US010682419B2

(12) United States Patent
Phiasivongsa et al.

(10) Patent No.: US 10,682,419 B2
(45) Date of Patent: *Jun. 16, 2020

(54) PRODRUGS OF PEPTIDE EPOXY KETONE PROTEASE INHIBITORS

(71) Applicant: Onyx Therapeutics, Inc., Thousand Oaks, CA (US)

(72) Inventors: Pasit Phiasivongsa, Brentwood, CA (US); Gary W. Luehr, Hayward, CA (US); Ge Peng, Mountain View, CA (US); Kolbot By, Hayward, CA (US); Shabbir T. Anik, San Francisco, CA (US)

(73) Assignee: ONYX THERAPEUTICS, INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,919

(22) Filed: Jan. 29, 2018

(65) Prior Publication Data

US 2018/0147291 A1 May 31, 2018

Related U.S. Application Data

(60) Division of application No. 15/065,347, filed on Mar. 9, 2016, now Pat. No. 9,878,047, which is a continuation of application No. 14/041,953, filed on Sep. 30, 2013, now Pat. No. 9,315,542, which is a continuation-in-part of application No. PCT/US2013/049804, filed on Jul. 9, 2013.

(60) Provisional application No. 61/790,106, filed on Mar. 15, 2013, provisional application No. 61/669,509, filed on Jul. 9, 2012.

(51) Int. Cl.

| | |
|---|---|
| A61K 47/64 | (2017.01) |
| A61K 47/68 | (2017.01) |
| C07K 5/10 | (2006.01) |
| A61K 47/60 | (2017.01) |
| C07K 5/083 | (2006.01) |
| C07K 5/065 | (2006.01) |
| C07K 5/103 | (2006.01) |
| C07K 5/107 | (2006.01) |
| C07K 5/097 | (2006.01) |
| C07K 5/117 | (2006.01) |
| C07K 7/06 | (2006.01) |
| A61K 38/07 | (2006.01) |
| C07K 5/113 | (2006.01) |
| A61K 47/54 | (2017.01) |
| C07K 5/08 | (2006.01) |
| A61K 38/06 | (2006.01) |

(52) U.S. Cl.
CPC ............ *A61K 47/64* (2017.08); *A61K 38/07* (2013.01); *A61K 47/549* (2017.08); *A61K 47/60* (2017.08); *A61K 47/6889* (2017.08); *C07K 5/06078* (2013.01); *C07K 5/08* (2013.01); *C07K 5/081* (2013.01); *C07K 5/0806* (2013.01); *C07K 5/0821* (2013.01); *C07K 5/10* (2013.01); *C07K 5/1008* (2013.01); *C07K 5/1016* (2013.01); *C07K 5/1021* (2013.01); *C07K 5/1024* (2013.01); *C07K 7/06* (2013.01); *A61K 38/06* (2013.01)

(58) Field of Classification Search
CPC ........ A61K 38/00; A61K 38/07; A61K 38/55; C07K 5/10; C07K 1/1075; C07K 2317/94
See application file for complete search history.

(56) References Cited

U.S. PATENT DOCUMENTS

| | | | |
|---|---|---|---|
| 4,733,665 | A | 3/1988 | Palmaz |
| 4,990,448 | A | 2/1991 | Konishi et al. |
| 5,071,957 | A | 12/1991 | Konishi et al. |
| 5,134,127 | A | 7/1992 | Stella et al. |
| 5,135,919 | A | 8/1992 | Folkman et al. |
| 5,340,736 | A | 8/1994 | Goldberg |
| 5,376,645 | A | 12/1994 | Stella et al. |
| 5,441,944 | A | 8/1995 | Weisz et al. |
| 5,723,492 | A | 3/1998 | Chandrakumar et al. |
| 5,756,764 | A | 5/1998 | Fenteany et al. |
| 5,831,081 | A | 11/1998 | Reuscher |
| 5,874,418 | A | 2/1999 | Stella et al. |
| 6,046,177 | A | 4/2000 | Stella et al. |
| 6,066,730 | A | 5/2000 | Adams et al. |
| 6,075,150 | A | 6/2000 | Wang et al. |
| 6,099,851 | A | 8/2000 | Weisman et al. |
| 6,133,248 | A | 10/2000 | Stella |
| 6,133,308 | A | 10/2000 | Soucy et al. |
| 6,150,415 | A | 11/2000 | Hammock et al. |
| 6,204,257 | B1 | 3/2001 | Stella et al. |
| 6,235,717 | B1 | 5/2001 | Leban et al. |
| 6,294,560 | B1 | 9/2001 | Soucy et al. |
| 6,297,217 | B1 | 10/2001 | Adams et al. |

(Continued)

FOREIGN PATENT DOCUMENTS

| | | |
|---|---|---|
| EP | 0 411 660 A1 | 2/1991 |
| EP | 1 136 498 A1 | 9/2001 |

(Continued)

OTHER PUBLICATIONS

Definition of Cancer, [Retrieved from] <http://www.medterms.com>, 1 page [retrieved on Sep. 16, 2005].

(Continued)

*Primary Examiner* — James H Alstrum-Acevedo
*Assistant Examiner* — Kaipeen E Yang
(74) *Attorney, Agent, or Firm* — Marshall, Gerstein & Borun LLP

(57) ABSTRACT

This disclosure features compounds that are useful as prodrugs of epoxy ketone protease inhibitors.

19 Claims, 48 Drawing Sheets

(56) References Cited

U.S. PATENT DOCUMENTS

| | | |
|---|---|---|
| 6,410,512 B1 | 6/2002 | Mundy et al. |
| 6,462,019 B1 | 10/2002 | Mundy et al. |
| 6,492,333 B1 | 12/2002 | Mundy |
| 6,548,668 B2 | 4/2003 | Adams et al. |
| 6,613,541 B1 | 9/2003 | Vaddi et al. |
| 6,617,309 B2 | 9/2003 | Tung et al. |
| 6,656,904 B2 | 12/2003 | Mundy et al. |
| 6,660,268 B1 | 12/2003 | Palombella et al. |
| 6,699,835 B2 | 3/2004 | Plamondon et al. |
| 6,740,674 B2 | 5/2004 | Klimko et al. |
| 6,781,000 B1 | 8/2004 | Wang et al. |
| 6,794,516 B2 | 9/2004 | Soucy et al. |
| 6,831,099 B1 | 12/2004 | Crews et al. |
| 6,838,252 B2 | 1/2005 | Mundy et al. |
| 6,838,436 B1 | 1/2005 | Mundy et al. |
| 6,849,743 B2 | 2/2005 | Soucy et al. |
| 6,884,769 B1 | 4/2005 | Mundy et al. |
| 6,902,721 B1 | 6/2005 | Mundy et al. |
| 7,109,323 B2 | 9/2006 | Plamondon et al. |
| 7,189,740 B2 | 3/2007 | Zeldis |
| 7,388,017 B2 | 6/2008 | Tung et al. |
| 7,417,042 B2 | 8/2008 | Smyth et al. |
| 7,442,830 B1 | 10/2008 | Olhava et al. |
| 7,491,704 B2 | 2/2009 | Smyth et al. |
| 7,531,526 B2 | 5/2009 | Adams et al. |
| 7,687,456 B2 | 3/2010 | Zhou et al. |
| 7,691,852 B2 | 4/2010 | Shenk et al. |
| 7,700,588 B2 | 4/2010 | Merkus |
| 7,737,112 B2 | 6/2010 | Lewis et al. |
| 7,863,297 B2 | 1/2011 | Zeldis |
| 7,968,569 B2 | 6/2011 | Zeldis |
| 8,080,545 B2 | 12/2011 | Shenk et al. |
| 8,080,576 B2 | 12/2011 | Shenk et al. |
| 8,088,741 B2 | 1/2012 | Smyth et al. |
| 8,129,346 B2 | 3/2012 | Smyth et al. |
| 8,198,262 B2 | 6/2012 | Zeldis |
| 8,198,270 B2 | 6/2012 | Smyth et al. |
| 8,198,306 B2 | 6/2012 | Zeldis |
| 8,207,124 B2 | 6/2012 | Smyth et al. |
| 8,207,125 B2 | 6/2012 | Smyth et al. |
| 8,207,126 B2 | 6/2012 | Smyth et al. |
| 8,207,127 B2 | 6/2012 | Smyth et al. |
| 8,207,297 B2 | 6/2012 | Smyth et al. |
| 8,324,174 B2 | 12/2012 | Smyth et al. |
| 8,357,683 B2 | 1/2013 | Shenk et al. |
| 8,367,617 B2 | 2/2013 | Phiasivongsa et al. |
| 8,431,571 B2 | 4/2013 | Shenk et al. |
| 2002/0103127 A1 | 8/2002 | Mundy et al. |
| 2002/0107203 A1 | 8/2002 | Mundy et al. |
| 2002/0111292 A1 | 8/2002 | Mundy et al. |
| 2003/0224469 A1 | 12/2003 | Buchholz et al. |
| 2003/0236223 A1 | 12/2003 | Wagner et al. |
| 2004/0097420 A1 | 5/2004 | Palombella et al. |
| 2004/0116329 A1 | 6/2004 | Epstein |
| 2004/0138153 A1 | 7/2004 | Ramesh et al. |
| 2004/0167139 A1 | 8/2004 | Potter |
| 2004/0171556 A1 | 9/2004 | Purandare et al. |
| 2004/0254118 A1 | 12/2004 | He et al. |
| 2004/0266664 A1 | 12/2004 | Crews et al. |
| 2005/0025734 A1 | 2/2005 | Garrett et al. |
| 2005/0101781 A1 | 5/2005 | Agoulnik et al. |
| 2005/0245435 A1 | 11/2005 | Smyth et al. |
| 2005/0256324 A1 | 11/2005 | Laidig et al. |
| 2006/0030533 A1 | 2/2006 | Smyth et al. |
| 2006/0088471 A1 | 4/2006 | Bennett et al. |
| 2006/0128611 A1 | 6/2006 | Lewis et al. |
| 2006/0241056 A1 | 10/2006 | Orlowski et al. |
| 2007/0105786 A1 | 5/2007 | Zhou et al. |
| 2007/0207950 A1 | 9/2007 | Yao et al. |
| 2008/0090785 A1 | 4/2008 | Smyth et al. |
| 2009/0099132 A1 | 4/2009 | Olhava et al. |
| 2009/0131421 A1 | 5/2009 | Smyth et al. |
| 2009/0156473 A1 | 6/2009 | Schubert |
| 2009/0182149 A1 | 7/2009 | Kawahara et al. |
| 2009/0203698 A1 | 8/2009 | Zhou et al. |
| 2009/0215093 A1 | 8/2009 | Bennett et al. |
| 2010/0144648 A1 | 6/2010 | Shenk et al. |
| 2010/0240903 A1 | 9/2010 | Phiasivongsa et al. |
| 2011/0236428 A1 | 9/2011 | Kirk et al. |
| 2012/0077855 A1 | 3/2012 | Phiasivongsa et al. |
| 2012/0088903 A1 | 4/2012 | Phiasivongsa et al. |
| 2012/0101025 A1 | 4/2012 | Smyth et al. |
| 2012/0101026 A1 | 4/2012 | Smyth et al. |
| 2012/0277146 A1 | 11/2012 | Smyth et al. |
| 2012/0329705 A1 | 12/2012 | Smyth et al. |
| 2013/0035295 A1 | 2/2013 | Kirk et al. |
| 2013/0041008 A1 | 2/2013 | Shenk et al. |
| 2013/0053303 A1 | 2/2013 | Shenk et al. |
| 2013/0065827 A1 | 3/2013 | Phiasivongsa |
| 2013/0072422 A1 | 3/2013 | Shenk et al. |
| 2013/0130968 A1 | 5/2013 | Zhou et al. |
| 2013/0150289 A1 | 6/2013 | Phiasivongsa et al. |
| 2013/0150290 A1 | 6/2013 | Phiasivongsa et al. |

FOREIGN PATENT DOCUMENTS

| | | |
|---|---|---|
| WO | WO-1991/013904 A1 | 9/1991 |
| WO | WO-1994/015956 A1 | 7/1994 |
| WO | WO-1995/023797 A1 | 9/1995 |
| WO | WO-1995/024914 A1 | 9/1995 |
| WO | WO-1996/013266 A1 | 5/1996 |
| WO | WO-1996/032105 A1 | 10/1996 |
| WO | WO-1998/010779 A1 | 3/1998 |
| WO | WO-2000/002548 A2 | 1/2000 |
| WO | WO-2000/061167 A2 | 10/2000 |
| WO | WO-2001/028579 A2 | 4/2001 |
| WO | WO-2003/059898 A2 | 7/2003 |
| WO | WO-2004/089341 A1 | 10/2004 |
| WO | WO-2005/065649 A1 | 7/2005 |
| WO | WO-2005/105827 A2 | 11/2005 |
| WO | WO-2005/111008 A2 | 11/2005 |
| WO | WO-2005/111009 A2 | 11/2005 |
| WO | WO-2006/017842 A1 | 2/2006 |
| WO | WO-2006/045066 A2 | 4/2006 |
| WO | WO-2006/063154 A1 | 6/2006 |
| WO | WO-2006/086600 A1 | 8/2006 |
| WO | WO-2006/099261 A2 | 9/2006 |
| WO | WO-2006/113470 A2 | 10/2006 |
| WO | WO-2007/021666 A2 | 2/2007 |
| WO | WO-2007/056464 A1 | 5/2007 |
| WO | WO-2007/067976 A2 | 6/2007 |
| WO | WO-2007/149512 A2 | 12/2007 |
| WO | WO-2008/033807 A2 | 3/2008 |
| WO | WO-2008/091620 A2 | 7/2008 |
| WO | WO-2008/140782 A2 | 11/2008 |
| WO | WO-2009/020448 A1 | 2/2009 |
| WO | WO-2009/045497 A1 | 4/2009 |
| WO | WO-2009/051581 A1 | 4/2009 |
| WO | WO-2009/067453 A1 | 5/2009 |
| WO | WO-2009/154737 A1 | 12/2009 |
| WO | WO-2010/036357 A1 | 4/2010 |
| WO | WO-2010/048298 A1 | 4/2010 |
| WO | WO-2010/108172 A1 | 9/2010 |
| WO | WO-2010/145376 A1 | 12/2010 |
| WO | WO-2011/060179 A1 | 5/2011 |
| WO | WO-2011/109355 A1 | 9/2011 |
| WO | WO-2011/123502 A1 | 10/2011 |
| WO | WO-2011/136905 A2 | 11/2011 |

OTHER PUBLICATIONS

Acharyya et al., Cancer cachexia is regulated by selective targeting of skeletal muscle gene products. *J. Clin. Invest.* 114: 370-8 (2004).

Adams et al., Proteasome inhibitors: A novel class of potent and effective antitumor agents. *Cancer Res.* 59: 2615-22 (1999).

Adams, Cancer Drug Discovery and Development, Protease Inhibitors in Cancer Therapy, Human Press, Chapter 20, Phase I trials, pp. 271-282 (2004).

Adams, The development of proteasome inhibitors as anticancer drugs. *Cancer Cell*, 5: 417-21 (2003).

Almond et al., The proteasome: a novel target for cancer chemotherapy. *Leukemia*, 16(4): 433-43 (2002).

(56) References Cited

OTHER PUBLICATIONS

Altun et al., Effects of PS-341 on the activity and composition of proteasomes in multiple myeloma cells. *Cancer Res.* 65: 7896 (2005).
Alves et al., Diels-alder reactions of alkyl 2H-azirine-3-carboxylates with furans. *J. Chem. Soc. Perkin Trans.* 1: 2969-76 (2001).
Arastu Kapur et al., Nonproteasomal targets of the proteasome inhibitors bortezomib and carfilzomib: A link to clinical adverse events. *Clin Cancer Res.* 17: 2734-43 (2011).
Argiriadi, Binding of alkylurea inhibitors to epoxide hydrolase implicates active site tyrosines in substrate activation. *J. Biol. Chem.* 275(20): 15265-70 (2000).
Bao et al., PR-39 and PR-11 peptides inhibit ischemia-reperfusion injury by blocking proteasome-mediated IKBa degradation. Am. J. Physiol. Heart Circ. Physiol. 281: H2612-8 (2001).
Benedetti et al., Versatile and stereoselective synthesis of diamino diol dipeptide isosteres, core units of pseudopeptide HIV protease inhibitors. *J. Org* <http://J.Org>. Chem. 62: 9348-53 (1997).
Berge et al., Pharmaceutical salts. *J. Pharm. Sci.* 66(1): 1-19 (1977).
Bernier et al., A methionine aminopeptidase-2 inhibitor, PPI-2458, for the treatment of rheumatoid arthritis. *Proc. Natl. Acad. Sci. USA*, 101(29): 10768-73 (2004).
Bis et al., Defining & Addressing Solid-State Risks After the Proof-of-Concept Stage of Pharmaceutical Development. *Drug Development & Delivery*, 32-34 (2011).
Blackburn et al., Characterization of a new series of non-covalent proteasome inhibitors with exquisite potency and selectivity for the 20S 135-subunit. *Biochem J.* 430: 461-76 (2010).
Boccadoro et al., Preclinical evaluation of the proteasome inhibitor bortezomib in cancer therapy. *Cancer Cell Internatl.* 5(18): Jun. 1, 2005.
Bogyo et al., Biochemistry. *Proc. Natl. Acad. Sci. USA*, 94: 6629-34 (1997).
Bogyo et al., Substrate binding and sequence preference of the proteasome revealed by active-site-directed affinity probes. *Chem. Biol.* 5(6): 307-20 (1998).
Bougauchi et al., Catalytic asymmetric epoxidation of α, β-unsaturated ketones promoted by lanthanoid complexes. J. Am. Chem. Soc. 119: 2329-30 (1997).
Brinkley, A brief survey of methods for preparing protein conjugates with dyes, haptens, and cross-linking reagents. *Bioconjug. Chem.* 3: 2-13 (1992).
Brittain et al., Physical characterization of pharmaceutical solids. *Pharma. Res.* 8(8): 963-73 (1991).
Brown et al., Selective seductions. 37. Asymmetric reduction of prochiral ketones with β-(3-Pmanyl)-9- borabicyclo[3.3.1]nonane. *J. Org* <http://J.Org>. Chem. 50: 1384-94 (1985).
Byrn et al., Pharmaceutical solids: A strategic approach to regulatory considerations. *Pharma. Res.* 12(7): 945-54 (1995).
Caira, Crystalline polymorphism of organic compounds. *Topics Curr. Chem.* 198: 163-208 (1998).
Cancer [online], [retrieved on Jul. 6, 2007] Retrieved from the Internet, URL: http://www.nlm.nih.gov/medlineplus/cancer.html.
Cascio et al., 26S proteasomes and immunoproteasomes produce mainly N-extended versions of an antigenic peptide. *EMBO J.* 20: 2357-66 (2001).
Center for Drug Evaluation and Research, Application No. 21-602, Medical Review, Clinical NDA Review, "NDA 21-602 VELCADETM (bortexomib) for injection," Clinical Review, 1-34 (2003).
Center for Drug Evaluation and Research, Application No. 21-602, Medical Review, Clinical NDA Review, "NDA 21-602 VELCADETM (bortexomib) for injection," Clinical Review, 1-47 (2003).
Center for Drug Evaluation and Research, Application No. 21-602, Medical Review, Clinical NDA Review, "NDA 21-602 VELCADETM (bortexomib) for injection," Clinical Review, 81-125 (2003).
Ciechanover, The ubiquitin-proteasome proteolytic pathway. *Cell*, 79: 13-21 (1994).
Cohen, AIDS mood upbeat-for a change. *Science*, 267: 959-60 (1995).
Collins, Endothelial nuclear factor—KB and the initiation of the atherosclerotic lesion. *Lab. Invest.* 68(5): 499-508 (1993).
Concise Encyclopedia Chemistry, p. 490 (1993).
Corey et al., A general, catalytic, and enantioselective synthesis of α-amino acids. *J. Am. Chem. Soc.* 114: 1906-8 (1992).
Corey et al., Highly enantioselective borane reduction of ketones catalyzed by chiral oxazaborolidines. mechanism and synthetic implications. J. Am. Chem. Soc. 109: 5551-3 (1987).
Craiu et al., Lactacyustin and clasto-lactacystin β-lactone modify multiple proteasome β-subunits and inhibit intracellular protein degradation and major hisotcompatibility complex class I antigen presentation. *J. Biol. Chem.* 272(20): 13437-45 (1997).
Dana et al., A stereoselective route to hydroxyethylamine dipeptide isosteres. *J. Am. Chem. Soc.* 65: 7609-11 (2000).
Dasmahapatra et al., Carfilzomib interacts synergistically with histone deacetylase inhibitors in mantle cell lymphoma cells in vitro and in vivo. *Mol. Cancer. Ther.* 10: 1686-97 (2011).
Demo et al., Antitumor activity of PR-171, a novel irreversible inhibitor of the proteasome. *Cancer Res.* 67(13): 6383-91 (2007).
Dess et al., A useful 12-I-5 iriacetoxyperiodinane (the Dess-Martin Periodinane) for the selective oxidation of primary or secondary alcohols and a variety of related 12-I-5 species. *J. Am. Chem. Soc.* 113: 7277-87 (1991).
Dess et al., Readily accessible 12-I-5 oxidant for the conversion of primary and secondary alcohols to aldehydes and ketones. *J. Org. Chem.* 48: 4155-6 (1983).
Diaz-Hernandez et al., Neuronal induction of the immunoproteasome in Huntington's Disease. *J. Neurosci.* 23: 11653-61 (2003).
Dimopoulos et al., Lenalidomide plus dexamethasone for relapsed or refractory multiple myeloma. *N. Engl. J. Med.* 357(21): 2123-32 (2007).
Dinger et al., Some crystal growing tips, http://xray.chem.ufl.edu/growing%20tips.htm <http://xray.chem.ufl.edu/growing%2520tips.htm>, 3 pages (2006).
Dobler, Total synthesis of (+)-epopromycin B and its analogues-studies on the inhibition of cellulose biosynthesis. *Tetrahedron Lett.* 42(2): 215-8 (2001).
Egerer et al., Tissue-specific up-regulation of the proteasome subunit beta5i (LMP7) in Sjogren's Syndrome. Arthritis Rheum. 54: 1501-8 (2006).
Elliott et al., The proteasome a new target for novel drug therapies. *Am J Clin Pathol.* 116: 637-46 (2001).
Elofsson et al., Towards subunit-specific proteasome inhibitors: synthesis and evaluation of peptide α, β-epoxyketones. *Chem. Biol.* 6: 811-22 (1999).
European Search Report, EP 08 16 4241, completed Jan. 22, 2009, 5 pages.
European Search Report, EP 09 00 6228, completed Aug. 25, 2009, 7 pages.
European Search Report, EP 09822636.8, dated Aug. 1, 2012, 6 pages.
Extended European Search Report, EP 12189466.1, dated Jul. 23, 2013, 10 pages.
Extended European Search Report, EP 13167148.9, dated Aug. 2, 2013, 7 pages.
Favit et al., Prevention of β-amyloid neurotoxicity by blockade of the ubiquitin-proteasome protealytic pathway. *J. Neurochem.* 75(3): 1258-63 (2000).
FDA mulls drug to slow late-stage Alzheimers[Online], [retrieved on Sep. 23, 2003]. Retrieved from the Internet,; U RL: http://www.cnn.com/2003/HEALTH/conditions/09/24/alzheimers.drug.ap/index.html>.
Fenteany et al., A β-lactone related to lactacystin induces neurite outgrowth in a neuroblastoma cell line and inhibits cell cycle progression in an osteosarcoma cell line. *Proc. Natl. Acad. Sci. USA*, 91: 3358-62 (1994).
Figueiredo-Pereira et al., The antitumor drug aclacinomycin A, which inhibits the degradation of ubiquitinated proteins, shows selectivity for the chymotrypsin-like activity of the bovine pituitary 20 S proteasome. *J. Biol. Chem.* 271(2): 16455-9 (1996).
First Vitality (2008, updated) Alzheimer's & Senile Dementia, http://www.lstvitality.co.uk/health/alzheimers/carnosine_proteasomal_alzheimers.htm, p. 1.

(56) References Cited

OTHER PUBLICATIONS

Fox et al.. Organic Chemistry, Publisher: Jones & Bartlett Pub, Sec. 5-6, pp. 177-178, Published Jun. 15, 2004.
Gan et al., Identification of cathepsin B as a mediator of neuronal death induced by A-activated microglial cells using a functional genomics approach. J. Biol. Chem. 279: 5565-72 (2004).
Gao et al., Inhibition of ubiquitin-proteasome pathway-mediated IκBα degradation by a naturally occurring antibacterial peptide. *J. Clin. Invest.* 106: 439-48 (2000).
Garcia-Echeverria, Peptide and peptide-like modulators of 20S proteasome enzymatic activity in cancer cells. *Internatl. J. Peptide Res. Ther.* 12(1): 49-64 (2006).
Garrett et al., Selective inhibitors of the osteoblast proteasome stimulate bone formation in vivo and in vitro. *J. Clin. Invest.* 111: 1771-82 (2003).
Gennaro, Remington: Practice of The Science of Pharmacy, 19th Edition, Mack Publishing Company, Chapter 83, pp. 1447-1462 (1995).
Golub et al., Molecular classification of cancer: Class discovery and class prediction by genes expression monitoring. *Science*, 286: 531-7 (1999).
Gonzales et al., Pain relief in chronic pancreatitis by pancreatico-jejunostomy. An institutional experience. *Arch. Med. Res.* 28(3): 387-90 (1997).
Gordon et al. 1207 results of study PX-171-007 a phase 1b/2 study of carfilzomib, a selective proteasome inhibitor, in patients with selected advanced metastatic solid tumors. *Eur. J. Cancer Suppl.* 7(2): 122-3 (2009).
Graz University of Technology, Database of fluorescent dyes properties and applications, www.Fluorophonres.org <http://www.Fluorophonres.org>, 33 pgs, Exhibit B to response filed with US Patent office on Sep. 16, 2008 for U.S. Appl. No. 11/254,541 (now abandoned).
Green et al., Protective groups in organic synthesis, 2nd Ed., Wiley & Sons, Inc., New York (1991).
Griffith et al., Molecular recognition of angiogenesis inhibitors fumagillin and ovalicin by methionine aminopeptidase. *Proc. Natl. Acad. Sci. USA*, 95: 15183-88 (1998).
Groettrup et al., Selective proteasome inhibitors: Modulators of antigen presentation? *Drug Discov. Today*, 4(2): 63-71 (1999).
Groll et al., Crystal structure of epoxomicin: 20S proteasome reveals a molecular basis for selectivity of r,â-epoxyketone proteasome inhibitors. *J. Am. Chem. Soc.* 122: 1237-8 (2000).
Gura, Systems for identifying new drugs are often faulty. *Science*, 278(5340): 1041-2 (1997).
Hanada et al., Epoxomicin, A new antitumor agent of microhial origin. *J. Antibiotics*, 45(11): 1746- 52 (1992).
Hanson et al., Synthesis of new dipeptide analogues containing novel ketovinyl and hydroxyethylidene isosteres via Grignard addition to chiral α-amino aldehydes. J. Org <http://J.Org>. Chem. 50: 5399-5401 (1985).
Harding et al., Novel dipeptide aldehydes are proteasome inhibitors and block the MHC-1 antigen-processing pathway. *J. Immunol.* 155: 1767-75 (1995).
Hardy, The secret life of the hair follicle. *Trends Genet.* 8: 55-61 (1992).
Harris et al., Effects of transforming growth factor 3 on bone nodule formation and expression of bone morphogenetic protein 2, osteocalcin, osteopontin, alkaline phosphatase, and type I collagen mRNA in long-term cultures of fetal rat calvarial osteoblasts. *J. Bone Miner. Res.* 9(6): 855-63 (1994).
Haugland, Coupling of monoclonal antibodies with fluorophores. *Methods Mol. Biol.* 45: 205-21 (1995).
*Hawley's Condensed Chemical Dictionary*, p. 594 (1993).
Hilfiker, Ed., *Polymorphism in the Pharmaceutical Industry*, pp. 12-15 (2006).
Hoffman et al., Highly stereoselective syntheses of syn- and anti- 1,2-amino alcohols. J. Org. <http://J.Org>. Chem. 67: 1045-56 (2002).
Holbeck et al., Analysis of food and drug administration— Approved anticancer agents in the NC160 panel of human tumor cell lines. *Mol. Cancer Ther.* 9: 1451-60 (2010).
Huff, HIV Protease: A novel chemotherapeutic target for AIDS. *J. Med. Chem.* 34(8): 2305-14 (1991).
International Preliminary Report on Patentability for corresponding PCT Application No. PCT/US2005/012740, dated Oct. 19, 2006, 11 pgs.
International Preliminary Report on Patentability for corresponding PCT Application No. PCT/US2005/016335, dated Nov. 14, 2006, 11 pgs.
International Preliminary Report on Patentability for PCT/US2005/017000, dated Nov. 21, 2006, 12 pages.
International Preliminary Report on Patentability for PCT/US2005/028246, dated Feb. 6, 2007, 8 pages.
International Preliminary Report on Patentability for PCT/US2005/037966, dated Apr. 24, 2007, 12 pages.
International Preliminary Report on Patentability for PCT/US2005/044451, dated Jun. 13, 2007, 8 pages.
International Preliminary Report on Patentability for PCT/US2008/005997, dated Nov. 10, 2009, 7 pages.
International Preliminary Report on Patentability for PCT/US2008/011443, dated Apr. 7, 2010, 12 pages.
International Preliminary Report on Patentability for PCT/US2010/056395, dated May 24, 2012, 8 pages.
International Preliminary Report on Patentability for PCT/US2011/026629, dated Sep. 4, 2012, 11 pages.
International Preliminary Report on Patentability PCT/US2007/014427, dated Dec. 22, 2008, 8 pages.
International Preliminary Report on Patentability PCT/US2009/061498, dated May 5, 2011, 9 pages.
International Preliminary Report on Patentability PCT/US2011/031436, dated Oct. 9, 2012, 5 pages.
International Search Report (Partial) for PCT/US2008/011443, dated Dec. 9, 2008, 6 pages.
International Search Report and Written Opinion for corresponding PCT Application No. PCT/US2005/012740, dated Jan. 9, 2006, 16 pgs.
International Search Report and Written Opinion for corresponding PCT Application No. PCT/US2005/016335, dated Jan. 2, 2006, 17 pgs.
International Search Report and Written Opinion for PCT/US2007/014427, dated Dec. 3, 2007, 12 pages.
International Search Report and Written Opinion for PCT/US2010/056395, dated Mar. 15, 2011, 10 pages.
International Search Report and Written Opinion for PCT/US2011/026629, dated Jun. 30, 2011, 18 pages.
International Search Report and Written Opinion for PCT/US2011/031436, dated Nov. 28, 2011, 5 pages.
International Search Report and Written Opinion of the International Searching Authority for PCT/US2005/017000, dated Feb. 3, 2006, 12 pages.
International Search Report and Written Opinion of the International Searching Authority for PCT/US2005/028246, dated Jan. 19, 2006, 11 pages.
International Search Report and Written Opinion of the International Searching Authority for PCT/US2005/037966, dated Jan. 24, 2006, 17 pages.
International Search Report and Written Opinion of the International Searching Authority for PCT/US2005/044451, dated May 2, 2006, 12 pages.
International Search Report and Written Opinion of the International Searching Authority for PCT/US2006/043503, dated Feb. 19, 2007, 17 pages.
International Search Report and Written Opinion of the International Searching Authority for PCT/US2008/005997, dated Nov. 7, 2008, 8 pages.
International Search Report and Written Opinion of the International Searching Authority for PCT/US2008/011443, dated Mar. 25, 2009, 16 pages.
International Search Report and Written Opinion of the International Searching Authority for PCT/US2010/028126, dated Jun. 9, 2010, 13 pages.

(56) References Cited

OTHER PUBLICATIONS

International Search Report and Written Opinion of the International Searching Authority for PCT/US2012/055127, dated Dec. 18, 2012, 10 pages.
International Search Report and Written Opinion of the International Searching Authority for PCT/US2013/040127, dated Oct. 22, 2013, 15 pages.
International Search Report for PCT/US2009/061498, dated Dec. 10, 2009, 5 pages.
Iqbal et al., Potent inhibitors of proteasome. *J. Med Chem.* 38: 2276-7 (1995).
Iqbal et al., Potent α-ketocarbonyl and boronic ester derived inhibitors of proteasome. *Bioorg. Med. Chem. Lett.* 6: 287-90 (1996).
Ivanisevic et al., Uses of X-ray powder diffraction in the pharmaceutical Industry. *Pharmaceutical Sciences Encyclopedia: Drug Discovery, Development, and Manufacturing*, Edited by Shayne C. Gad, pp. 1-42 (2010).
Jacobsen et al., Asymmetric dihydroxylation via ligand-accelerated catalysis. *J. Am. Chem. Soc.* 110: 1968-70 (1988).
Jain, Delivery of molecular medicine to solid tumors. *Science*, 271(5252): 1079-80 (1996).
Jones et al., Total synthesis of the immunosuppressant (−)-FK-506. *J. Am. Chem. Soc.* 111: 1157-9 (1989).
Jung et al., Melatonin in cancer management: Progress and promise. *Cancer Res.* 66(22): 9789-93 (2006).
Kessler et al., Extended peptide-based inhibitors efficiently target the proteasome and reveal overlapping specificities of the catalytic β-subunits. *Chem. Biol.* 8(9): 913-29 (2001).
Khan et al., Immunoproteasomes largely replace constitutive proteasomes during an antiviral and antibacterial immune response in the liver. *J. Immunol.* 5 167: 6859-68 (2001).
Kijima et al., Trapoxin, an antitumor cyclic tetrapeptide, is an irreversible inhibitor of mammalian histone Deacetylase. *J. Biol. Chem.* 268(30): 22429-35 (1993).
Kim et al., Proteasome inhibition by the natural products epoxomicin and dihydroeponemycin: insights into specificity and potency. *Bioorg. Med. Chem. Lett.* 9: 3335-40 (1999).
Kisselev et al., Proteasome inhibitors: From research tools to drug candidates. *Chem. Biol.* 8(8): 739-58 (2001).
Kojima et al., Two-way cleavage of β-amyloid protein precursor by multicatalytic proteinase. *Fed. Eur. Biochem. Soc.* 304: 57-60 (1992).
Koong et al., Hypoxia causes the activation of nuclear factor-κB through the phosphorylation of IκBα on tyrosine residues. *Cancer Res.* 54: 1425-30 (1994).
Koong et al., Hypoxic activation of nuclear factor-κB is mediated by a Ras and Raf signaling pathway and does not involve MAP kinase (ERK1 or ERK2)1. *Cancer Res.* 54: 5273-9 (1994).
Kreidenweiss et al., Comprehensive study of proteasome nhibitors against Plasmodium falciparum laboratory strains and field isolates from Gabon, Malar J., 7(187):1-8, 2008.
Krise et al., A novel prodrug approach for tertiary amines: Synthesis and preliminary evaluation of N-phosphonooxymethyl prodrugs. *J. Med. Chem.* 42: 3094-100 (1999).
Kuhn et al., Potent activity of carfilzomib, a novel, irreversible inhibitor of the ubiquitin-proteasome pathway, against preclinical models of multiple myeloma. *Blood*, 110(9): 3281-90, prepublished online: Jun. 25, 2007.
Kumatori et al., Abnormally high expression of proteasomes in human leukemic cells. *Proc. Natl. Acad. Sci. USA*, 87: 7071-5 (1990).
Lala et al., Role of notric oxide in tymor progression: Lessons from experimental tumors. *Cancer Metastasis Rev.* 17: 91-106 (1998).
Le Blanc et al., Growth in vivo and prolongs survival in a murine model proteasome inhibitor PS-341 inhibits human myeloma cell. *Cancer Res.* 62: 4996-5000, Published online Sep. 1, 2002.
Lecker et al., Multiple types of skeletal muscle atrophy involve a common program of changes in gene expression. *FASEB J.* 18: 39-51 (2004).
Lee et al., Proteasome inhibitors: Valuable new tools for cell biologists. *Trends in Cell Biol.*, 8: 397-403 (1988).
Liang et al., Synthesis of cryptophycin 52 using the sharpless asymmetric dihydroxylation: Diol to epoxide transformation optimized for a base-sensitive substrate. *J. Am. Chem. Soc.* 65: 3143-7 (2000).
Lin et al., Alteration of substrate and inhibitor specificity of feline immunodeficiency virus protease. *J. Virol.* 74(10): 4710-20 (2000).
Loftsson et al., Pharmaceutical applications of cyclodextrins. 1. Drug solubilization and stabilization. *J. Pharmaceut. Sci.* 85(10): 1017-25 (1996).
Luke et al., Review of the basic and clinical pharmacology of sulfobutylether-13-0cyclodextrin (SBECD). *J. Pharmaceut. Sci.* 99: 3291-301 (2010).
MacAry et al., Mobilization of MHC class I molecules from late endosomes to the cell surface following activation of CD34-derived human Langerhans cells. *Proc. Natl. Acad. Sci. USA*, 98: 3982-7 (2001).
Mandel et al., Neuroprotective strategies in Parkinson's Disease. *CNS Drugs*, 17(10): 729-62 (2003).
Marx et al., Reactivity-selectivity in the Swern Oxidation of alcohols using dimethyl sulfoxide-oxalyl chloride. *J. Org. Chem.* 49: 788-93 (1984).
McGraw-Hill Dictionary of Chemical Terms, p. 282 (1990).
Meng et al., Eponemycin exerts its antitumor effect through the inhibition of proteasome function. *Cancer Res.* 59: 2798-801 (1999).
Meng et al., Epoxomicin, a potent and selective proteasome inhibitor, exhibits in vivo antimflamatory activity. *Proc. Natl. Acad. Sci. USA*, 96: 10403-8 (1999).
Min et al., Bortezomib in combination with conventional chemotherapeutic agents for multiple myeloma compared with bortezomib alone. *Jap. J. Clin. Oncol.* 37(12): 961-8 (2007).
Mishto et al., Immunoproteasome and LMP2 polymorphism in aged and Alzheimer's disease brains. *Neurobiol. Aging*, 27: 54-66 (2006).
Molecular biology and biotechnology a comprehensive desk reference: Edited by R A Meyers. pp. 658-664. VCH, Weinheim, Germany, 1995, DM89 ISBN 1-56081-925-1.
Molecular Probes, Inc. , Introduction to Fluorescence techniques, invitrogen detection technologies, 11 pgs, Molecular Probes, Inc. (2007), Exhibit A to response filed with US Patent Office on Sep. 16, 2008 for U.S. Appl. No. 11/254,541 (now abandoned).
Morissette et al., High-throughput crystallization: Polymorphs, salts, co-crystals and solvates of pharmaceutical solids, Adv. Drug Deliv. Rev. 56(3): 276 (2004).
Morris, Structural Aspects of Hydrates and Solvates in Polymorphism in Pharmaceutical Solids, Polymorphism in Pharmaceutical Solids, Ed H. G. Nbrittain, Marcel Dekker, New York, pp. 125181 (1999).
Muchamuel et al., A selective inhibitor of the immunoproteasome subunit NMP7 blocks cytokine production and attenuates progression of experimental arthritis. *Nature Med.* 15: 781-7 (1999).
Myung et al., Lack of proteasome active site allostery as revealed by subunit-specific inhibitors. *Molec. Cell*, 7(2): 411-20 (2001).
Myung et al., The ubiquitin-proteasome pathway and proteasome inhibitors. *Med. Res. Rev.* 21(4): 245-73 (2001).
Nemoto et al., Catalytic asymmetric epoxidation of enones using La-BINOL-Triphenylarsine oxide complex: Structural determination of the asymmetric catalyst. *J. Am. Chem. Soc.* 123: 2725-32 (2001).
Newman et al.,Solid-state analysis of the active pharmaceutical ingredient in drug products. *Drug Disc. Today*, 8(19): 898-905 (2003).
Oishi et al., Diastereoselective synthesis of new psi '(E)-CH=CMel- and psi '(Z)-CH=CMel- type alkene dipeptide isosteres by organocopper reagents and application to conformationally restricted cyclic RGD peptidomimetics. *J. Org. Chem.* 67: 6162-73 (2002).
Orlowski et al., Phase I trial of the proteasome inhibitor PS-341 in patients with refractory hematologic malignancies. *J. Clin. Oncol.* 20(22): 4420-7 (2002).
Orlowski et al., Proteasome inhibitors in cancer therapy: lessons from the first decade. *Clin. Canc. Res.* 14: 1649-165 (2008).

(56) References Cited

OTHER PUBLICATIONS

Overkleeft et al., Solid phase synthesis of peptide vinyl sulfone and peptide expoxyketone proteasome inhibitors. *Tetrahedron Lett.* 41(32): 6005-9 (2000).
Palombella et al., The ubiquitin-proteasome pathway is required for processing the NF-.kappa.B1 precursor protein and the activation of NF-.kappa.B. *Cell*, 78: 773-85 (1994).
Paoluzzi et al., Targeting Bcl-2 family members with the BH3 mimetic AT-101 markedly enhances the therapeutic effects of chemotherapeutic agents in in vitro and in vivo models of B-cell lymphoma. *Blood*, 111(11): 5350-8 (2008).
Pasut et al., PEG conjugates in clinical development or use as anticancer agents: an overview. *Adv. Drug Deliv. Rev.* 61: 1177-88 (2009).
Paugam et al., Characterization and role of protozoan parasite proteasomes. *Trends Parasitol.* 19:55-9 (2003).
Pivazyan et al., Inhibition of HIC-1 protease by a boron-modified polypeptide. *Biochem. Pharm.* 60: 927-36 (2000).
Polymorphism in Pharmaceutical Solids, edited by Brittain, 1999, Marcel Dekker Inc., p. 228-229, 236.
Pye et al., Proteasome inhibition ablates activation of NF-KB in myocardial reperfusion and reduces reperfusion of injury. *Am. J. Physiol. Heart Circ. Physiol.* 284: H919-26 (2003).
Qureshi et al., The proteasome as a lipopolysaccharide-binding protein in macrophages: Differential effects of proteasome inhibition on lipopolysaccharide-induced signaling events. *J. Immunol.* 171: 1515-25 (2003).
Raw et al., Regulatory considerations of pharmaceutical solid polymorphism in Abbreviated New Drug Applications (ANDAs). *Adv. Drug Deliv. Rev.* 56: 397-414 (2004).
Reidlinger et al., Catalytic properties of 26 S and 20 S proteasomes and radiolabling of MB 1, LMP7, and C7 subunits associated with trypsin-like and chymotrypsin-like activities. *J. Biol. Chem.* 272(40): 24899-905 (1997).
Roccaro et al., Selective inhibition of chymotrypsin-like activity of the immunoproteasome and constitutive proteasome in Waldenstrom macroglobulimia. *Blood*, 115: 4051-60 (2010).
Rossi et al., Proteasome inhibitors in cancer therapy: death by indigestion. *Cell Death Differ.* as: 1255-7 (2005).
Rouhi, Chemical & Engineering News, p. 32-35, Feb. 24, 2004.
Safadi et al., Phosphoryloxymet hyl carbarnates and carbonates-novel water-soluble prodrugs for amines and hindered alcohols. *Pharma. Res.* 10(9): 1350-5 (1993).
Schwarz et al., The selective proteasome inhibitors lactacystin and epoxomicin can be used to either up- or down-regulate antigen presentation at nontoxic doses. *J. Immunol.* 164: 6148-57 (2000).
Shah et al., Analytical techniques for quantification of amorphous/crystalline phases in pharmaceutical solids. *J. Pharma. Sci.* 95(8): 1641-65 (2006).
Shao et al., A new asymmetric synthesis of .alpha.-methylcysteines via chiral aziridines . . . *J. Org. Chem.* 60: 790-1 (1995).
Sharpless et al., High stereo- and regioselectivities in the transition metal catalyzed epoxidations of olefinic alcohols by tert-butyl hydroperoxide. *J. Am. Chem. Soc.* 95: 6136-7 (1973).
Shoemaker, The NCI60 human tumour cell line anticancer drug screen. *Nat. Rev. Cancer*, 6: 813-23 (2006).
Simsek et al., Hepatitis B virus large and middle glycoproteins are degraded by a proteasome pathway in glucosidase-inhibited cells but not in cells with functional glucosidase enzyme. *J. Virol.* 79(20): 12914-20 (2005).
Sin et al., Eponymycin analogues: Syntheses and use as probes of angiogenesis. *Bioorg. Med. Chem. Lett.* 6(8): 1209-17 (1998).
Sin et al., Total synthesis of the potent proteasome inhibitor epoxomicin: a useful tool for understanding proteasome biology. *Bioorg. Med. Chem. Lett.* 9: 2283-8 (1999).
Singhal et al.,Drug polymorphism and dosage form design: A practical perspective. *Adv. Drug Deliv. Rev.* 56: 335-47 (2004).
Spaltenstein et al., Design and synthesis of novel protease inhibitors. Tripeptide .alpha.',.beta.'-epoxyketones as nanomolar inactivators of the proteasome. *Tetrahedron Lett.* 37: 1343-6 (1996).

Stahl and Wermuth, Handbook of Pharmaceutical Salts: Properties, Selection, and Use, pp. 198-200 (2002).
Stein et al., Kinetic characterization of the chymotryptic activity of the 20S proteasome. *Biochemistry*, 35: 3899-908 (1996).
Stoklosa et al., Prospects for p53-based cancer therapy. *Acta Biochim Pol.* 52(2): 321-8 (2005).
Strickley, Solubilizing excipients in oral and injectable formulations. *Pharma. Res.* 21(2): 201-30 (2004).
Sun et al., Inhibition of acute graft-versus-host disease with retention of graft-versus-tumor effects by the proteasome inhibitor bortezomib. *Proc. Natl. Acad. Sci. USA*, 101(21): 8120-5 (2004).
Szalay et al., Ongoing coxsackievirus myocarditis is associated with increased formation and activity of myocardial immunoproteaseomes. *Am. J. Pathol.* 168(5): 1542-52 (2006).
Tawa et al., Inhibitors of the proteasome reduce the accelerated proteolysis in atrophying rat skeletal muscles. *J. Chem. Invest.* 100: 197-203 (1997).
Terato et al., Induction of arthritis with monoclonal antibodies to collagens. *J. Immunol.* 148(7): 2103-8 (1992).
Thanos et al., NF-.kappa.B: A lesson in family values. *Cell*, 80: 529-53 (1995).
Thompson., Cyclodextrins-enabling excipients: Their present and future use in pharmaceuticals. *Crit. Rev. Therap. Drug Carrier Syst.* 14(1): 1-104 (1997).
Tong, Applications of complexation in the formulation of insoluble compounds. R. Liu, Ed., pp. 111-139 (2000).
Traenckner et al., A proteasome inhibitor prevents activation of NF-.kappa.B and stabilizes a newly phosphorylated form of I.kappa.B-.alpha. that is still bound to NF-.kappa.B. *EMBO J.* 13: 5433-41 (1994).
Tu et al., An efficient assymettric epoxidation method for trans-olefins mediated by a fructose-derived ketone. *J. Am. Chem. Soc.* 118: 9806-7 (1996).
U.S. Pharmacopia #23, National Formulary #18, p. 1843-4 (1995).
Vogel's textbook of practical organic chemistry, 5th Ed. See p. 135, "2.20 Recrystallisation Techniques" and p. 141, 2nd paragraph onwards, Feb. 1996.
Voskoglou-Nomikos, Clinical predictive value of the in vitro cell line, human xenograft, and mouse allograft preclinical cancer models. *Clin. Cancer Res.* 9(11): 4227-39 (2003).
Wang et al., A New Type of Ketone Catalyst for Asymmetric Epoxidation. *J. Org. Chem.* 62: 8622-3 (1997).
Watanabe et al., Synthesis of boronic acid derivatives of tyropeptin: Proteasome inhibitors. *Bioorg. & Med. Chem.* 19(8): 2343-5 (2009).
WebMD "HIV and Aids", www.webmd.com/hiv-aids/guide/sexual-health-aids <http://www.webmd.com/hiv-aids/guide/sexual-health-aids> pp. 1-2 (2009).
Wilson et al., Novel disease targets and management approaches for diffuse large B-cell lymphoma. *Leuk. Lymph.* 51(suppl. 1): 1-10 (2010). Abstract Only.
Wipf et al., Methyl- and (trifluoromethyl)alkene peptide isosteres: Synthesis and evaluation of their potential as .beta.-turn promoters and peptide mimetics. *J. Org. Chem.* 63: 6088-9 (1998).
Xu et al., Mutations in the tumor suppressors Smad2 and Smad4 inactivate transforming growth factor 13 signaling by targeting Smads to the ubiquitin-proteasome pathway., *Proc. Natl. Acad. Sci. USA*, 97(9): 4820-5 (2000).
Yang et al., Pharmacokinetics, pharmacodynamics, metabolism, distribution, and excretion of carfilzomib in rats. *Drug Metabol. Disposition*, 39: 1873-82 (2011).
Yu et al., The ubiquitin-proteasome system facilitates the transfer of murine coronavirus from endosome to cytoplasm during virus entry. *J. Virol.* 79(1): 644-8 (2005).
Zhou et al., Design and synthesis of an orally bioavailable and selective peptide epoxyketone proteasome inhibitor (PR-047). *J. Med. Chem.* 52(9): 3028-38 (2009).
Zhu et al., 3D-QSAR studies of boron-containing dipeptides as proteasome inhibitors with CoMFA and CoMSIA methods. *Eur. J. Med. Chem.* 44(4): 1486-99 (2009).
Zhu et al., Design synthesis and biological evaluation of tripeptide boronic acid proteasome inhibitors. *Bioorg & Med. Chem.* 17(19): 6851-61 (2009).

(56) References Cited

OTHER PUBLICATIONS

Zollner et al., Proteasome inhibition reduces superantigen-mediated T cell activation and the severity of psoriasis in a SCID-hu model. *J. Clin. Invest.* 109(5): 671-9 (2002).

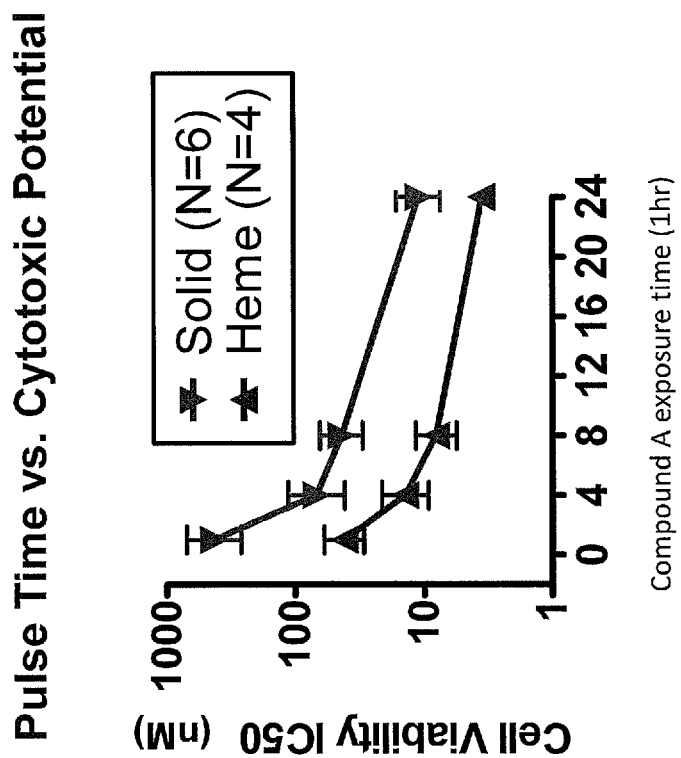
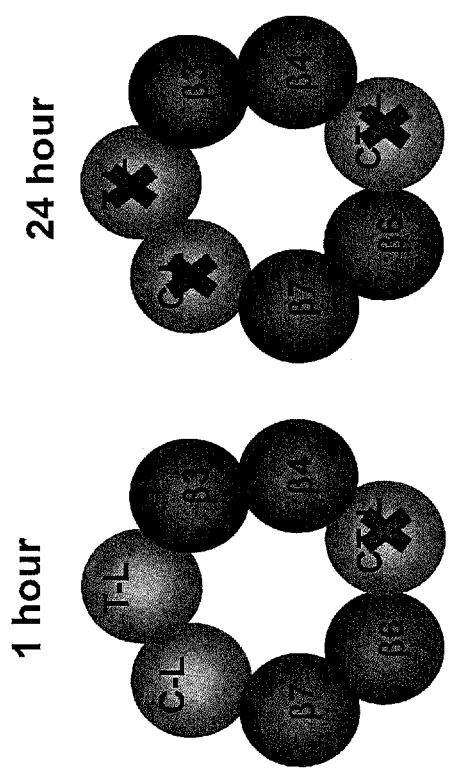
FIG. 3

FIG. 46

| Activated linker/group (can drive reformation of active epoxide) | Spacer (optional, can separate the activated group from conjugates to facilitate release and can improve target specificity) | Conjugate (can improve solubility, stability/half-life, permeability/volume of distribution and target specificity) |
|---|---|---|
| sulfonyl-ethyl | succinate diester | PEG-O-methyl |
| sulfonyl-dimethyl-ketone | fumarate diester | amino-PEG-O-methyl |
| bis-sulfonyl-ethyl | fumaramide | Human Serum Albumin |
| sulfonyl-propanone | Human Serum Albumin (X = S, O, NH) | Monoclonal Antibodies |
| sulfonyl-phenyl-ketone | PEG diether | $N^+$-CH$_2$(CH$_2$)$_{14}$CH$_3$ |
| fluoro-sulfonyl-phenyl-ketone | amino-PEG-amine | Cyclodextrins |

FIG. 46 CONTINUED
| | | |
|---|---|---|
| | | 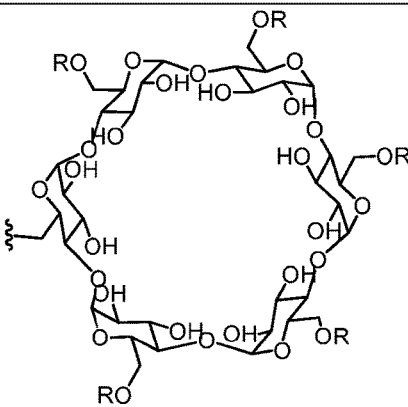 |
| 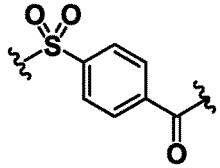 | Cyclodextrins<br>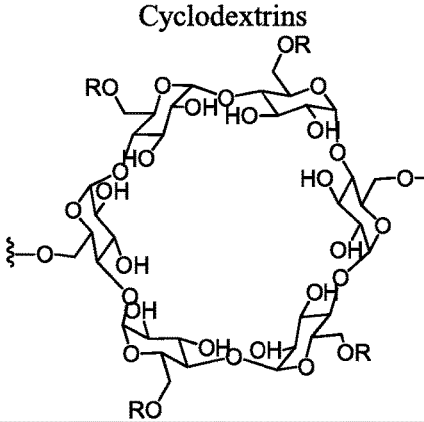 | 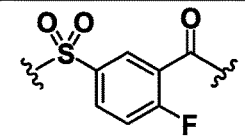(Arg)₈—NH₂ |
| 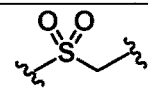 | Amino acid mimetics | Docosahexaenoic acid (DHA) |
| 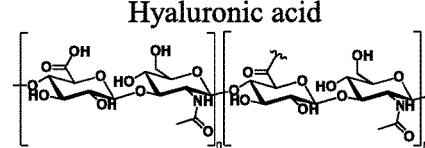 | D-Amino acids | Hyaluronic acid<br>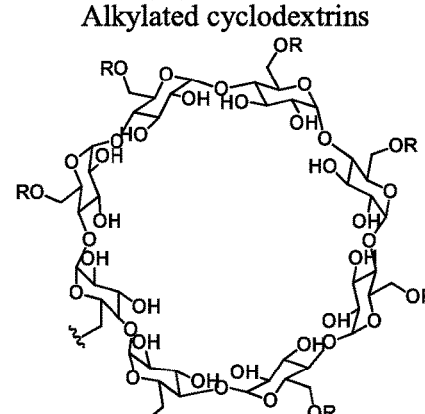 |
| F, Cl, Br, I | Hydrazone linker | Alkylated cyclodextrins |

FIG. 46 CONTINUED

| | Phenylalanine-lysine linker | Poly(L-glutamic acid) |
|---|---|---|
| | Valine-citrulline linker | N-(2-Hydroxypropryl)methacrylamide copolymer |
| | Single atom linker | Dendrimers (example with nitro reduction trigger) |

PRODRUGS OF PEPTIDE EPOXY KETONE PROTEASE INHIBITORS

CROSS REFERENCE TO RELATED APPLICATIONS

This application is a continuation-in-part of PCT/US2013/049804, filed Jul. 9, 2013, which claims the benefit of U.S. Provisional Application 61/669,509, filed on Jul. 9, 2012 and U.S. Provisional Application 61/790,106, filed on Mar. 15, 2013, each of these prior applications is incorporated herein by reference in its entirety.

TECHNICAL FIELD

This disclosure features compounds that are useful as pro-drugs of epoxy ketone protease inhibitors.

BACKGROUND

The proteasome has been validated as a therapeutic target, as demonstrated by the FDA approval of bortezomib, a boronic acid proteasome inhibitor, for the treatment of various cancer indications, including multiple myeloma. However, other more highly proteasome-specific inhibitors that could have fewer toxic side effects have recently been described. These compounds include peptide epoxy ketones such as epoxomicin, described in U.S. Pat. No. 6,831,099, the contents of which are hereby incorporated by reference, and those described in U.S. Pat. Nos. 7,687,456; 7,737,112; 7,232,818; 7,417,042; 8,080,576; 8,088,741; and 8,357,683, the contents of each is hereby incorporated by reference in its entirety.

SUMMARY

This disclosure features compounds that are useful as pro-drugs of epoxy ketone protease inhibitors (e.g., such as those described in U.S. Pat. Nos. 7,687,456; 7,737,112; 7,232,818; 7,417,042; 8,080,576; 8,088,741; and 8,357,683). In some embodiments, the compounds described herein include one or more moieties that (i) can confer enhanced solubility, permeability, pharmacokinetics and/or pharmacodynamics properties to the compounds when compared with the corresponding epoxy ketone protease inhibitors that do not contain such moieties; and (ii) can be removed in vivo upon administration to a subject.

In some embodiments, the compounds described herein themselves exhibit lower therapeutic activity when compared with said corresponding epoxy ketone protease inhibitors.

In some embodiments, the compounds described herein themselves exhibit lower therapeutic activity when compared with said corresponding epoxy ketone protease inhibitors and exhibit enhanced solubility, permeability, pharmacokinetics and/or pharmacodynamics properties in vivo when compared with said corresponding epoxy ketone protease inhibitors.

In some embodiments, the epoxy moiety of the epoxy ketone protease inhibitors is replaced with an activated diol. In some embodiments, the activated diol contains a PEG moiety. In some embodiments, the epoxy moiety of the epoxy ketone protease inhibitors is replaced with an activated halohydrin (e.g., iodohydrin). In some embodiments, the ketone moiety of the epoxy ketone protease inhibitors is replaced with a masked ketone moiety, e.g., acylhydrazones, oximes, oxazolidine, or thiazolidine. In some embodiments, the masked ketone moiety contains a PEG moiety. In some embodiments, the backbone amide of the epoxy ketone protease inhibitors is replaced with N-acyloxymethyl, N-acyloxymethylcarbamate or sulfonamide. In some embodiments, the N-acyloxymethyl, N-acyloxymethylcarbamate, or sulfonamide moiety contains PEG. In some embodiments, the N-terminal "cap" of the epoxy ketone protease inhibitors (e.g., the morpholino and 2-methylthiazole cap) is converted to a quaternary salts (e.g., by the addition of a N-acyloxymethyl group). In some embodiments, the quaternary salt contains a PEG moiety. In some embodiments, the prodrugs are cleavable by pH change and/or enzymes such as, but not limited to, esterases, cytochrome P450, phosphodiesterase, phosphoamidase, phosphatase, and DT-diaphorase, or any combination thereof. In some embodiments, the PEG is a linear PEG. In some embodiments, the PEG is a bifunctional PEG, that can conjugate 1-2 compounds per PEG. In some embodiments, the PEG is a four-arm PEG that can conjugate 1-4 compounds per PEG. In some embodiments, the PEG is an eight-arm PEG with a hexaglycerin core, that can conjugate 1-8 compounds per PEG. In some embodiments, the PEG is an eight-arm PEG with a tripentaerythritol core, that can conjugate 1-8 compounds per PEG. In some embodiments, the PEG is a branched two-arm PEG. In some embodiments, the PEG is a branched four-arm PEG. In addition, the compounds can further include solubilizers, permeability enhancers, masking agents, macromolecular carriers, targeting moieties, and biologics to improve half-life and disease specificity that are attached directly to the compound or indirectly attached via a spacer moiety.

While not wishing to be bound by theory, it is believed that having the protease inhibitory activity temporarily masked until the compounds described herein have reached and released the active into system circulation can reduce side effects associated with routes of administration. This can also facilitate subcutaneous administration and extend half-life, e.g., to beyond four hours. In some embodiments, the human plasma half-life of the prodrug is longer than 0.5 hr. In some embodiments, the human plasma half-life of the prodrug is between 0.5 and 5 hr. In some embodiments, the human plasma half-life of the prodrug is longer than 5 hr. In some embodiments, the human plasma half-life of the prodrug is between 5 and 100 hr. In some embodiments, the human plasma half-life of the prodrug is longer than 100 hr. In some embodiments, the human plasma half-life of the prodrug is between 100 and 836 hr. In some embodiments, the human plasma half-life of the prodrug is between 200 and 300 hr. In some embodiments, the human plasma half-life of the prodrug is about 267 hr. In some embodiments, the human plasma half-life of the prodrug is up to 836 hr. In some embodiments, this will improve both dosing and patient convenience and compliance.

In one aspect, compounds of formula (I) are featured:

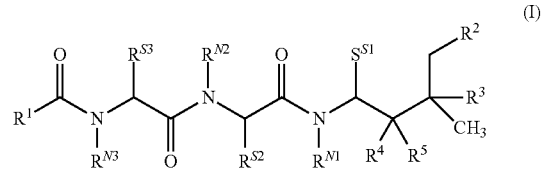

or a pharmaceutically acceptable salt thereof, in which:
R$^1$ is defined according to (A) or (B) below:
(A) R$^1$ has formula (II):

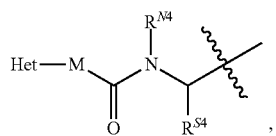

(II)

wherein Het is heterocyclyl that includes from 5-6 ring atoms, wherein at least one ring atom is a nitrogen atom selected from —N(H)—, —N(M)-, or —N(C$_1$-C$_3$ alkyl)-, wherein said ring nitrogen atom is further optionally substituted with a group R$^{11}$, thereby forming a quaternary nitrogen atom and wherein the positive charge associated with the quaternary nitrogen atom is balanced by a pharmaceutically acceptable anion; and M is C$_1$-C$_{12}$ alkyl; or (B) R$^1$ is heteroaryl that includes from 5-6 ring atoms, wherein at least one ring atom is a nitrogen atom selected from =N— and —N(C$_1$-C$_3$ alkyl)-, wherein said ring nitrogen atom is further optionally substituted with a group R$^{11}$, thereby forming a quaternary nitrogen atom and wherein the positive charge associated with the quaternary nitrogen atom is balanced by a pharmaceutically acceptable anion;

R$^2$ and R$^3$, together with the carbon atoms to which each is attached, form an epoxide ring; or R$^2$ is R$^{12}$, and R$^3$ is hydroxyl or activated hydroxyl;

R$^4$ and R$^5$, together with the carbon atom to which both are attached, form a carbonyl group; or R$^4$ and R$^5$, together with the carbon atom to which both are attached, form R$^{13}$, R$^{S1}$, R$^{S2}$, R$^{S3}$, and R$^{S4}$ are each independently selected from C$_{1-6}$alkyl, C$_{1-6}$hydroxyalkyl, C$_{1-6}$alkoxyC$_{1-6}$alkyl, C$_{6-10}$aryl, and C$_{7-12}$aralkyl, each of which is optionally substituted with a group selected from amide, amine, carboxylic acid or a pharmaceutically acceptable salt thereof, carboxyl ester, thiol, and thioether;

R$^{N1}$, R$^{N2}$, R$^{N3}$, and R$^{N4}$ are each independently selected from H and R$^{14}$;

R$^{11}$ is a moiety that is removable at a pH>7 or in the presence of an esterase;

R$^{12}$ is a leaving group;

R$^{13}$ is a masked carbonyl group that is removable at a pH<6.5 or in the presence of an enzyme selected from esterase, amidase, phosphodiesterase or phosphoamidase and CYP P450, or any combination thereof;

each R$^{14}$ is, independently, a moiety that is removable at a pH>7 or in the presence of an esterase;

provided that at least one group selected from R$^{11}$, R$^{12}$, R$^{13}$, and R$^{14}$ is present.

In another aspect, compounds having the formula (SM)$_m$-PEG, or a pharmaceutically acceptable salt thereof, are featured, in which each SM is an independently selected compound of formula (I) as defined in above and anywhere herein and is attached to PEG (e.g. covalently attached to PEG); and m is 2-10. Examples of such compounds are provided below:

Formula (III), Formula 1B':

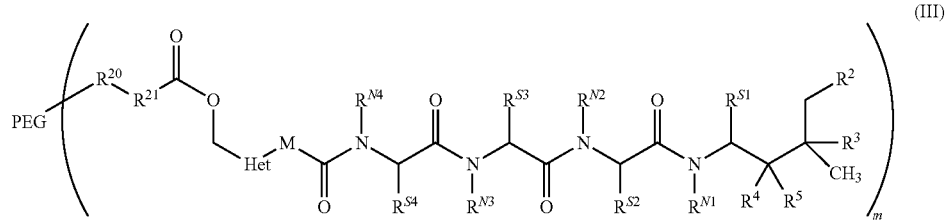

(III)

Formula (IV), Formula 1D:

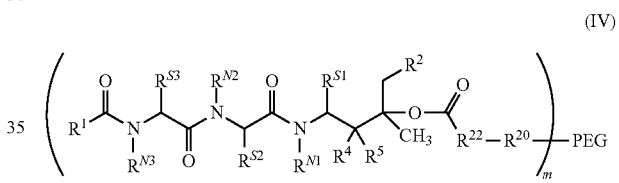

(IV)

Formula (V) (where Q=SO$_2$, Formula 1F; Q=R$^{16}$O (P=O), Formula 1 G):

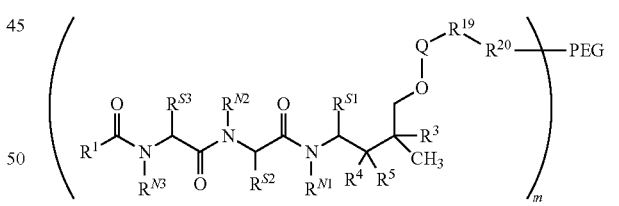

(V)

Formula (VI), Formula 1H:

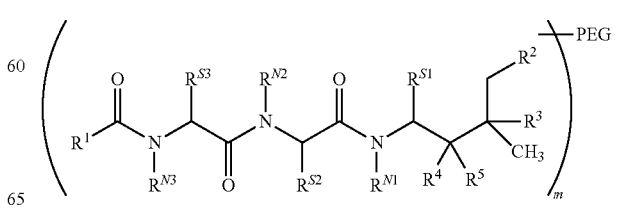

(VI)

Formula (VII) Formula 1I:

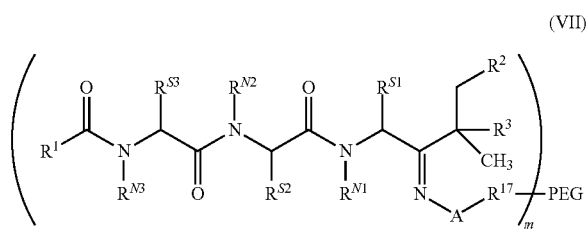

(VII)

and
Formula (VIII)

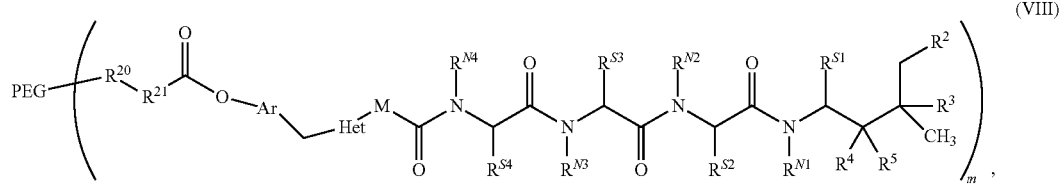

(VIII)

in which each of the attendant variables in each of said formula can be independently as defined anywhere herein.

In one aspect, a therapeutic agent is featured, which is prepared by a process that includes reacting a compound as described anywhere herein under conditions sufficient to remove any one or more of $R^{11}$, $R^{12}$, $R^{13}$, and $R^{14}$.

In one aspect, a pharmaceutical composition is featured, which includes a compound as described anywhere herein and a pharmaceutically acceptable carrier.

In one aspect, methods are featured for treating a disease or condition selected from the group consisting of cancer, autoimmune disease, graft or transplant-related condition, neurodegenerative disease, fibrotic-associated condition, ischemic-related conditions, infection (viral, parasitic or prokaryotic) and diseases associated with bone loss, the method includes administering to a patient a therapeutically effective amount of a compound as described anywhere herein.

In one aspect, methods for treating cancer (e.g., multiple myeloma, e.g., multiple myeloma that is relapsed and/or refractory) in a patient are featured, which include administering to a patient a therapeutically effective amount of a compound as described anywhere herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and from the claims.

BRIEF DESCRIPTION OF THE DRAWINGS

FIG. 3 is a line graph showing that more intensive dosing of epoxy ketone protease inhibitors can yield greater efficacy in both solid and hematologic tumor models.

FIG. 40 is a scheme showing the synthesis of an embodiment of an alkyl sulfonate precursor to a prodrug of epoxy ketone proteasome inhibitors.

FIG. 46 provides a table showing examples of activated diol leaving groups (with different combinations of spacer and conjugate) in epoxy ketone protease inhibitors designed, for example, for subcutaneous and intravenous administration. The leaving groups can include (i) polymers such as, but not limited to, hyaluronic acid, poly(ethylene glycol), carboxymethylcyclodextran, poly(L-glutamic acid), and N-(2-hydroxypropryl)methacrylamide copolymer; (ii) proteins; (iii) dendrimers; or (iv) antibodies and antibody fragments. In some embodiments, the epoxy ketone protease inhibitors of FIG. 46 are suitable for subcutaneous and intravenous administration.

DETAILED DESCRIPTION

Figure 1:
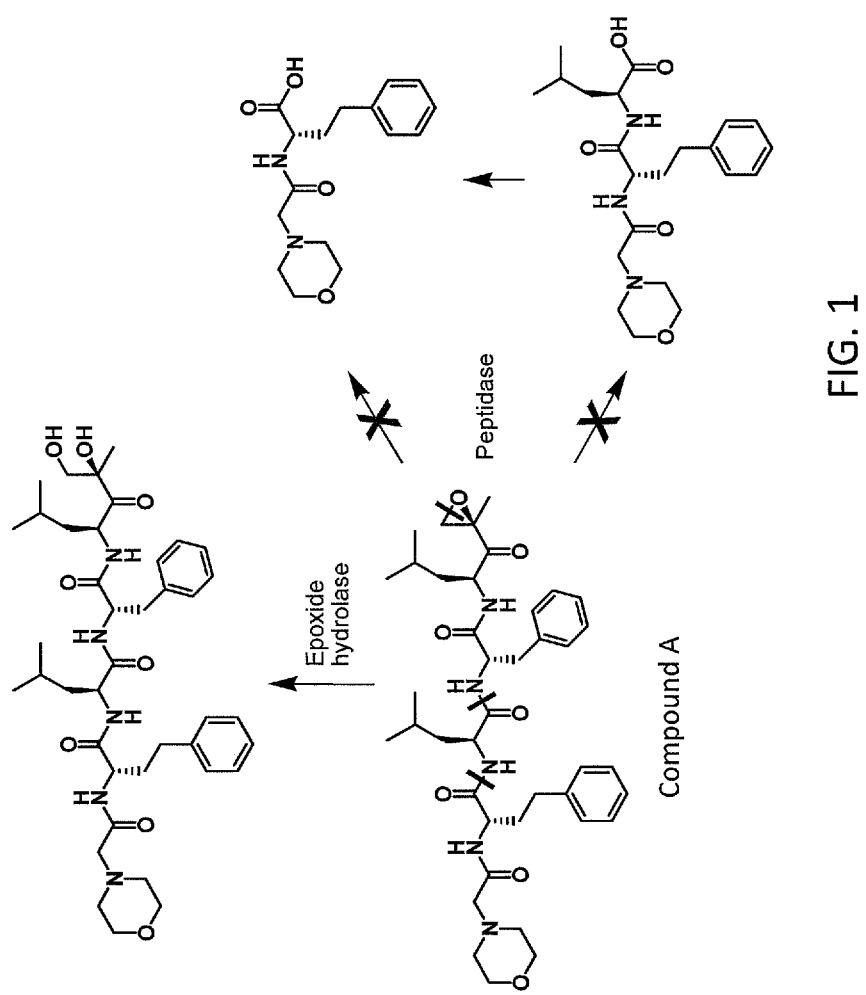
FIG. 1 is a scheme showing cleavage of an embodiment of an epoxy ketone protease inhibitor by peptidases and epoxide hydrolase to inactive metabolites.

This disclosure features compounds that are useful as pro-drugs of epoxy ketone protease inhibitors (e.g., such as those described in U.S. Pat. Nos. 7,687,456; 7,737,112; 7,232,818; 7,417,042; 8,080,576; 8,088,741; and 8,357,683). In some embodiments, the compounds described herein include one or more moieties that (i) can confer enhanced solubility, permeability, pharmacokinetics and/or pharmacodynamics properties relative to compounds that do not contain such moieties; and (ii) can be removed in vivo. In some embodiments, the epoxy moiety of the epoxy ketone protease inhibitors is replaced with an activated diol. In some embodiments, the epoxy moiety of the epoxy ketone protease inhibitors is replaced with an activated halohydrin. In some embodiments, the epoxy moiety of the epoxy ketone protease inhibitor is replaced an activated diol that is conjugated to polyethylene glycol (PEG). In some embodiments, the ketone moiety of the epoxy ketone protease inhibitors is replaced with a masked ketone moiety, e.g., acylhydrazones, oximes, oxazolidine, or thiazolidine. In some embodiments, the masked ketone moiety contains a PEG moiety. In some embodiments, the backbone amide of the epoxy ketone protease inhibitors is replaced with N-acyloxymethyl, N-acyloxymethylcarbamate or sulfonamide. In some embodiments, the N-acyloxymethyl, N-acyloxymethylcarbamate, or sulfonamide moiety contains PEG. In some embodiments, the N-terminal "cap" of the epoxy ketone protease inhibitors (e.g., the morpholino and 2-methylthiazole cap) is converted to a quaternary salts (e.g., by the addition of a N-acyloxymethyl group). In some embodiments, the quaternary salt contains a PEG moiety. In some embodiments, the prodrugs are cleavable by pH change and/or enzymes such as, but not limited to, esterases, cytochrome P450, phosphodiesterase, phosphoamidase, phosphatase, and DT-diaphorase, or any combination thereof. In some embodiments, the PEG is a linear PEG. In some embodiments, the PEG is a bifunctional PEG, that can conjugate 1-2 compounds per PEG. In some embodiments, the PEG is a four-arm PEG that can conjugate 1-4 compounds per PEG. In some embodiments, the PEG is an eight-arm PEG with a hexaglycerin core, that can conjugate 1-8 compounds per PEG. In some embodiments, the PEG is an eight-arm PEG with a tripentaerythritol core, that can conjugate 1-8 compounds per PEG. In some embodiments, the PEG is a branched two-arm PEG. In some embodiments, the PEG is a branched four-arm PEG. In addition, the compounds can further include solubilizers, permeability enhancers, masking agents, macromolecular carriers, targeting moieties, and biologics to improve half-life and disease specificity that are attached directly to the compound or indirectly attached via a spacer moiety.

Compound Scaffolds

In some embodiments, the compounds (or a pharmaceutically acceptable salt thereof) can have Formula I, in which $R^1$, $R^2$, $R^3$, $R^4$, $R^5$, $R^{N1}$, $R^{N2}$, $R^{N3}$, $R^{N4}$, $R^{S1}$, $R^{S2}$, $R^{S3}$, and $R^{S4}$ can be as defined anywhere herein.

In other embodiments, the compounds can have the formula $(SM)_m$-PEG, or a pharmaceutically acceptable salt thereof, in which each SM is an independently selected compound of formula (I) as defined in above and anywhere herein and is attached to PEG; and m is 2-10 (e.g., compounds having any one of formulas III-VIII).

Variables $R^1$ and $R^{11}$

In some embodiments, $R^1$ has formula (II):

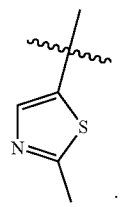

(II)

wherein Het is heterocyclyl that includes from 5-6 ring atoms, wherein at least one ring atom is a nitrogen atom selected from —N(H)—, —N(M)-, or —N(C$_1$-C$_3$ alkyl)-, wherein said ring nitrogen atom is further optionally substituted with a group $R^{11}$, thereby forming a quaternary nitrogen atom and wherein the positive charge associated with the quaternary nitrogen atom is balanced by a pharmaceutically acceptable anion; and M is $C_1$-$C_{12}$ alkyl.

In some embodiments, Het is:

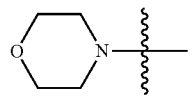

In some embodiments, M is CH$_2$.

In some embodiments, the ring nitrogen atom is further substituted with a group $R^{11}$, thereby forming a quaternary nitrogen atom and wherein the positive charge associated with the quaternary nitrogen atom is balanced by a pharmaceutically acceptable anion.

In some embodiments, when $R^1$ has formula (II), $R^{S1}$ and $R^{S3}$ are each independently $C_{1-6}$alkyl, and $R^{S2}$ and $R^{S4}$ are each independently $C_{7-12}$aralkyl.

In some embodiments, when $R^1$ has formula (II), $R^{S1}$ and $R^{S3}$ are both isobutyl, $R^{S4}$ is phenylethyl, and $R^{S2}$ is phenylmethyl.

In other embodiments, $R^1$ is heteroaryl that includes from 5-6 ring atoms, wherein at least one ring atom is a nitrogen atom selected from =N— and —N(C$_1$-C$_3$ alkyl)-, wherein said ring nitrogen atom is further optionally substituted with a group $R^{11}$, thereby forming a quaternary nitrogen atom and wherein the positive charge associated with the quaternary nitrogen atom is balanced by a pharmaceutically acceptable anion.

In some embodiments, $R^1$ is:

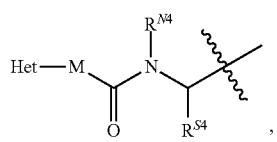

In some embodiments, when $R^1$ is heteroaryl that includes from 5-6 ring atoms, $R^{S2}$ and $R^{S3}$ are each independently $C_{1-6}$alkoxy$C_{1-6}$alkyl, and $R^{S1}$ is $C_{1-6}$aralkyl.

In some embodiments, when $R^1$ is heteroaryl that includes from 5-6 ring atoms, $R^{S2}$ and $R^{S3}$ are both methoxymethyl, and $R^{S1}$ is phenylmethyl.

In some embodiments, the $R^1$ Het or heteroaryl ring nitrogen atom is substituted with a group $R^{11}$, thereby forming a quaternary nitrogen atom and wherein the positive charge associated with the quaternary nitrogen atom is balanced by a pharmaceutically acceptable anion.

In some embodiments, $R^{11}$ is:

(i) —CH$_2$OC(=O)R$^{15}$;
(ii) —C(=O)OCH$_2$OC(=O)R$^{15}$;
(iii) —SR$^{15}$; or
(iv) —CH$_2$Ar—R$^{15}$;

wherein:

Ar is $C_{6-10}$aryl, optionally substituted with from 1-3 substituents independently selected from $C_{1-6}$alkyl, $C_{1-6}$alkoxy, and halo;

$R^{15}$ is $C_{1-6}$alkyl, $C_{1-6}$haloalkyl, $C_{1-6}$alkoxy$C_{1-6}$alkyl, $C_{6-10}$aryl, $C_{7-12}$aralkyl, $C_{3-7}$cycloalkyl, heteroaryl including from 5-10 ring atoms (wherein from 1-3 of the ring atoms are independently selected from N, NH, N—C$_1$-C$_6$ alkyl, O, and S), or heterocyclyl including from 3-7 ring atoms (wherein from 1-2 of the ring atoms are independently selected from N, NH, N—C$_1$-C$_6$ alkyl, and O), each of which is optionally substituted with from 1-3 R$^a$;

wherein: R$^a$ at each occurrence is, independently selected from halo, cyano, nitro, hydroxyl, $C_{1-6}$ alkoxy, heteroalkyl, $C_{6-10}$ aryloxy, $C_{7-12}$ aralkoxy, CF$_3$, quaternary ammonium ion, sugar, —Y'$_p$—Z', $C_{1-6}$ alkyl, —C(=O)(C$_{1-6}$ alkyl), —SO$_2$(C$_{1-6}$ alkyl), —C(=O)O(C$_{1-6}$ alkyl), —C(=O)O(heteroalkyl), —C(=O)NH(C$_{1-6}$ alkyl), —C(=O)NH(heteroalkyl), —C(=O)(phenyl), —SO$_2$(phenyl), phosphate (or a salt thereof), —C(=O)—Y$_n$—Z, and —SO$_2$—Y$_n$—Z; or R$^{15}$ is Y$_n$—Z; wherein:

Y is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, C$_{6-10}$ arylene, heteroarylene from 5-10 ring atoms (wherein from 1-3 of the ring atoms are independently selected from N, NH, N—C$_1$-C$_6$ alkyl, O, and S), heteroalkylene chain, polyheteroalkylene chain, alkenylene chain, —OC(=O)—, —C(=O)O—, —NHC(=O)—, —C(=O)NH—, —C(=O)—, cyclodextrin, human serum albumin, amino acid, amino acid mimetic, or hydrazine;

Z is conjugate for enhancing solubility, stability, half-life, permeability, volume of distribution, and/or target specificity, which comprises one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): alkylene chain, heteroalkylene chain, polyheteroalkylene chain, alkenylene chain, cyclodextrin, alkylated cyclodextrin, human serum albumin, —OC(=O)—, —C(=O)O—, —NHC(=O)—, —C(=O)NH—, —C(=O)—, monoclonal anti-body, quaternary ammonium ion, NH$_2$, docosahexenoic acid, hyaluronic acid, poly(L-glutamic acid), N-(2-hydroxypropyl) methacrylamide copolymer, or dendrimers (e.g., nitro-substituted dendrimers); and n is 0 or 1.

In some embodiments, R$^{11}$ is: (i) —CH$_2$OC(=O)R$^{15}$; (ii) —C(=O)OCH$_2$OC(=O)R$^{15}$; or (iii) —SR$^{15}$.

In certain embodiments, R$^{11}$ is —CH$_2$OC(=O)R$^{15}$.

In certain embodiments, R$^{11}$ is —CH$_2$OC(=O)R$^{15}$, and R$^{15}$ is C$_{1-6}$alkyl, C$_{1-6}$ haloalkyl, C$_{1-6}$alkoxyC$_{1-6}$alkyl, C$_{6-10}$aryl, C$_{7-12}$aralkyl, C$_{3-7}$cycloalkyl, heteroaryl including from 5-10 ring atoms (wherein from 1-3 of the ring atoms are independently selected from N, NH, N—C$_1$-C$_6$ alkyl, O, and S), or heterocyclyl including from 3-7 ring atoms (wherein from 1-2 of the ring atoms are independently selected from N, NH, N—C$_1$-C$_6$ alkyl, and O), each of which is optionally substituted.

In some embodiments, R$^{11}$ is —CH$_2$OC(=O)R$^{15}$, and R$^{15}$ is C$_{1-6}$alkyl. In certain embodiments, R$^{15}$ is tert-butyl.

In some embodiments, the pharmaceutically acceptable anion is selected from chloride, iodide, acetate, mesylate, tosylate, and citrate.

In some embodiments, R$^{11}$ is —CH$_2$OC(=O)R$^{21}$—R$^{20}$-PEG or —CH$_2$OSO$_2$R$^{21}$—R$^{20}$-PEG.

In some embodiments, R$^{11}$ is —CH$_2$OC(=O)R$^{21}$—R$^{20}$-PEG.

In some embodiments, R$^{11}$ is —CH$_2$OSO$_2$R$^{21}$—R$^{20}$-PEG.

For ease of exposition, the term "PEG" refers to a polyethylene glycol (PEG) chain and includes oligomers and polymer of ethylene oxide polyethylene glycol chain (linear or branched) having a molecular weight of from 300 g/mol to 10,000,000 g/mol. The PEG can have any one of the architectures described herein (e.g., formulas 2A-2H; table AA).

Further, it is understood that one or more compound can be conjugated to a polyethylene glycol (PEG) polymer chain.

In some embodiments, the prodrug has Formula 1B:

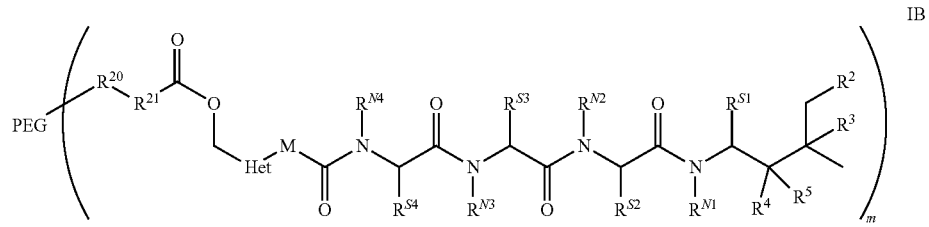

wherein m is 1, 2, 3, 4, 5, 6, 7, 8, 9, or 10, e.g., 2, 3, 4, 5, 6, 7, 8, 9, or 10.

In some embodiments, the prodrug has Formula 1B':

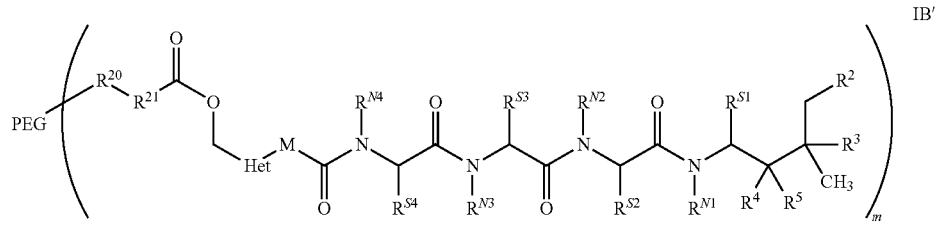

wherein m is 1, 2, 3, 4, 5, 6, 7, 8, 9, or 10, e.g., 2, 3, 4, 5, 6, 7, 8, 9, or 10.

In some embodiments, the prodrug has Formula 1C:

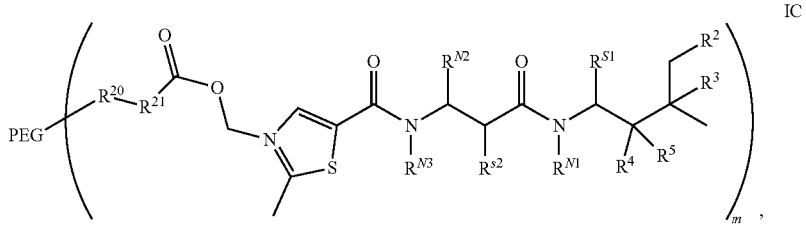

wherein m is 1, 2, 3, 4, 5, 6, 7, 8, 9, or 10, e.g., 2, 3, 4, 5, 6, 7, 8, 9, or 10.

In some embodiments, m is 4.
In some embodiments, m is 2.
In some embodiment, m is 1.
In some embodiments, the prodrug has Formula (VIII):

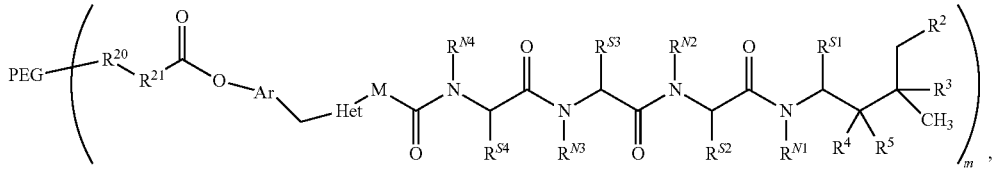

in which Ar is $C_{6-10}$ aryl (e.g., phenyl), optionally substituted with from 1-3 substituents independently selected from $C_{1-6}$alkyl, $C_{1-6}$alkoxy, and halo; and wherein m is 1, 2, 3, 4, 5, 6, 7, 8, 9, or 10, e.g., 2, 3, 4, 5, 6, 7, 8, 9, or 10.

The following definitions apply to formulas 1B, 1B', 1C, and VIII as well as —CH$_2$OC(=O)R$^{21}$—R$^{20}$-PEG and —CH$_2$OSO$_2$R$^{21}$—R$^{20}$-PEG. For purposes of clarification, it is understood that the R$^{20}$/R$^{21}$-containing substituent in each of these formulas 1B, 1B', 1C, and VIII is attached to the Het or heteroaryl ring nitrogen atom, thereby forming a quaternary nitrogen atom and wherein the positive charge associated with the quaternary nitrogen atom is balanced by a pharmaceutically acceptable anion.

R$^{20}$ is a heteroarylene including 5-6 ring atoms ((wherein from 1-4 of the ring atoms are independently selected from N, NH, N—C$_1$-C$_6$ alkyl, O, and S; e.g., containing one or more, e.g., from 1-4, 1-3, 1-2 nitrogen atoms), optionally substituted with 1, 2, or 3 substituents independently selected from C$_{1-6}$alkyl, C$_{1-6}$hydroxyalkyl, C$_{1-6}$alkoxyC$_{1-6}$alkyl, C$_{6-10}$aryl, or C$_{7-12}$aralkyl, each of which is optionally substituted with a group selected from amide, amine, carboxylic acid or a pharmaceutically acceptable salt thereof; or R$^{20}$ is absent (e.g., R$^{20}$ is present and is as defined above).

In some embodiments, R$^{20}$ is

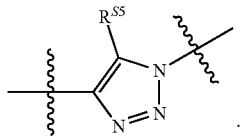

In some embodiments, R$^{S5}$ is H, C$_{1-6}$alkyl, C$_{1-6}$hydroxyalkyl, C$_{1-6}$alkoxyC$_{1-6}$alkyl, C$_{6-10}$aryl, or C$_{7-12}$aralkyl, each of which is optionally substituted with a group selected from amide, amine, carboxylic acid or a pharmaceutically acceptable salt thereof, carboxyl ester, thiol, and thioether.

In certain embodiments, R$^{S5}$ is H or C$_{1-6}$alkyl.
In certain embodiments, R$^{S5}$ is H.
In other embodiments, R$^{20}$ is absent.

R$^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, polyheteroalkylene chain, alkenylene chain, arylene including 6-10 ring atoms, heteroarylene including from 5-10 ring atoms (wherein from 1-3 of the ring atoms are independently selected from N, NH, N—C$_1$-C$_6$ alkyl, O, and S), heterocycloalkylene including 3-9 ring atoms (wherein from 1-3 of the ring atoms are independently selected from N, NH, N—C$_1$-C$_6$ alkyl, O, and S), —OC(=O)—, —C(=O)O—, —NHC(=O)—, —C(=O)NH—, —N(C1-6 alkyl)C(=O), —C(=O)N(C$_{1-6}$ alkyl)-, —C(=O)—, —NHC(=O)NH—, cyclodextrin, human serum albumin, amino acid, amino acid mimetic, or hydrazine, wherein arylene including 6-10 ring atoms, heteroarylene including from 5-10 ring atoms, and heterocycloalkylene including 3-9 ring atoms are each optionally substituted with 1, 2, or 3 substituents each independently selected from the group consisting of halo, cyano, nitro, hydroxyl, C$_{1-6}$ alkoxy, heteroalkyl, C$_{6-10}$ aryloxy, C$_{7-12}$ aralkoxy, CF$_3$, quaternary ammonium ion, sugar, C$_{1-6}$ alkyl, —C(=O)(C$_{1-6}$ alkyl), —SO$_2$(C$_{1-6}$ alkyl), —C(=O)O(C$_{1-6}$ alkyl), —C(=O)O(heteroalkyl), —C(=O)NH(C$_{1-6}$ alkyl), —C(=O)NH(heteroalkyl), —C(=O)(phenyl), —SO$_2$(phenyl), and phosphate (or a salt thereof);

In some embodiments, R$^{21}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—C$_1$-C$_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, cyano, $C_{1-6}$ alkoxy, heteroalkyl, $CF_3$, and $C_{1-6}$ alkyl.

In some embodiments, $R^{21}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, phenylene, indolylene, indolinylene, thiophenylene, or furanylene, wherein phenylene, indolylene, indolinylene, thiophenylene, and furanylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, or phenylene, wherein phenylene is optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, —C(=O)—, or phenylene, wherein phenylene is optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, or —C(=O)—.

In some embodiments, $R^{21}$ is a phenylene optionally substituted with 1, 2, or 3 substituents each independently selected from the group consisting of halo, $C_{1-6}$ alkoxy, heteroalkyl, $CF_3$, and $C_{1-6}$ alkyl.

The PEG can have any one of the architectures described herein (e.g., formulas 2A-2H; table AA).

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

Variables $R^2$, $R^{12}$, and $R^3$

In some embodiments, $R^{12}$ is present (i.e., $R^2$ is $R^{12}$).

In some embodiments, when $R^{12}$ is present, $R^3$ is activated hydroxyl as defined anywhere herein.

In some embodiments, when $R^{12}$ is present, $R^3$ is hydroxyl.

In some embodiments, $R^2$ and $R^3$, together with the carbon atoms to which each is attached, form an epoxide ring.

In some embodiments, $R^{12}$ is:
(i) halo;
(ii) —$OSO_2$—$R^{16}$;
(iii) —OC(=O)$R^{16}$;
(iv) —OP(=O)($R^{16}$)$_2$,
(v) —OP(=O)(O$R^{16}$)$_2$;
(vi) —OP(=O)($R^{16}$)(O$R^{16}$); or
(vii) —O—(N-linked heteroaryl);
wherein:
$R^{16}$ is $C_{1-6}$alkyl, $C_{1-6}$haloalkyl, heteroalkyl, $C_{6-10}$aryl, $C_{7-12}$aralkyl, $C_{3-7}$cycloalkyl, heteroaryl including from 5-10 ring atoms (wherein from 1-3 of the ring atoms are independently selected from N, NH, N—$C_1$-$C_6$ alkyl, O, and S), or heterocyclyl including from 3-7 ring atoms (wherein from 1-2 of the ring atoms are independently selected from N, NH, N—$C_1$-$C_6$ alkyl, and O), each of which is optionally substituted with from 1-3 $R^a$; or $R^{16}$ is —$Y'_p$—$Z'$; wherein:

Y' is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, polyheteroalkylene chain, alkenylene chain, —OC(=O)—, —C(=O)O—, —NHC(=O)—, —C(=O)NH—, —C(=O)—, cyclodextrin, human serum albumin, amino acid, amino acid mimetic, or hydrazine;

Z' is conjugate for enhancing solubility, stability, half-life, permeability, volume of distribution, and/or target specificity, which comprises one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): alkylene chain, heteroalkylene chain, polyheteroalkylene chain, alkenylene chain, cyclodextrin, alkylated cyclodextrin, human serum albumin, —OC(=O)—, —C(=O)O—, —NHC(=O)—, —C(=O)NH—, —C(=O)—, monoclonal anti-body, quaternary ammonium ion, $NH_2$, docosahexenoic acid, hyaluronic acid, poly(L-glutamic acid), N-(2-hydroxypropyl) methacrylamide copolymer, or dendrimers (e.g., nitro-substituted dendrimers);

p is 0 or 1; and $R^a$ at each occurrence is, independently selected from halo, cyano, nitro, hydroxyl, $C_{1-6}$ alkoxy, heteroalkyl, $C_{6-10}$ aryloxy, $C_{7-12}$ aralkoxy, $CF_3$, quaternary ammonium ion, sugar, —$Y'_p$—$Z'$, $C_{1-6}$ alkyl, —C(=O)($C_{1-6}$ alkyl), —$SO_2$($C_{1-6}$ alkyl), —C(=O)O($C_{1-6}$ alkyl), —C(=O)O(heteroalkyl), —C(=O)NH($C_{1-6}$ alkyl), —C(=O)NH(heteroalkyl), —C(=O)(phenyl), —$SO_2$(phenyl), phosphate (or a salt thereof), —C(=O)—$Y'_p$—$Z'$, and —$SO_2$—$Y'_p$—$Z'$.

In some embodiments, $R^{12}$ is —$OSO_2$—$R^{16}$. In some embodiments, $R^{16}$ is $C_{1-6}$alkyl (e.g., $CH_3$) or $C_{6-10}$aryl (e.g., phenyl).

In some embodiments, $R^{12}$ is halo (e.g., iodo).

In some embodiments, $R^{12}$ is halo (e.g., iodo), and $R^3$ is activated hydroxyl.

In some embodiments, $R^{12}$ is halo (e.g., iodo), and $R^3$ is hydroxyl.

In some embodiments, $R^3$ is hydroxyl.

In some embodiments, $R^3$ is activated hydroxyl, e.g., —O—C(=O)—$R^{22}$—$R^{20}$-PEG or —O—$SO_2$—$R^{22}$—$R^{20}$-PEG In certain embodiments, $R^3$ is —O—C(=O)—$R^{22}$—$R^{20}$-PEG.

In certain embodiments, $R^3$ is —O—$SO_2$—$R^{22}$—$R^{20}$-PEG.

It is understood that one or more prodrugs can be conjugated to a polyethylene glycol (PEG) polymer chain. In some embodiments, the prodrug has Formula 1D:

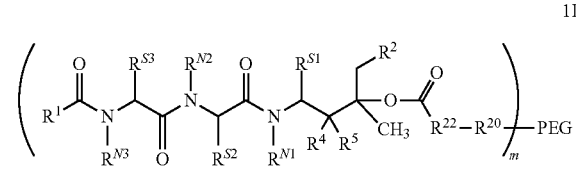

1D

In some embodiments, the prodrug has Formula 1E:

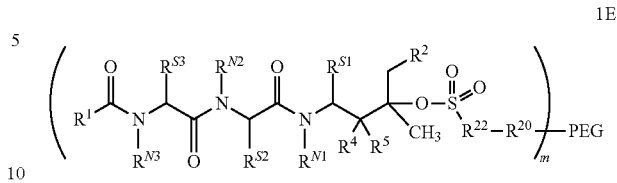

1E

In some embodiments, m is 1, 2, 3, 4, 5, 6, 7, 8, 9, or 10, e.g., 2, 3, 4, 5, 6, 7, 8, 9, or 10.

In some embodiments, m is 4.

In some embodiments, m is 2.

In some embodiment, m is 1.

$R^{20}$ is a heteroarylene including 5-6 ring atoms ((wherein from 1-4 of the ring atoms are independently selected from N, NH, N—$C_1$-$C_6$ alkyl, O, and S; e.g., containing one or more, e.g., from 1-4, 1-3, 1-2 nitrogen atoms), optionally substituted with 1, 2, or 3 substituents independently selected from $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof; or $R^{20}$ is absent (e.g., $R^{20}$ is present and is as defined above).

In some embodiments, $R^{20}$ is

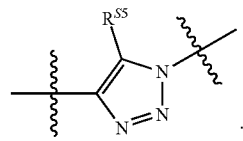

In some embodiments, $R^{S5}$ is H, $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof, carboxyl ester, thiol, and thioether.

In certain embodiments, $R^{S5}$ is H or $C_{1-6}$alkyl.

In certain embodiments, $R^{S5}$ is H.

In other embodiments, $R^{20}$ is absent.

$R^{22}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, polyheteroalkylene chain, alkenylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O), —C(=O)N($C_{1-6}$ alkyl)-, —C(=O)—, —NHC(=O)NH—, cyclodextrin, human serum albumin, amino acid, amino acid mimetic, or hydrazine, wherein arylene including 6-10 ring atoms, heteroarylene including from 5-10 ring atoms, and heterocycloalkylene including 3-9 ring atoms are each optionally substituted with 1, 2, or 3 substituents each independently selected from the group consisting of halo, cyano, nitro, hydroxyl, $C_{1-6}$ alkoxy, heteroalkyl, $C_{6-10}$ aryloxy, $C_{7-12}$ aralkoxy, $CF_3$, quaternary ammonium ion, sugar, $C_{1-6}$ alkyl, —C(=O)($C_{1-6}$ alkyl), —SO$_2$($C_{1-6}$ alkyl), —C(=O)O($C_{1-6}$ alkyl), —C(=O)O (heteroalkyl), —C(=O)NH($C_{1-6}$ alkyl), —C(=O)NH(heteroalkyl), —C(=O)(phenyl), —SO$_2$(phenyl), and phosphate (or a salt thereof).

In some embodiments, $R^{22}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-9 membered heteroarylene, and 6-10 membered cycloalkylene are each optionally substituted with 1, 2, or 3 substituents each independently selected from the group consisting of halo, cyano, $C_{1-6}$ alkoxy, heteroalkyl, $CF_3$, and $C_{1-6}$ alkyl.

In some embodiments, $R^{22}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{22}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, phenylene, indolylene, indolinylene, thiophenylene, or furanylene, wherein phenylene, indolylene, indolinylene, thiophenylene, and furanylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{22}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, or phenylene, wherein phenylene is optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{22}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, or heteroalkylene chain.

In some embodiments, $R^{22}$ is a heteroalkylene chain.

The PEG can have any one of the architectures described herein (e.g., formulas 2A-2H; table AA).

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments, $R^{12}$ is —OSO$_2$—$R^{19}$—$R^{20}$-PEG or OC(=O)—$R^{19}$—$R^{20}$-PEG.

In certain embodiments, $R^{12}$ is —OSO$_2$—$R^{19}$—$R^{20}$-PEG.

In certain embodiments, $R^{12}$ is OC(=O)—$R^{19}$—$R^{20}$-PEG.

It is understood that one or more prodrugs can be conjugated to a polyethylene glycol (PEG) polymer chain. In some embodiments, the prodrug has Formula 1F:

1F

In some embodiments, the prodrug has Formula 1G:

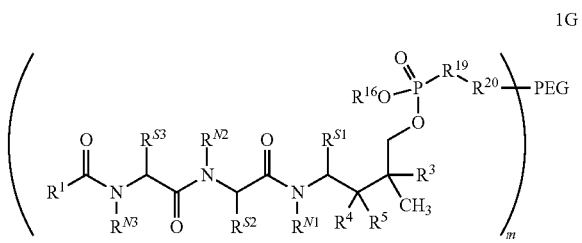

1G

In some embodiments, m is 1, 2, 3, 4, 5, 6, 7, 8, 9, or 10, e.g., 2, 3, 4, 5, 6, 7, 8, 9, or 10.

In some embodiments, m is 8.

In some embodiments, m is 4.

In some embodiments, m is 2.

In some embodiment, m is 1

$R^{19}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, polyheteroalkyl chain, alkenylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O), —C(=O)N($C_{1-6}$ alkyl)-, —C(=O)—, —NHC(=O)NH—, cyclodextrin, human serum albumin, amino acid, amino acid mimetic, or hydrazine, wherein arylene including 6-10 ring atoms, heteroarylene including from 5-10 ring atoms, and heterocycloalkylene including 3-9 ring atoms are each optionally substituted with 1, 2, or 3 substituents each independently selected from the group consisting of halo, cyano, nitro, hydroxyl, $C_{1-6}$ alkoxy, heteroalkyl, $C_{6-10}$ aryloxy, $C_{7-12}$ aralkoxy, $CF_3$, quaternary ammonium ion, sugar, $C_{1-6}$ alkyl, —C(=O)($C_{1-6}$ alkyl), —$SO_2$($C_{1-6}$ alkyl), —C(=O)O($C_{1-6}$ alkyl), —C(=O)O(heteroalkyl), —C(=O)NH($C_{1-6}$ alkyl), —C(=O)NH(heteroalkyl), —C(=O)(phenyl), —$SO_2$(phenyl), and phosphate (or a salt thereof).

In some embodiments, $R^{19}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, cyano, $C_{1-6}$ alkoxy, heteroalkyl, $CF_3$, and $C_{1-6}$ alkyl.

In some embodiments, $R^{19}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, cyano, $C_{1-6}$ alkoxy, heteroalkyl, $CF_3$, and $C_{1-6}$ alkyl.

In some embodiments (e.g., when $R^{20}$ is present), $R^{19}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, phenylene, indolylene, indolinylene, thiophenylene, or furanylene (e.g., phenylene), wherein phenylene, indolylene, indolinylene, thiophenylene, and furanylene are optionally substituted with 1, 2, or 3 substituents each independently selected from the group consisting of halo, $C_{1-6}$ alkoxy, heteroalkyl, $CF_3$, and $C_{1-6}$ alkyl.

In some embodiments (e.g., when $R^{20}$ is absent), $R^{19}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, —NHC(=O)—, —C(=O)NH—, heteroalkylene chain, phenylene, indolylene, indolinylene, thiophenylene, or furanylene, wherein phenylene, indolylene, indolinylene, thiophenylene, and furanylene are optionally substituted with 1, 2, or 3 substituents each independently selected from the group consisting of halo, $C_{1-6}$ alkoxy, heteroalkyl, $CF_3$, and $C_{1-6}$ alkyl. In certain embodiments, when either of —NHC(=O)— or —C(=O)NH— is present, —NHC(=O)— or —C(=O)NH— is linked to PEG.

In some embodiments, $R^{19}$, $R^{21}$, or $R^{22}$ (and $R^{14'}$ and $R^{17'}$ defined herein) each is a divalent linker independently selected from the group consisting of

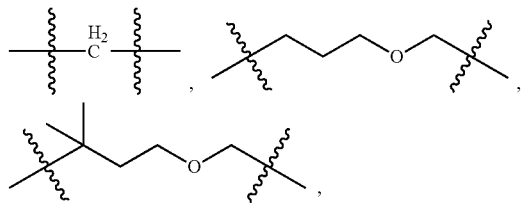

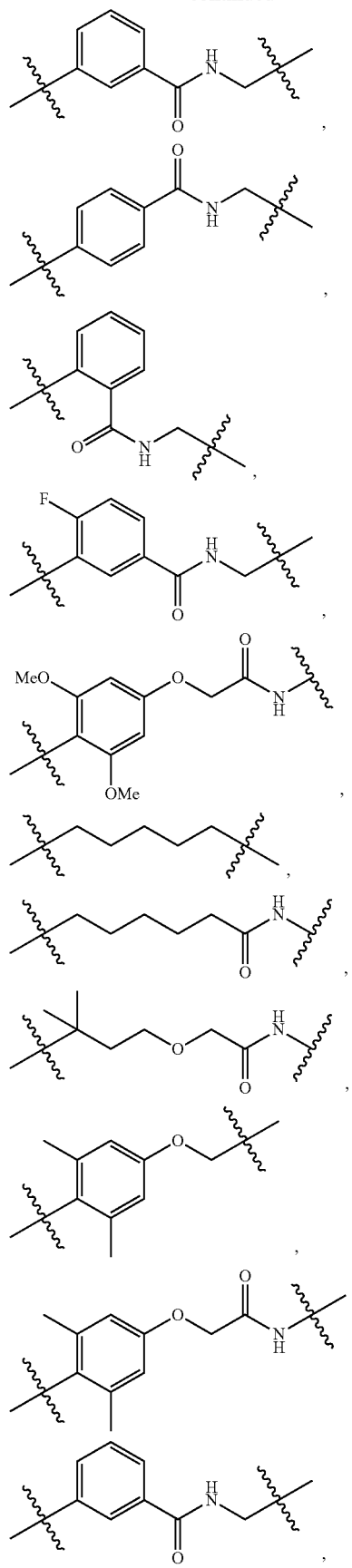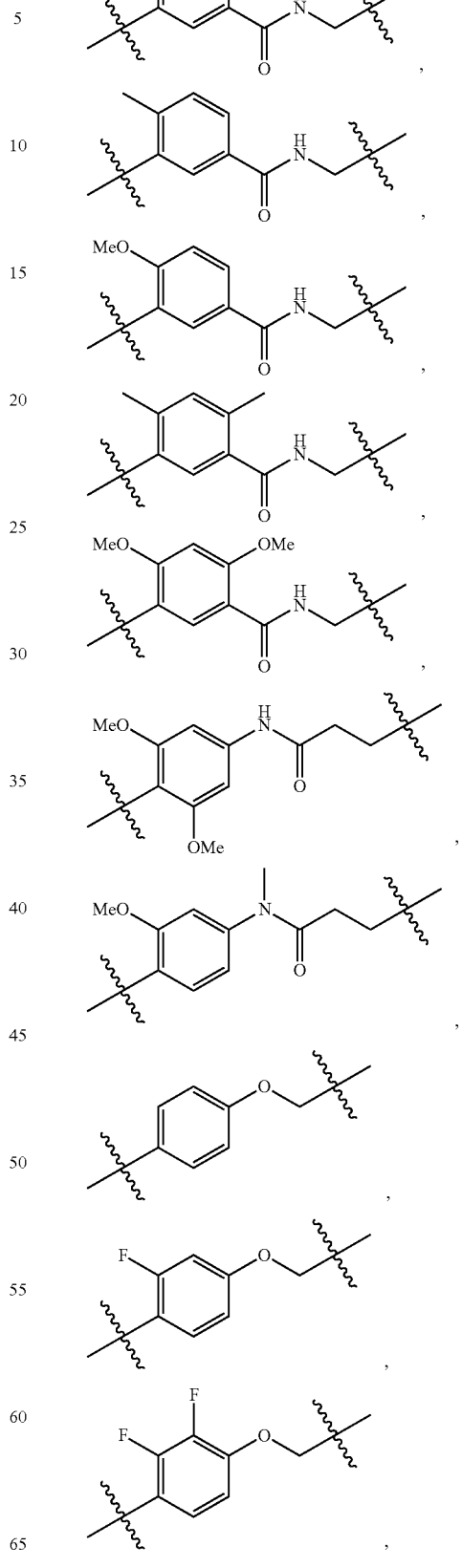

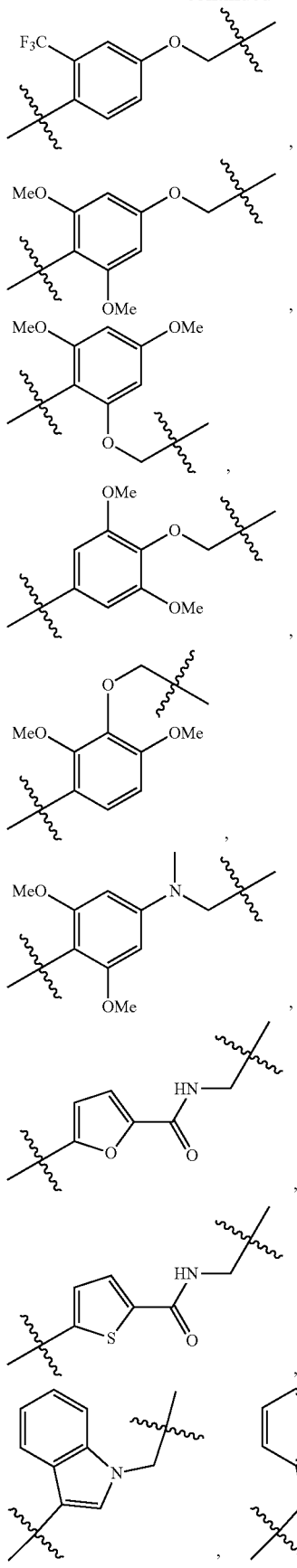

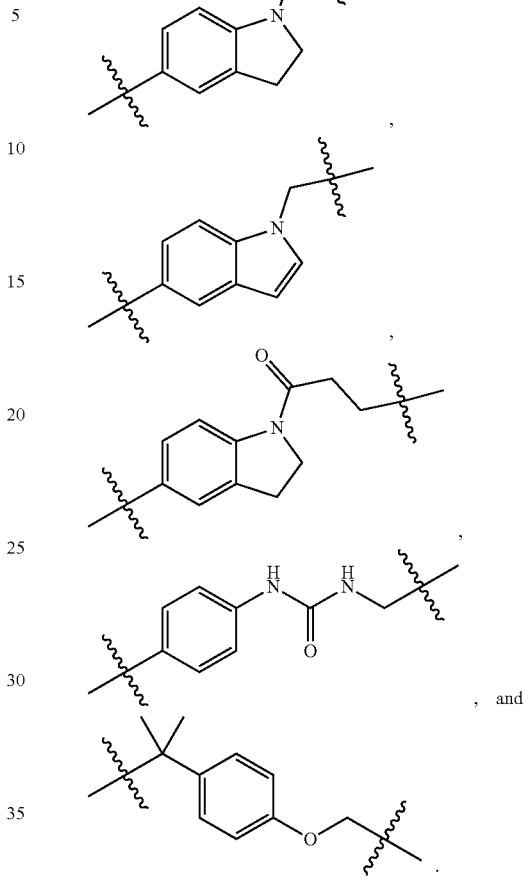

$R^{20}$ is a heteroarylene including 5-6 ring atoms ((wherein from 1-4 of the ring atoms are independently selected from N, NH, N—$C_1$-$C_6$ alkyl, O, and S; e.g., containing one or more, e.g., from 1-4, 1-3, 1-2 nitrogen atoms), optionally substituted with 1, 2, or 3 substituents independently selected from $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof; or $R^{20}$ is absent.

In some embodiments, $R^{20}$ is

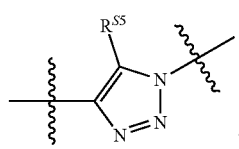

In some embodiments, $R^{S5}$ is H, $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof, carboxyl ester, thiol, and thioether.

In certain embodiments, $R^{S5}$ is H or $C_{1-6}$ alkyl.
In certain embodiments, $R^{S5}$ is H.
In other embodiments, $R^{20}$ is absent.

The PEG can have any one of the architectures described herein (e.g., formulas 2A-2H; table AA).

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

Variable $R^{13}$

In some embodiments, $R^{13}$ is present.

In some embodiments, $R^{13}$ is selected from acylhydrazone, acyloxime, carbamoyl oxime, acyloxyaklyl oxime, acyloxyalkyloxy oxime, oximinophosphate, oximinophosponate, oximinophosphoramidate, oxazolidine or thiazolidine, protected hydroxyl, and protected hydroxymethyl.

In some embodiments, $R^{13}$ is =N-A-$R^{17}$; wherein A is NH or O, and $R^{17}$ is H, $C_{1-6}$alkyl, $C_{1-6}$haloalkyl, $C_{1-6}$alkoxy$C_{1-6}$alkyl, $C_{6-10}$aryl, $C_{7-12}$aralkyl, $C_{3-7}$cycloalkyl, heteroaryl including from 5-10 ring atoms (wherein from 1-3 of the ring atoms are independently selected from N, NH, N—$C_1$-$C_6$ alkyl, O, and S), heterocyclyl including from 3-7 ring atoms (wherein from 1-2 of the ring atoms are independently selected from N, NH, N—$C_1$-$C_6$ alkyl, and O), —C(=O)$C_{1-6}$alkyl, —C(=O)$C_{1-6}$haloalkyl, —C(=O)$C_{6-10}$aryl, —C(=O)$C_{7-12}$aralkyl, —C(=O)$C_{3-7}$cycloalkyl, —C(=O)heteroaryl, or —C(=O)heterocyclyl, each of which is optionally substituted; or $R^{17}$ is —Y"$_q$—Z" or —C(=O)—Y"$_q$—Z"; wherein:

Y" is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, polyheteroalkylene chain, alkenylene chain, —OC(=O)—, —C(=O)O—, —NHC(=O)—, —C(=O)NH—, —C(=O)—, cyclodextrin, human serum albumin, amino acid, amino acid mimetic, or hydrazine;

Z" is conjugate for enhancing solubility, stability, half-life, permeability, volume of distribution, and/or target specificity, which comprises one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): alkylene chain, heteroalkylene chain, polyheteroalkylene chain, alkenylene chain, cyclodextrin, alkylated cyclodextrin, human serum albumin, —OC(=O)—, —C(=O)O—, —NHC(=O)—, —C(=O)NH—, —C(=O)—, monoclonal anti-body, quaternary ammonium ion, $NH_2$, docosahexenoic acid, hyaluronic acid, poly(L-glutamic acid), N-(2-hydroxypropyl) methacrylamide copolymer, or dendrimers (e.g., nitrosubstituted dendrimers); and q is 0 or 1.

In certain embodiments, A is NH, and $R^{17}$ is —C(=O)$C_{1-6}$alkyl, —C(=O)$C_{1-6}$ haloalkyl, —C(=O)$C_{6-10}$aryl, —C(=O)$C_{7-12}$aralkyl, —C(=O)$C_{3-7}$cycloalkyl, —C(=O)heteroaryl, or —C(=O)heterocyclyl (e.g., —C(=O)$C_{1-6}$alkyl).

In certain embodiments, A is O, and $R^{17}$ is H, $C_{1-6}$alkyl, $C_{1-6}$haloalkyl, $C_{1-6}$ alkoxy$C_{1-6}$alkyl, $C_{6-10}$aryl, $C_{7-12}$aralkyl, $C_{3-7}$cycloalkyl (e.g., H or $C_{1-6}$alkyl).

In certain embodiments, $R^{17}$ is —Y"$_q$—Z" or —C(=O)—Y"$_q$—Z".

In certain embodiments, $R^2$ and $R^3$, together with the carbon atoms to which each is attached, form an epoxide ring.

In some embodiments, the prodrug has Formula 1I:

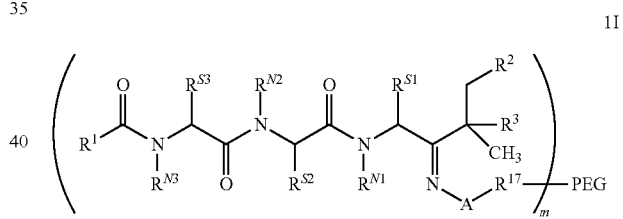

1I

When present as a divalent moiety in formula 1I, $R^{17}$ is —$R^{17'}$—$R^{20}$, in which $R^{20}$ is connected to PEG, and $R^{17'}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{17'}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): alkylene chain, heteroalkylene chain, —NHC(=O)—, —C(=O)NH—, —N($C_{1-6}$ alkyl)C (=O), —C(=O)N($C_{1-6}$ alkyl)-, —C(=O)—, or —NHC (=O)NH—.

In some embodiments, $R^{17'}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): alkylene chain, heteroalkylene chain, or —C(=O)— (e.g., alkylene chain or —C(=O)—). In certain embodiments (e.g., when A is NH), the —C(=O)— is attached to A.

In certain embodiments, $R^{17'}$ is —C(=O)-alkylene chain. In certain embodiments, A is NH, $R^{17'}$ is —C(=O)-alkylene chain, and the —C(=O)— is attached to A.

m is 1, 2, 3, 4, 5, 6, 7, 8, 9, or 10, e.g., 2, 3, 4, 5, 6, 7, 8, 9, or 10.

$R^{20}$ is a heteroarylene including 5-6 ring atoms ((wherein from 1-4 of the ring atoms are independently selected from N, NH, N—$C_1$-$C_6$ alkyl, O, and S; e.g., containing one or more, e.g., from 1-4, 1-3, 1-2 nitrogen atoms), optionally substituted with 1, 2, or 3 substituents independently selected from $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof; or $R^{20}$ is absent (e.g., $R^{20}$ is present and is as defined above).

In some embodiments, $R^{20}$ is

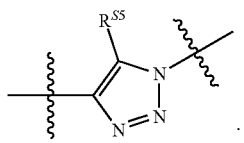

In some embodiments, $R^{S5}$ is H, $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof, carboxyl ester, thiol, and thioether.

In certain embodiments, $R^{S5}$ is H or $C_{1-6}$alkyl.
In certain embodiments, $R^{S5}$ is H.
In other embodiments, $R^{20}$ is absent.
m is 1, 2, 3, 4, 5, 6, 7, 8, 9, or 10, e.g., 2, 3, 4, 5, 6, 7, 8, 9, or 10.
In certain embodiments, m is 8.
In certain embodiments, m is 4.
In certain embodiments, m is 2.
In certain embodiments, m is 1.

The PEG can have any one of the architectures described herein (e.g., formulas 2A-2H; table AA).

In some embodiments, PEG has a molecular weight of greater than 1 kDa.
In some embodiments, PEG has a molecular weight of about 1 kDa.
In some embodiments, PEG has a molecular weight of greater than 2 kDa.
In some embodiments, PEG has a molecular weight of about 2 kDa.
In some embodiments, PEG has a molecular weight of greater than 5 kDa.

In some embodiments, PEG has a molecular weight of about 5 kDa.
In some embodiments, PEG has a molecular weight of greater than 10 kDa.
In some embodiments, PEG has a molecular weight of about 10 kDa.
In some embodiments, PEG has a molecular weight of greater than 20 kDa.
In some embodiments, PEG has a molecular weight of about 20 kDa.
In some embodiments, PEG has a molecular weight of greater than 30 kDa.
In some embodiments, PEG has a molecular weight of about 30 kDa.
In some embodiments, PEG has a molecular weight of greater than 40 kDa.
In some embodiments, PEG has a molecular weight of about 40 kDa.
In some embodiments, PEG has a molecular weight of greater than 50 kDa.

In some embodiments, prior to conjugation to epoxy ketone protease inhibitors, PEG has a plurality of reactive functional groups (e.g., azide groups).
In some embodiments, prior to conjugation to epoxy ketone protease inhibitors, PEG has 1, 2, 3, 4, 5, 6, 7, 8, 9, or 10 reactive functional groups (e.g., azide groups).

Variable $R^{14}$
In some embodiments, $R^{14}$ is present.
In some embodiments, $R^{14}$ is:
(i) —CH$_2$OC(=O)R$^{18}$;
(ii) —C(=O)OCH$_2$OC(=O)R$^{18}$; or
(iii) —SR$^{18}$;
wherein:
$R^{18}$ is $C_{1-6}$alkyl, $C_{1-6}$haloalkyl, $C_{1-6}$alkoxy$C_{1-6}$alkyl, $C_{6-10}$aryl, $C_{7-12}$aralkyl, $C_{3-7}$cycloalkyl, heteroaryl including from 5-10 ring atoms, or heterocyclyl including from 3-7 ring atoms, each of which is optionally substituted; or
$R^{15}$ is —Y'''$_r$—Z'''; wherein:
Y''' is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, heteroalkylene chain, polyheteroalkylene chain, alkenylene chain, —OC(=O)—, —C(=O)O—, —NHC(=O)—, —C(=O)NH—, —C(=O)—, cyclodextrin, human serum albumin, amino acid, amino acid mimetic, or hydrazine;
Z''' is conjugate for enhancing solubility, stability, half-life, permeability, volume of distribution, and/or target specificity, which comprises one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): alkylene chain, heteroalkylene chain, polyheteroalkylene chain, alkenylene chain, cyclodextrin, alkylated cyclodextrin, human serum albumin, —OC(=O)—, —C(=O)O—, —NHC(=O)—, —C(=O)NH—, —C(=O)—, monoclonal anti-body, quaternary ammonium ion, NH$_2$, docosahexenoic acid, hyaluronic acid, poly(L-glutamic acid), N-(2-hydroxypropyl) methacrylamide copolymer, or dendrimers (e.g., nitro-substituted dendrimers); and
r is 0 or 1.
In some embodiments, each of Y, Y', Y'', and Y''' is independently a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, heteroalkylene chain, polyheteroalkylene chain, alkenylene chain, —OC(=O)—, —C(=O)O—, —NHC (=O)—, —C(=O)NH—, —C(=O)—, amino acid, or amino acid mimetic.

In some embodiments, each of Z, Z', Z", and Z'" is independently a conjugate for enhancing solubility, stability, half-life, permeability, volume of distribution, and/or target specificity, which comprises one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): alkylene chain, heteroalkylene chain, polyheteroalkylene chain, alkenylene chain, —OC(=O)—, —C(=O)O—, —NHC (=O)—, —C(=O)NH—, —C(=O)—, quaternary ammonium ion, $NH_2$, docosahexenoic acid, hyaluronic acid, poly (L-glutamic acid), N-(2-hydroxypropyl) or methacrylamide copolymer.

In some embodiments, the prodrug has Formula 1H:

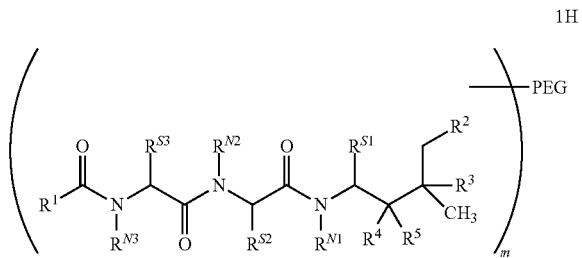

1H wherein m is 1, 2, 3, 4, 5, 6, 7, 8, 9, or 10, e.g., 2, 3, 4, 5, 6, 7, 8, 9, or 10;

and the compound is attached to the PEG through one of $R^{N1}$, $R^{N2}$, $R^{N3}$ or $R^{N4}$, wherein at least one of $R^{N1}$, $R^{N2}$, $R^{N3}$ or $R^{N4}$ is $R^{14}$.

In certain embodiments, m is 8.
In certain embodiments, m is 4.
In certain embodiments, m is 2.
In certain embodiments, m is 1.

When present as a divalent moiety in formula 1H, $R^{14}$ is —$R^{14'}$—$R^{20}$—, in which $R^{20}$ is connected to PEG, and $R^{14'}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, 3, 4, or 5 of the following moieties): heteroatom (e.g., N, O, or S), alkylene chain, heteroalkylene chain, polyheteroalkylene chain, alkenylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O)—, —C(=O)N($C_{1-6}$ alkyl)-, —C(=O)—, —NHC(=O)NH—, cyclodextrin, human serum albumin, amino acid, amino acid mimetic, or hydrazine, wherein arylene including 6-10 ring atoms, heteroarylene including from 5-10 ring atoms, and heterocycloalkylene including 3-9 ring atoms are each optionally substituted with 1, 2, or 3 substituents each independently selected from the group consisting of halo, cyano, nitro, hydroxyl, $C_{1-6}$ alkoxy, heteroalkyl, $C_{6-10}$ aryloxy, $C_{7-12}$ aralkoxy, $CF_3$, quaternary ammonium ion, sugar, $C_{1-6}$ alkyl, —C(=O)($C_{1-6}$ alkyl), —$SO_2$($C_{1-6}$ alkyl), —C(=O)O($C_{1-6}$ alkyl), —C(=O)O(heteroalkyl), —C(=O)NH($C_{1-6}$ alkyl), —C(=O)NH(heteroalkyl), —C(=O)(phenyl), —$SO_2$(phenyl), and phosphate (or a salt thereof).

In some embodiments, $R^{14'}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —OC(=O)—, —C(=O)O—, —NHC(=O)—, —C(=O)NH—, —N($C_{1-6}$ alkyl)C(=O)—, —C(=O)N($C_{1-6}$ alkyl)-, —C(=O)—, or —NHC(=O) NH—, wherein 6-10 membered arylene, 5-10 membered heteroarylene, and 6-10 membered cycloalkylene are each optionally substituted with 1, 2, or 3 substituents each independently selected from the group consisting of halo, cyano, $C_{1-6}$ alkoxy, heteroalkyl, $CF_3$, and $C_{1-6}$ alkyl.

In some embodiments, $R^{14'}$ is divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH. N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O. and S), —NHC(=O)—, —C(=O) NH—, —N($C_{1-6}$ alkyl)C(=O)—, —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{14'}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, —C(=O)—, —NHC(=O)—, —C(=O)NH—, heteroalkylene chain, phenylene, indolylene, indolinylene, thiophenylene, or furanylene, wherein phenylene, indolylene, indolinylene, thiophenylene, and furanylene are optionally substituted with 1, 2, or 3 substituents each independently selected from the group consisting of halo, $C_{1-6}$ alkoxy, heteroalkyl, $CF_3$, and $C_{1-6}$ alkyl. In certain embodiments, when alkylene chain is present, the alkylene chain is linked to the backbone nitrogen.

In certain embodiments, $R^{14'}$ is -alkylene(e.g., $C_1$-$C_6$, $C_1$-$C_3$) chain-O—C(O)— phenylene-, e.g., —$CH_2$—O—C (O)-phenylene-. In embodiments, the alkylene chain is linked to the backbone nitrogen (i.e., nitrogen attached to one of $R^{N1}$, $R^{N2}$, $R^{N3}$ or $R^{N4}$).

$R^{20}$ is a heteroarylene including 5-6 ring atoms ((wherein from 1-4 of the ring atoms are independently selected from N, NH, N—$C_1$-$C_6$ alkyl, O, and S; e.g., containing one or more. e.g., from 1-4, 1-3, 1-2 nitrogen atoms), optionally substituted with 1, 2, or 3 substituents independently selected from $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof; or $R^{20}$ is absent (e.g., $R^{20}$ is present and is as defined above).

In some embodiments, $R^{20}$ is

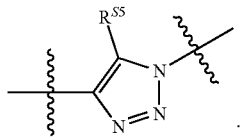

In some embodiments, $R^{S5}$ is H, $C_{1-6}$alkyl, $C_{1-6}$hydroxyalkyl, $C_{1-6}$alkoxy$C_{1-6}$alkyl, $C_{6-10}$aryl, or $C_{7-12}$aralkyl, each of which is optionally substituted with a group selected from amide, amine, carboxylic acid or a pharmaceutically acceptable salt thereof, carboxyl ester, thiol, and thioether.

In certain embodiments, $R^{S5}$ is H or $C_{1-6}$alkyl.

In certain embodiments, $R^{S5}$ is H.

In other embodiments, $R^{20}$ is absent.

The PEG can have any one of the architectures described herein (e.g., formulas 2A-2H; table AA).

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

Variables $R^{N1}$, $R^{N2}$, $R^{N3}$, and $R^{N4}$

In some embodiments, each of $R^{N1}$, $R^{N2}$, $R^{N3}$, and $R^{N4}$ is H.

Variables $R^4$ and $R^5$

In some embodiments, $R^4$ and $R^5$, together with the carbon atom to which both are attached, form a carbonyl group.

Non-Limiting $R^{11}$, $R^{12}$, $R^{13}$, and $R^{14}$ Combinations

In some embodiments, one of $R^{11}$, $R^{12}$, $R^{13}$, and $R^{14}$ is present.

In some embodiments, one of $R^{11}$, $R^{12}$, $R^{13}$, and $R^{14}$ is present, wherein $R^{11}$ is present, and $R^2$ and $R^3$ together form an epoxide ring.

In some embodiments, one of $R^{11}$, $R^{12}$, $R^{13}$, and $R^{14}$ is present, $R^3$ is hydroxyl, and wherein $R^{12}$ is present and is a leaving group.

In some embodiments, one of $R^{11}$, $R^{12}$, $R^{13}$, and $R^{14}$ is present, $R^3$ activated hydroxyl, and wherein $R^{12}$ is present and is a leaving group.

In some embodiments, one of $R^{13}$ and $R^{14}$ is present, $R^3$ is hydroxyl, $R^{11}$ is present, and wherein $R^{12}$ is present is a leaving group.

In some embodiments, one of $R^{13}$ and $R^{14}$ is present, $R^3$ is activated hydroxyl, $R^{11}$ is present, and wherein $R^{12}$ is present is a leaving group.

In some embodiments, one of $R^{11}$ and $R^{14}$ is present, $R^3$ is hydroxyl, $R^{13}$ is present, and wherein $R^{12}$ is present is a leaving group.

In some embodiments, one of $R^{11}$ and $R^{14}$ is present, $R^3$ is activated hydroxyl, $R^{13}$ is present, and wherein $R^{12}$ is present is a leaving group.

In some embodiments, one of $R^{11}$ and $R^{13}$ is present, $R^3$ is hydroxyl, $R^{14}$ is present, and wherein $R^{12}$ is present is a leaving group.

In some embodiments, one of $R^{11}$ and $R^{13}$ is present, $R^3$ is activated hydroxyl, $R^{14}$ is present, and wherein $R^{12}$ is present is a leaving group.

In some embodiments, each of $R^{11}$, $R^{12}$, $R^{13}$, and $R^{14}$ is present, $R^3$ is hydroxyl, and wherein $R^{12}$ is a leaving group.

In some embodiments, each of $R^{11}$, $R^{12}$, $R^{13}$, and $R^{14}$ is present, $R^3$ is activated hydroxyl, and wherein $R^{12}$ is a leaving group.

In some embodiments, $R^{11}$ is present.

In some embodiments, $R^{13}$ is present.

In some embodiments, $R^{14}$ is present.

PEG Architecture

It is understood that one or more independently selected formula (1) compounds (i.e., each of the compounds can be the same or different) can be conjugated to a polyethylene glycol (PEG) polymer chain.

In some embodiments, the PEG has a molecular weight between about 1 kDa and about 40 kDa.

In some embodiments, the PEG has a molecular weight of about 1 kDa.

In some embodiments, PEG has a molecular weight of greater than 1 kDa.

In some embodiments, PEG has a molecular weight of about 2 kDa.

In some embodiments, the PEG has a molecular weight of greater than 2 kDa.

In some embodiments, the PEG has a molecular weight of about 5 kDa.

In some embodiments, PEG has a molecular weight of greater than 5 kDa.

In some embodiments, the PEG has a molecular weight of about 10 kDa.

In some embodiments, the PEG has a molecular weight of greater than 10 kDa.

In some embodiments, the PEG has a molecular weight of about 20 kDa.

In some embodiments, PEG has a molecular weight of greater than 20 kDa.

In some embodiments, the PEG has a molecular weight of about 40 kDa.

In some embodiments, PEG has a molecular weight of greater than 40 kDa.

In some embodiments, PEG has a molecular weight of greater than 50 kDa.

In some embodiments, the prodrug has Formula 2A:

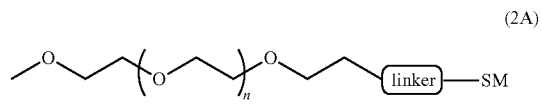

(2A)

wherein SM is a compound of Formula (I) attached to the PEG through a linker.

In some embodiments, the prodrug is attached to a bifunctional PEG and has Formula 2B:

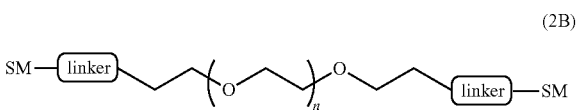

(2B)

wherein each SM is an independently selected compound of Formula (I) attached to the PEG through an independently selected linker.

In some embodiments, the prodrug is a four-arm PEG of Formula 2C:

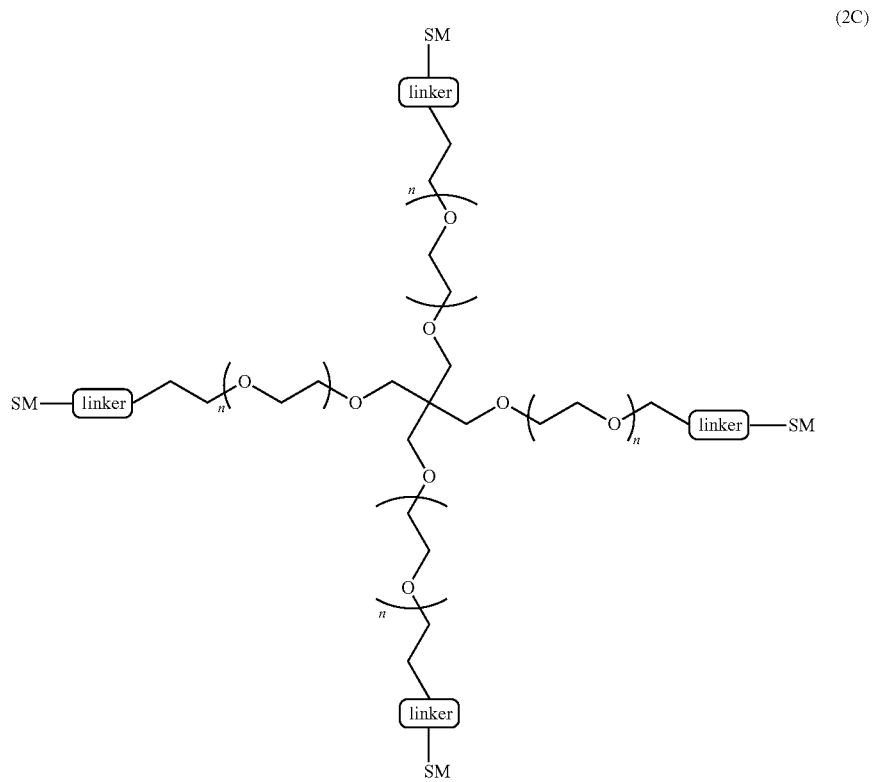

(2C)

wherein each SM is an independently selected compound of Formula (I) attached to the PEG through an independently selected linker.

In some embodiments, the prodrug has an eight-arm hexaglycerin core and is of Formula 2D:

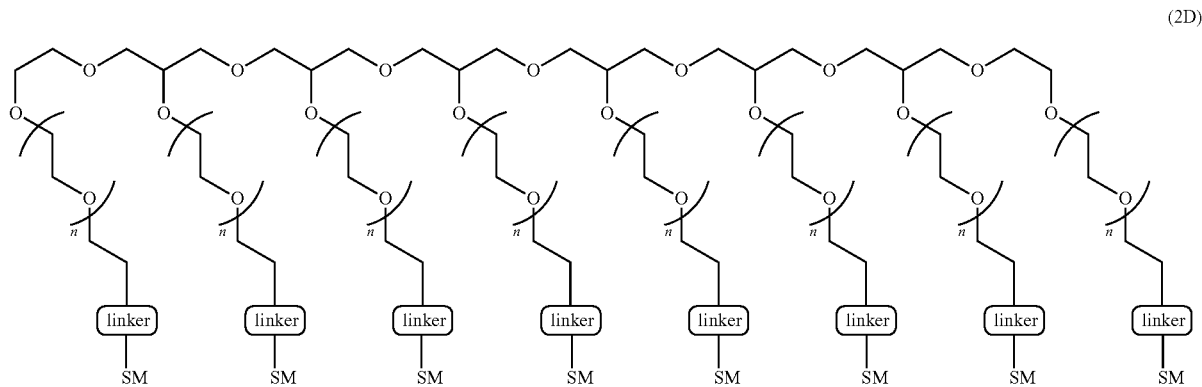

(2D)

wherein each SM is an independently selected compound of Formula (I) attached to the PEG through an independently selected linker.

In some embodiments, the prodrug has an eight-arm tripentaerythritol core, and is of Formula 2E:

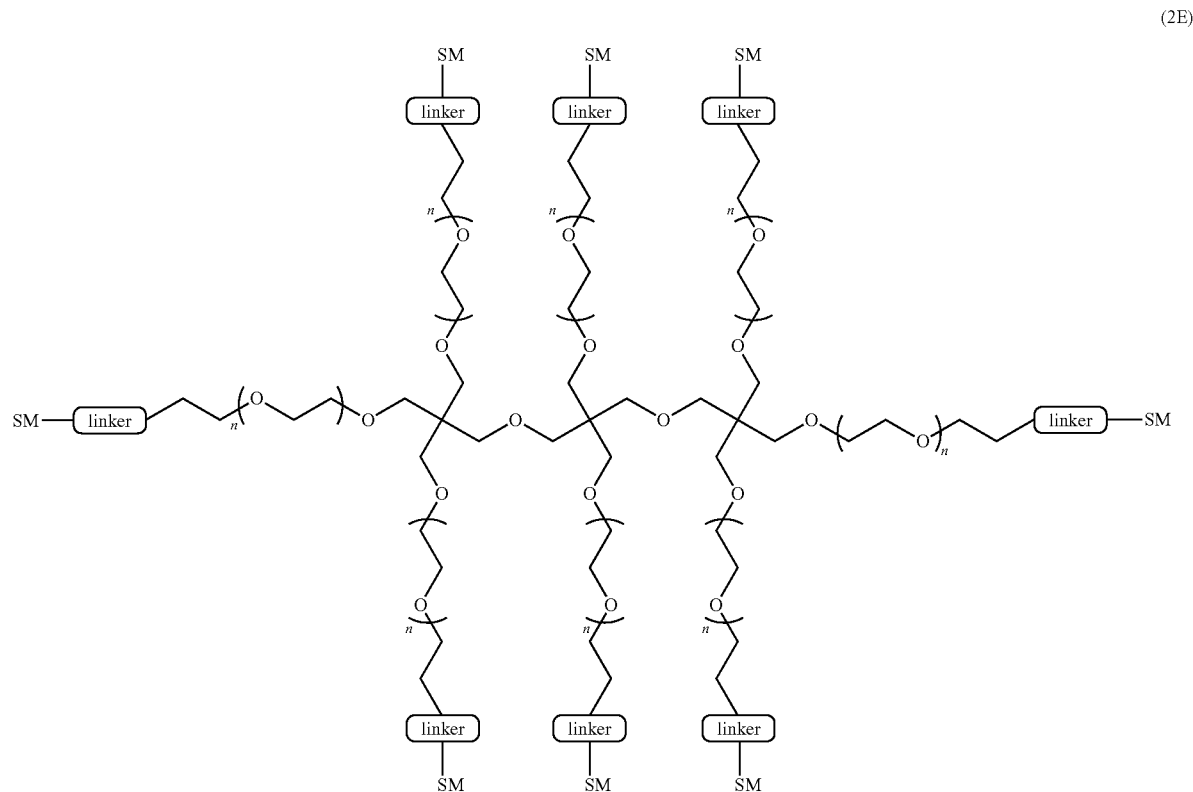

(2E)

wherein each SM is an independently selected compound of Formula (I) attached to the PEG through an independently selected linker.

In some embodiments, the prodrug has a branched two-arm PEG; and is of Formula 2F:

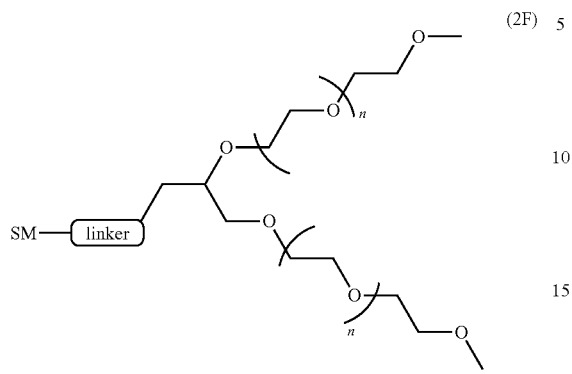

(2F)

wherein each SM is an independently selected compound of Formula (I) attached to the PEG through an independently selected linker.

In some embodiments, the prodrug has a branched four-arm PEG, and is of Formula 2G:

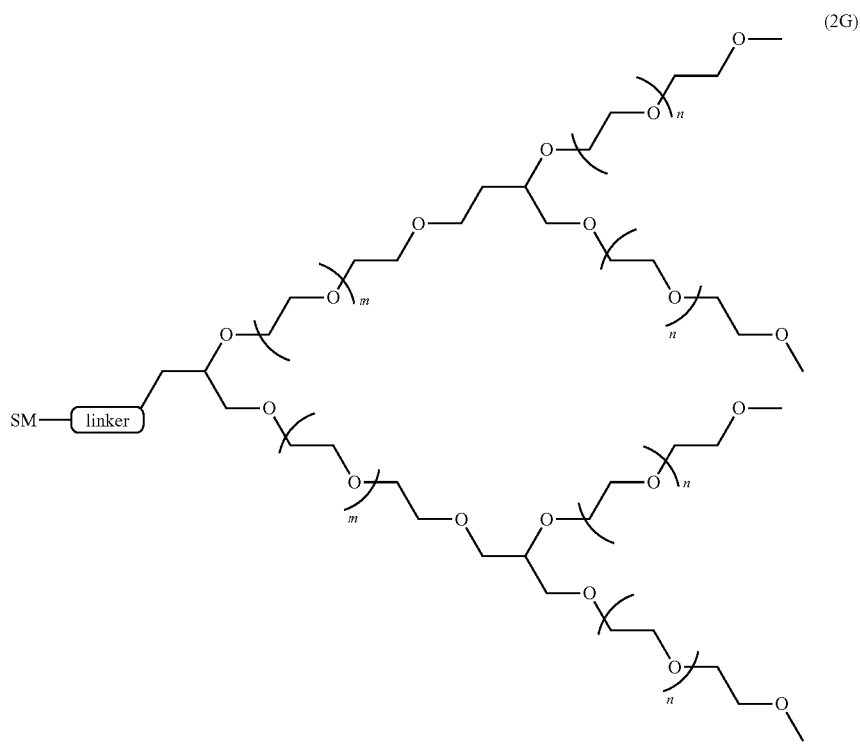

(2G)

wherein each SM is an independently selected compound of Formula (I) attached to the PEG through an independently selected linker.

In some embodiments, the prodrug has a branched four-arm PEG and is of Formula 2H:

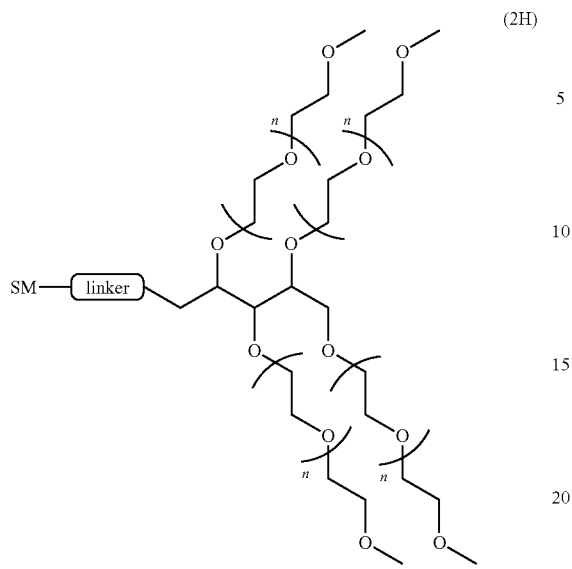
(2H)
wherein each SM is an independently selected compound of Formula (I) attached to the PEG through an independently selected linker.
In some embodiments, the PEG architecture of the prodrugs is disclosed in Table AA.
TABLE AA
| Formula | Structure | PEG Architecture |
|---|---|---|
| 2A | 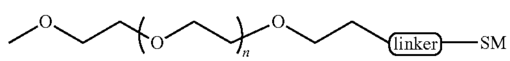 | Linear |
| 2B | 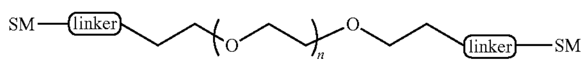 | Bifunctional |
| 2C | 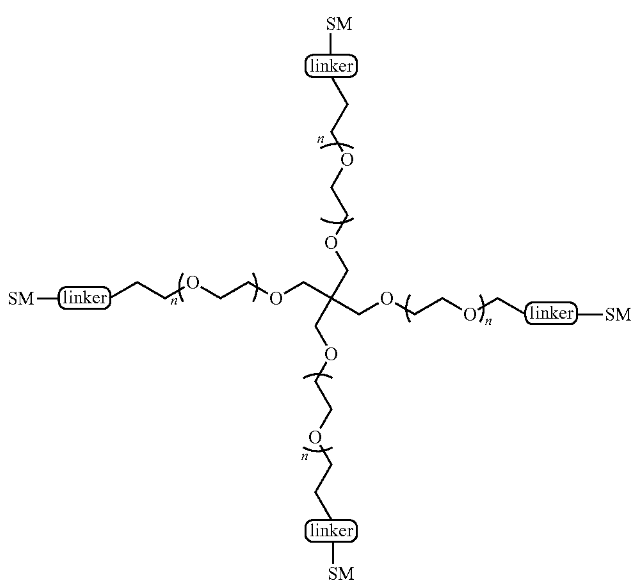 | 4-Arm |

TABLE AA-continued

| Formula | Structure | PEG Architecture |
|---|---|---|
| 2D | 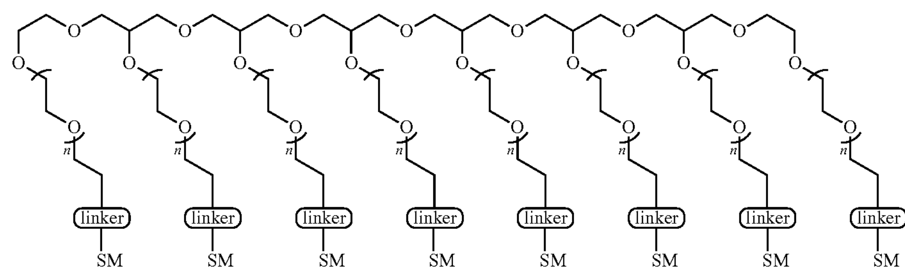 | 8-Arm hexaglycerin core |
| 2E | 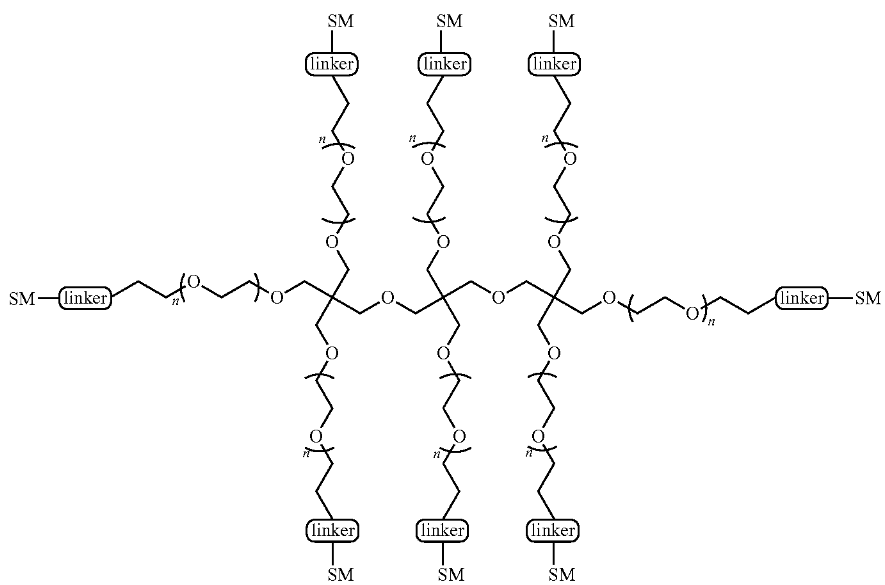 | 8-Arm tripentaerythitol core |
| 2F | 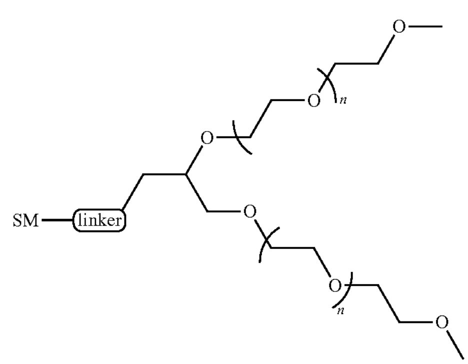 | Branched 2-Arm |

TABLE AA-continued
| Formula | Structure | PEG Architecture |
|---|---|---|
| 2G | 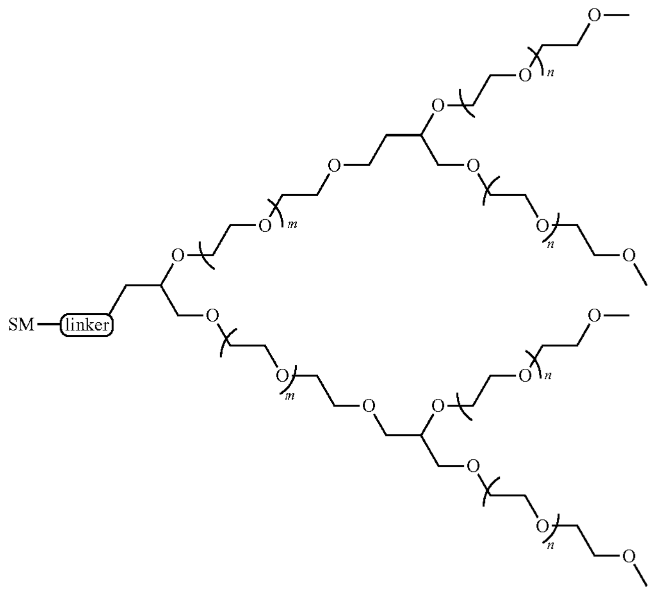 | Branched 4-Arm |
| 2H | 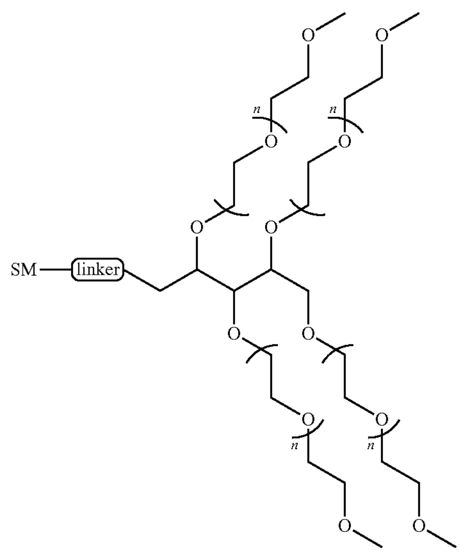 | Branched 4-Arm |
In some embodiments, the compound is a prodrug of compound A:
In some embodiments, the compound is a prodrug of compound B:
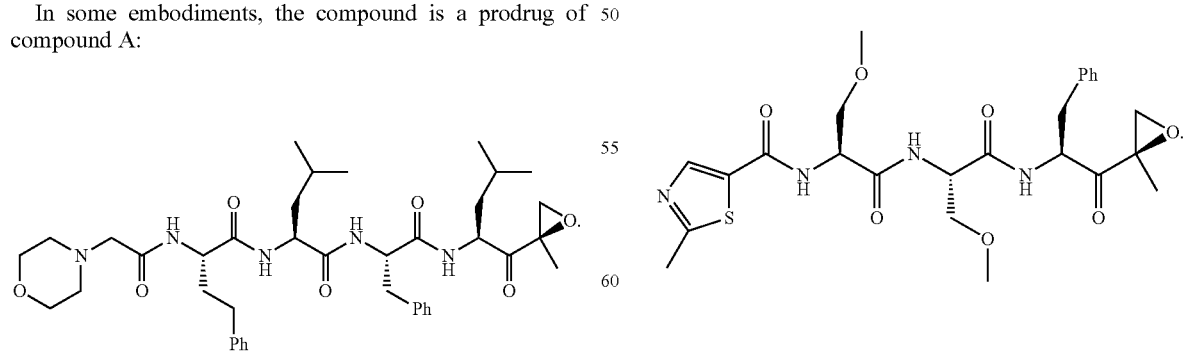
Non-Limiting Combinations
[A] In some embodiments, the compound has formula (I); and $R^1$ has formula (II):

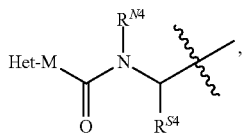

wherein Het is heterocyclyl that includes from 5-6 ring atoms, wherein at least one ring atom is a nitrogen atom selected from —N(H)—, —N(M)-, or —N($C_1$-$C_3$ alkyl)- (e.g., morpholino), and M is $C_1$-$C_{12}$ alkyl (e.g., $CH_2$);

$R^{S1}$ and $R^{S3}$ are each independently $C_{1-6}$alkyl, and $R^{S2}$ and $R^{S4}$ are each independently $C_{7-12}$aralkyl (e.g., $R^{S1}$ and $R^{S3}$ are both isobutyl, $R^{S4}$ is phenylethyl, and $R^{S2}$ is phenylmethyl).

$R^{N1}$, $R^{N2}$, $R^{N3}$, and $R^{N4}$ are each H;

$R^4$ and $R^5$, together with the carbon atom to which both are attached, form a carbonyl group;

$R^3$ is hydroxyl, and $R^{12}$ is present and is selected from: (i) —$OSO_2$—$R^{16}$ (e.g., $R^{16}$ is $C_{1-6}$alkyl (e.g., $CH_3$) or $C_{6-10}$aryl (e.g., phenyl); (ii) halo (e.g., iodo); and (iii) —$OSO_2$—$R^{19}$—$R^{20}$-PEG.

In some embodiments, the PEG can have PEG architecture 2A.

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments (e.g., when $R^{20}$ is present), $R^{19}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, heteroalkylene chain, phenylene, indolylene, indolinylene, thiophenylene, or furanylene (e.g., phenylene), wherein phenylene, indolylene, indolinylene, thiophenylene, and furanylene are optionally substituted with 1, 2, or 3 substituents each independently selected from the group consisting of halo, $C_{1-6}$ alkoxy, heteroalkyl, $CF_3$, and $C_{1-6}$ alkyl. In embodiments, R20 is

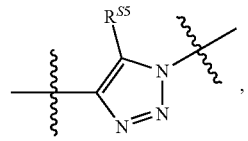

e.g., $R^{S5}$ is hydrogen.

In some embodiments, the compound is selected from the group consisting of:

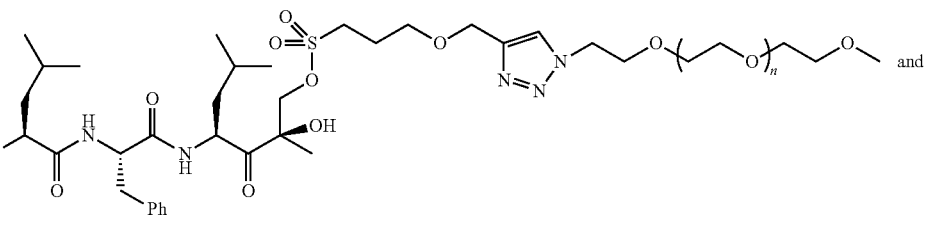

and

-continued

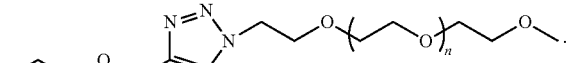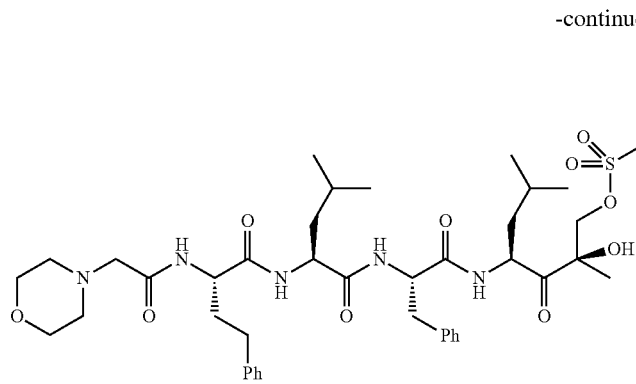

[A'] In some embodiments, the compound has formula (I); and R$^1$ has formula (II):

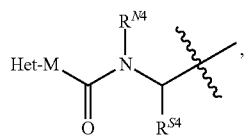

wherein Het is heterocyclyl that includes from 5-6 ring atoms, wherein at least one ring atom is a nitrogen atom selected from —N(H)—, —N(M)-, or —N(C$_1$-C$_3$ alkyl)- (e.g., morpholino), and M is C$_1$-C$_{12}$ alkyl (e.g., CH$_2$);

R$^{S1}$ and R$^{S3}$ are each independently C$_{1-6}$alkyl, and R$^{S2}$ and R$^{S4}$ are each independently C$_{7-12}$aralkyl (e.g., R$^{S1}$ and R$^{S3}$ are both isobutyl, R$^{S4}$ is phenylethyl, and R$^{S2}$ is phenylmethyl).

R$^{N1}$, R$^{N2}$, R$^{N3}$, and R$^{N4}$ are each H;

R$^4$ and R$^5$, together with the carbon atom to which both are attached, form a carbonyl group;

R$^2$ and R$^3$, together with the carbon atoms to which each is attached, form an epoxide ring, and R$^{11}$ is present (e.g., R$^{11}$ is —CH$_2$OC(=O)R$^{21}$—R$^{20}$-PEG or —CH$_2$Ar—R$^{21}$—R$^{20}$-PEG. In certain embodiments, R$^{11}$ is attached to a morpholino ring nitrogen atom, which in turn is also attached to moiety M).

In some embodiments, the PEG can have PEG architecture 2A.

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments, R$^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, —C(=O)—, or phenylene, wherein phenylene is optionally substituted with 1, 2, or 3 substituents each independently selected from the group consisting of halo, C$_{1-6}$ alkoxy, heteroalkyl, CF$_3$, and C$_{1-6}$ alkyl.

In some embodiments, R$^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, or —C(=O)—.

In certain embodiments, R$^{21}$ is —O—C(O)-alkylene chain (e.g., C$_2$).

In some embodiments, R$^{20}$ is present; e.g., R$^{20}$ is

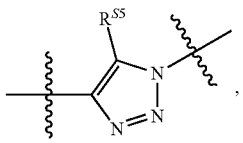

e.g., R$^{S5}$ is H. In some embodiments, R$^{20}$ is absent.

In some embodiments, the compound is selected from the group consisting of:
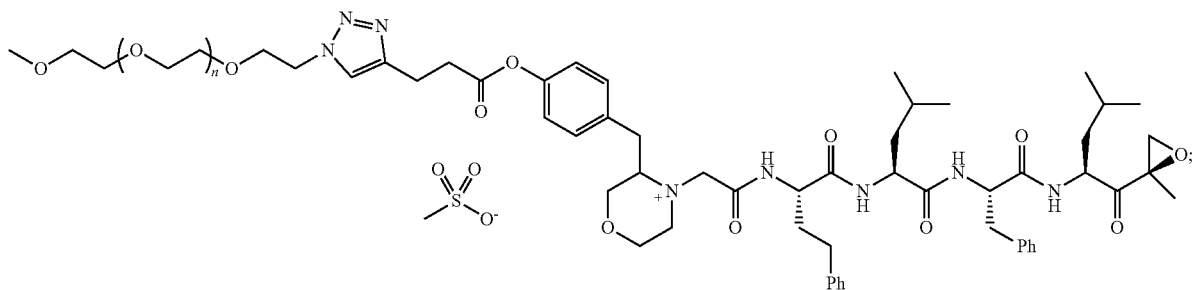
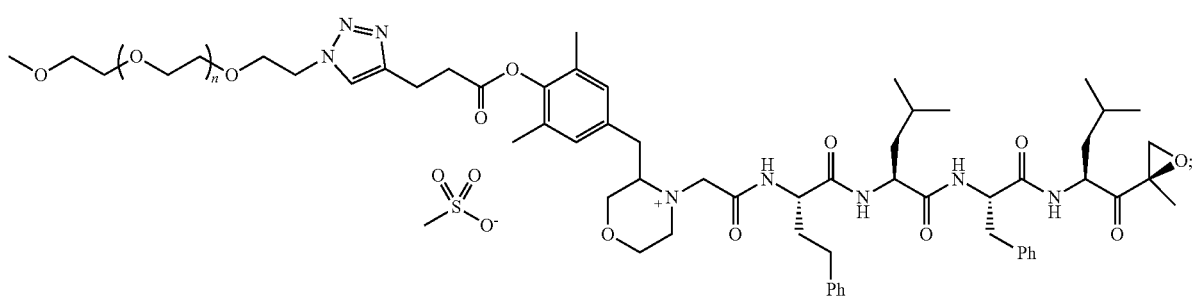
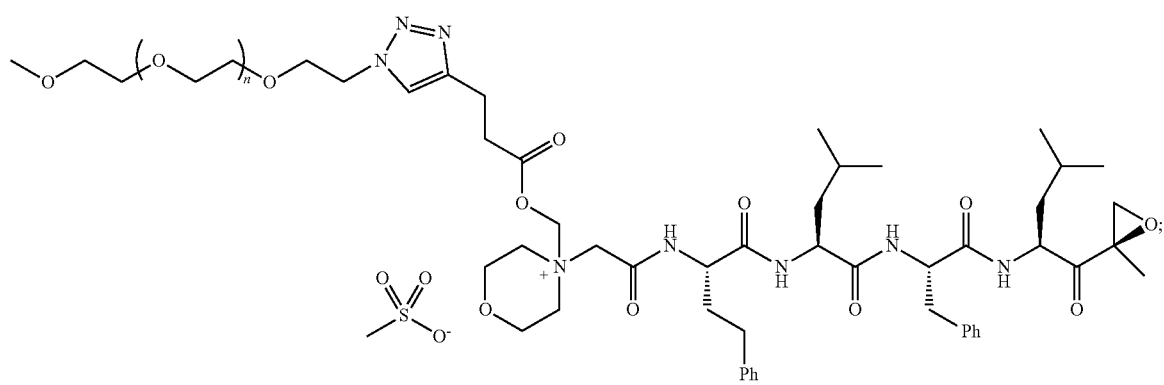
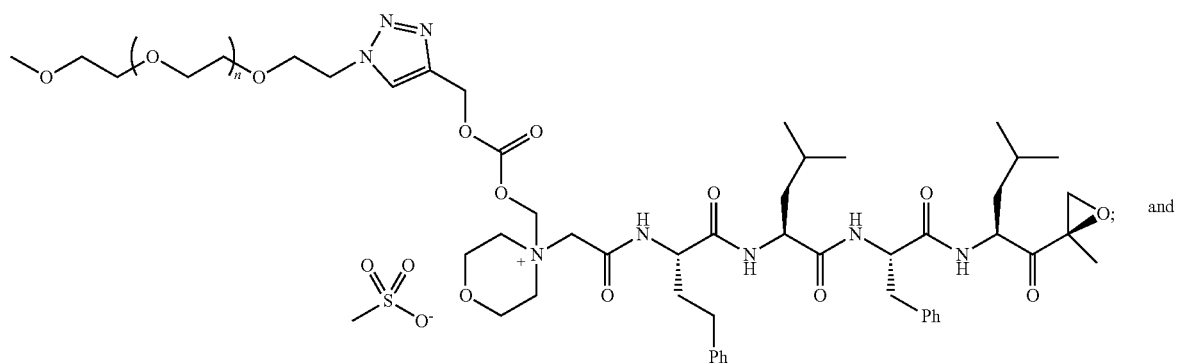

-continued

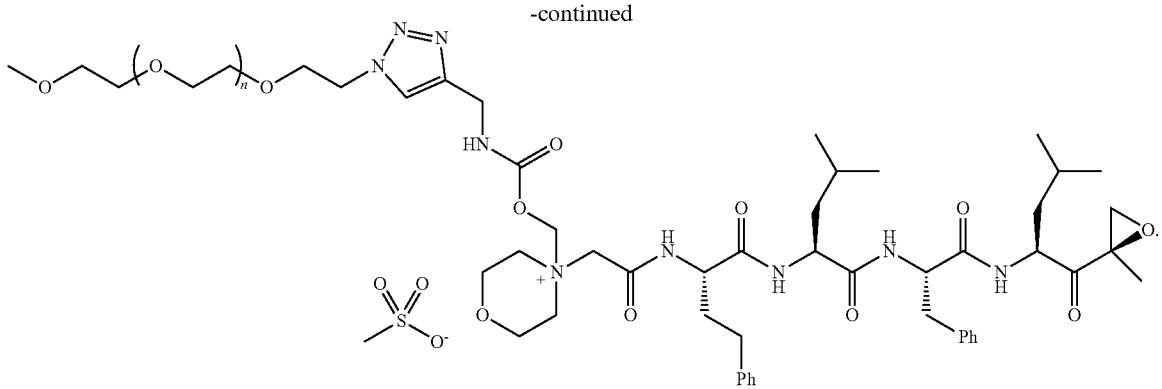

[B] In some embodiments, the compound has formula (V); and
Q is SO$_2$;
R$^1$ has formula (II):

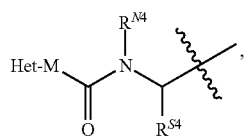

wherein Het is heterocyclyl that includes from 5-6 ring atoms, wherein at least one ring atom is a nitrogen atom selected from —N(H)—, —N(M)-, or —N(C$_1$-C$_3$ alkyl)- (e.g., morpholino), and M is C$_1$-C$_{12}$ alkyl (e.g., CH$_2$);
R$^{S1}$ and R$^{S3}$ are each independently C$_{1-6}$alkyl, and R$^{S2}$ and R$^{S4}$ are each independently C$_{7-12}$aralkyl (e.g., R$^{S1}$ and R$^{S3}$ are both isobutyl, R$^{S4}$ is phenylethyl, and R$^{S2}$ is phenylmethyl).
R$^{N1}$, R$^{N2}$, R$^{N3}$, and R$^{N4}$ are each H;
R$^4$ and R$^5$, together with the carbon atom to which both are attached, form a carbonyl group; and
R$^3$ is hydroxyl.
In some embodiments, m is 2, 4, or 8;
In some embodiments, R$^{20}$ is present; e.g., R$^{20}$ is

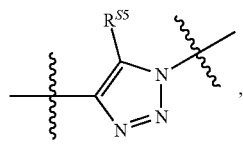

e.g., R$^{S5}$ is H.
In some embodiments, R$^{20}$ is absent.
In some embodiments, the PEG can have PEG architecture 2B or 2C.
In some embodiments, PEG has a molecular weight of greater than 1 kDa.
In some embodiments, PEG has a molecular weight of about 1 kDa.
In some embodiments, PEG has a molecular weight of greater than 2 kDa.
In some embodiments, PEG has a molecular weight of about 2 kDa.
In some embodiments, PEG has a molecular weight of greater than 5 kDa.
In some embodiments, PEG has a molecular weight of about 5 kDa.
In some embodiments, PEG has a molecular weight of greater than 10 kDa.
In some embodiments, PEG has a molecular weight of about 10 kDa.
In some embodiments, PEG has a molecular weight of greater than 20 kDa.
In some embodiments, PEG has a molecular weight of about 20 kDa.
In some embodiments, PEG has a molecular weight of greater than 30 kDa.
In some embodiments, PEG has a molecular weight of about 30 kDa.
In some embodiments, PEG has a molecular weight of greater than 40 kDa.
In some embodiments, PEG has a molecular weight of about 40 kDa.
In some embodiments, PEG has a molecular weight of greater than 50 kDa.
In some embodiments, prior to conjugation to epoxy ketone protease inhibitors, PEG has a plurality of reactive functional groups (e.g., azide groups).
In some embodiments, prior to conjugation to epoxy ketone protease inhibitors, PEG has 1, 2, 3, 4, 5, 6, 7, 8, 9, or 10 reactive functional groups (e.g., azide groups).
In some embodiments (e.g., when R$^{20}$ is present, e.g., as defined above), R$^{19}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, heteroalkylene chain, phenylene, indolylene, indolinylene, thiophenylene, or furanylene (e.g., phenylene), wherein phenylene, indolylene, indolinylene, thiophenylene, and furanylene are optionally substituted with 1, 2, or 3 (e.g., 2) substituents each independently selected from the group consisting of halo, C$_{1-6}$ alkoxy, heteroalkyl, CF$_3$, and C$_{1-6}$ alkyl (e.g., C$_{1-6}$ alkoxy, e.g., methoxy or C$_{1-6}$ alkyl, e.g., methyl). In certain embodiments, R$^{19}$ is.

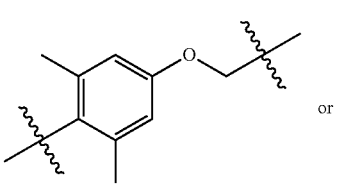

or

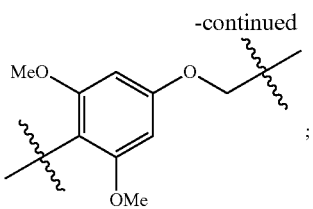

in embodiments, $R^{20}$ is present, e.g., as defined above.

In some embodiments (e.g., when $R^{20}$ is absent), $R^{19}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, —NHC(=O)—, —C(=O)NH—, heteroalkylene chain, phenylene, indolylene, indolinylene, thiophenylene, or furanylene, wherein phenylene, indolylene, indolinylene, thiophenylene, and furanylene are optionally substituted with 1, 2, or 3 substituents each independently selected from the group consisting of halo, $C_{1-6}$ alkoxy, heteroalkyl, $CF_3$, and $C_{1-6}$ alkyl. In certain embodiments, when either of —NHC(=O)— or —C(=O)NH— is present, —NHC(=O)— or —C(=O)NH— is linked to PEG.

[C] In some embodiments, the compound has formula (IV); and $R^1$ has formula (II):

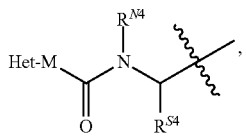

(II)

wherein Het is heterocyclyl that includes from 5-6 ring atoms, wherein at least one ring atom is a nitrogen atom selected from —N(H)—, —N(M)-, or —N($C_1$-$C_3$ alkyl)- (e.g., morpholino), and M is $C_1$-$C_{12}$ alkyl (e.g., $CH_2$);

$R^{S1}$ and $R^{S3}$ are each independently $C_{1-6}$alkyl, and $R^{S2}$ and $R^{S4}$ are each independently $C_{7-12}$aralkyl (e.g., $R^{S1}$ and $R^{S3}$ are both isobutyl, $R^{S4}$ is phenylethyl, and $R^{S2}$ is phenylmethyl).

$R^{N1}$, $R^{N2}$, $R^{N3}$, and $R^{N4}$ are each H;

$R^4$ and $R^5$, together with the carbon atom to which both are attached, form a carbonyl group;

$R^2$ is hydroxyl, or $R^{12}$ is present and is selected from: (i) —OSO$_2$—$R^{16}$ (e.g., $R^{16}$ is $C_{1-6}$alkyl (e.g., $CH_3$) or $C_{6-10}$aryl (e.g., phenyl); and (ii) halo (e.g., iodo).

In some embodiments, m is 2, 4, or 8.

In some embodiments, $R^{20}$ is present; e.g., $R^{20}$ is

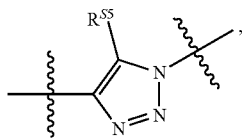

e.g., $R^{S5}$ is H.

In some embodiments, $R^{20}$ is absent.

In some embodiments, the PEG can have PEG architecture 2B or 2C.

In some embodiments, the PEG can have PEG architecture 2D.

In some embodiments, the PEG can have PEG architecture 2E or 2F.

In some embodiments, the PEG can have PEG architecture 2G or 2H.

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments, $R^{22}$ is divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): heteroatom (e.g., N, O, or S), alkylene chain, heteroalkylene chain, arylene including 6-10 ring atoms, heteroarylene including from 5-10 ring atoms (wherein from 1-3 of the ring atoms are independently selected from N, NH, N—$C_1$-$C_6$ alkyl, O, and S), heterocycloalkylene including 3-9 ring atoms (wherein from 1-3 of the ring atoms are independently selected from N, NH, N—$C_1$-$C_6$ alkyl, O, and S), —NHC(=O)—, —C(=O)NH—, —N($C_{1-6}$ alkyl)C(=O), —C(=O)N($C_{1-6}$ alkyl)-, —C(=O)—, or —NHC(=O)NH—, wherein 6-10 membered arylene, 5-10 membered heteroarylene, and 6-10 membered cycloalkylene are each optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{22}$ is one selected from the group consisting of:

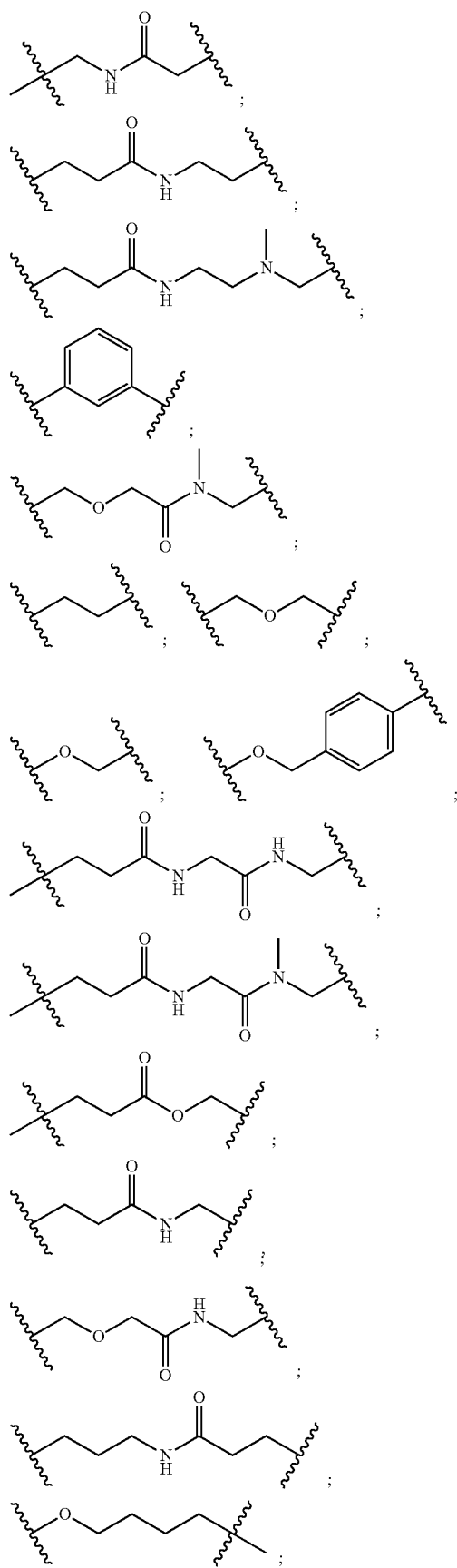

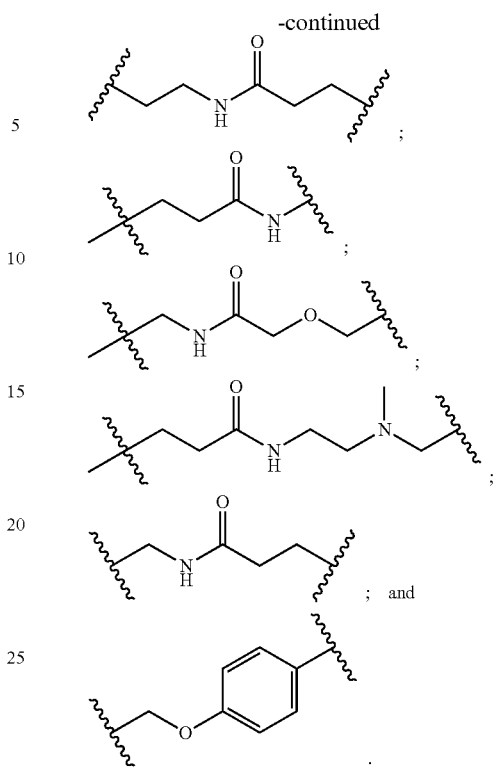

[D] In some embodiments, the compound has formula (1H); and
$R^1$ has formula (II):

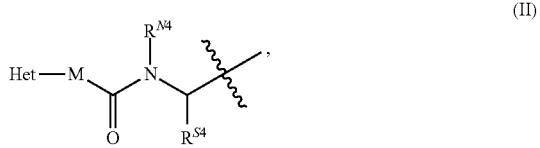

wherein Het is heterocyclyl that includes from 5-6 ring atoms, wherein at least one ring atom is a nitrogen atom selected from —N(H)—, —N(M)-, or —N($C_1$-$C_3$ alkyl)- (e.g., morpholino), and M is $C_1$-$C_{12}$ alkyl (e.g., $CH_2$);
$R^{S1}$ and $R^{S3}$ are each independently $C_{1-6}$alkyl, and $R^{S2}$ and $R^{S4}$ are each independently $C_{7-12}$aralkyl (e.g., $R^{S1}$ and $R^{S3}$ are both isobutyl, $R^{S4}$ is phenylethyl, and $R^{S2}$ is phenylmethyl).

One of $R^{N1}$, $R^{N2}$, $R^{N3}$, and $R^{N4}$ is $R^{14}$, and the others are each H;
$R^4$ and $R^5$, together with the carbon atom to which both are attached, form a carbonyl group; and
$R^2$ and $R^3$, together with the carbon atoms to which each is attached, form an epoxide ring.
In some embodiments, m is 2, 4, or 8;
In some embodiments, $R^{20}$ is present; e.g., $R^{20}$ is

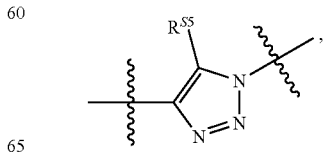

e.g., $R^{S5}$ is H.

In some embodiments, $R^{20}$ is absent.

In some embodiments, the PEG can have PEG architecture 2B or 2C.

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments, $R^{14}$ is —$R^{14'}$—$R^{20}$—, in which $R^{20}$ is connected to PEG, and $R^{14'}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, —C(=O)—, —NHC(=O)—, —C(=O)NH—, heteroalkylene chain, phenylene, indolylene, indolinylene, thiophenylene, or furanylene, wherein phenylene, indolylene, indolinylene, thiophenylene, and furanylene are optionally substituted with 1, 2, or 3 substituents each independently selected from the group consisting of halo, $C_{1-6}$ alkoxy, heteroalkyl, $CF_3$, and $C_{1-6}$ alkyl. In certain embodiments, when alkylene chain is present, the alkylene chain is linked to the backbone nitrogen.

In certain embodiments, $R^{14'}$ is -alkylene chain (e.g., $CH_2$—O—C(O)-phenylene-. In embodiments, the alkylene chain is linked to the backbone nitrogen.

In some embodiments, one $R^{N1}$ and $R^{N4}$ is $R^{14}$ (e.g., $R^{N1}$) and the other is hydrogen, and $R^{N2}$ and $R^{N3}$ are each hydrogen.

In some embodiments, one $R^{N2}$ and $R^{N3}$ is $R^{14}$, and the other is hydrogen, and $R^{N1}$ and $R^{N4}$ are each hydrogen.

[E] In some embodiments, the compound has formula (VIII); and

Het is heterocyclyl that includes from 5-6 ring atoms, wherein at least one ring atom is a nitrogen atom selected from —N(H)—, —N(M)-, or —N($C_1$-$C_3$ alkyl)- (e.g., morpholino), and M is $C_1$-$C_{12}$ alkyl (e.g., $CH_2$);

the $R^{20}$/$R^{21}$-containing substituent in formula VIII is attached to the Het ring nitrogen atom, thereby forming a quaternary nitrogen atom and wherein the positive charge associated with the quaternary nitrogen atom is balanced by a pharmaceutically acceptable anion;

Ar is phenyl, optionally substituted with from 1-3 substituents independently selected from $C_{1-6}$alkyl, $C_{1-6}$alkoxy, and halo;

$R^{S1}$ and $R^{S3}$ are each independently $C_{1-6}$alkyl, and $R^{S2}$ and $R^{S4}$ are each independently $C_{7-12}$aralkyl (e.g., $R^{S1}$ and $R^{S3}$ are both isobutyl, $R^{S4}$ is phenylethyl, and $R^{S2}$ is phenylmethyl).

$R^{N1}$, $R^{N2}$, $R^{N3}$, and $R^{N4}$ are each H;

$R^4$ and $R^5$, together with the carbon atom to which both are attached, form a carbonyl group; and $R^2$ and $R^3$, together with the carbon atoms to which each is attached, form an epoxide ring.

In some embodiments, m is 2, 4, or 8;

In some embodiments, $R^{20}$ is present; e.g., $R^{20}$ is

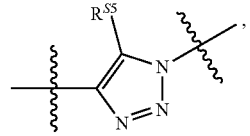

e.g., $R^{S5}$ is H.

In some embodiments, $R^{20}$ is absent.

In some embodiments, the pharmaceutically acceptable anion is selected from chloride, iodide, acetate, mesylate, tosylate, and citrate.

In some embodiments, the PEG can have PEG architecture 2B or 2C.

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments, $R^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, —C(=O)—, or phenylene, wherein phenylene is optionally substituted with 1, 2, or 3 substituents each independently selected from the group consisting of halo, $C_{1-6}$ alkoxy, heteroalkyl, $CF_3$, and $C_{1-6}$ alkyl.

In some embodiments, $R^{21}$ is a divalent spacer comprising one or more of the following moieties (e.g., comprise 1, 2, 3, 4, or 5 of the following moieties; e.g., comprise 1, 2, or 3 of the following moieties; e.g., consist of 1, 2, 3, 4, or 5 of the following moieties; e.g., consist of 1, 2, or 3 of the following moieties): heteroatom (e.g., N, O, or S), alkylene chain, heteroalkylene chain, or —C(=O)—.

In certain embodiments, $R^{21}$ is —O—C(O)-alkylene chain (e.g., $C_2$).

[F] In some embodiments, the compound has formula (1I); and
$R^1$ has formula (II):

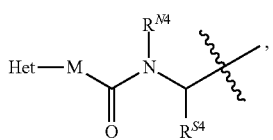

(II)

wherein Het is heterocyclyl that includes from 5-6 ring atoms, wherein at least one ring atom is a nitrogen atom selected from —N(H)—, —N(M)-, or —N($C_1$-$C_3$ alkyl)- (e.g., morpholino), and M is $C_1$-$C_{12}$ alkyl (e.g., $CH_2$);

$R^{S1}$ and $R^{S3}$ are each independently $C_{1-6}$alkyl, and $R^{S2}$ and $R^{S4}$ are each independently $C_{7-12}$aralkyl (e.g., $R^{S1}$ and $R^{S3}$ are both isobutyl, $R^{S4}$ is phenylethyl, and $R^{S2}$ is phenylmethyl).

$R^{N1}$, $R^{N2}$, $R^{N3}$, and $R^{N4}$ are each H; and $R^2$ and $R^3$, together with the carbon atoms to which each is attached, form an epoxide ring.

In some embodiments, m is 2, 4, or 8;

In some embodiments, $R^{20}$ is present; e.g., $R^{20}$ is

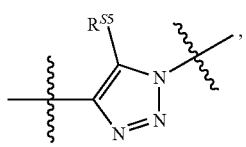

e.g., $R^{S5}$ is H.

In some embodiments, $R^{20}$ is absent.

In some embodiments, the PEG can have PEG architecture 2B or 2C.

In some embodiments, PEG has a molecular weight of greater than 1 kDa.

In some embodiments, PEG has a molecular weight of about 1 kDa.

In some embodiments, PEG has a molecular weight of greater than 2 kDa.

In some embodiments, PEG has a molecular weight of about 2 kDa.

In some embodiments, PEG has a molecular weight of greater than 5 kDa.

In some embodiments, PEG has a molecular weight of about 5 kDa.

In some embodiments, PEG has a molecular weight of greater than 10 kDa.

In some embodiments, PEG has a molecular weight of about 10 kDa.

In some embodiments, PEG has a molecular weight of greater than 20 kDa.

In some embodiments, PEG has a molecular weight of about 20 kDa.

In some embodiments, PEG has a molecular weight of greater than 30 kDa.

In some embodiments, PEG has a molecular weight of about 30 kDa.

In some embodiments, PEG has a molecular weight of greater than 40 kDa.

In some embodiments, PEG has a molecular weight of about 40 kDa.

In some embodiments, PEG has a molecular weight of greater than 50 kDa.

In some embodiments, prior to conjugation to epoxy ketone protease inhibitors, PEG has a plurality of reactive functional groups (e.g., azide groups).

In some embodiments, prior to conjugation to epoxy ketone protease inhibitors, PEG has 1, 2, 3, 4, 5, 6, 7, 8, 9, or 10 reactive functional groups (e.g., azide groups).

In some embodiments, $R^{17}$ is —$R^{17'}$—$R^{20}$—, in which $R^{20}$ is connected to PEG, and $R^{17'}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties; e.g., consisting of 1, 2, or 3 of the following moieties): alkylene chain, heteroalkylene chain, —NHC(=O)—, —C(=O)NH—, —N($C_{1-6}$ alkyl)C(=O), —C(=O)N($C_{1-6}$ alkyl)-, —C(=O)—, or —NHC(=O)NH—.

In some embodiments, $R^{17'}$ is a divalent spacer comprising one or more of the following moieties (e.g., comprising 1, 2, 3, 4, or 5 of the following moieties; e.g., comprising 1, 2, or 3 of the following moieties; e.g., consisting of 1, 2, 3, 4, or 5 of the following moieties: e.g., consisting of 1, 2, or 3 of the following moieties): alkylene chain, heteroalkylene chain, or —C(=O)— (e.g., alkylene chain or —C(=O)—).

In certain embodiments (e.g., when A is NH), the —C(=O)— is attached to A.

In certain embodiments, $R^{17'}$ is —C(=O)-alkylene chain.

In certain embodiments, A is NH, $R^{17'}$ is —C(=O)-alkylene chain, and the —C(=O)— is attached to A.

In some embodiments, the compound is selected from the compounds disclosed in Tables A and B.

TABLE A

| Compound number | Structure |
| --- | --- |
| 1 | (structure) |
| 2 | (structure) |
| 3 | (structure) |
| 4 | (structure) |
| 5 | (structure) |

TABLE A-continued

| Compound number | Structure |
|---|---|
| 6 | 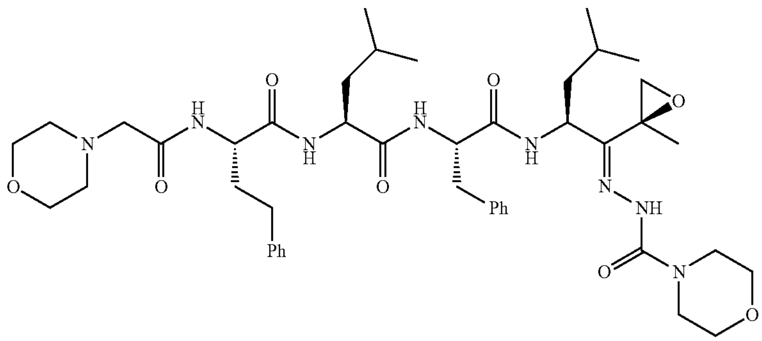 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)/C(=N/NC(=O)N1CCOCC1)[C@@]1(C)CO1] |
| 7 | 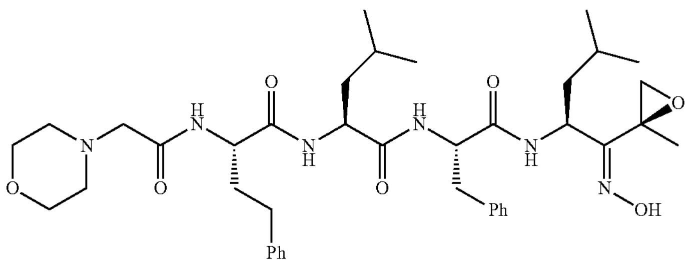 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)/C(=N/O)[C@@]1(C)CO1] |
| 8 | 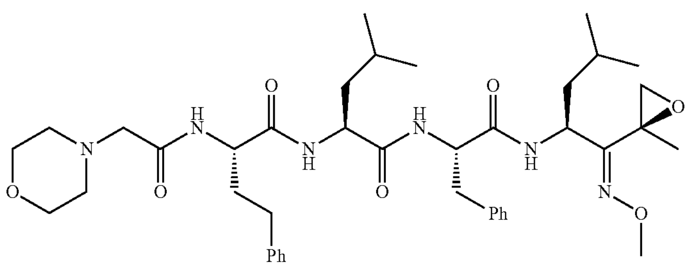 [SMILES: CO/N=C(/[C@H](CC(C)C)NC(=O)[C@H](Cc1ccccc1)NC(=O)[C@H](CC(C)C)NC(=O)[C@H](CCc1ccccc1)NC(=O)CN1CCOCC1)[C@@]1(C)CO1] |
| 9 | 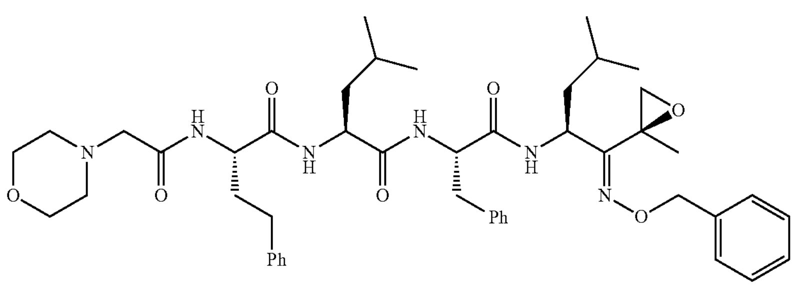 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)/C(=N/OCc1ccccc1)[C@@]1(C)CO1] |
| 10 | 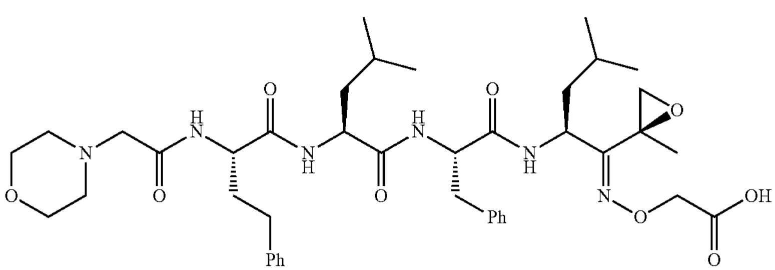 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)/C(=N/OCC(=O)O)[C@@]1(C)CO1] |

TABLE A-continued
| Compound number | Structure |
|---|---|
| 11 | 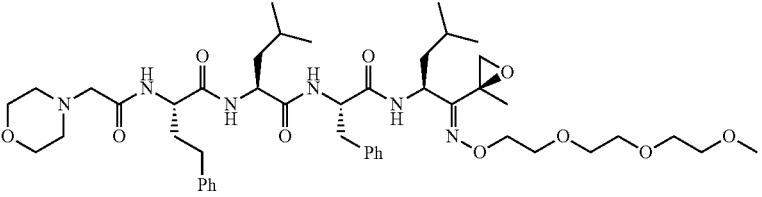 [SMILES: COCCOCCOCCO/N=C(/[C@H](CC(C)C)NC(=O)[C@H](Cc1ccccc1)NC(=O)[C@H](CC(C)C)NC(=O)[C@H](CCc1ccccc1)NC(=O)CN1CCOCC1)[C@@]1(C)CO1] |
| 12 | 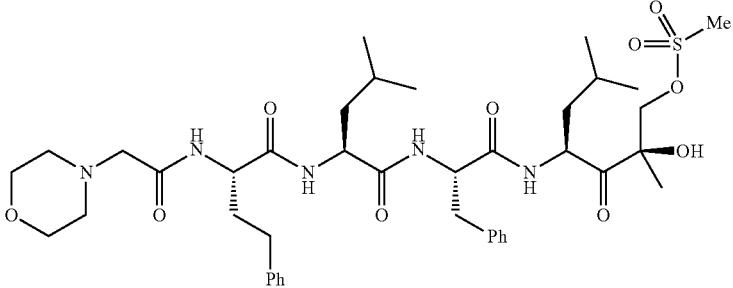 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COS(C)(=O)=O] |
| 13 | 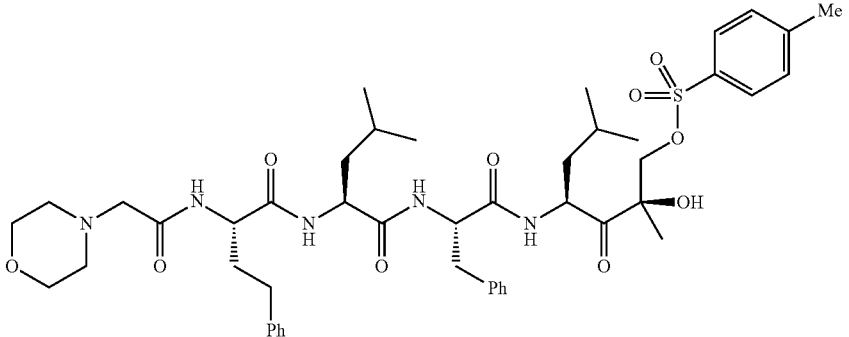 [SMILES: Cc1ccc(S(=O)(=O)OC[C@@](C)(O)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)cc1] |
| 14 | 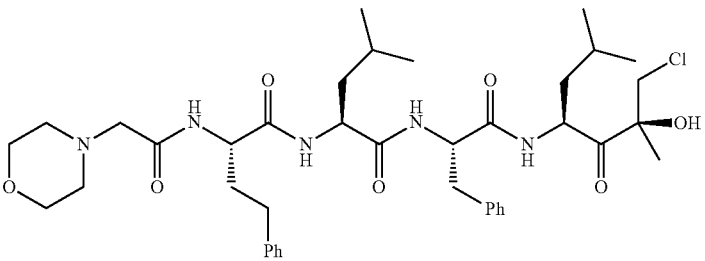 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)CCl] |
| 15 | 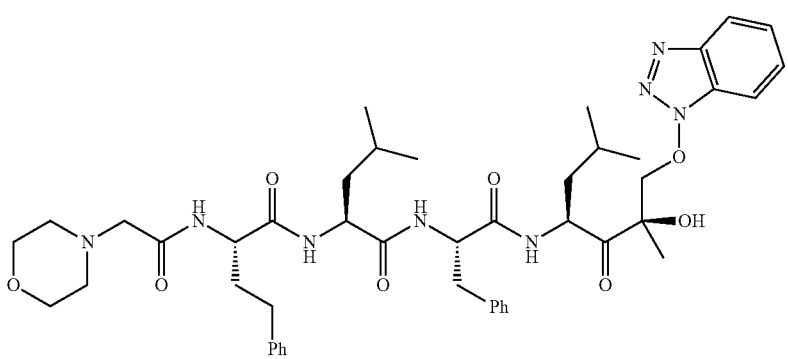 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COn1nnc2ccccc21] |

TABLE A-continued
| Compound number | Structure |
|---|---|
| 16 | 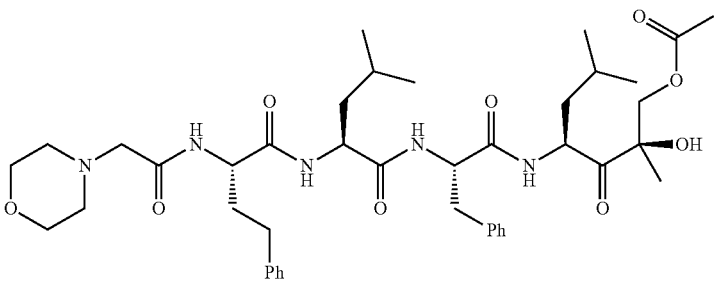 [SMILES: CC(=O)OC[C@@](C)(O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1] |
| 17 | 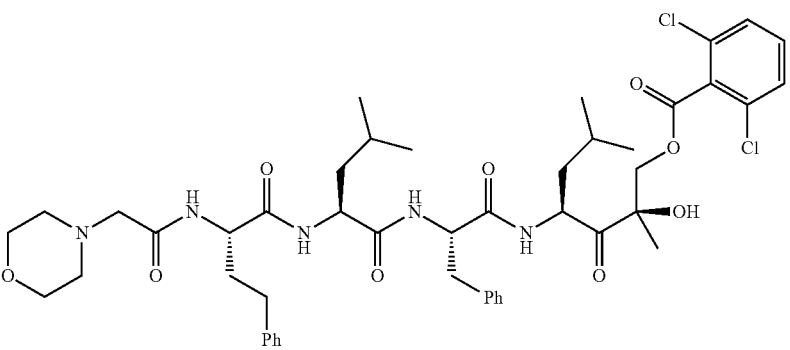 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COC(=O)c1c(Cl)cccc1Cl] |
| 18 | 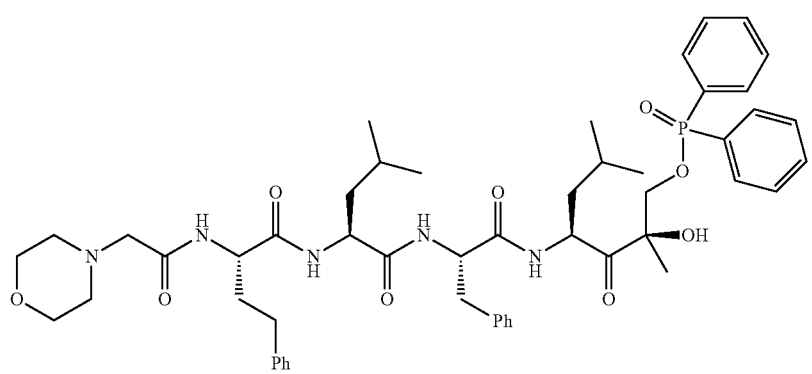 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COP(=O)(c1ccccc1)c1ccccc1] |
TABLE B
| Compound name | Structure |
|---|---|
| 19 | 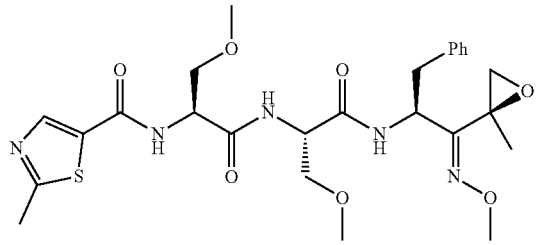 [SMILES: COC[C@H](NC(=O)c1cnc(C)s1)C(=O)N[C@@H](COC)C(=O)N[C@@H](Cc1ccccc1)/C(=N/OC)[C@@]1(C)CO1] |

TABLE B-continued
| Compound name | Structure |
|---|---|
| 20-1 | 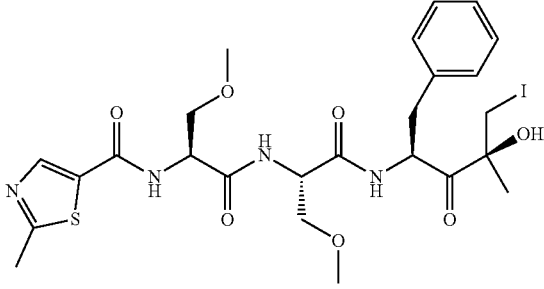 [SMILES: COC[C@H](NC(=O)c1cnc(C)s1)C(=O)N[C@@H](COC)C(=O)N[C@@H](Cc1ccccc1)C(=O)[C@](C)(O)CI] |
| 20-2 | 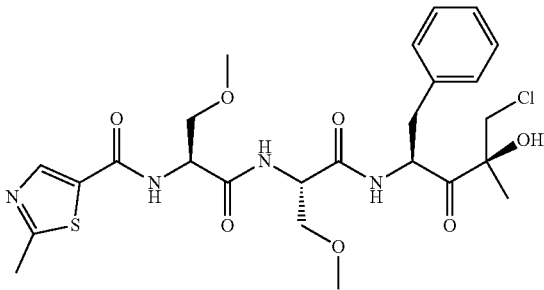 |
| 20-3 | 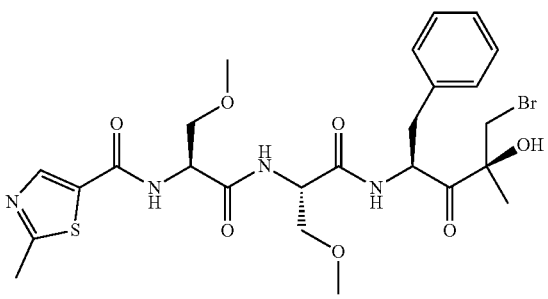 |
| 20-4 | 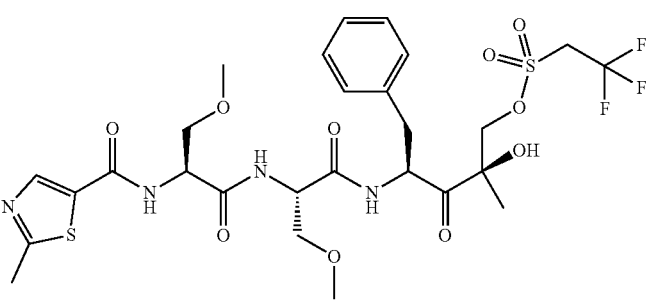 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)CC(F)(F)F] |
| 20-5 | 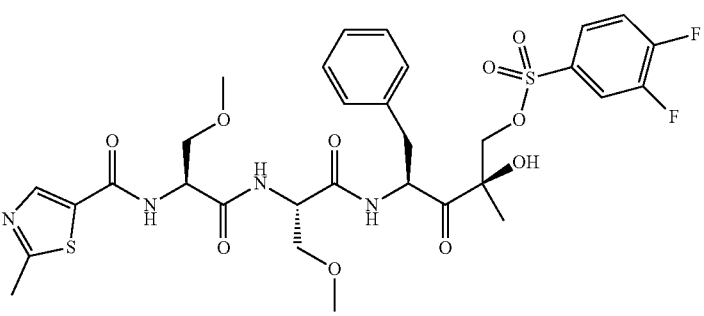 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(F)c(F)c1] |

TABLE B-continued
| Compound name | Structure |
|---|---|
| 20-6 | 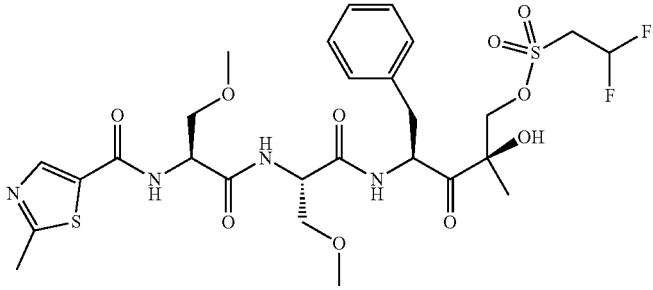 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)CC(F)F] |
| 20-7 | 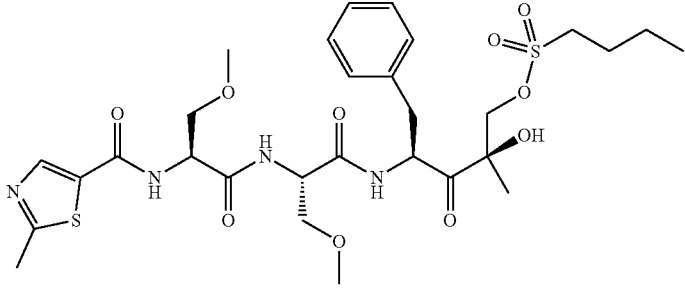 [SMILES: CCCCS(=O)(=O)OC[C@@](C)(O)C(=O)[C@H](Cc1ccccc1)NC(=O)[C@H](COC)NC(=O)[C@H](COC)NC(=O)c1cnc(C)s1] |
| 20-8 | 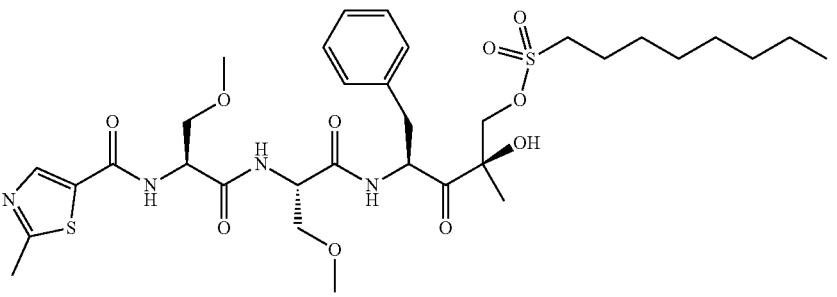 [SMILES: CCCCCCCCS(=O)(=O)OC[C@@](C)(O)C(=O)[C@H](Cc1ccccc1)NC(=O)[C@H](COC)NC(=O)[C@H](COC)NC(=O)c1cnc(C)s1] |
| 20-9 | 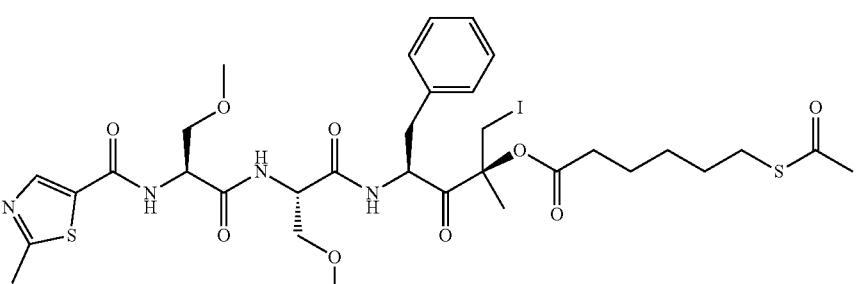 |
| 20-10 | 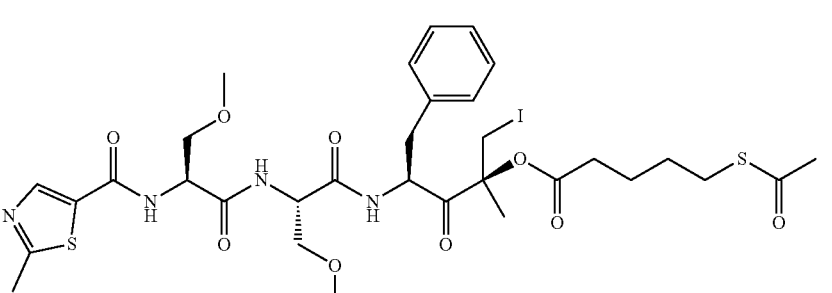 |

TABLE B-continued

| Compound name | Structure |
|---|---|
| 20-11 | 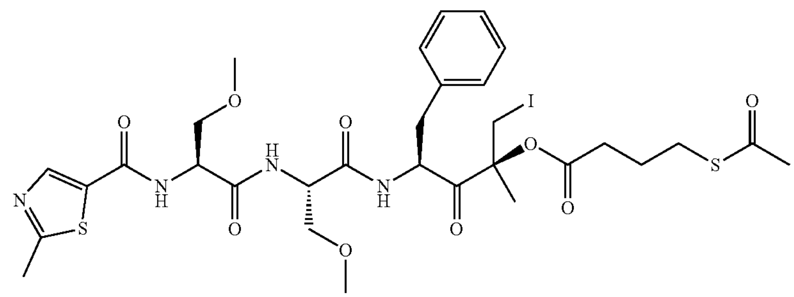 |
| 20-12 | 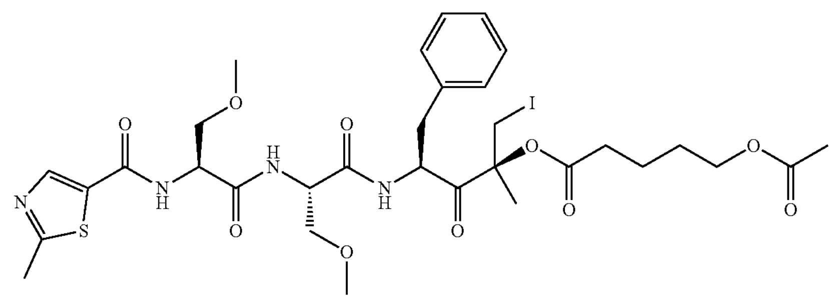 |
| 20-13 | 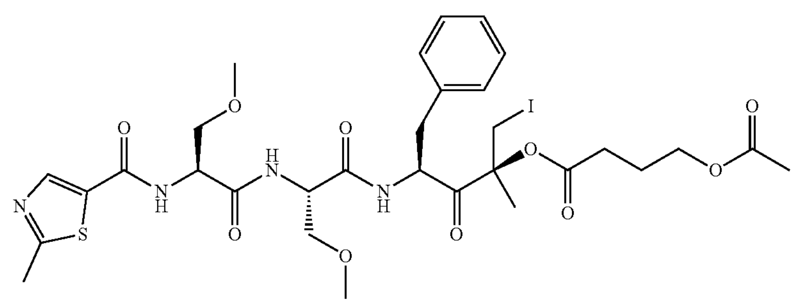 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCCSC(C)=O] |
| 20-14 | 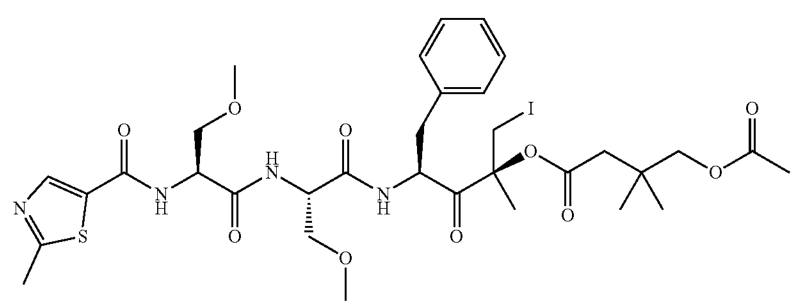 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CC(C)(C)COC(C)=O] |
| 20-15 | 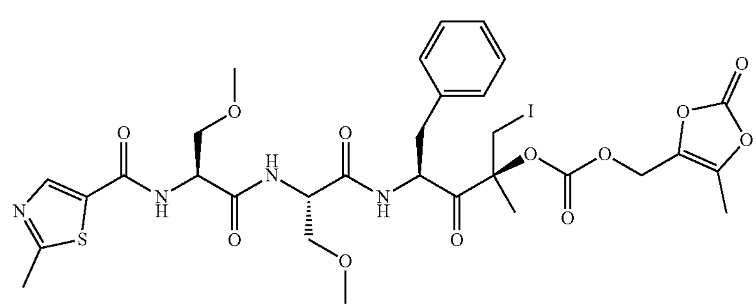 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)OCc1oc(=O)oc1C] |

TABLE B-continued

| Compound name | Structure |
|---|---|
| 20-16 | 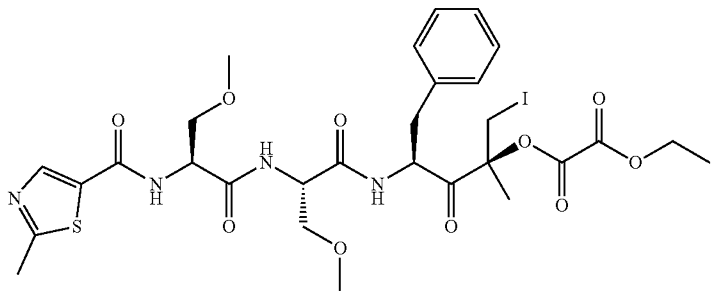 [SMILES: CCOC(=O)C(=O)O[C@](C)(CI)C(=O)[C@H](Cc1ccccc1)NC(=O)[C@H](COC)NC(=O)[C@H](COC)NC(=O)c1cnc(C)s1] |
| 20-17 | 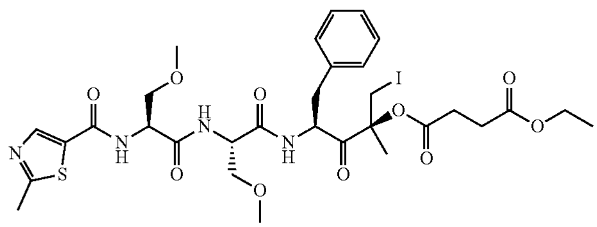 [SMILES: CCOC(=O)CCC(=O)O[C@](C)(CI)C(=O)[C@H](Cc1ccccc1)NC(=O)[C@H](COC)NC(=O)[C@H](COC)NC(=O)c1cnc(C)s1] |
| 20-18 | 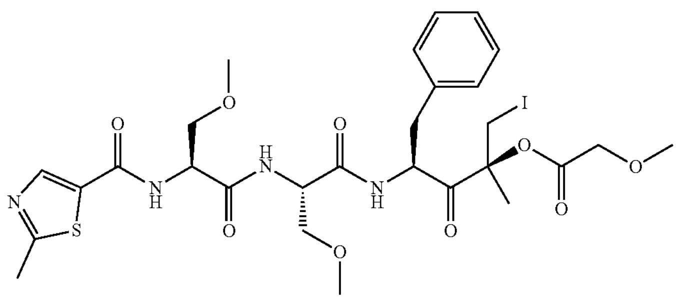 [SMILES: COCC(=O)O[C@](C)(CI)C(=O)[C@H](Cc1ccccc1)NC(=O)[C@H](COC)NC(=O)[C@H](COC)NC(=O)c1cnc(C)s1] |
| 20-19 | 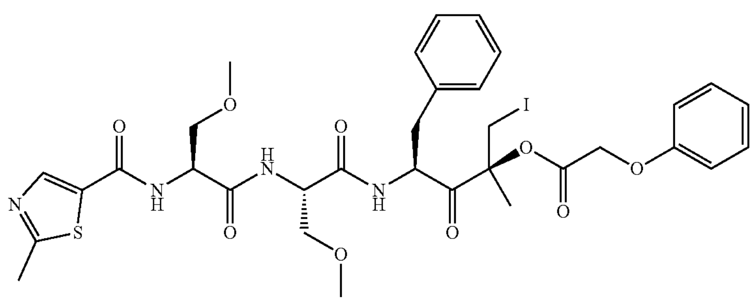 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)COc1ccccc1] |
| 20-20 | 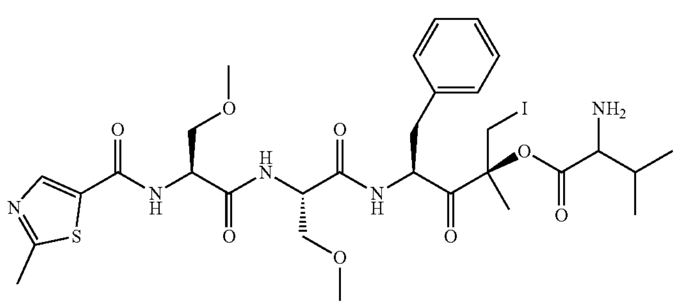 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)C(N)C(C)C] |

TABLE B-continued

| Compound name | Structure |
| --- | --- |
| 20-21 | 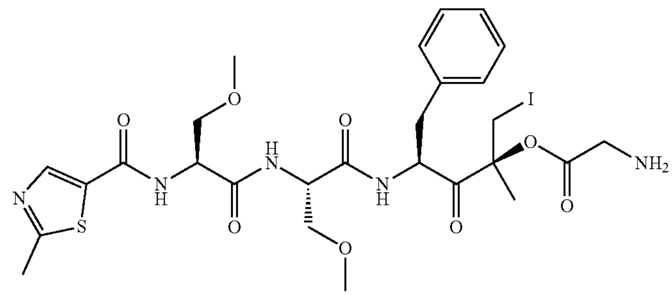 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CN] |
| 20-22 | 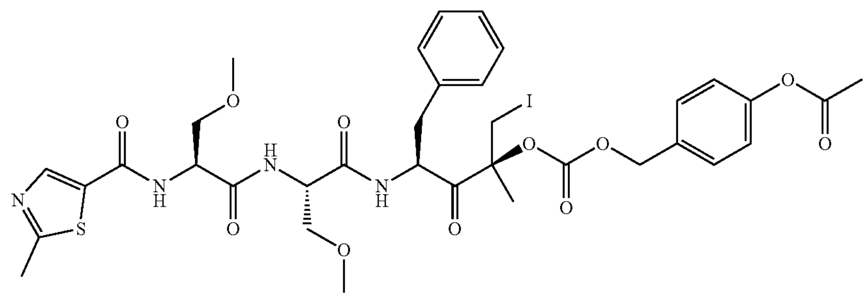 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)OCc1ccc(OC(C)=O)cc1] |
| 20-23 | 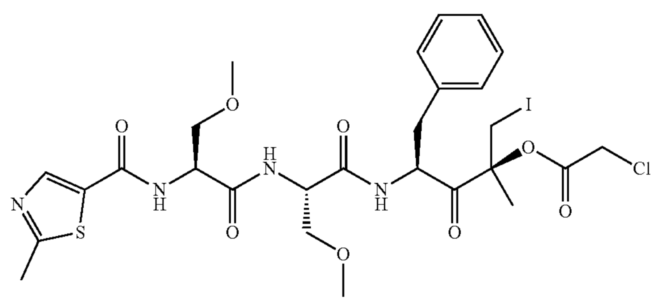 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCl] |
| 20-24 | 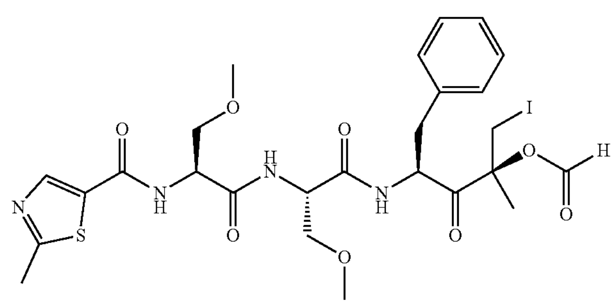 [SMILES: COC[C@H](NC(=O)c1cnc(C)s1)C(=O)N[C@@H](COC)C(=O)N[C@@H](Cc1ccccc1)C(=O)[C@@](C)(CI)OC=O] |
| 20-25 | 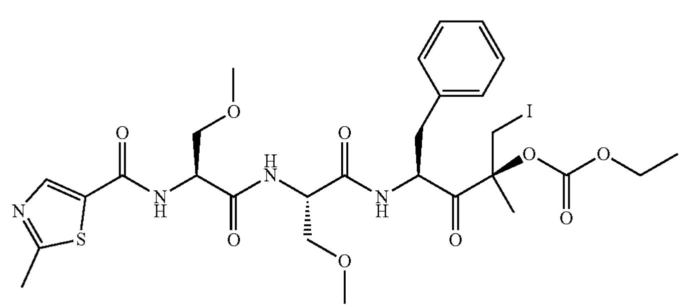 [SMILES: CCOC(=O)O[C@](C)(CI)C(=O)[C@H](Cc1ccccc1)NC(=O)[C@H](COC)NC(=O)[C@H](COC)NC(=O)c1cnc(C)s1] |

TABLE B-continued

| Compound name | Structure |
|---|---|
| 20-26 | 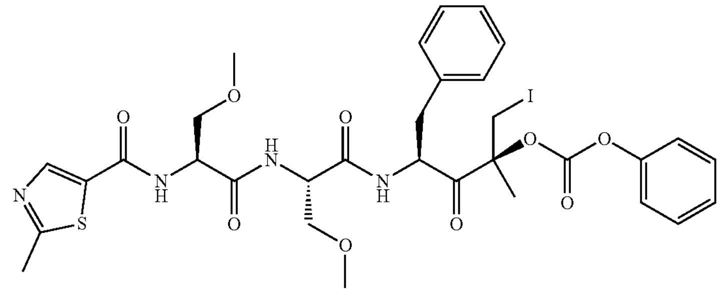 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)Oc1ccccc1] |
| 20-27 | 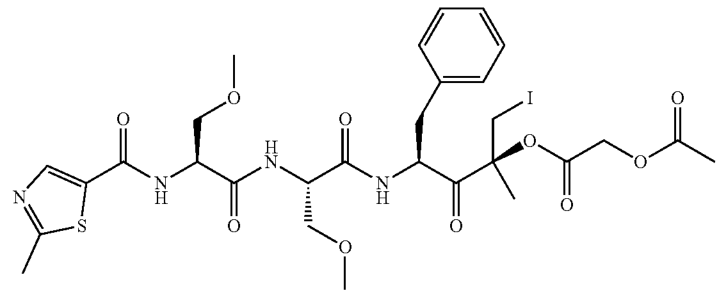 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)COC(C)=O] |
| 20-28 | 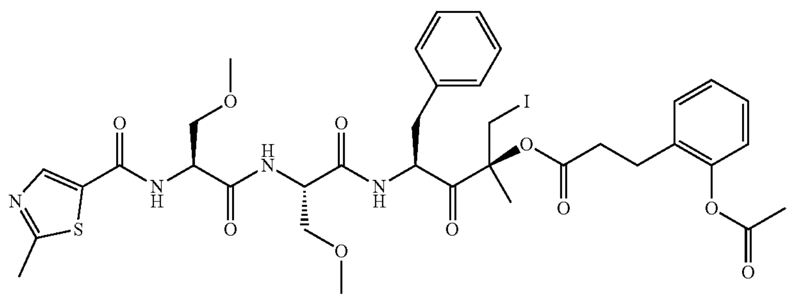 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCc1ccccc1OC(C)=O] |
| 20-29 | 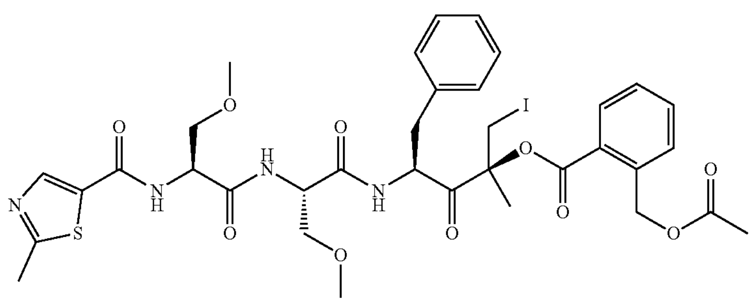 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)c1ccccc1COC(C)=O] |
| 20-30 | 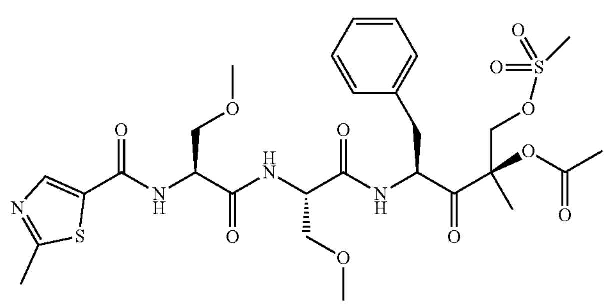 [SMILES: COC[C@H](NC(=O)c1cnc(C)s1)C(=O)N[C@@H](COC)C(=O)N[C@@H](Cc1ccccc1)C(=O)[C@@](C)(COS(C)(=O)=O)OC(C)=O] |

TABLE B-continued
| Compound name | Structure |
|---|---|
| 20-31 | 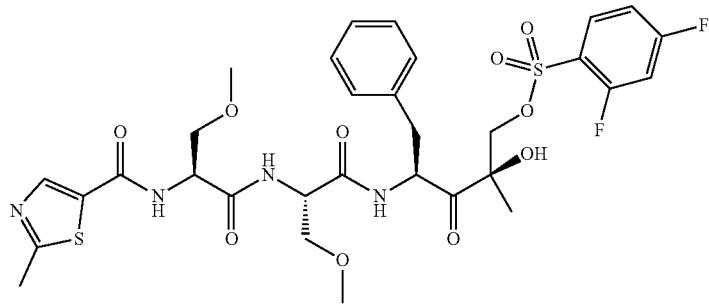 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(F)cc1F] |
| 20-32 | 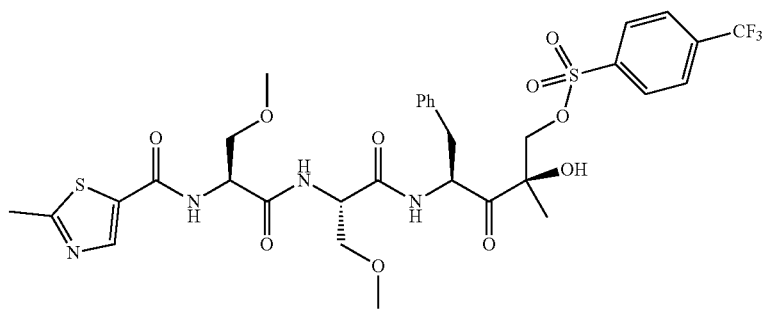 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(C(F)(F)F)cc1] |
| 20 | 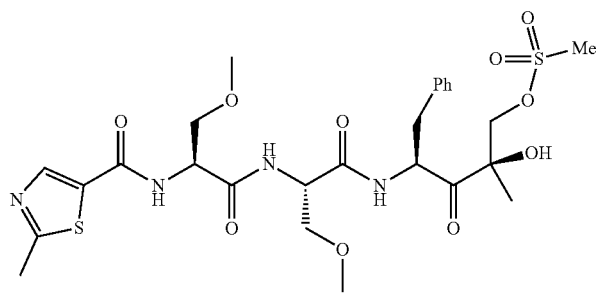 [SMILES: COC[C@H](NC(=O)c1cnc(C)s1)C(=O)N[C@@H](COC)C(=O)N[C@@H](Cc1ccccc1)C(=O)[C@](C)(O)COS(C)(=O)=O] |
| 21 | 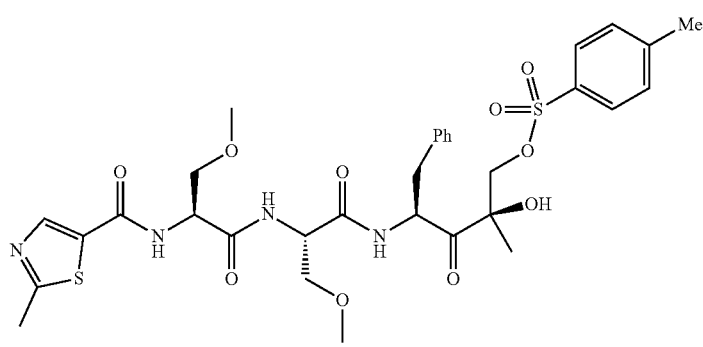 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(C)cc1] |
| 22 | 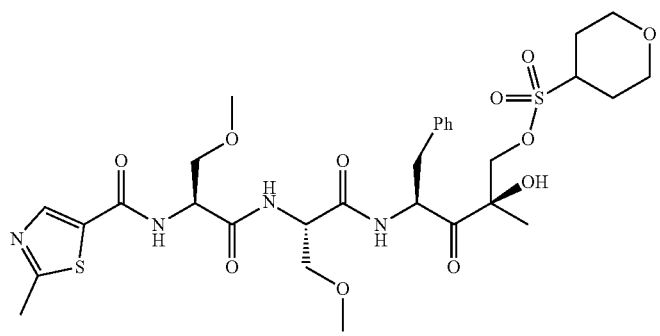 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)C1CCOCC1] |

TABLE B-continued
| Compound name | Structure |
|---|---|
| 23 | 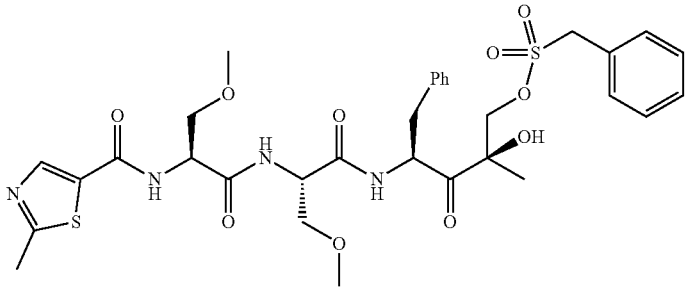 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)Cc1ccccc1] |
| 24 | 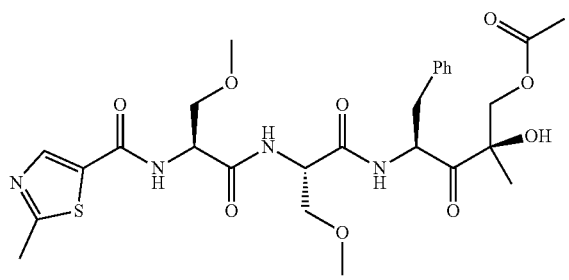 [SMILES: COC[C@H](NC(=O)c1cnc(C)s1)C(=O)N[C@@H](COC)C(=O)N[C@@H](Cc1ccccc1)C(=O)[C@](C)(O)COC(C)=O] |
| 25 | 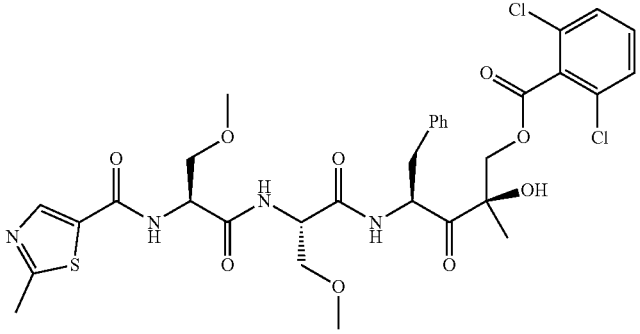 [SMILES: COC[C@H](NC(=O)c1cnc(C)s1)C(=O)N[C@@H](COC)C(=O)N[C@@H](Cc1ccccc1)C(=O)[C@](C)(O)COC(=O)c1c(Cl)cccc1Cl] |
| 26 | 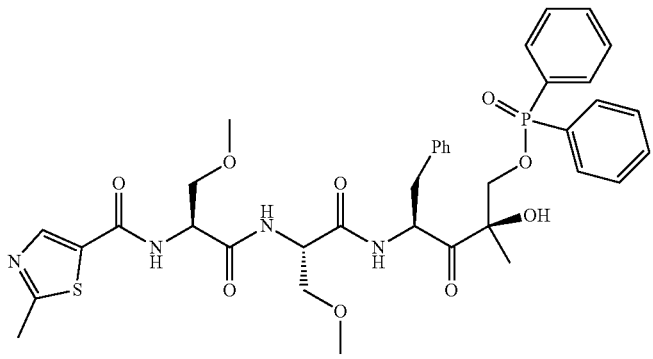 [SMILES: COC[C@H](NC(=O)c1cnc(C)s1)C(=O)N[C@@H](COC)C(=O)N[C@@H](Cc1ccccc1)C(=O)[C@](C)(O)COP(=O)(c1ccccc1)c1ccccc1] |

In some embodiments, the compound is selected from the compounds disclosed in Table C.

TABLE C

| Compound number | Structure |
|---|---|
| 27 | (structure with PEG$_{2K}$) |
| 28 | (structure with PEG$_{5K}$) |
| 29 | (structure with PEG$_{1K}$) |
| 30 | (structure with PEG$_{2K}$) |
| 31 | (structure with PEG$_{5K}$) |

TABLE C-continued
| Compound number | Structure |
|---|---|
| 32 | 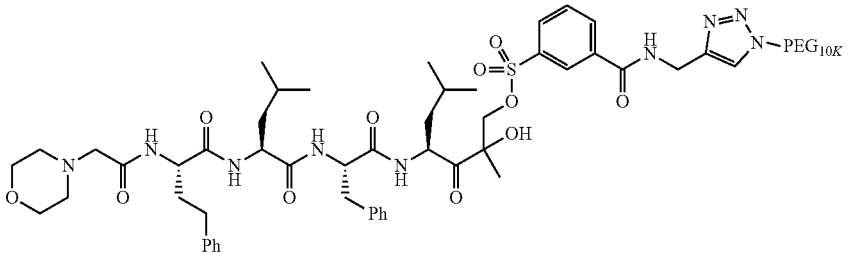 |
| 33 | 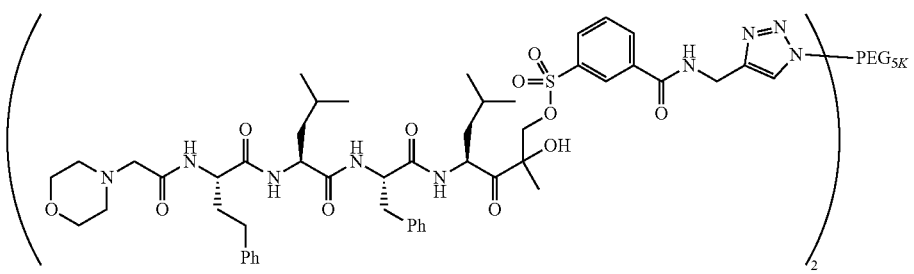 |
| 34 | 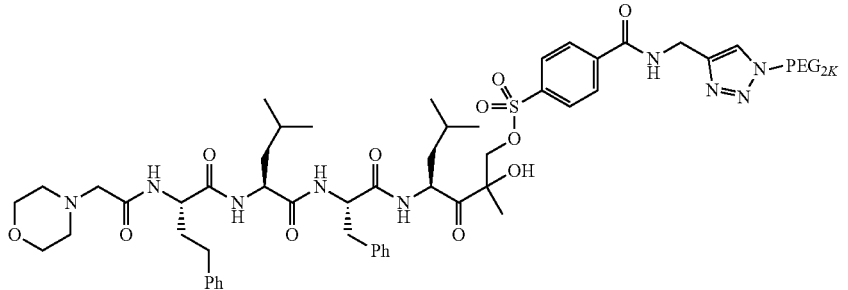 |
| 35 | 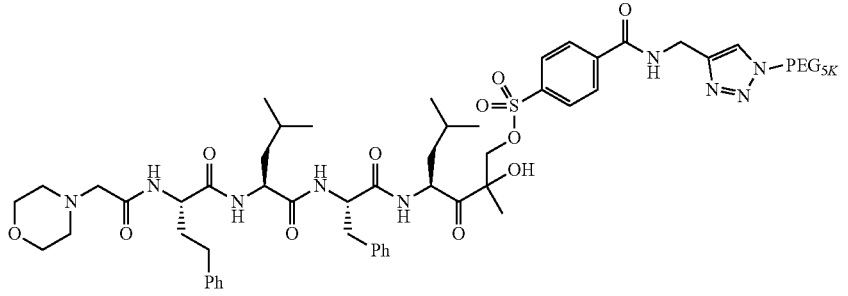 |
| 36 | 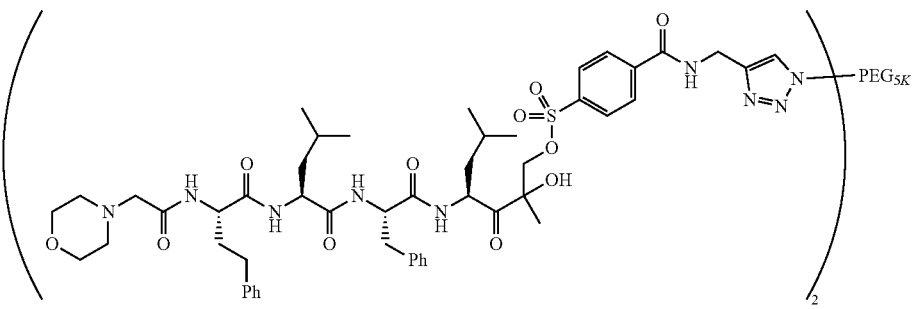 |

TABLE C-continued

| Compound number | Structure |
|---|---|
| 37 | (structure with morpholine-Gly-homoPhe-Leu-Phe-Leu-epoxyketone-like core bearing -O-SO₂-C₆H₄-C(O)NH-CH₂-triazole-PEG₁₀ₖ)₄ |
| 38 | morpholine-Gly-homoPhe-Leu-Phe-Leu core with -O-SO₂-(2-F-C₆H₃)-C(O)NH-CH₂-triazole-PEG₂ₖ |
| 39 | morpholine-Gly-homoPhe-Leu-Phe-Leu core with -O-SO₂-(2-F-C₆H₃)-C(O)NH-CH₂-triazole-PEG₅ₖ |
| 40 | (morpholine-Gly-homoPhe-Leu-Phe-Leu core with -O-SO₂-(2-F-C₆H₃)-C(O)NH-CH₂-triazole-PEG₅ₖ)₂ |
| 41 | (morpholine-Gly-homoPhe-Leu-Phe-Leu core with -O-SO₂-(2-F-C₆H₃)-C(O)NH-CH₂-triazole-PEG₂₀ₖ)₄ |

TABLE C-continued
| Compound number | Structure |
|---|---|
| 42 | 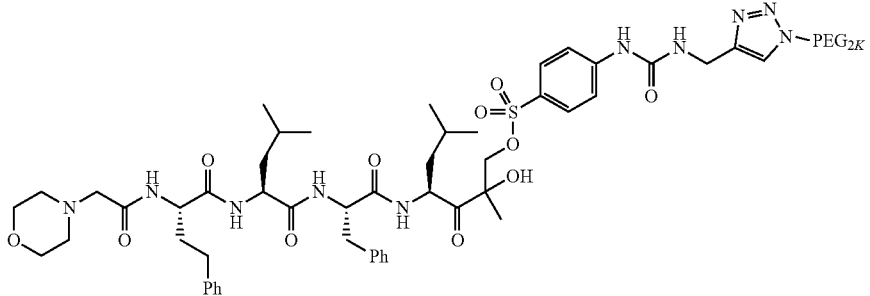 |
| 43 | 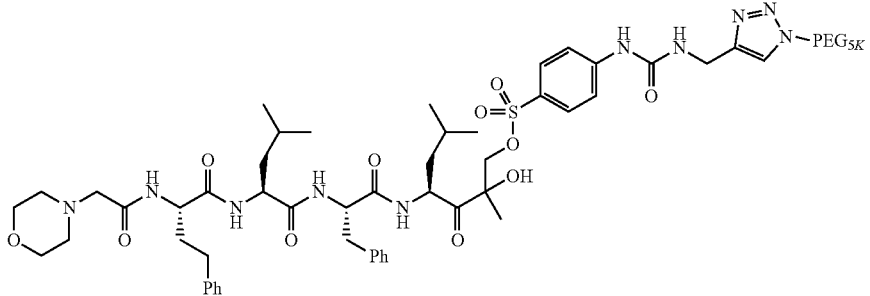 |
| 44 | 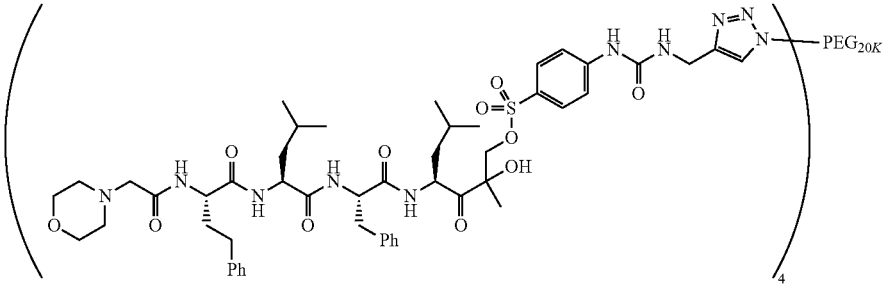 |
| 45 | 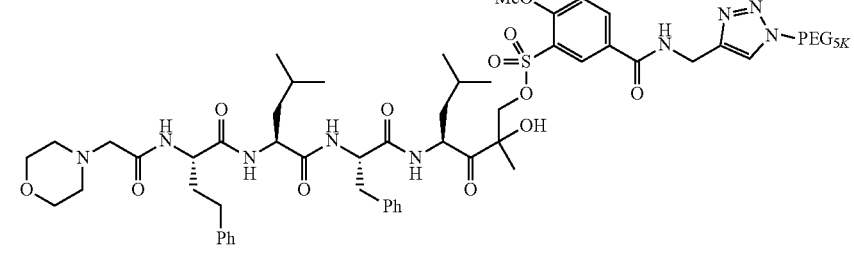 |
| 46 | 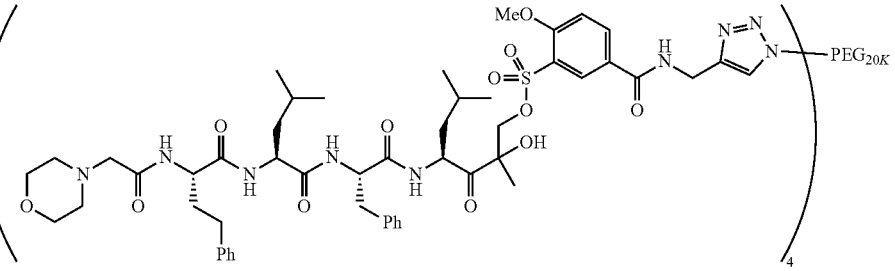 |

TABLE C-continued
| Compound number | Structure |
|---|---|
| 47 | 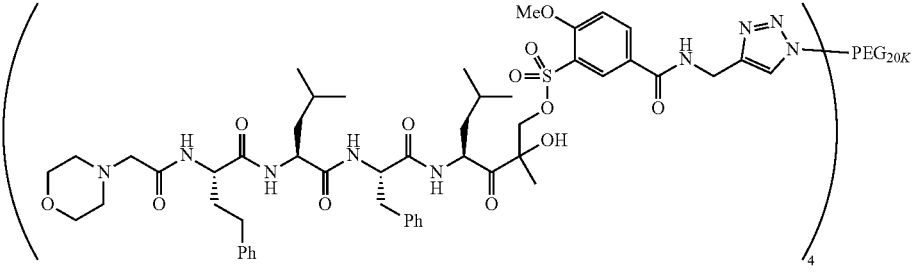 |
| 48 | 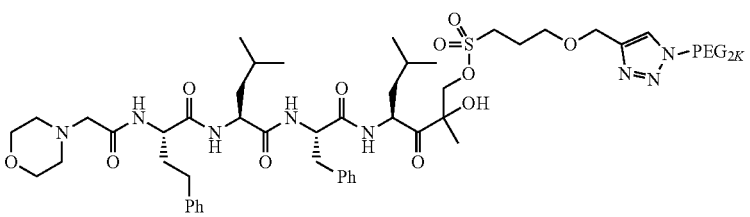 |
| 49 | 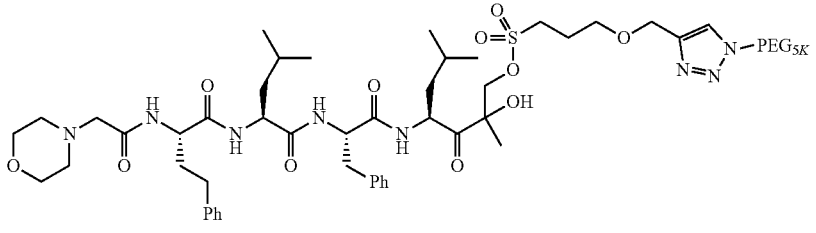 |
| 50 | 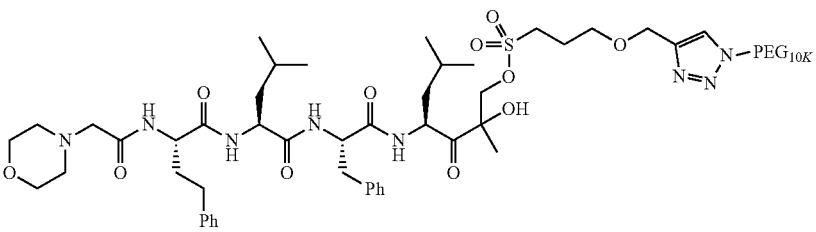 |
| 51 | 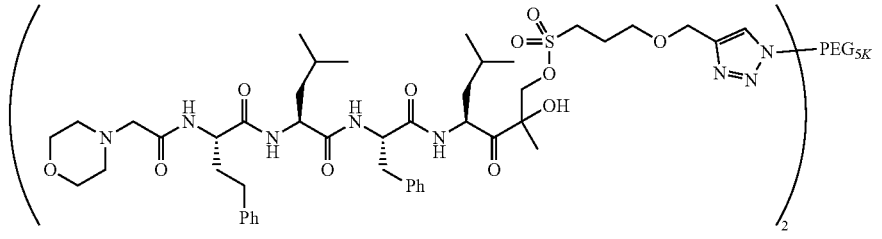 |
| 52 | 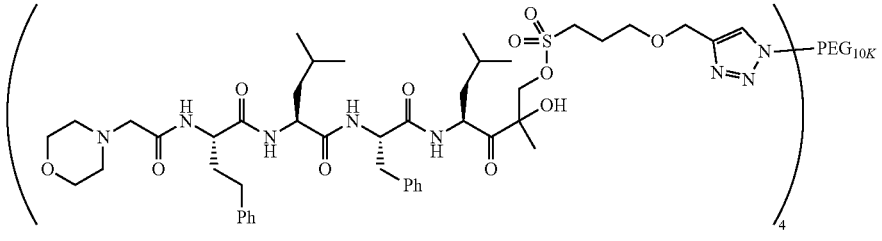 |

TABLE C-continued
| Compound number | Structure |
|---|---|
| 53 | 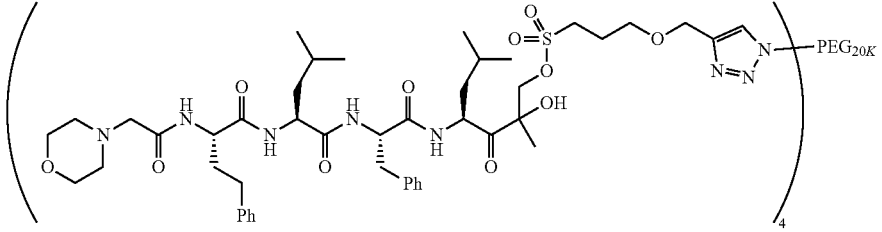 |
| 54 | 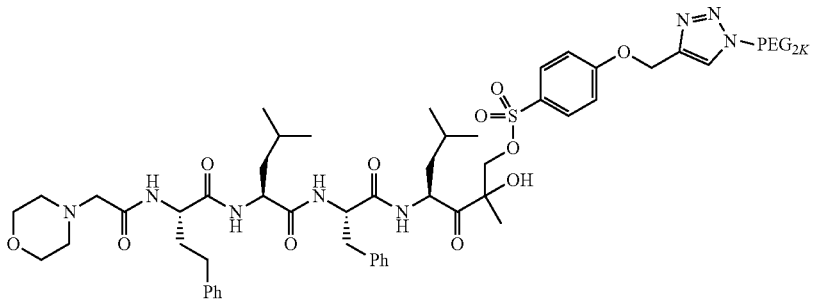 |
| 55 | 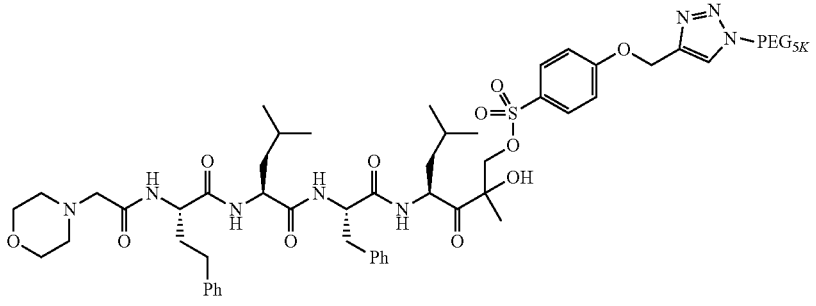 |
| 56 | 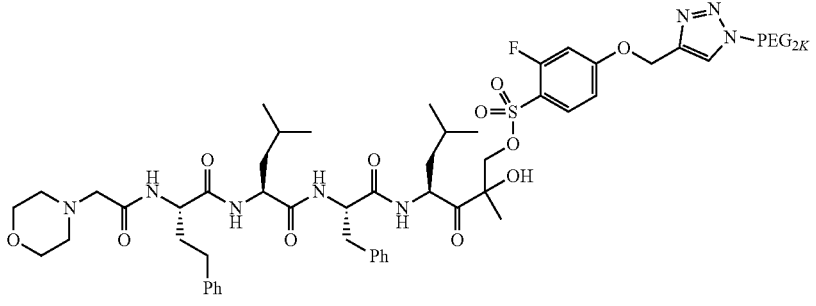 |
| 57 | 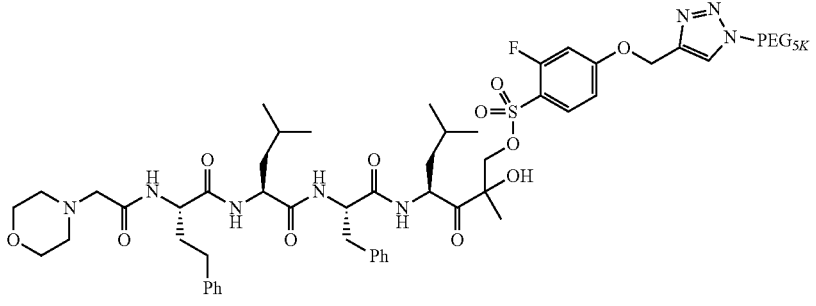 |

TABLE C-continued
| Compound number | Structure |
|---|---|
| 58 | 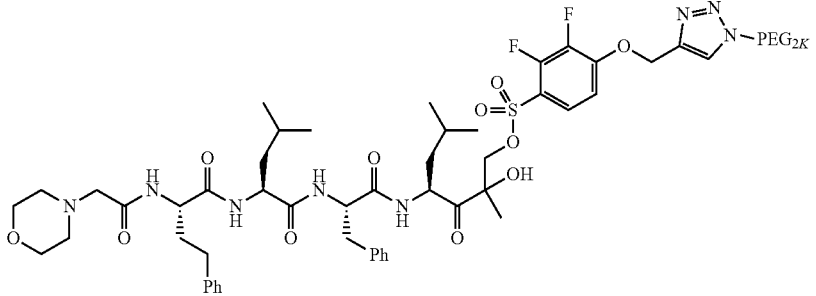 |
| 59 | 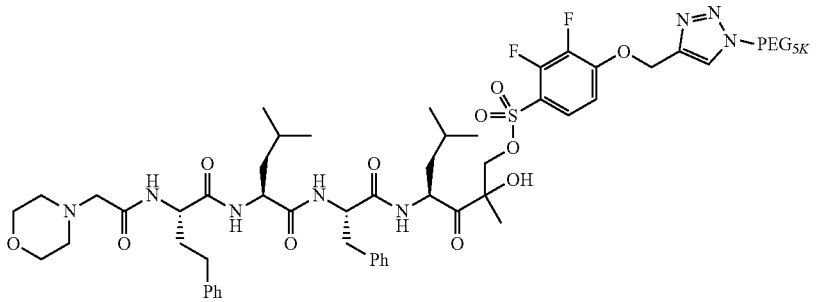 |
| 60 | 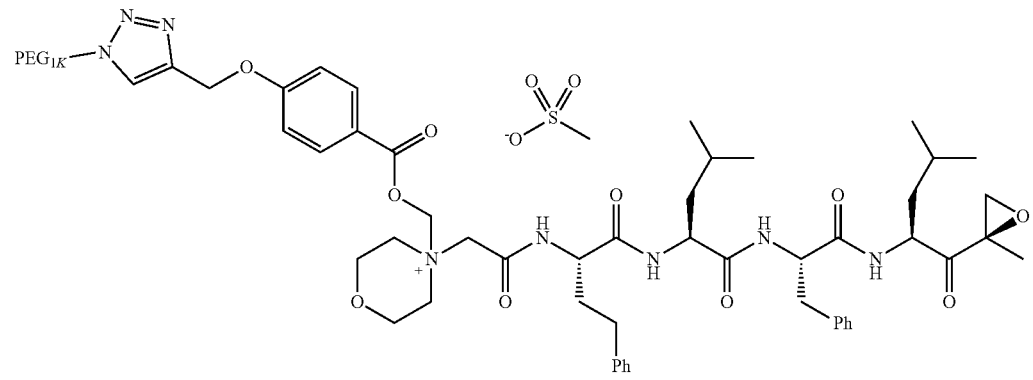 |
| 61 | 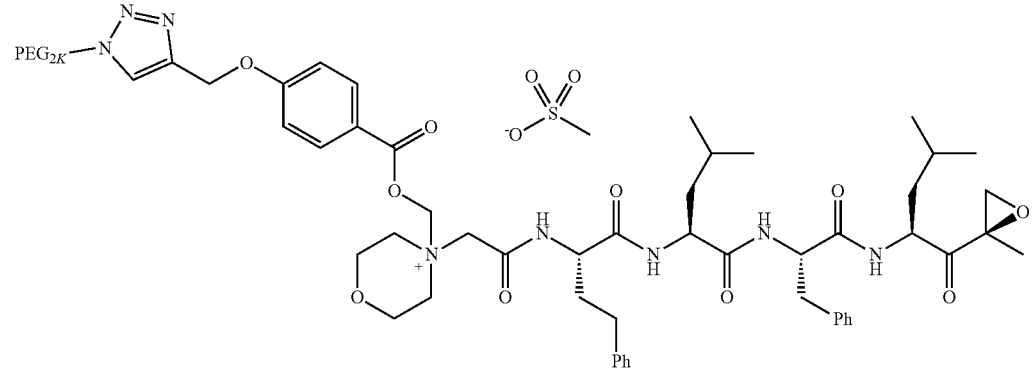 |

TABLE C-continued

| Compound number | Structure |
|---|---|
| 62 | 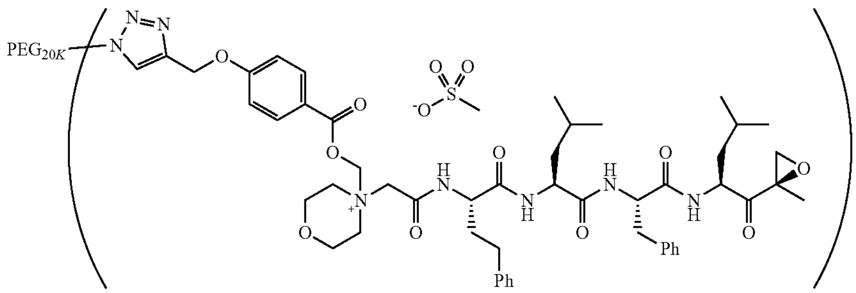 |
| 63 | 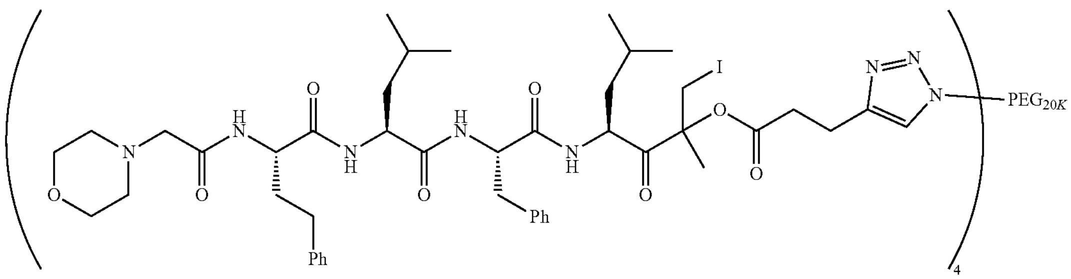 |
| 64 | 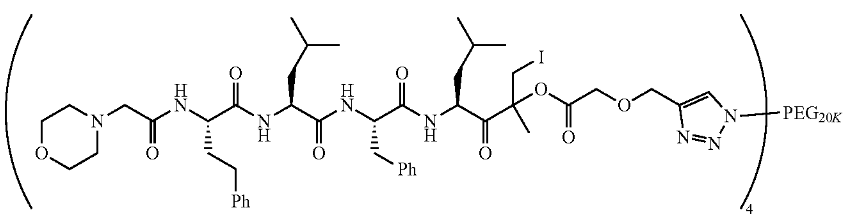 |
| 65 | 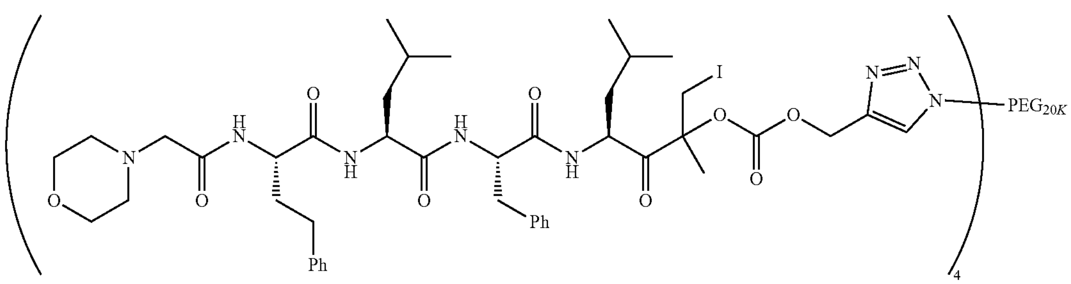 |
| 66 | 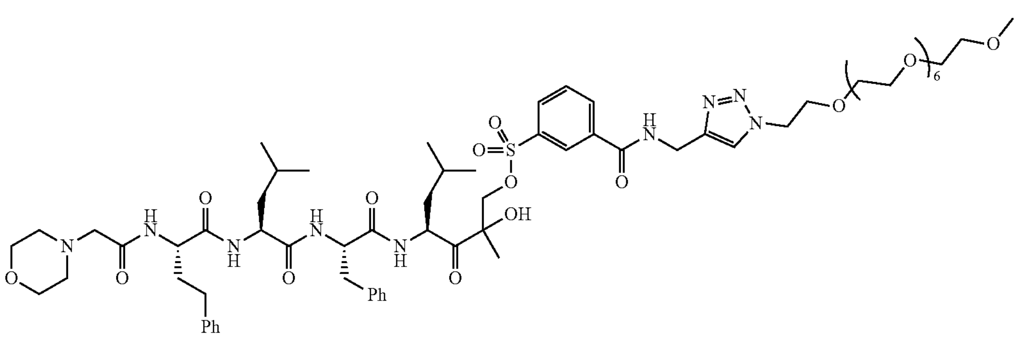 |

TABLE C-continued
| Compound number | Structure |
|---|---|
| 67 | 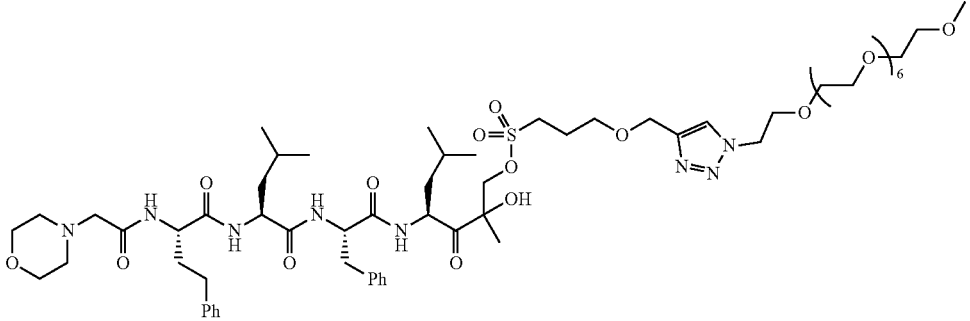 |
| 68 | 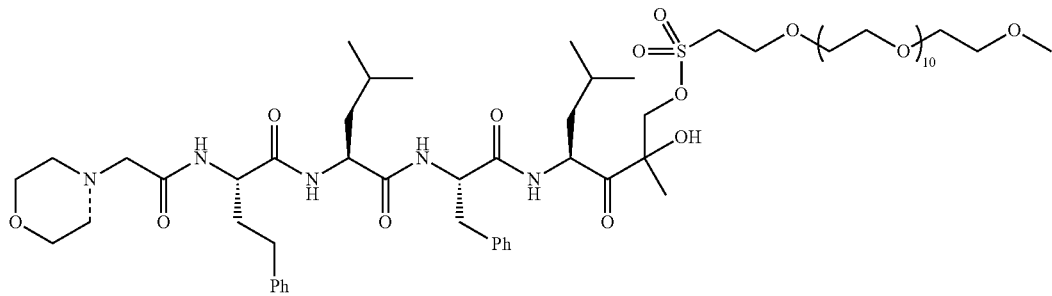 |
| 69 | 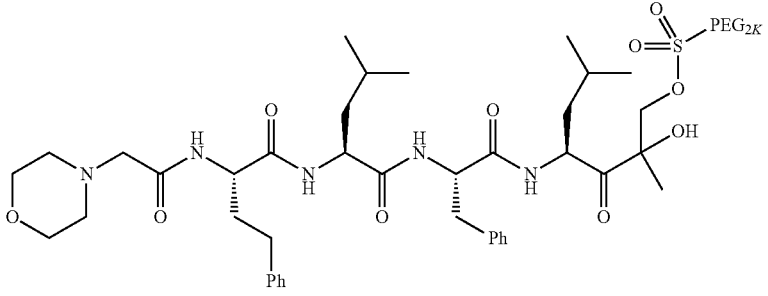 |
| 70 | 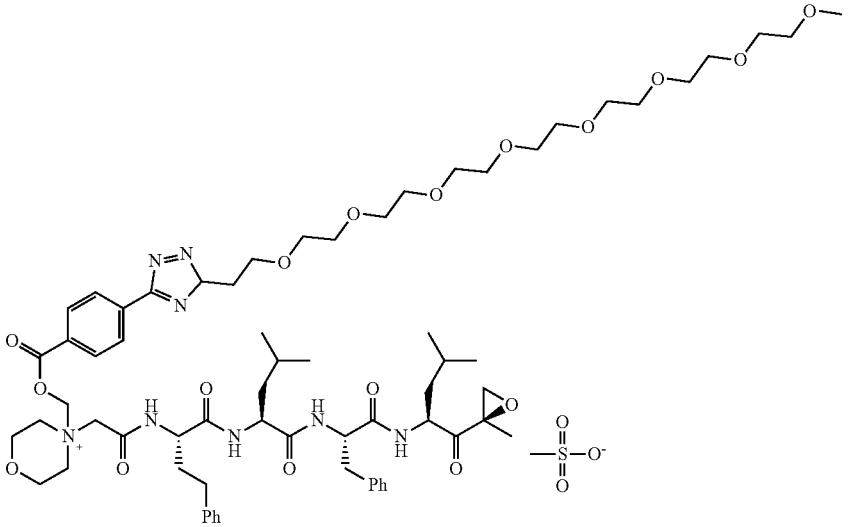 |

TABLE C-continued
| Compound number | Structure |
|---|---|
| 71 | 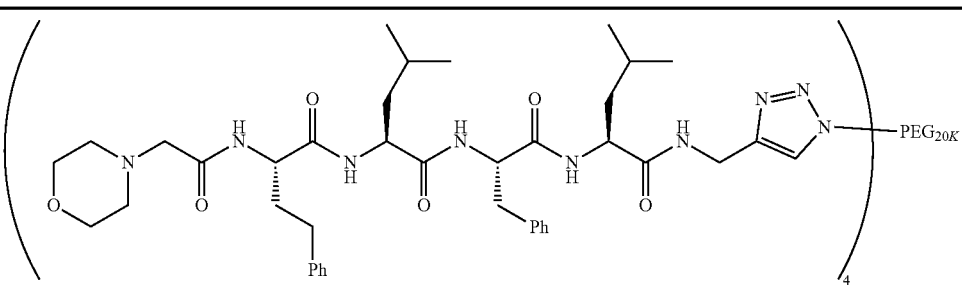 |
| 72 | 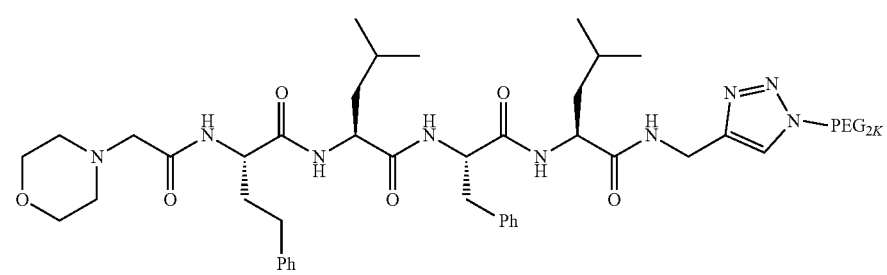 |
In some embodiments, the compound is selected from the compounds disclosed in Table C1.
TABLE C1
| Compound Number | Structure | PEG architecture (see Table AA) |
|---|---|---|
| 73 | 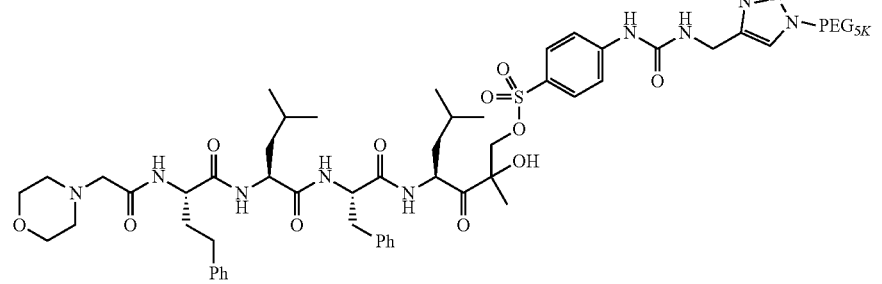 | 2A |
| 74 | 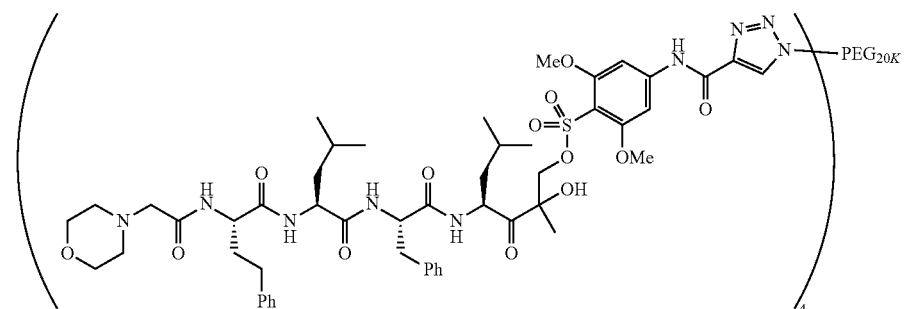 | 2C |

TABLE C1-continued

| Compound Number | Structure | PEG architecture (see Table AA) |
|---|---|---|
| 75 | 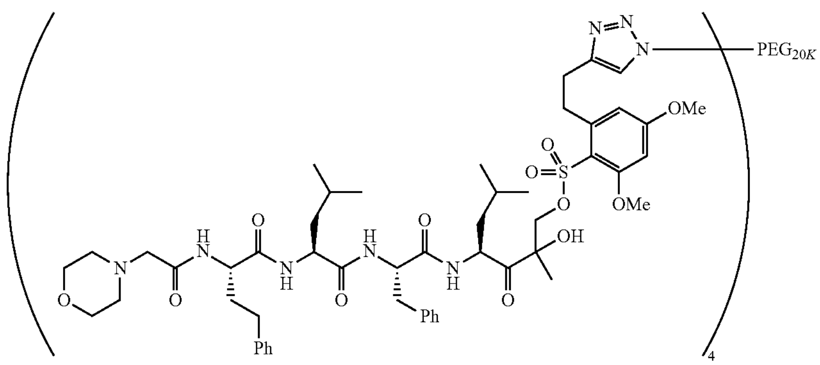 | 2C |
| 76 | 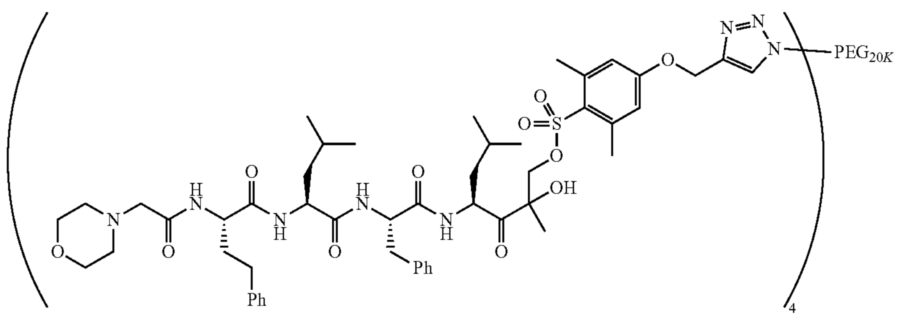 | 2C |
| 77 | 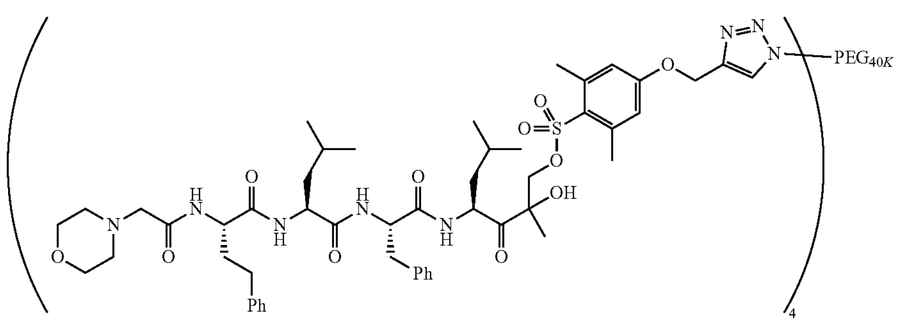 | 2C |
| 78 | 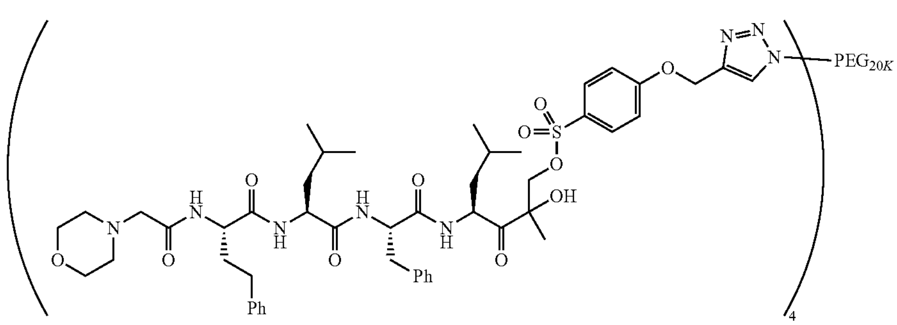 | 2C |

TABLE C1-continued

| Compound Number | Structure | PEG architecture (see Table AA) |
|---|---|---|
| 79 | 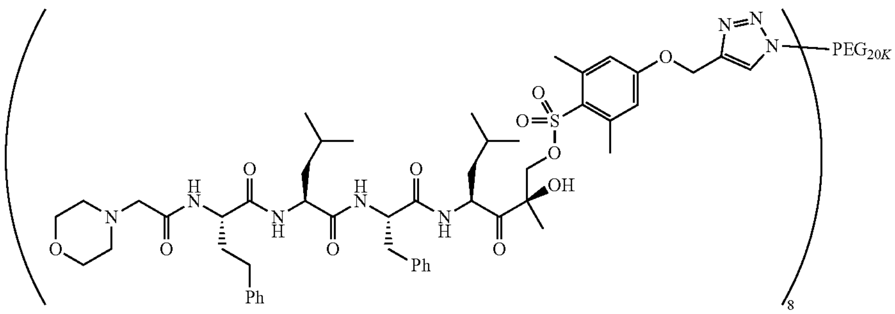 | 2D |
| 80 | 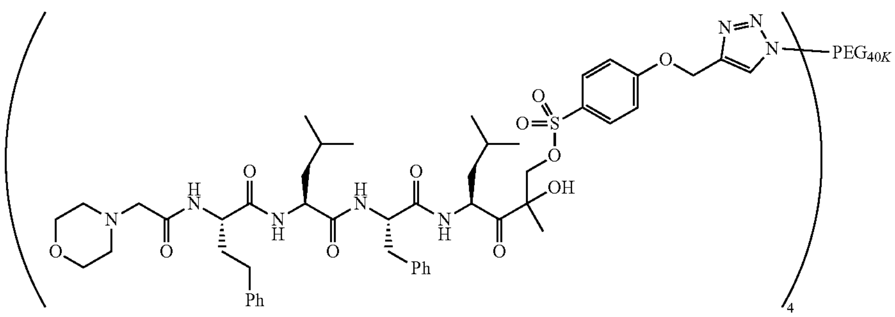 | 2C |
| 81 | 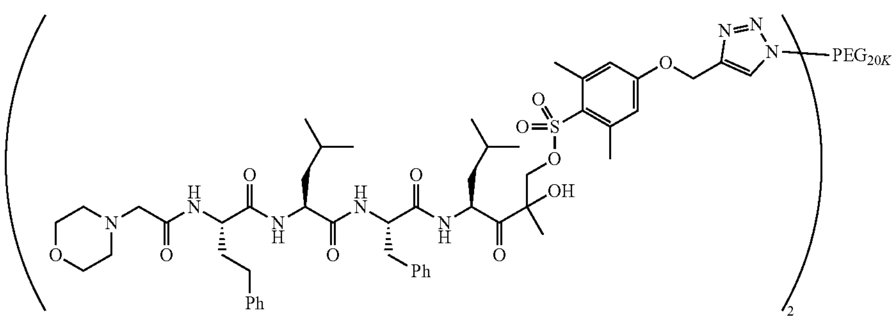 | 2B |
| 82 | 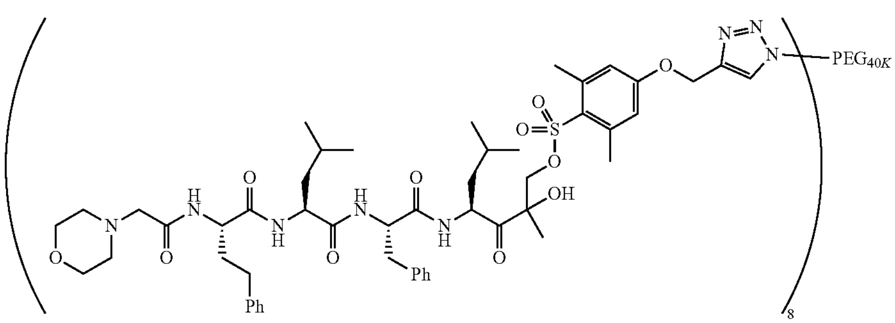 | 2D |
| 83 | 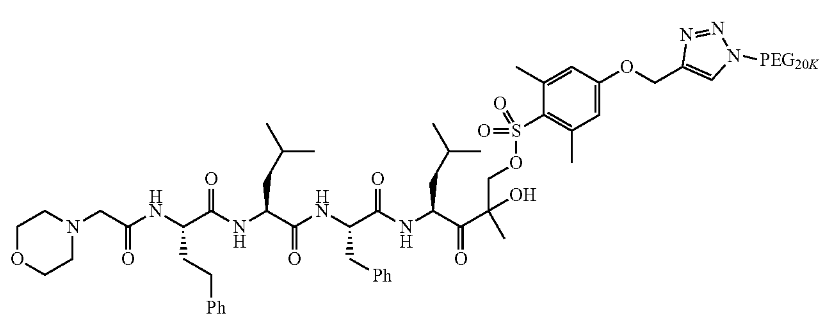 | 2A |

TABLE C1-continued
| Compound Number | Structure | PEG architecture (see Table AA) |
|---|---|---|
| 84 | 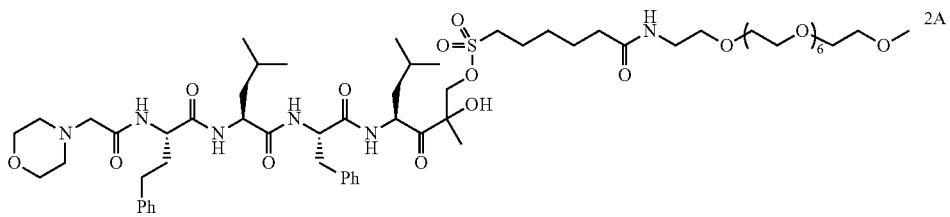 | 2A |
| 85 | 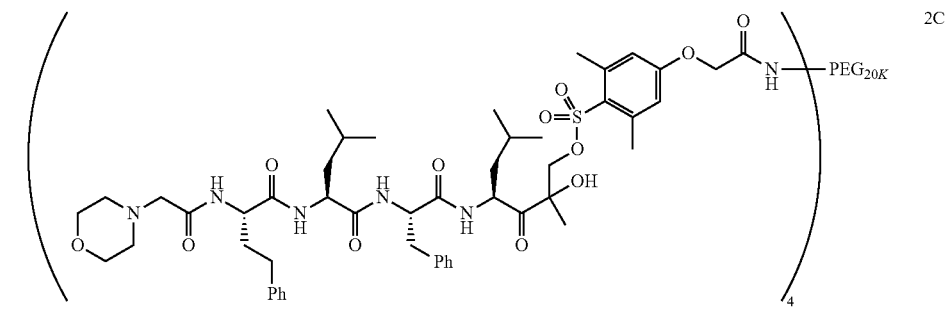 | 2C |
| 86 | 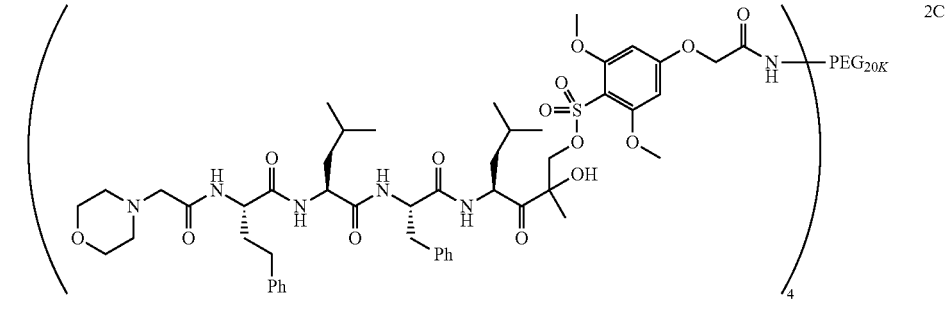 | 2C |
| 87 | 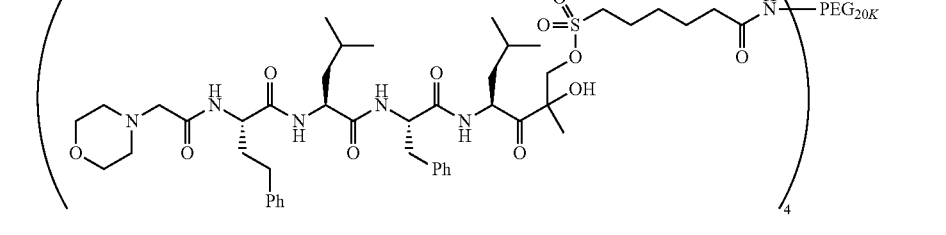 | 2C |
| 88 | 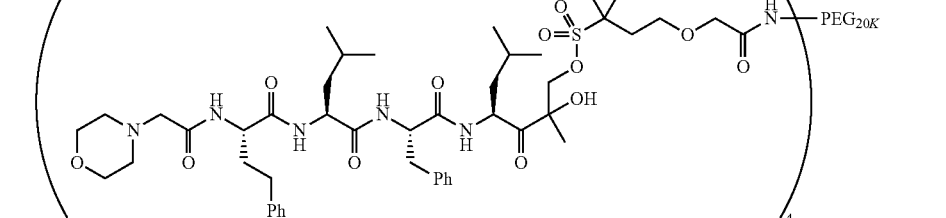 | 2C |

TABLE C1-continued
| Compound Number | Structure | PEG architecture (see Table AA) |
|---|---|---|
| 89 | 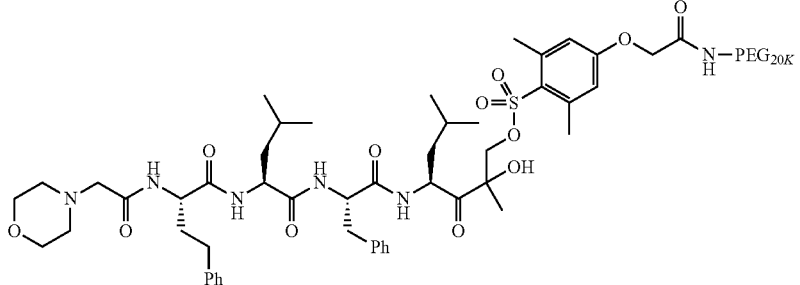 | 2A |
| 90 | 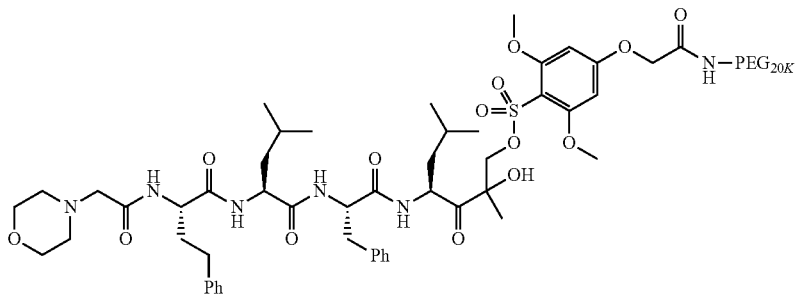 | 2A |
| 91 | 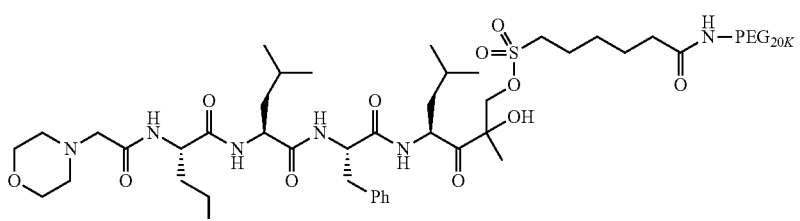 | 2A |
| 92 | 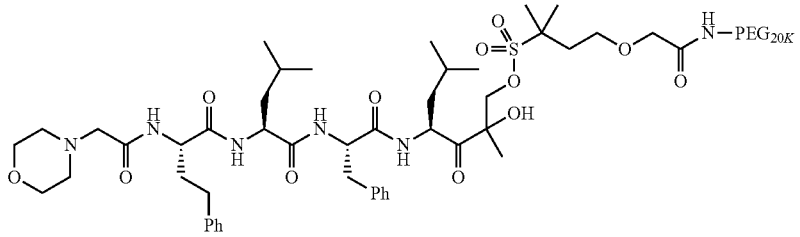 | 2A |
| 93 | 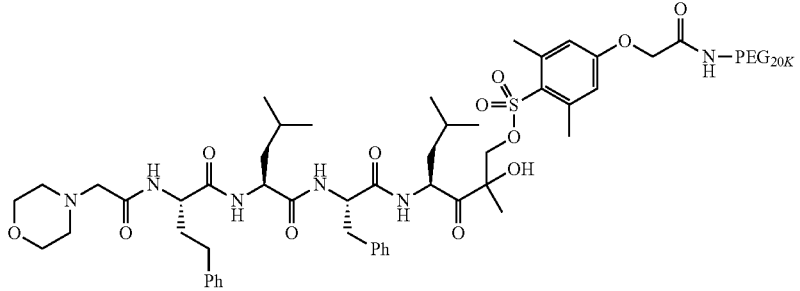 | 2F |

TABLE C1-continued
| Compound Number | Structure | PEG architecture (see Table AA) |
|---|---|---|
| 94 | 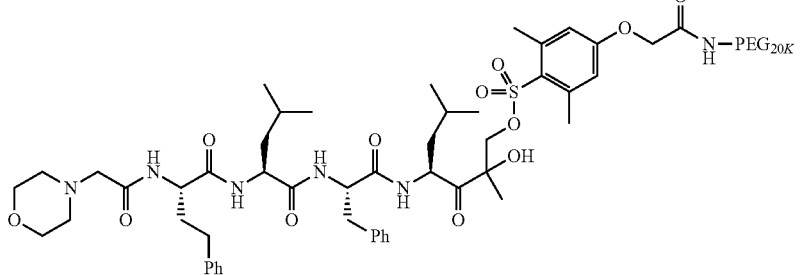 | 2G |
| 95 | 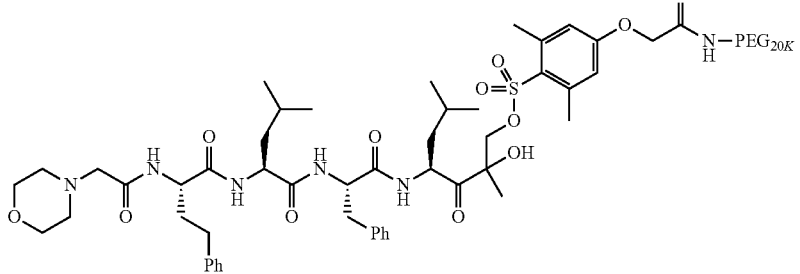 | 2H |
| 96 | 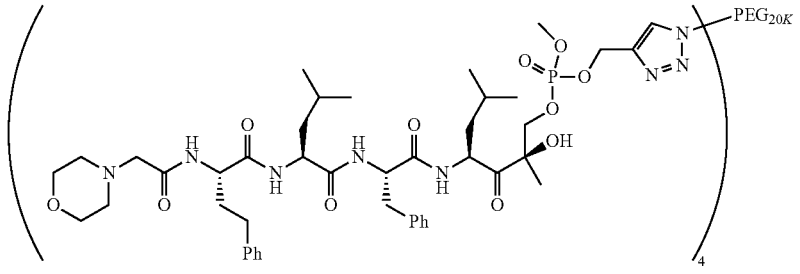 | 2C |
| 97 | 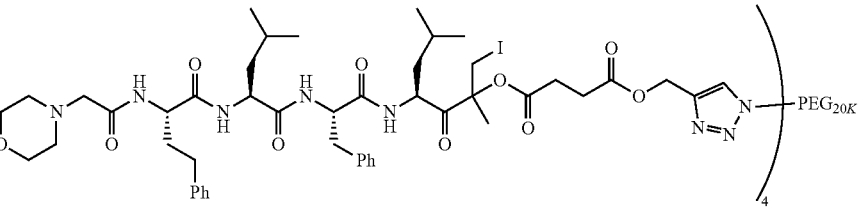 | 2C |
| 98 | 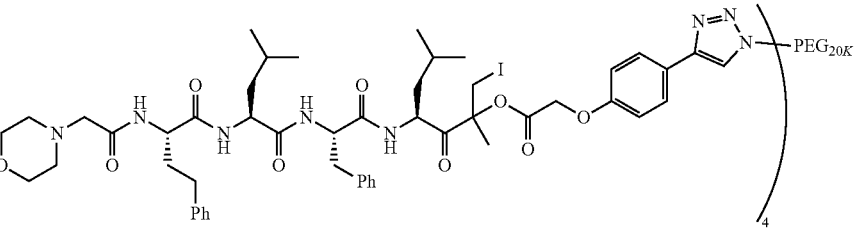 | 2C |
| 99 | 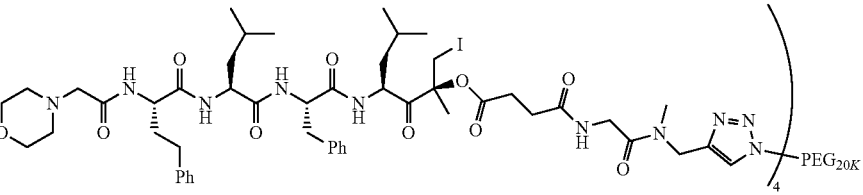 | 2C |

TABLE C1-continued

| Compound Number | Structure | PEG architecture (see Table AA) |
|---|---|---|
| 100 | 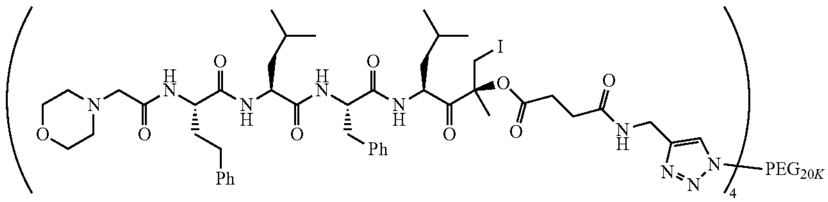 | 2C |
| 101 | 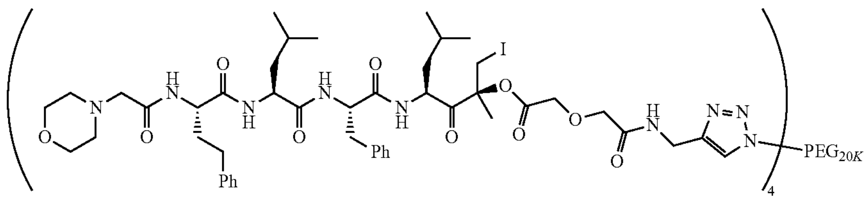 | 2C |
| 102 | 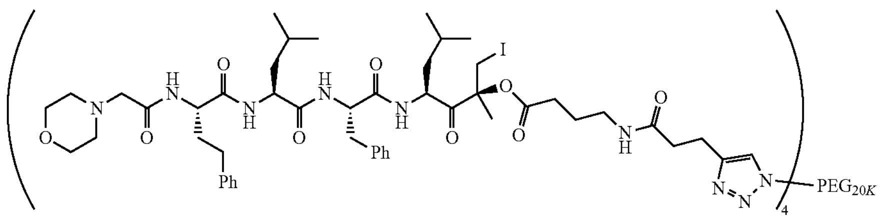 | 2C |
| 103 | 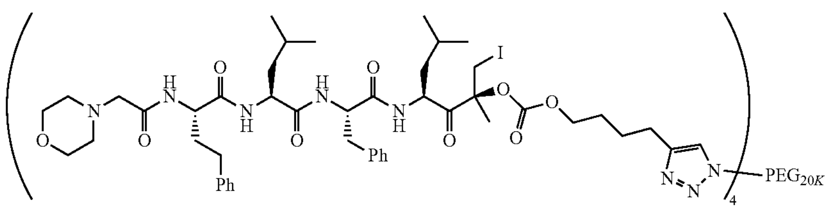 | 2C |
| 104 | 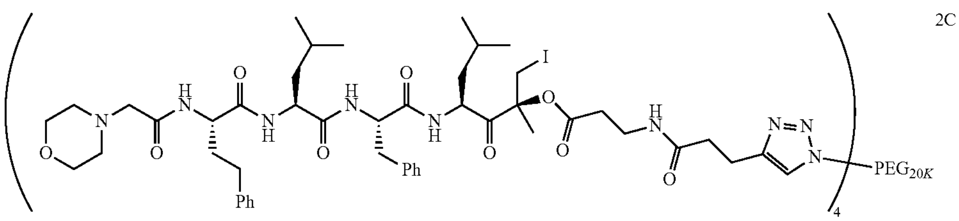 | 2C |
| 105 | 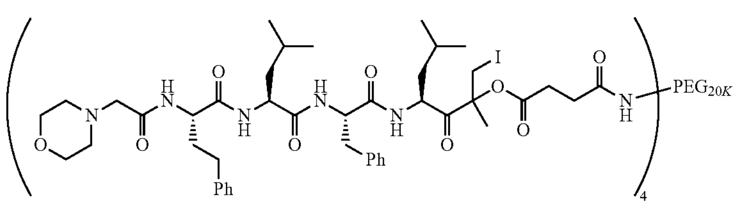 | 2C |
| 106 | 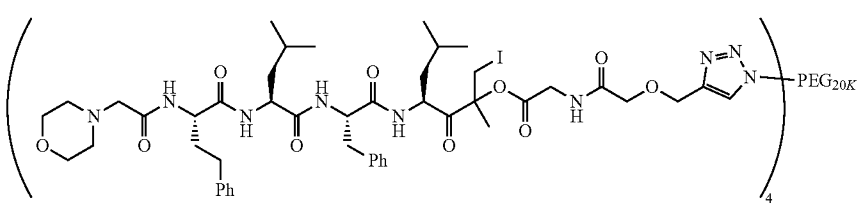 | 2C |

TABLE C1-continued

| Compound Number | Structure | PEG architecture (see Table AA) |
|---|---|---|
| 107 | 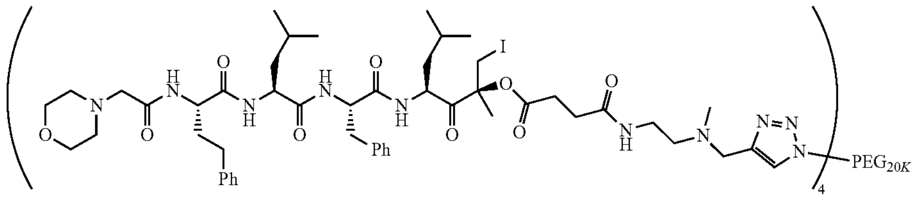 | 2C |
| 108 | 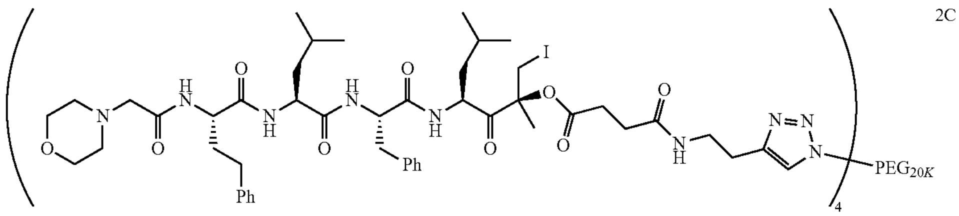 | 2C |
| 109 | 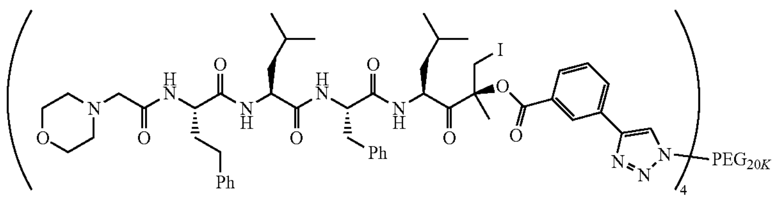 | 2C |
| 110 | 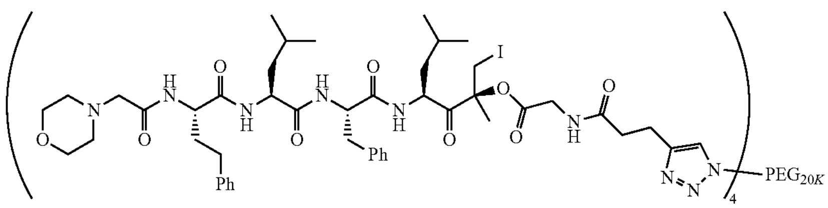 | 2C |
| 111 | 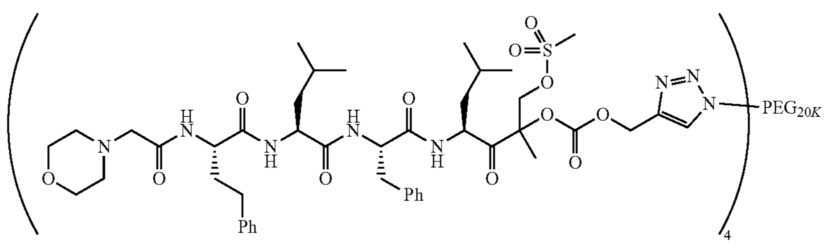 | 2C |
| 112 | 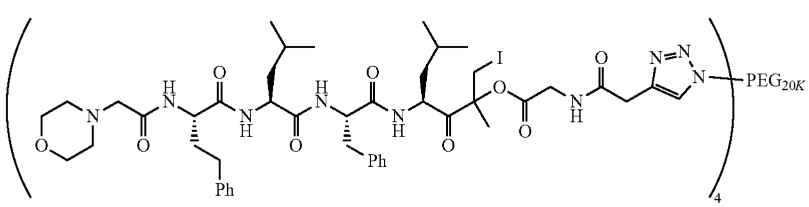 | 2C |
| 113 | 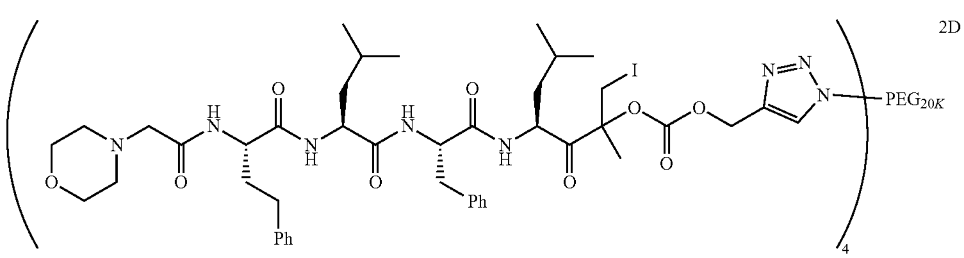 | 2D |

TABLE C1-continued

| Compound Number | Structure | PEG architecture (see Table AA) |
|---|---|---|
| 114 | (structure) | 2C |
| 115 | (structure) | 2C |
| 116 | (structure) | 2C |
| 117 | (structure) | 2C |
| 118 | (structure) | 2C |

TABLE C1-continued

| Compound Number | Structure | PEG architecture (see Table AA) |
|---|---|---|
| 119 | 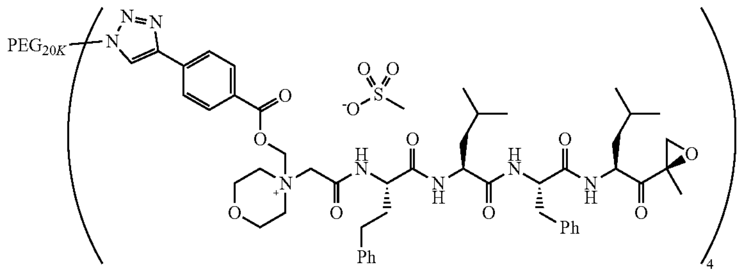 | 2C |
| 120 | 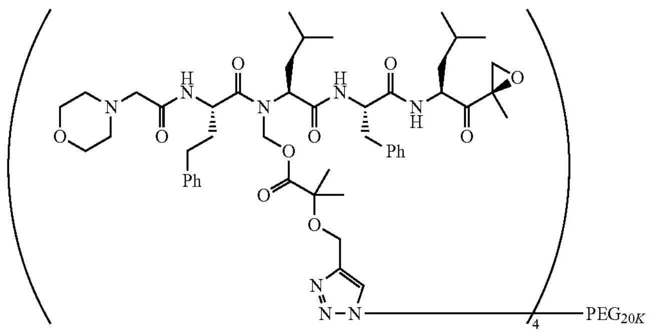 | 2C |
| 121 | 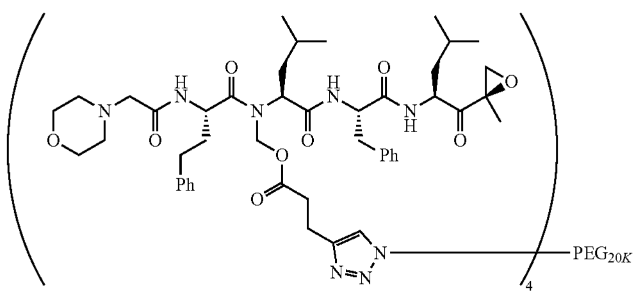 | 2C |
| 122 | 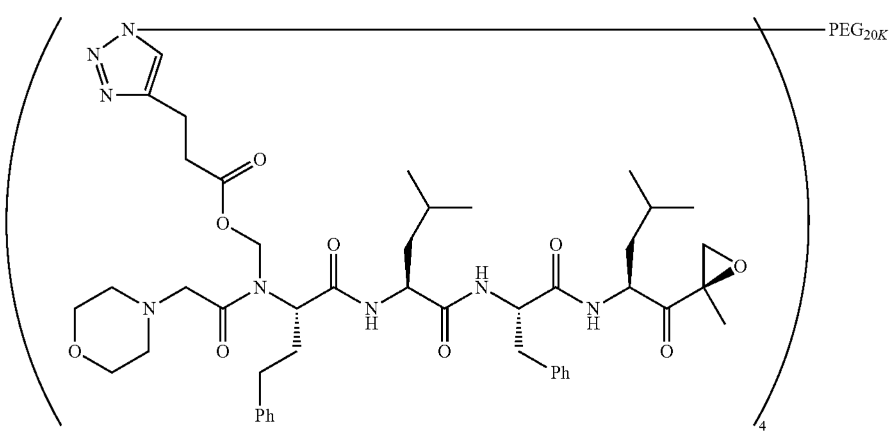 | 2C |

TABLE C1-continued

| Compound Number | Structure | PEG architecture (see Table AA) |
|---|---|---|
| 123 | (chemical structure with morpholine-acetyl-peptide containing epoxyketone warhead, with meta-substituted benzoate linker and triazole, connected via 4-arm to PEG20K) | 2C |
| 124 | (chemical structure with meta-triazolyl benzoate linked through methylene to N of peptide bearing morpholine-acetyl group and epoxyketone warhead, 4-arm PEG20K) | 2C |
| 125 | (chemical structure with morpholine-acetyl-peptide containing epoxyketone warhead, with succinate/N-methyl-triazole linker, 4-arm PEG20K) | 2C |

TABLE C1-continued

| Compound Number | Structure | PEG architecture (see Table AA) |
|---|---|---|
| 126 | 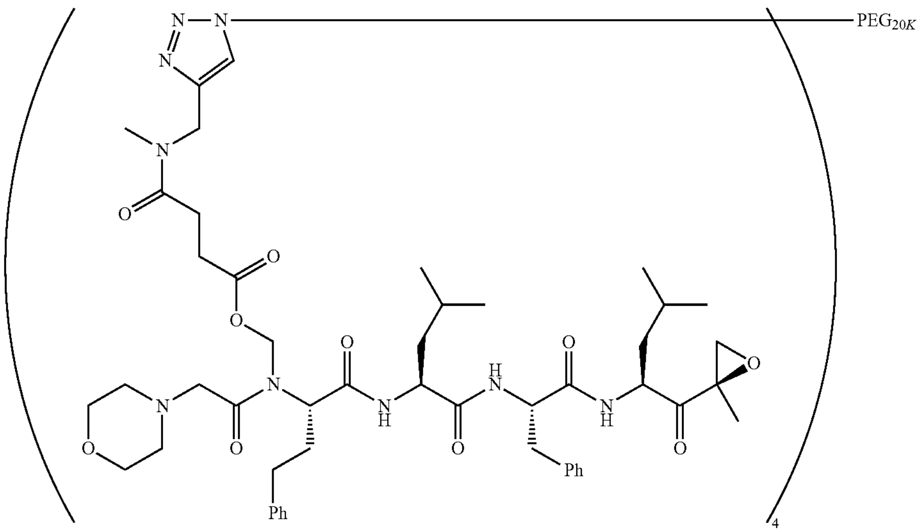 | 2C |
| 127 | 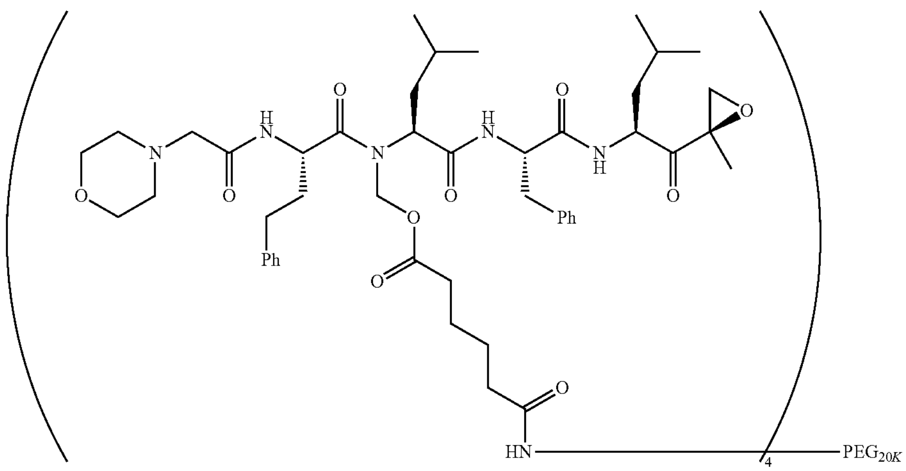 | 2C |
| 128 | 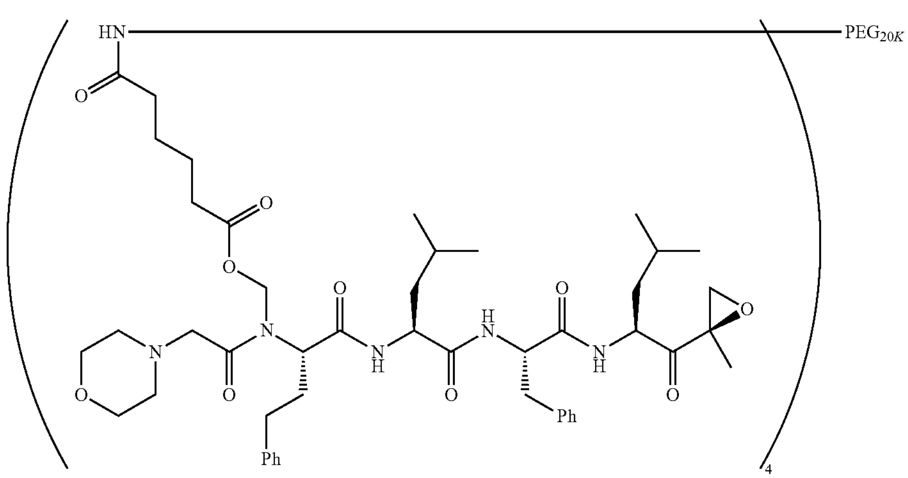 | 2C |

TABLE C1-continued

| Compound Number | Structure | PEG architecture (see Table AA) |
|---|---|---|
| 129 | 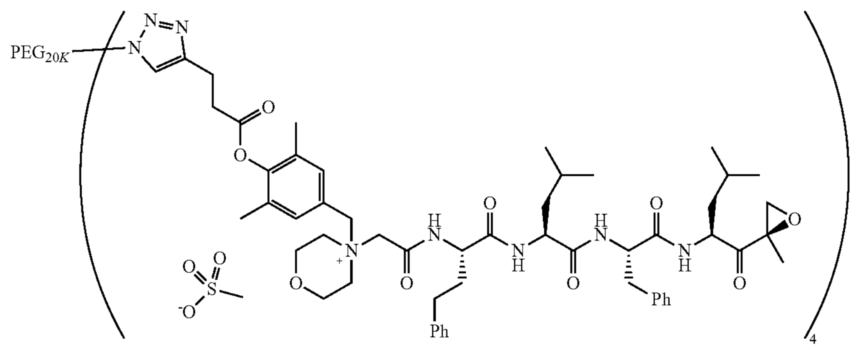 | 2C |
| 130 | 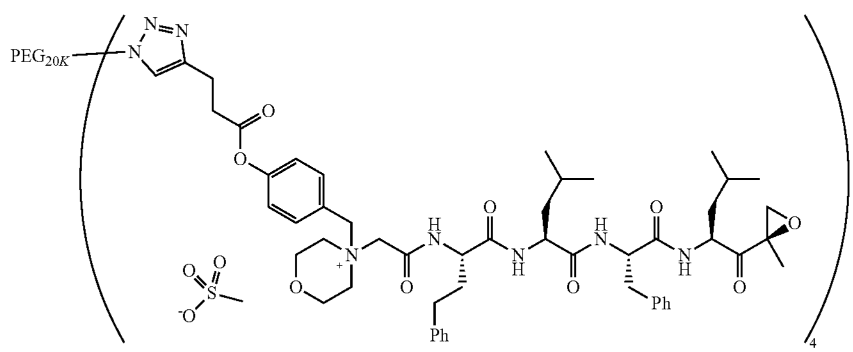 | 2C |
| 131 | 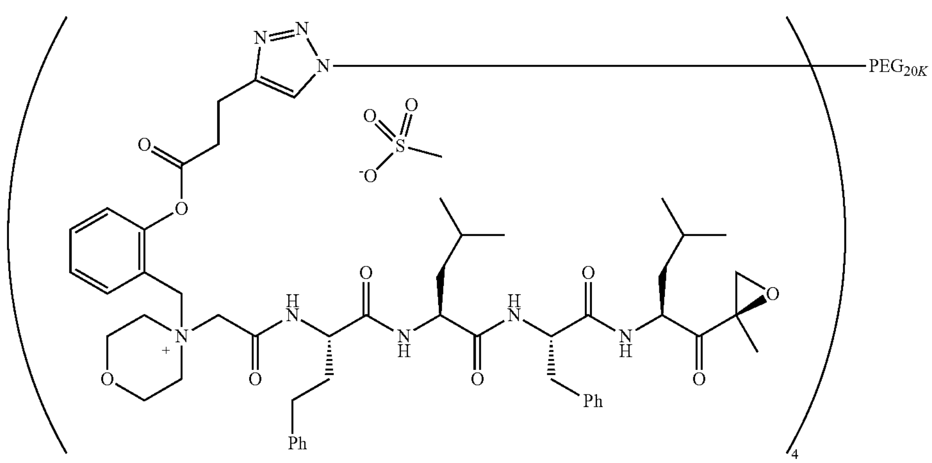 | 2C |
| 132 | 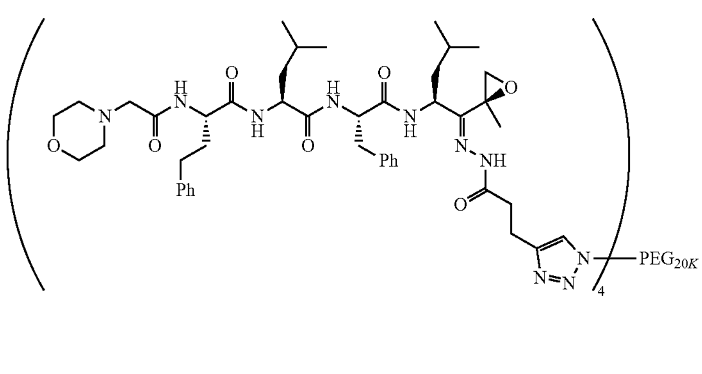 | 2C |

TABLE C1-continued

| Compound Number | Structure | PEG architecture (see Table AA) |
|---|---|---|
| 133 | 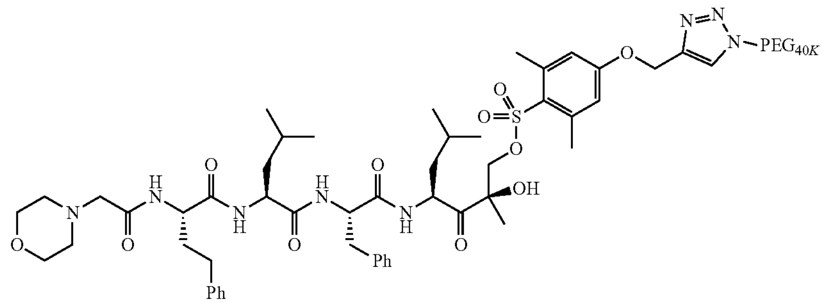 | 2A |
| 134 | 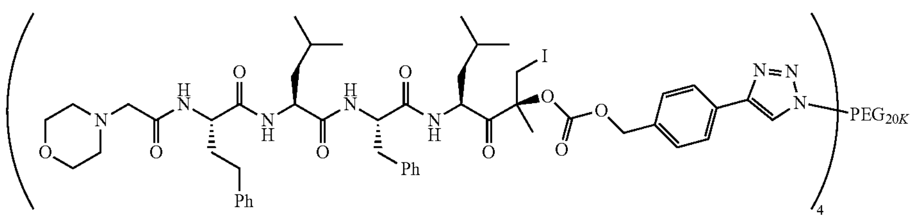 | 2C |
| 135 | 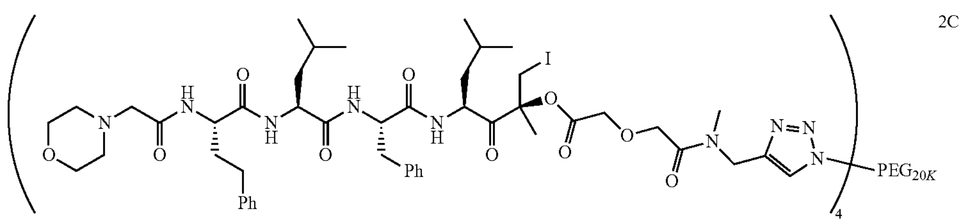 | 2C |
| 136 | 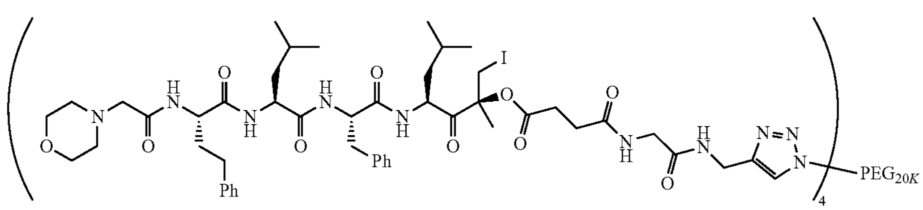 | 2C |
| 137 | 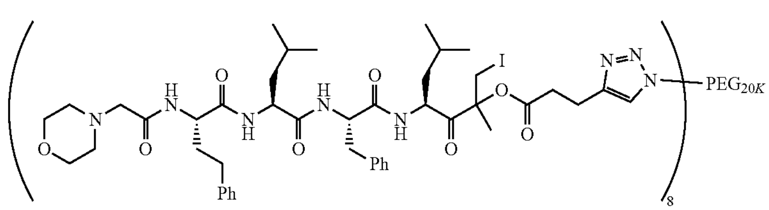 | 2D |

TABLE C1-continued
| Compound Number | Structure | PEG architecture (see Table AA) |
|---|---|---|
| 138 | 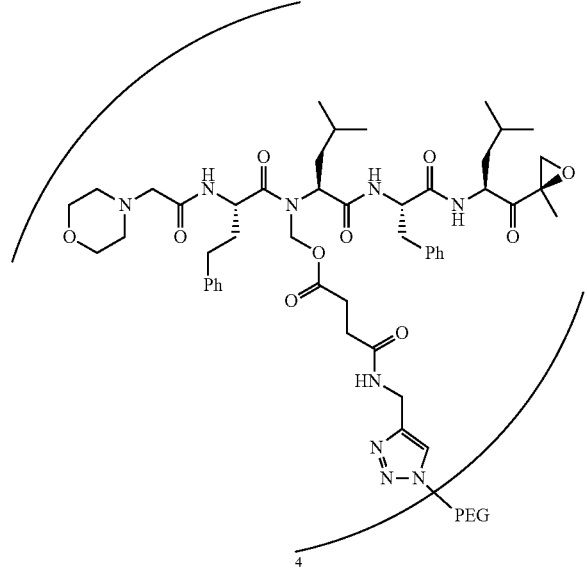 | 2C |
| 139 | 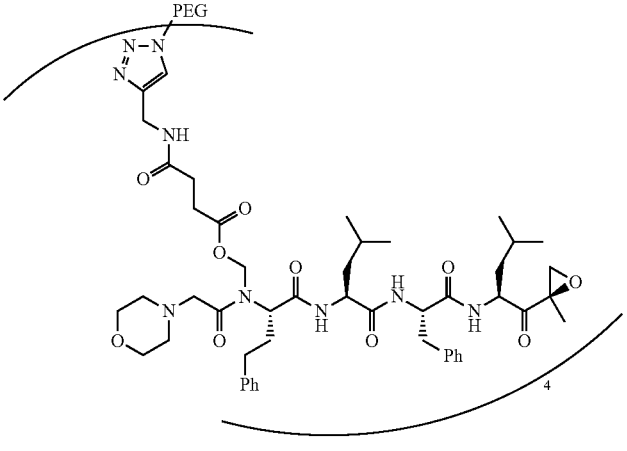 | 2C |
| 140 | 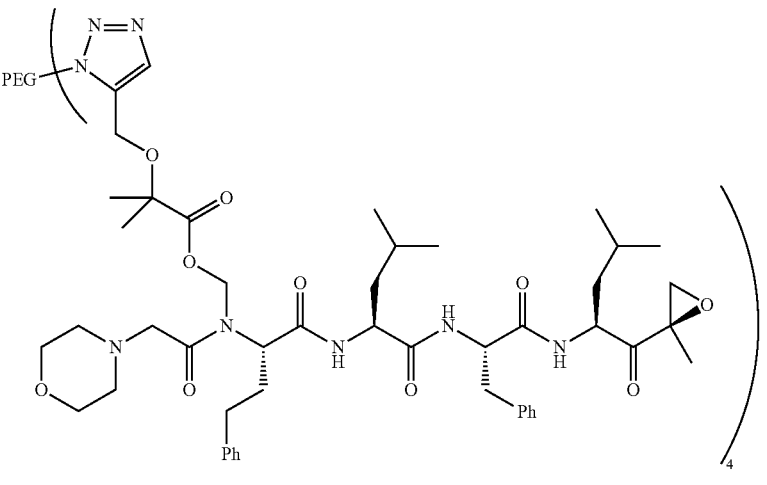 | 2C |

The disclosure provides, inter alia, a process for preparing a therapeutic agent comprising reacting the compound under conditions sufficient to remove any one or more of $R^3$, $R^{11}$, $R^{12}$, $R^{13}$, and $R^{14}$.

active form by undergoing cyclization and re-formation of the epoxide at a target pH (e.g., a physiological pH). Scheme I illustrates an example activated diol undergoing pH-driven epoxide re-formation.

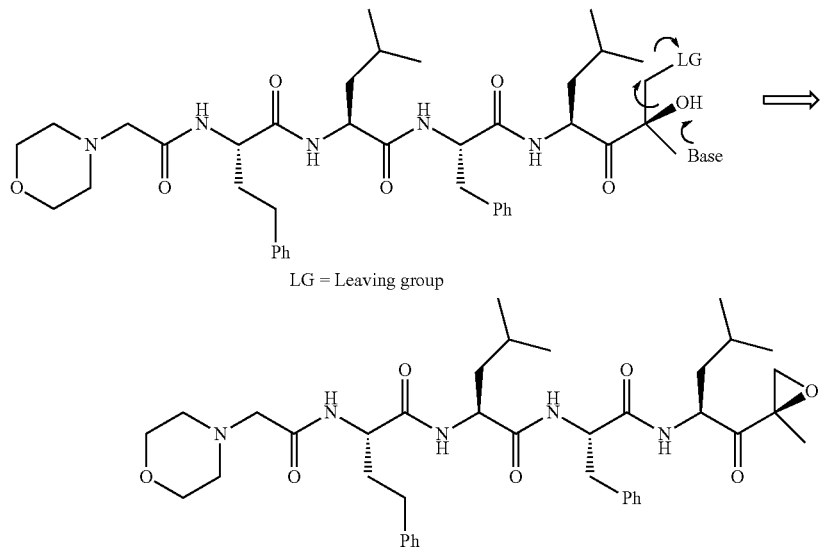

Scheme 1

LG = Leaving group

In some embodiments, the present disclosure provides a process for preparing a therapeutic agent comprising reacting a compound described herein under conditions sufficient to remove any one or more of $R^{11}$, $R^{12}$, $R^{13}$, and $R^{14}$.

The disclosure provides, inter alia, a pharmaceutical composition including any one or more of the compounds described herein and a pharmaceutically acceptable carrier.

The present disclosure provides, inter alia, a method for treating a disease or condition selected from the group consisting of cancer, autoimmune disease, graft or transplant-related condition, neurodegenerative disease, fibrotic-associated condition, ischemic-related conditions, infection (viral, parasitic or prokaryotic) and diseases associated with bone loss, the method comprising administering to a patient a therapeutically effective amount of any one or more of the compounds or pharmaceutical compositions described herein and a pharmaceutically acceptable carrier.

In some embodiments, the disease or condition is cancer.
In some embodiments, the cancer is multiple myeloma.
Preparation of Compounds and Prodrug Activation The compound scaffolds described herein can be prepared using, e.g., methods of preparation described in one or more of U.S. Pat. Nos. 7,687,456; 7,737,112; 7,232,818, and 7,417,042. The compound scaffolds can be modified as described herein and using conventional methods known in the art.

Figure 2:
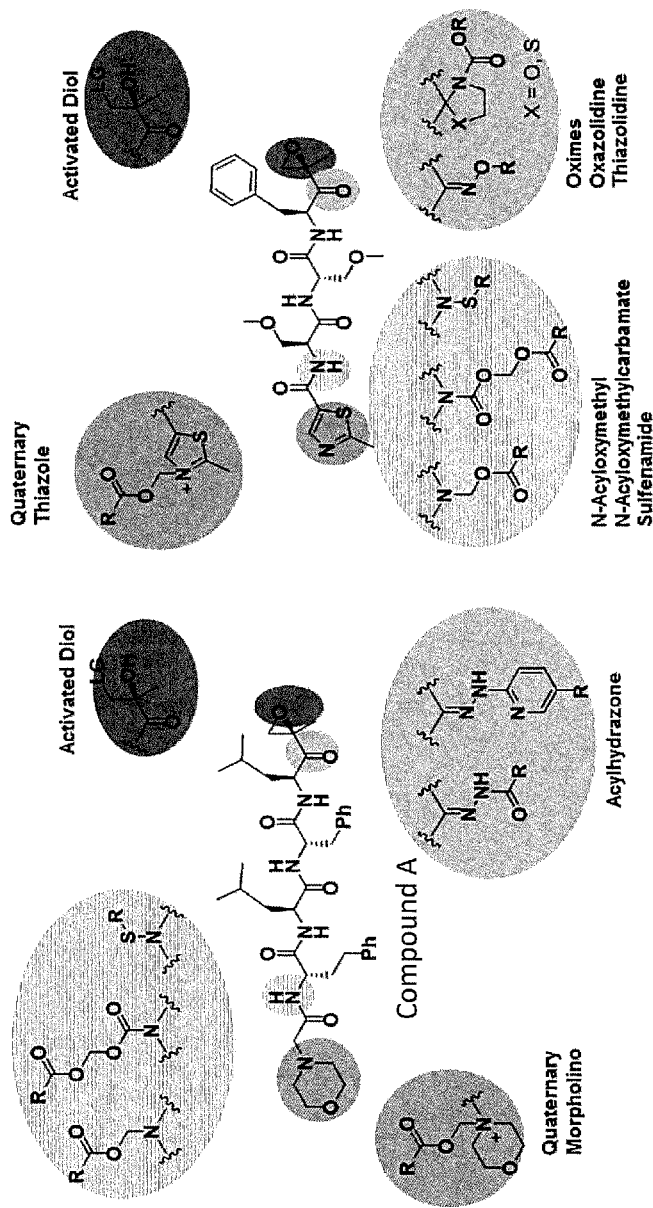
FIG. 2 is a scheme showing embodiments of modifications of peptide epoxy ketone protease inhibitors.

Examples of modifications of epoxy ketone protease inhibitors are shown, for example, in FIG. 2.
Activated Diols Referring to FIG. 1, in some embodiments, the epoxy moiety of the epoxy ketone protease inhibitor can be deactivated by replacing the epoxide with a diol (e.g., by cleaving the epoxide to a diol). The diol can be activated and the epoxy ketone protease inhibitor can be converted to an Epoxy ketone protease inhibitor prodrugs having an activated diol can include a leaving group. In some embodiments, the leaving groups include an activated linker, a spacer, a conjugate, or combination thereof. FIG. 46 shows examples of activated diol leaving groups (with different combinations of spacer and conjugate) in epoxy ketone protease inhibitors designed, for example, for subcutaneous and intravenous administration. Referring to FIG. 46, the leaving groups can include (i) polymers such as, but not limited to, hyaluronic acid, poly(ethylene glycol), carboxymethylcyclodextran, poly(L-glutamic acid), and N-(2-hydroxypropryl)methacrylamide copolymer; (ii) proteins; (iii) dendrimers; or (iv) antibodies and antibody fragments. In some embodiments, the epoxy ketone protease inhibitors of FIG. 46 are suitable for subcutaneous and intravenous administration.

In some embodiments, the activated diol prodrugs can be converted to an active form by cleavage at a target pH and/or using enzymes such as, but not limited to, esterases, cytochrome P450, phosphodiesterase, phosphoamidase, phosphatase, and DT-diaphorase, or any combination thereof. In some embodiments, the epoxy ketone protease inhibitor prodrugs are designed for oral administration.

Figure 11:
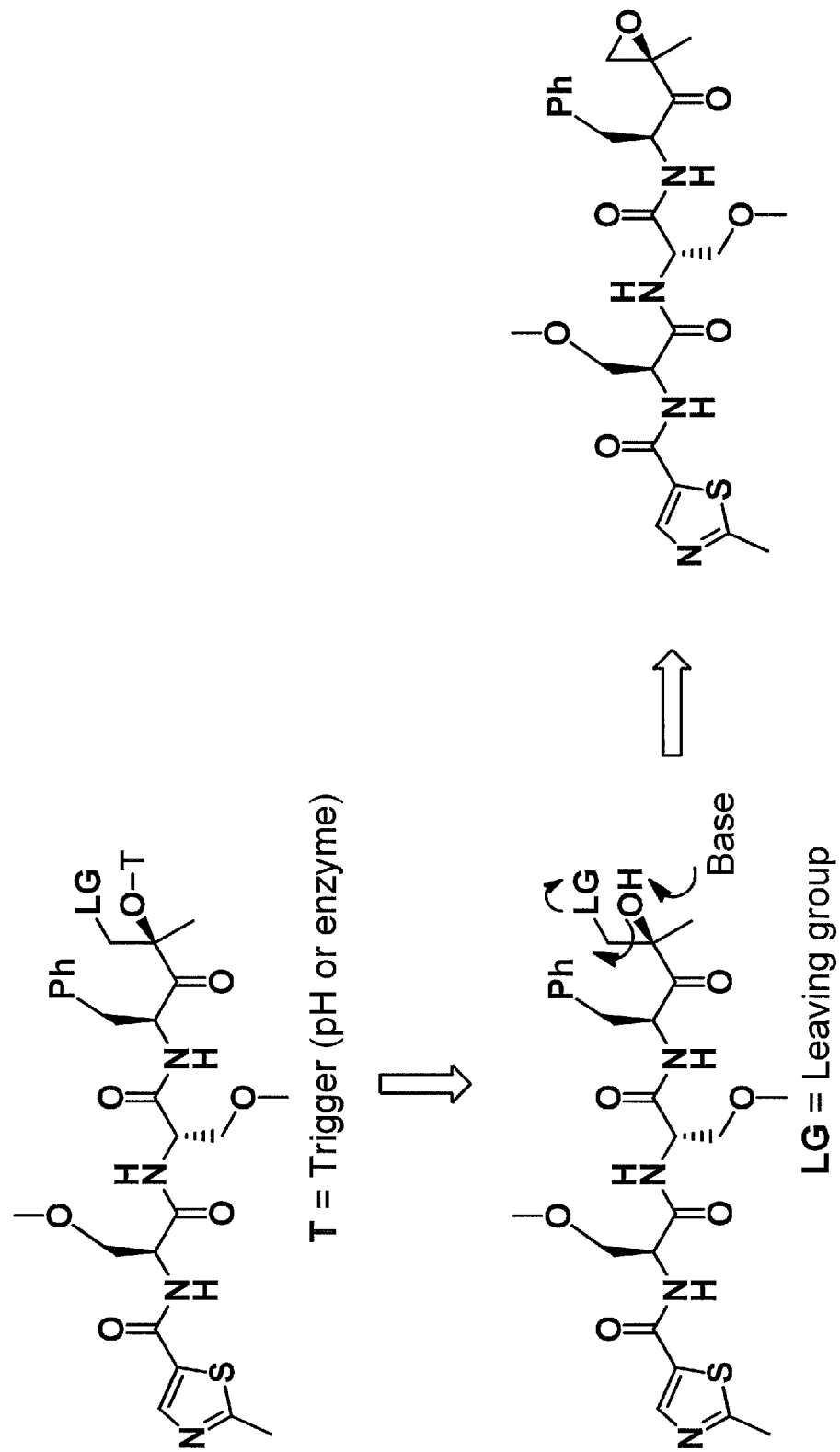
FIG. 11 is a scheme showing embodiments of epoxy ketone proteasome inhibitor prodrug undergoing pH driven reconversion to the active inhibitor.

Referring to FIG. 11, the scheme illustrates an example epoxy ketone protease inhibitor prodrug undergoing pH driven reconversion, tandem to activation by an enzyme trigger.

Table E1 lists examples of activated diol leaving groups suitable for various pH and/or enzyme triggers.

TABLE E1

| Leaving group | Leaving group | Trigger (pH, enzyme) |
|---|---|---|
| | | pH > 6 |
| | | (esterases) |
| | | (esterases) |
| | | (esterases) |
| | | (DT-diaphorase) |
| | | (phosphatases) |
| | | |
| | | |
| | | |

TABLE E1-continued

| Leaving group | Leaving group | Trigger (pH, enzyme) |
|---|---|---|
| [sulfonyl-4-fluorophenyl] | [sulfonyl-2-fluorophenyl] | |
| [sulfonyl-2,6-difluorophenyl] | [sulfonyl-2,4-difluorophenyl] | |
| [sulfonyl-8-quinolinyl] | [sulfonyl-CH2-C(O)-O-benzyl] | |
| [sulfonyl-phenyl-C(O)-X-octyl], X = O, NH | [sulfonyl-propyl-N+(CH3)2-CH2(CH2)14CH3] | |
| [sulfonyl-(4-F)phenyl-C(O)-X-PEG3-OMe], X = O, NH | [sulfonyl-(2-F)phenyl-C(O)-X-PEG3-OMe], X = O, NH | |
| [sulfonyl-phenyl-C(O)-X-PEG3-OMe], X = O, NH | [sulfonyl-CH2-C(O)-X-PEG3-OMe], X = O, NH | |
| F, Cl, Br, I | | |

PEG Conjugates

In some embodiments, the epoxy ketone protease inhibitor prodrugs can include a PEG (polyethylene glycol) conjugate. PEG conjugates can allow for an increased circulating half-life, reduced proteolytic degradation and/or an extended duration of action.

Figure 12:
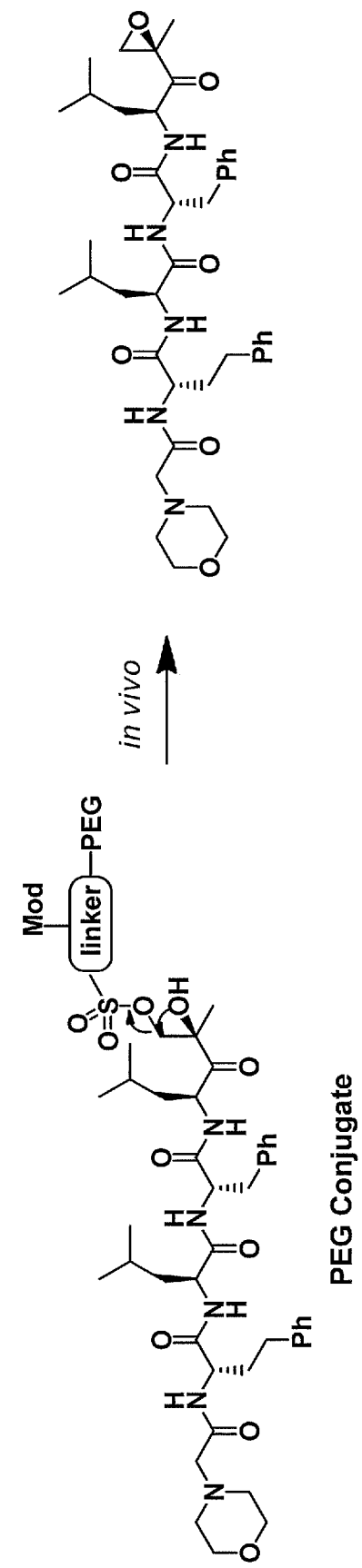
FIG. 12 is a scheme showing embodiments of epoxy ketone proteasome inhibitor prodrug being released by hydroxide-driven reconversion to the active inhibitor.

The PEG conjugates can include releasable PEG carriers of epoxy ketone protease inhibitors. Referring to FIG. 12, the epoxy ketone protease inhibitor prodrugs can be chemically released (e.g., in vivo) from the PEG conjugates by a hydroxide-catalyzed intramolecular α-oxyanion displacement of a PEG tethered alkyl or aryl sulfonate leaving group. The PEG conjugate itself can be inactive as a proteasome inhibitor and active epoxy ketone protease inhibitors can be released when the conjugate is exposed to a slightly basic environment. The rate of intramolecular cyclization and displacement can be varied over a time range by the introduction of an electron density modulating group. Electron withdrawing groups increase the rate of displacement and electron donating groups decrease it.

In some embodiments that are found in the present application, the PEG architecture of the conjugate may differ between prodrugs of epoxy ketone proteasome inhibitors. The various PEG architectures are described in Table AA (see above). Architecture type 2A describes a linear PEG, with one conjugation point. Architecture type 2B describes a bifunctional PEG, with as many as two possible conjugation points. Architecture type 2C describes a four-arm PEG, with as many as four possible conjugation points. Architecture type 2D describes a PEG with an eight-arm hexaglycerin core, with as many as eight possible conjugation points. Architecture type 2E describes a PEG with an eight-arm tripentaerythritol core, with as many as eight possible conjugation points. Architecture type 2F describes a branched two-arm PEG, with one conjugation point. Architecture type 2G describes a branched four-arm PEG, with one conjugation point. Architecture type 2H describes an alternate embodiment of a branched four-arm PEG, with one conjugation point. In some non-limiting embodiments, one architecture type may provide an advantage with respect to ease of synthesis, physicochemical properties, pharmacokinetic stability, or volume of distribution. (See, for example, Sim, S L et al. *Biotechnol. Bioeng.* (2012), 109 (3), 736-46; Prencipe, G. et al. "PEG Branched Polymer for Functionalization of Nanomaterials with Ultralong Blood Circulation," *J. Am. Chem. Soc.* (2009), 131 (13), 4783-4787; Roth, P J et al. *Soft Matter* (2013), 9, 1825-1834; and Dhawan, S. et al. PEGylation. In *Development of Therapeutic Agents Handbook*; Gad, S. C., Ed.; Wiley: Hoboken, 2012; Chap. 19.)

Synthesis of PEG Conjugates of Epoxy Ketone Protease Inhibitors

Figure 13:
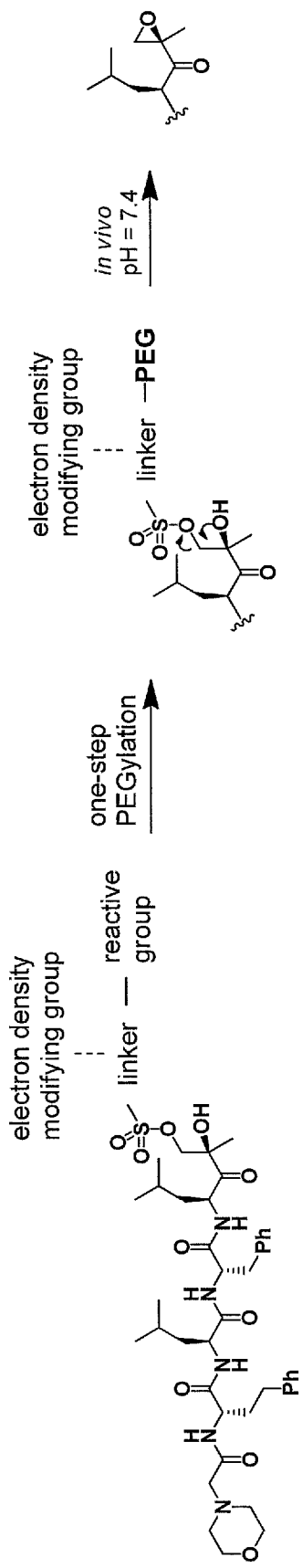
FIG. 13 is a scheme showing an embodiment of an epoxy ketone proteasome inhibitor prodrug containing a sulfonate-linking group that is conjugated to a PEG, which is then released.

In some embodiments, referring to FIG. 13, a epoxy ketone protease inhibitor includes a diol that is activated with a sulfonate leaving group. The epoxy ketone protease inhibitor can undergo quantitative cyclization to a biologically active epoxide in buffer (pH=7.4) and/or plasma. The cyclization and/or cleavage rate can be adjusted by including electron withdrawing or donating group(s) in the epoxy ketone protease inhibitor, where electron donating groups can decrease cyclization rate; while electron withdrawing groups can increase cyclization rate.

Figure 14:
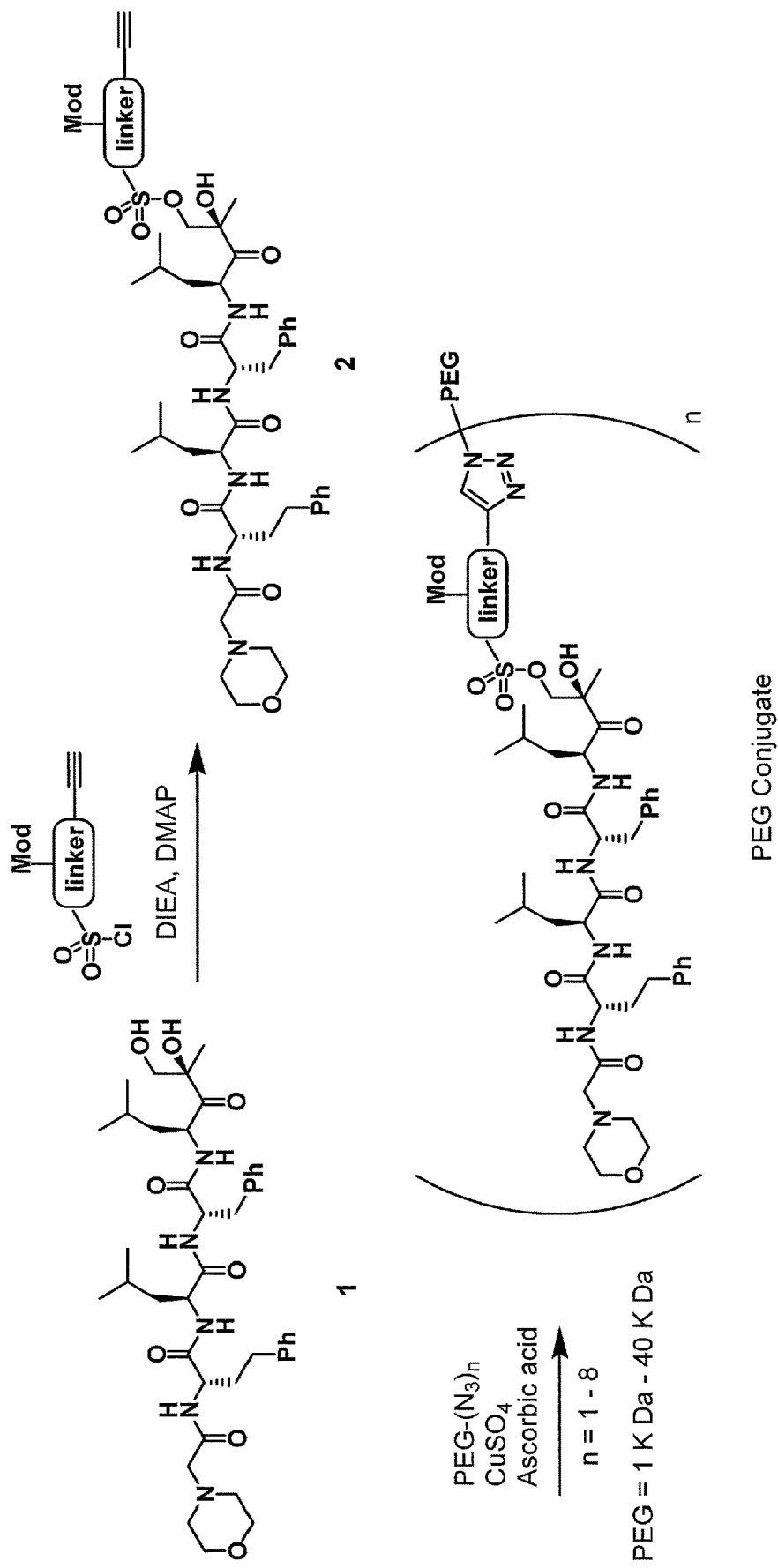
FIG. 14 is a scheme showing an embodiment of an epoxy ketone proteasome inhibitor prodrug conjugated to a sulfonate-linking group containing a PEG moiety by way of the PEG-containing sulfonyl chloride.

As discussed above, the epoxy moiety of the epoxy ketone protease inhibitor can be converted to a diol. The PEG conjugate can be formed by the linkage of the diol to PEG, via an electron density modulated alkyl or aryl sulfonate bearing a functional group compatible with known PEG attachment chemistries. Referring to FIG. 14, the sulfonate linkage is formed by the reaction of a diol (e.g., diol 1) with an appropriately substituted sulfonyl chloride in the presence of a base such as DIEA and a catalytic amount of DMAP. Functionalized PEG reagents are commercially available for attachment via a variety of different chemistries. "Click" chemistry methods, particularly the [3+2] cycloaddition of an azide and an alkyne, are desirable for their large thermodynamic driving force, high yields and lack of offensive byproducts. The reaction of example intermediate 2 with azide functionalized PEG reagents in the presence of a copper(I) catalyst provides the PEG conjugates in high yield. The reaction can be carried out, for example, by mixing the PEG azide reagent, compound 2, copper sulfate, and a reducing agent such as ascorbic acid or sodium ascorbate in organic solvents such as DMF, or in mixtures of DMF and water. The product can be purified by precipitation, reverse phase chromatography or size exclusion chromatography. The use of copper catalyst can be avoided if desired via copper-free click chemistry involving the cycloaddition of azides and dibenzocyclooctyne derivatized reagents. Linear and multi-arm PEG azide reagents are commercially available in sizes ranging from 1 KDa to 40 KDa, and are appended with 1-8 reactive azide functional groups. In some embodiments, large, multi-arm PEGs are advantageous since they are capable of providing a higher drug loading, provide greater protection against proteolytic degradation, and/or their hydrodynamic size precludes renal clearance. The synthetic route described is suitable for the preparation of large multi-arm PEG conjugates.

Figure 15:
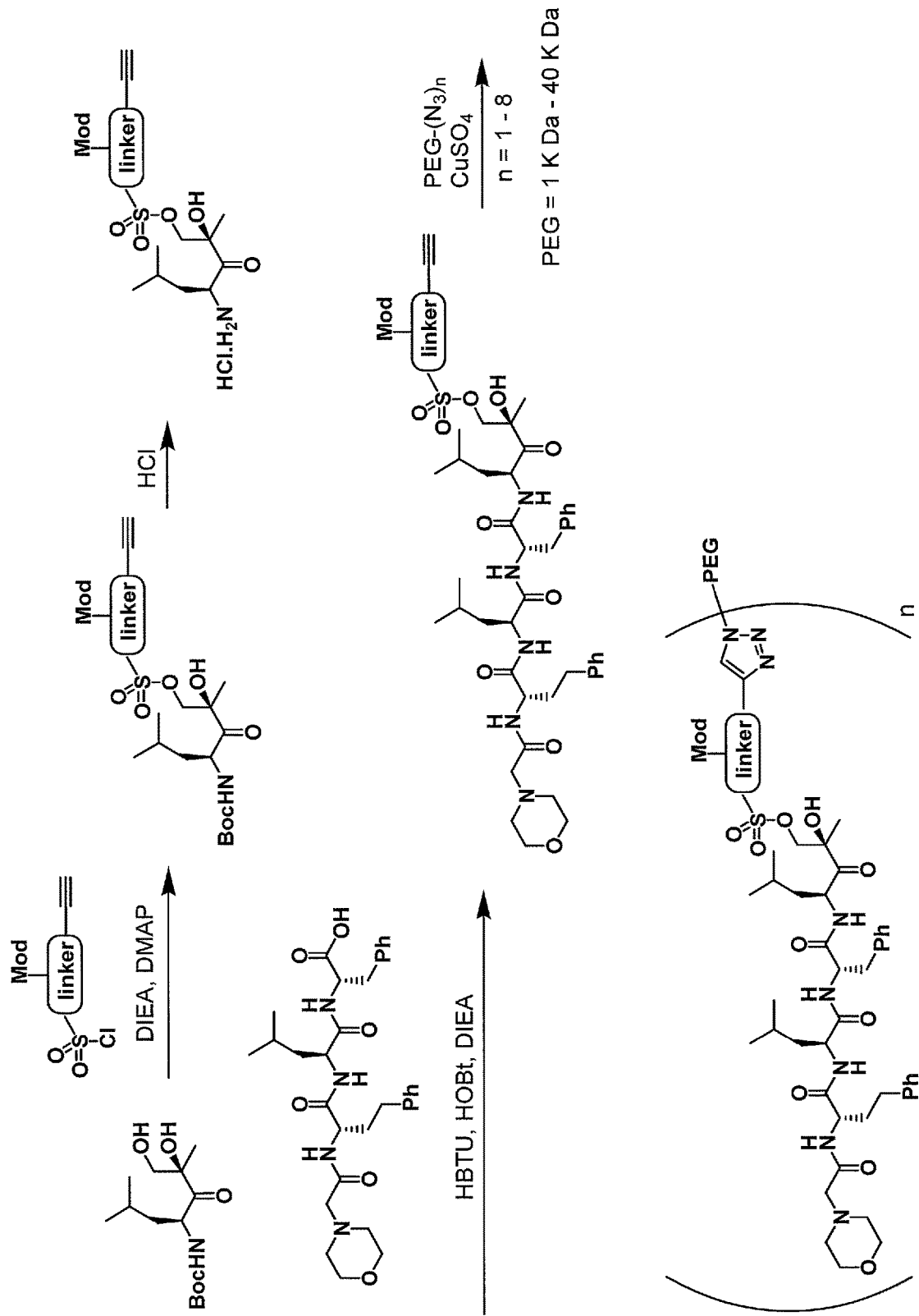
FIG. 15 is a scheme showing the conjugation of a PEG of molecular weight between 1-40 kDa onto a sulfonate-containing epoxy ketone proteasome inhibitor prodrug.

Referring to FIG. 15, in some embodiments, the PEG conjugates are prepared in a step-wise fashion as shown with an exemplary epoxy ketone protease inhibitor.

Sulfonate Linkers for PEG Conjugates

The rate of cyclization and displacement can be controlled, for example, by tuning the electron density of the sulfonate linker group. Table F shows sulfonate linker groups having a variety of electron rich and electron poor groups, prior to cyclization with PEG-(N$_3$)$_n$ using click chemistry.

TABLE F

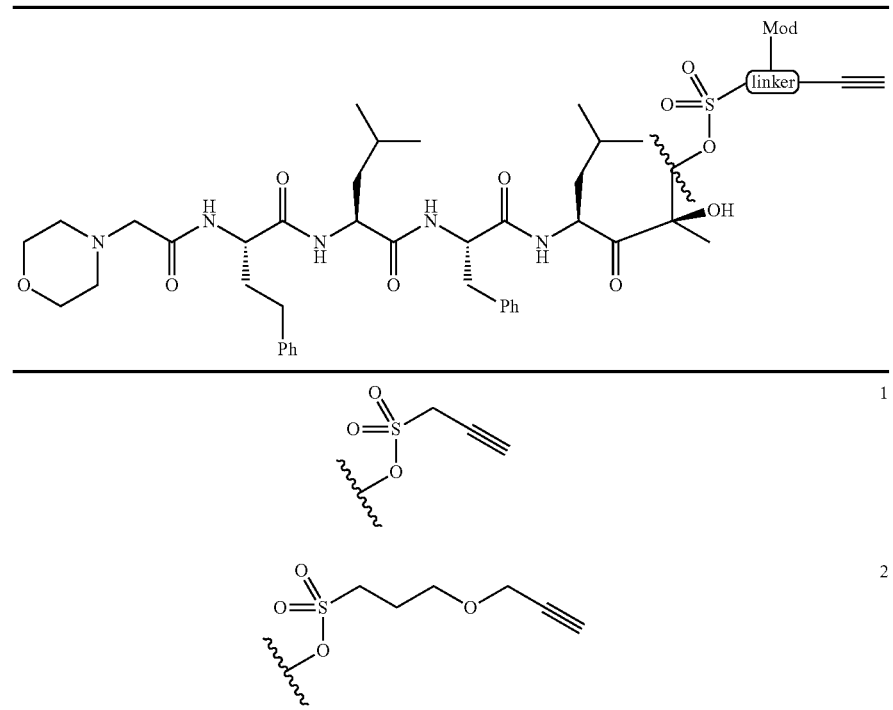

TABLE F-continued
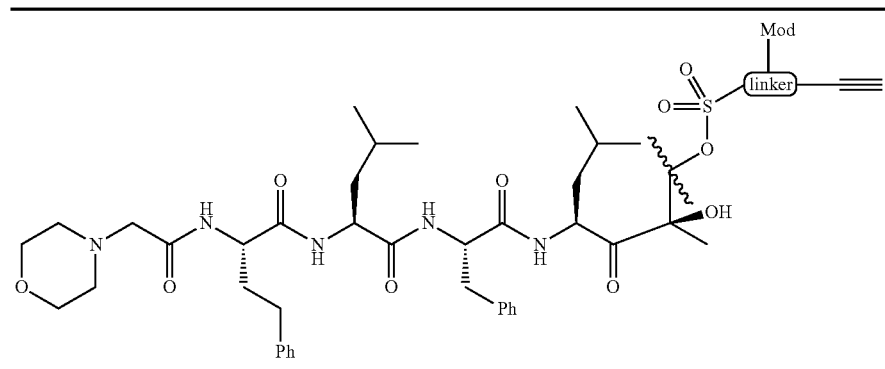
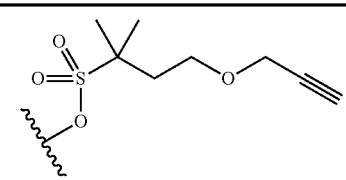  3
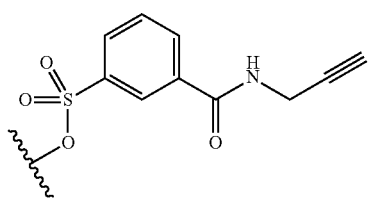 [SMILES: *OS(=O)(=O)c1cccc(C(=O)NCC#C)c1]  4
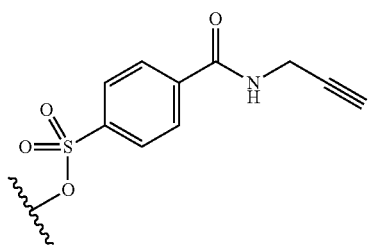 [SMILES: *OS(=O)(=O)c1ccc(C(=O)NCC#C)cc1]  5
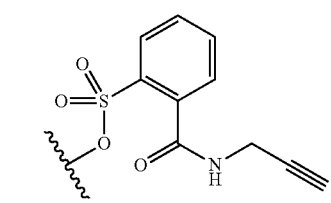 [SMILES: *OS(=O)(=O)c1ccccc1C(=O)NCC#C]  6
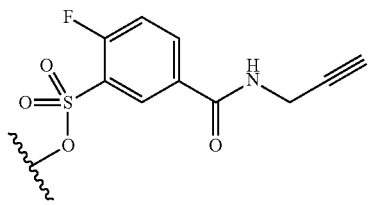 [SMILES: *OS(=O)(=O)c1cc(C(=O)NCC#C)ccc1F]  7
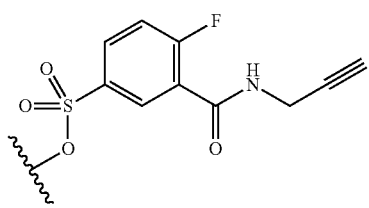 [SMILES: *OS(=O)(=O)c1ccc(F)c(C(=O)NCC#C)c1]  8

TABLE F-continued
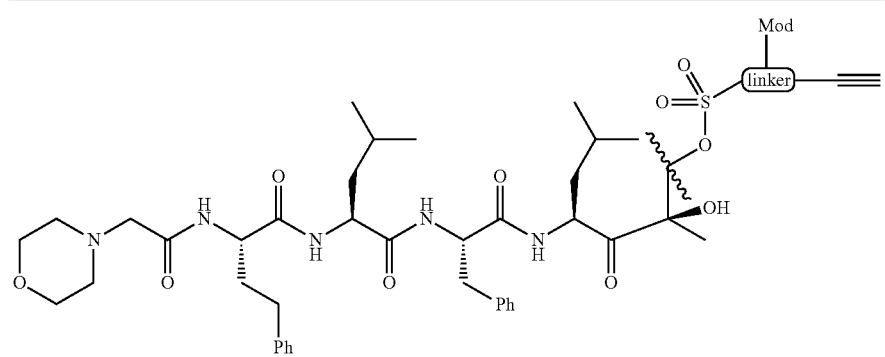
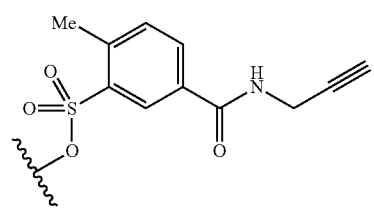 [SMILES: *OS(=O)(=O)c1cc(C(=O)NCC#C)ccc1C]
9
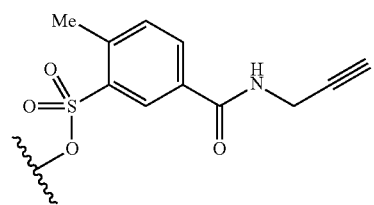 [SMILES: *OS(=O)(=O)c1cc(C(=O)NCC#C)ccc1C]
10
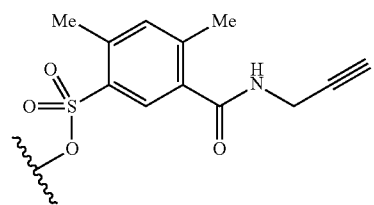 [SMILES: *OS(=O)(=O)c1cc(C(=O)NCC#C)c(C)cc1C]
11
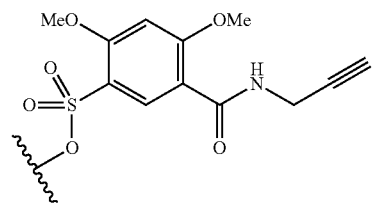 [SMILES: *OS(=O)(=O)c1cc(C(=O)NCC#C)c(OC)cc1OC]
12
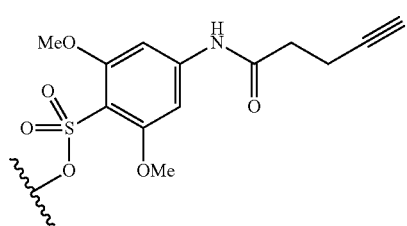 [SMILES: *OS(=O)(=O)c1c(OC)cc(NC(=O)CCC#C)cc1OC]
13

TABLE F-continued
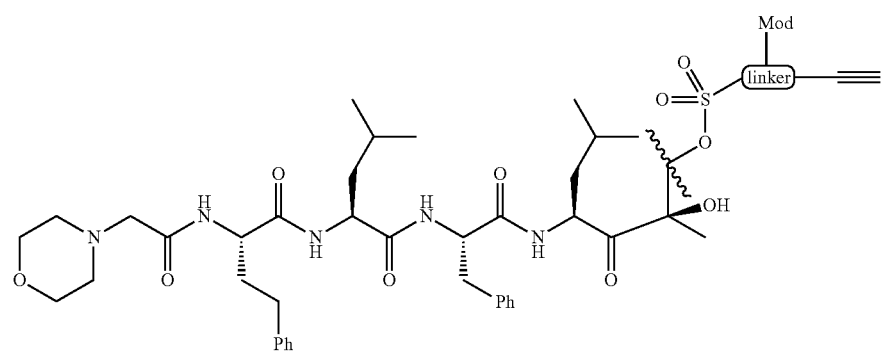
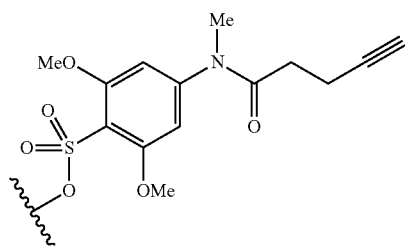 [SMILES: *OS(=O)(=O)c1c(OC)cc(N(C)C(=O)CCC#C)cc1OC]
14
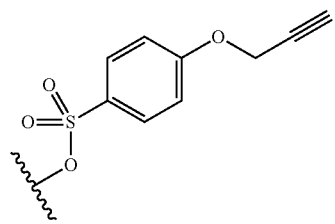 [SMILES: *OS(=O)(=O)c1ccc(OCC#C)cc1]
15
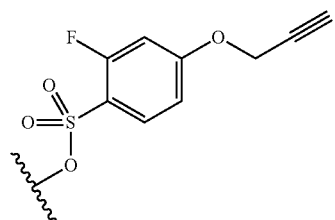 [SMILES: *OS(=O)(=O)c1ccc(OCC#C)cc1F]
16
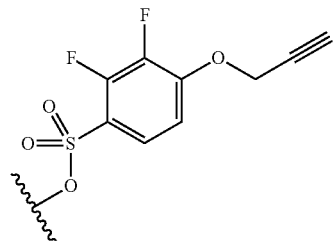 [SMILES: *OS(=O)(=O)c1ccc(OCC#C)c(F)c1F]
17
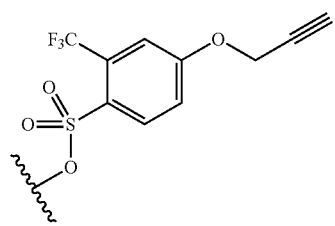 [SMILES: *OS(=O)(=O)c1ccc(OCC#C)cc1C(F)(F)F]
18

TABLE F-continued
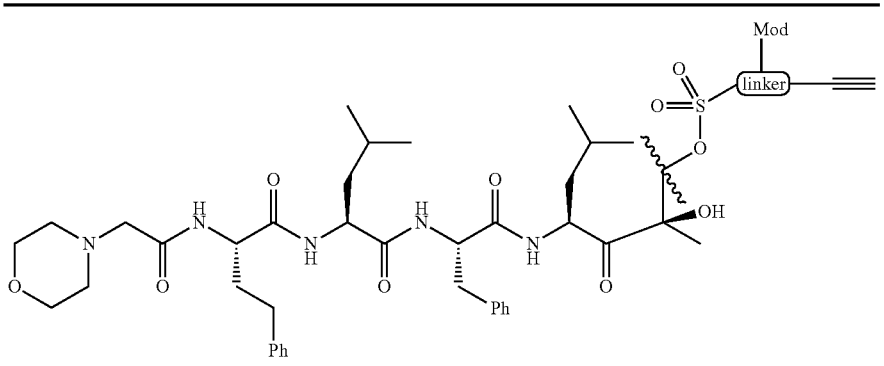
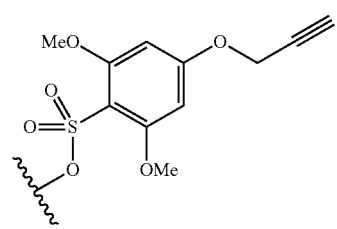 [SMILES: *OS(=O)(=O)c1c(OC)cc(OCC#C)cc1OC]
19
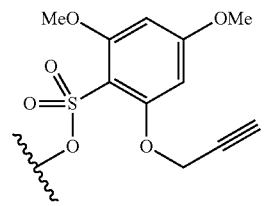 [SMILES: *OS(=O)(=O)c1c(OC)cc(OC)cc1OCC#C]
20
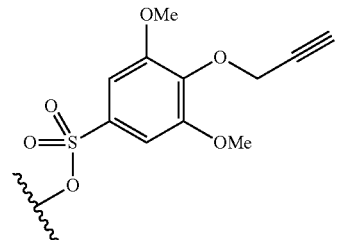 [SMILES: *OS(=O)(=O)c1cc(OC)c(OCC#C)c(OC)c1]
21
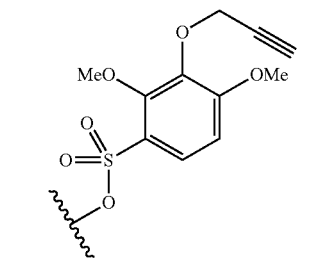 [SMILES: *OS(=O)(=O)c1ccc(OC)c(OCC#C)c1OC]
22
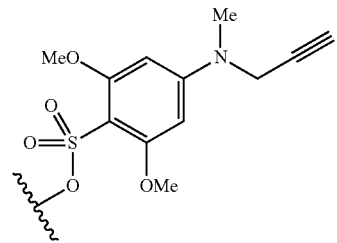 [SMILES: *OS(=O)(=O)c1c(OC)cc(N(C)CC#C)cc1OC]
23

TABLE F-continued
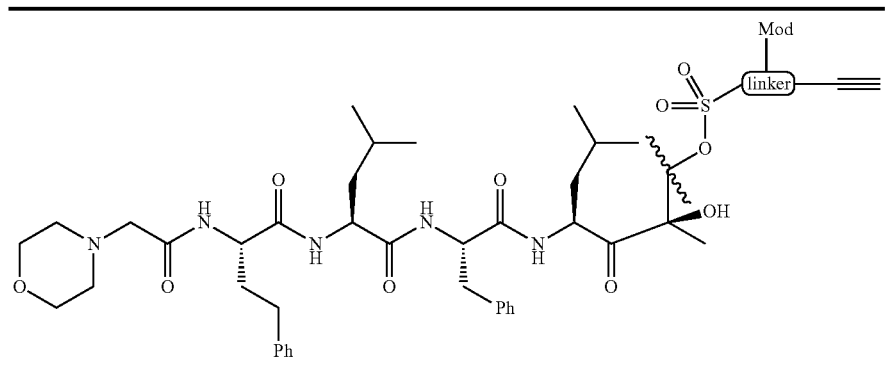
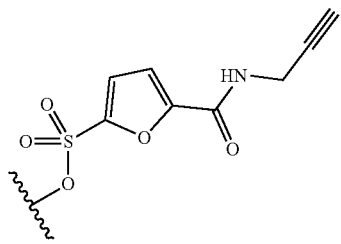 [SMILES: *OS(=O)(=O)c1ccc(C(=O)NCC#C)o1]
24
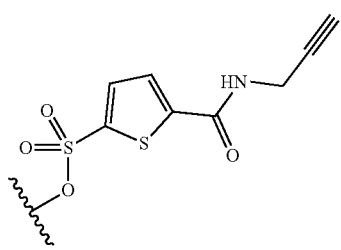 [SMILES: *OS(=O)(=O)c1ccc(C(=O)NCC#C)s1]
25
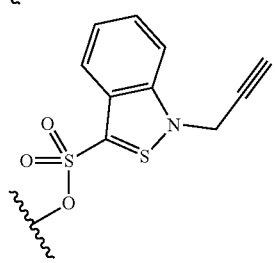
26
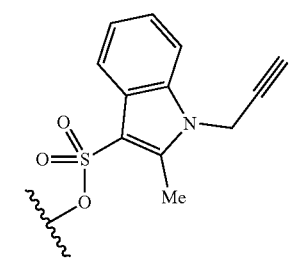 [SMILES: *OS(=O)(=O)c1c(C)n(CC#C)c2ccccc12]
27
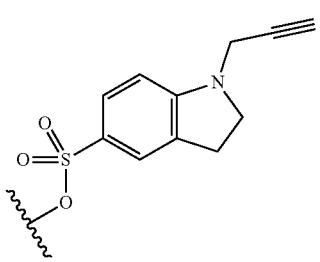 [SMILES: *OS(=O)(=O)c1ccc2c(c1)CCN2CC#C]
28

TABLE F-continued
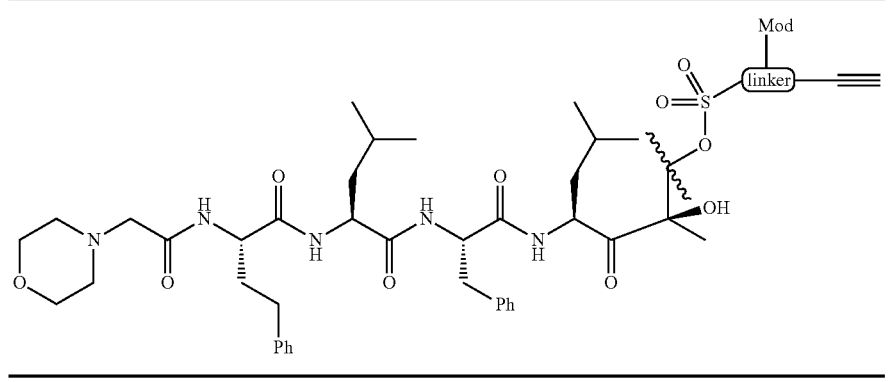
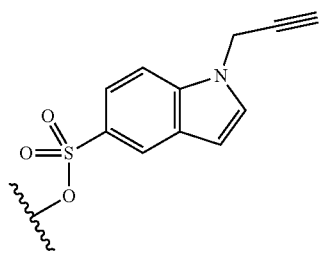 [SMILES: *OS(=O)(=O)c1ccc2c(ccn2CC#C)c1]
29
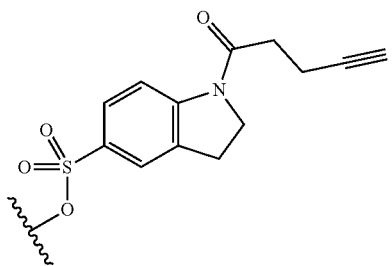 [SMILES: *OS(=O)(=O)c1ccc2c(c1)CCN2C(=O)CCC#C]
30
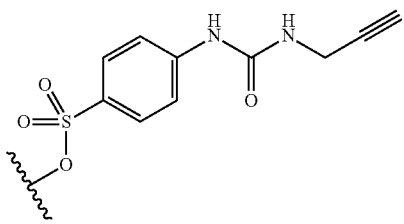 [SMILES: *OS(=O)(=O)c1ccc(NC(=O)NCC#C)cc1]
31
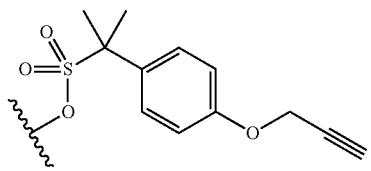 [SMILES: *OS(=O)(=O)C(C)(C)c1ccc(OCC#C)cc1]
32
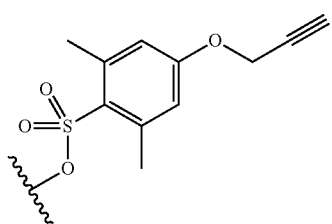 [SMILES: *OS(=O)(=O)c1c(C)cc(OCC#C)cc1C]
33

TABLE F-continued
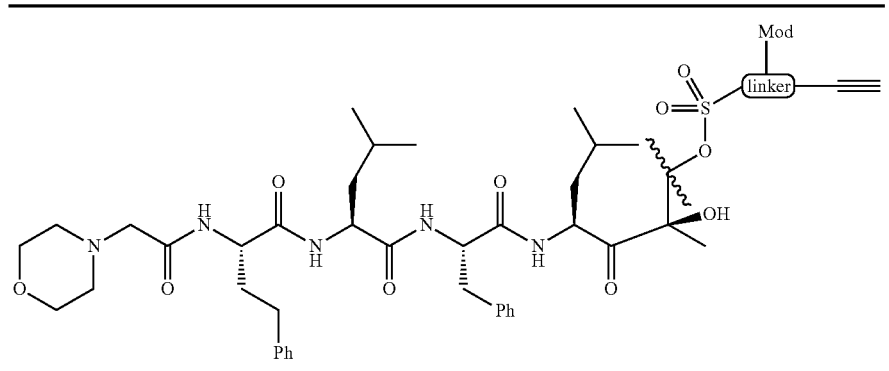
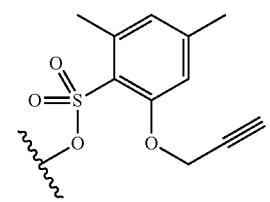 [SMILES: *OS(=O)(=O)c1c(C)cc(C)cc1OCC#C]
34
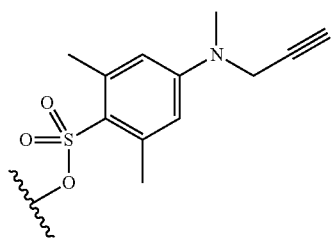 [SMILES: *OS(=O)(=O)c1c(C)cc(N(C)CC#C)cc1C]
35
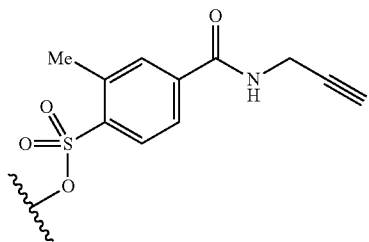 [SMILES: *OS(=O)(=O)c1ccc(C(=O)NCC#C)cc1C]
36
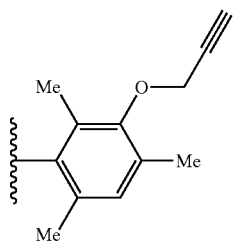 [SMILES: *c1c(C)cc(C)c(OCC#C)c1C]
37
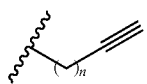
38
n = 1-10
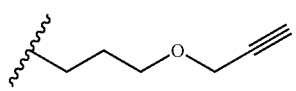 [SMILES: *CCCOCC#C]
39

TABLE F-continued

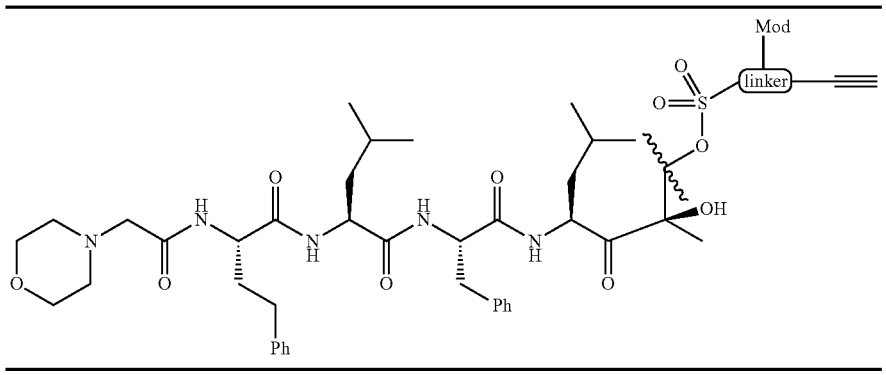

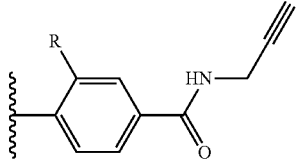

40

R = Me, Ome, hao

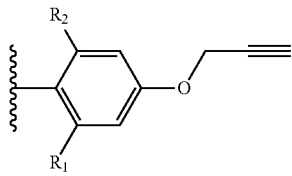

41

$R_1, R_2 = H$ or $R_1$ = alkyl, $R_2 = H$ or
$R_1, R_2$ = alky or $R_1$ = Oalky, $R_2 = H$ or
$R_1, R_2$ = Oalky or $R_1$ = halo. $R_2 = H$ Alternatively, the sulfonate group may be attached by an alkylene or heteroalkylene linker to a carboxylic acid prior to coupling with an amino-substituted PEG. Table F' shows some examples of linkers prior to coupling with PEG-$(NH_2)_n$ using standard amide coupling chemistry.

TABLE F'

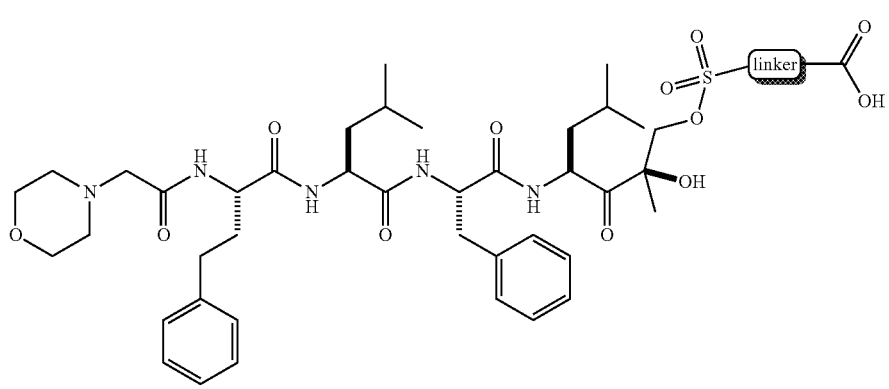

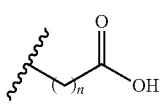

1 n = 1-11

TABLE F'-continued

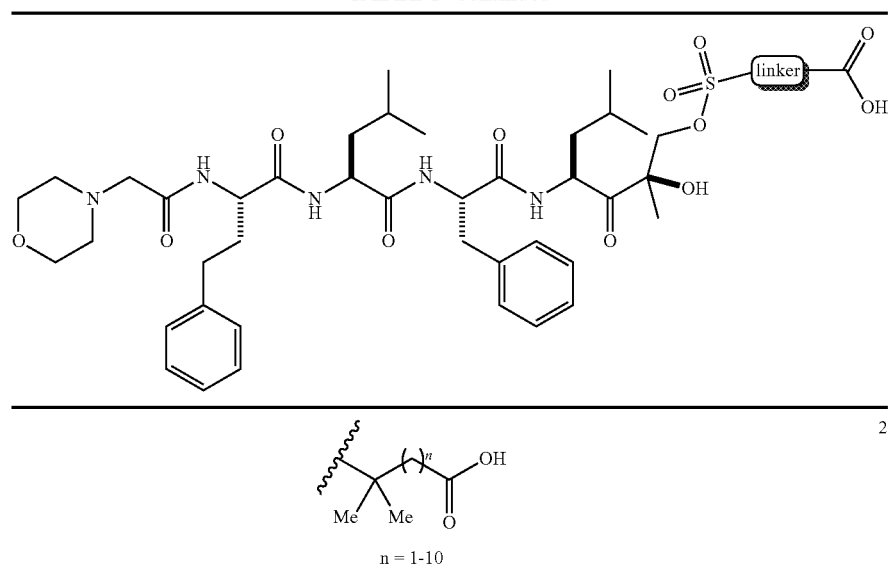

n = 1-10

Figure 16:
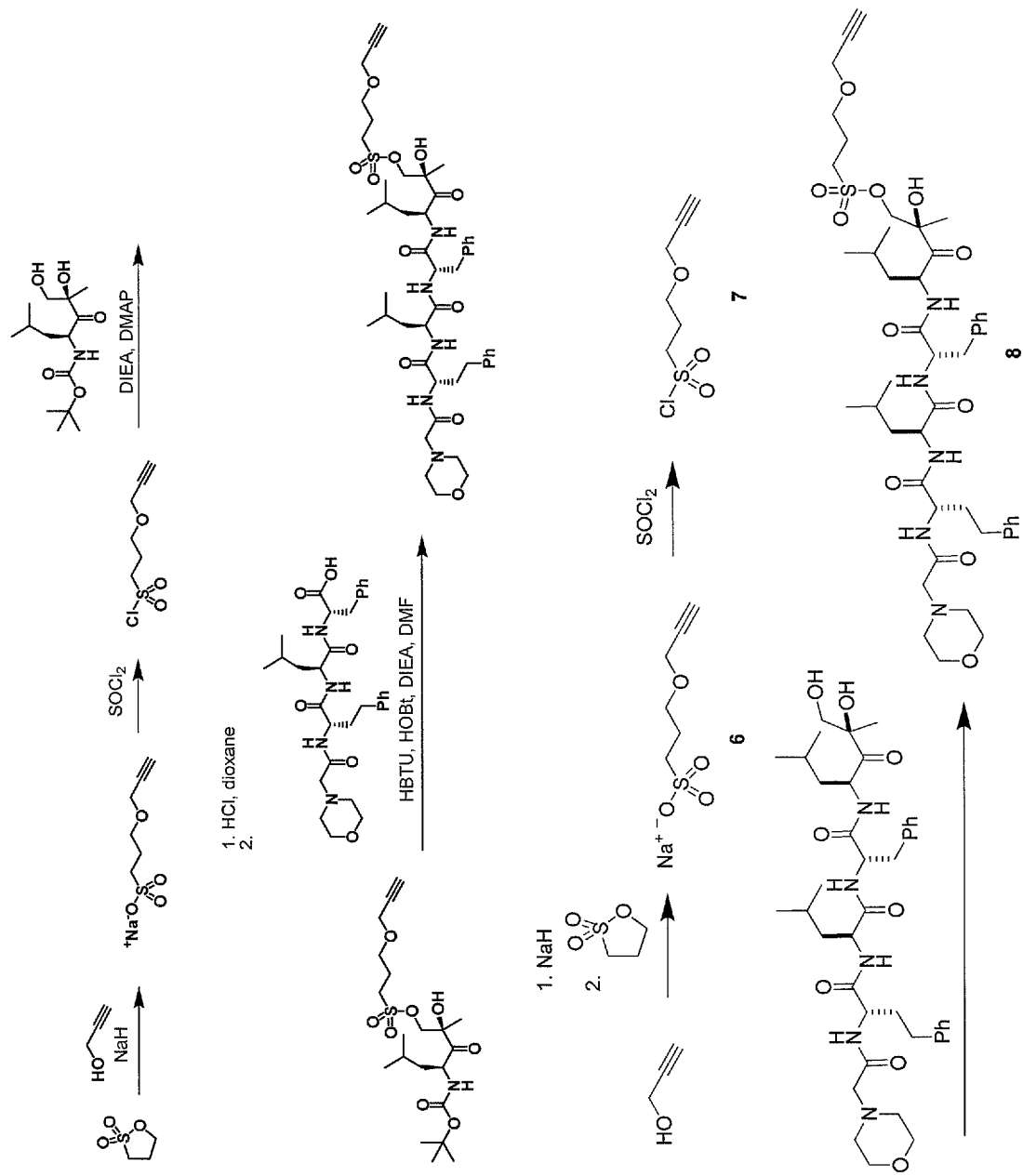
FIG. 16 is a scheme showing the general synthesis of an alkyl sulfonate-containing epoxy ketone proteasome inhibitor prodrug.
Figure 17:
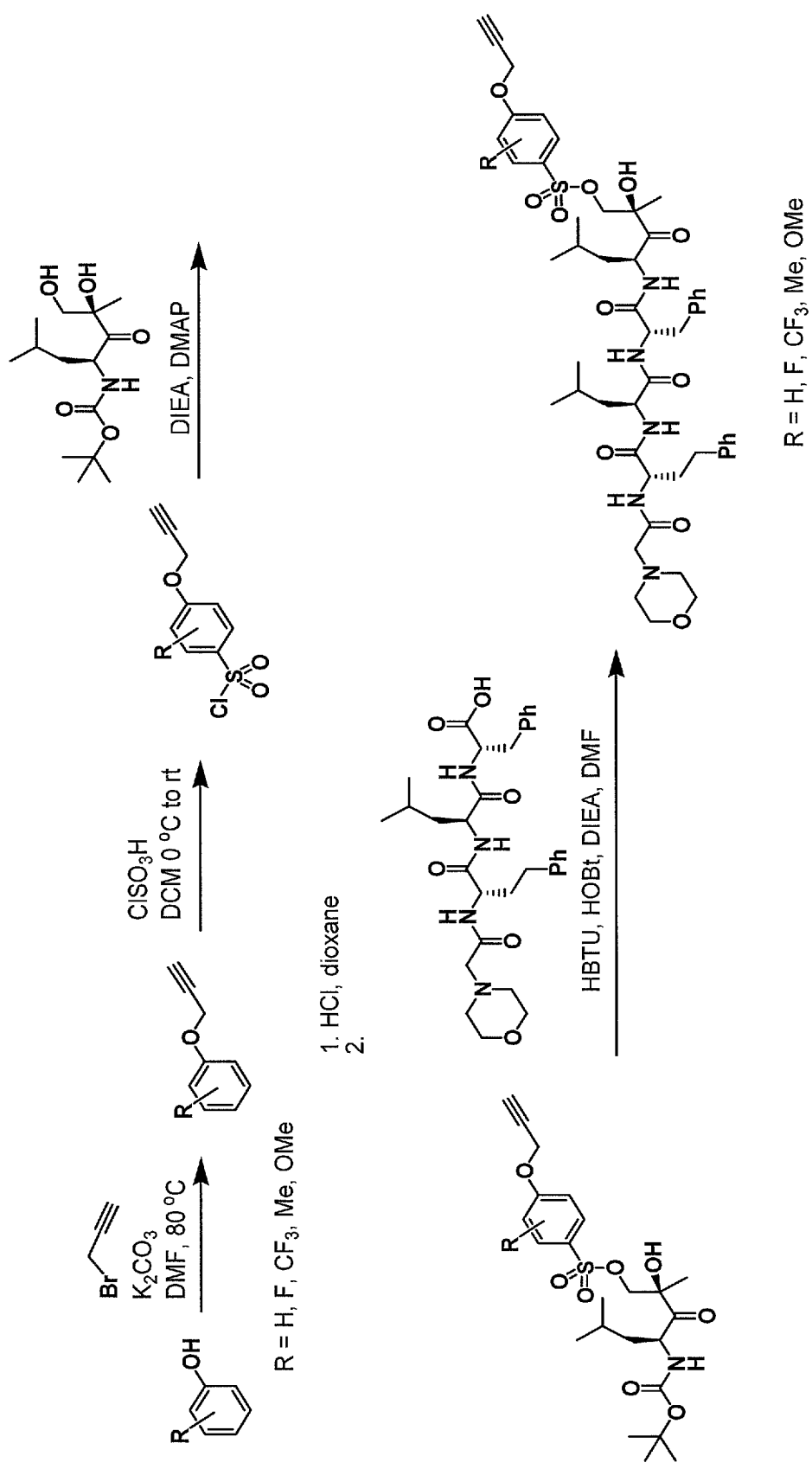
FIG. 17 is a scheme showing the general synthesis of a phenoxysulfonate-containing epoxy ketone proteasome inhibitor prodrug.
Figure 18:
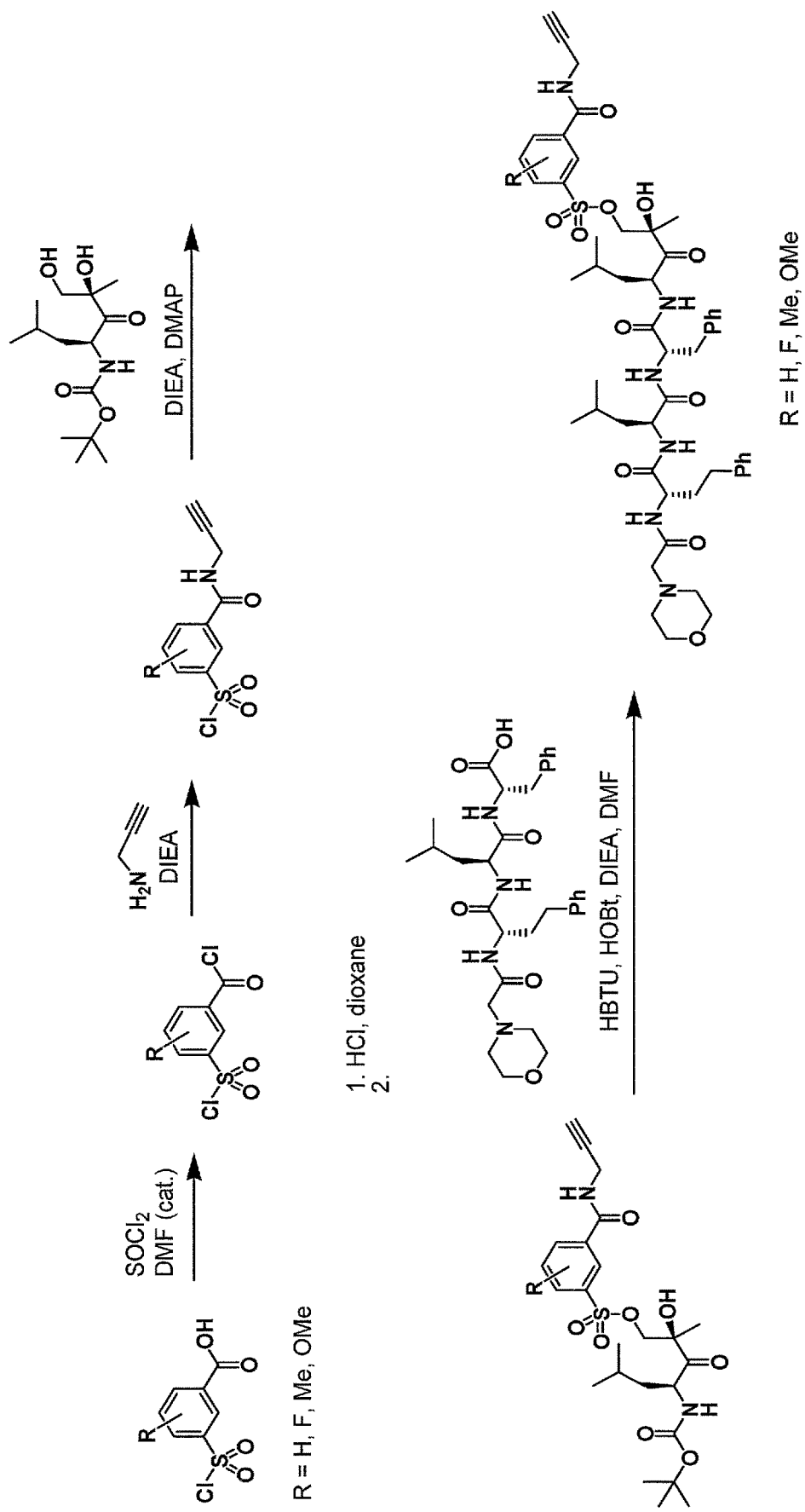
FIG. 18 is a scheme showing the general synthesis of an aryl sulfonate-containing epoxy ketone proteasome inhibitor prodrug.

Referring to FIGS. 16-18, in some embodiments, the synthesis of the required sulfonate building blocks are carried out according to the example schemes. FIG. 16 shows the general synthesis of alkyl sulfonate building blocks. FIG. 17 shows the general synthesis of a phenoxy sulfonate building block. FIG. 18 shows the general synthesis of a benzamide sulfonate building block.

Figure 4:
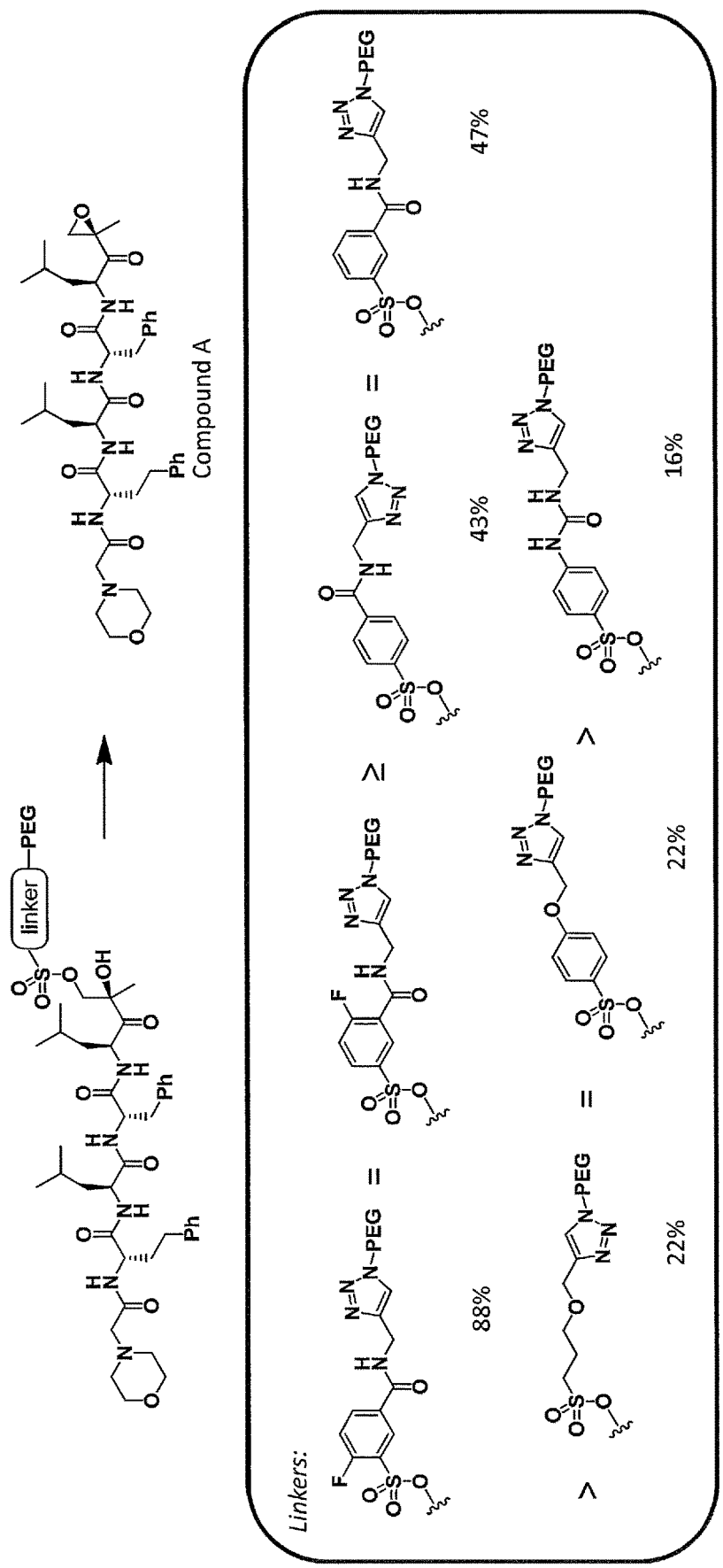
FIG. 4 is a scheme showing cyclization rates of embodiments of epoxy ketone protease inhibitor prodrugs in pH 7.4 buffer.

The release capabilities of PEG conjugates can be assessed by quantitation of epoxy ketone protease inhibitors released in a basic buffer solution, by NMR, and by MALDI-TOF NMR. Reformation rates of various example PEG conjugates are shown, for example, in FIG. 4.

Ketone Modified Prodrugs

In some embodiments, the ketone moiety of the epoxy ketone protease inhibitors is replaced with a masked ketone moiety, a spacer, and a conjugate. The ketone modified prodrugs can revert back to an active epoxide form under certain conditions.

Figure 19:
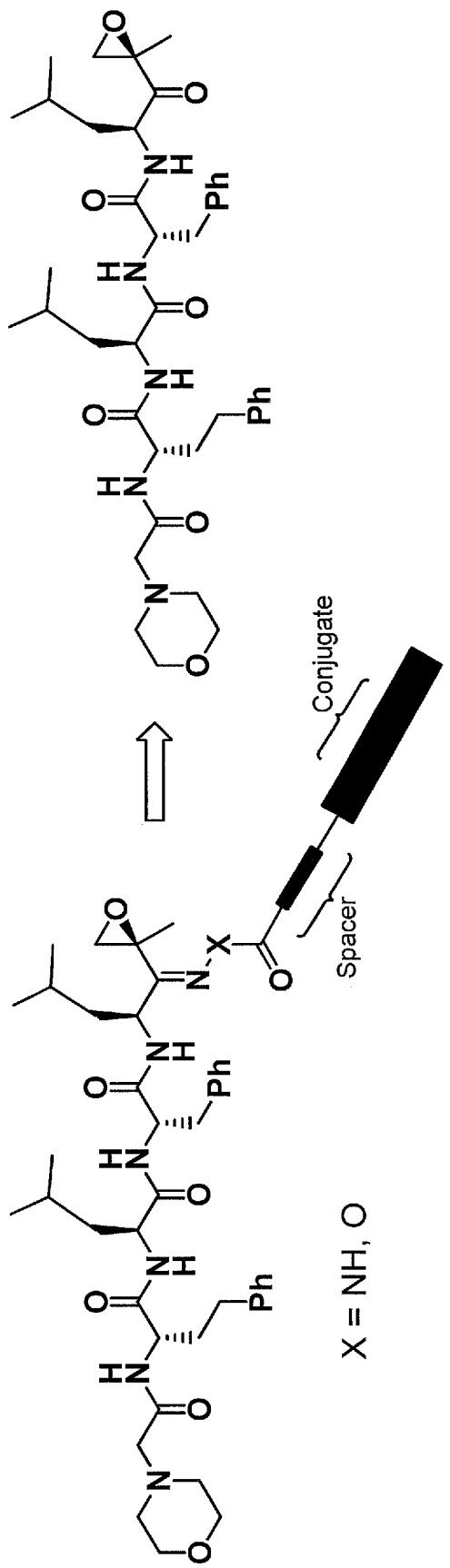
FIG. 19 is a scheme showing an embodiment of epoxy ketone proteasome inhibitor prodrug containing a masked ketone, which undergoes pH driven reconversion to the active inhibitor.

Examples of spacers and conjugates are as listed in FIG. 46. In some embodiments, referring to FIG. 19, where X is either NH or O, epoxy ketone protease inhibitor prodrugs can revert back to the active form at a suitable pH (e.g., a pH of less than 6.5) and/or by enzymatic cleavage (e.g, cleavage by CYP P450). The epoxy ketone protease inhibitor prodrugs can be suitable for subcutaneous and intravenous administration.

Figure 20:
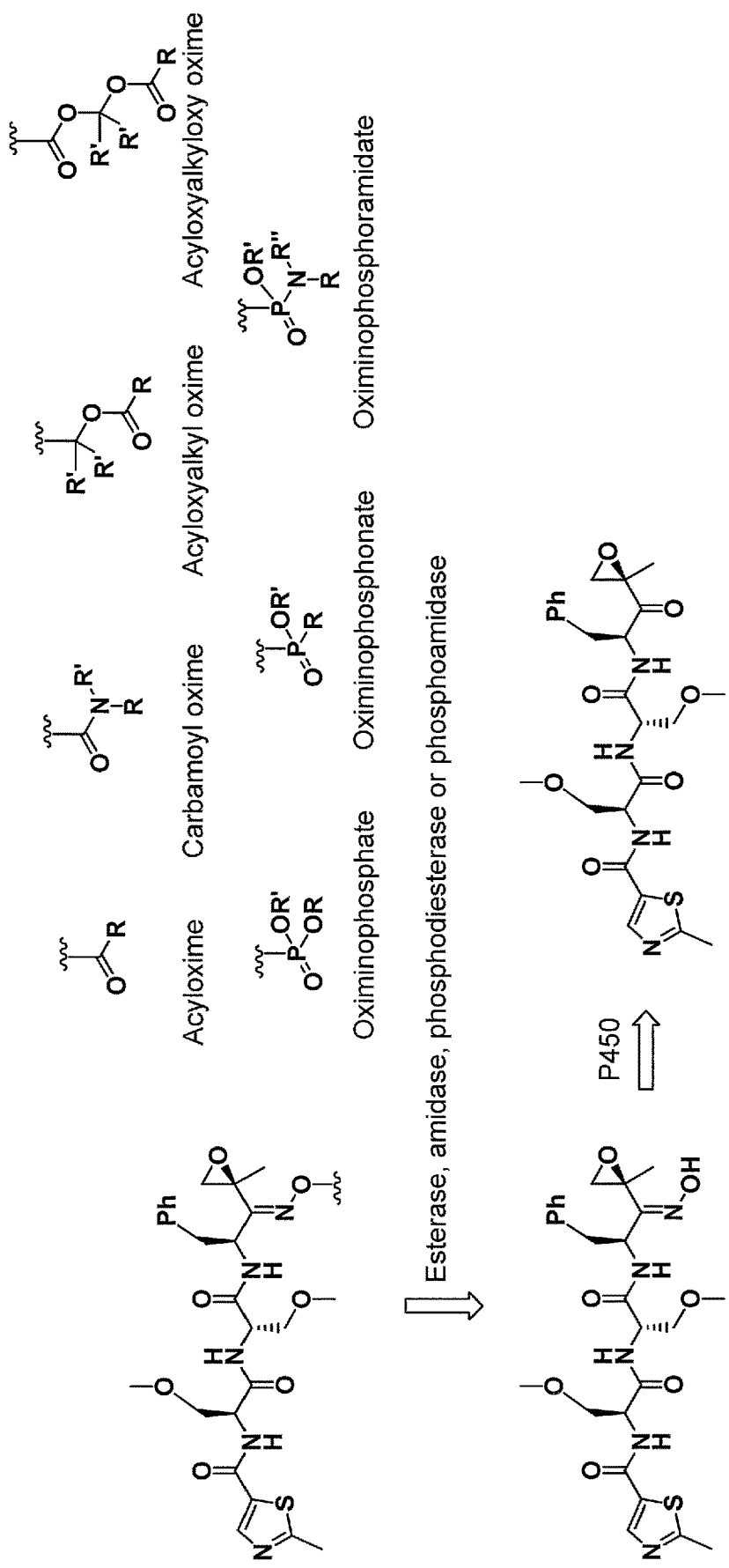
FIG. 20 is a scheme showing an embodiment of epoxy ketone proteasome inhibitor prodrug containing a masked ketone, which undergoes reconversion to the active inhibitor through an esterase, amidase, phosphodiesterase, or phosphoamidase.

In some embodiments, referring to FIG. 20, the ketone is modified by oximes such as, but not limited to, acyloxime, carbamoyl oxime, acyloxyaklyl oxime, acyloxyalkyloxy oxime, oximinophosphate, oximinophosponate and oximinophosphoramidate. R is, but not limited to, alkyl, aryl, or a permeability enhancer. The prodrugs can revert back to the active form by cleavage with an enzyme such as esterase, amidase, phosphodiesterase, or phosphoamidase, and subsequently by CYP P450. The prodrugs can be suitable for oral administration.

Figure 21:
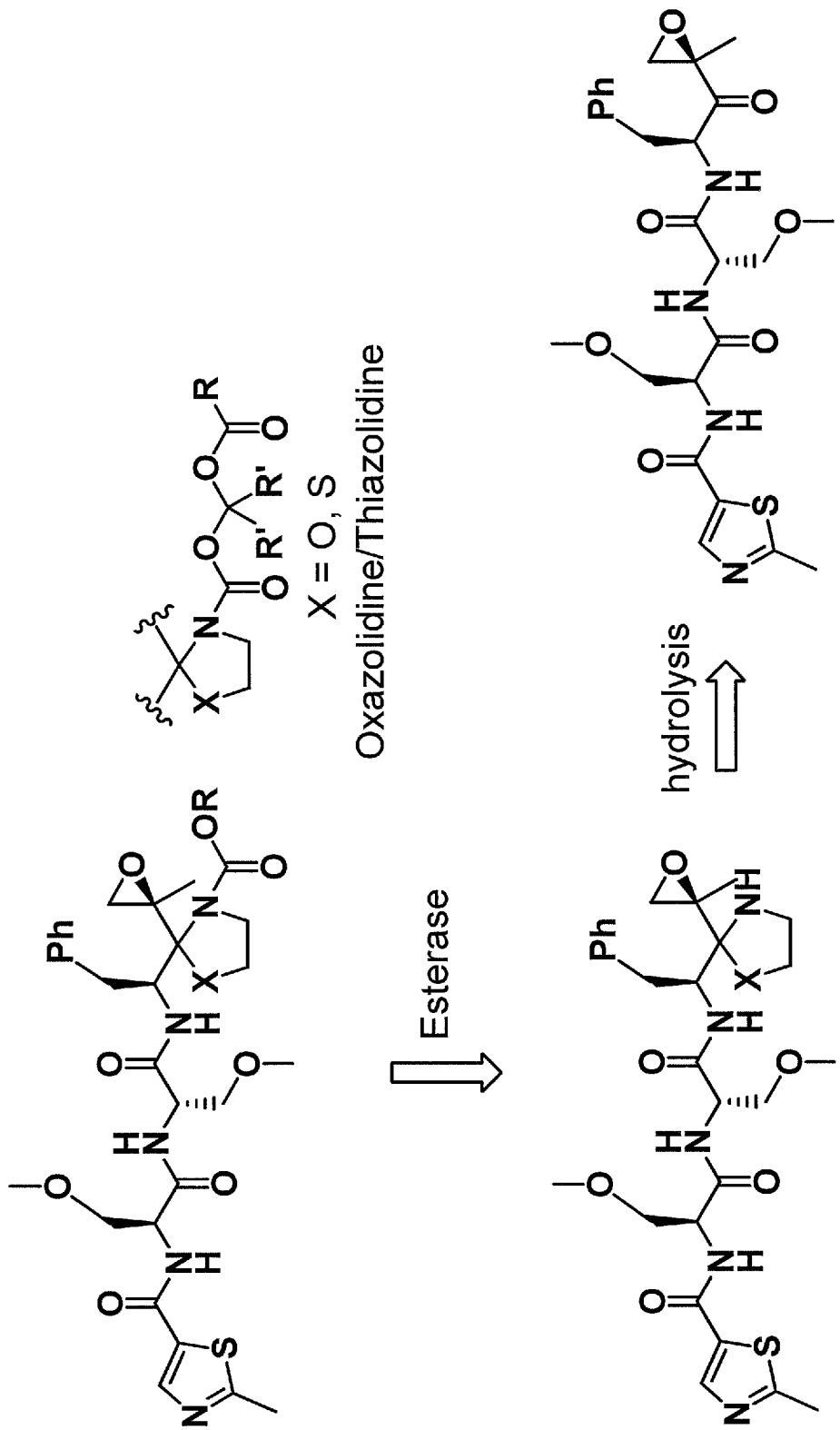
FIG. 21 is a scheme showing an embodiment of epoxy ketone proteasome inhibitor prodrug containing a masked ketone, which undergoes hydrolysis to the active inhibitor.

In some embodiments, referring to FIG. 21, the ketone is modified by oxazolidine or thiazolidine; and R is, but not limited to, alkyl, aryl or a permeability enhancer. The ketone modified prodrugs can revert back to the active form in tandem to esterase activation. The prodrugs can be suitable for oral administration.

Figure 22:
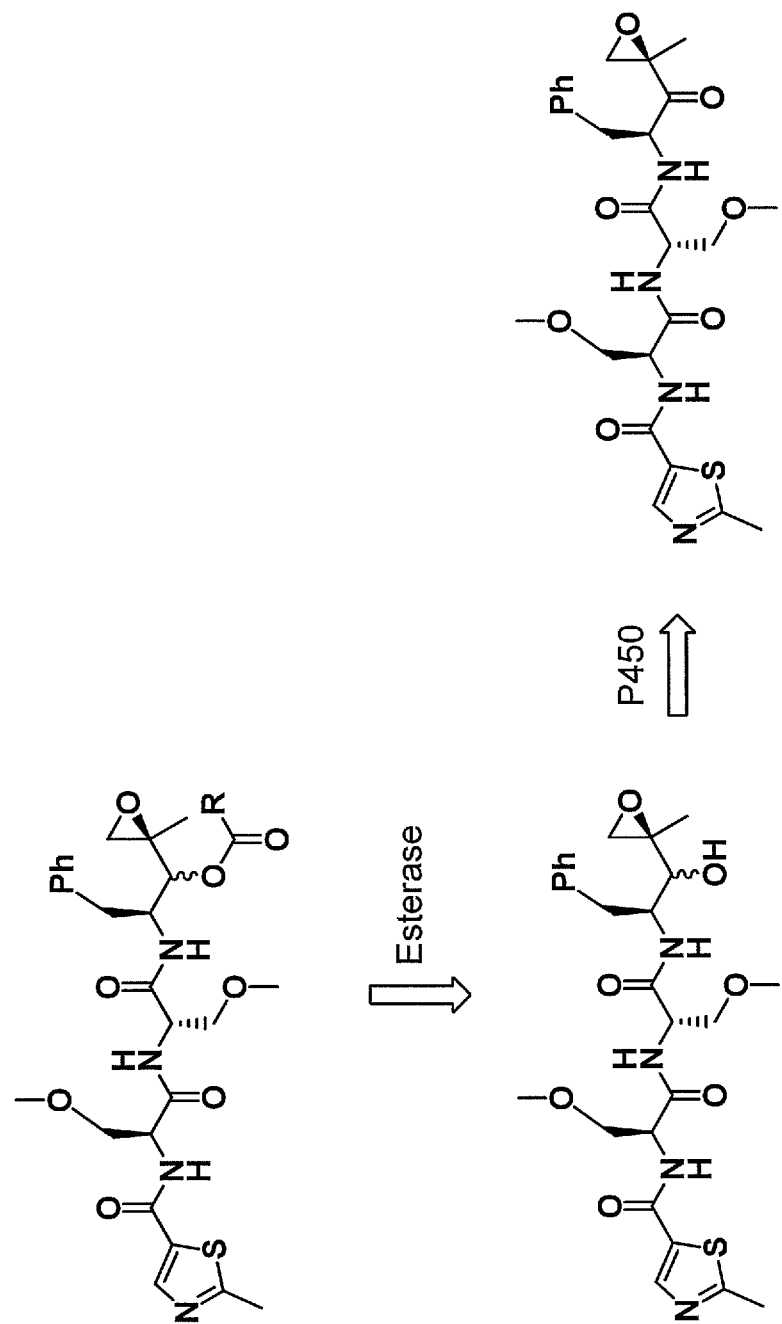
FIG. 22 is a scheme showing an embodiment of epoxy ketone proteasome inhibitor prodrug containing a masked ketone, which undergoes hydrolysis by an esterase then oxidation to the active inhibitor.

In some embodiments, referring to FIG. 22, the ketone is a modified epoxy alcohol and R is, but not limited to, alkyl, aryl or a permeability enhancer. The ketone modified prodrugs can revert back to the active form in tandem to esterase activation, followed by CYP P450 oxidation. The prodrugs can be suitable for oral administration.

N-Acyloxymethyl Prodrugs

In some embodiments, the backbone amide of the epoxy ketone protease inhibitors is masked by a group including a N-acyloxymethyl linker at one of the four amides, a spacer, and a conjugate. The epoxy ketone protease inhibitor prodrugs can be unmasked to reveal the active form by exposing the prodrug to a pH of greater than about 7 and/or by esterase cleavage.

Figure 23:
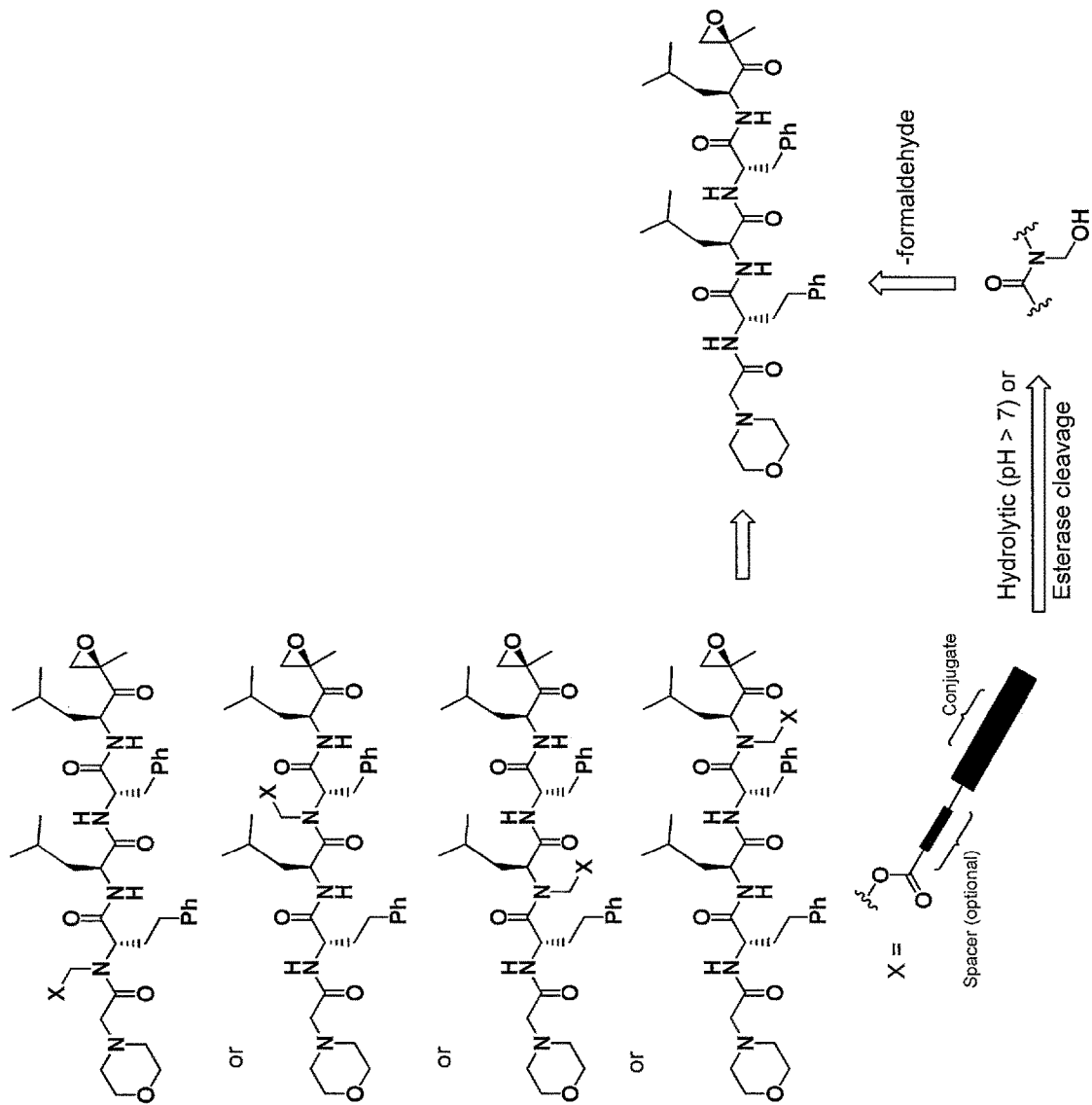
FIG. 23 is a scheme showing embodiments of N-acyloxymethyl-linked epoxy ketone proteasome inhibitor prodrugs containing a morpholine moiety.

FIG. 46 lists examples of spacers and conjugates. Referring to FIG. 23, the N-acyloxymethyl linker can be attached at four different amides. The scheme also shows pH and esterase-driven re-formation of an active form of an exemplary epoxy ketone protease inhibitor. The epoxy ketone protease inhibitors can be suitable for subcutaneous and intravenous administration.

Figure 24:
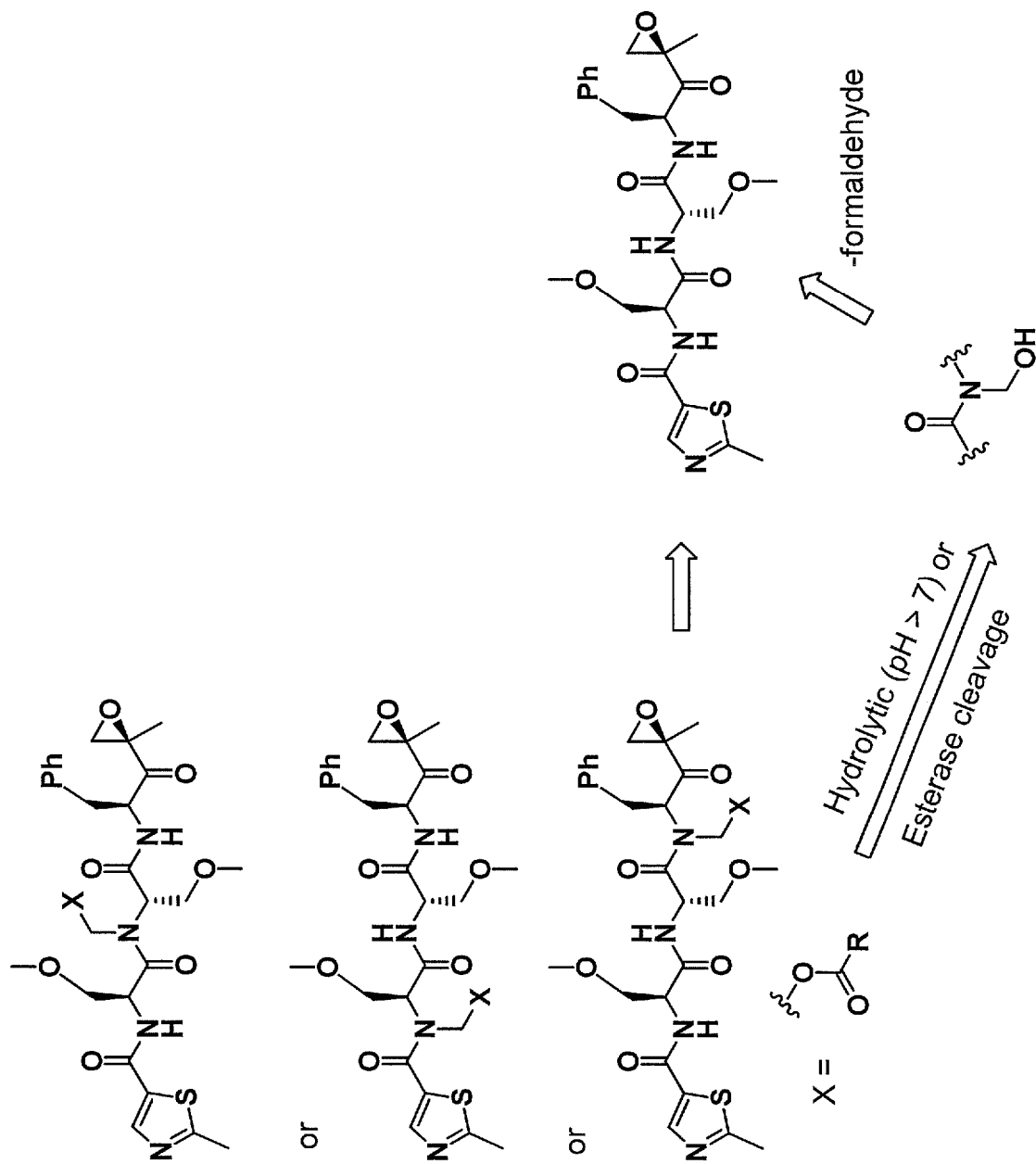
FIG. 24 is a scheme showing embodiments of N-acyloxymethyl-linked epoxy ketone proteasome inhibitor prodrugs containing a thiazole moiety.

Referring to FIG. 24, the N-acyloxymethyl linker can be attached at one of three different amides. R can be, but not limited to, alkyl, aryl or a permeability enhancer. The scheme also shows pH and esterase-driven re-formation of an active form of an exemplary epoxy ketone protease inhibitor. The prodrugs can be designed for oral administration.

Figure 25:
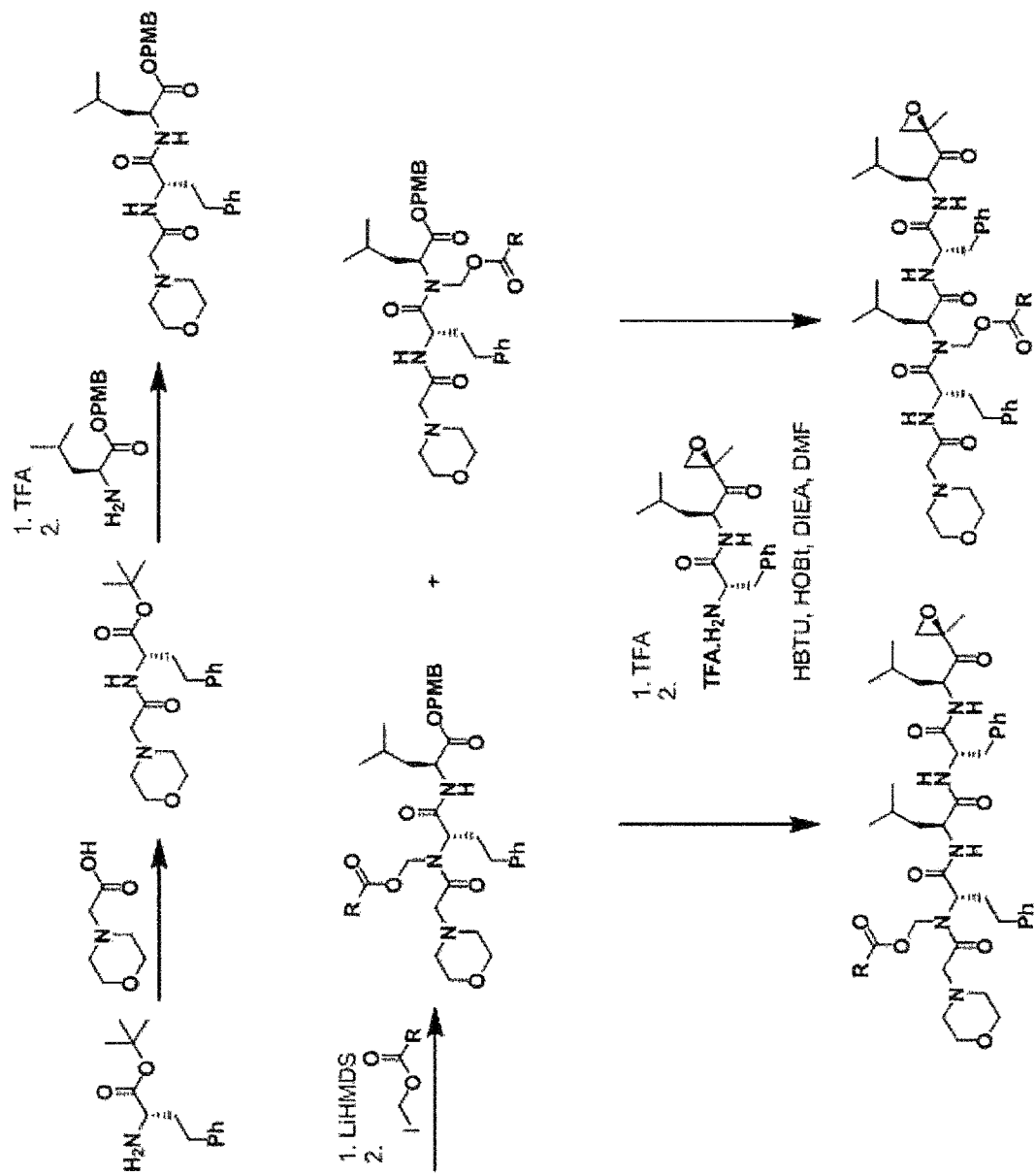
FIG. 25 is a scheme showing an approach to regioselective syntheses of N-acyloxymethyl-linked epoxy ketone proteasome inhibitor prodrugs.
Figure 26:
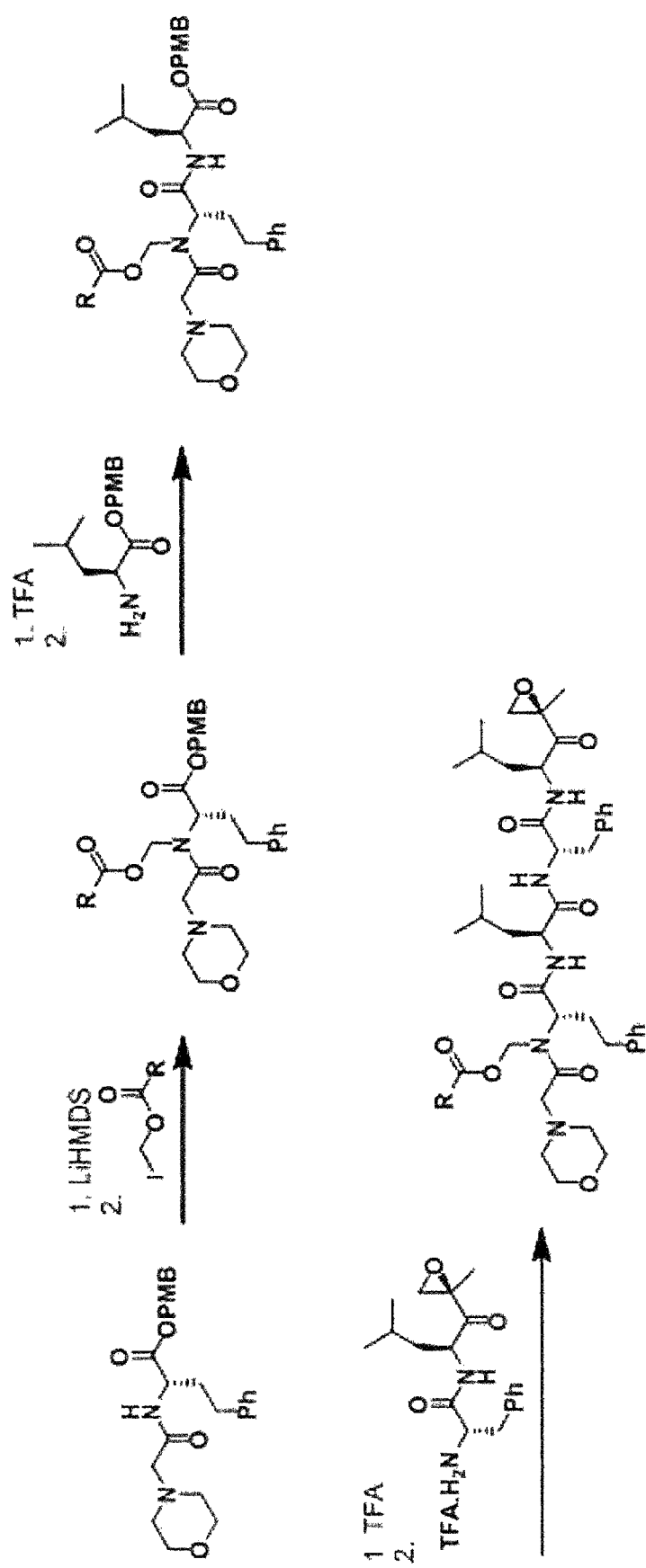
FIG. 26 is a scheme showing an alternate approach to regioselective syntheses of N-acyloxymethyl-linked epoxy ketone proteasome inhibitor prodrugs.

Referring to FIGS. 25-26, the N-acyloxymethyl linker may be attached, in some embodiments, regioselectively. The scheme describes the attachment of the N-acyloxymethyl linker onto $R^{N3}$ and $R^{N4}$, as well as the regiospecific synthesis of an N-acyloxymethyl group on $R^{N4}$.

In some embodiments, the prodrug is one selected from Table E.

TABLE E

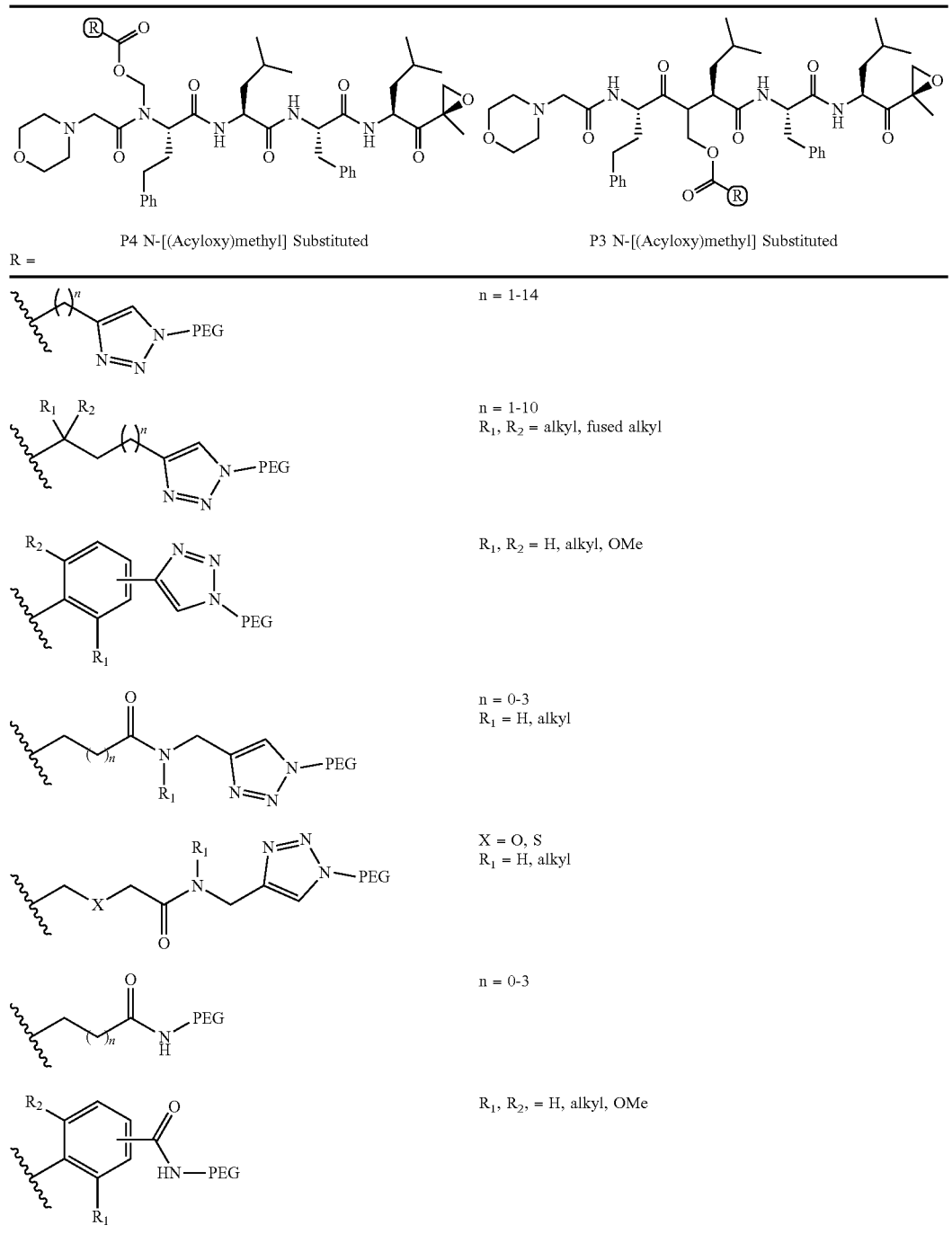

Quaternary Prodrugs

In some embodiments, the N-terminal "cap" of the epoxy ketone protease inhibitors (e.g., the morpholino and 2-methylthiazole cap) is converted to a quaternary salts (e.g., by the addition of a N-acyloxymethyl group). The N-terminal cap can be masked by a group including N-acyloxymethyl linker, optionally a spacer, and a conjugate. The epoxy ketone protease inhibitor prodrugs can be unmasked to the active form exposing the prodrug to a pH of greater than 7 and by esterase cleavage.

Figure 27:
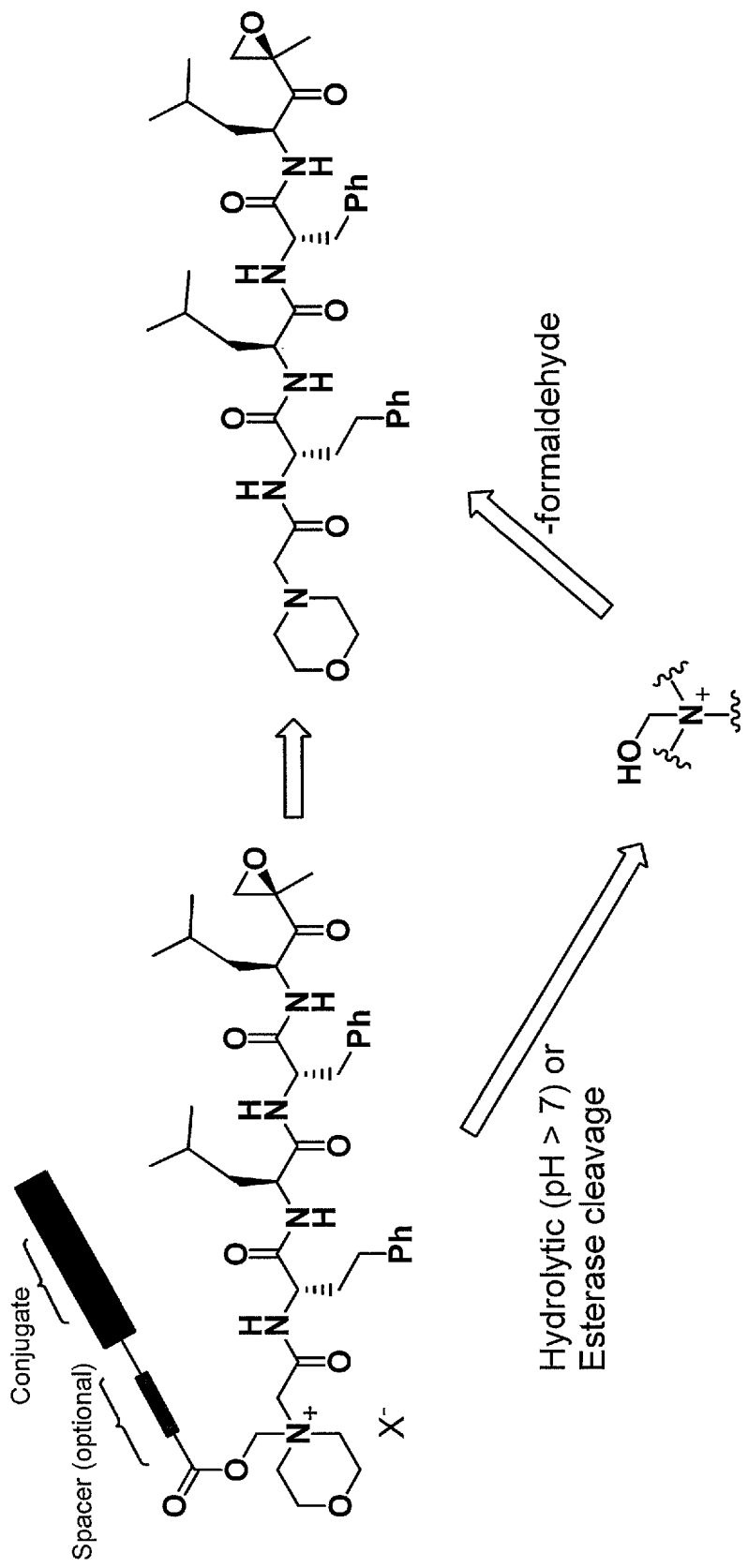
FIG. 27 is a scheme showing embodiments of N-acyloxymethyl-linked quaternary epoxy ketone proteasome inhibitor prodrugs.

Referring to FIG. 27, the N-acyloxymethyl linker can form a quaternary salt with the morpholino N-cap. X can be, but is not limited to, chloride, acetate, mesylate, tosylate, or citrate. Examples of spacers and conjugates are as listed in FIG. 46. The epoxy ketone protease inhibitor prodrugs can be designed for subcutaneous and intravenous administration.

Figure 28:
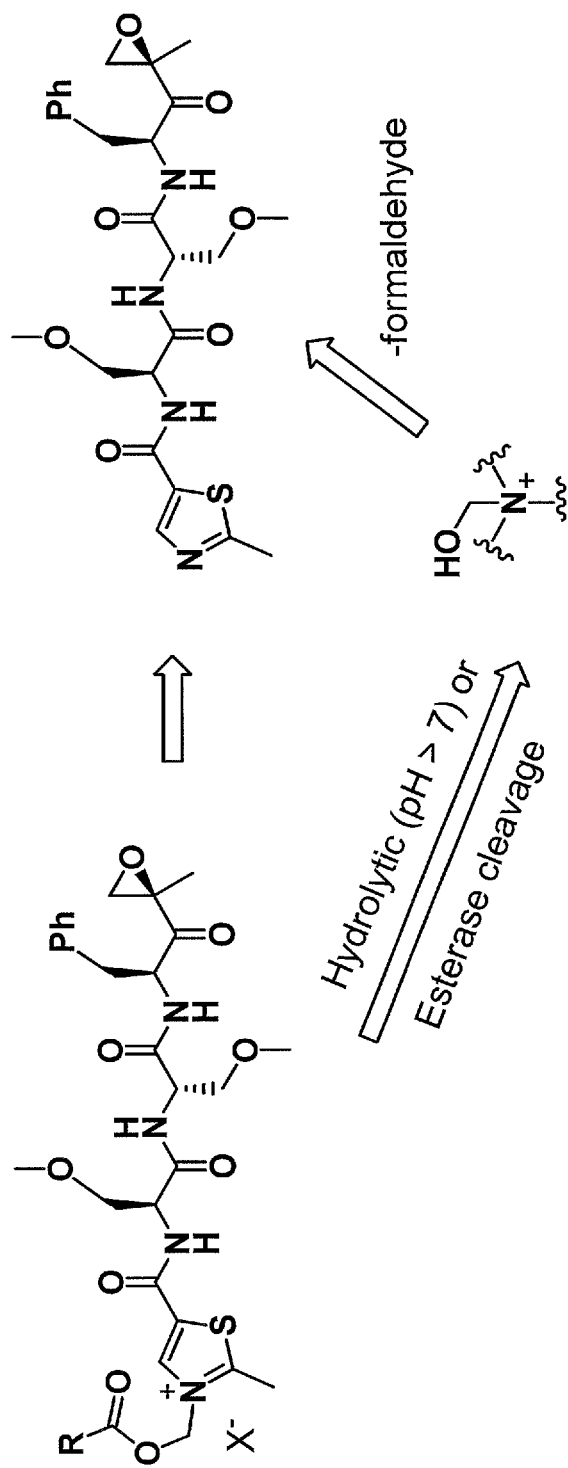
FIG. 28 is a scheme showing embodiments of N-acyloxymethyl-linked quaternary epoxy ketone proteasome inhibitor prodrugs, with the quaternary ion forming with an aryl ring nitrogen.

Referring to FIG. 28, the N-acyloxymethyl linker forms a quaternary ion with methylthiazo N-cap, where X is, but not limited to, chloride, acetate, mesylate, tosylate, or citrate (and where R is, but not limited to, alkyl, aryl or a permeability enhancer), oprozomib prodrugs designed for oral administration.

Figure 29:
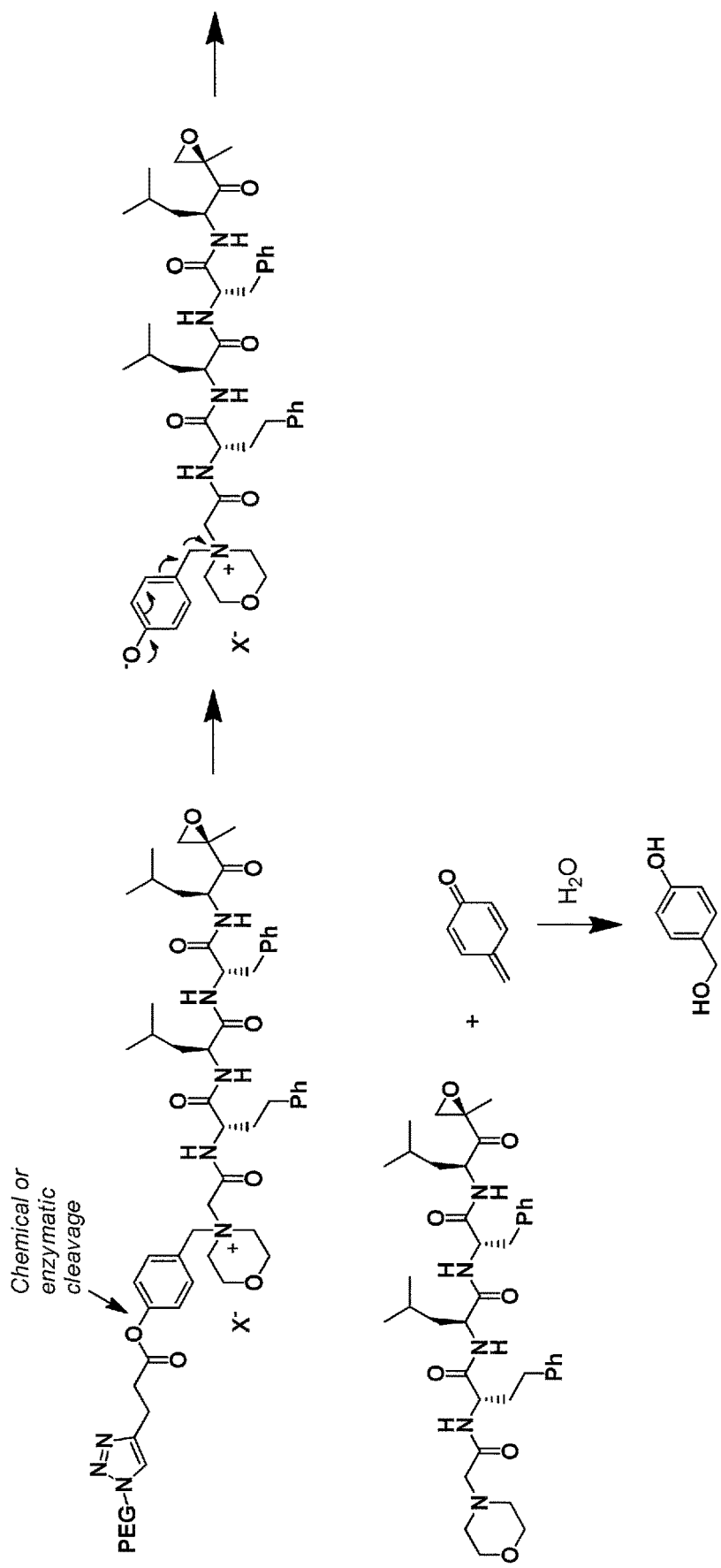
FIG. 29 is a scheme showing embodiments of N-benzyloxy-linked quaternary epoxy ketone proteasome inhibitor prodrugs.
Figure 30:
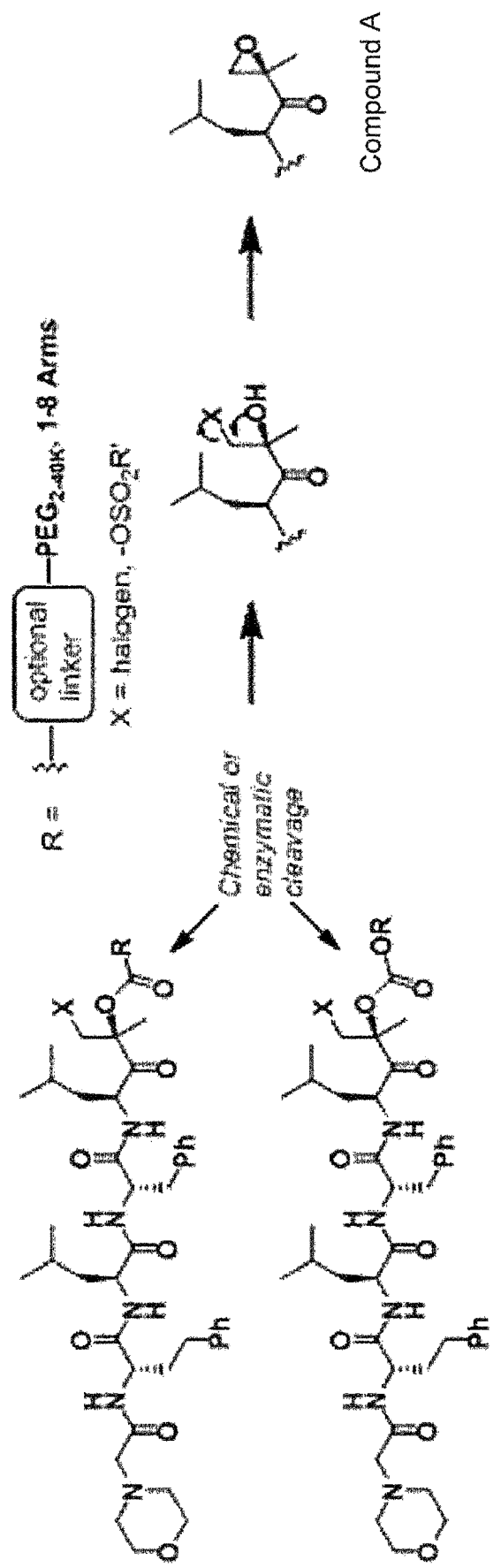
FIG. 30 is a scheme showing embodiments of iodohydrin ester or carbonate epoxy ketone proteasome inhibitor prodrugs.

Referring to FIG. 29, the cleavage of the benzyl quaternary salt analogs is driven by the release of a quinone methide intermediate after enzymatic or chemical cleavage at pH>7.

Table F'" shows some examples of quaternary benzyl group linkers prior to cyclization with PEG-($N_3$) using click chemistry.

TABLE F'"

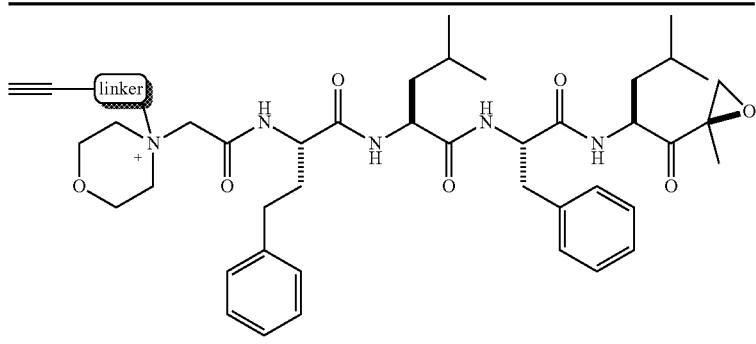

esterases or pH mediated chemical hydrolysis to give a hydroxy intermediate bearing an α-leaving group substituent X, which is then capable of cyclization to an epoxide at physiological pH (see Scheme 20). The leaving group, X, may be, but is not limited to, a halogen, alkylsulfonate, or arylsulfonate group. It should be noted that these PEG conjugates themselves are inactive as a proteasome inhibi-

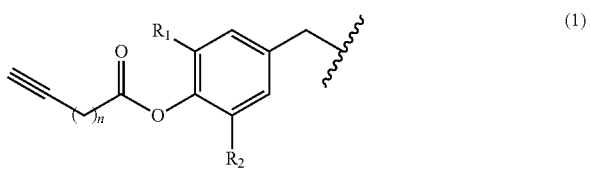

(1)

wherein $R_1$, $R_2$ are independently H or Me

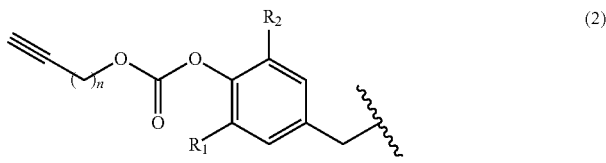

(2)

wherein $R_1$, $R_2$, are independently H or Me

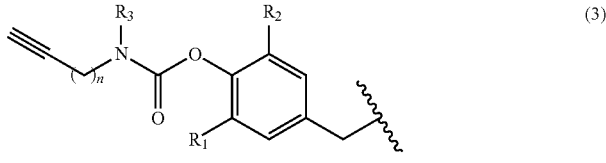

(3)

wherein $R_1$, $R_2$, $R_3$ are independently H or Me

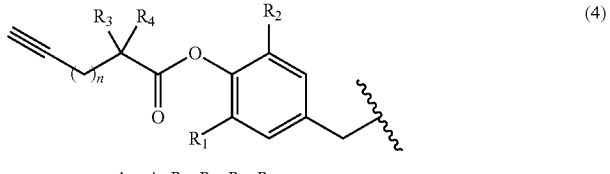

(4)

wherein $R_1$, $R_2$, $R_3$, $R_4$ are independently H or Me

Iodohydrin Esters/Carbonates

In some embodiments, the conjugates described in this invention are releasable PEG carriers of Compound A. Compound A is released in a two step process from an ester or carbonate linked conjugate by the action of endogenous esterases or pH mediated chemical hydrolysis to give a hydroxy intermediate bearing an α-leaving group substituent X, which is then capable of cyclization to an epoxide at physiological pH (see Scheme 20). The leaving group, X, may be, but is not limited to, a halogen, alkylsulfonate, or arylsulfonate group. It should be noted that these PEG conjugates themselves are inactive as a proteasome inhibitors. The rate of ester and/or carbonate hydrolysis and subsequent intramolecular cyclization to epoxide may be varied by the introduction of an electron density modulating group or a cleavage assisting neighboring group. The linker may also contain a reactive functional group such as amino, aldehyde, azido, alkyne, or carboxylic acid which allows for facile attachment of a complimentary carboxylic acid, alkoxyamine, alkyne, azido or amine substituted PEG reagent.

Figure 31:
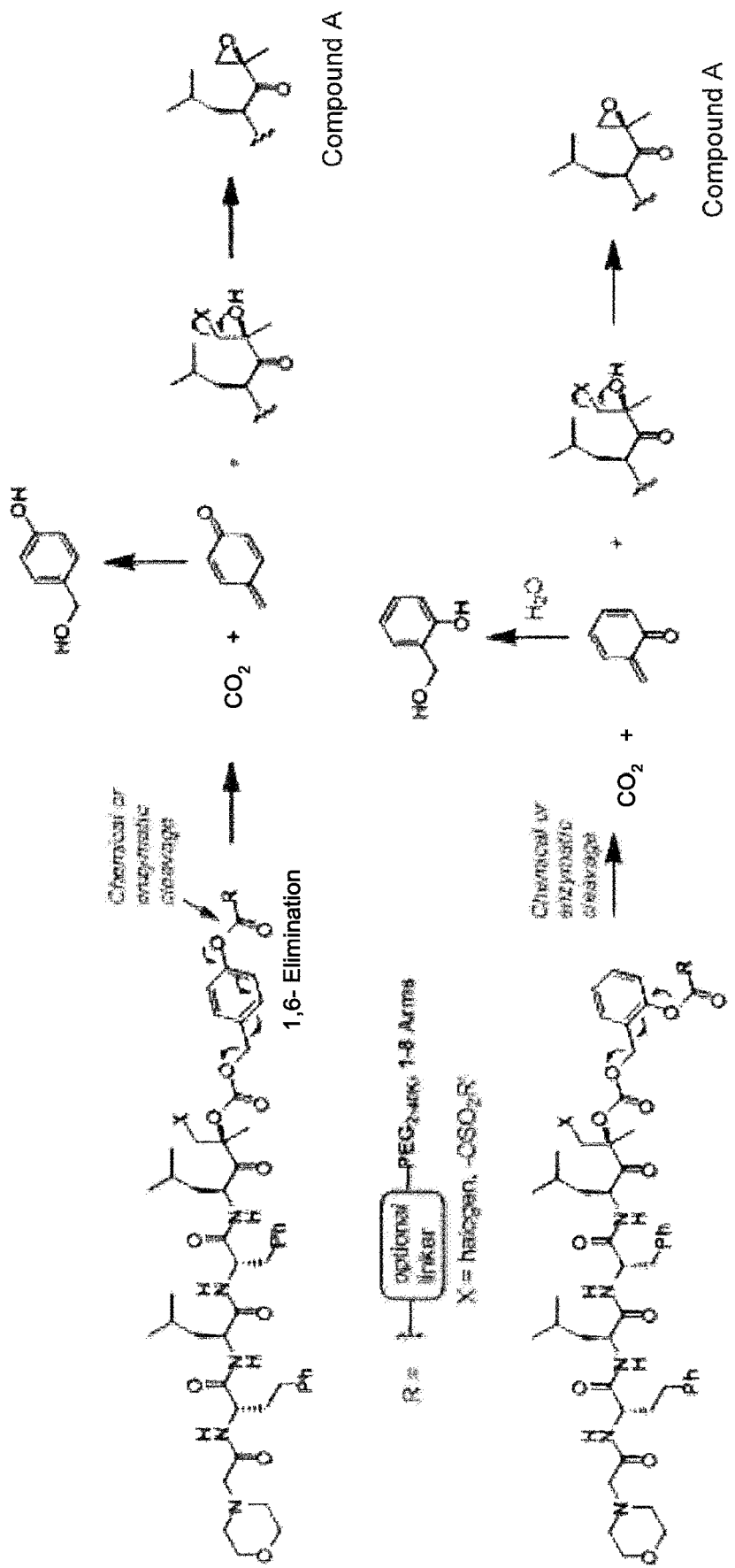
FIG. 31 is a scheme showing the putative mechanism of iodohydrin phenoxy ester or carbonate epoxy ketone proteasome inhibitor prodrug release.

Referring to FIG. 31, cleavage may be facilitated by the introduction of an ortho or para-hydroxy benzyl alcohol linker capable of undergoing self-immolative elimination. Chemical or enzymatic cleavage of the phenol ester bond and deprotonation of the corresponding phenol generates a strongly electron-donating phenoxide that facilitates the formation of quinine methide intermediates following a 1,4- or 1,6-elimination process. Spontaneous decarboxylation and carbon dioxide release liberates the iodohydrin which is then capable of cyclization to the epoxide at physiological pH.

Figure 32:
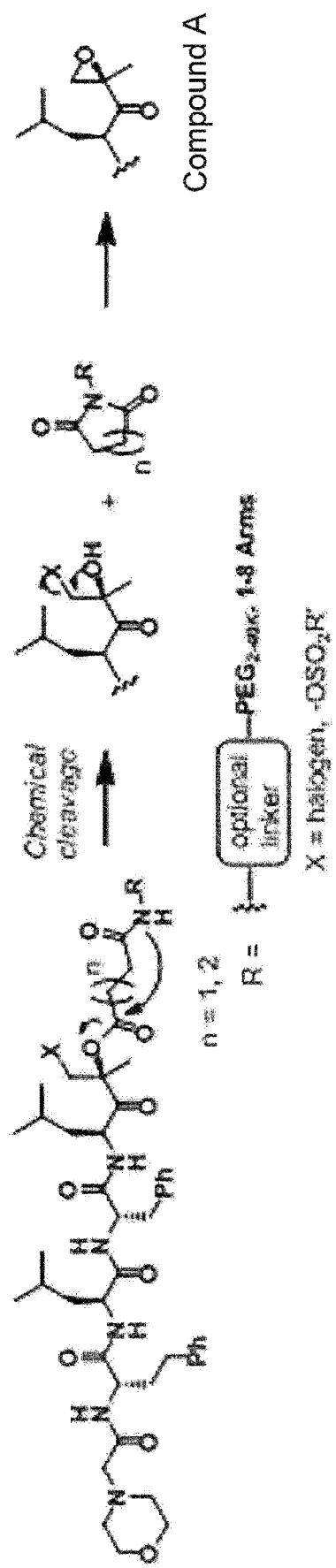
FIG. 32 is a scheme showing the putative mechanism of iodohydrin succinamide ester or carbonate epoxy ketone proteasome inhibitor prodrug release.

Alternatively, referring to FIG. 32, a substituted succinamide or glutaramide may be used to link the halohydrin (X=Cl, Br, or I) or sulfonate diol (X=—OSO$_2$R') and PEG. Under physiological conditions (pH=7.4) the spacer group spontaneously cyclizes to the imide derivative thereby releasing the halohydrin or sulfonate diol which then cyclizes to Compound A.

Figure 33:
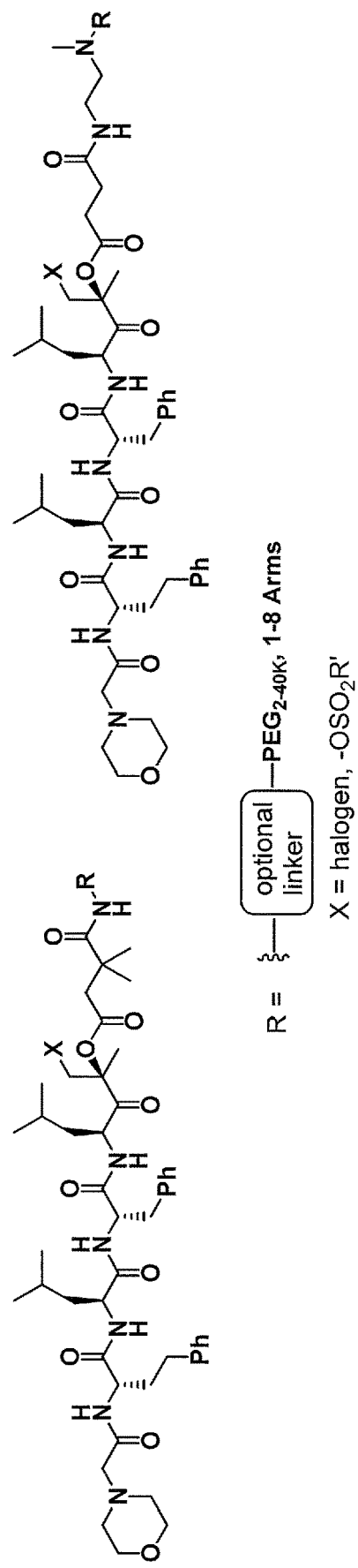
FIG. 33 is a scheme showing embodiments of iodohydrin succinamide ester or carbonate epoxy ketone proteasome inhibitor prodrugs.

Referring to FIG. 33, the succinamide prodrug cleavage rate may be adjusted by the incorporation of conformational restriction ("gem dimethyl effect") and/or an adjacent charged group within the linker. The presence of a negative charge (a carboxylic acid, for example) in the same part of the molecule may reduce the nucleophilicity of the amide nitrogen and inhibit the cyclization reaction to imide. Conversely, the presence of an amine group facilitates cyclization to imide and drug release.

Figure 34:
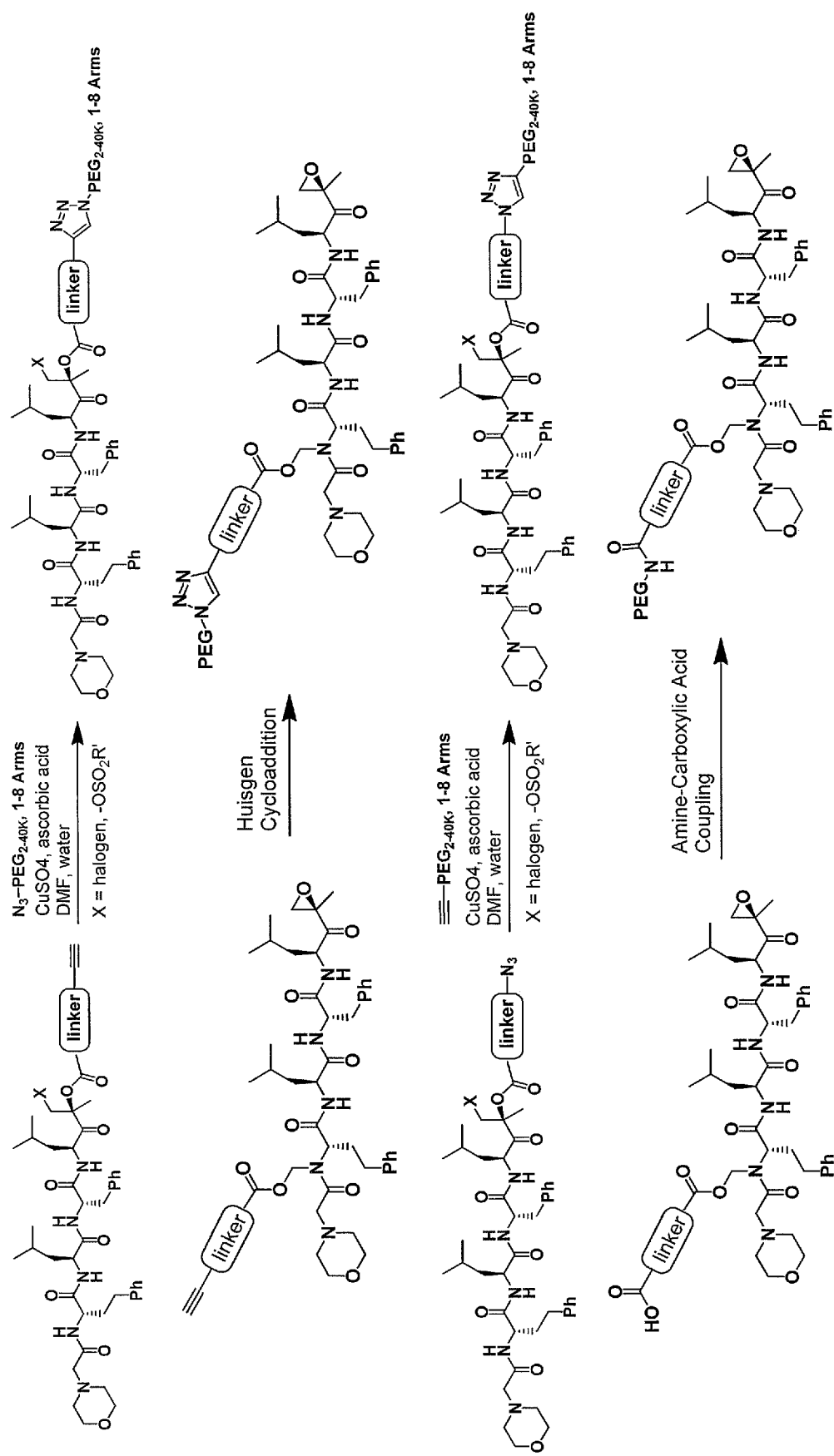
FIG. 34 is a scheme showing embodiments of N-acylmethyloxy ester and iodohydrin succinamide ester/carbonate linked PEG prodrugs of epoxy ketone proteasome inhibitors.
Figure 35:
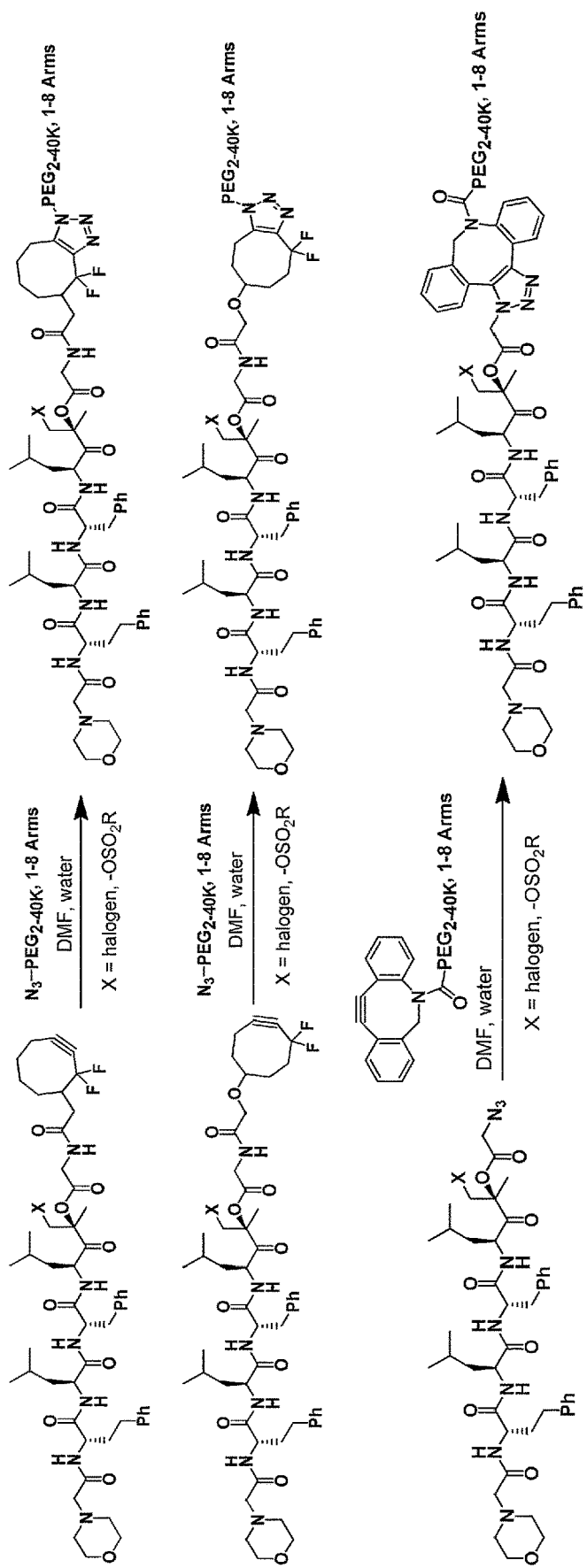
FIG. 35 is a scheme showing embodiments of copper-free [3+2] cycloaddition conditions to form PEG prodrugs of epoxy ketone proteasome inhibitors.
Figure 36:
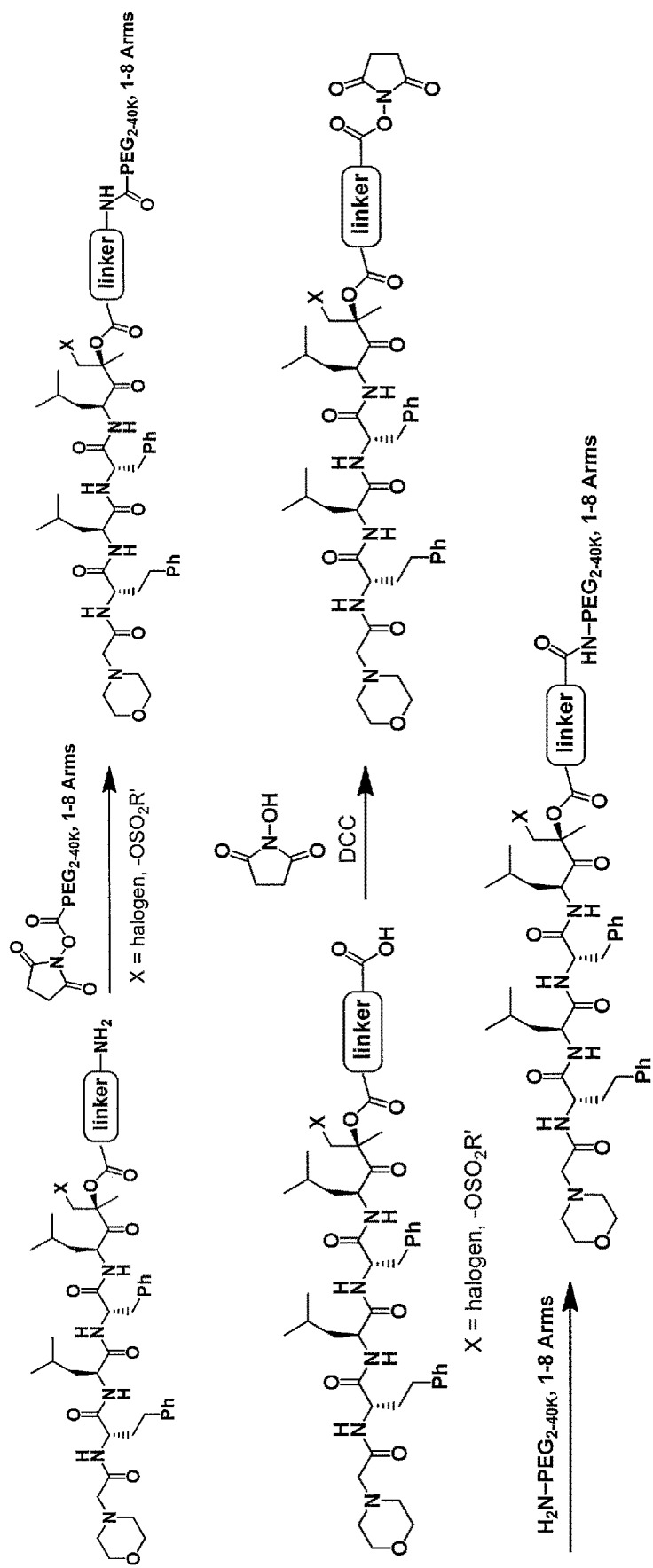
FIG. 36 is a scheme showing a general approach to embodiments of amide-linked PEG prodrugs of epoxy ketone proteasome inhibitors.

Referring to FIGS. 34-36, functionalized PEG reagents are commercially available for attachment via a variety of different chemistries. In some embodiments, "click" chemistry methods, particularly the [3+2] cycloaddition of an azide and an alkyne, are desirable for their large thermodynamic driving force, high yields and lack of offensive byproducts. The reaction of the Compound A-linker-alkyne intermediate with an azide functionalized PEG reagent in the presence of a copper(I) catalyst provides the PEG conjugates in high yield. The reaction is most practically carried out by mixing the PEG azide reagent, Compound A-linker-azide intermediate, copper sulfate, and a reducing agent such as ascorbic acid or sodium ascorbate in organic solvents such as DMF, or in mixtures of DMF and water. The product may be purified by precipitation, reverse phase chromatography or size exclusion chromatography. Alternatively, the reverse cycloaddition reaction may be conducted with a Compound A-linker-azide and an alkyne containing PEG reagent. The use of copper catalyst may be avoided if desired via copper-free click chemistry involving the cycloaddition of azides and dibenzocyclooctyne derivatized reagents. Linear and multi-arm PEG azide reagents are commercially available in sizes ranging from 1 KDa to 40 KDa, and are appended with 1-8 reactive azide functional groups. Alternatively, PEG may be attached via an amide bond linkage formed from a Compound A-linker-amine reagent and a carboxylic acid derivatized PEG or a Compound A-linker-acid reagent and an amine derivatized PEG in the presence of a suitable coupling agent. Large, multi-arm PEGs are advantageous since they are capable of providing a higher drug loading, provide greater protection against proteolytic degradation, and their hydrodynamic size precludes renal clearance. The synthetic route described is suitable for the preparation of large multi-arm PEG conjugates.

Definitions

The term "C$_{x-y}$alkyl" refers to substituted or unsubstituted saturated hydrocarbon groups, including straight-chain alkyl and branched-chain alkyl groups that contain from x to y carbons in the chain. The term "haloalkyl" refers to alkyl groups in which at least one hydrogen atom is replace by a halo (e.g., fluoro, chloro, bromo, iodo), e.g., trifluoromethyl and 2,2,2-trifluoroethyl.

The term "alkylene" refers to substituted or unsubstituted saturated hydrocarbon divalent groups, including straight-chain alkyl and branched-chain alkyl groups. In some embodiments, alkylene includes from 1 to 12 carbon atoms. In certain embodiments, alkylene includes from 1 to 10 carbon atoms. In certain embodiments, alkylene includes from 1 to 6 carbon atoms (e.g., 1, 2, 3, 4, 5, or 6 carbon atoms).

The term "heteroalkylene" refers to alkylene groups inserted with one or more (e.g., two or more) heteroatoms (e.g., N, O, or S, e.g., O). In some embodiments, heteroalkylene includes from 1 to 12 atoms. In certain embodiments, heteroalkylene includes from 1 to 10 atoms. In certain embodiments, heteroalkylene includes from 1 to 8 atoms (e.g., 1, 2, 3, 4, 5, 6, 7, or 8 atoms).

The terms "C$_{2-y}$alkenyl" and "C$_{2-y}$alkynyl" refer to substituted or unsubstituted unsaturated aliphatic groups analogous in length and possible substitution to the alkyls TO described above, but that contain at least one double or triple bond, respectively. In some embodiments, divalent groups alkenylene and alkynylene include from 2 to 12 carbon atoms. In certain embodiments, alkylene and alkynylene include from 2 to 10 carbon atoms. In certain embodiments, alkylene and alkynylene include from 2 to 6 carbon atoms (e.g., 2, 3, 4, 5, or 6 carbon atoms).

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "C$_{1-6}$alkoxyalkyl" refers to a C$_{1-6}$alkyl group substituted with an alkoxy group, thereby forming an ether.

The term "C$_{1-6}$aralkyl", as used herein, refers to a C$_{1-6}$alkyl group substituted with an aryl group.

The terms "amine" and "amino" are art-recognized and refer to both unsubstituted and substituted amines and quaternary salts thereof, e.g., a moiety that can be represented by the general formulae:

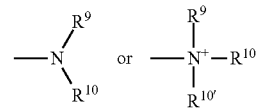

where R$^9$, R$^{10}$ and R$^{10'}$ each independently represent a hydrogen, an alkyl, an alkenyl, —(CH$_2$)$_m$—R$^8$, or R$^9$ and R$^{10}$ taken together with the N atom to which they are attached complete a heterocycle having from 4 to 8 atoms in the ring structure; R$^8$ represents an aryl, a cycloalkyl, a cycloalkenyl, a heterocyclyl or a polycyclyl; and m is zero or an integer from 1 to 8. In some embodiments, only one of R$^9$ or R$^{10}$ is a carbonyl, e.g., R$^9$, R$^{10}$ and the nitrogen together do not form an imide. In some embodiments, R$^9$ and R$^{10}$ (and optionally R$^{10'}$) each independently represent a hydrogen, an alkyl, an alkenyl, or —(CH$_2$)—R$^8$. In certain embodiments, an amino group is basic, meaning its protonated form has a pKa above 7.00.

The terms "amide" and "amido" are art-recognized as an amino-substituted carbonyl and includes a moiety that can be represented by the general formula:

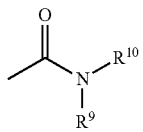

wherein $R^9$, $R^{10}$ are as defined above. In some embodiments, the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "cycloalkyl", as used herein, refer to a saturated substituted or unsubstituted ring in which each atom of the ring is carbon.

The term "carbonyl" is art-recognized and refers to carbon doubly bonded to oxygen (sometimes represented herein as "C=O" or "C(=O)").

The term "$C_{1-6}$heteroaralkyl", as used herein, refers to a $C_{1-6}$alkyl group substituted with a heteroaryl group.

The term "heteroaryl" includes substituted or unsubstituted aromatic 5- to 7-membered ring structures, for example, 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. For example, heteroatoms include nitrogen, oxygen, phosphorus, and sulfur.

The term "heteroalkyl" refers to alkyl groups inserted with one or more (e.g., two or more) heteroatoms.

The term "heterocyclyl" or "heterocyclic group" refers to substituted or unsubstituted non-aromatic 3- to 10-membered ring structures, for example, 3- to 7-membered rings, whose ring structures include one to four heteroatoms. The term "heterocyclyl" or "heterocyclic group" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$hydroxyalkyl" refers to a $C_{1-6}$alkyl group substituted with a hydroxy group.

The term "thioether" refers to an alkyl group, as defined above, having a sulfur moiety attached thereto. In some embodiments, the "thioether" is represented by —S-alkyl. Representative thioether groups include methylthio, ethylthio, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As used herein, the term "peptide" refers to a chain of amino acids that is about two to about ten amino acids in length.

As used herein, the term "natural" or "naturally occurring" amino acid refers to one of the twenty most common occurring amino acids. Natural amino acids are referred to by their standard one- or three-letter abbreviations.

The term "non-natural amino acid" or "non-natural" refers to any derivative or structural analogue of a natural amino acid including D forms, and β and γ amino acid derivatives. It is noted that certain amino acids, e.g., hydroxyproline, that are classified as a non-natural amino acid herein, may be found in nature within a certain organism or a particular protein. Non-limiting examples of non-natural amino acids include: β-Alanine (β-Ala), γ-Aminobutyric Acid (GABA), 2-Aminobutyric Acid (2-Abu), α,β-Dehydro-2-aminobutyric Acid (Δ-Abu), 1-Aminocyclopropane-1-carboxylic Acid (ACPC), Aminoisobutyric Acid (Aib), 2-Amino-thiazoline-4-carboxylic Acid, 5-Aminovaleric Acid (5-Ava), 6-Aminohexanoic Acid (6-Ahx), 8-Aminooctanoic Acid (8-Aoc), 11-Aminoundecanoic Acid (11-Aun), 12-Aminododecanoic Acid (12-Ado), 2-Aminobenzoic Acid (2-Abz), 3-Aminobenzoic Acid (3-Abz), 4-Aminobenzoic Acid (4-Abz), 4-Amino-3-hydroxy-6-methylheptanoic Acid (Statine, Sta), Aminooxyacetic Acid (Aoa), 2-Aminotetraline-2-carboxylic Acid (Atc), 4-Amino-5-cyclohexyl-3-hydroxypentanoic Acid (ACHPA), para-Aminophenylalanine (4-$NH_2$-Phe), Biphenylalanine (Bip), para-Bromophenylalanine (4-Br-Phe), ortho-Chlorophenylalanine (2-Cl-Phe), meta-Chlorophenylalanine (3-Cl-Phe), para-Chlorophenylalanine (4-Cl-Phe), meta-Chlorotyrosine (3-Cl-Tyr), para-Benzoylphenylalanine (Bpa), tert-Butylglycine (Tle), Cyclohexylalanine (Cha), Cyclohexylglycine (Chg), 2,3-Diaminopropionic Acid (Dpr), 2,4-Diaminobutyric Acid (Dbu), 3,4-Dichlorophenylalanine (3,4-Cl2-Phe), 3,4-Diflurorphenylalanine (3,4-F2-Phe), 3,5-Diiodotyrosine (3,5-12-Tyr), ortho-Fluorophenylalanine (2-F-Phe), meta-Fluorophenylalanine (3-F-Phe), para-Fluorophenylalanine (4-F-Phe), meta-fluorotyrosine (3-F-Tyr), Homoserine (Hse), Homophenylalanine (Hfe), Homotyrosine (Htyr), 5-Hydroxytryptophan (5-OH-Trp), Hydroxyproline (Hyp), para-Iodophenylalanine (4-1-Phe), 3-Iodotyrosine (3-I-Tyr), Indoline-2-carboxylic Acid (Idc), Isonipecotic Acid (Inp), meta-methyltyrosine (3-Me-Tyr), I-Naphthylalanine (1-NaI), 2 Naphthylalanine (2-NaI), para-Nitrophenylalanine (4-$NO_2$-Phe), 3-Nitrotyrosine (3-$NO_2$-Tyr), Norleucine (Nle), Norvaline (Nva), Omithine (Orn), ortho-Phosphotyrosine ($H_2PO_3$-Tyr), Octahydroindole-2-carboxylic Acid (Oic), Penicillamine (Pen), Pentafluorophenylalanine (F5-Phe), Phenylglycine (Phg), Pipecolic Acid (Pip), Propargylglycine (Pra), Pyroglutamic Acid (pGlu), Sarcosine (Sar), Tetrahydroisoquinoline-3-carboxylic Acid (Tic), and Thiazolidine-4-carboxylic Acid (Thioproline, Th). Stereochemistry of amino acids may be designated by preceding the name or abbreviation with the designation "D" or "d" or "L" or "1" as appropriate. Alternately, chiral centers may be represented with conventional (S)-, or (R)-designations. Additionally, αN-alkylated amino acids may be employed, as well as amino acids having amine-containing side chains (such as Lys and Orn) in which the amine has been acylated or alkylated. See, for example, "Peptides and Mimics, Design of Conformationally Constrained" by Hruby and Boteju, in Molecular Biology and Biotechnology: A Comprehensive Desk Reference, ed. Robert A. Meyers, VCH Publishers (1995), pp. 658-664, which is hereby incorporated by reference.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

As used herein, the term "inhibitor" is meant to describe a compound that blocks or reduces an activity of an enzyme or system of enzymes, receptors, or other pharmacological target (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

Pharmaceutical Compositions

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include sterile water for injection, sterile buffers, such as citrate buffer, bacteriostatic water, and Cremophor EL™ (BASF, Parsippany, N.J.). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation is freeze-drying (lyophilization), which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alia, Hamajima et al., *Clin. Immunol. Immunopathol.*, 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

The pharmaceutical compositions can be included in a container, pack, or dispenser together with instructions for administration.

In some embodiments, the compounds provided herein can be formulated as described in U.S. Pat. No. 7,737,112.

Methods of Use

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations for very potent, proteasome-specific compounds, such as the epoxy ketone class of molecules, provide a means of administering a drug to a patient and treating these conditions.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these compositions are useful for treating cancer.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., *J. Mol. Med* (1997) 75:5-17; Adams, *Nature* (2004) 4: 349-360). Therefore, provided herein is a method of treating cancers comprising administering to a patient in need of such treatment a therapeutically effective amount of a peptide proteasome inhibitor as provided herein.

As used herein, the term "cancer" includes, but is not limited to, blood borne and solid tumors. Cancer refers to disease of blood, bone, organs, skin tissue and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplamacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, mycloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

In some embodiments, a peptide proteasome inhibitor as provided herein, or a pharmaceutical composition comprising the same, can be administered to treat multiple myeloma in a patient. For example, multiple myeloma can include refractory and/or refractory multiple myeloma.

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, use of a proteasome inhibitor for the treatment of such diseases is attractive and being examined (Cilloni et al., *Haematologica* (2007) 92: 1124-1229). CMPD can include chronic myelogenous leukemia, chronic neutrophilic leukemia, chronic eosinophilic leukemia, polycythaemia vera, chronic idiopathic myelofibrosis, essential thrombocythaemia and unclassifiable chronic myeloproliferative disease. Provided herein is a method of treating CMPD comprising administering to a patient in need of such treatment an effective amount of the proteasome inhibitor compound disclosed herein.

Myelodisplastic/mycloproliferative diseases, such as chronic myelomonocytic leukemia, atypical chronic myeloid leukemia, juvenile myelomonocytic leukemia and unclassifiable myelodysplastic/myeloproliferative disease, are characterized by hypercellularity of the bone marrow due to proliferation in one or more of the myeloid lineages. Inhibiting the proteasome with a composition described herein, can serve to treat these myelodisplatic/myeloproliferative diseases by providing a patient in need of such treatment an effective amount of the composition.

Myelodysplastic syndromes (MDS) refer to a group of hematopoietic stem cell disorders characterized by dysplasia and ineffective haematopoiesis in one or more of the major myeloid cell lines. Targeting NF-kB with a proteasome inhibitor in these hematologic malignancies induces apoptosis, thereby killing the malignant cell (Braun et al. *Cell Death and Differentiation* (2006) 13:748-758). Further provided herein is a method to treat MDS comprising administering to a patient in need of such treatment an effective amount of a compound provided herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del (5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extracutaneous mastocytoma. Further provided herein is a method to treat mastocytosis comprising administering an effect amount of the compound disclosed herein to a patient diagnosed with mastocytosis.

The proteasome regulates NF-κB, which in turn regulates genes involved in the immune and inflammatory response. For example, NF-κB is required for the expression of the immunoglobulin light chain K gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Thus, provided herein are methods of affecting the level of expression of IL-2, MHC-I, IL-6, TNFα, IFN-β or any of the other previously-mentioned proteins, each method comprising administering to a patient an effective amount of a proteasome inhibitor composition disclosed herein.

Also provided herein is a method of treating an autoimmune disease in a patient comprising administering a therapeutically effective amount of the compound described herein. An "autoimmune disease" herein is a disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation or present unfamiliar peptides on their surface. Intracellular proteolysis generate small peptides for presentation to T-lymphocytes to induce MHC class I-mediated immune responses. Thus, provided herein is a method of using a proteasome inhibitor provided herein as an immunomodulatory agent for inhibiting or altering antigen presentation in a cell, comprising exposing the cell (or administering to a patient) to the compound described herein. Specific embodiments include a method of treating graft or transplant-related diseases, such as graft-versus-host disease or host versus-graft disease in a patient, comprising administering a therapeutically effective amount of the compound described herein. The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same patient. In some embodiments, the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. *Cancer Res*. (2006) 66:5461-5468). In some embodiments, a composition provided herein can be administered to a patient with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor and non-specified dendritic cell sarcoma.

Inhibition of the proteasome has been shown to be beneficial to treat diseases whereby a cell type is proliferating and immune disorders; thus, in some embodiments, the treatment of lymphoproliferative diseases (LPD) associated with primary immune disorders (PID) is provided comprising administering an effective amount of the disclosed compound to a patient in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in patients who have received solid organ or bone marrow allografts, and iatrogenis immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Proteasome inhibition has also been associated with inhibition of NF-κB activation and stabilization of p53 levels. Thus, compositions provided herein may also be used to inhibit NF-κB activation, and stabilize p53 levels in cell culture. Since NF-κB is a key regulator of inflammation, it is an attractive target for anti-inflammatory therapeutic intervention. Thus, compositions provided herein may be useful for the treatment of conditions associated with inflammation, including, but not limited to COPD, psoriasis, asthma, bronchitis, emphysema, and cystic fibrosis.

The disclosed compositions can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

In some embodiments, a composition provided herein is useful for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the n-subunit of human macropain (Kojima, S. et al., Fed. Eur. Biochem. Soc., (1992) 304:57-60). The APP-processing enzyme cleaves at the Gnl15-Lys16 bond; in the presence of calcium ion, the enzyme also cleaves at the Met-1-Asp1 bond, and the Asp1-Ala2 bonds to release the extracellular domain of β-AP.

One embodiment, therefore, is a method of treating Alzheimer's disease, including administering to a patient an effective amount of a composition provided herein. Such treatment includes reducing the rate of β-AP processing, reducing the rate of β-AP plaque formation, reducing the rate of β-AP generation, and reducing the clinical signs of Alzheimer's disease.

Also provided herein are methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Peptide proteasome inhibitors as provided herein are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736. Methods of treatment include: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a patient) with an effective amount of a pharmaceutical composition disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity. However, accelerated degradation of the TGF-β signaling components has been observed in cancers and other hyperproliferative conditions. Thus, in certain embodiments, a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders) is provided. The treatment of burn victims is often hampered by fibrosis, thus, in some embodiments an inhibitor provided herein may be administered by topical or systemic administration to treat burns. Wound closure following surgery is often associated with disfiguring scars, which may be prevented by inhibition of fibrosis. Thus, in certain embodiments, a method for the prevention or reduction of scarring is provided herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., Cell (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain K gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., Cell (1994) 78:773-785). Some embodiments include methods of affecting the level of expression of IL-2, MHC-I, IL-6, TNFα, IFN-β, or any of the other previously-mentioned proteins, each method including administering to a patient an effective amount of a composition disclosed herein. Complexes including p50 are rapid mediators of acute inflammatory and immune responses (Thanos, D. and Maniatis, T., Cell (1995) 80:529-532).

NF-κB also participates in the expression of the cell adhesion genes that encode E-selectin, P-selectin, ICAM, and VCAM-1 (Collins, T., Lab. Invest. (1993) 68:499-508). In some embodiments, a method for inhibiting cell adhesion (e.g., cell adhesion mediated by E-selectin, P-selectin, ICAM, or VCAM-1) is provided, including contacting a cell with (or administering to a patient) an effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Thus, provided herein is a method of treating an ischemic condition or reperfusion injury comprising administering to a patient in need of such treatment an effective amount of a compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science*, (1995) 267:960). Provided herein is a method for inhibiting or reducing HIV infection in a patient, and a method for decreasing the level of viral gene expression, each method including administering to the patient an effective amount of a composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, *Am J Pathol* 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (*J Virol* 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, *J Virol* 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, a method for treating viral infection, such as SARS or hepatitis A, B, C, D and E, is provided comprising contacting a cell with (or administering to a patient) an effective amount of the compound disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, compositions as provided herein may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. A further embodiment is a method for suppressing the immune system of a patient (e.g., inhibiting transplant rejection, allergy, asthma), including administering to the patient an effective amount of a composition described herein. Compositions provided herein can also be used to treat autoimmune diseases such as lupus, rheumatoid arthritis, multiple sclerosis, and inflammatory bowel diseases such as ulcerative colitis and Crohn's disease.

Another embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., *EMBO J.* (1994) 13:5433-5441). In some embodiments, a method for inhibiting IκB-α degradation is provided, including contacting the cell with a composition described herein. A further embodiment is a method for reducing the cellular content of NF-κB in a cell, muscle, organ, or patient, including contacting the cell, muscle, organ, or patient with a composition described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Further provided herein are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, GI cyclins, and cyclin B. Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAAL-GNISEN-50 (destruction box). There is evidence that cyclin is converted to a form vulnerable to a ubiquitin ligase or that a cyclin-specific ligase is activated during mitosis (Ciechanover, A., *Cell*, (1994) 79:13-21). Inhibition of the proteasome inhibits cyclin degradation, and therefore inhibits cell proliferation, for example, in cyclin-related cancers (Kumatori et al., *Proc. Natl. Acad Sci. USA* (1990) 87:7071-7075). Provided herein is a method for treating a proliferative disease in a patient (e.g., cancer, psoriasis, or restenosis), including administering to the patient an effective amount of a composition disclosed herein. Also provided herein is a method for treating cyclin-related inflammation in a patient, including administering to a patient a therapeutically effective amount of a composition described herein.

Additional embodiments include methods for affecting the proteasome-dependent regulation of oncoproteins and methods of treating or inhibiting cancer growth, each method including exposing a cell (in vivo, e.g., in a patient, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a patient an effective amount of a composition disclosed herein.

In another embodiment, the disclosed compositions are useful for the treatment of a parasitic infection, such as infections caused by protozoan parasites. The proteasome of these parasites is considered to be involved primarily in cell differentiation and replication activities (Paugam et al., *Trends Parasitol.* 2003, 19(2): 55-59). Furthermore, entamoeba species have been shown to lose encystation capacity when exposed to proteasome inhibitors (Gonzales, et al., *Arch. Med. Res.* 1997, 28, Spec No: 139-140). In certain such embodiments, the disclosed compositions are useful for the treatment of parasitic infections in humans caused by a protozoan parasite selected from *Plasmodium* sps. (including *P. falciparum, P. vivax, P. malariae,* and *P. ovale,* which cause malaria), *Trypanosoma* sps. (including *T. cruzi,* which causes Chagas' disease, and *T. brucei* which causes African sleeping sickness), *Leishmania* sps. (including *L. amazonesis, L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia.* In certain embodiments, the disclosed compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona,* and *Neurospora crassa.* Other compounds useful as proteasome inhibitors in the treatment of parasitic diseases are described in WO 98/10779, which is incorporated herein in its entirety.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the n-subunits. In some embodiments, a method of treating prokaryotic infections is provided, comprising administering to a patient an effective amount of the proteasome inhibitor composition disclosed herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteoporosis.

Provided herein is a method for treating a disease or condition selected from cancer, autoimmune disease, graft or transplant-related condition, neurodegenerative disease, fibrotic-associated condition, ischemic-related conditions, infection (viral, parasitic or prokaryotic) and diseases associated with bone loss, comprising administering a proteasome inhibitor as provided herein. For example, a compound of formula (5).

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, compounds provided herein may also be useful for hair follicle growth stimulation.

Finally, the disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

Administration

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent in addition to a cyclodextrin and a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect. In general, compositions intended for parenteral use (e.g., intravenous, subcutaneous injection) include a substituted cyclodextrin. Compositions administered via other routes, particularly the oral route, include a substituted or unsubstituted cyclodextrin.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified peptide proteasome inhibitor in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm Sci. 66: 1-19.)

In some embodiments, the peptide proteasome inhibitors provided herein may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A peptide proteasome inhibitor can be administered by aerosol. This is accomplished by preparing an aqueous aerosol, liposomal preparation, or solid particles containing the composition. A nonaqueous (e.g., fluorocarbon propellant) suspension could be used. In some embodiments, sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions suitable for parenteral administration comprise one or more peptide proteasome inhibitors in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), ethanol, polyols (such as glycerol, propylene glycol, polyethylene glycol, and the like), buffer (such as citrate buffer), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Pharmaceutical compositions typically include a pharmaceutically acceptable carrier. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. In some embodiments, a pharmaceutically acceptable carrier is a buffer (e.g., citrate buffer). In some embodiments, a pharmaceutically acceptable carrier is sterile water for injection. In some embodiments, a pharmaceutically acceptable carrier comprises citric acid.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

The peptide proteasome inhibitors described herein may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, a peptide proteasome inhibitor, which may be used in a suitable hydrated form, and/or the pharmaceutical compositions provided herein, is formulated into a pharmaceutically acceptable dosage form by conventional methods known to those of skill in the art.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions provided herein may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds. The dosage will be an effective amount depending on several factors including the overall health of a patient, and the formulation and route of administration of the selected compound(s).

In another embodiment, the pharmaceutical composition is an oral solution or a parenteral solution. Another embodiment is a freeze-dried preparation that can be reconstituted prior to administration. As a solid, this formulation may also include tablets, capsules or powders.

Also provided herein is a conjoint therapy wherein one or more other therapeutic agents are administered with a peptide proteasome inhibitor prodrug described herein or a pharmaceutical composition comprising a peptide proteasome inhibitor prodrug described herein. Such conjoint treatment may be achieved by way of the simultaneous, sequential, or separate dosing of the individual components of the treatment.

In certain embodiments, a peptide proteasome inhibitor prodrug described herein is conjointly administered with one or more other proteasome inhibitor(s).

In certain embodiments, peptide proteasome inhibitor prodrug described herein is conjointly administered with one or more chemotherapeutics. Suitable chemotherapeutics may include, natural products such as vinca alkaloids (i.e. vinblastine, vincristine, and vinorelbine), taxanes (e.g., docetaxel, paclitaxel, e.g., docetaxel), epidipodophyllotoxins (i.e. etoposide, teniposide), antibiotics (dactinomycin (actinomycin D) daunorubicin, doxorubicin and idarubicin; e.g., doxorubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, ifosphamide, cyclophosphamide and analogs, melphalan, chlorambucil, e.g., melphalan), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); platinum coordination complexes (cisplatin, carboplatin), procarbazine, hydroxyurea, mitotane, aminoglutethimide; DNA binding/Cytotoxic agents (e.g., Zalypsis); histone deacetylase (HDAC) inhibitors (e.g., trichostatin, sodium butyrate, apicidan, suberoyl anilide hydroamic acid (SAHA (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxy-carbonyl)aminomethyl]benzamide), LAQ824/LBH589, CI994, MGCD0103, ACY-1215, Panobinostat); hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a peptide proteasome inhibitor prodrug described herein is conjointly administered with a cytokine. Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In certain embodiments, a peptide proteasome inhibitor prodrug described herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In some embodiments, a peptide proteasome inhibitor prodrug described herein is conjointly administered with an immunotherapeutic agent. Suitable immunotherapeutic agents may include, but are not limited to, MDR modulators (verapamil, valspordar, biricodar, tariquidar, laniquidar), cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

In certain embodiments, a peptide proteasome inhibitor prodrug described herein is conjointly administered with one or more histone deacetylase (HDAC) inhibitors (e.g., trichostatin, sodium butyrate, apicidan, suberoyl anilide hydroamic acid ("SAHA" (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxy-carbonyl)aminomethyl]benzamide), LAQ824/LBH589, CI994, MGCD0103, ACY-1215, Panobinostat; e.g., SAHA, ACY-1215, Panobinostat).

In certain embodiments, a peptide proteasome inhibitor prodrug described herein is conjointly administered with one or more nitrogen mustards (mechlorethamine, ifosphamide, cyclophosphamide and analogs, melphalan, chlorambucil, e.g., melphalan).

In certain embodiments, a peptide proteasome inhibitor prodrug described herein is conjointly administered with one or more DNA binding/Cytotoxic agents (e.g., Zalypsis).

In certain embodiments, a peptide proteasome inhibitor prodrug described herein is conjointly administered with one or more taxanes (e.g., docetaxel, paclitaxel, e.g., docetaxel).

In certain embodiments, a peptide proteasome inhibitor prodrug described herein is conjointly administered with one or more antibiotics (dactinomycin (actinomycin D) daunorubicin, doxorubicin and idarubicin; e.g., doxorubicin).

In some embodiments, a peptide proteasome inhibitor prodrug described herein is conjointly administered with one or more cytokines. Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In some embodiments, a peptide proteasome inhibitor prodrug described herein is conjointly administered with one or more steroids. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof (e.g., hydrocortisone, dexamethasone, methylprednisolone and prednisolone; e.g., dexamethasone).

In certain embodiments, peptide proteasome inhibitor prodrugs described herein are conjointly administered with dexamethasone. In certain embodiments, conjoint therapy includes the dosing regimens provided on the KYPROLIS (carfilzomib) label, e.g.:

1. KYPROLIS (carfilzomib) is administered intravenously over 2 to 10 minutes, on two consecutive days, each week for three weeks (Days 1, 2, 8, 9, 15, and 16), followed by a 12-day rest period (Days 17 to 28). Each 28-day period is considered one treatment cycle (Table A).

In Cycle 1, KYPROLIS (carfilzomib) is administered at a dose of 20 mg/m². If tolerated in Cycle 1, the dose should be escalated to 27 mg/m² beginning in Cycle 2 and continued at 27 mg/m² in subsequent cycles. Treatment may be continued until disease progression or until unacceptable toxicity occurs.

The dose is calculated using the patient's actual body surface area at baseline. Patients with a body surface area greater than 2.2 m² should receive a dose based upon a body surface area of 2.2 m². Dose adjustments do not need to be made for weight changes of less than or equal to 20%.

TABLE A1

KYPROLIS (carfilzomib) Dosage Regimen for Patients with Multiple Myeloma

| | Cycle 1 | | | | | | | | | |
|---|---|---|---|---|---|---|---|---|---|---|
| | Week 1 | | | Week 2 | | | Week 3 | | | Week 4 |
| KYPROLIS (20 mg/m²): | Day 1 | Day 2 | Days 3-7 | Day 8 | Day 9 | Days 10-14 | Day 15 | Day 16 | Days 17-21 | Days 22-28 |
| | 20 | 20 | No Dosing | 20 | 20 | No Dosing | 20 | 20 | No Dosing | No Dosing |
| | Cycles 2 and Beyond*a* | | | | | | | | | |
| | Week 1 | | | Week 2 | | | Week 3 | | | Week 4 |
| KYPROLIS (27 mg/m²): | Day 1 | Day 2 | Days 3-7 | Day 8 | Day 9 | Days 10-14 | Day 15 | Day 16 | Days 17-21 | Days 22-28 |
| | 27 | 27 | No Dosing | 27 | 27 | No Dosing | 27 | 27 | No Dosing | No Dosing |

*a*If previous cycle dosage is tolerated.

2. Hydrate patients to reduce the risk of renal toxicity and of tumor lysis syndrome (TLS) with KYPROLIS (carfilzomib) treatment Maintain adequate fluid volume status throughout treatment and monitor blood chemistries closely. Prior to each dose in Cycle 1, give 250 mL to 500 mL of intravenous normal saline or other appropriate intravenous fluid. Give an additional 250 mL to 500 mL of intravenous fluids as needed following KYPROLIS (carfilzomib) administration. Continue intravenous hydration, as needed, in subsequent cycles. Also monitor patients during this period for fluid overload.

3. Pre-medicate with dexamethasone 4 mg orally or intravenously prior to all doses of KYPROLIS (carfilzomib) during Cycle 1 and prior to all KYPROLIS (carfilzomib) doses during the first cycle of dose escalation to 27 mg/m² to reduce the incidence and severity of infusion reactions. Reinstate dexamethasone premedication (4 mg orally or intravenously) if these symptoms develop or reappear during subsequent cycles.

In some embodiments, a peptide proteasome inhibitor prodrug described herein is conjointly administered with one or more immunotherapeutic agents. Suitable immunotherapeutic agents may include, but are not limited to, MDR modulators (verapamil, valspordar, biricodar, tariquidar, laniquidar), cyclosporine, thalidomide, CC-4047 (Actimid), lenalidomide (Revlimid) and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab. In certain embodiments, a peptide proteasome inhibitor prodrug described herein is conjointly administered with lenalidomide (Revlimid).

In some embodiments, a peptide proteasome inhibitor prodrug described herein is conjointly administered with one or more topoisomerase inhibitors (e.g., irinotecan, topotecan, camptothecin, lamellarin D, and etoposide).

In some embodiments, a peptide proteasome inhibitor prodrug described herein is conjointly administered with one or more m-TOR inhibitors (e.g., CCI-779, AP23573 and RAD-001).

In some embodiments, a peptide proteasome inhibitor prodrug described herein is conjointly administered with one or more protein kinase inhibitor (e.g., sorafenib, imatinib, dasatinib, sunitinib, pazopanib, and nilotinib; e.g., sorafenib).

In some embodiments, a peptide proteasome inhibitor prodrug described herein is conjointly administered with one or more CDK Inhibitors (e.g., Dinaciclib).

In some embodiments, a peptide proteasome inhibitor prodrug described herein is conjointly administered with one or more KSP(Eg5) Inhibitors (e.g., Array 520).

In some embodiments, a peptide proteasome inhibitor prodrug described herein is conjointly administered with one or more PI13 delta Inhibitors (e.g., GS-1101 PI3K).

In some embodiments, a peptide proteasome inhibitor prodrug described herein is conjointly administered with one or more Dual Inhibitor: PI3K delta and gamma Inhibitors (e.g., CAL-130).

In some embodiments, a peptide proteasome inhibitor prodrug described herein is conjointly administered with one or more multi-kinase Inhibitors (e.g., TG02).

In some embodiments, a peptide proteasome inhibitor prodrug described herein is conjointly administered with one or more PI3K delta Inhibitors (e.g., TGR-I202).

In some embodiments, a peptide proteasome inhibitor prodrug described herein is conjointly administered with
  (i) one or more of the following:
    one or more second chemotherapeutic agents (e.g., one or more HDAC inhibitors, e.g., SAHA, ACY-1215, Panobinostat; one or more nitrogen mustards e.g., melphalan; one or more DNA binding/cytotoxic agents, e.g., Zylapsis; one or more taxanes, e.g., docetaxel; one or more antibiotics (dactinomycin (actinomycin D) daunorubicin, doxorubicin and idarubicin; e.g., doxorubicin);

one or more other proteasome inhibitor(s) (e.g., another compound of formulae (1)-(5));

one or more cytokines;

one or more immunotherapeutic agents (e.g., Revlimid);

one or more topoisomerase inhibitors;

one or more m-TOR inhibitors;

protein kinase inhibitor (e.g., sorafenib);

one or more CDK Inhibitors (e.g., Dinaciclib);

one or more KSP(Eg5) Inhibitors (e.g., Array 520);

one or more PI13 delta Inhibitors (e.g., GS-101 PI3K);

one or more Dual Inhibitor: PI3K delta and gamma Inhibitors (e.g., CAL-130);

one or more multi-kinase Inhibitors (e.g., TG02);

one or more PI3K delta Inhibitors (e.g., TGR-1202);

and (ii) one or more steroids (e.g., dexamethasone).

In certain embodiments, a peptide proteasome inhibitor prodrug described herein is conjointly administered with (i) one of the following:

one or more second chemotherapeutic agents (e.g., one or more HDAC inhibitors, e.g., SAHA, ACY-1215, Panobinostat; one or more nitrogen mustards e.g., melphalan; one or more DNA binding/cytotoxic agents, e.g., Zylapsis; one or more taxanes, e.g., docetaxel; one or more antibiotics (dactinomycin (actinomycin D) daunorubicin, doxorubicin and idarubicin; e.g., doxorubicin);

one or more other proteasome inhibitor(s) (e.g., another compound of formulae (1)-(5));

one or more cytokines;

one or more immunotherapeutic agents (e.g., Revlimid);

one or more topoisomerase inhibitors;

one or more m-TOR inhibitors;

protein kinase inhibitor (e.g., sorafenib);

one or more CDK Inhibitors (e.g., Dinaciclib);

one or more KSP(Eg5) Inhibitors (e.g., Array 520);

one or more PI13 delta Inhibitors (e.g., GS-1101 PI3K);

one or more Dual Inhibitor: PI3K delta and gamma Inhibitors (e.g., CAL-130);

one or more multi-kinase Inhibitors (e.g., TG02);

one or more PI3K delta Inhibitors (e.g., TGR-1202);

and (ii) dexamethasone.

EXAMPLES

Example 1—Exemplary Compounds

Exemplary compounds and their respective IC50 slope values are listed in Tables G and H.

TABLE G

| Structure | MW | Purified PI IC$_{50}$ Slope (nM) c20s | i20s |
|---|---|---|---|
| Quaternary Salts | | | |
| [structure] | 961.96 | 8.915 | 49.8 |
| Acylhydrazones | | | |
| [structure] | 775.98 | 678 | 2185* |

TABLE G-continued

| Structure | MW | Purified PI IC$_{50}$ Slope (nM) c20s | i20s |
|---|---|---|---|
| 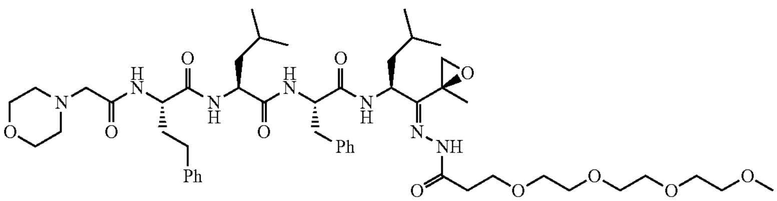 [SMILES: COCCOCCOCCOCCC(=O)N/N=C(/[C@H](CC(C)C)NC(=O)[C@H](Cc1ccccc1)NC(=O)[C@H](CC(C)C)NC(=O)[C@H](CCc1ccccc1)NC(=O)CN1CCOCC1)[C@@]1(C)CO1] | 952.19 | inactive | 3242* |
| 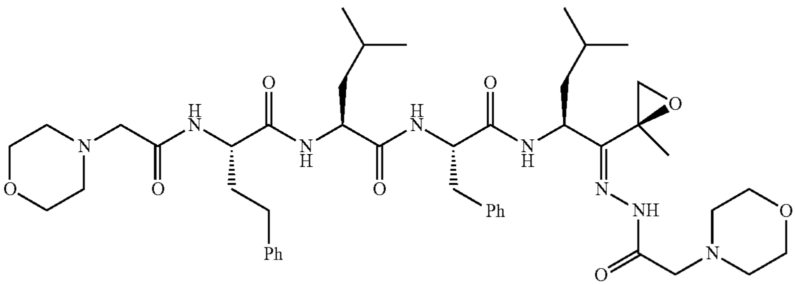 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)/C(=N/NC(=O)CN1CCOCC1)[C@@]1(C)CO1] | 861.08 | | |
| 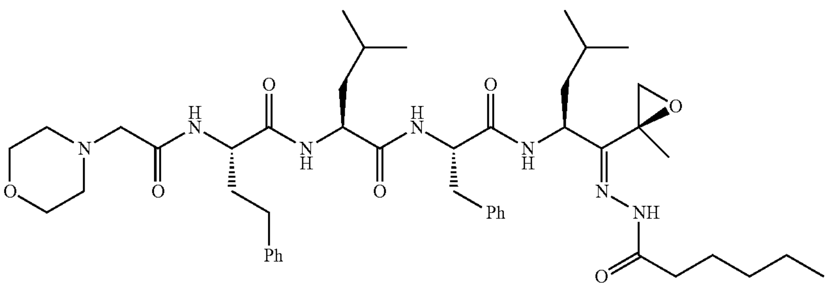 [SMILES: CCCCCC(=O)N/N=C(/[C@H](CC(C)C)NC(=O)[C@H](Cc1ccccc1)NC(=O)[C@H](CC(C)C)NC(=O)[C@H](CCc1ccccc1)NC(=O)CN1CCOCC1)[C@@]1(C)CO1] | 832.08 | | |
| 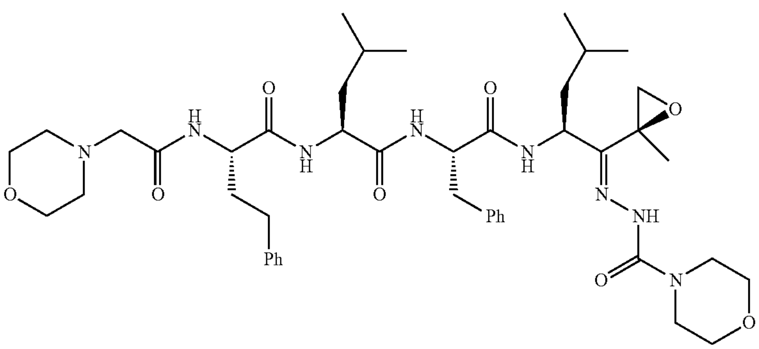 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)/C(=N/NC(=O)N1CCOCC1)[C@@]1(C)CO1] | 847.05 | | |

Oximes

| | 734.92 | 278.6* | 2293* |

TABLE G-continued

| Structure | MW | Purified PI IC$_{50}$ Slope (nM) c20s | i20s |
|---|---|---|---|
| (structure) | 348.95 | 2612* | inactive |
| (structure) | 825.05 | 539 | 2181 |
| (structure) | 792.96 | inactive | inactive |
| (structure) | 881.11 | | |

Activated Diols

| Structure | MW | c20s | i20s |
|---|---|---|---|
| (structure) | 816.02 | 37.66 | 98.68 |

TABLE G-continued

| Structure | MW | Purified PI IC$_{50}$ Slope (nM) c20s | i20s |
|---|---|---|---|
| 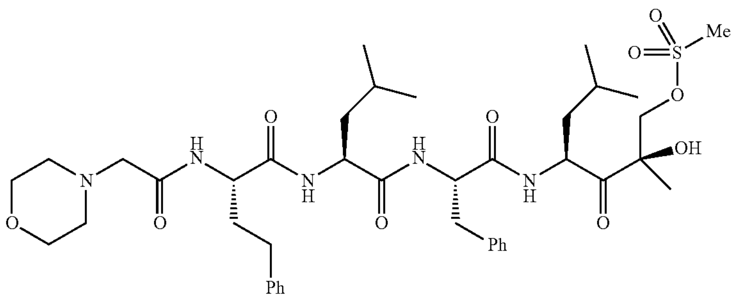 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COS(C)(=O)=O] | 892.11 | 73.67 | 316.4 |
| 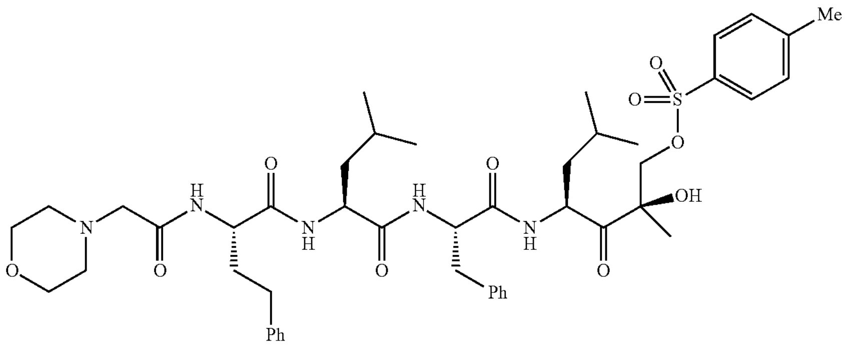 [SMILES: Cc1ccc(S(=O)(=O)OC[C@@](C)(O)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)cc1] | 756.37 | 614.5 | 143.1 |
| 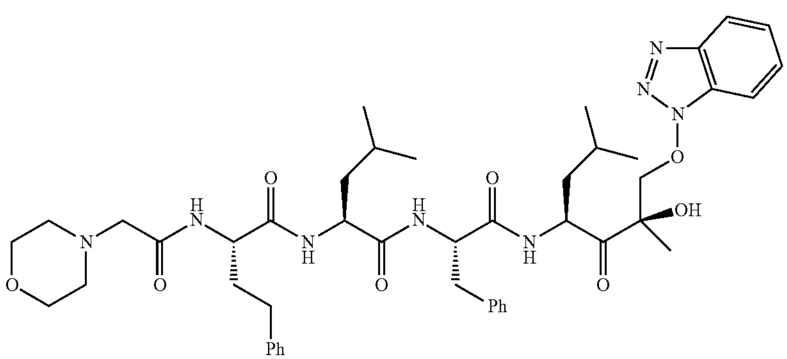 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COn1nnc2ccccc21] | 855.03 | 2473* | 2818* |
| 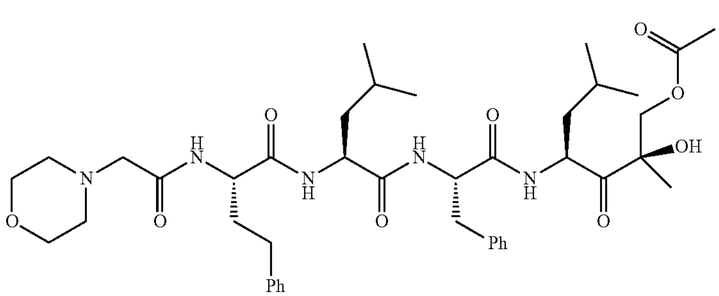 [SMILES: CC(=O)OC[C@@](C)(O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1] | 779.96 | 2444* | 8186 |

TABLE G-continued
| Structure | MW | Purified PI IC$_{50}$ Slope (nM) c20s | i20s |
|---|---|---|---|
| 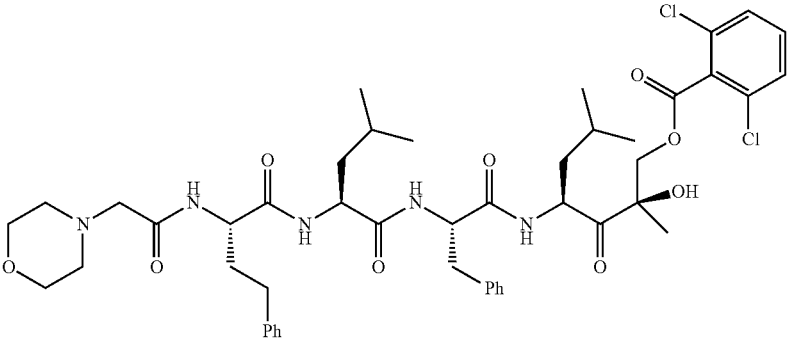 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COC(=O)c1c(Cl)cccc1Cl] | 910.92 | inactive | 659.8 |
| 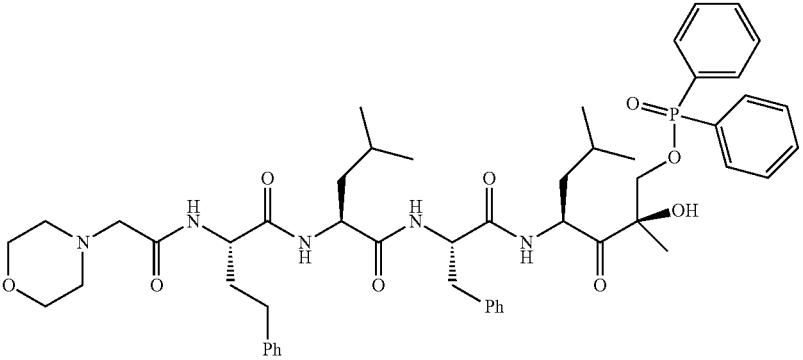 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COP(=O)(c1ccccc1)c1ccccc1] | 938.1 | 2670 | 2547* |
*did not converge
TABLE H
| Structure | MW | IC$_{50}$ Slope (nM) c20s | i20s | Purified PI IC$_{50}$ 60 minute point (nM) c20s | i20s |
|---|---|---|---|---|---|
| Oximes | | | | | |
| 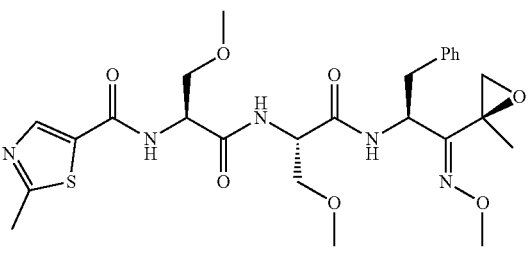 [SMILES: COC[C@H](NC(=O)c1cnc(C)s1)C(=O)N[C@@H](COC)C(=O)N[C@@H](Cc1ccccc1)/C(=N/OC)[C@@]1(C)CO1] | 561.65 | inactive | inactive | 2560* | inactive |

TABLE H-continued
| | | Purified PI | | | |
| | | IC$_{50}$ Slope (nM) | | IC$_{50}$ 60 minute point (nM) | |
| Structure | MW | c20s | i20s | c20s | i20s |
Activated Diols (sulfonates)
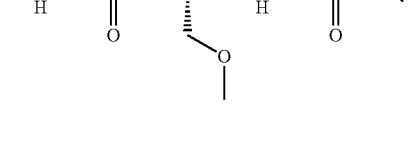 628.71 102.7 179.4 458.5 614.1
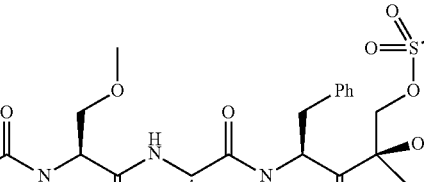 704.81 140.8 251.9 747.9 637.3
 698.81 192.7 278.5*
 704.81 95.37 inactive

TABLE H-continued

| Structure | MW | IC$_{50}$ Slope (nM) Purified PI c20s | IC$_{50}$ Slope (nM) Purified PI i20s | IC$_{50}$ 60 minute point (nM) c20s | IC$_{50}$ 60 minute point (nM) i20s |
|---|---|---|---|---|---|
| (structure 1) | 592.66 | inactive | inactive | inactive | inactive |
| (structure 2) | 723.62 | inactive | inactive | inactive | inactive |
| (structure 3) | 750.8 | inactive | inactive | inactive | inactive |

N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide

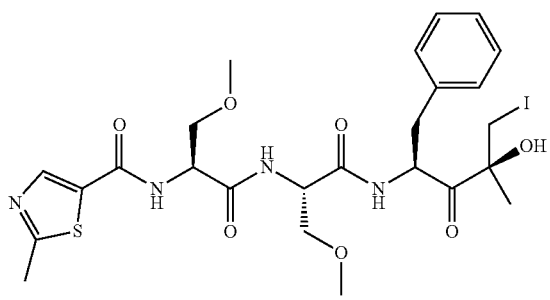 [SMILES: COC[C@H](NC(=O)c1cnc(C)s1)C(=O)N[C@@H](COC)C(=O)N[C@@H](Cc1ccccc1)C(=O)[C@](C)(O)CCl]

Cerium chloride heptahydrate (488 mg, 1.32 mmol) and sodium iodide (423 mg, 2.82 mmol) were added to a solution of compound N—((S)-3-methoxy-1-(((S)-3-methoxy-1-(((S)-1-((R)-2-methyloxiran-2-yl)-1-oxo-3-phenylpropan-2-yl)amino)-1-oxopropan-2-yl)amino)-1-oxopropan-2-yl)-2-methylthiazole-5-carboxamide (1.0 g, 1.88 mmol) in acetonitrile (50 mL). The reaction mixture was stirred at room temperature for 2 h and TLC analysis showed a complete conversion of the starting material. Then saturated sodium hydrogensulfite solution (50 mL) was added and the resulting mixture was extracted with EtOAc (100 mL). The organic phase was separated, washed with brine (50 mL), dried over anhydrous MgSO4 and concentrated under reduced pressure to afford iodohydrin (1.2 g, yield 96%) as a white solid without further purification.

$^1$H NMR (CDCl$_3$): δ 8.06 (s, 1H), 7.28-7.19 (m, 6H), 7.00 (d, J=7.2 Hz, 1H), 6.82 (d, J=6.4 Hz, 1H), 5.42-5.38 (m, 1H), 4.69-4.66 (m, 1H), 4.51-4.48 (m, 1H), 3.94 (s, 1H), 3.85-3.76 (m, 2H), 3.59-3.53 (m, 2H), 3.44-3.39 (m, 4H), 3.31 (s,

3H), 3.22-3.18 (m, 1H), 2.93-2.89 (m, 1H), 2.74 (s, 3H), 1.21 (s, 3H); MS for $C_{25}H_{33}IN_4O7S$ m/z: 661 (M+H)$^+$.

N—((S)-1-(((S)-1-(((2S,4S)-5-Chloro-4-hydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide

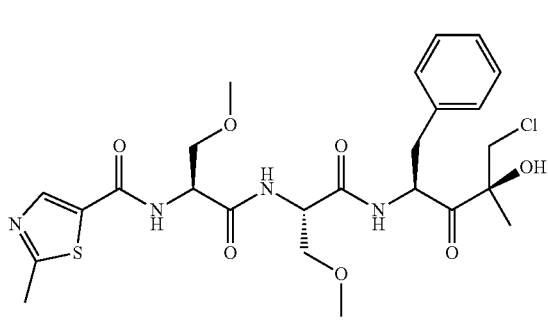

Diethyl chlorophosphate (120 mg, 0.7 mmol) was dissolved in dichloromethane (5 mL). A solution of TiCl$_4$ (1 mg, catalytic) in dichloromethane (2 mL) was added, followed by N—((S)-3-methoxy-1-(((S)-3-methoxy-1-(((S)-1-((R)-2-methyloxiran-2-yl)-1-oxo-3-phenylpropan-2-yl)amino)-1-oxopropan-2-yl)amino)-1-oxopropan-2-yl)-2-methylthiazole-5-carboxamide (300 mg, 0.58 mmol) in dichloromethane (10 mL). The reaction mixture was stirred 9 h at room temperature, then diluted with dichloromethane (10 mL) and water (10 mL). The organic layer was separated and washed with brine (5 mL) and dried over MgSO4. It was concentrated to dryness, and the residue purified on silica gel column (dichloromethane:methanol=100:1 to 80:1) to give product as a white solid (200 mg, yield 63%); MS for $C_{25}H_{33}ClN_4O7S$ m/z: 570 (M+H)$^+$.

N—((S)-1-(((S)-1-(((2S,4S)-5-bromo-4-hydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide

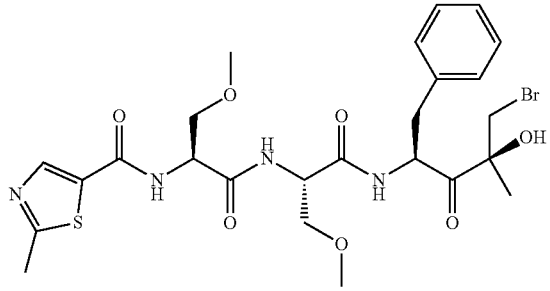 [SMILES: COC[C@H](NC(=O)c1cnc(C)s1)C(=O)N[C@@H](COC)C(=O)N[C@@H](Cc1ccccc1)C(=O)[C@](C)(O)CBr]

Hydrobromic acid (2 eq., 0.314 mL) was added to N—((S)-3-methoxy-1-(((S)-3-methoxy-1-(((S)-1-((R)-2-methyloxiran-2-yl)-1-oxo-3-phenylpropan-2-yl)amino)-1-oxopropan-2-yl)amino)-1-oxopropan-2-yl)-2-methylthiazole-5-carboxamide (1.0 g, 1.88 mmol) in dioxane (20 mL) at 0° C., the reaction allowed to warm to room temperature and stirred overnight. The mixture was diluted with DCM, washed with aqueous saturated sodium bicarbonate, brine, dried (Na$_2$SO$_4$) and evaporated. The residue was purified by Biotage flash column chromatography to give product as a white solid (0.722 g, 48%); $^1$H NMR (CDCl$_3$): δ 8.06 (s, 1H), 7.28-7.18 (m, 6H), 7.02 (d, J=7.6 Hz, 1H), 6.85 (d, J=6.4 Hz, 1H), 5.45-5.40 (m, 1H), 4.71-4.66 (m, 1H), 4.53-4.48 (m, 1H), 4.20 (s, 1H), 3.85-3.75 (m, 3H), 3.57-3.52 (m, 2H), 3.44-3.39 (m, 4H), 3.31 (s, 3H), 3.23-3.18 (m, 1H), 2.94-2.89 (m, 1H), 2.75 (s, 3H), 1.18 (s, 3H); MS for $C_{25}H_{33}BrN_4O7S$ m/z 614 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 6-(acetylthio)hexanoate

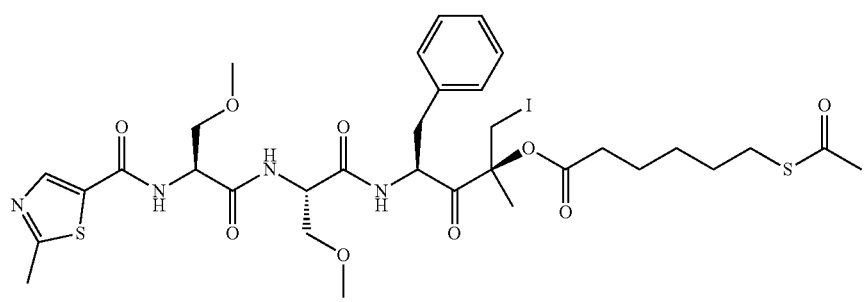 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCCCCSC(C)=O]

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (300 mg, 0.45 mmol) and DMAP (166 mg, 1.5 mmol) in pyridine (15 mL) was kept in a 30° C. oil bath. 6-(Acetylthio)hexanoic anhydride (ca 7 mmol) in pyridine (1 mL) was added and the mixture was stirred 30 min at 30° C. It was diluted with water (20 mL) and dichloromethane (150 mL). The dichloromethane layer was separated and washed with 1N HCl (20 mL) and brine (20 mL). It was dried over sodium sulfate then concentrated to dryness. The residue was purified on silica gel column (dichloromethane:ethyl acetate=1.5:1) to give product as a pale yellow powder (150 mg, 18%); MS for $C_{33}H_{45}IN_4O_9S_2$ m/z: 833 $(M+H)^+$.

(2S,4S)-1-Iodo-4-((S)-3-methoxy-2-((S)-3-methoxy-2-(2-methylthiazole-5-carboxamido)propanamido)propanamido-2-methyl-3-oxo-5-phenylpentan-2-yl 5-(acetylthio)pentanoate

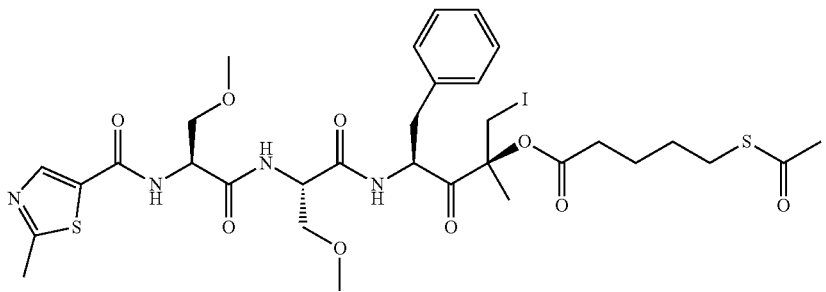 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCCCSC(C)=O]

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (500 mg, 0.76 mmol) and DMAP (300 mg, 2.28 mmol) in pyridine (5 mL) was kept in a 30° C. oil bath. 5-(Acetylthio)pentanoic anhydride 1 (ca 7 mmol) in pyridine (1 mL) was added and the mixture was stirred 30 min at 30° C. It was diluted with water (20 mL) and dichloromethane (50 mL). The dichloromethane layer was separated and washed with 1N HCl (10 mL) and brine (10 mL). It was dried over sodium sulfate then concentrated to dryness. The residue was purified on silica gel column (dichloromethane:ethyl acetate=1.5:1) to give product as a pale yellow powder (240 mg, yield 37%); MS for $C_{32}H_{43}IN_4O_9S_2$ m/z: 819 $(M+H)^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 4-(acetylthio)butanoate

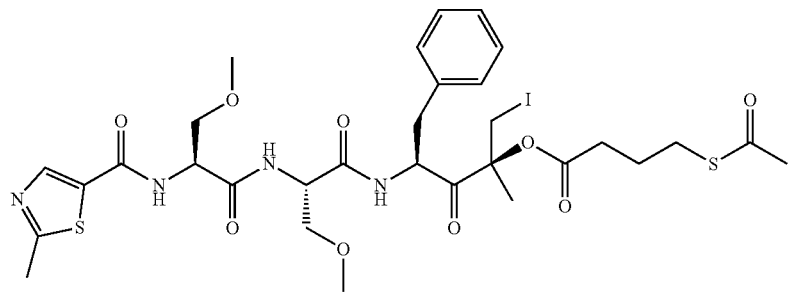 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCCSC(C)=O]

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (500 mg, 0.76 mmol) and DMAP (300 mg, 2.28 mmol) in pyridine (2 mL) 2 was kept in a 30° C. oil bath. 4-(Acetylthio)butanoic anhydride (ca 7 mmol) in pyridine (1 mL) was added and the mixture was stirred 30 min at 30° C. It was diluted with water (20 mL) and dichloromethane (50 mL). The dichloromethane layer was separated and washed with 1N HCl (10 mL) and brine (10 mL). It was dried over sodium sulfate then concentrated to dryness. The residue was purified on silica gel column (dichloromethane:ethyl acetate=1.5:1) to give product as a pale yellow powder (300 mg, 50%); MS for $C_{31}H_{41}IN_4O_9S_2$ m/z: 805 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 5-acetoxypentanoate

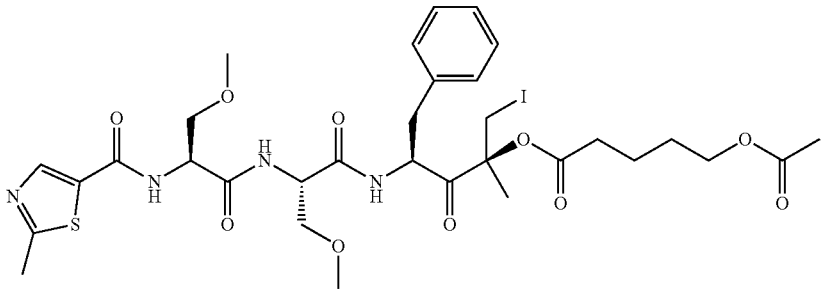

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (500 mg, 0.76 mmol) and DMAP (300 mg, 2.28 mmol) in pyridine (2 mL) was kept in a 30° C. oil bath. 5-(Acetoxy)pentanoic anhydride (ca 7 mmol) in pyridine (I mL) was added and the mixture was stirred 30 min at 30° C. It was diluted with water (20 mL) and dichloromethane (50 mL). The dichloromethane layer was separated and washed with 1N HCl (10 mL) and brine (10 mL). It was dried over sodium sulfate then concentrated to dryness. The residue was purified on silica gel column (dichloromethane:ethyl acetate=1.5:1) to give product as a brownish powder (340 mg, 55%); MS for $C_{32}H_{43}IN_4O_{10}S$ m/z: 803 (M+H)$^+$.

5-(Acetoxy)pentanoic Anhydride

General procedure for anhydride preparation: To a solution of acid (1 mmol) in dichloromethane (2 mL) under $N_2$ was added DCC (0.5 mmol). The reaction mixture was stirred overnight then filtered to remove DCU. The filtrate was concentrated to dryness to give the crude anhydride.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 4-acetoxybutanoate

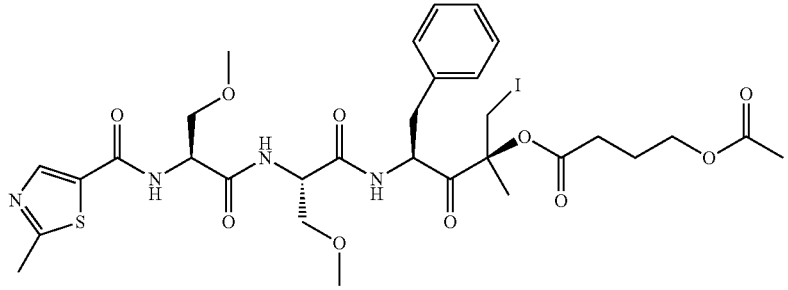 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCCOC(C)=O]

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (500 mg, 0.76 mmol) and DMAP (300 mg, 2.28 mmol) in pyridine (2 mL) was kept in a 30° C. oil bath. 4-(Acetoxy)butanoic anhydride (ca 7 mmol) in pyridine (1 mL) was added and the mixture was stirred 30 min at 30° C. It was diluted with water (20 mL) and dichloromethane (50 mL). The dichloromethane layer was separated and washed with 1N HCl (10 mL) and brine (10 mL). It was dried over sodium sulfate then concentrated to dryness. The residue was purified on silica gel column (dichloromethane:ethyl acetate=1.5:1) to give product as a white powder (300 mg, 50%); $^1$H NMR (300 MHz, CDCl$_3$): δ 8.12 (s, 1H), 7.29-7.10 (m, 6H), 7.06-6.95 (m, 2H), 5.38-5.30 (m, 1H), 4.78-4.70 (m, 1H), 4.51-4.45 (m, 1H), 4.15 (t, J=6.6 Hz, 1H), 3.91-3.72 (m, 3H), 3.65-3.73 (m, 1H), 3.66-3.55 (m, 2H), 3.48 (s, 3H), 3.46-3.39 (m, 1H), 3.30 (s, 3H), 3.14-3.05 (m, 1H), 2.90-2.83 (m, 1H), 2.77 (s, 3H), 2.58-2.52 (m, 2H), 1.97-1.92 (m, 2H), 1.35 (s, 3H); MS for C$_{31}$H$_{41}$IN$_4$O$_{10}$S m/z: 789 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 4-acetoxy-3,3-dimethylbutanoate

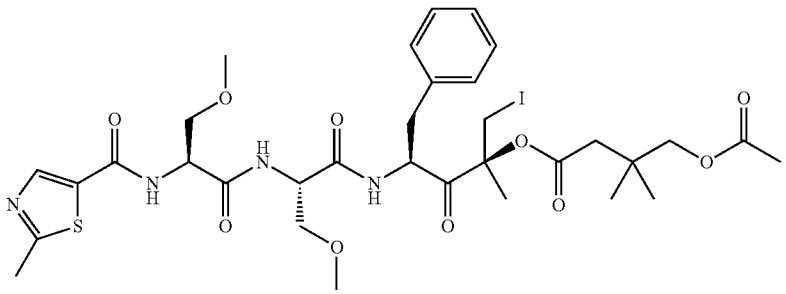 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CC(C)(C)COC(C)=O]

Prepared according to the procedures described above, by reacting 4-acetoxy-3,3-dimethylbutanoic anhydride with N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. $^1$H NMR (300 MHz, CDCl$_3$): δ 8.10 (s, 1H), 7.29-7.11 (m, 6H), 7.05 (d, J=6.6 Hz, 1H), 6.92 (d, J=7.8 Hz, 1H), 5.37-5.29 (m, 1H), 4.78-4.68 (m, 1H), 4.51-4.46 (m, 1H), 3.96 (s, 2H), 3.85-3.73 (m, 3H), 3.64-3.52 (m, 2H), 3.47 (s, 3H), 3.43-3.39 (m, 1H), 3.28 (s, 3H), 3.18-3.09 (m, 1H), 2.93-2.83 (m, 1H), 2.76 (s, 3H), 2.45 (d, J=8.4 Hz, 2H), 2.11 (s, 3H), 1.45 (s, 3H), 1.11 (s, 3H), 1.09 (s, 3H); MS for C$_{33}$H$_{45}$IN$_4$O$_{10}$S m/z: 817 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl ((5-methyl-2-oxo-1,3-dioxol-4-yl)methyl) carbonate

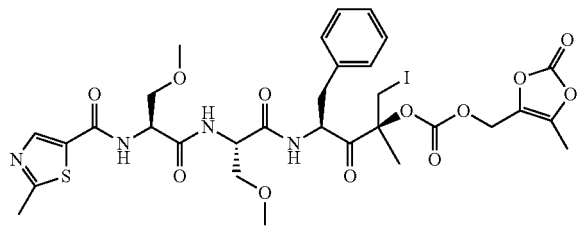 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)OCc1oc(=O)oc1C]

A solution of N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (500 mg, 0.76 mmol) and DMAP (180 mg, 1.5 mmol) in dichloromethane (7.5 mL) was kept at 0° C. in an ice-water bath. A solution of triphosgene (150 mg, 1.5 mmol) in toluene (7.5 mL) was added. The solution was stirred 10 min, then DMAP (90 mg, 0.75 mmol) was added. The solution was stirred another 10 min, then another portion of DMAP (180 mg, 1.5 mmol) was added. The reaction mixture was stirred 10 min, then 4-(hydroxymethyl)-5-methyl-1,3-dioxol-2-one (1 g, 7.6 mmol) was added. The mixture was allowed to stirred over night, then diluted with water (20 mL) and dichloromethane (50 mL). The dichloromethane layer was separated and washed with 1N HCl (10 mL) and brine (10 mL). It was dried over sodium sulfate then concentrated to dryness. Three similar batches were combined, and the residue was purified on reverse-phase prep-HPLC to give product as a white powder (75 mg) as white powder; $^1$H NMR (300 MHz, CDCl$_3$): δ 8.12 (s, 1H), 7.29-7.10 (m, 6H), 6.95 (m, 2H), 5.48-5.37 (m, 1H), 4.93 (m, 2H), 4.78-4.69 (m, 1H), 4.51-4.42 (m, 1H), 3.87-3.82 (m, 2H), 3.79-3.73 (m, 1H), 3.66-3.55 (m, 2H), 3.48 (s, 3H), 3.47-3.44 (m, 1H), 3.28 (s, 3H), 3.18-3.11 (m, 1H), 2.90-2.82 (m, 1H), 2.77 (s, 3H), 2.22 (s, 3H), 1.48 (s, 3H); MS for C$_{31}$H$_{37}$IN$_4$O$_{12}$S m/z: 817 (M+H)$^+$.

Ethyl ((2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl) oxalate

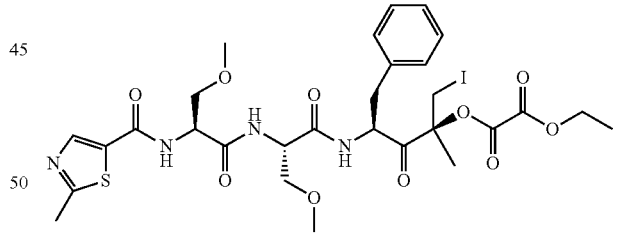

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (300 mg, 0.46 mmol) and DMAP (150 mg, 1.14 mmol) in pyridine (5 mL) was kept in a 30° C. oil bath. 2-Ethoxy-2-oxoacetic anhydride (ca 10 mmol) in pyridine (2 mL) was 3 Journal of Medicinal Chemistry 35, 11, 1992, p 2113-2129 4 European Journal of Medicinal Chemistry 47, 2012, p 485-492 added and the mixture was stirred 30 min at 30° C. It was diluted with water (20 mL) and dichloromethane (50 mL). The dichloromethane layer was separated and washed with 1N HCl (10 mL) and brine (10 mL). It was dried over sodium sulfate then concentrated to dryness. The residue was purified on silica gel column (dichloromethane:ethyl acetate=2:1 to 1:1) to give product as a yellow powder (180 mg, 53%); $^1$H NMR (300 MHz, CDCl$_3$): δ 8.10 (s, 1H), 7.29-7.18 (m, 6H), 7.05 (d, J=7.5 Hz, 1H), 6.96 (d, J=6.9 Hz, 1H), 5.42-5.31 (m, 1H), 4.78-4.69 (m, 1H), 4.65-4.56 (m, 1H), 4.45-4.37 (m, 2H), 3.78-3.64 (m, 3H), 3.68-3.65 (m, 1H), 3.62-3.53 (m, 1H), 3.45-3.42 (m, 1H), 3.44 (s, 3H), 3.31 (s, 3H), 3.25-3.16 (m, 1H), 2.98-2.91 (m, 1H), 2.76 (s, 3H), 1.53 (s, 3H), 1.42 (t, J=7.2 Hz, 3H); MS for C$_{29}$H$_{37}$IN$_4$O$_{10}$S m/z: 761 (M+H)$^+$.

Ethyl ((2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl) succinate

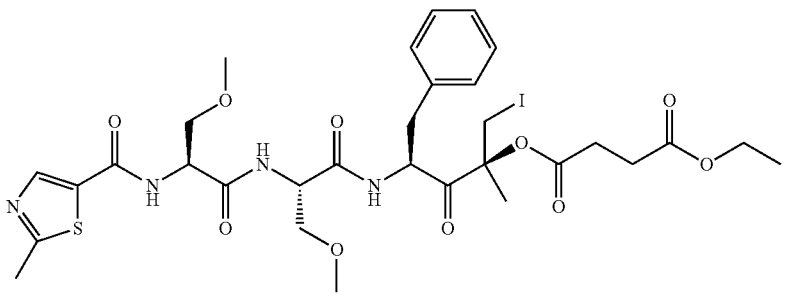 [SMILES: CCOC(=O)CCC(=O)O[C@](C)(CI)C(=O)[C@H](Cc1ccccc1)NC(=O)[C@H](COC)NC(=O)[C@H](COC)NC(=O)c1cnc(C)s1]

A solution of N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (300 mg, 0.46 mmol) and DMAP (166 mg, 1.36 mmol) in pyridine (2 mL) was kept in a 30° C. oil bath. 4-Ethoxy-4-oxobutanoic anhydride (ca 8.5 mmol) in pyridine (I mL) was added and the mixture was stirred 30 min at 30° C. It was diluted with water (20 mL) and dichloromethane (50 mL). The dichloromethane layer was separated and washed with 1N HCl (10 mL) and brine (10 mL). It was dried over sodium sulfate then concentrated to dryness. The residue was purified on silica gel column (dichloromethane:ethyl acetate=2:1) to give product as a white powder (200 mg, 55%); $^1$H NMR (300 MHz, CDCl$_3$): δ 8.10 (s, 1H), 7.29-7.10 (m, 6H), 7.05 (m, 2H), 5.39-5.29 (m, 1H), 4.78-4.69 (m, 1H), 4.63-4.56 (m, 1H), 4.20-4.11 (m, 2H), 3.89-3.81 (m, 2H), 3.76-3.72 (m, 1H), 3.62-3.53 (m, 2H), 3.46 (s, 3H), 3.43 (m, 1H), 3.31 (s, 3H), 3.15-3.05 (m, 1H), 2.90-2.78 (m, 3H), 2.76 (s, 3H), 2.71-2.72 (m, 2H), 1.37 (s, 3H), 1.27 (t, J=7.2 Hz, 3H); MS for C$_{31}$H$_{41}$IN$_4$O$_{10}$S m/z: 789 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 2-methoxyacetate

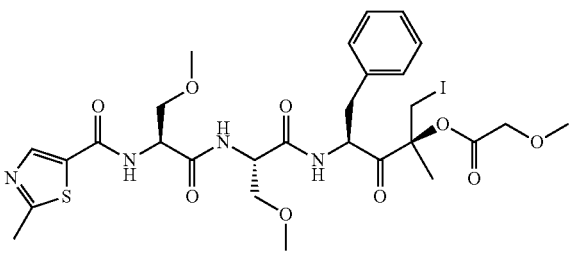 [SMILES: COCC(=O)O[C@](C)(CI)C(=O)[C@H](Cc1ccccc1)NC(=O)[C@H](COC)NC(=O)[C@H](COC)NC(=O)c1cnc(C)s1]

Prepared according to the procedures described above, by reacting 2-methoxyacetic anhydride with N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. $^1$H NMR (300 MHz, CDCl$_3$): δ 8.09 (s, 1H), 7.29-7.15 (m, 6H), 7.09 (d, J=7.5 Hz, 1H), 6.98 (d, J=6.9 Hz, 1H), 5.41-5.32 (m, 1H), 4.75-4.69 (m, 1H), 4.51-4.45 (m, 1H), 4.25 (d, J=16.8 Hz, 1H), 4.11 (d, J=16.8 Hz, 1H), 3.91-3.82 (m, 2H), 3.78-3.74 (m, 1H), 3.65-3.58 (m, 2H), 3.51 (s, 3H), 3.47 (m, 1H), 3.45 (s, 3H), 3.32 (s, 3H), 3.18-3.09 (m, 1H), 2.95-2.86 (m, 1H), 2.76 (s, 3H), 1.33 (s, 3H); MS for $C_{28}H_{37}IN_4O_9S$ m/z: 733.14 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 2-phenoxyacetate

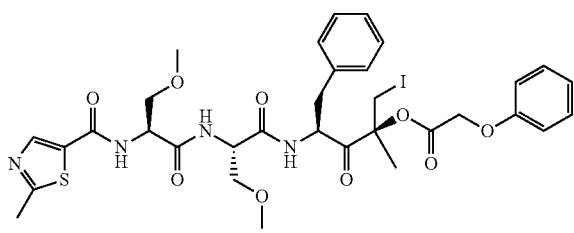 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)COc1ccccc1]

2-Phenoxyacetic acid (1.5 g, 9.9 mmol) was dissolved in dry DCM (50 mL) under N2 and DCC (0.93 g, 4.45 mmol) was added at 0° C. The reaction mixture was stirred overnight at room temperature. The precipitated white solid was filtered off and the filtration was concentrated under reduced pressure to give the corresponding anhydride. The anhydride was added to a solution of N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (300 mg, 0.46 mmol) and DMAP (180 mg, 1.3 mmol) in pyridine (3 mL) at 0° C. The reaction mixture was allowed to warm to room temperature and stirred for 5 h. The mixture was poured into a mixture of DCM (70 mL) and 2N HCl (50 mL). The organic layer was separated, washed with saturated NaHCO3 (50 mL), dried over sodium sulfate and concentrated to dryness. The residue was purified on silica gel column (dichloromethane:ethyl acetate=1.5:1) to give product as a white powder (200 mg, 54%); MS for $C_{33}H_{39}IN_4O_9S$ m/z: 795 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 2-amino-3-methylbutanoate, Hydrochloride Salt

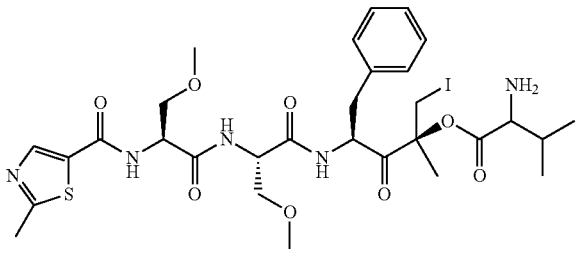 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)C(N)C(C)C]

Boc-Val-OH (3.0 g, 13.8 mmol) was dissolved in dry DCM (20 mL) under N$_2$ and DCC (1.42 g, 6.9 mmol) was added. The reaction mixture was stirred overnight at room temperature. The precipitated white solid was filtered off and the filtrate was concentrated under reduced pressure to give the corresponding anhydride. The anhydride was added to a solution of N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (300 mg, 0.45 mmol) and DMAP (166 mg, 1.36 mmol) in pyridine (5 mL). The reaction mixture was stirred at 30° C. for 4 h. The mixture was diluted with DCM (50 mL) and then washed with 2N HCl (2×30 mL) and saturated NaHCO3 (40 mL), respectively. The organic layer was separated, dried over sodium sulfate and concentrated to dryness. The residue was purified on silica gel column (dichloromethane:ethyl acetate-1.5:1) to give the desired Boc-ester (150 mg, yield 39%) as white powder. Boc-ester (150 mg, 0.17 mmol) was dissolved in 10 mL of HCl-EtOAc (2M) and the mixture was stirred for 2 h at room temperature. The solvent was removed under reduced pressure and the residue was triturated with ether. The resulting precipitate was collected by filtration to give product as a pale yellow powder (110 mg, 79%); MS for $C_{30}H_{42}IN_5O_8S$ m/z: 760 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 2-aminoacetate, Hydrochloride Salt

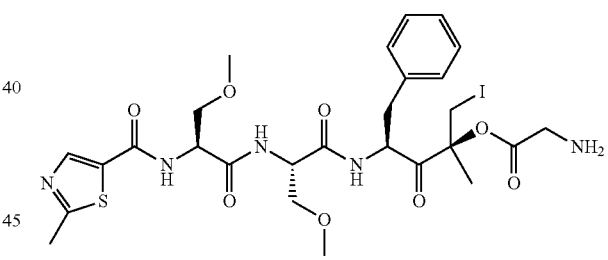

Prepared according to the methods described above, by reacting 2-((tert-butoxycarbonyl)amino)acetic anhydride with N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. $^1$H NMR (300 MHz, DMSO-d$_6$): δ 8.85 (d, J=8.1 Hz, 1H), 8.66 (d, J=9.0 Hz, 1H), 8.46 (m, 3H), 8.30 (d, J=7.5 Hz, 1H), 7.30-7.15 (m, 5H), 5.09-4.97 (m, 1H), 4.78-4.69 (m, 1H), 4.47-4.39 (m, 1H), 3.99-3.89 (m, 2H), 3.88-3.75 (m, 2H), 3.61-3.30 (m, 4H), 3.25 (s, 3H), 3.21 (s, 3H), 3.09-2.98 (m, 1H), 2.85-2.76 (m, 1H), 2.78 (s, 3H), 1.47 (s, 3H); MS for $C_{27}H_{36}IN_5O_8S$ m/z: 718 (M+H)$^+$.

4-((5S,7S,10S,13S)-7-Benzyl-5-(iodomethyl)-10-(methoxymethyl)-5-methyl-13-(2-methylthiazole-5-carboxamido)-3,6,9,12-tetraoxo-2,4,15-trioxa-8,11-diazahexadecyl)phenyl Acetate

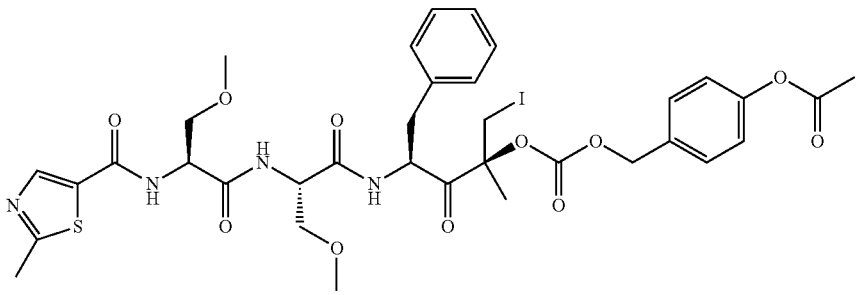 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)OCc1ccc(OC(C)=O)cc1]

A solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (1.0 g, 1.5 mmol) and DMAP (360 mg, 3 mmol) in dichloromethane (15 mL) was kept at 0° C. in an ice-water bath. A solution of triphosgene (300 mg, 3 mmol) in toluene (10.0 mL) was added. The solution was stirred for 10 min and new portion of DMAP (180 mg, 1.5 mmol) was added. The solution was stirred for 10 min and another portion of DMAP (180 mg, 1.5 mmol) was added. The mixture was stirred for 10 min and 4-(hydroxymethyl)phenyl acetate (2.49 g, 15 mmol) [4-(Hydroxymethyl)phenyl acetate was prepared from 4-hydroxybenzaldehyde in two steps (reaction with acetic anhydride followed by hydrogenation.] was added. The reaction mixture was allowed to warm to room temperature and stirred overnight. The mixture was diluted with water (30 mL) and dichloromethane (100 mL). The organic layer was separated, washed with 1N HCl (30 mL) and brine (20 mL), dried over sodium sulfate and concentrated to dryness. The residue was purified on prep-HPLC to give product as an off-white powder (190 mg, 15%); $^1$H NMR (300 MHz, CDCl$_3$): δ 8.09 (s, 1H), 7.47 (d, J=8.4 Hz, 2H), 7.29-7.10 (m, 6H), 7.15 (d, J=8.4 Hz, 2H), 6.97-6.91 (m, 2H), 5.47-5.40 (m, 1H), 5.21 (s, 2H), 4.77-4.67 (m, 1H), 4.53-4.46 (m, 1H), 3.87-3.75 (m, 3H), 3.68-3.54 (m, 2H), 3.47 (s, 3H), 3.46-3.43 (m, 1H), 3.28 (s, 3H), 3.18-3.14 (m, 1H), 2.95-2.86 (m, 1H), 2.76 (s, 3H), 2.31 (s, 3H), 1.52 (s, 3H); MS for C$_{35}$H$_{41}$IN$_4$O$_{11}$S m/z: 853 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 2-chloroacetate

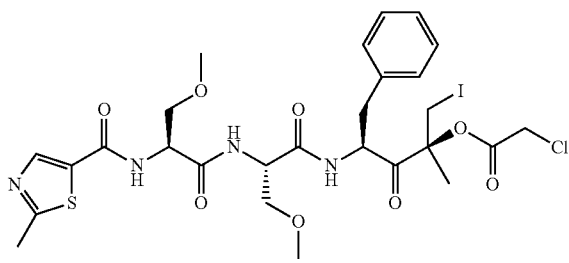 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCl]

To a solution of N—((S)-1-(((S)-1-(((2S,4S)-4-Hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide (300 mg, 0.46 mmol) and DMAP (300 mg, 230 mmol) in DCM (10 mL) was added dropwise a solution of 2-chloroacetic anhydride (0.78 g, 4.6 mmol) in DCM (1 mL) at 5~10° C. and the reaction mixture was stirred for 2 h. The mixture was diluted with DCM (50 mL) and then washed with 2N HCl (25 mL) and saturated NaHCO3 (25 mL), respectively. The organic layer was separated, dried over sodium sulfate and concentrated to dryness. The residue was purified on silica gel column (dichloromethane:ethyl acetate=1.5:1) to give product as a white powder (200 mg, 59%); $^1$H NMR (300 MHz, CDCl$_3$): δ 8.10 (s, 1H), 7.29-7.10 (m, 6H), 7.05 (d, J=7.5 Hz, 1H), 6.93 (d, J=6.6 Hz, 1H), 5.41-5.32 (m, 1H), 4.78-4.69 (m, 1H), 4.53-4.46 (m, 1H), 4.24 (m, 2H), 3.93-3.75 (m, 3H), 3.75-3.63 (m, 2H), 3.49 (s, 3H), 3.48-3.45 (m, 1H), 3.32 (s, 3H), 3.18-3.09 (m, 1H), 2.95-2.86 (m, 1H), 2.76 (s, 3H), 1.28 (s, 3H); MS for C$_{27}$H$_{34}$ClN$_4$O$_8$S m/z: 738 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl Formate

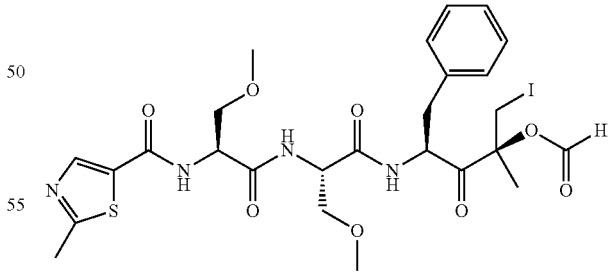

$^1$H NMR (300 MHz, CDCl$_3$): δ 8.08 (s, 1H), 8.04 (s, 1H), 7.29-7.10 (m, 6H), 6.97-6.87 (m, 1H), 5.42-5.34 (m, 1H), 4.78-4.69 (m, 1H), 4.53-4.46 (m, 1H), 3.90-3.75 (m, 3H), 3.65-3.54 (m, 2H), 3.49 (s, 3H), 3.48-3.45 (m, 1H), 3.32 (s, 3H), 3.18-3.09 (m, 1H), 2.95-2.86 (m, 1H), 2.76 (s, 3H), 1.48 (s, 3H); MS for C$_{26}$H$_{33}$IN$_4$O$_8$S m/z: 689 (M+H)$^+$.

Figure 38:
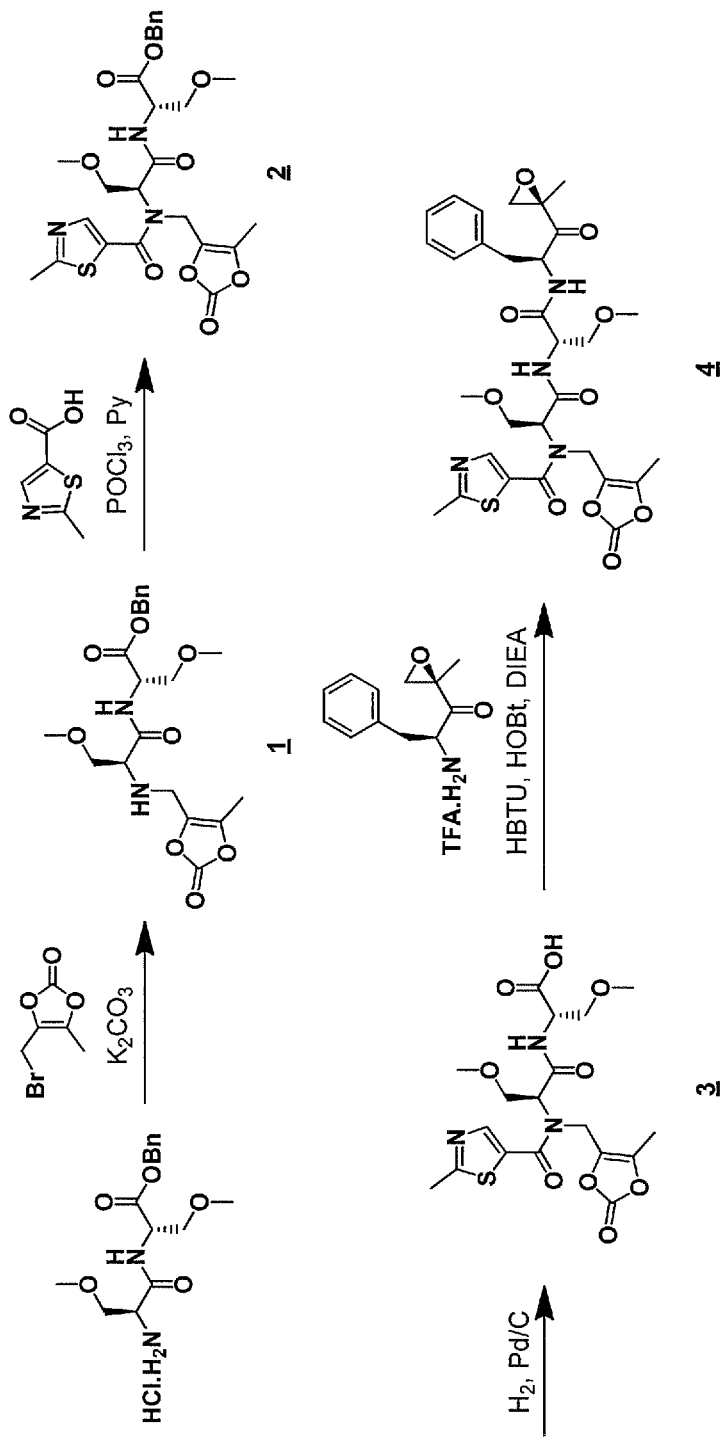
FIG. 38 is a scheme showing the synthesis of an embodiment of a thiazole carboxamide prodrug of epoxy ketone proteasome inhibitors.

N—((S)-3-Methoxy-1-((S)-3-methoxy-1-((S)-1-((R)-2-methyloxiran-2-yl)-1-oxo-3-phenylpropan-2-yl)amino)-1-oxopropan-2-yl)amino)-1-oxopropan-2-yl)-2-methyl-N-((5-methyl-2-oxo-1,3-dioxol-4-yl)methyl)thiazole-5-carboxamide (S)-Benzyl 3-methoxy-2-((S)-3-methoxy-2-(((5-methyl-2-oxo-1,3-dioxol-4-yl)methyl)amino)propanamido)propanoate Referring to FIG. 38, 4-(bromomethyl)-5-methyl-1,3-dioxo-2-one (278 mg, 1.44 mmol) was added to (S)-benzyl 2-((S)-2-amino-3-methoxypropanamido)-3-methoxypropanoate hydrochloride salt (1.0 g, 2.88 mmol) and potassium carbonate (400 mg, 2.88 mmol) in DMF (15 mL) at 0° C. The reaction was stirred at 00 for 2.5 hours and then diluted with water and extracted with EtOAc. The extract was washed with brine, dried (Na$_2$SO$_4$) and evaporated. The residue was purified by Biotage flash column chromatography to give product as a yellow oil. MS for C$_{20}$H$_{26}$N$_2$O$_8$ m/z: 423 (M+H)$^+$.

(S)-Benzyl 3-methoxy-2-((S)-3-methoxy-2-(2-methyl-N-((5-methyl-2-oxo-1,3-dioxol-4-yl)methyl)thiazole-5-carboxamido)propanamido)propanoate Referring to FIG. 38, phosphorous oxychloride (323 μL, 3.46 mmol) was added dropwise to (S)-benzyl 3-methoxy-2-((S)-3-methoxy-2-(((5-methyl-2-oxo-1,3-dioxol-4-yl)methyl)amino)propanamido)propanoate (1.46 g, 3.46 mmol), 2-methylthiazole-5-carboxylic acid (248 mg, 3.46 mmol) and pyridine (1.07 mL, 10 mmol) in DCM (20 ml) at 0° C. The reaction mixture was stirred at 0° C. for 3 hours, diluted with 1N HCl, and extracted with DCM. The organic layer was separated, dried (Na$_2$SO$_4$) and evaporated. The residue was purified by flash column chromatography to give the product as a white solid (346 mg, 22%).

(S)-3-Methoxy-2-((S)-3-methoxy-2-(2-methyl-N-((5-methyl-2-oxo-1,3-dioxol-4-yl)methyl)thiazole-5-carboxamido)propanamido)propanoic Acid Referring to FIG. 38, (S)-benzyl 3-methoxy-2-((S)-3-methoxy-2-(2-methyl-N-((5-methyl-2-oxo-1,3-dioxol-4-yl)methyl)thiazole-5-carboxamido)propanamido)propanoate (346 mg, 0.632 mmol) and palladium on carbon (10%, 70 mg) in methanol was stirred under hydrogen (balloon) overnight. The reaction was filtered and evaporated to give product suitable for use directly in the next step.

Referring to FIG. 38, diisopropylethylamine (0.32 mL, 1.84 mmol) was added to (S)-3-methoxy-2-((S)-3-methoxy-2-(2-methyl-N-((5-methyl-2-oxo-1,3-dioxol-4-yl)methyl)thiazole-5-carboxamido)propanamido)propanoic acid (0.28 g, 0.612 mmol), (S)-2-amino-1-((R)-2-methyloxiran-2-yl)-3-phenylpropan-1-one, hydrochloride (0.15 g, 0.612 mmol), HBTU (0.35 g, 0.918 mmol), and HOBt (0.124 g, 0.918 mmol) in DMF (4 mL) at 0° C. The reaction was stirred at 0° C. for 30 minutes, diluted with EtOAc, washed with 2N HCl, sat. aq. sodium bicarbonate and brine, dried (Na$_2$SO$_4$) and evaporated. The residue was purified by flash column chromatography to give product as a white solid (0.24 g, 60%); $^1$H NMR (300 MHz, CDCl$_3$): δ 7.92 (s, 1H), 7.41-7.11 (m, 7H), 4.92-4.82 (m, 1H), 4.61-4.55 (m, 1H), 4.47-4.39 (m, 1H), 3.99-3.91 (m, 1H), 3.84-3.75 (m, 1H), 3.43 (s, 3H), 3.41 (s, 3H), 3.18-3.12 (m, 1H), 2.95-2.89 (m, 2H), 2.74 (s, 2H), 2.18 (s, 3H), 1.55 (s, 3H); MS for C$_{30}$H$_{36}$N$_4$O$_{10}$S m/z: 645 (M+H)$^+$.

Ethyl ((2S,4S)-1-iodo-4-((S)-3-methoxy-2-((S)-3-methoxy-2-(2-methylthiazole-5-carboxamido)propanamido)propanamido)-2-methyl-3-oxo-5-phenylpentan-2-yl) carbonate

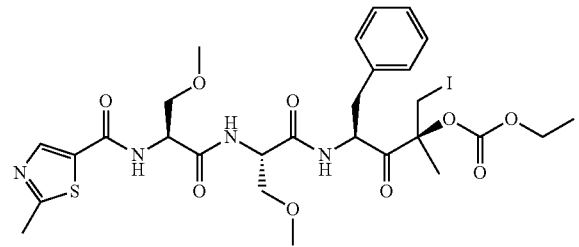 [SMILES: CCOC(=O)O[C@](C)(CI)C(=O)[C@H](Cc1ccccc1)NC(=O)[C@H](COC)NC(=O)[C@H](COC)NC(=O)c1cnc(C)s1]

Prepared according to procedures described above, by reacting ethanol with the intermediate (2S,4S)-1-iodo-4-((S)-3-methoxy-2-((S)-3-methoxy-2-(2-methylthiazole-5-carboxamido)propanamido)propanamido)-2-methyl-3-oxo-5-phenylpentan-2-yl carbonochloridate. $^1$H NMR (CDCl$_3$): δ 8.05 (s, 1H), 7.28-7.16 (m, 5H), 7.08 (d, J=9.2 Hz, 1H), 6.96 (d, J=7.2 Hz, 1H), 6.84 (d, J=6 Hz, 1H), 5.44-5.40 (m, 1H), 4.71-4.66 (m, 1H), 4.48-4.44 (m, 1H), 4.21 (q, J=7.2 Hz, 2H), 3.84-3.79 (m, 2H), 3.75-3.72 (m, 1H), 3.62 (d, J=11.2 Hz, 1H), 3.55 (t, J=4.8 Hz, 1H), 3.45 (s, 3H), 3.41-3.38 (m, 1H), 3.28 (s, 3H), 3.19-3.14 (m, 1H), 2.89-2.83 (m, 1H), 2.74 (s, 3H), 1.51 (s, 3H), 1.35 (t, J=7.2 Hz, 3H); MS for C$_{28}$H$_{37}$IN$_4$O$_9$S m/z: 733 (M+H)$^+$.

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl phenyl carbonate

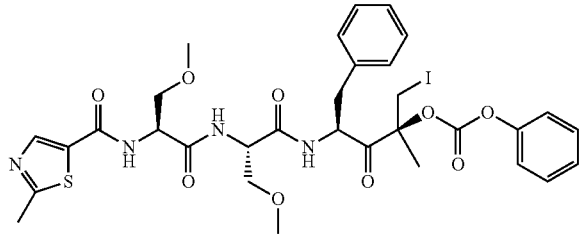 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)Oc1ccccc1]

Prepared according to procedures described above, using phenol with the intermediate (2S,4S)-1-iodo-4-((S)-3-methoxy-2-((S)-3-methoxy-2-(2-methylthiazole-5-carboxamido)propanamido)propanamido)-2-methyl-3-oxo-5-phenylpentan-2-yl carbonochloridate. $^1$H NMR (CDCl$_3$): δ 8.02 (s, 1H), 7.40 (t, J=8 Hz, 2H), 7.29-7.10 (m, 10H), 6.98 (d, J=7.2 Hz, 1H), 6.82 (d, J=6 Hz, 1H), 5.51-5.45 (m, 1H), 4.67-4.62 (m, 1H), 4.45-4.41 (m, 1H), 3.83-3.78 (m, 2H), 3.70-3.64 (m, 2H), 3.50 (t, J=4.8 Hz, 1H), 3.45 (s, 3H), 3.32-3.28 (m, 1H), 3.27 (s, 3H), 3.19-3.14 (m, 1H), 2.91-2.86 (m, 1H), 2.74 (s, 3H), 1.55 (s, 3H); MS for C$_{32}$H$_{37}$IN$_4$O$_9$S m/z: 782 (M+H)$^+$.

223

(2S,4S)-1-Iodo-4-((S)-3-methoxy-2-((S)-3-methoxy-2-(2-methylthiazole-5-carboxamido)propanamido)propanamido)-2-methyl-3-oxo-5-phenylpentan-2-yl 2-acetoxyacetate

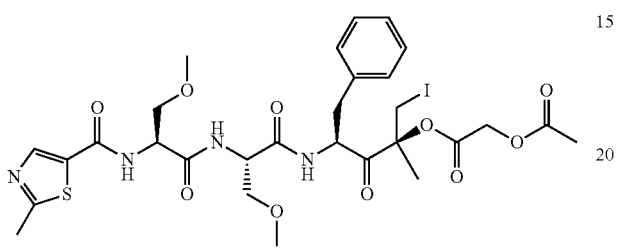

Prepared according to procedures described above, by reacting 2-acetoxyacetic anhydride with N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. $^1$H NMR (300 MHz, CDCl$_3$): δ 8.09 (s, 1H), 7.31-7.15 (m, 6H), 7.05 (d, J=7.5 Hz, 1H), 6.96 (d, J=6.3 Hz, 1H), 5.39-5.34 (m, 1H), 4.78-4.70 (m, 3H), 4.55-4.46 (m, 1H), 3.89-3.82 (m, 2H), 3.78-3.72 (m, 1H), 3.62-3.53 (m, 2H), 3.48 (s, 3H), 3.45-3.42 (m, 1H), 3.32 (s, 3H), 3.18-3.09 (m, 1H), 2.95-2.86 (m, 1H), 2.76 (s, 3H), 2.18 (s, 3H), 1.27 (s, 3H); MS for C$_{29}$H$_{37}$IN$_4$O$_{10}$S nm/z: 762 (M+H)$^+$.

(2S,4S)-1-iodo-4-((S)-3-methoxy-2-((S)-3-methoxy-2-(2-methylthiazole-5-carboxamido)propanamido)propanamido)-2-methyl-3-oxo-5-phenylpentan-2-yl 3-(2-acetoxyphenyl)propanoate

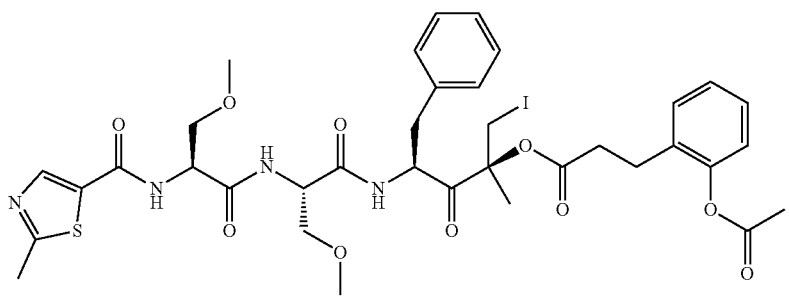 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCc1ccccc1OC(C)=O]

224

Prepared according to procedures described above, by reacting 3-(2-acetoxyphenyl)propanoic anhydride with N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for C$_{36}$H$_{43}$IN$_4$O$_{10}$S m/z: 851 (M+H)$^+$.

(2S,4S)-1-Iodo-4-((S)-3-methoxy-2-((S)-3-methoxy-2-(2-methylthiazole-S-carboxamido)propanamido)propanamido)-2-methyl-3-oxo-5-phenylpentan-2-yl 2-(acetoxymethyl)benzoate

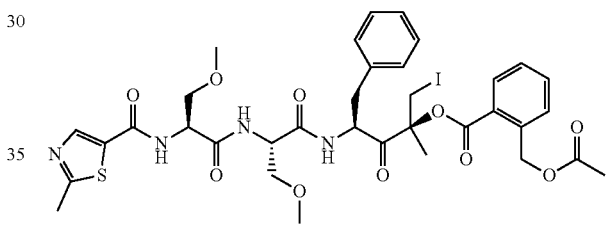

Prepared according to procedures described above, by reacting 2-(acetoxymethyl)benzoic anhydride with N—((S)-1-(((S)-1-(((2S,4S)-4-hydroxy-5-iodo-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for C$_{35}$H$_{41}$IN$_4$O$_{10}$S m/z: 837 (M+H)$^+$.

(2R,4S)-2-Hydroxy-4-((S)-3-methoxy-2-((S)-3-methoxy-2-(2-methylthiazole-5-carboxamido)propanamido)propanamido)-2-methyl-3-oxo-5-phenyl-pentyl 4-(trifluoromethyl)benzenesulfonate

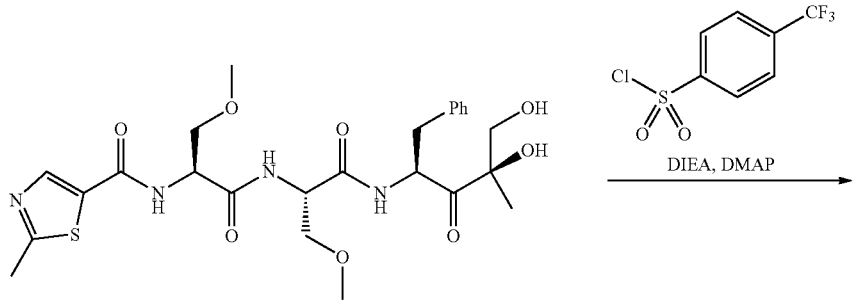

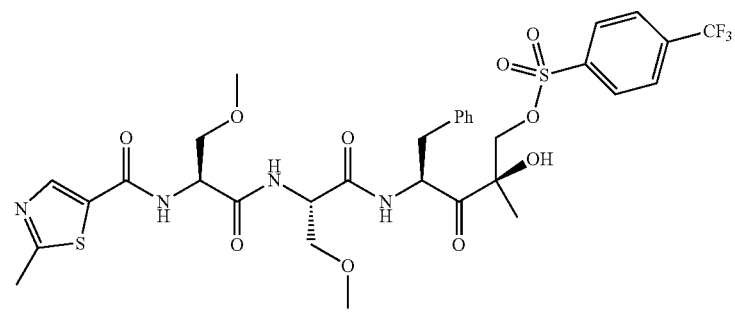

4-(Trifluoromethyl)benzenesulfonyl chloride (0.71 g, 2.89 mmol) in DCM (5 mL) was added dropwise to N—((S)-1-(((S)-1-(((2S,4R)-4,5-dihydroxy-4-methyl-3-oxo-1-phenyl-pentan-2-yl)amino)-3-methoxy-1-oxopropan-2-yl)amino)-3-methoxy-1-oxopropan-2-yl)-2-methylthiazole-5-carboxamide (1.59 g, 0.00289 mol), DMAP (0.1 g) and DIEA (0.60 mL, 3.47 mmol) in DCM (15 mL) at 0° C. The reaction was allowed to warm to room temperature and stirred overnight. The mixture was washed with 2N aqueous HCl, brine, dried (MgSO$_4$) and evaporated. The residue was purified by Biotage flash column chromatography (5% MeOH/25% EtOAc, DCM) to give product as a white solid (1.1 g, 52%); $^1$H NMR (CDCl3): δ 8.08-8.03 (m, 3H), 7.82 (d, J=8.4 Hz, 2H), 7.32 (d, J=7.6 Hz, 1H), 7.28-7.15 (m, 5H), 7.02 (d, J=8.4 Hz, 1H), 6.94 (d, J=6.8 Hz, 1H), 5.40-5.32 (m, 1H), 4.76-4.72 (m, 1H), 4.58-4.52 (m, 1H), 4.30 (d, J=9.2 Hz, 1H), 3.86-3.80 (m, 3H), 3.63-3.59 (m, 1H), 3.50-3.36 (m, 7H), 3.12-3.06 (m, 1H), 2.95-2.90 (m, 1H), 2.70 (s, 3H), 0.74 (s, 3H); MS for C$_{32}$H$_{37}$F3N$_4$O$_{10}$S$_2$ m/z: 759 (M+H)$^+$.

(2R,4S)-2-Hydroxy-4-((S)-3-methoxy-2-((S)-3-methoxy-2-(2-methylthiazole-5-carboxamido)propanamido)propanamido)-2-methyl-3-oxo-5-phenyl-pentyl Methanesulfonate

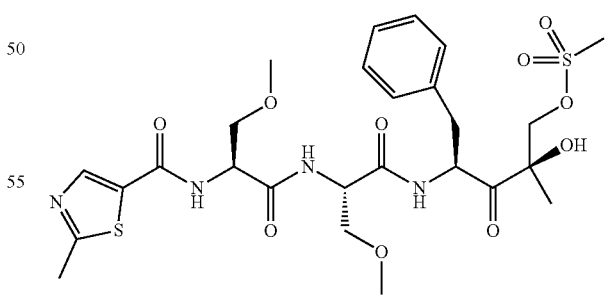

Prepared according to procedures described above, by reacting methanesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for C$_{26}$H$_{36}$N$_4$O$_{10}$S$_2$ m/z: 629 (M+H)$^+$.

227

(2R,4S)-1-(methanesulfonyloxy)-4-[(2S)-3-methoxy-2-[(2S)-3-methoxy-2-[(2-methyl-1,3-thiazol-5-yl)formamido]propanamido]propanamido]-2-methyl-3-oxo-5-phenylpentan-2-yl Acetate

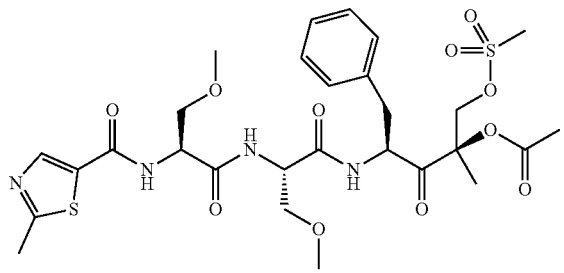 [SMILES: COC[C@H](NC(=O)c1cnc(C)s1)C(=O)N[C@@H](COC)C(=O)N[C@@H](Cc1ccccc1)C(=O)[C@@](C)(COS(C)(=O)=O)OC(C)=O]

Prepared according to procedures described above, by reacting acetic anhydride with (2R,4S)-2-hydroxy-4-((S)-3-methoxy-2-((S)-3-methoxy-2-(2-methylthiazole-5-carboxamido)propanamido)propanamido)-2-methyl-3-oxo-5-phenylpentyl methanesulfonate. MS for $C_{28}H_{38}N_4O_{11}S_2$ m/z: 671 (M+H)$^+$.

(2R,4S)-2-Hydroxy-4-((S)-3-methoxy-2-((S)-3-methoxy-2-(2-methylthiazole-5-carboxamido)propanamido)propanamido-2-methyl-3-oxo-5-phenylpentyl 2,2,2-trifluoroethanesulfonate

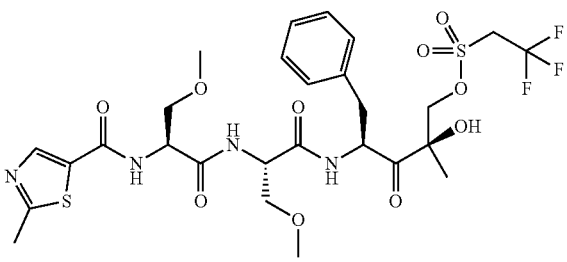 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)CC(F)(F)F]

Prepared according to procedures described above, by reacting 2,2,2-trifluoroethanesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{27}H_{35}F_3N_4O_{10}S_2$ m/z: 697 (M+H)$^+$.

228

(2R,4S)-2-Hydroxy-4-((S)-3-methoxy-2-((S)-3-methoxy-2-(2-methylthiazole-5-carboxamido)propanamido)propanamido)-2-methyl-3-oxo-5-phenylpentyl 3,4-difluorobenzenesulfonate

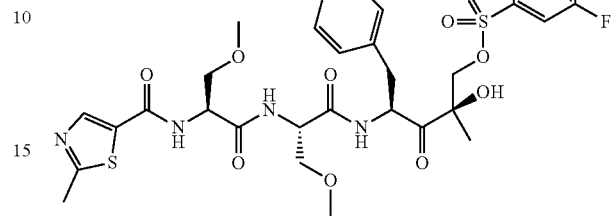

Prepared according to procedures described above, by reacting 3,4-difluorobenzenesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{31}H_{36}F_2N_4O_{10}S_2$ m/z: 727 (M+H)$^+$.

(2R,4S)-2-Hydroxy-4-((S)-3-methoxy-2-((S)-3-methoxy-2-(2-methylthiazole-5-carboxamido)propanamido)propanamido)-2-methyl-3-oxo-S-phenylpentyl 2,2-difluoroethanesulfonate

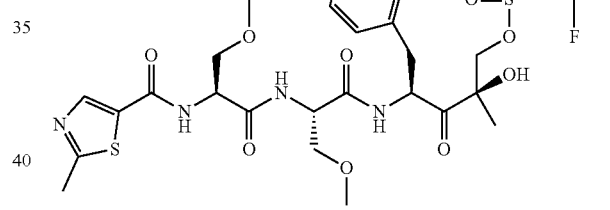

Prepared according to procedures described above, by reacting 2,2-difluoroethanesulfonyl chloride with N—((S)-1-(((S)-1-(((2S,4R)-4,5-dihydroxy-1-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{27}H_{36}F_2N_4O_{10}S_2$ m/z: 679 (M+H)$^+$.

(2R,4S) 2-Hydroxy-4-((S)-3-methoxy-2-((S)-3-methoxy-2-(2-methylthiazole-S-carboxamido)propanamido)propanamido)-2-methyl-3-oxo-5-phenylpentyl Phenylmethanesulfonate

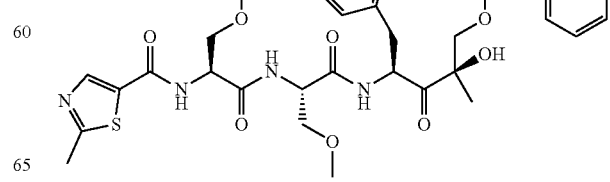

Prepared according to procedures described above, by reacting phenylmethanesulfonyl chloride with N—((S)-1-(((S)-1-(((2S,4R)-4,5-dihydroxy-4-methyl-3-oxo-1-phenyl-pentan-2-yl)amino)-3-methoxy-1-oxopropan-2-yl)amino)-3-methoxy-1-oxopropan-2-yl)-2-methylthiazole-5-carboxamide. MS for $C_{32}H_{40}N_4O_{10}S_2$ m/z: 705 (M+H)$^+$.

(2R,4S)-2-Hydroxy-4-((S)-3-methoxy-2-((S)-3-methoxy-2-(2-methylthiazole-5-carboxamido)propanamido)propanamido)-2-methyl-3-oxo-1-phenyl-pentyl octane-1-sulfonate

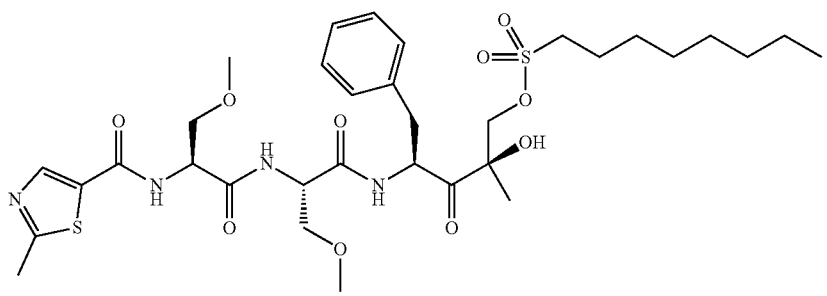 [SMILES: CCCCCCCCS(=O)(=O)OC[C@@](C)(O)C(=O)[C@H](Cc1ccccc1)NC(=O)[C@H](COC)NC(=O)[C@H](COC)NC(=O)c1cnc(C)s1]

Prepared according to procedures described above, by reacting octanesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{33}H_{50}N_4O_{10}S_2$ m/z: 727 (M+H)$^+$.

(2R,4S)-2-Hydroxy-4-((S)-3-methoxy-2-((S)-3-methoxy-2-(2-methylthiazole-5-carboxamido)propanamido)propanamido-2-methy-3-oxo-5-phenyl-pentyl tetrahydro-2H-pyran-4-sulfonate

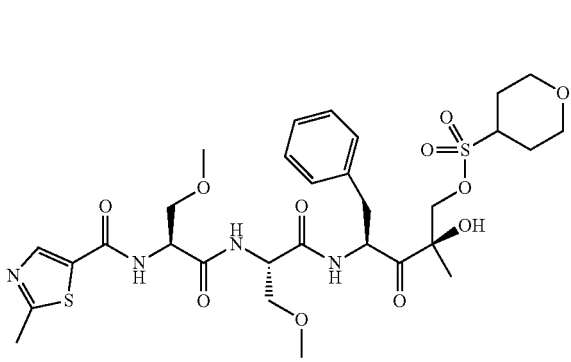 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)C1CCOCC1]

Prepared according to procedures described above, by reacting tetrahydro-2H-pyran-4-sulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{30}H_{42}N_4O_{11}S_2$ m/z: 699 (M+H)$^+$.

(2R,4S)-2-hydroxy-4-((S)-3-methoxy-2-((S)-3-methoxy-2-(2-methylthiazole-5-carboxamido)propanamido)propanamido-2-methyl-3-ox-5-phenylpentyl 4-methylbenzenesulfonate

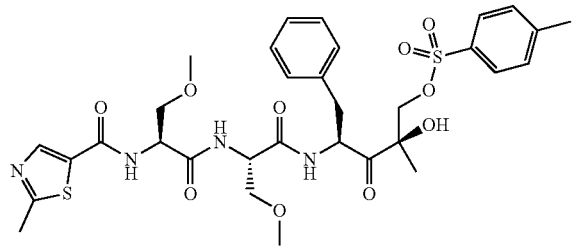 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(C)cc1]

Prepared according to procedures described above, by reacting p-toluenesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{32}H_{40}N_4O_{10}S_2$ m/z: 705 (M+H)$^+$.

231

(2R,4S)-2-hydroxy-4-((S)-3-methoxy-2-((S)-3-methoxy-2-(2-methylthiazole-S-carboxamido)propanamido)propanamido)-2-methyl-3-oxo-5-phenylpentyl butane-1-sulfonate

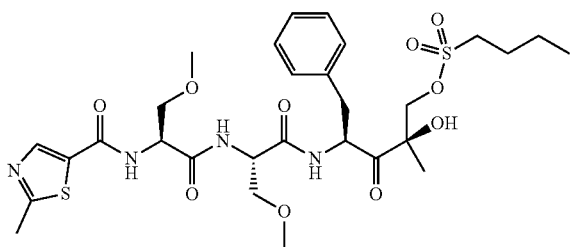

Prepared according to procedures described above, by reacting butanesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{29}H_{42}N_4O_{10}S_2$ m/z: 671 (M+H)$^+$.

(2R,4S)-2-hydroxy-4-((S)-3-methoxy-2-((S)-3-methoxy-2-(2-methylthiazole-5-carboxamido)propanamido)propanamido)-2-methyl-3-oxo-S-phenylpentyl 2,4-difluorobenzenesulfonate

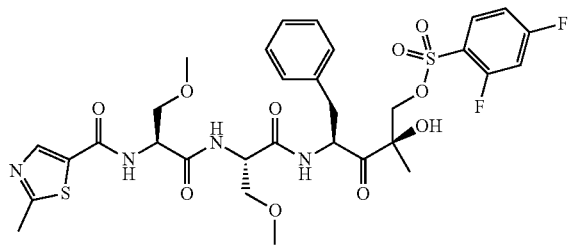 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(F)cc1F]

232

Prepared according to procedures described above, by reacting 2,4-difluorobenzenesulfonyl chloride with N—((S)-1-(((S)-1-(((2S,4R)-4,5-dihydroxy-4-methyl-3-oxo-1-phenylpentan-2-yl)amino)-3-methoxy-1-oxopropan-2-yl)amino)-3-methoxy-1-oxopropan-2-yl)-2-methylthiazole-5-carboxamide. MS for $C_{31}H_{36}F_2N_4O_{10}S_2$ m/z: 727 (M+H)$^+$.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-methylbenzenesulfonate

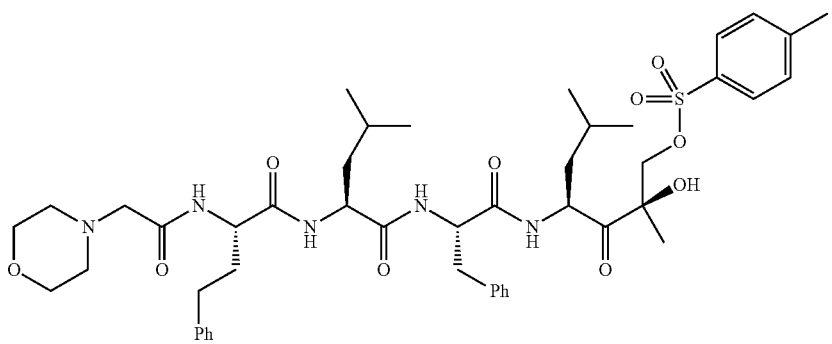 [SMILES: Cc1ccc(S(=O)(=O)OC[C@@](C)(O)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)cc1]

Prepared according to procedures described above, by reacting p-toluenesulfonyl chloride with (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide. MS for $C_{47}H_{65}N_5O_{10}S$ m/z: 892 (M+H)$^+$.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl methanesulfonate

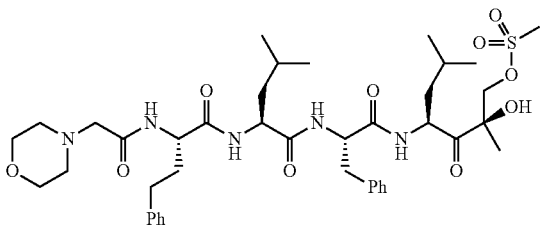 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COS(C)(=O)=O]

Prepared according to procedures described above, by reacting methanesulfonyl chloride with (S)—N—((S)-1-(((2R,4S)-1,2-dihydroxy-2,6-di methyl-3-oxoheptan-4-yl) amino)-1-oxo-3-phenylpropan-2-yl)-4-methyl-2-((S)-2-(2-morpholinoacetamido)-4-phenylbutanamido)pentanamide. MS for $C_{41}H_{61}N_5O_{10}S$ m/z: 816 (M+H)$^+$.

Xenograft studies showed (see FIG. 3) that more intensive dosing of epoxy kinase protease inhibitors can yield greater efficacy in both solid and hematologic tumor models.

Example 2—Examples of PEG-Conjugates

General PEGylation Conditions
Method A:

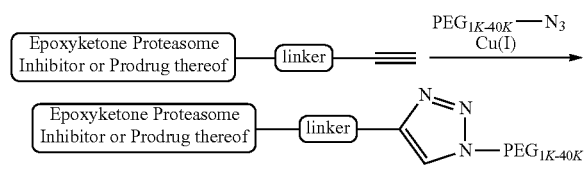

Copper sulfate (0.1M aqueous solution, 1.8 eq.) was added to alkyne (1.5 eq.), $PEG_{20K}$-$N_3$ (1 eq.) and ascorbic acid (3.6 eq.) in DMF (7 mL/g PEG) and water (3.5 mL/g PEG at room temperature. After 4 hours the reaction mixture began to darken to the characteristic green color of Cu(II), and another portion of ascorbic acid (1.6 eq.) was added. The resultant mixture was stirred overnight at room temperature. The crude solution was submitted for preparative HPLC on a C18 column using a 0.1% formic acid water/acetonitrile gradient (25% B→65% B over 60 min.). Fractions were combined on the basis of LC/MS analysis. Acetonitrile was largely stripped from the combined solution at 25° C. and the resultant concentrate was frozen and lyophilized.

Method B:

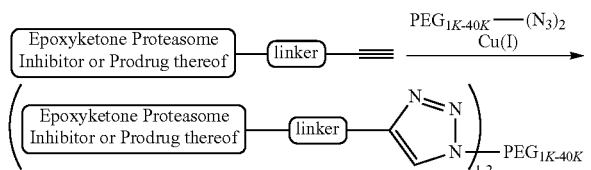

Copper sulfate (0.1M aqueous solution, 1.8 eq.) was added to alkyne (3 eq.), 4-arm $PEG_{20K}$-$N_3$ (1 eq.) and ascorbic acid (3.6 eq.) in DMF (7 mL/g PEG) and water (3.5 mL/g PEG at room temperature. After 4 hours the reaction mixture began to darken to the characteristic green color of Cu(II), and another portion of ascorbic acid (1.6 eq.) was added. The resultant mixture was stirred overnight at room temperature. The crude solution was submitted for preparative HPLC on a C18 column using a 0.1% formic acid water/acetonitrile gradient (25% B→65% B over 60 min.). Fractions were combined on the basis of LC/MS analysis. Acetonitrile was largely stripped from the combined solution at 25° C. and the resultant concentrate was frozen and lyophilized.

Method C:

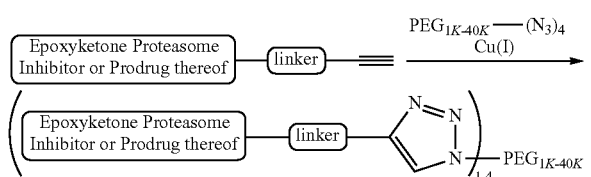

Copper sulfate (0.1M aqueous solution, 1.8 eq.) was added to alkyne (6 eq.), $PEG_{20K}$-$(N_3)_4$ (1 eq., Creative PEGworks Catalog # PSB-493) or $PEG_{40K}$-$(N_3)_4$ (1 eq., JenKem Technologies), and ascorbic acid (3.6 eq.) in DMF (7 mL/g PEG) and water (3.5 mL/g PEG at room temperature. A homogeneous pale yellow solution was obtained within 20 min. After 4 hours the reaction mixture began to darken to the characteristic green color of Cu(II), and another portion of ascorbic acid (1.6 eq.) was added. The resultant mixture was stirred overnight at room temperature. The crude solution was submitted for preparative HPLC on a C18 column using a 0.1% formic acid water/acetonitrile gradient (25% B→65% B over 60 min.). Fractions were combined on the basis of LC/MS analysis. Acetonitrile was largely stripped from the combined solution at 25° C. (no decomposition observed) and the resultant concentrate was frozen and lyophilized over 48 hrs. to give products as fluffy white solids.

Method D:

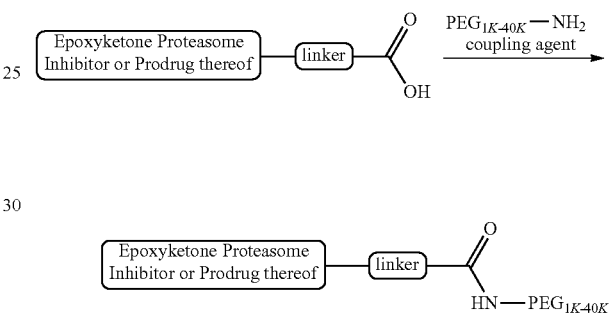

Propylphosphonic anhydride (T3P, 7.5 eq, 50% EA solution) was added to the acid (5 eq.) and $PEG_{20K}$/4-Arm-$NH_2$ (1 eq.) in a mixture of pyridine (12 eq.) and ethyl acetate (twice the volume of pyridine) at −10° C. and then stirred at 0° C. overnight. The reaction was evaporated under vacuum and the residue purified by preparative HPLC (C18 column).

Method E:

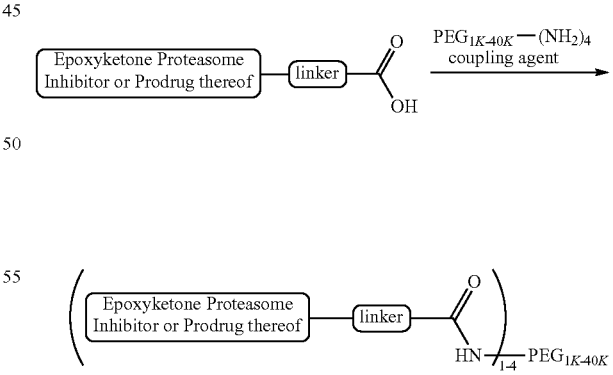

Propylphosphonic anhydride (T3P, 2.5 eq, 50% EA solution) was added to the acid (1.5 eq.) and $PEG_{20K}$/4-Arm-$NH_2$ (1 eq.) in a mixture of pyridine (12 eq.) and ethyl acetate (twice the volume of pyridine) at −10° C. and then stirred at 0° C. overnight. The reaction was evaporated under vacuum and the residue purified by preparative HPLC (C18 column).

Standard PEGylation Conditions

Preparation of (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraaza-hexadecan-16-yl 2-fluoro-5-(((1-PEG$_{2K}$-1H-1,2,3-triazol-4-yl)methyl)carbamoyl)benzenesulfonate Cu(II) and a 0.004 g charge of ascorbic acid was added. The resultant mixture was stirred overnight at RT. After 18 hrs, LC/MS analysis of the reaction solution showed little change. The crude solution was submitted for preparative HPLC on a C18 column using a 0.1% formic acid water/acetonitrile gradient (25% B→65% B over 60 min.). Fractions were combined on the basis of LC/MS analysis. Acetonitrile was largely stripped from the combined solu-

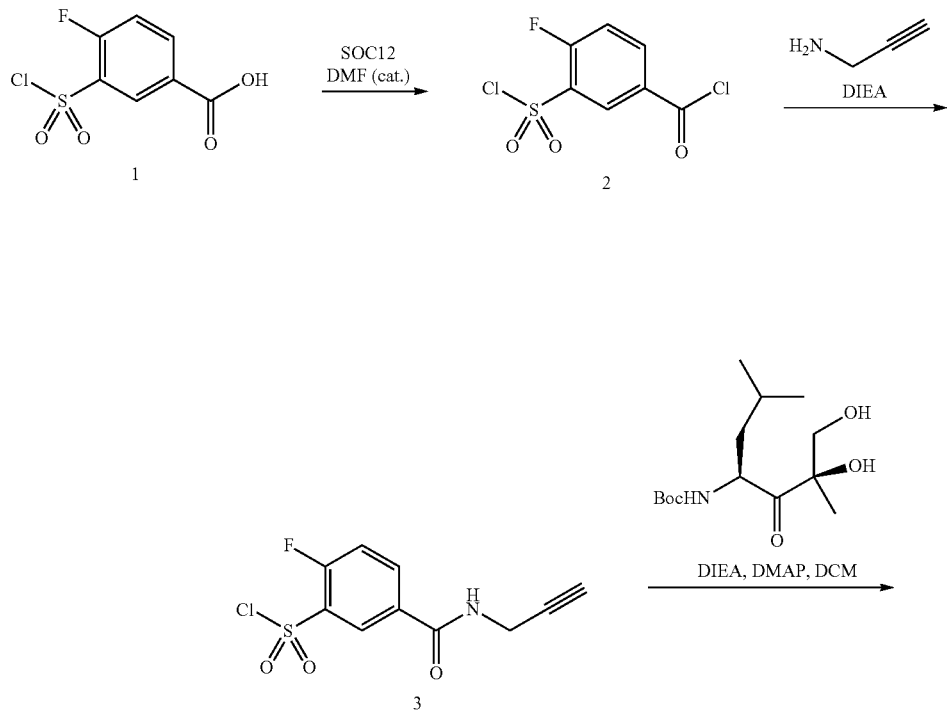

To a solid mixture of alkyne (0.080 g, 0.082 mmol), 4-arm PEG$_{20k}$N$_3$ (6 eq., 0.284 g, 0.0137 mmol) and ascorbic acid (0.009 g, 0.0492 mmol) in a 20 dram vial was added a mixture of 2.0 mL DMF and 1.0 mL water. To the resultant stirred pale yellow slurry was added 246 μL of 0.1 M CuSO$_4$(aq) and the reaction mixture was stirred in the capped vial at ambient temperature. A homogeneous pale yellow solution was obtained within 20 min. Analysis of an aliquot after 1 hr by LC/MS showed the continued presence of alkyne (present in excess). After 4 hours the reaction mixture began to darken to the characteristic green color of tion at 25° C. (no decomposition observed) and the resultant concentrate was frozen and lyophilized over 48 hrs. to give a fluffy white solid (0.221 g, 66% based on PEG azide).

Preparation of (4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraaza-hexadecan-16-yl 2-fluoro-5-(prop-2-yn-1-ylcarbamoyl)benzenesulfonate (5)

Scheme 18

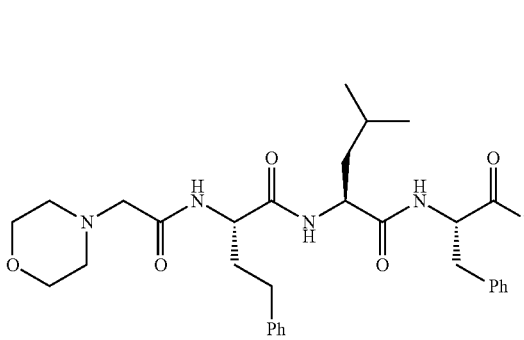

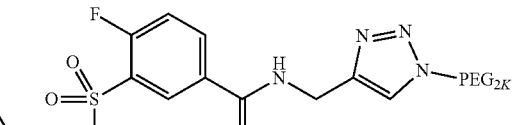

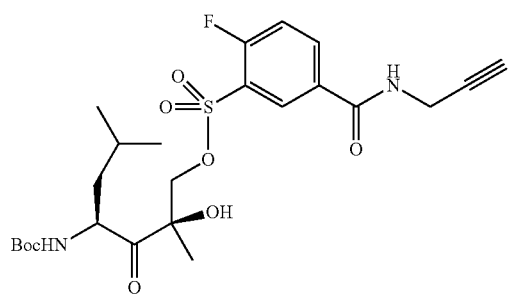

4

-continued
1. HCl, dioxane
2.

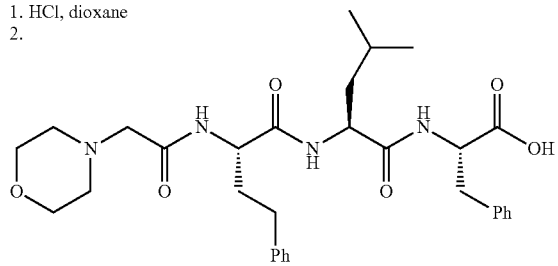

HBTU, HOBt, DIEA

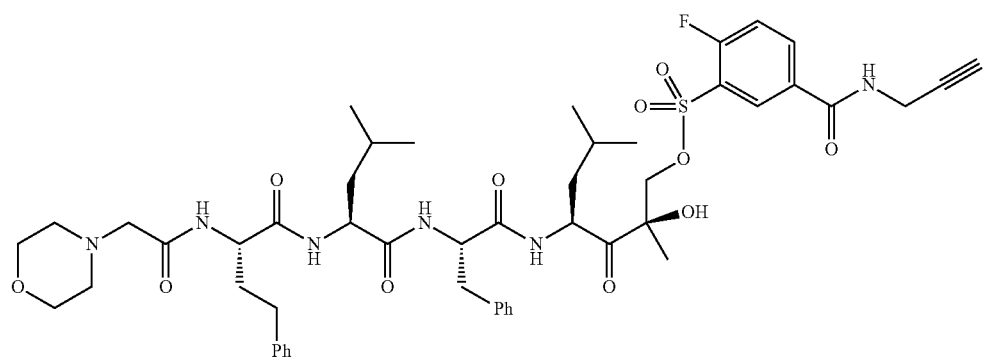

5

3-(Chlorosulfonyl)-4-fluorobenzoyl Chloride (2)

3-(Chlorosulfonyl)-4-fluorobenzoic acid (1, 2.50 g, 10.5 mmol), thionyl chloride (10 mL) and DMF (1 drop) were heated at 90° C. for 1 hour and then the mixture evaporated to dryness. The material was used directly in the next step.

2-Fluoro-5-(prop-2-yn-1l-ylcarbamoyl)benzene-1-sulfonyl Chloride (3)

Propargylamine (0.67 mL, 10.5 mmol) and DIEA (1.83 mL, 10.5 mmol) in DCM (10 mL) were added dropwise to 3-(chlorosulfonyl)-4-fluorobenzoyl chloride (2) in DCM (10 mL) at 0° C. The mixture was allowed to warm to room temperature and stirred for 15 minutes. The reaction was washed with 2N HCl and brine, dried (MgSO$_4$) and evaporated. The residue was purified by Biotage flash column chromatography (30% EtOAc/Hep) to give product as an oil (2.52 g, 87%).

(2R,4S)-4-((tert-Butoxycarbonyl)amino)-2-hydroxy-2,6-dimethyl-3-oxoheptyl 2-fluoro-5-(prop-2-yn-1-ylcarbamoyl)benzenesulfonate (4)

2-Fluoro-5-(prop-2-yn-1-ylcarbamoyl)benzene-1-sulfonyl chloride (3, 2.52 g, 9.14 mmol) was added dropwise to tert-butyl ((2R,4S)-1,2-dihydroxy-2,6-dimethyl-3-oxoheptan-4-yl)carbamate (2.65 g, 9.14 mmol), DIEA (1.91 mL, 10 mmol) and DMAP (0.1 g, 0.914 mmol) in DCM (30 mL) at 0° C. The mixture was allowed to warm to room temperature and stirred overnight. The reaction was washed with 2N HCl and brine, dried (MgSO$_4$) and evaporated. The residue was purified by Biotage flash column chromatography (30% EtOAc/Hep) to give product as an oil (3.62 g, 75%).

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-5-(prop-2-yn-1-ylcarbamoyl)benzenesulfonate (5)

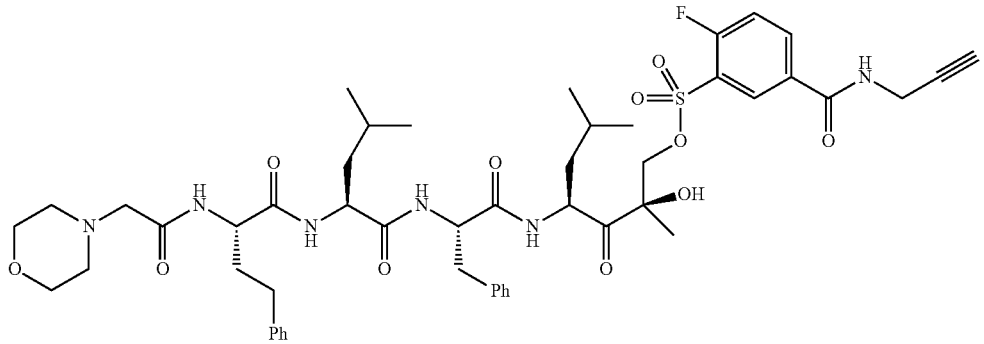 [SMILES: C#CCNC(=O)c1ccc(F)c(S(=O)(=O)OC[C@@](C)(O)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)c1]

(2R,4S)-4-((tert-Butoxycarbonyl)amino)-2-hydroxy-2,6-dimethyl-3-oxoheptyl 2-fluoro-5-(prop-2-yn-1-ylcarbamoyl)benzenesulfonate (4, 3.62 g, 6.85 mmol) was stirred with 4M HCl in dioxane for 1 hour and then evaporated to dryness. HBTU (3.91 g, 10.3 mmol) and HOBt (1.39 g, 10.3 mmol) were added, the mixture dissolved in DMF (30 mL) and cooled to 0° C. DIEA (3.59 mL, 20.6 mmol) was added dropwise and the reaction stirred at 0° C. for 20 minutes. The mixture was diluted with 2N HCl/EtOAc. The EtOAc layer was separated, washed with sat. aq. NaHCO$_3$ and brine, dried (MgSO$_4$) and evaporated. The residue was purified by Biotage flash column chromatography (10% MeOH/DCM) to give product as foam (2.14 g, 32%).

The following analogs were prepared similarly to the preparation of (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-5-(((1-PEG$_{2K}$-1H-1,2,3-triazol-4-yl)methyl)carbamoyl)benzenesulfonate, above.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-5-(((1-PEG$_{2K}$-1H-1,2,3-triazol-4-yl)methyl)carbamoyl)benzenesulfonate

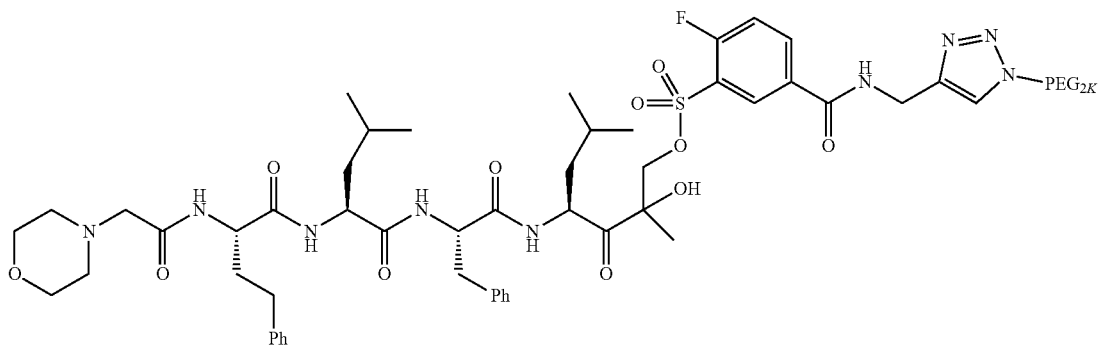

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-5-(prop-2-yn-1-ylcarbamoyl)benzenesulfonate and PEG$_{2k}$-N$_3$ (Creative PEGworks Catalog # PSB-2022) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-5-(((1-PEG$_{5K}$-1H-1,2,3-triazol-4-yl)methyl)carbamoyl)benzenesulfonate

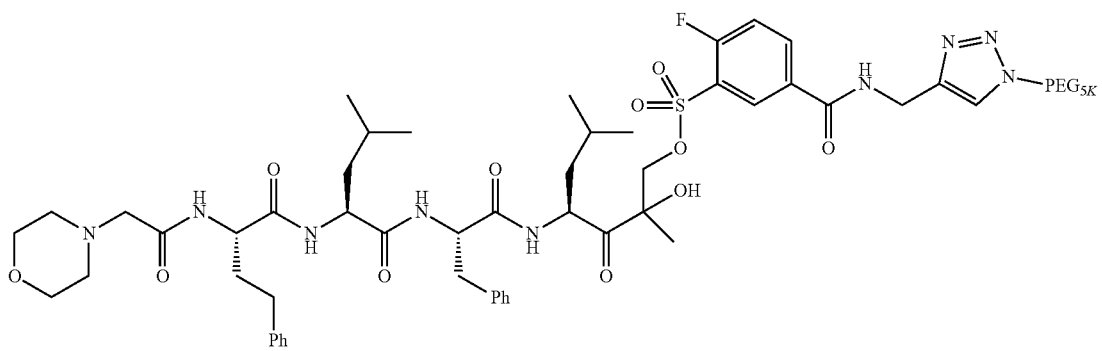

(4S,7S,10S,13S,15R)-10-Benzyl-5-hydroxy-7,13-diisobutyl-15-methyl-1-morpholino-2,5,8,11,14-pentaoxo-4-phenethyl-3,6,9,12-tetraazahexadecan-16-yl 2-fluoro-5-(prop-2-yn-1-ylcarbamoyl)benzenesulfonate and PEG$_{5k}$-N$_3$ (Creative PEGworks Catalog # PSB-2024) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(((1-PEG$_{1K}$-1H-1,2,3-triazol-4-yl)methyl)carbamoyl)benzenesulfonate

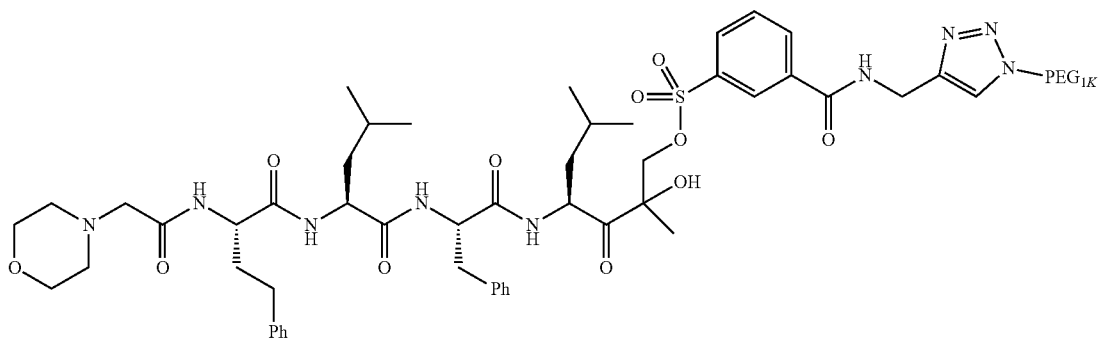

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{1k}$-N$_3$ (Creative PEGworks Catalog # PSB-2026) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(((1-PEG$_{2K}$-1H-1,2,3-triazol-4-yl)methyl)carbamoyl)benzenesulfonate

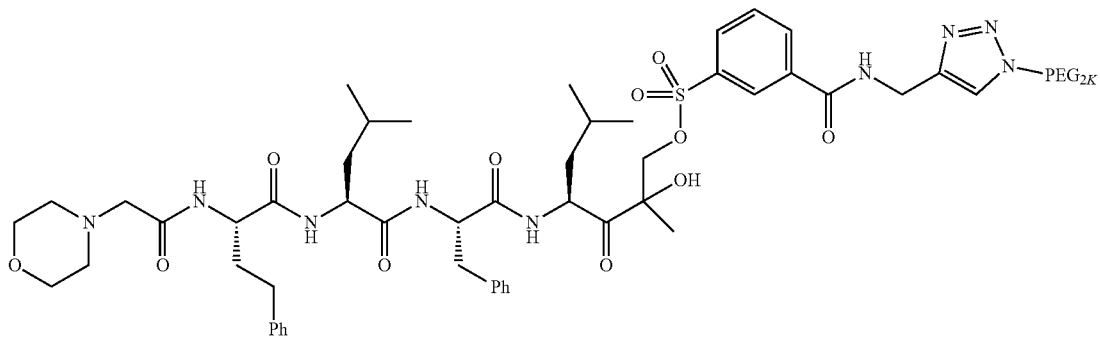

4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-yl-carbamoyl)benzenesulfonate and PEG$_{2k}$-N$_3$ (Creative PEGworks Catalog # PSB-2025) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(((1-PEG$_{5K}$-1H-1,2,3-triazol-4-yl)methyl)carbamoyl)benzenesulfonate

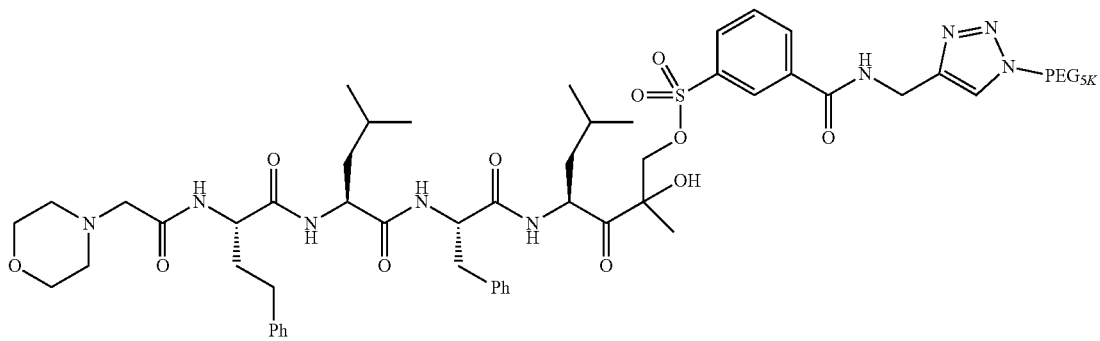

(4S,7S,10S,13S)-10-Benzyl-5-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-yl-carbamoyl)benzenesulfonate and PEG$_{5k}$-N$_3$ (Creative PEGworks Catalog # PSB-2024) were reacted following General PEGylation Conditions, Method A; 1H NMR (DMSO-d$_6$): δ 9.40 (t, J=7.0 Hz, 1H), 8.39 (t, J=2.0 Hz, 1H), 8.26 (d, J=10 Hz, 1H), 8.07-8.00 (m, 4H), 7.97 (s, 1H), 7.77 (t, J=10 Hz, 1H), 7.29-7.03 (m, 1H), 6.54 (s, 1H), 6.03 (s, 1H), 5.03 (m, 1H), 4.54-4.47 (m, 5H), 4.38-4.27 (m, 2H), 4.08 (d, J=11.5 Hz, 1H), 3.87 (d, J=1.5 Hz, 1H), 3.79 (t, J=6.5 Hz, 2H), 3.69-3.54 (m, 570H), 3.34-3.32 (m, 12H), 3.24 (s, 4H), 3.02-2.72 (m, 2H), 1.92-1.73 (m, 2H), 1.65-1.46 (m, 4H), 1.40-1.22 (m, 2H), 1.14 (s, 3H), 0.85-0.79 (m, 12H)

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(((1-PEG$_{10K}$-1H-1,2,3-triazol-4-yl)methyl)carbamoyl)benzenesulfonate

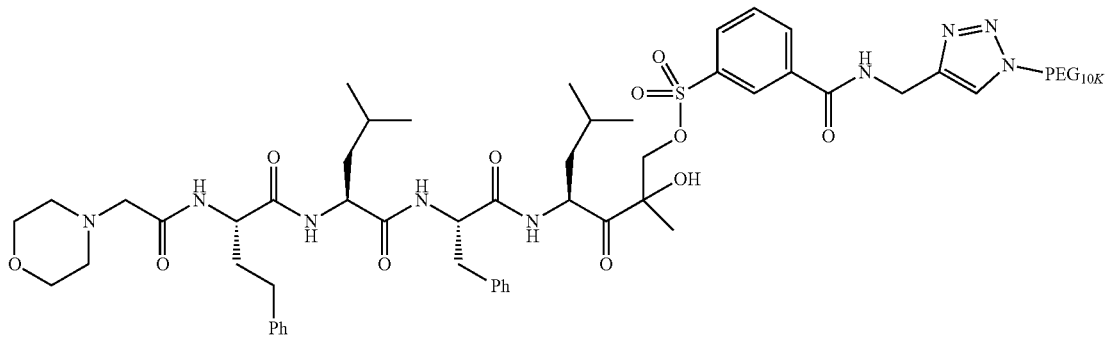

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{10k}$-N$_3$ (Creative PEGworks Catalog # PSB-2023) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(((1-PEG$_{5K}$/2-Arm-1H-1,2,3-triazol-4-yl)methyl)carbamoyl)benzenesulfonate

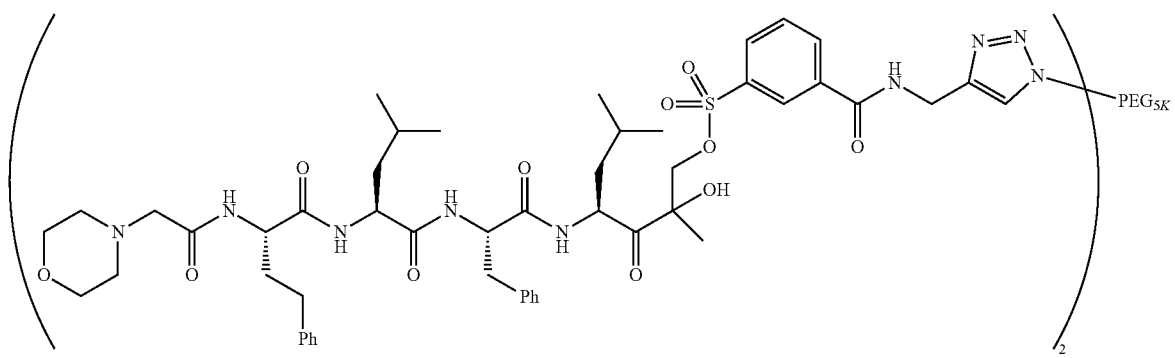

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{5k}$-(N$_3$)$_2$ (Creative PEGworks Catalog # PSB-327) were reacted following General PEGylation Conditions, Method B.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(((1-PEG$_{2K}$-1H-1,2,3-triazol-4-yl)methyl)carbamoyl)benzenesulfonate

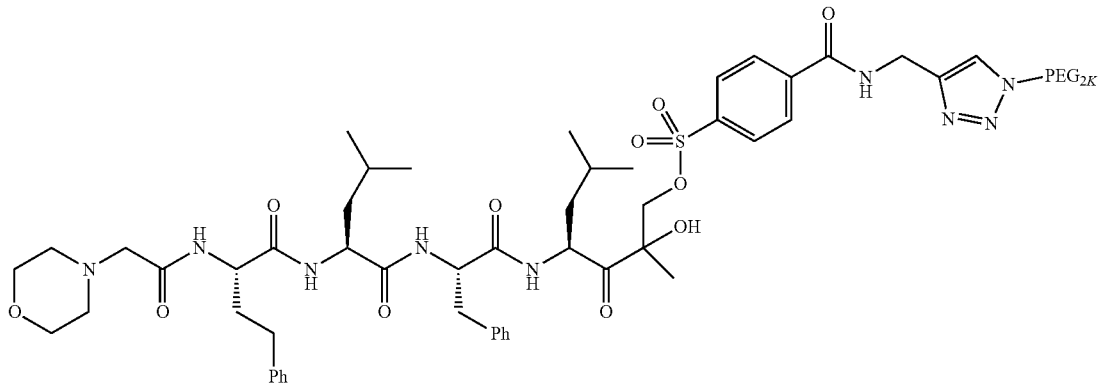

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(prop-2-yn-1-ylcarbamoyl)benzenesulfonate and PEG$_{2K}$-N$_3$ (Creative PEGworks Catalog # PSB-2025) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(((1-PEG$_{5K}$-1H-1,2,3-triazol-4-yl)methyl)carbamoyl)benzenesulfonate

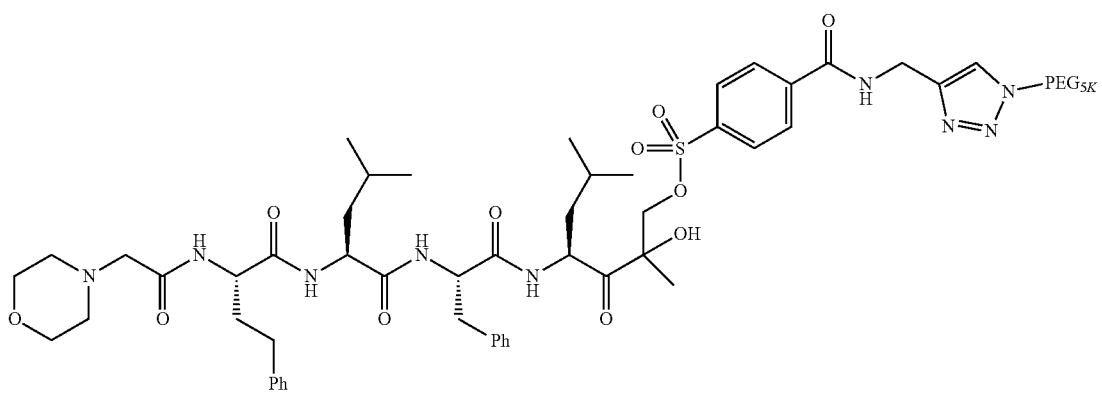

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(prop-2-yn-1-ylcarbamoyl)benzenesulfonate and PEG$_{5K}$-N$_3$ (Creative PEGworks Catalog # PSB-2024) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(((1-PEG$_{5K}$/2-Arm-1H-1,2,3-triazol-4-yl)methyl)carbamoyl)benzenesulfonate

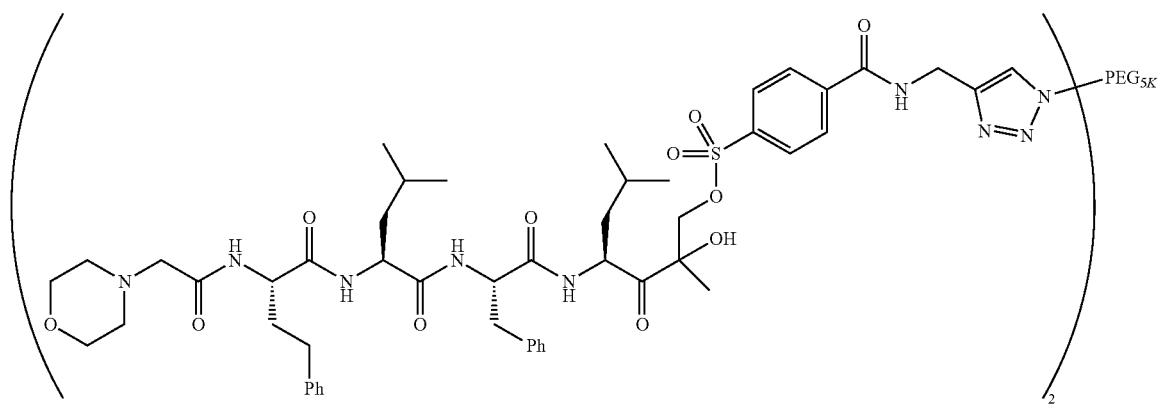

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(prop-2-yn-1-yl-carbamoyl)benzenesulfonate and PEG$_{5k}$-(N$_3$)$_2$ (Creative PEGworks Catalog # PSB-327) were reacted following General PEGylation Conditions, Method B.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(((f-PEG$_{10K}$/4-Arm-1H-1,2,3-triazol-4-yl)methyl)carbamoyl)benzenesulfonate

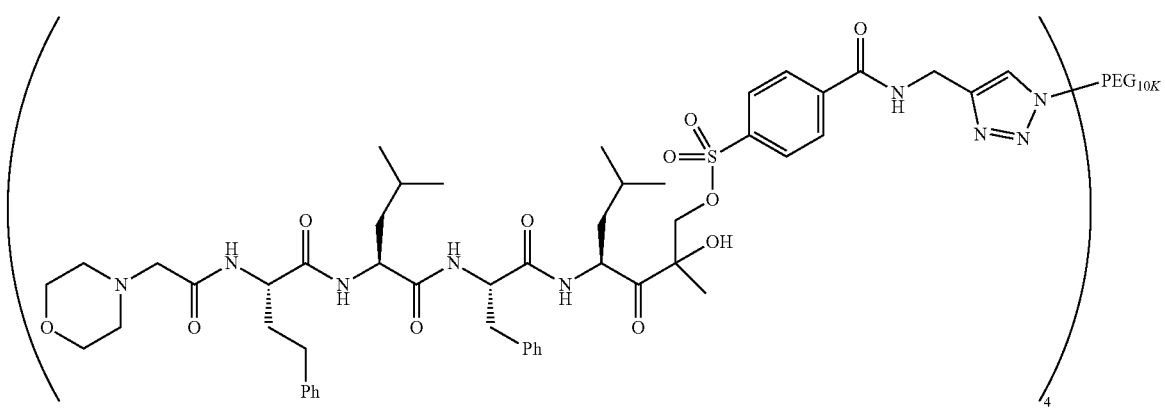

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(prop-2-yn-1-yl-carbamoyl)benzenesulfonate and PEG$_{10k}$-(N$_3$)$_4$ (Creative PEGworks Catalog # PSB-492) were reacted following General PEGylation Conditions, Method C.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(((1-PEG$_{2K}$-1H-1,2,3-triazol-4-yl)methyl)carbamoyl)benzenesulfonate

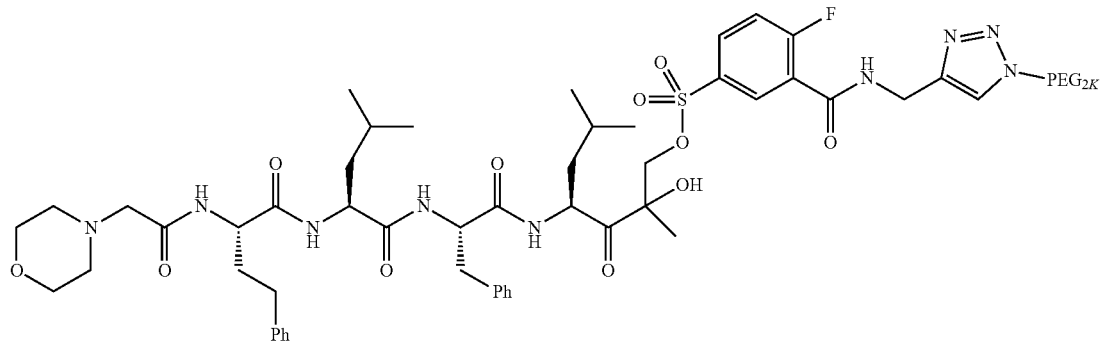

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(prop-2-yn-1-ylcarbamoyl)benzenesulfonate and PEG$_{2k}$-N$_3$ (Creative PEGworks Catalog # PSB-2025) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4 fluoro-3-(((1-PEG$_{5K}$-1H-1,2,3-triazol-4-yl)methyl)carbamoyl)benzenesulfonate

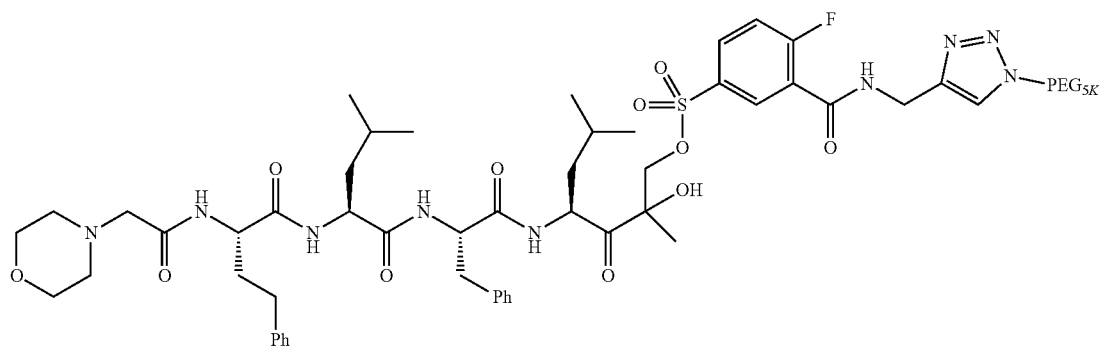

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(prop-2-yn-1-ylcarbamoyl)benzenesulfonate and PEG$_{5k}$-N$_3$ (Creative PEGworks Catalog # PSB-2024) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(((1-PEG$_{5K}$/2-Arm-1H-1,2,3-triazol-4-yl)methyl)carbamoyl)benzenesulfonate

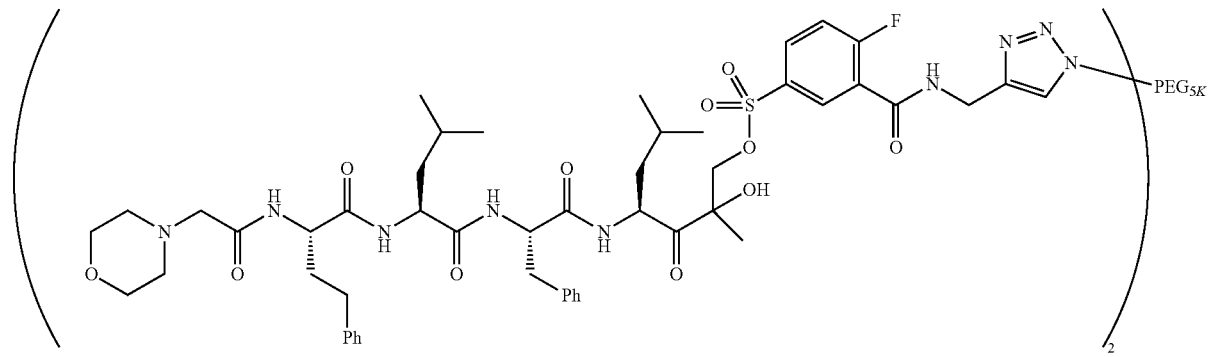

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(prop-2-yn-1-ylcarbamoyl)benzenesulfonate and PEG$_{5k}$-(N$_3$)$_2$ (Creative PEGworks Catalog # PSB-327) were reacted following General PEGylation Conditions, Method B.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(((1-PEG$_{20K}$/4-Arm-1H-1,2,3-triazol-4-yl)methyl)carbamoyl)benzenesulfonate

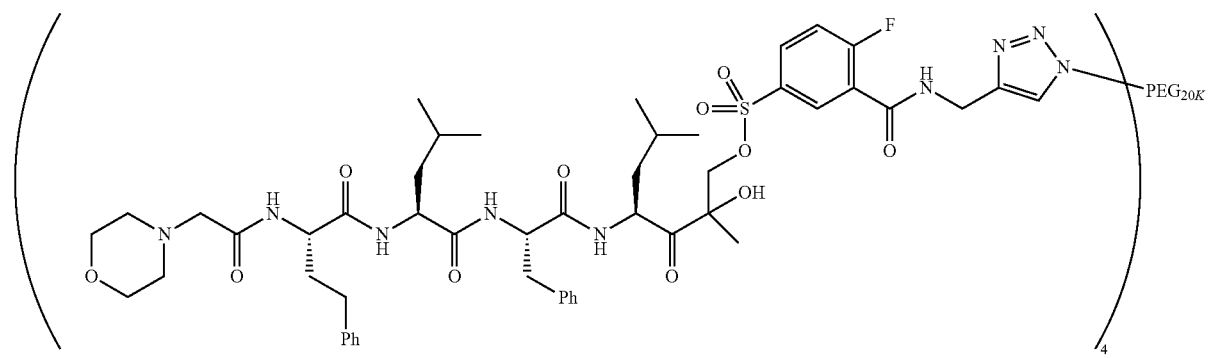

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-fluoro-3-(prop-2-yn-1-ylcarbamoyl)benzenesulfonate and PEG$_{20k}$-(N$_3$)$_4$ (Creative PEGworks Catalog # PSB-493) were reacted following General PEGylation Conditions, Method C; $^1$H NMR (DMSO-d$_6$): δ 9.11 (t, J=7 Hz, 1H), 8.10-7.82 (m, 7H), 7.59 (t, J=9.5 Hz, 1H), 7.29-7.03 (m, 10H), 6.03 (s, 1H), 5.03 (m, 1H), 4.54-4.47 (m, 5H), 4.38-4.27 (m, 2H), 4.10 (d, J=9.5 Hz, 1H), 3.87 (d, J=9.5 Hz, 1H), 3.79 (t, J=5 Hz, 2H), 3.69-3.24 (m, 618H), 3.02-2.72 (m, 4H), 2.50-2.38 (m, 4H), 1.92-1.73 (m, 2H), 1.65-1.46 (m, 4H), 1.40-1.22 (m, 4H), 1.15 (s, 3H), 0.85-0.79 (m, 12H).

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(3-((1-PEG$_{2K}$-1H-1,2,3-triazol-4-yl)methyl)ureido)benzenesulfonate

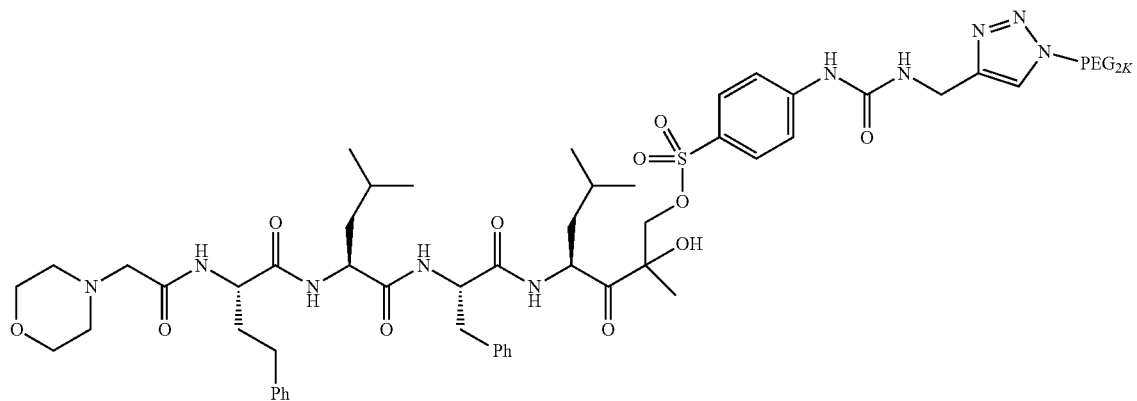

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(3-(prop-2-yn-1-yl)ureido)benzenesulfonate and PEG$_{2k}$-N$_3$ (Creative PEGworks Catalog # PSB-2025) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(3-((1-PEG$_{5K}$-1H-1,2,3-triazol-4-yl)methyl)ureido)benzenesulfonate

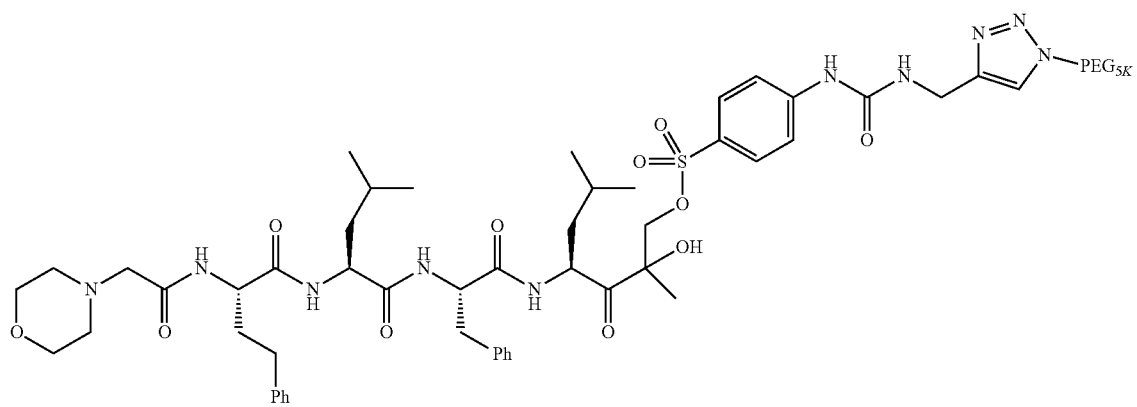

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(3-((1-PEG$_{20K}$/4-Arm-1H-1,2,3-triazol-4-yl)methyl)ureido)benzenesulfonate

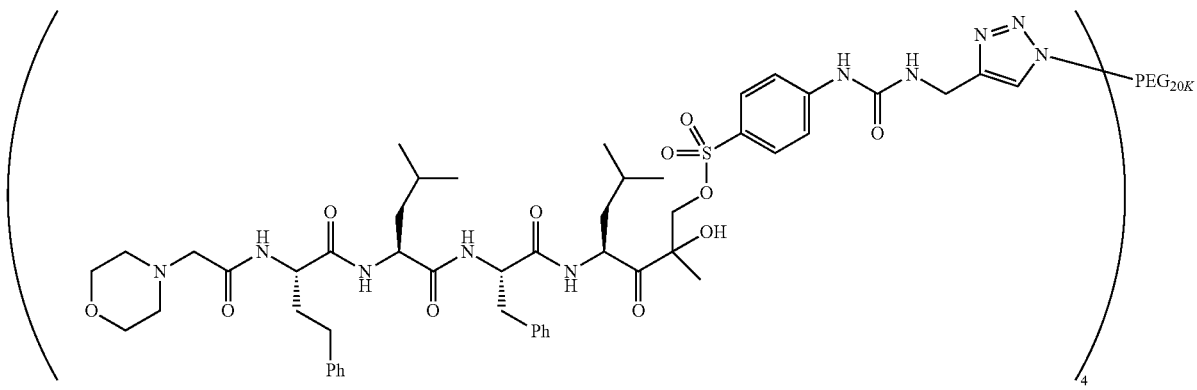

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(3-(prop-2-yn-1-yl)ureido)benzenesulfonate and PEG$_{20k}$-(N$_3$)$_4$ (Creative PEGworks Catalog # PSB-493) were reacted following General PEGylation Conditions, Method C.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-methoxy-5-(((1-PEG$_{5K}$-1H-1,2,3-triazol-4 yl)methyl)carbamoyl)benzenesulfonate

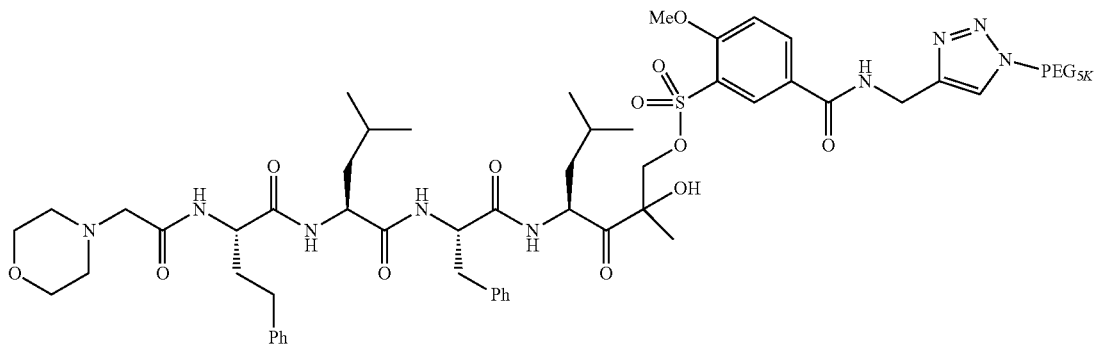

(4S,7S,10S,13S)-10-Benzyl-5-hydroxy-7,13-diisobutyl-15-methyl-1-morpholino-2,5,8,11,14-pentaoxo-4-phenethyl-3,6,9,12-tetraazahexadecan-16-yl 2-methoxy-5-(prop-2-yn-1-ylcarbamoyl)benzenesulfonate and PEG$_{5k}$-N$_3$ (Creative PEGworks Catalog # PSB-2024) were reacted following General PEGylation Conditions, Method A.

(4S,7S,10S,13S, R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-methoxy-5-(((1-PEG$_{20K}$/4-Arm-1H-1,2,3-triazol-4-yl)methyl)carbamoyl)benzenesulfonate

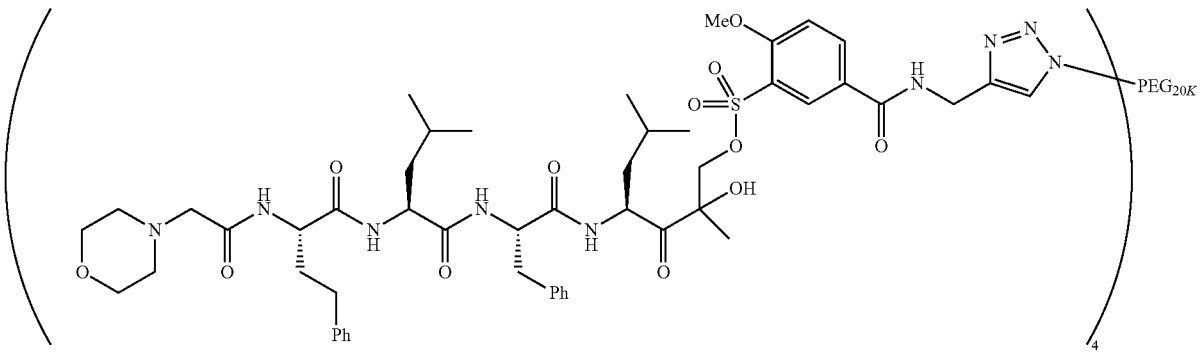

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2-methoxy-5-(prop-2-yn-1-ylcarbamoyl)benzenesulfonate and PEG$_{20K}$-(N$_3$)$_4$ (Creative PEGworks Catalog # PSB-493) were reacted following General PEGylation Conditions, Method C; PEG Loading (NMR): ¾ Arms, 8.9% small molecule.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-methyl-5-(((1-PEG$_{20K}$/4-Arm-1H-1,2,3-triazol-4-yl)methyl)carbamoyl)benzenesulfonate

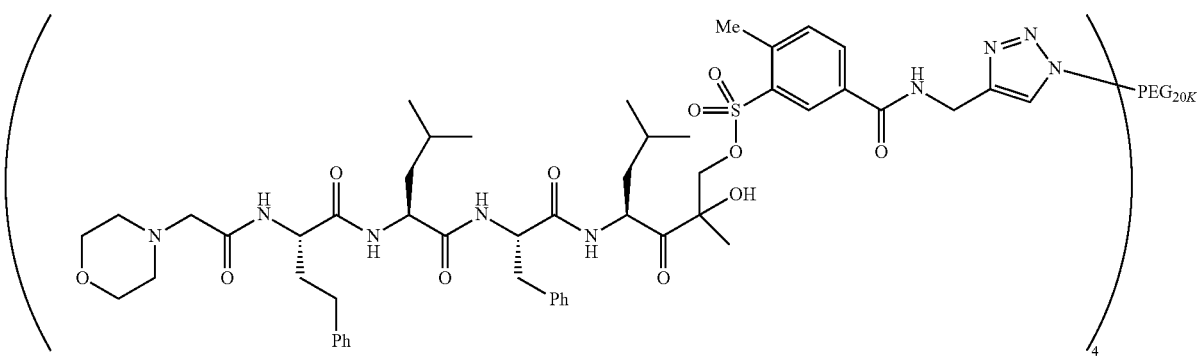

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2-methyl-5-(prop-2-yn-1-ylcarbamoyl)benzenesulfonate and PEG$_{20K}$-(N$_3$)$_4$ (Creative PEGworks Catalog # PSB-493) were reacted following General PEGylation Conditions, Method C.

(4S,7S,10S,13S)-10-Benzyl-15-((ethoxycarbonyl)oxy)-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate

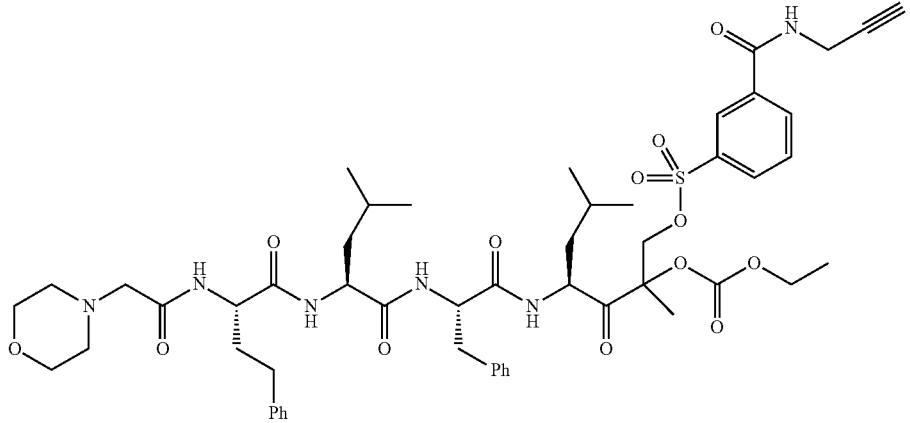 [SMILES: C#CCNC(=O)c1cccc(S(=O)(=O)OCC(C)(OC(=O)OCC)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)c1]

Prepared using methods described above from ethanol and (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate.

(4S,7S,10S,13S)-10-benzyl-5-hydroxy-7,13-diisobutyl-15-methyl-1-morpholino-2,5,8,11,14-pentaoxo-4-phenethyl-3,6,9,12-tetraazahexadecan-16-yl 4-(3-((1-PEG$_{5K}$-1H-1,2,3-triazol-4-yl)methyl)ureido)benzenesulfonate

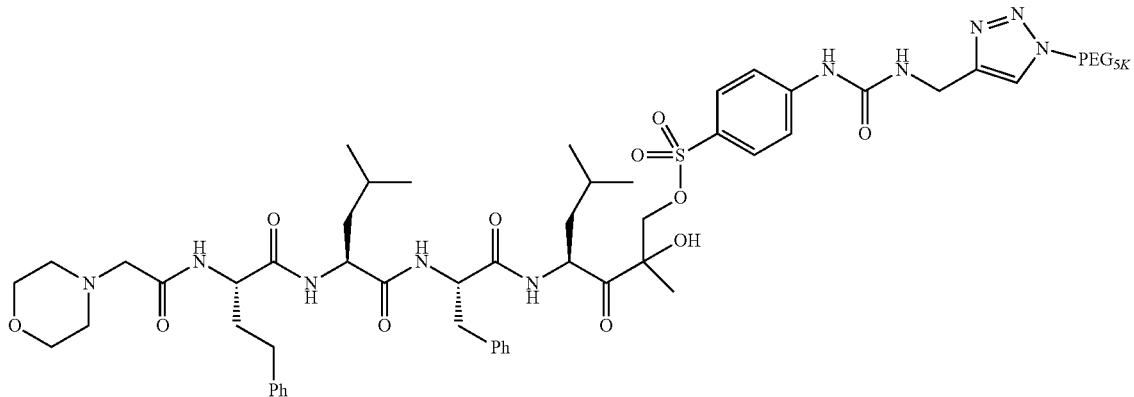

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 4-(3-(prop-2-yn-1-yl)ureido)benzenesulfonate and PEG$_{5k}$-N$_3$ (Creative PEGworks Catalog # PSB-2024) were reacted following General PEGylation Conditions, Method A.

Preparation of (4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate (13)

(Prop-2-yn-1-yloxy)benzene (10)

Figure 39:
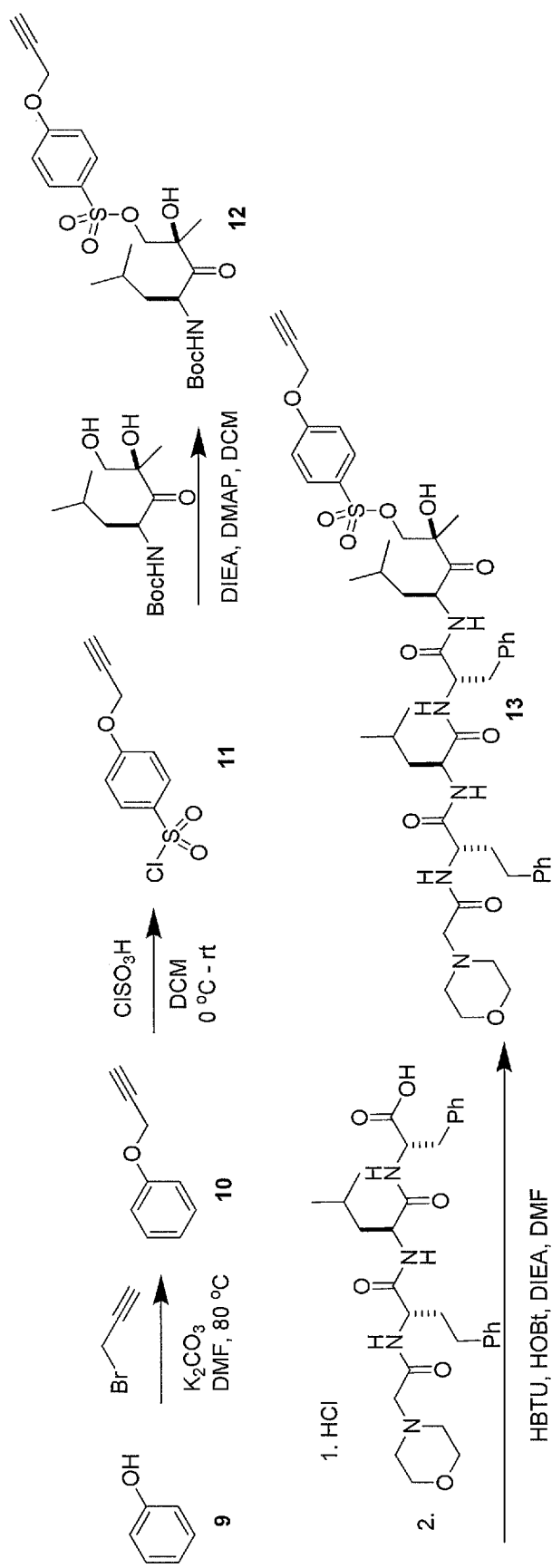
FIG. 39 is a scheme showing the synthesis of an embodiment of an alkynyl sulfonate precursor to a prodrug of epoxy ketone proteasome inhibitors.
Figure 4F:
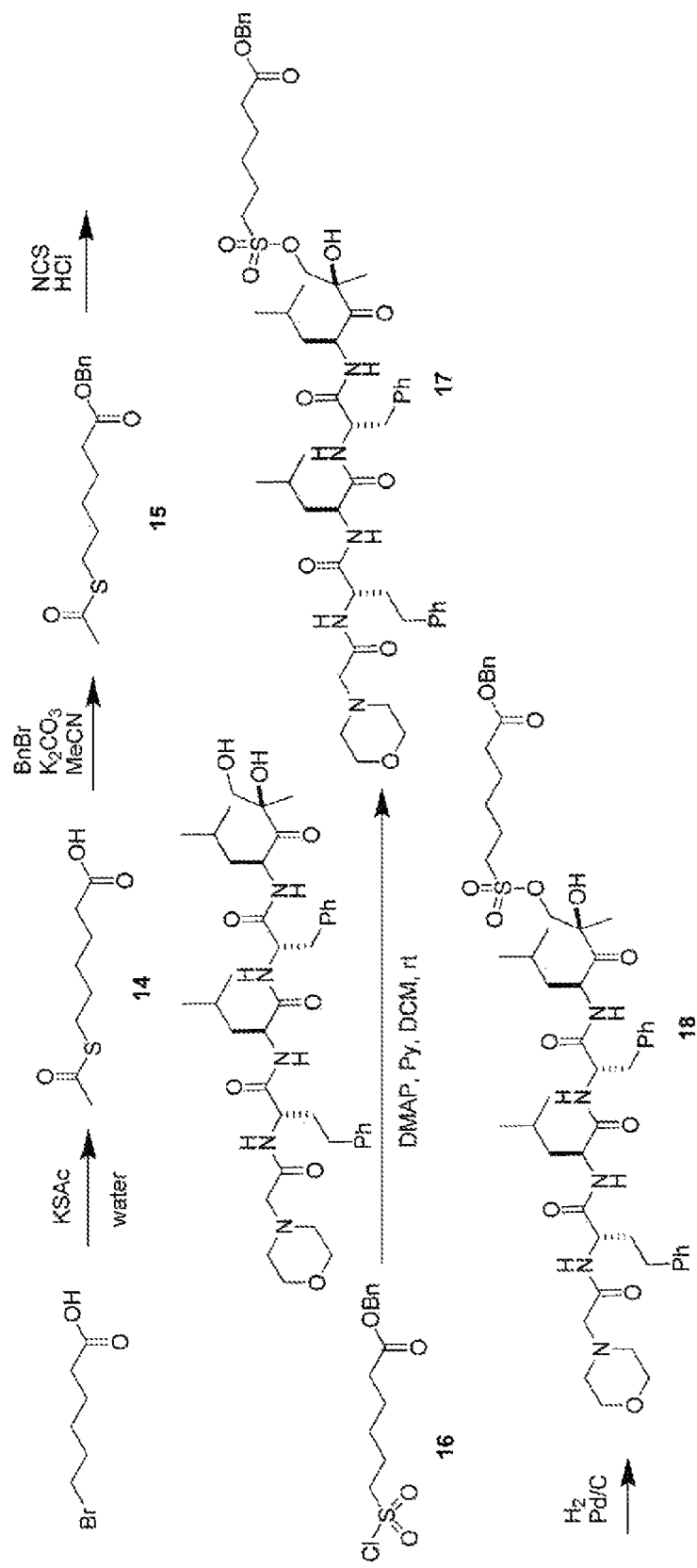

Referring to FIG. 39, phenol (14.6 g, 0.155 mol), propargyl bromide (19 mL, 0.171 mol) and potassium carbonate (32.1 g, 0.232 mol) in DMF (100 mL) were heated at 85° C. overnight. The reaction was diluted with water and extracted with ether. The extract was washed with brine, dried (MgSO$_4$) and evaporated. The residue was purified by Biotage flash column chromatography (10% EtOAc/Hep) to give product as an oil (17.2 g, 84%).

4-(Prop-2-yn-1-yloxy)benzene-1-sulfonyl Chloride (11)

Referring to FIG. 39, chlorosulfonic acid (19.9 mL, 0.299 mol) was added dropwise to (prop-2-yn-1-yloxy)benzene (17.2 g, 0.130 mol) in dichloromethane (100 mL) at 0° C. The reaction was stirred at 0° C. for 1 hour and then poured into ice-water and extracted with dichloromethane. The extract was washed with water, dried (MgSO₄), and evaporated. The residue was purified by Biotage flash column chromatography (30% EtOAc/Hep) to give product as an oil (17.9 g, 60%).

(2R,4S)-4-((tert-Butoxycarbonyl)amino)-2-hydroxy-2,6-dimethyl-3-oxoheptyl 3-(prop-2-yn-1-yloxy)propane-1-sulfonate (12)

Referring to FIG. 39, 4-(prop-2-yn-1-yloxy)benzene-1-sulfonyl chloride (2.39 g, 0.0104 mol) in dichloromethane (10 mL) was added to tert-butyl ((2R,4S)-1,2-dihydroxy-2,6-dimethyl-3-oxoheptan-4-yl)carbamate (3.00 g, 0.0104 mol), DMAP (0.13 g) and DIEA (2.17 mL, 0.0125 mol) in dichloromethane (40 mL) at 0° C., allowed to warm to room temperature and stirred overnight. The mixture was washed with 2N HCl, brine, dried (MgSO4) and evaporated. The residue was purified by Biotage flash column chromatography (30% EtOAc/Hep) to give product as a foam (4.13 g, 82%).

Referring to FIG. 39. (2R,4S)-4-((tert-butoxycarbonyl)amino)-2-hydroxy-2,6-dimethyl-3-oxoheptyl 3-(prop-2-yn-1-yloxy)propane-1-sulfonate (4.13 g, 0.00854 mol) and 4N hydrogen chloride in dioxane (50 mL) were stirred at room temperature for 1 hour and then evaporated to dryness. (S)-2-((S)-4-methyl-2-((S)-2-(2-morpholinoacetamido)-4-phenylbutanamido)pentanamido)-3-phenylpropanoic acid (4.84 g, 0.00854 mol), HBTU (4.86 g, 0.0128 mol), HOBt (1.73 g, 0.0128 mol) and DMF (50 mL) were added to the residue and stirred until dissolved. The reaction was cooled to 0° C. and DIEA (4.46 mL, 0.0256 mol) added dropwise. The mixture was stirred at 0° C. for 30 minutes, diluted with 2N HCl, and extracted with ethyl acetate. The extract was washed with sat. aq. sodium bicarbonate, brine, dried (MgSO₄) and evaporated. The residue was purified by Biotage flash column chromatography (5% MeOH/30% EtOAc/DCM) to give product 13 as a foam (6.4 g, 80%).

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethoxy-4-(prop-2-yn-1-yloxy)benzenesulfonate

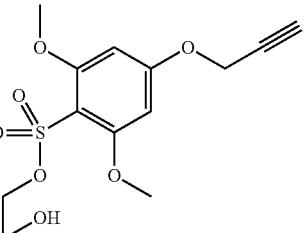
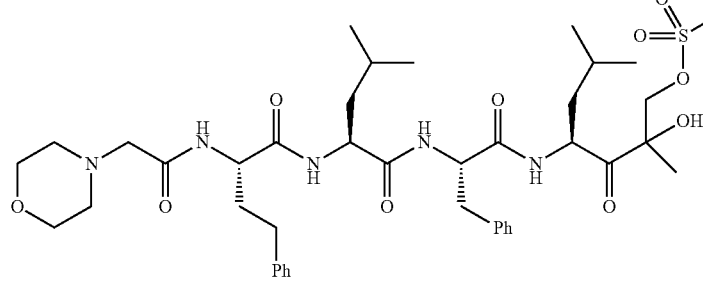

Prepared in a similar manner to compound 13, except from 4-propargyloxy)-2,6-dimethoxybenzene-1-sulfonyl chloride and (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide.

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,4-dimethoxy-6-(prop-2-yn-1-yloxy)benzenesulfonate

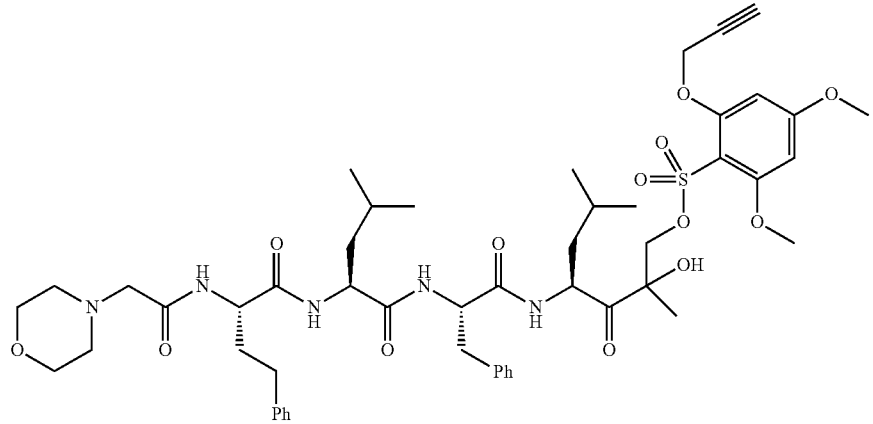 [SMILES: C#CCOc1cc(OC)cc(OC)c1S(=O)(=O)OCC(C)(O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Prepared in a similar manner to compound 13, except from 2,4-dimethoxy-6-(prop-2-yn-1-yloxy)benzene-1-sulfonyl chloride and (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide.

(4S,7S,10S,13S)-10-Benzyl-15-hydroxy-7,13-diisobutyl-15-methyl-1-morpholino-2,5,11,14-pentaoxo-4-phenethyl-3,6,9,12-tetraazahexadecan-16-yl 2,6-dimethyl-4-(prop-2-yn-1-yloxy)benzenesulfonate

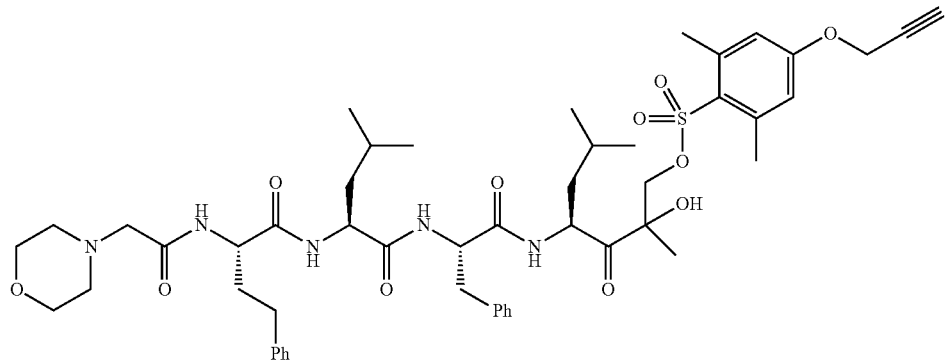 [SMILES: C#CCOc1cc(C)c(S(=O)(=O)OCC(C)(O)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)c(C)c1]

Prepared in a similar manner to compound 13, except from 4-(propargyloxy)-2,6-dimethylbenzene-1-sulfonyl chloride and (S)—N—((S)-1-(((2R,4S)-1,2-dihydroxy-2,6-dimethyl-3-oxoheptan-1-yl)amino)-1-oxo-3-phenylpropan-2-yl)-4-methyl-2-((S)-2-(2-morpholinoacetamido)-4-phenylbutanamido)pentanamide.

(4S,7S,10S,13S)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-((1-PEG$_{20K}$/2-Arm-1H-1,2,3-triazol-4-yl)methoxy)benzenesulfonate

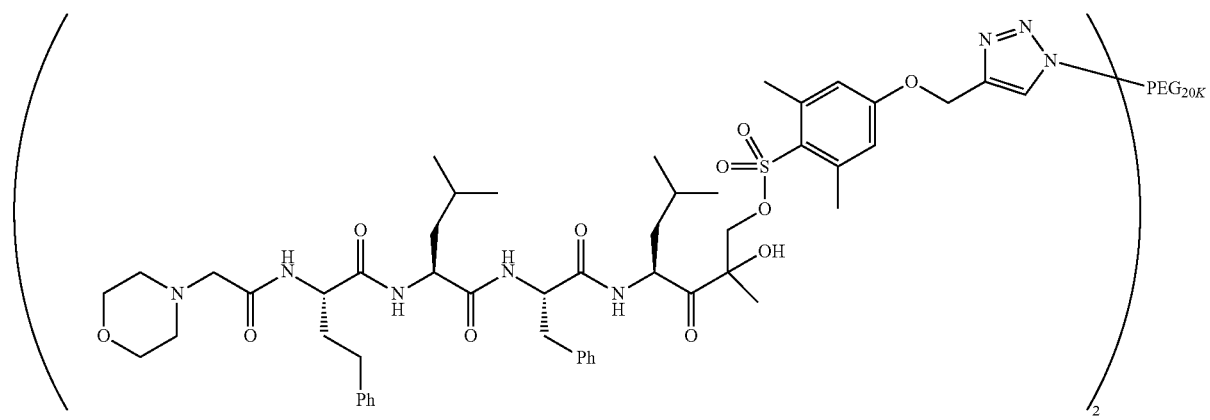

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-(prop-2-yn-1-yloxy)benzenesulfonate and PEG$_{20K}$-(N$_3$)$_2$ (Creative PEGworks Catalog # PSB-329) were reacted following General PEGylation Conditions, Method B.

(4S,7S,10S,13S)-10-benzyl-15-hydroxy-7,13-di-
isobutyl-15-methyl-1-morpholino-2,5,8,11,14-pen-
taoxo-4-phenethyl-3,6,9,12-tetraazahexadecan-16-yl
2,6-dimethyl-4-((1-PEG$_{40K}$/8-Arm-1H-1,2,3-triazol-
4-yl)methoxy)benzenesulfonate

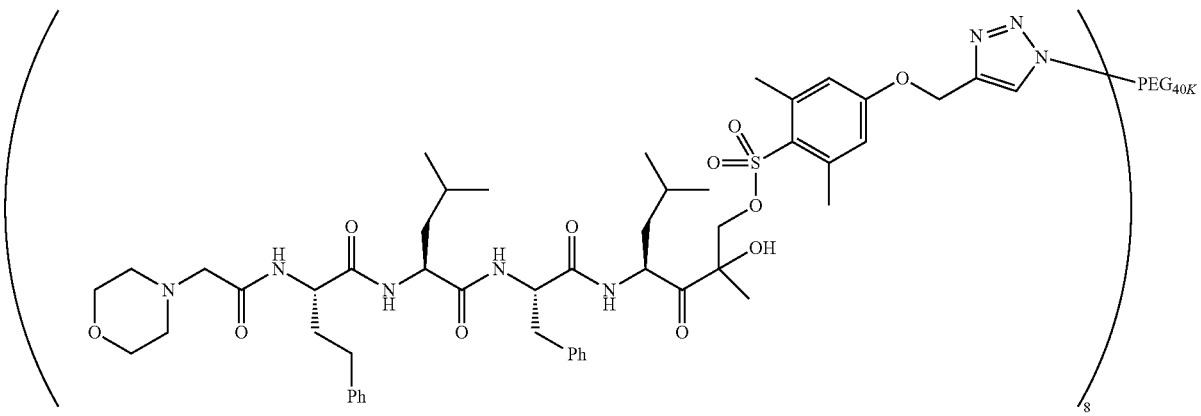

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-(prop-2-yn-1-yloxy)benzenesulfonate and PEG$_{40K}$-(N$_3$)$_8$ (Creative PEGworks Catalog # PSB-884) were reacted following General PEGylation Conditions, Method C; PEG Loading (NMR): 4.7/8 Arms, 7.1% small molecule.

(4S,7S,10S,13S)-10-benzyl-15-hydroxy-7,13-di-
isobutyl-15-methyl-1-morpholino-2,5,8,11,14-pen-
taoxo-4-phenethyl-3,6,9,12-tetraazahexadecan-16-yl
2,6-dimethyl-4-((1-PEG$_{20K}$-1H-1,2,3-triazol-4-yl)
methoxy)benzenesulfonate

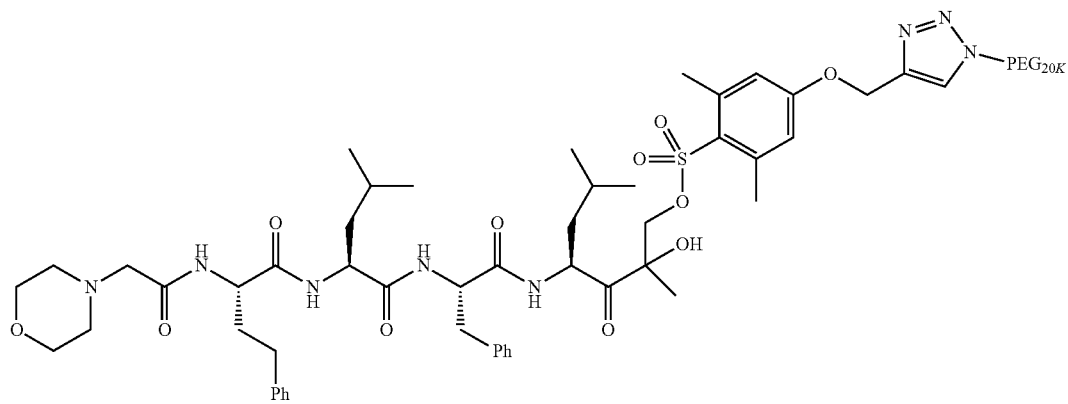

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-(prop-2-yn-1-yloxy)benzenesulfonate and PEG$_{20K}$-N$_3$ (Creative PEGworks Catalog # PSB-2022) were reacted following General PEGylation Conditions, Method A.

2-(4-(((((4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetic Acid 2-(4-(((((4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl)oxy)sulfonyl)-3,5-dimethoxyphenoxy)acetic Acid

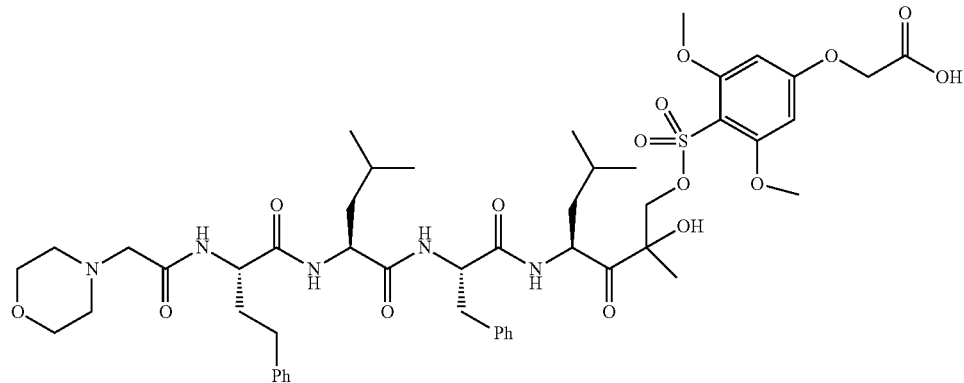 [SMILES: COc1cc(OCC(=O)O)cc(OC)c1S(=O)(=O)OCC(C)(O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S)-10-benzyl-15-hydroxy-7,13-diisobutyl-15-methyl-1-morpholino-2,5,8,11,14-pentaoxo-4-phenethyl-3,6,9,12-tetraazahexadecan-16-yl-2,6-dimethyl-4-(2-($PEG_{20K}$/4-Arm)-amino)-2-oxoethoxy)benzenesulfonate

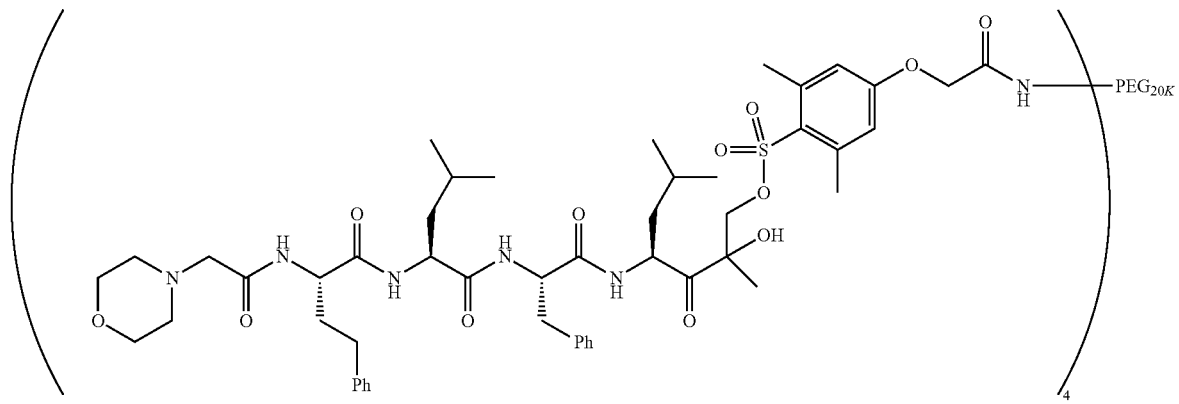

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-(prop-2-yn-1-yloxy)benzenesulfonate and $PEG_{20k}$-$(N_3)_4$ (Creative PEGworks Catalog # PSB-493) were reacted following General PEGylation Conditions, Method C; 1H NMR (DMSO-d6): δ 8.21 (s, 1H), 8.08-8.01 (m, 3H), 7.87 (d, J=8.5 Hz, 1H), 7.27 (t, J=7 Hz, 2H), 7.18-7.03 (m, 8H), 6.98 (s, 2H), 6.02 (s, 1H), 5.21 (s, 2H), 5.12-5.04 (m, 1H), 4.55-4.53 (m, 3H), 4.38-4.26 (m, 2H), 3.92 (d, J=9 Hz, 1H), 3.81 (t, J=5 Hz, 2H), 3.71 (d, J=9.5 Hz, 1H), 3.65-3.63 (m, 2H), 3.60-3.35 (m, 437H), 2.99-2.92 (m, 3H), 2.76-2.75 (m, 1H), 2.53 (s, 6H), 2.47-2.42 (m, 6H), 1.91-1.76 (m, 2H), 1.65-1.48 (m, 3H), 1.40-1.33 (m, 2H), 1.29-1.22 (m, 1H), 1.17 (s, 3H), 0.85-0.79 (m, 12H); PEG Loading (NMR): 4/4 Arms, 11.9% small molecule.

(4S,7S,10S,13S)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl 2,6-dimethyl-4-(2-PEG$_{20K}$/4-Arm amino-2-oxoethoxy)benzenesulfonate

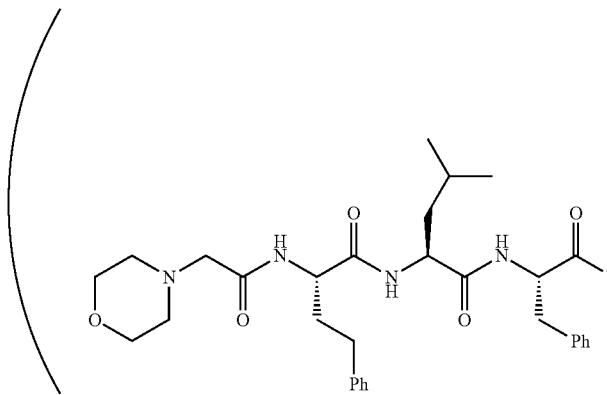
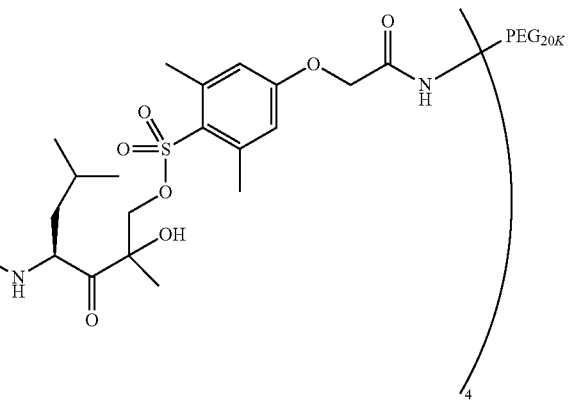

2-(4-((((4S,7S,10S,13S)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetic acid and PEG$_{20K}$-(NH$_2$)$_4$ (Creative PEGworks Catalog # PSB-435) were reacted following General PEGylation Conditions, Method E.

Ethyl 2-(3,5-dimethylphenoxy)acetate (1)

Figure 37:
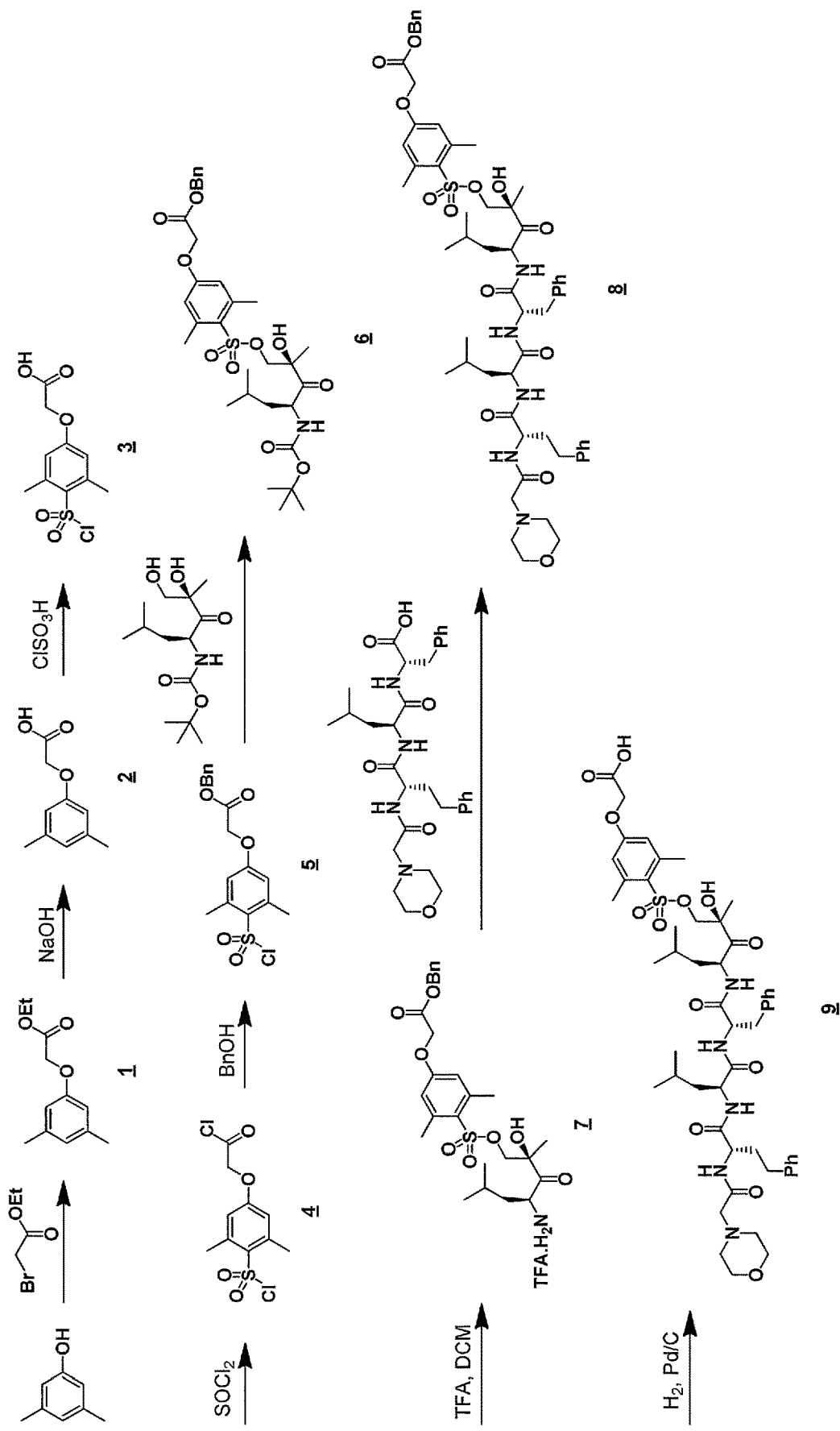
FIG. 37 is a scheme showing the synthesis of an embodiment of a precursor to a sulfonate-linked PEG prodrug of epoxy ketone proteasome inhibitors.

Referring to FIG. 37, to a solution of 3,5-dimethylphenol (10 g, 82 mmol) in CH3CN (150 mL) were added ethyl 2-bromoacetate (14.9 g, 90 mmol) and K$_2$CO$_3$ (16.9 g, 123 mmol). The reaction mixture was stirred overnight at room temperature. The mixture was poured into water (200 mL) and the resulting mixture was extracted with ethyl acetate (150 mL×2). The combined extracts were washed with brine, dried over anhydrous Na2SO4 and concentrated under reduced pressure to give product as a yellow oil, which was used in the next step without further purification (19 g); $^1$H NMR (CDCl$_3$, 300 MHz): δ 6.13 (s, 1H), 6.11 (s, 2H), 4.59 (s, 2H), 4.30 (q, J=7.2 Hz, 2H), 3.77 (s, 6H), 1.31 (t, J=7.2 Hz, 3H).

2-(3,5-Dimethylphenoxy)acetic Acid (2)

Referring to FIG. 37, to a solution of ethyl 2-(3,5-dimethylphenoxy)acetate (19 g, obtained from the previous step) in methanol (150 mL) was added NaOH solution (6 N, 50 mL). The reaction mixture was stirred at room temperature for 4 h and then adjusted to pH=1~2 with 2 N HCl solution. The resulting mixture was extracted with ethyl acetate (150 mL×2). The combined extracts were washed with brine, dried over anhydrous Na2SO4 and concentrated under reduced pressure to give a solid, which was washed with ethyl acetate/hexane (1:15, 40 mL) to give product (14 g, 95% yield over two steps); $^1$H NMR (CDCl$_3$, 300 MHz): δ 6.69 (s, 1H), 6.58 (s, 2H), 4.68 (s, 2H), 2.31 (s, 6H).

2-(4-(Chlorosulfonyl)-3,5-dimethylphenoxy)acetic Acid (3)

Referring to FIG. 37, to a solution of 2-(3,5-dimethylphenoxy)acetic acid (13 g, 72 mmol) in DCM (130 mL) was added dropwise a solution of ClSO$_3$H (19.2 g, 166 mmol) in DCM (20 mL) at 0° C. The reaction mixture was stirred at 0° C. for 0.5 h. Water (100 mL) and THF (30 mL) were added and the resulting mixture was stirred for 5 min. The two layers were separated and the organic layer was washed with brine (100 mL), dried over anhydrous Na$_2$SO$_4$ and concentrated under reduced pressure to give product as a white solid (6 g, 30% yield); $^1$H NMR (CDCl$_3$, 300 MHz): δ 6.79 (s, 2H), 4.79 (s, 2H), 2.77 (s, 6H).

2-(4-(Chlorosulfonyl)-3,5-dimethylphenoxy)acetyl Chloride (4)

Referring to FIG. 37, 2-(4-(Chlorosulfonyl)-3,5-dimethylphenoxy)acetic acid (6 g, 21.6 mmol) was dissolved in SOCl$_2$ (50 mL) and the reaction mixture was refluxed overnight. Proton NMR analysis on a sample from the reaction mixture exhibited the conversion went completion. Concentration of the mixture under reduced pressure gave product as a white solid (6.4 g, quantitative); $^1$H NMR (CDCl3, 300 MHz): δ 6.71 (s, 2H), 5.03 (s, 2H), 2.80 (s, 6H).

Benzyl 2-(4-(chlorosulfonyl)-3,5-dimethylphenoxy)acetate (5)

Referring to FIG. 37, to a solution of 2-(4-(chlorosulfonyl)-3,5-dimethylphenoxy)acetyl chloride (6 g, 20.3 mmol) in THF (60 mL) were added dropwise a solution of BnOH (2.2 g, 20.3 mmol), Et3N (3.44 mL, 24.3 mmol) and DMAP (25 mg, 0.2 mmol) in THF (30 mL) at −78° C. The reaction mixture was stirred for 5 h at −78° C. and then poured into HCl solution (1 N, 100 mL). The resulting mixture was extracted with ethyl acetate (100 mL×2). The combined extracts were washed with brine, dried over anhydrous Na2SO4 and concentrated under reduced pressure. The residue was purified by flash column chromatography (petroleum ether/EtOAc=60:1) to give product as a white powder (1.2 g, 16% yield), 2-(4-(Chlorosulfonyl)-3,5-dimethylphenoxy)acetyl chloride (2.0 g) was recovered. $^1$H NMR (CDCl$_3$, 300 MHz): δ 7.42-7.32 (m, 5H), 6.67 (s, 2H), 5.32 (s, 2H), 4.74 (s, 2H) 2.72 (s, 6H).

Benzyl 2-(4-(((((2R,4S)-4-((tert-butoxycarbonyl)amino)-2-hydroxy-2,6-dimethyl-3-oxoheptyl)oxy)sulfonyl)-3,5-dimethylphenoxy)acetate (6)

Referring to FIG. 37, to a solution of the tert-butyl ((2R,4S)-1,2-dihydroxy-2,6-dimethyl-3-oxoheptan-4-yl)

carbamate (0.72 g, 2.5 mmol) in DCM (30 mL) were added benzyl 2-(4-(chlorosulfonyl)-3,5-dimethylphenoxy)acetate (1.1 g, 3 mmol), Et$_3$N (0.52 mL, 3.7 mmol) and DMAP (63 mg, 0.5 mmol). The reaction mixture was stirred at room temperature for 7 h (TLC analysis showed some starting material was left). DCM (50 mL) was added and the resulting mixture was washed with HCl solution (1 N, 30 mL) and saturated aqueous NaHCO$_3$ (30 mL). The organic layer was dried over anhydrous Na$_2$SO$_4$ and concentrated under reduced pressure. The residue was purified by flash column chromatography (petroleum ether/EtOAc=10:1) to give product as a white powder (540 mg, 34.8%). LC-MS analysis confirmed the structure.

Benzyl 2-(4-((((2R,4S)-4-amino-2-hydroxy-2,6-dimethyl-3-oxoheptyl)oxy)sulfonyl)-3,5-dimethylphenoxy)acetate (7)

Referring to FIG. 37, to a solution of benzyl 2-(4-((((2R,4S)-4-((tert-butoxycarbonyl)amino)-2-hydroxy-2,6-dimethyl-3-oxoheptyl)oxy)sulfonyl)-3,5-dimethylphenoxy)acetate (540 mg, 0.87 mmol) in DCM (15 mL) was added TFA (5 mL). The reaction mixture was stirred at room temperature for 3 h. Removal of the solvent under reduced pressure gave product, which was used directly in the next step without further purification. LC-MS analysis confirmed the structure.

Benzyl 2-(4-((((4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetate (8)

Referring to FIG. 37, to a solution of (S)-2-((S)-4-methyl-2-((S)-2-(2-morpholinoacetamido)-4-phenylbutanamido)-3-phenylpropanoic acid (0.59 g, 1 mmol) in DCM (30 mL) were added DMTMM (0.44 g, 1.5 mmol) and benzyl 2-(4-((((2R,4S)-4-amino-2-hydroxy-2,6-dimethyl-3-oxoheptyl)oxy)sulfonyl)-3,5-dimethylphenoxy)acetate (obtained from 540 mg of compound 6). The mixture was adjusted to pH=8 with 4-methylmorpholine. The reaction mixture was stirred at room temperature for 4 h and then diluted with DCM (40 mL). The resulting mixture was washed with HCl solution (1 N, 40 mL) and saturated aqueous NaHCO3 (30 mL). The organic layer was washed with brine, dried over anhydrous Na2SO4 and concentrated under reduced pressure. The residue was purified by flash column chromatography (DCM/EtOAc=3:1) to give product (770 mg, 82.8% yield). LC-MS analysis confirmed the structure.

2-(4-((((4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetic Acid (9)

Referring to FIG. 37, benzyl 2-(4-((((4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetate (110 mg, 0.1 mmol) was dissolved in dioxane (10 mL) and Pd/C (50 mg) was added. The mixture was stirred for 3 h under H2 atmosphere (15 psi). The catalyst was filtered off and the filtrate was concentrated under reduced pressure to give compound (100 mg, quantitative); $^1$H NMR (DMSO-d$_6$, 300 MHz): δ 8.12-8.02 (m, 3H), 7.99-7.89 (m, 1H), 7.32-7.02 (m, 10H), 6.88 (s, 2H), 6.05 (s, 1H), 5.11-5.02 (m, 1H), 5.75 (s, 2H), 4.61-4.22 (m, 4H), 3.65 (m, 4H), 2.95 (m, 2H), 2.78-2.70 (m, 1H), 2.55 (s, 6H), 2.45 (m, 4H), 1.94-1.55 (m, 4H), 0.92-0.74 (m, 12H).

(4S,7S,10S,13S)-10-benzyl-15-hydroxy-7,13-diisobutyl-1-methyl-1-morpholino-2,5,8,11,14-pentaoxo-4-phenethyl-3,6,9,12-tetraazahexadecan-16-yl-2,6-dimethoxy-4-(2-(PEG$_{20K}$/4-Arm)-amino)-2-oxoethoxy)benzenesulfonate

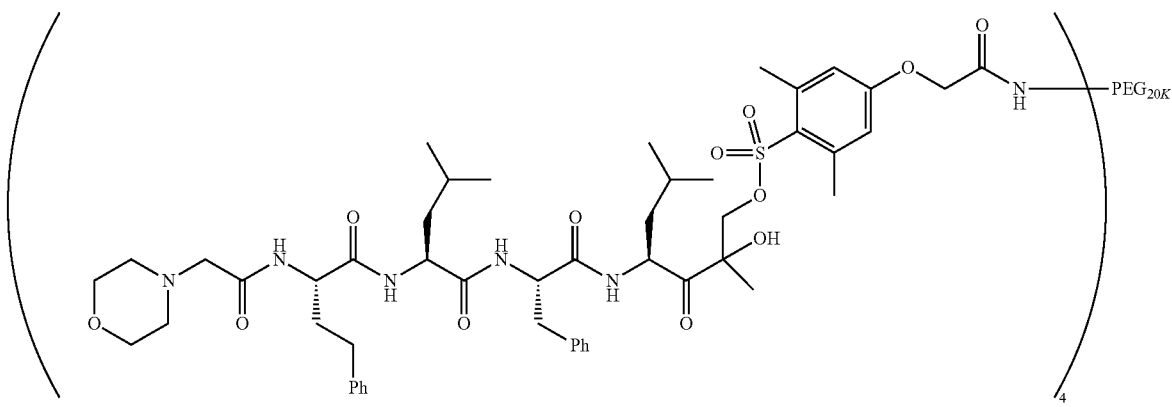

2-(4-((((4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl)oxy)sulfonyl)-3,5-dimethoxyphenoxy)acetic acid and PEG$_{20k}$-(NH$_2$)$_4$ (Creative PEGworks Catalog # PSB-435) were reacted following General PEGylation Conditions, Method E.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl-2,6-dimethyl-4-(2-(N-PEG$_{20K}$-amino)-2-oxoethoxy)benzenesulfonate

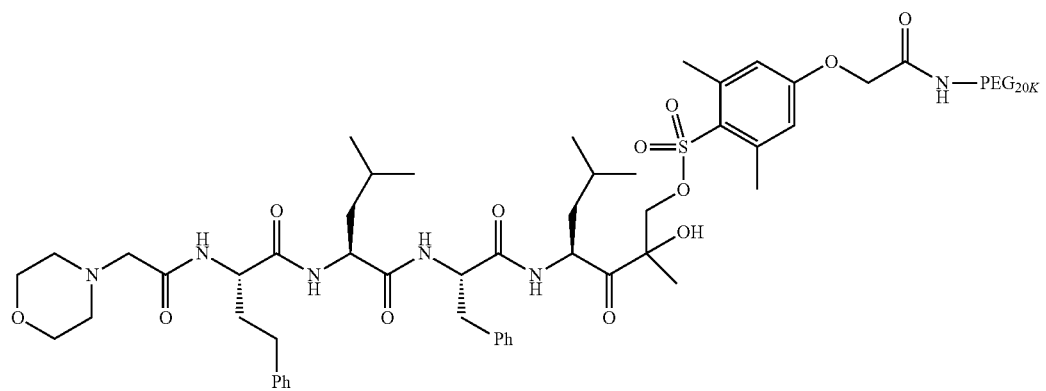

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl-2,6-dimethoxy-4-(2-(N-PEG$_{20K}$-amino)-2-oxoethoxy)benzenesulfonate

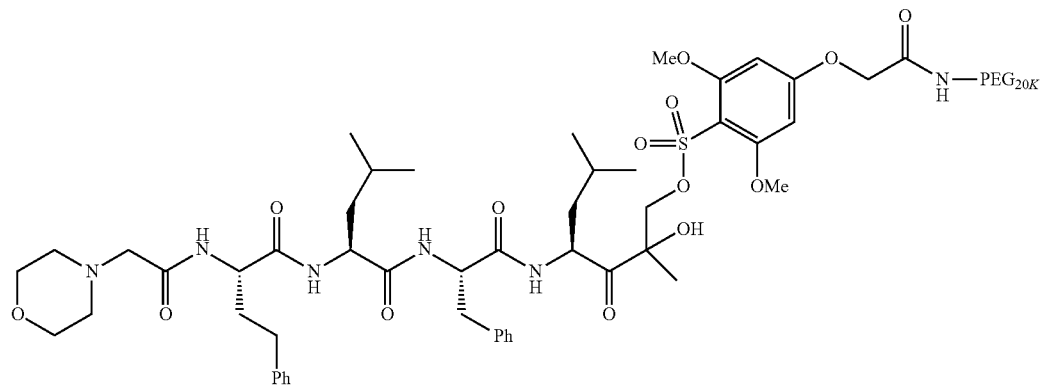

2-(4-((((4S,7S,10S,13S)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl)oxy)sulfonyl)-3,5-dimethoxyphenoxy)acetic acid and PEG$_{20K}$-NH$_2$ (Creative PEGworks Catalog # PJK-265) were reacted following General PEGylation Conditions, Method D.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl-2,6-dimethyl-4-(2-((N-PEG$_{20K}$/Branched 2-Arm)-amino)-2-oxoethoxy)benzenesulfonate

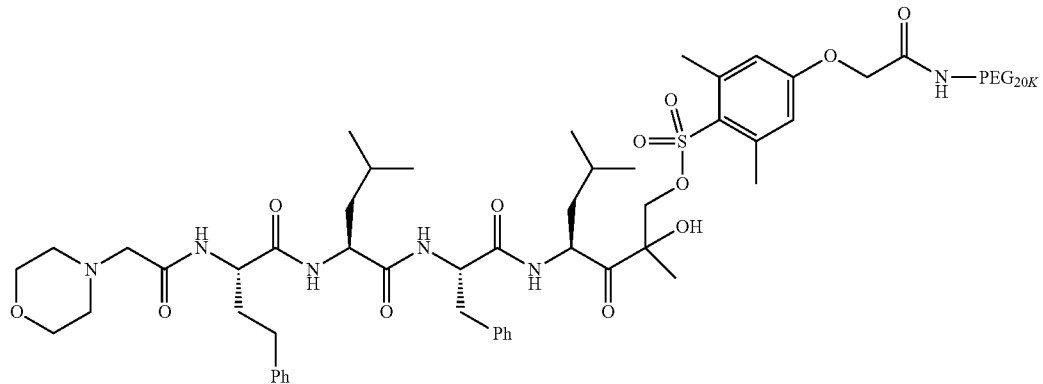

(4S,7S,10S,13S)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl 2,6-dimethyl-4-(2-PEG$_{40K}$ amino-2-oxoethoxy)benzenesulfonate

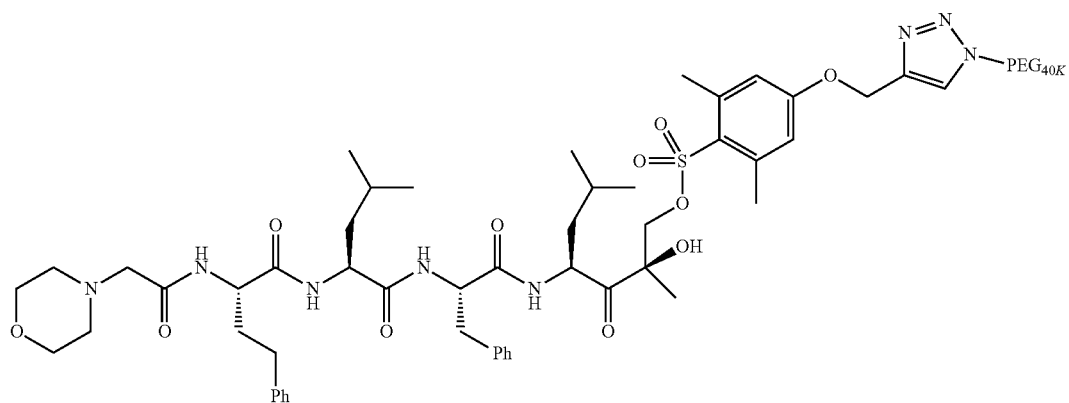

2-(4-((((4S,7S,10S,13S)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetic acid and PEG$_{40K}$-NH$_2$ (4-Arm Branched, NOF America, Sunbright GL4-400PA) were reacted following ethynylphenoxy)acetate Conditions, Method A.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl-2,6-dimethyl-4-(2-((N-PEG$_{20K}$/Branched 4-Arm)-amino)-2-oxoethoxy)benzenesulfonate (PEG Architecture Formula 2G)

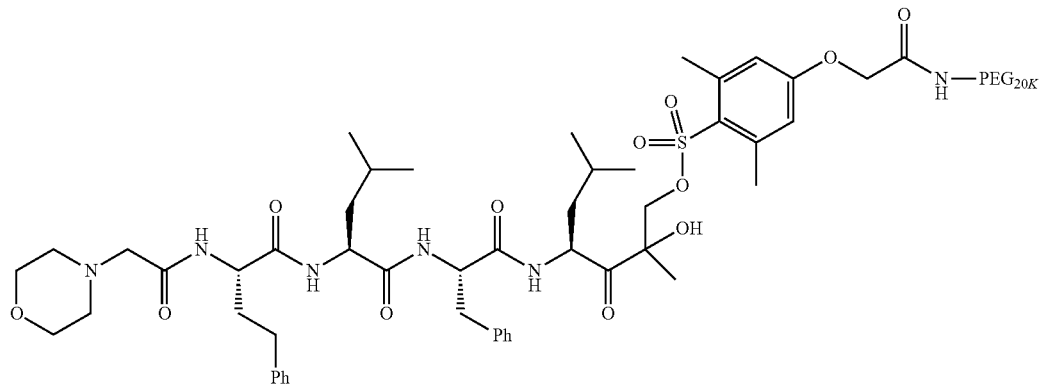

2-(4-((((4S,7S,10S,13S)-10-Benzyl-5-hydroxy-7,13-di-isobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetic acid and PEG$_{20K}$-NH$_2$ (Creative PEGworks Catalog # PJK-265) were reacted following General PEGylation Conditions, Method D.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl-2,6-dimethyl-4-(2-((N-PEG$_{20K}$/Branched 4-Arm)-amino)-2-oxoethoxy)benzenesulfonate (PEG Architecture Formula 2H)

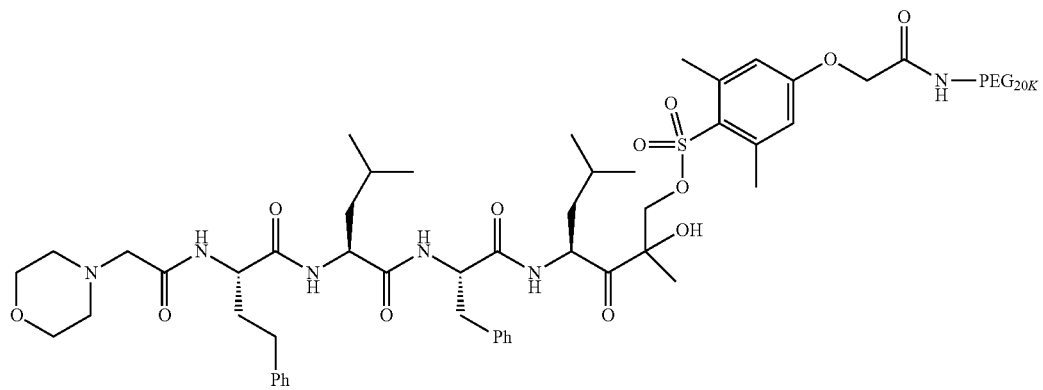

2-(4-((((4S,7S,10S,13S)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl)oxy)sulfonyl)-3,5-dimethylphenoxy)acetic acid and PEG$_{20K}$-NH$_2$ (4-Arm Branched, NOF America, Sunbright XY4-200PA) were reacted following General PEGylation Conditions, Method D.

Aliphatic Sulfonates

Preparation of (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-((1-PEG$_{2K}$-1H-1,2,3-triazol-4-yl)methoxy)propane-1-sulfonate

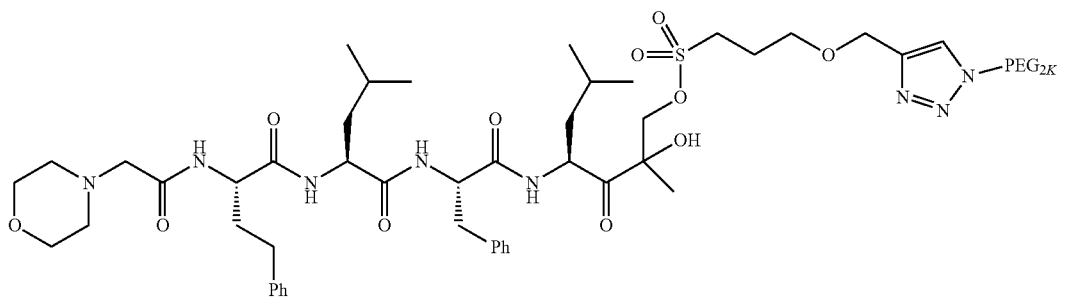

Final compounds were prepared using the standard PEGylation conditions.

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate and PEG$_{2K}$-N$_3$ (Creative PEGworks Catalog # PSB-2025) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate Scheme 19

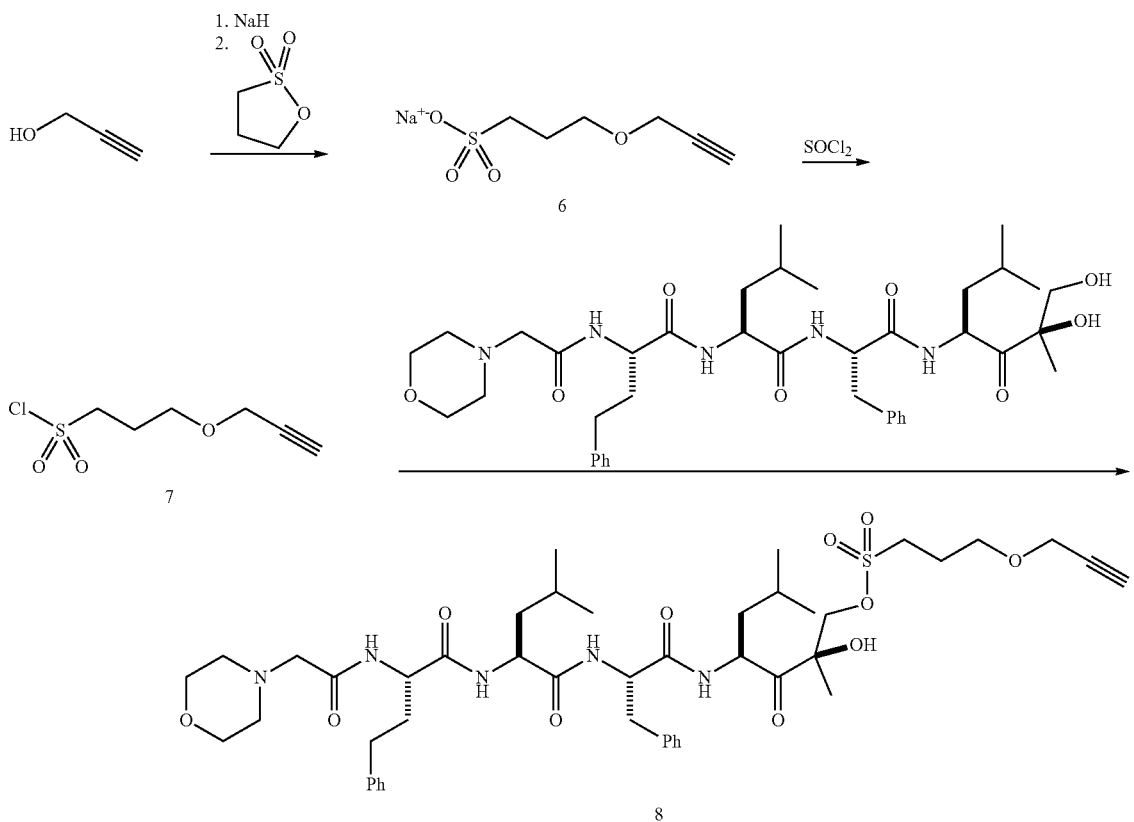

3-(Prop-2-yn-1-yloxy)propane-1-sulfonyl Chloride (6)

Referring to FIG. 16, a slurry of sodium 3-(propargyloxy) propyl sulfonate (5.0 g, 25.0 mmol, 1.0 equiv.) and thionyl chloride (25 mL, 344 mmol, 13.8 equiv.) was heated to 100° C. under $N_2$ for three hours. The mixture was concentrated to a thick oil, diluted with 50 mL benzene, and concentrated again by rotavap to obtain a waxy solid. The material was slurried in 50 mL dichloromethane and filtered. The solids were discarded and the mother liquor concentrated on rotavap to obtain product as an orange oil (4.7 g, 95%). $^1$H NMR (300 MHz, CDCl$_3$) δ 4.17 (d, 2H), 3.82 (t, 2H), 3.70 (t, 2H), 2.47 (t, 1H), 2.34 (m, 2H).

Sodium 3-(prop-2-yn-1-yloxy)propane-1-sulfonate (7)

Referring to FIG. 16, to a chilled (5° C.) slurry of NaH (60% in mineral oil, 1.60 g, 40.9 mmol, 1.0 equiv.) in dry DMF (30 mL) was added dropwise a solution of propargyl alcohol (2.4 mL, 40.9 mmol, 1.0 equiv.) in dry DMF (30 mL) over a ten minute period. 1,3-Propanesultone (5.0 g, 40.9 mmol, 1.0 equiv.) was dissolved in dry DMF (30 mL), and the resulting solution added dropwise over a five minute period to the chilled sodium propargylate solution. After stirring for ten minutes in the ice bath, the flask was transferred to an oil bath and heated at 60° C. for three hours. Most of the DMF was then removed by rotavap, and the remaining oil was triturated with 200 mL diethyl ether to yield a white solid, which was collected by vacuum filtration. The product was dried under vacuum to provide product as a white powder (7.4 g, 90%).

Referring to FIG. 16, to a solution of (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide (1.50 g, 2.0 mmol, 1.0 equiv.) in dry pyridine (15 mL) was added dropwise a solution of 3-(prop-2-yn-1-yloxy)propane-1-sulfonyl chloride (0.9 g, 4.4 mmol, 2.2 equiv) in DCM (15 mL) over a fifteen minute period. The resultant mixture was stirred at room temperature for three hours, concentrated via rotavap, and partitioned between ca. 100 mL dichloromethane and 50 ml water. The aqueous phase was discarded and the organic phase was concentrated and purified on a CombiFlash chromatograph (40 g silica column, 0-10% IPA/DCM, 60 min.) to provide product 8 as an off-white solid (1.2 g, 67%). LC/MS: M+H=898.6.

The following analogs were prepared similarly:

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-((1-PEG$_{5K}$-1H-1,2,3-triazol-4-yl)methoxy)propane-1-sulfonate

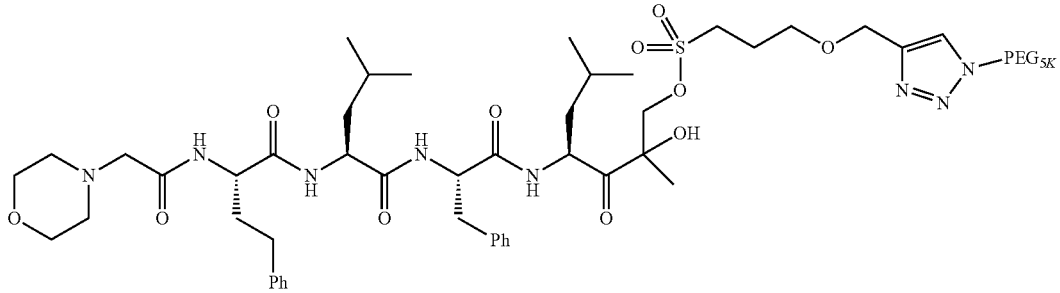

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate and PEG$_{5k}$-N$_3$ (Creative PEGworks Catalog # PSB-2024) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-((1-PEG$_{10K}$-1H-1,2,3-triazol-4-yl)methoxy)propane-1-sulfonate

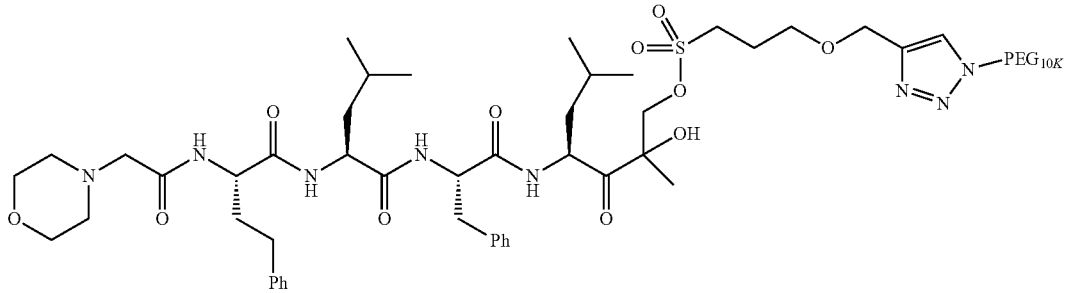

(4S,7S,10S,13S,15R)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate and PEG$_{10k}$-N$_3$ (Creative PEGworks Catalog # PSB-2023) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-((1-PEG$_{5K}$/2-Arm-1H-1,2,3-triazol-4-yl)methoxy)propane-1-sulfonate

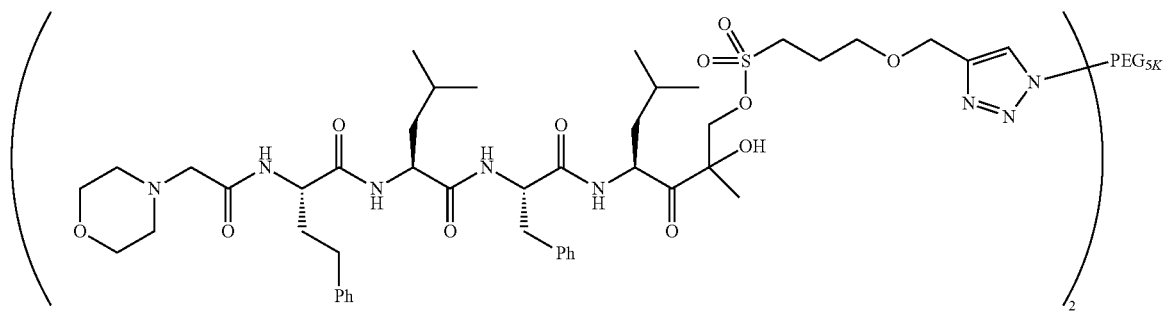

(4S,7S,10S,13S,15R)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate and PEG$_{5k}$-(N$_3$)$_2$ (Creative PEGworks Catalog # PSB-327) were reacted following General PEGylation Conditions, Method B.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-((1-PEG$_{10K}$/4-Arm-1H-1,2,3-triazol-4-yl)methoxy)propane-1-sulfonate

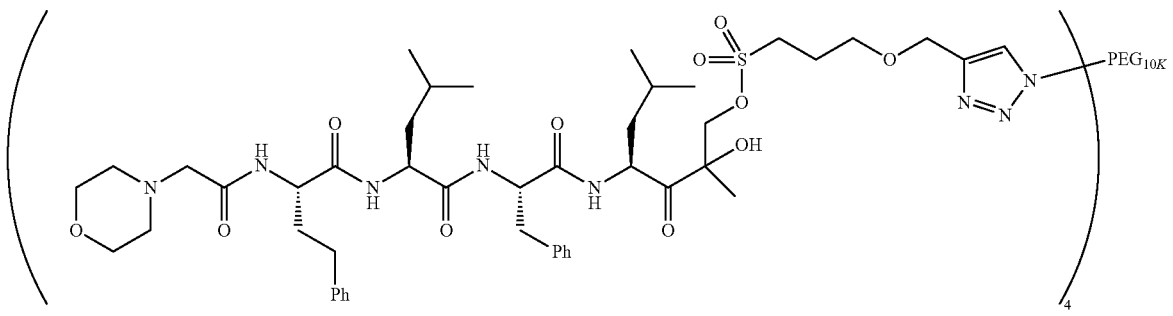

(4S,7S,10S,13S,15R)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate and PEG$_{10k}$-(N$_3$)$_4$ (Creative PEGworks Catalog # PSB-492) were reacted following General PEGylation Conditions, Method C; $^1$H NMR (DMSO-d$_6$): δ 8.08-8.01 (m, 4H), 7.87 (d, J=6.8 Hz, 1H), 7.28-7.03 (m, 10H), 5.08 (m, 1H), 4.55-4.49 (m, 6H), 4.35-4.21 (m, 4H), 4.05-3.90 (m, 6H), 3.81-3.80 (m, 3H), 3.65-3.36 (m, 336H), 3.32-3.31 (m, 10H), 3.05-2.77 (m, 4H), 2.50-2.27 (m, 10H), 1.93-1.19 (m, 13H), 0.87-0.77 (m, 12H).

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-((1-PEG$_{20K}$/4-Arm-1H-1,2,3-triazol-4-yl)methoxy)propane-1-sulfonate

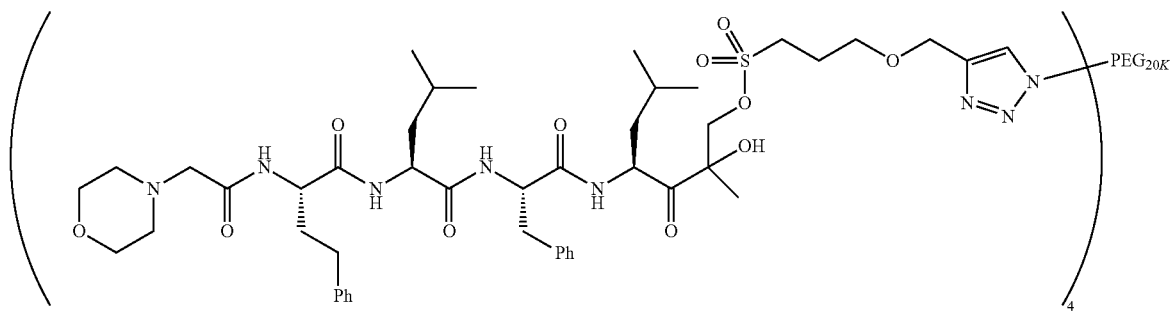

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-yloxy)propane-1-sulfonate and PEG$_{20K}$-(N$_3$)$_4$ (Creative PEGworks Catalog # PSB-493) were reacted following General PEGylation Conditions, Method C; $^1$H NMR (DMSO-d$_6$): δ 8.08-8.01 (m, 4H), 7.87 (d, J=8.5 Hz, 1H), 7.28-7.14 (m, 10H), 5.08 (m, 1H), 4.55-4.49 (m, 6H), 4.35-4.29 (m, 2H), 4.21 (d, J=0 Hz, 1H), 4.00 (d, J=10 Hz, 1H), 3.80 (t, J=5 Hz, 3H), 3.65-3.30 (m, 548H), 3.05-2.77 (m, 6H), 2.50-2.42 (m, 4H), 1.93-1.19 (m, 13H), 0.87-0.77 (m, 12H).

6-({[(2R,4S)-2-Hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3-oxoheptyl]oxy}sulfonyl)hexanoic acid (18)

6-(Acetylthio)hexanoic Acid (14)

Referring to FIG. 40, a mixture of 6-bromohexanoic acid (5 g, 25.8 mmol), AcSK (3.51 g, 30.7 mmol) and K$_2$CO$_3$ (3.54 g, 25.6 mmol) in water (15 mL) was stirred at room temperature overnight. The mixture was adjusted to pH-2 with 2N HCl solution and the resulting mixture was extracted with ethyl acetate (2×80 mL). The organic layers were combined, dried over anhydrous sodium sulfate and concentrated under reduced pressure to give the title compound (4.6 g, 94% yield).

Benzyl 6-(acetylthio)hexanoate (15)

Referring to FIG. 40, to a solution of 6-(acetylthio)hexanoic acid (3 g, 15.8 mmol) in CH3CN (80 mL) were added K2CO3 (4.3 g, 31.6 mmol) and benzyl bromide (2.68 g, 15.8 mmol). The reaction mixture was stirred at room temperature overnight and ethyl acetate (200 mL) and water (100 mL) were added. The organic layer was separated, dried over anhydrous sodium sulfate and concentrated under reduced pressure. The residue was purified by silica gel column chromatography to give the title compound (2.2 g, 50% yield) as a yellow oil.

Benzyl 6-(chlorosulfonyl)hexanoate (16)

Referring to FIG. 40, benzyl 6-(acetylthio)hexanoate (1.6 g, 5.7 mmol) was dissolved in CH3CN (40 mL) and 3N HCl solution (40 mL) and then NCS (3.05 g, 22.8 mmol) was added in portions over 0.5 h. The reaction mixture was stirred at room temperature for 3 hr and extracted with ethyl acetate (100 mL). The extract was washed with saturated NaHSO3 solution (3×50 mL) and water (3×50 mL), dried over anhydrous sodium sulfate and concentrated under reduced pressure to give the title compound (1.45 g, 83% yield) as a yellow oil.

Benzyl 6-({[(2R,4S)-2-hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3-oxoheptyl]oxy}sulfonyl)hexanoate (17)

Referring to FIG. 40, benzyl 6-(chlorosulfonyl)hexanoate (0.74 g, 2.44 mmol) was added to (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide (1.50 g, 2.03 mmol), DMAP (0.1 g) and pyridine (5 mL) in dichloromethane (20 mL) and the mixture stirred overnight at room temperature. The reaction was washed with 2N HCl, brine, dried (MgSO$_4$) and evaporated. The residue was purified by Biotage flash column chromatography (MeOH/EtOAc/DCM) to give product 17 as a white solid (0.93 g, 50%).

Referring to FIG. 40, to a solution of compound (0.0.49 g, 0.49 mmol) in methanol (10 mL) was added Pd/C (0.15 g). The mixture was stirred at ambient temperature under H$_2$ atmosphere (15 psi) for 5 hours. The catalyst was filtered off and the filtrate was concentrated under reduced pressure to dryness. The residue was purified on silica gel column (DCM/MeOH=100:1 to 50:1) to give compound 18 (0.25 g, yield 56%).

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl 27-oxo-2,5,8,11,14,17,20,23-octaoxa-26-azadotriacontane-32-sulfonate

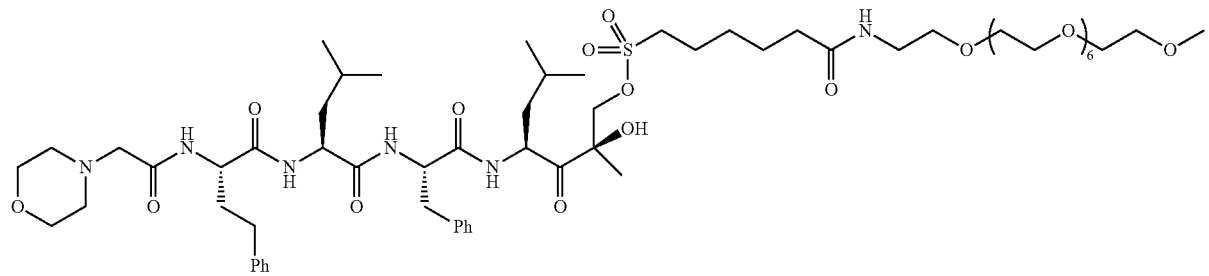

6-({[(2R,4S)-2-Hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3-oxoheptyl]oxy}sulfonyl)hexanoic acid and 2,5,8,11,14,17,20,23-octaoxapentacosan-25-amine (Quanta Biodesign) were reacted following General PEGylation Conditions, Method D.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl-6-((N-PEG$_{20K}$/4-Arm)amino)-6-oxohexane-1-sulfonate

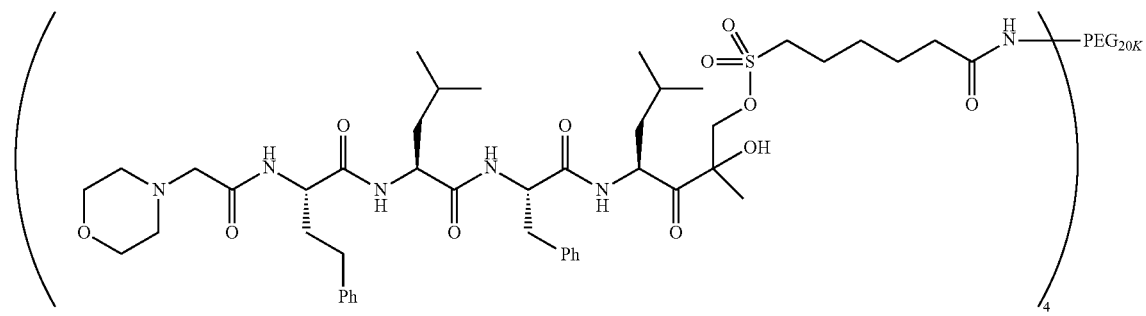

6-({[(2R,4S)-2-Hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3-oxoheptyl]oxy}sulfonyl)hexanoic acid and PEG$_{20k}$-(NH$_2$)$_4$ (Creative PEGworks Catalog # PSB-435) were reacted following General PEGylation Conditions, Method E.

(4S,7S,10S,13S)-10-benzyl-15-hydroxy-7,13-di-isobutyl-1S-methyl-1-morpholino-2,5,8,11,14-pentaoxo-4-phenethyl-3,6,9,12-tetraazahexadecan-16-yl-2-methyl-4-(2-((N-PEG$_{20K}$/4 Arm)amino)-2-oxoethoxy)butane-2-sulfonate

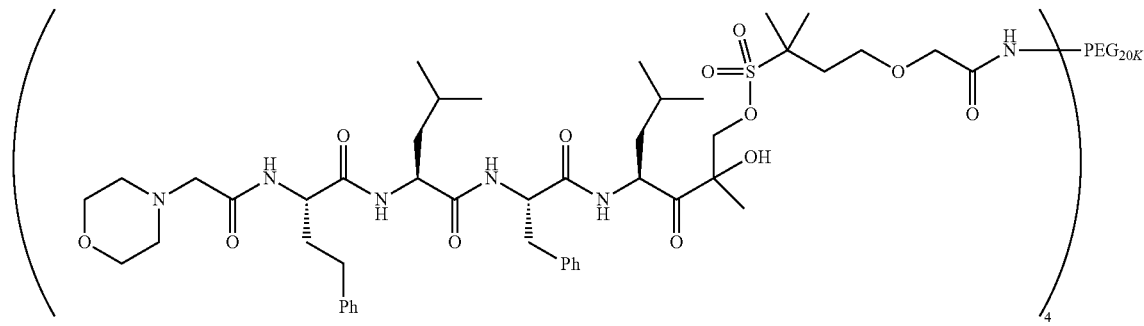

2-[3-({[(4S)-2-Hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3oxo-heptyl]oxy}sulfonyl)-3-methylbutoxy]acetic acid and PEG$_{20K}$-(NH$_2$)$_4$ (Creative PEGworks Catalog # PSB-435) were reacted following General PEGylation Conditions, Method E.

2-[3-(([(4S)-2-Hydroxy-2,6-dimethyl-4-[(2S)-2-[(2S)-4-methyl-2-[(2S)-2-[2-(morpholin-4 yl)acet-amido]-4 phenylbutanamido]pentanamido]-3 phenylpropanamido]-3oxoheptyl]oxy)sulfonyl)-3-methylbutoxy]acetic acid

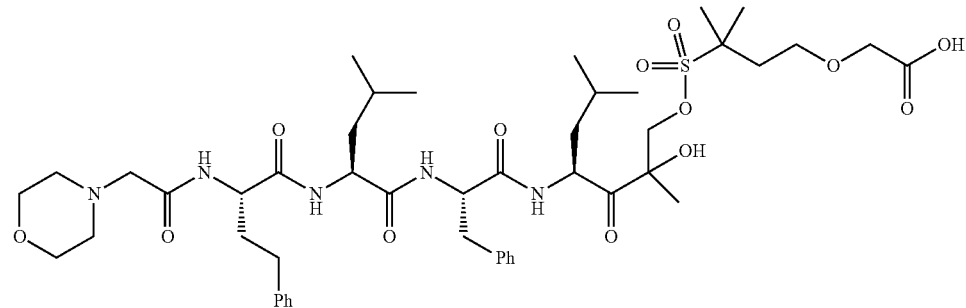 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)C(C)(O)COS(=O)(=O)C(C)(C)CCOCC(=O)O]

(4S,7S,10S,13S)-10-benzyl-15-hydroxy-7,13-di-isobutyl-15-methyl-1-morpholino-2,5,8,11,14-pentaoxo-4 phenethyl-3,6,9,12-tetraazahexadecan-16 yl-6-((N-PEG$_{20K}$)amino)-6-oxohexane-1-sulfonate

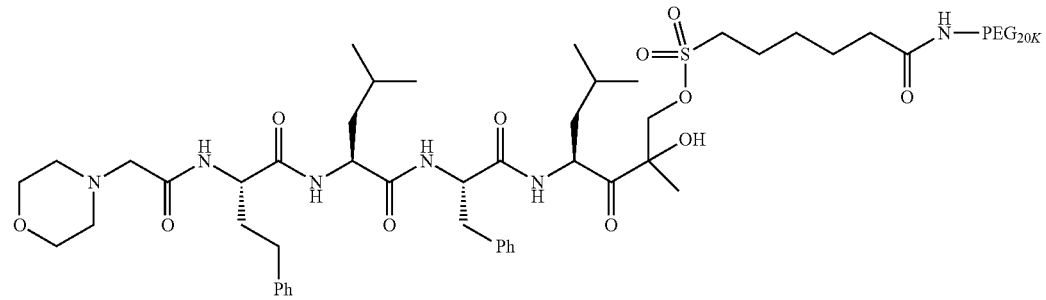

6-({[(2R,4S)-2-Hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3-oxoheptyl]oxy}sulfonyl)hexanoic acid and PEG$_{20K}$-NH$_2$ (Creative PEGworks Catalog # PJK-265) were reacted following General PEGylation Conditions, Method D.

(4S,7S,10S,13S)-10-benzyl-15-hydroxy-7,13-diisobutyl-15-methyl-1-morpholino-2,5,8,11,14-pentaoxo-4-phenethyl-3,6,9,12-tetraazahexadecan-)-16-yl-2-methyl-4-(2-((N-PEG20K)amino)-2-oxoethoxy)butane-2-sulfonate

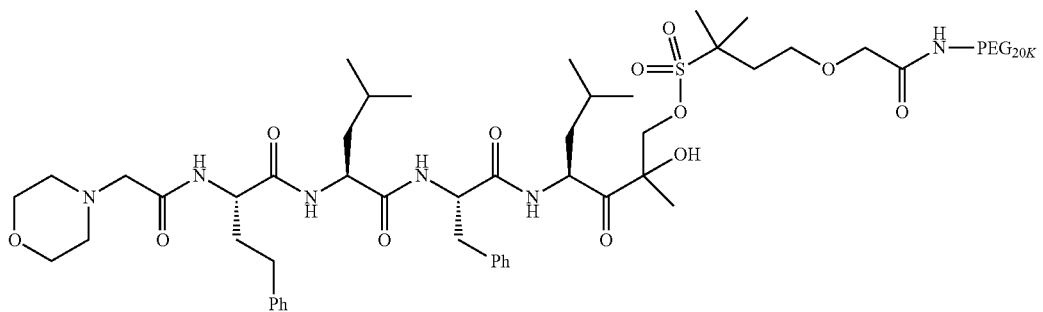

2-[3-({[(4S)-2-Hydroxy-2,6-dimethyl-4-[(2S)-2-[(2S)-4-methyl-2-[(2S)-2-[2-(morpholin-4-yl)acetamido]-4-phenylbutanamido]pentanamido]-3-phenylpropanamido]-3oxoheptyl]oxy}sulfonyl)-3-methylbutoxy]acetic acid and PEG$_{20K}$-NH$_2$ (Creative PEGworks Catalog # PJK-265) were reacted following General PEGylation Conditions, Method D.

Phenoxy Sulfonates (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-((1-PEG$_{2K}$-1H-1,2,3-triazol-1-yl)methoxy)benzenesulfonate

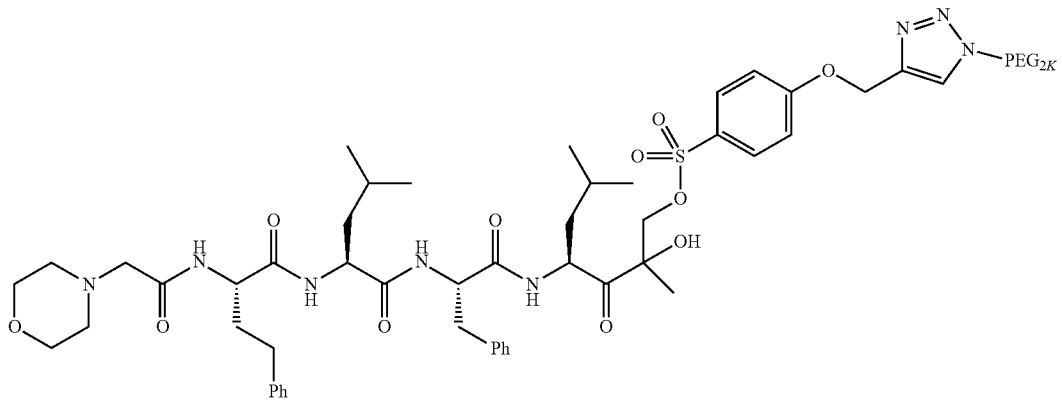

Final compounds were prepared using the standard PEGylation conditions.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{2K}$-N$_3$ (Creative PEGworks Catalog # PSB-2025) were reacted following General PEGylation Conditions, Method A.

Preparation of (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate (5)

The general synthesis of these compounds are shown referring to FIG. 17. The following analogs were prepared similarly, (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-((1-PEG$_{5K}$-1H-1,2,3-triazol-4-yl)methoxy)benzenesulfonate

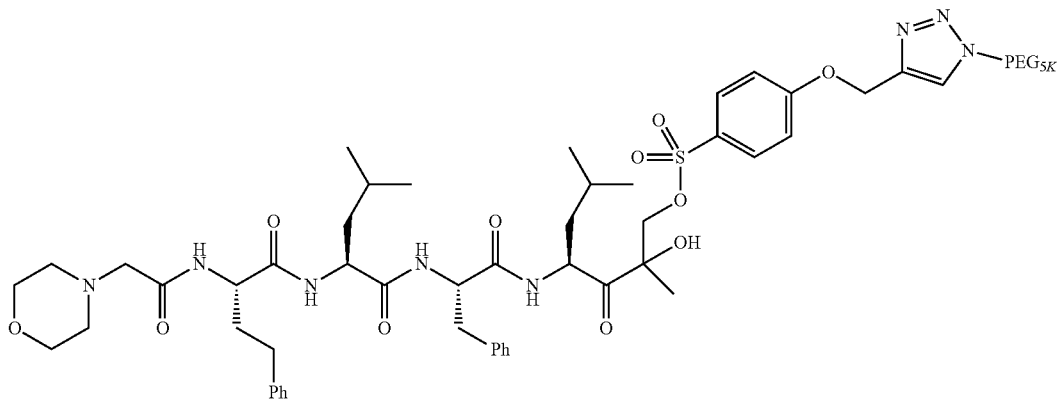

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{5K}$-N$_3$ (Creative PEGworks Catalog # PSB-2024) were reacted following General PEGylation Conditions, Method A.

(4S,7S,13S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-4-((1-PEG$_{2K}$-1H-1,2,3-triazol-4-yl)methoxy)benzenesulfonate

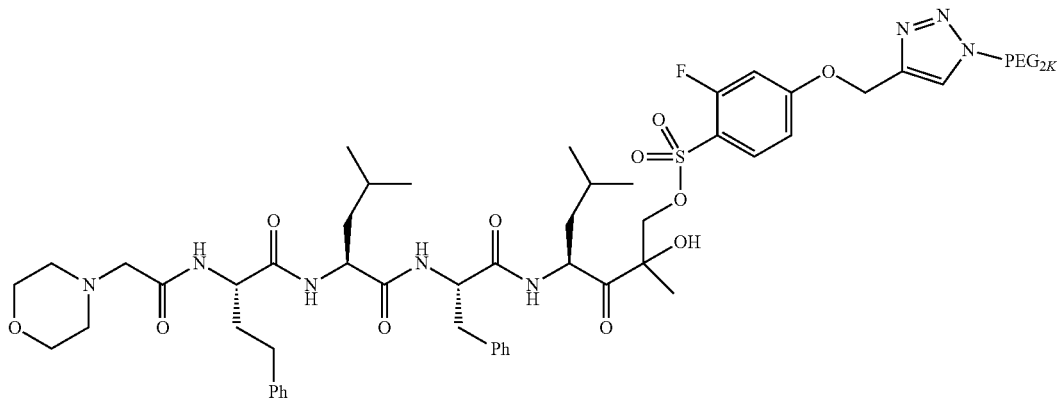

(4S,7S,10S,13S)-10-Benzyl-15-hydroxy-7,13-diisobutyl-15-methyl-1-morpholino-2,5,8,11,14-pentaoxo-1-phenethyl-3,6,9,12-tetraazahexadecan-16-yl 2-fluoro-4-(prop-2-yn-1-yloxy)benzenesulfonate and $PEG_{2K}$-$N_3$ (Creative PEGworks Catalog # PSB-2025) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-4-((1-$PEG_{5K}$-1H-1,2,3-triazol-4-yl)methoxy)benzenesulfonate

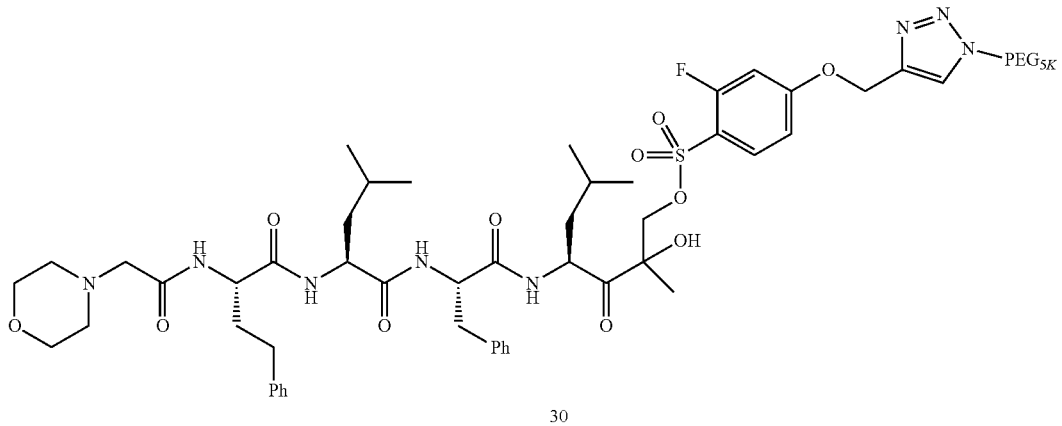

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2-fluoro-4-(prop-2-yn-1-yloxy)benzenesulfonate and $PEG_{5K}$-$N_3$ (Creative PEGworks Catalog # PSB-2024) were reacted following General PEGylation Conditions, Method A.

(4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2,3-difluoro-4-((1-$PEG_{2K}$-1H-1,2,3-triazol-4-yl)methoxy)benzenesulfonate

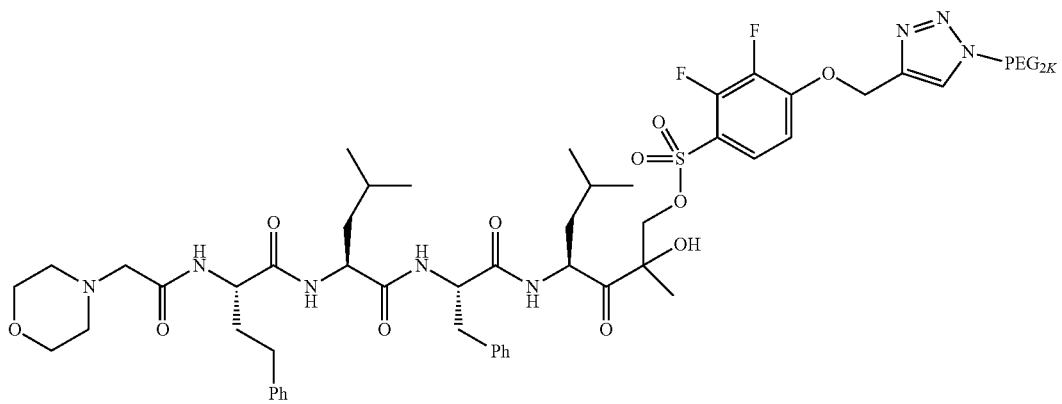

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,3-difluoro-4-(prop-2-yn-1-yloxy)benzenesulfonate and $PEG_{2K}$-$N_3$ (Creative PEGworks Catalog # PSB-2025) were reacted following General PEGylation Conditions, Method A.

(4S,7S,10S,13S,15R)-10-benzyl-15-hydroxy-7,13-
diisobutyl-15-methyl-1-morpholino-2,5,8,11,14-
pentaoxo-4-phenethyl-3,6,9,12-tetraazahexadecan-
16-yl 2,3-difluoro-4-((1-PEG$_{5K}$-1H-1,2,3-triazol-4-
yl)methoxy)benzenesulfonate

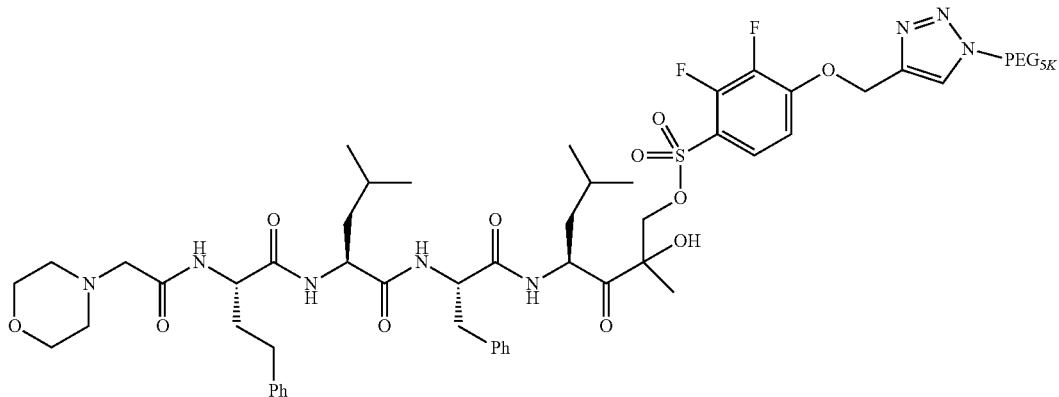

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,3-difluoro-4-(prop-2-yn-1-yloxy)benzenesulfonate and PEG$_{5k}$-N$_3$ (Creative PEGworks Catalog # PSB-2024) were reacted following General PEGylation Conditions, Method A.

(4S,7S,10S,13S)-10-benzyl-15-hydroxy-7,13-di-
isobutyl-15-methyl-1-morpholino-2,5,8,11,14-pen-
taoxo-4-phenethyl-3,6,9,12-tetraazahexadecan-16-yl
2,6-dimethoxy-4-((1-PEG$_{20K}$/4-Arm-1H-1,2,3-tri-
azol-4-yl)methoxy)benzenesulfonate

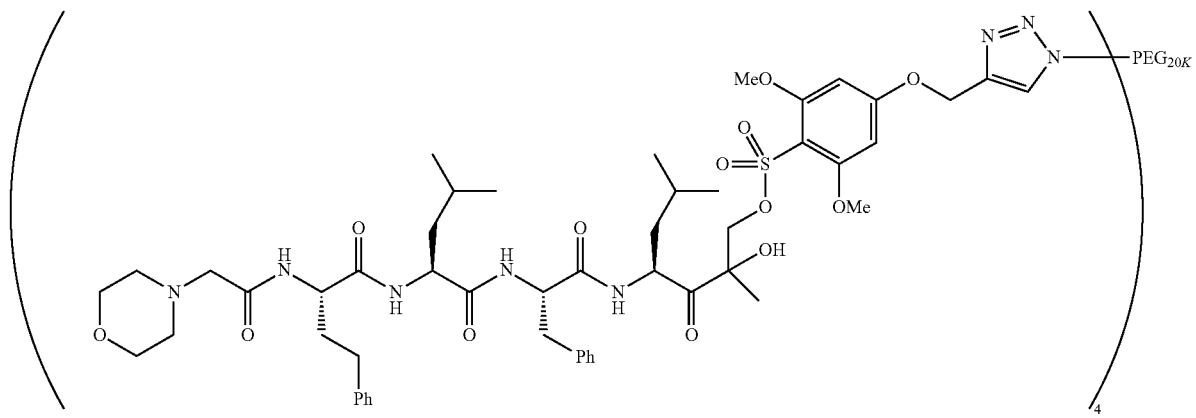

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethoxy-4-(prop-2-yn-1-yloxy)benzenesulfonate and PEG$_{20k}$-(N$_3$)$_4$ (Creative PEGworks Catalog # PSB-493) were reacted following General PEGylation Conditions, Method C; $^1$H NMR (DMSO-d6): δ 8.23 (s, 1H), 8.05-8.00 (m, 3H), 7.86 (d, J=8.5 Hz, 1H), 7.28-7.25 (m, 2H), 7.18-7.02 (m, 8H), 5.95 (s, 1H), 5.28 (s, 2H), 5.08-5.07 (m, 1H), 4.56-4.52 (m, 3H), 4.36-4.26 (m, 2H), 3.99 (d, J=10 Hz, 1H), 3.84-3.82 (m, 7H), 3.76 (d, J=9.5 Hz, 1H), 3.66-3.29 (m, 610H), 2.99-2.91 (m, 3H), 2.75-2.72 (m, 1H), 2.47-2.42 (m, 6H), 1.91-1.74 (m, 2H), 1.68-1.48 (m, 3H), 1.39-1.22 (m, 3H), 1.19 (s, 3H), 0.86-0.79 (m, 12H); PEG Loading (NMR): ¾ Arms, 8.9% small molecule.

(4S,10S,13S,15R)-10-benzyl-15-hydroxy-7,13-di-isobutyl-15-methyl-1-morpholino-2,5,8,11,14-pentaoxo-4-phenethyl-3,6,9,12-tetraazahexadecan-16-yl 2-methyl-5-(((1-PEG$_{20K}$/4-Arm-1H-1,2,3-triazol-4-yl)methyl)carbamoyl)benzenesulfonate

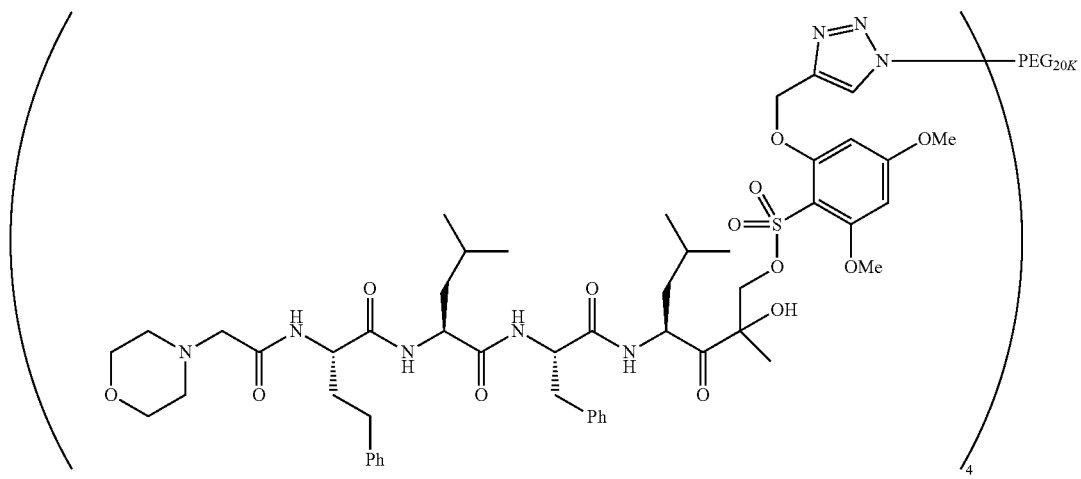

(4S,7S,10S,13S)-10-Benzyl-5-hydroxy-7,13-diisobutyl-15-methyl-1-morpholino-2,5,8,11,14-pentaoxo-4-phenethyl-3,6,9,12-tetraazahexadecan-16-yl 2,4-dimethoxy-6-(prop-2-yn-1-yloxy)benzenesulfonate and PEG$_{20k}$-(N$_3$)$_4$ (Creative PEGworks Catalog # PSB-493) were reacted following General PEGylation Conditions, Method C; $^1$H NMR (DMSO-d6): δ 8.14 (s, 1H), 8.04-7.98 (m, 3H), 7.86 (d, J=8.5 Hz, 1H), 7.28-7.25 (m, 2H), 7.19-7.01 (m, 8H), 6.59 (d, J=2.5 Hz, 1H), 6.51 (s, 1H), 6.35 (d, J=2.5 Hz, 1H), 5.95 (s, 1H), 5.27 (s, 2H), 5.08-5.07 (m, 1H), 4.55-4.49 (m, 3H), 4.37-4.26 (m, 2H), 3.98 (d, J=9.5 Hz, 1H), 3.86 (s, 3H), 3.81-3.78 (m, 5H), 3.75 (d, J=10 Hz, 1H), 3.66-3.30 (m, 508H), 2.99-2.91 (m, 3H), 2.76-2.71 (m, 1H), 2.47-2.42 (m, 6H), 1.91-1.74 (m, 2H), 1.67-1.47 (m, 3H), 1.38-1.22 (m, 3H), 1.16 (s, 3H), 0.85-0.79 (m, 12H); PEG Loading (NMR): 3.7/4 Arms, 11% small molecule.

(4S,7S,10S,13S)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-((1-PEG$_{20K}$/4-Arm-1H-1,2,3-triazol-4-yl)methoxy)benzenesulfonate

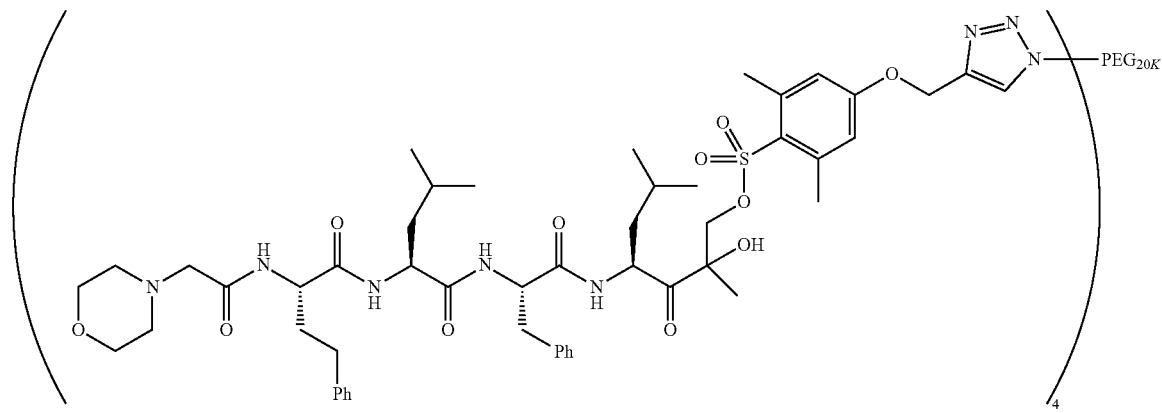

(4S,7S,10S,13S)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-((1-PEG$_{40K}$/4-Arm-1H-1,2,3-triazol-4-yl)methoxy)benzenesulfonate

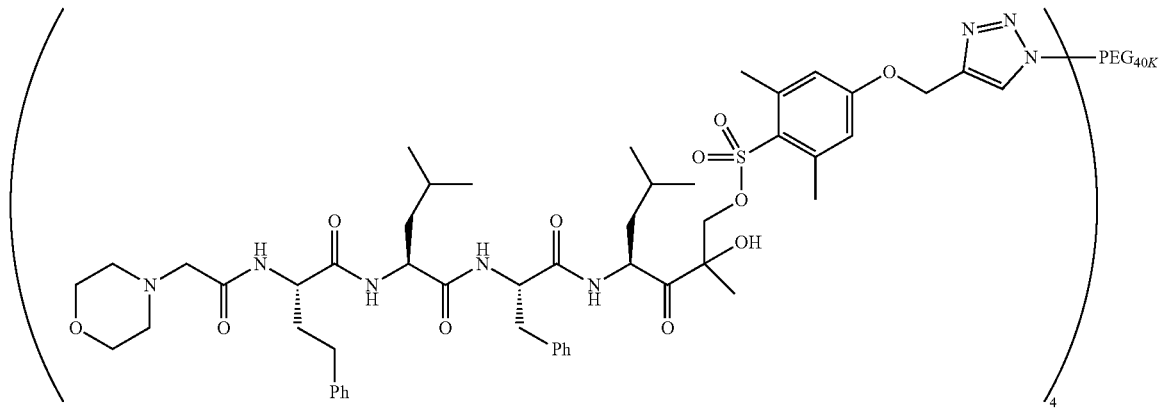

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-(prop-2-yn-1-yloxy)benzenesulfonate and PEG$_{40k}$-(N$_3$)$_4$ (JenKem Technologies) were reacted following General PEGylation Conditions, Method C; PEG Loading (NMR): 4/4 Arms, 6.1% small molecule.

(4S,7S,10S,13S)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-((1-PEG$_{20K}$/4-Arm-1H-1,2,3-triazol-4-yl)methoxy)benzenesulfonate

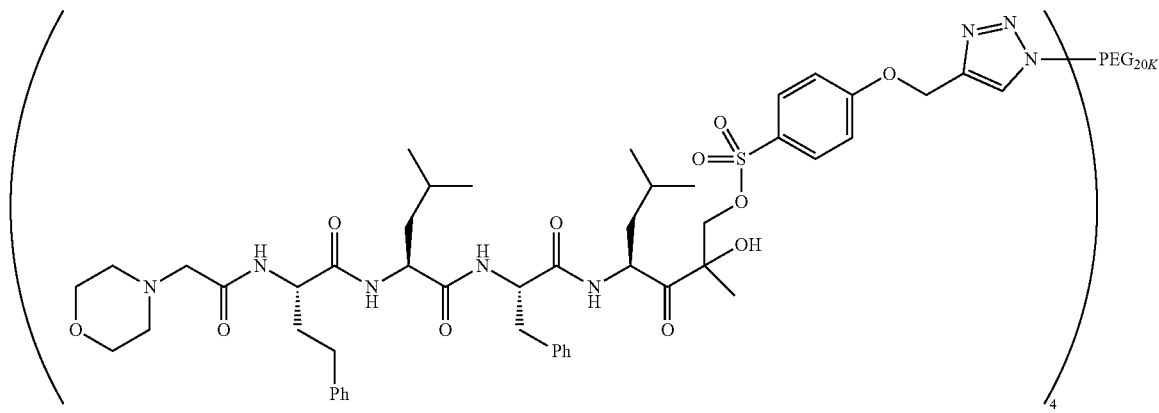

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{20k}$-(N$_3$)$_4$ (Creative PEGworks Catalog # PSB-493) were reacted following General PEGylation Conditions, Method C; $^1$H NMR [(CD$_3$)$_2$SO]: δ 8.23 (s, 1H), 8.06-8.01 (m, 3H), 7.86 (d, J=8.5 Hz, 1H), 7.82-7.80 (m, 2H), 7.29-7.25 (m, 4H), 7.18-7.04 (m, 7H), 6.01 (s, 1H), 5.26 (s, 2H), 5.05-4.98 (m, 1H), 4.55-4.53 (m, 3H), 4.35-4.28 (m, 2H), 4.00 (d, J=9.5 Hz, 1H), 3.83-3.78 (m, 3H), 3.66-3.34 (m, 428H), 3.01-2.91 (m, 3H), 2.79-2.74 (m, 1H), 2.49-2.42 (m, 6H), 1.92-1.75 (m, 2H), 1.66-1.48 (m, 3H), 1.38-1.22 (m, 3H), 1.14 (s, 3H), 0.85-0.79 (m, 12H); PEG Loading (NMR): 3.8/4 Arms, 11.4% small molecule.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl 2,6-dimethyl-4-((1-PEG$_{20K}$ Hexaglycerin/8-Arm-1H-1,2,3-triazol-4-yl)methoxy)benzenesulfonate

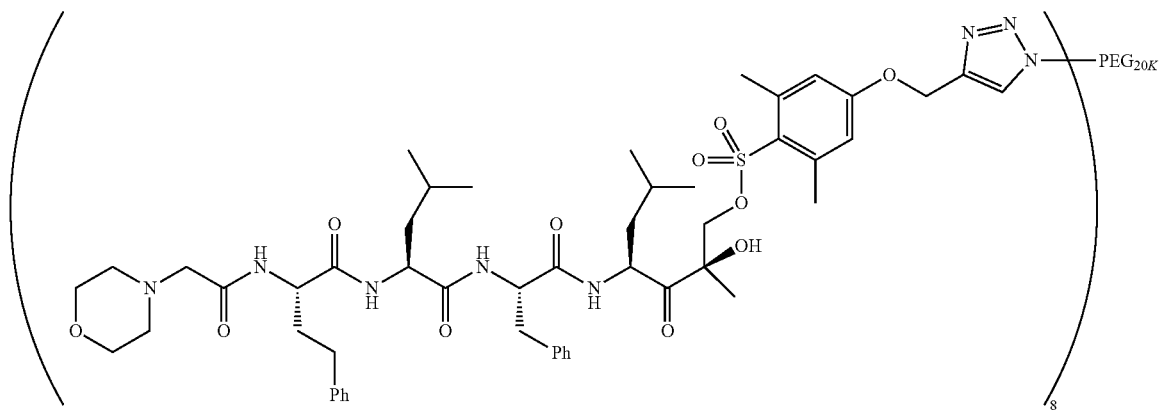

(4S,7S,10S,13S)-10-Benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-(prop-2-yn-1-yloxy)benzenesulfonate and PEG$_{20K}$-(N$_3$)$_8$ (Creative PEGworks Catalog # PSB-882) were reacted following General PEGylation Conditions. Method C; PEG Loading (NMR): 4.4/8 Arms, 11.3% small molecule.

(4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl 4-((1-PEG$_{40K}$/4-Arm-1H-1,2,3-triazol-4-yl)methoxy)benzenesulfonate

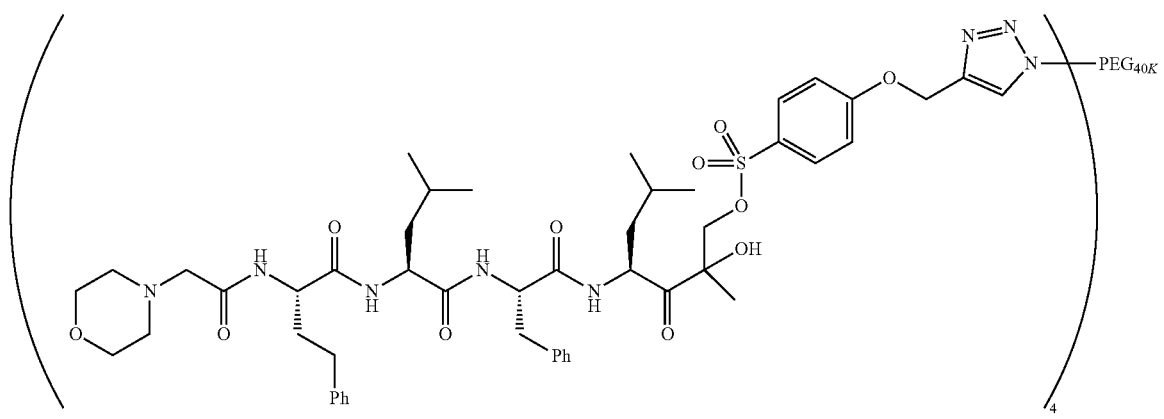

(4S,7S,10S,13S,15R)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{40K}$-(N$_3$)$_4$ (JenKem Technologies) were reacted following General PEGylation Conditions, Method C; PEG Loading (NMR): 4/4 Arms, 6.2% small molecule.

Phosphates (4S,7S,10S,13S)-10-benzyl-15-hydroxy-7,13-di-isobutyl-15-methyl-1-morpholino-2,5,8,11,14-pentaoxo-4-phenethyl-3,6,9,12-tetraazahexadecan-16-yl methyl (1-PEG$_{20K}$/4-Arm-1H-1,2,3-triazol-4-yl) methyl Phosphate

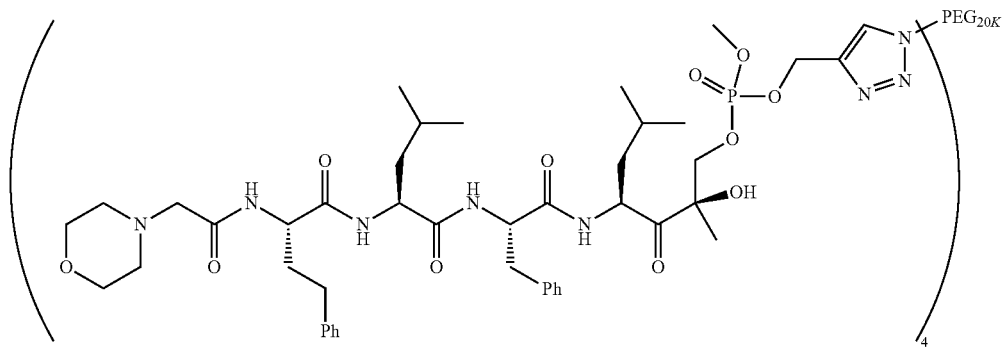

(4S,7S,10S,13S,15R)-10-Benzyl-15-hydroxy-7,13-di-isobutyl-15-methyl-1-morpholino-2,5,8,11,14-pentaoxo-4-phenethyl-3,6,9,12-tetraazahexadecan-16-yl methyl prop-2-yn-1-yl phosphate and PEG$_{20k}$-(N$_3$)$_4$ (Creative PEGworks Catalog # PSB-493) were reacted following General PEGylation Conditions, Method C.

(4S,7S,10S,13S,15R)-10-Benzyl-15-hydroxy-7,13-diisobutyl-15-methyl-1-morpholino-2,5,8,11,14-pentaoxo-4-phenethyl-3,6,9,12-tetraazahexadecan-16-yl methyl prop-2-yn-1-yl Phosphate

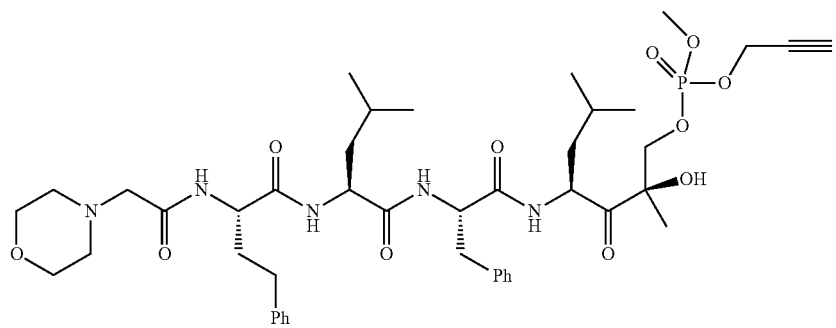 [SMILES: C#CCOP(=O)(OC)OC[C@@](C)(O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

To a solution of propargyl alcohol (0.5 g, 8.92 mmol) in pyridine (1 ml) and DCM (5 mL) at 0° C. was added methyl dichlorophosphate (0.89 mL, 8.92 mmol) dropwise maintaining the reaction temperature at 0° C. The mixture was stirred for 10 min and a solution of CFZ-diol (3.29 g, 4.48 mmol) in pyridine (15.0 mL) was added dropwise. The reaction mixture was allowed to warm to room temperature and stirred for 6 h. The reaction was quenched with methanol (3 mL) and then diluted with ethyl acetate. The resulting mixture was washed with 1N HCl solution and the aqueous layer was extracted with ethyl acetate. The combined organic layers were dried over anhydrous sodium sulfate and concentrated under reduced pressure. The resulting oil was purified by flash column chromatography on silica gel (DCM:ethyl acetate:MeOH=74:25:1 to 65:25:10) to afford desired compound (major spot, 1.2 g, 31% yield) as a white solid.

ESI-MS for $C_{44}H_{64}N_5O_{11}P$, found 870.1 [M+H]$^+$.

Acylhydrazones (S)-4-methyl-N—((S)-1-((S,Z)-4-methyl-1-(2-(3-(1-PEG$_{20K}$/4-Arm-1H-1,2,3-triazol-4-yl)propanoyl)hydrazono)-1-((S)-2-methyloxiran-2-yl)pentan-2-ylamino)-1-oxo-3-phenylpropan-2-yl)-2-((S)-2-(2-morpholinoacetamido)-4-phenylbutanamido)pentanamide

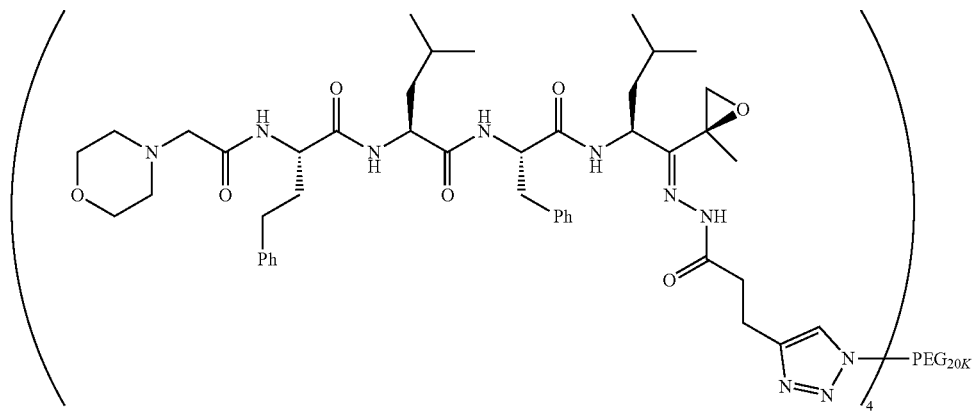

Quaternary Salt

Preparation of 4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-(1-PEG$_{1K}$-1H-1,2,3-triazol-4-yl)benzoyl)oxy)methyl)morpholin-4-ium Methanesulfonate

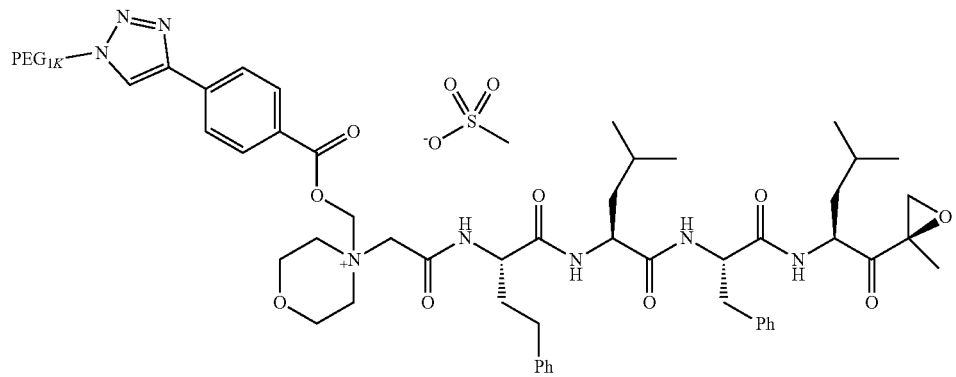

Final compounds were prepared using the standard PEGylation conditions. 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-ethynylbenzoyl)oxy)methyl)morpholin-4-ium methanesulfonate and PEG$_{1k}$-N$_3$ (Creative PEGworks Catalog # PSB-2026) were reacted following General PEGylation Conditions, Method A.

Figure 41:
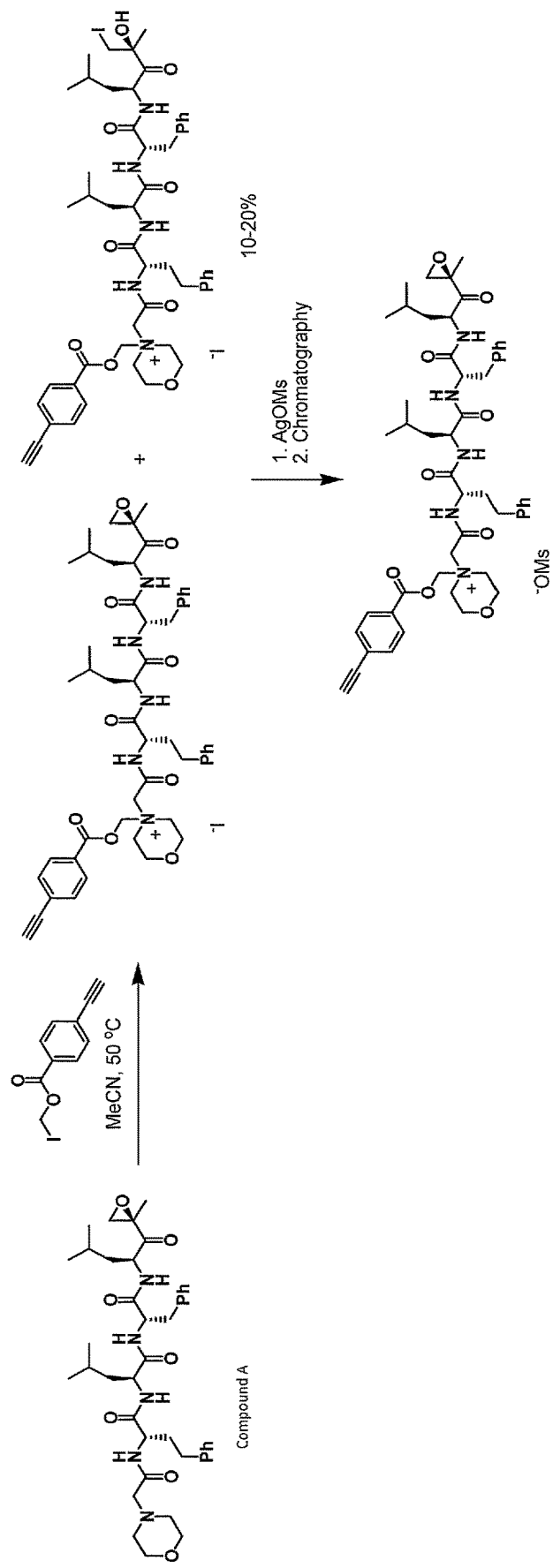
FIG. 41 is a scheme showing the synthesis of an embodiment of a quaternary ammonium precursor to prodrugs of epoxy ketone proteasome inhibitors.

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-ethynylbenzoyl)oxy)methyl)morpholin-4-ium Methanesulfonate Referring to FIG. 41, compound A (3.00 g, 0.00417 mol) and iodomethylester (2.38 g, 0.00833 mol) in acetonitrile (30 mL) were heated at 50° C. overnight. Silver methansulfonate (1.69 g, 0.00833 mol) was then added and the mixture was stirred and heated at 50° C. for 2 hours. The mixture was filtered through celite and evaporated. The residue was purified by Biotage flash column chromatography (5% MeOH, 25% EtOAc, DCM) to give product as a foam (3.25 g, 80%).

The following analogs were prepared similarly, 4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-(1-PEG$_{2K}$-1H-1,2,3-triazol-4-yl)benzoyl)oxy)methyl)morpholin-4-ium Methanesulfonate

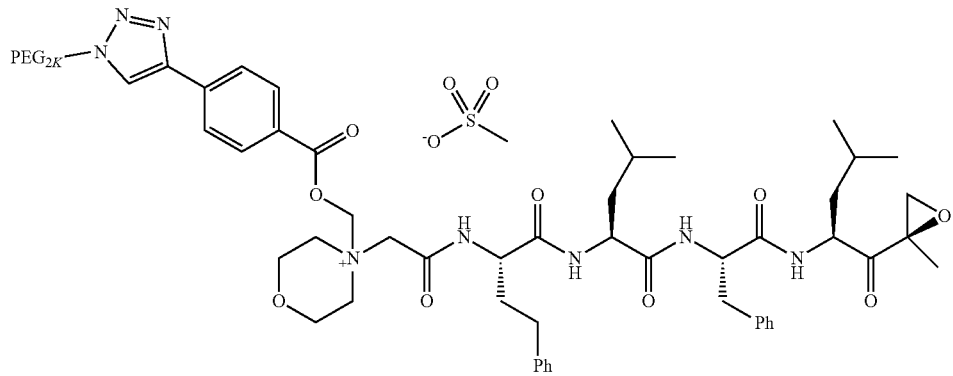

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-ethynylbenzoyl)oxy)methyl)morpholin-4-ium methanesulfonate and PEG$_{2K}$-N$_3$ (Creative PEGworks Catalog # PSB-2025) were reacted following General PEGylation Conditions, Method A.

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-(1-PEG$_{20K}$/4-Arm-1H-1,2,3-triazol-4-yl)benzoyl)oxy)methyl)morpholin-4-ium Methanesulfonate

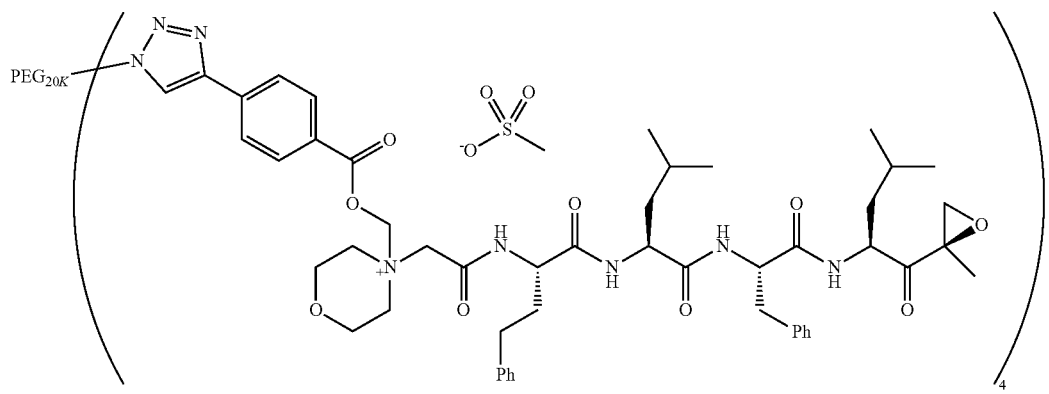

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(((4-ethynylbenzoyl)oxy)methyl)morpholin-4-ium methanesulfonate and PEG$_{20K}$-(N$_3$)$_4$ (Creative PEGworks Catalog # PSB-493) were reacted following General PEGylation Conditions, Method C; PEG Loading (NMR): 3.1/4 Arms, 9.2% small molecule.

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3,5-dimethyl-4-(3-(1-PEG$_{20K}$/4-Arm-1H-1,2,3-triazol-4-yl)propanoyloxy)benzyl)morpholin-4-ium Methanesulfonate

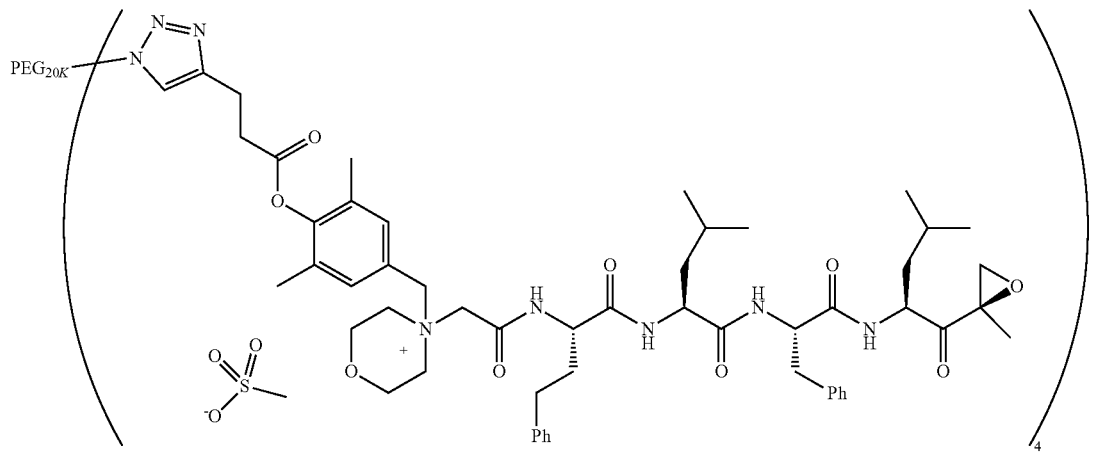

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3,5-dimethyl-4-(pent-4-ynoyloxy)benzyl)morpholin-4-ium methanesulfonate and PEG$_{20K}$-(N$_3$)$_4$ (Creative PEGworks Catalog # PSB-93) were reacted following General PEGylation Conditions, Method C.

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3,5-dimethyl-4-(pent-4-ynoyloxy)benzyl)morpholin-4-ium Methanesulfonate

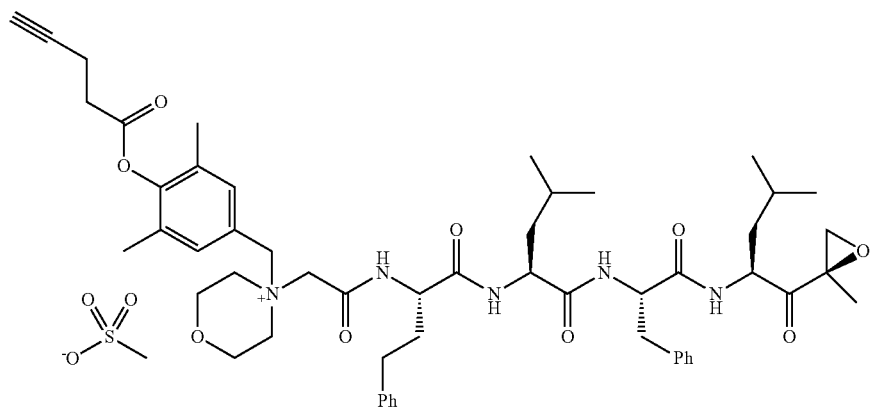

Prepared according to the procedure described for compound 28, from 4-(bromoethyl-2,6-dimethylphenyl pent-4-ynoate and (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide.

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(3-(1-PEG$_{20K}$/4-Arm-1H-1,2,3-triazol-4-yl)propanoyloxy)benzyl)morpholin-4-ium Methanesulfonate

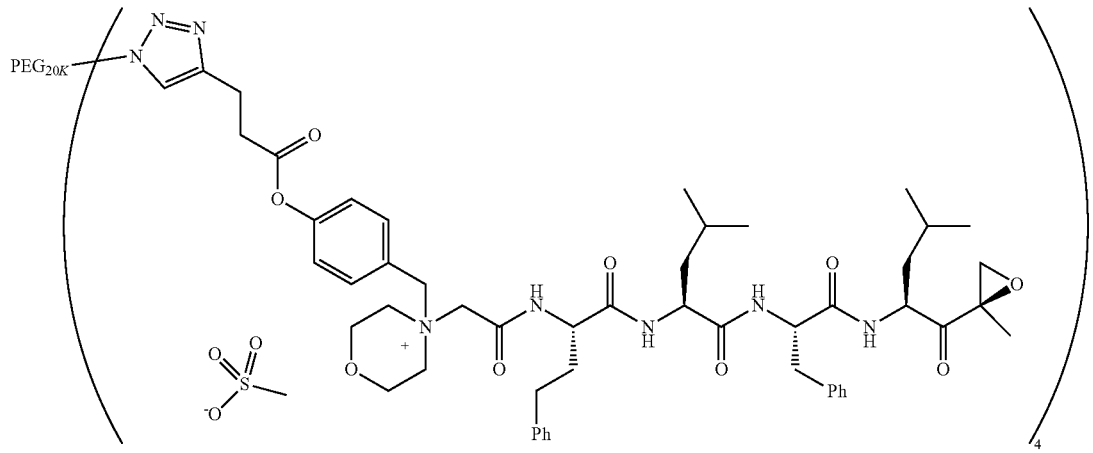

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(pent-4-ynoyloxy)benzyl)morpholin-4-ium methanesulfonate and PEG$_{20k}$-(N$_3$)$_4$ (Creative PEGworks Catalog # PSB-493) were reacted following General PEGylation Conditions, Method C.

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(pent-4-ynoyloxy)benzyl)morpholin-4-ium methanesulfonate (28)

4-(Hydroxymethyl)phenyl pent-4-ynoate (25)

Figure 42:
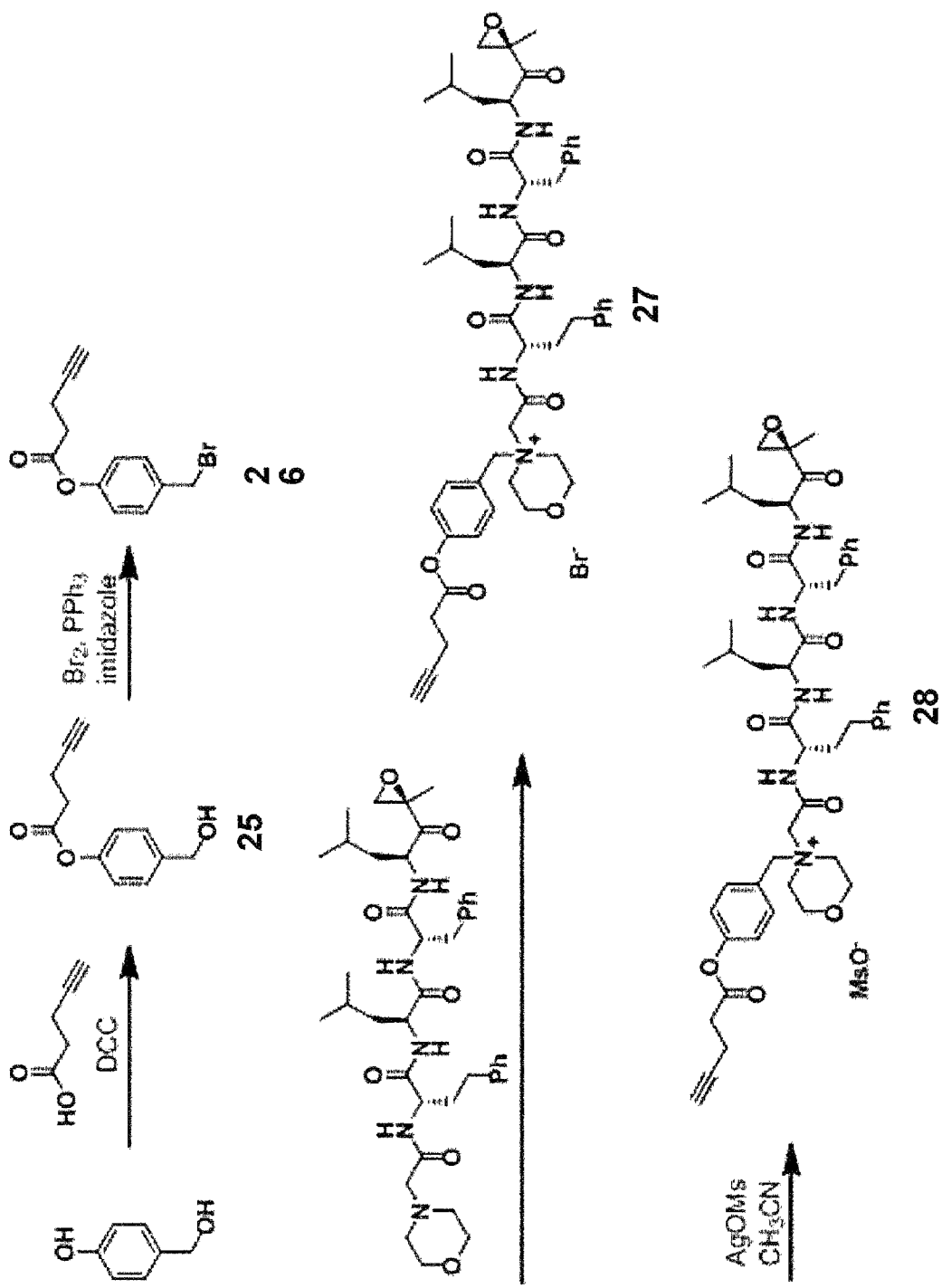
FIG. 42 is a scheme showing the synthesis of an alternative embodiment of a quaternary ammonium precursor to prodrugs of epoxy ketone proteasome inhibitors.

Referring to FIG. 42, a mixture of pent-4-ynoic acid (1.10 g, 11.2 mmol), 4-(hydroxymethyl)phenol (1.40 g, 11.2 mmol) and DCC (3.5 g, 16.8 mmol) in THF (30 mL) was stirred at room temperature overnight. Ethyl acetate was added to dilute the mixture and the white solid was filtered off. The filtrate was collected and concentrated under reduced pressure. The residue was purified by flash column chromatography on silica gel (petroleum ether/EtOAc=3:1 to 2:1) to afford compound 1 (0.91 g, 40% yield); $^1$H NMR (300 MHz, DMSO-d6): δ 7.35 (d, J=8.4 Hz, 2H), 7.06 (d, J=8.4 Hz, 2H), 5.23 (t, J=6.0 Hz, 1H), 4.49 (d, J=5.7 Hz, 2H), 2.90-2.89 (m, 1H), 2.81-2.76 (m, 2H), 2.55-2.50 (m, 2H).

4-(Bromomethyl)phenyl pent-4-ynoate (26)

Referring to FIG. 42, a mixture of PPh$_3$ (0.8 g, 3.0 mmol) and imidazole (0.3 g, 4.5 mmol) in DCM (20 mL) was stirred for 30 min at 0° C. Then a solution of Br$_2$ (0.7 g, 4.5 mmol) in DCM (5 mL) was added. The mixture was kept at 0° C. for 10 min and compound 1 (0.3 g, 1.5 mmol) was added. The reaction mixture was stirred at 0° C. for 10 min (monitored by TLC and UPLC analysis). The mixture was washed with diluted HCl solution (20 mL×2), saturated aqueous NaHSO$_3$ (20 mL) and brine (20 mL), respectively. The organic layer was concentrated under reduced pressure and the residue was purified by flash column chromatography on silica gel (petroleum ether/EtOAc=100:1 to 30:1) to afford the title compound 2 (0.2 g, 40% yield); $^1$H NMR (300 MHz, CDCl$_3$): δ 7.41 (d, J=8.4 Hz, 2H), 7.10 (d, J=8.4 Hz, 2H), 4.51 (s, 2H), 2.86-2.81 (m, 2H), 2.68-2.65 (m, 2H), 2.07-2.06 (m, 1H).

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(pent-4-ynoyloxy)benzyl)morpholin-4-ium Bromide (27)

Referring to FIG. 42, a mixture of compound 4-(bromomethyl)phenyl pent-4-ynoate (300 mg, 1.13 mmol) and (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (270 mg, 0.38 mmol) in MeCN (20 mL) was stirred at 50° C. overnight. The mixture was concentrated under reduced pressure and the residue was purified by flash column chromatography on silica gel (DCM/MeOH=10:1) to afford the bromide salt (70 mg, 21% yield); $^1$H NMR (300 MHz, DMSO-d$_6$): δ 9.12 (br s, 1H), 8.31 (t, J=8.4 Hz, 2H), 8.02 (d, J=7.8 Hz, 1H), 7.66 (d, J=8.1 Hz, 2H), 7.30-7.06 (m, 12H), 5.03 (m, 2H), 4.65-4.07 (m, 11H), 3.70-3.42 (m, 5H), 3.12-2.52 (m, 9H), 1.92-1.12 (m, 11H), 0.89-0.82 (m, 12H).

Referring to FIG. 42, to a solution of 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(pent-4-ynoyloxy)benzyl)morpholin-4-ium bromide (130 mg, 0.132 mmol) in THF (20 mL) was added MsOAg (58 mg, 0.286 mmol). The reaction mixture was stirred for 3 h at room temperature. The white solid was filtered off and the filtrate was concentrated under reduced pressure to give the title compound (123 mg, 93% yield); $^1$H NMR (300 MHz, CDCl$_3$): δ 9.61 (br s, 1H), 7.82 (br s, 1H), 7.55 (d, J=8.7 Hz, 2H), 7.31-7.15 (m, 12H), 7.92-7.85 (br s, 1H), 6.49-6.41 (br s, 1H), 5.19-4.89 (m, 3H), 4.53-4.15 (m, 8H), 4.05-3.70 (m, 5H), 3.50-3.24 (m, 2H), 3.22-3.02 (m, 3H), 2.92-2.65 (m, 9H), 2.31-1.23 (m, 12H), 0.89-0.82 (m, 12H).

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(2-(3-(1-PEG$_{20K}$/4-Arm-1H-1,2,3-triazol-4-yl)propanoyloxy)benzyl)morpholin-4-ium Methanesulfonate

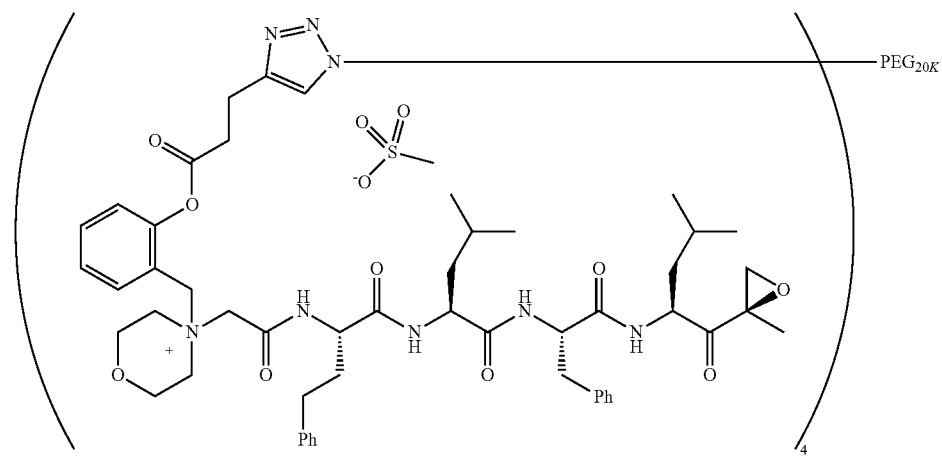

Backbone Acyloxyesters ((S)—N—((S)-4-methyl-1-((S)-1-((S)-4-methyl-1-((R)-2-methyloxiran-2-yl)-1-oxopentan-2-ylamino)-1-oxo-3-phenylpropan-2-ylamino)-1-oxopentan-2-yl)-2-(2-morpholinoacetamido)-4-phenylbutanamido)methyl 2-methyl-2-((1-PEG$_{20K}$/4-Arm-1H-1,2,3-triazol-4-yl)methoxy)propanoate

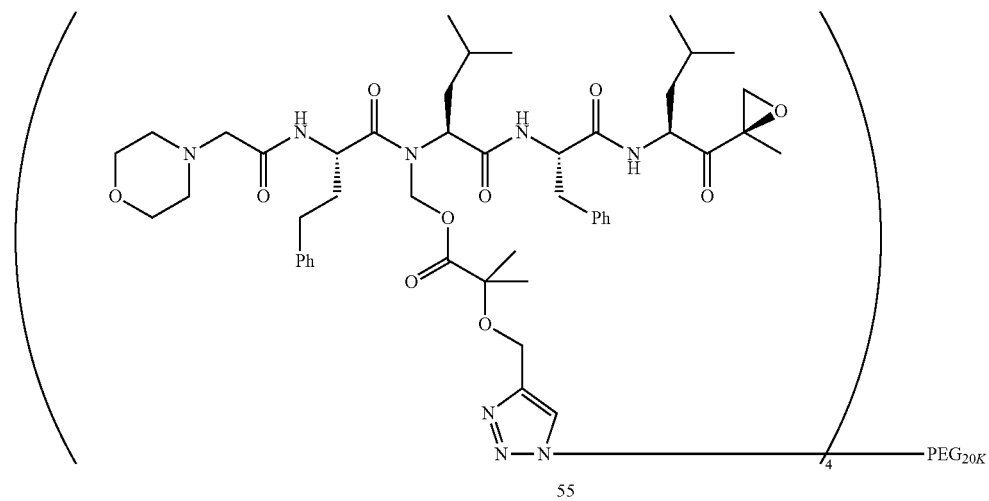

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl 2-methyl-2-(prop-2-yn-1-yloxy)propanoate and PEG$_{20K}$-(N$_3$)$_4$ (Creative PEGworks Catalog # PSB-493) were reacted following General PEGylation Conditions, Method C; $^1$H NMR (DMSO-d$_6$): δ 8.25-7.84 (m, 4H), 7.28-7.04 (m, 10H), 5.91 (d, J=12 Hz, 1H), 5.62 (d, J=12 Hz, 1H), 4.90-4.82 (m, 1H), 4.68-4.16 (m, 8H), 3.80-3.77 (m, 4H), 3.66-3.33 (m, 504H), 3.14-2.94 (m, 4H), 2.76-2.28 (m, 8H), 2.12-1.80 (m, 2H), 1.62-1.25 (m, 15H), 0.87-0.75 (m, 12H); PEG Loading (NMR): 3.6/4 Arms, 10.9% small molecule.

319

((S)—N—((S)-4-Methyl-1-(((S)-1-(((S)-4-methyl-1-((R)-2-methyloxiran-2-yl)-1-oxopentan-1-yl)amino)-1-oxo-3-phenylpropan-2-yl)amino)-1-oxopentan-2-yl)-2-(2-morpholinoacetamido)-4 phenylbutanamido)methyl 2-methyl-2-(prop-2-yn-1-yloxy)propanoate

320

(S)-4-methoxybenzyl 2-((S)-4-Methyl-2-((S)—N-(((2-methyl-2-(prop-2-yn-1-yloxy)propanoyl)oxy) methyl)-2-(2-morpholinoacetamido)-4-phenylbutanamido)pentanamido)-3-phenylpropanoate

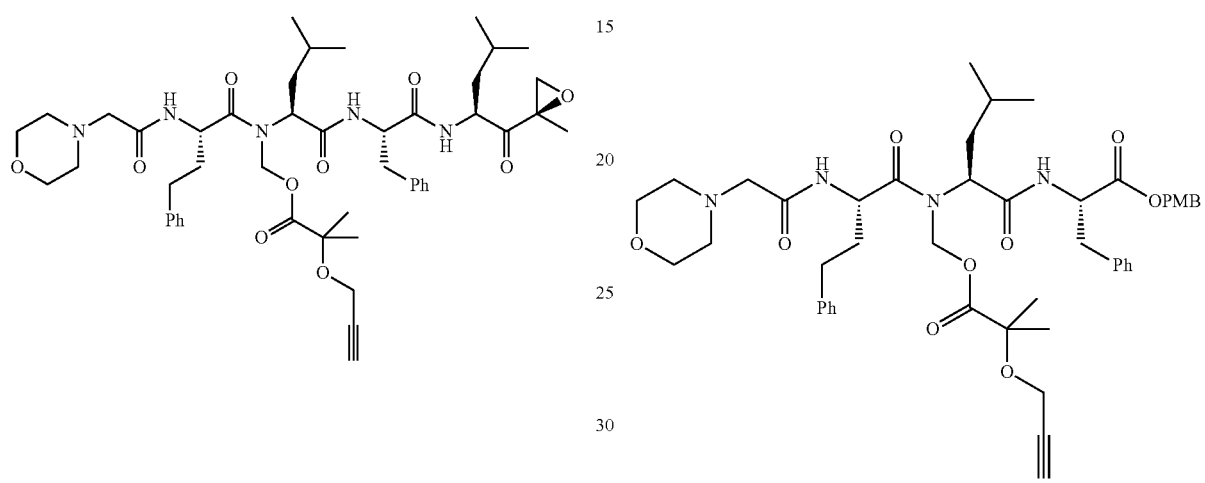

To a solution of (S)-4-methoxybenzyl 2-((S)-4-methyl-2-((S)—N-(((2-methyl-2-(prop-2-yn-1-yloxy)propanoyl)oxy) methyl)-2-(2-morpholinoacetamido)-4-phenylbutanamido) pentanamido)-3-phenylpropanoate (1.1 g, 1.3 mmol) in DCM (20 mL) was added TFA (5.0 mL). The mixture was stirred at room temperature for 2 h and then concentrated under reduced pressure to provide TFA salt (0.58 g, 52.7% yield) as a yellow solid, which was carried forward without further purification. To a solution of TFA salt (580 mg, 0.81 mmol) in DCM (25.0 mL) were added (S)-2-amino-4-methyl-1-((R)-2-methyloxiran-2-yl)pentan-1-one (459 mg, 1.61 mmol), DMTMM (444 mg, 1.61 mmol) and NMM (245 mg, 2.43 mmol) at 0° C. The reaction mixture was stirred at room temperature for 2 h. Saturated sodium bicarbonate solution was added to quench the reaction and the resulting mixture was extracted with ethyl acetate. The combined extracts were dried over anhydrous sodium sulfate and concentrated. Purification of the residue by flash column chromatography on silica gel provided compound (400 mg, 56.6% yield) as a light yellow solid; $^1$H NMR (300 MHz, CDCl$_3$): δ 7.31-7.16 (m, 10H), 6.72 (m, 1H), 6.50 (m, 1H), 6.30 (m, 1H), 5.85 (m, 1H), 5.65-5.55 (m, 1H), 4.62-4.51 (m, 3H), 4.28 (m, 1H), 4.15 (m, 2H), 3.74 (m, 4H), 2.86 (m, 2H), 2.64 (m, 2H), 2.61 (m, 1H), 2.55 (m, 4H), 2.39 (m, 2H), 2.05 (m, 2H), 1.64 (s, 6H), 1.49 (s, 6H), 1.30-1.16 (m, 4H), 0.89-0.85 (m, 12H). ESI-MS for C$_{48}$H$_{67}$N$_5$O$_{10}$, found 874.1 [M+H]$^+$.

To a solution of (S)-4-methoxybenzyl 4-methyl-2-((S)—N-(((2-methyl-2-(prop-2-yn-1-yloxy)propanoyl)oxy) methyl)-2-(2-morpholinoacetamido)-4-phenylbutanamido) pentanoate (1.9 g, 2.74 mmol) in DCM (20.0 mL) was added TFA (4.0 mL). The mixture was stirred at room temperature for 2 h and then concentrated under reduced pressure to provide TFA salt (1.85 g, quantitative) as yellow oil, which was carried forward without further purification.

To a solution of TFA salt (1.85 g, 2.74 mmol) in DCM (25 mL) were added (S)-4-methoxybenzyl 2-amino-3-phenylpropanoate (1.2 g, 4.2 mmol) and HATU (1.5 g, 3.95 mmol). The mixture was cooled to 0° C. and DIPEA (0.88 g, 6.8 mmol) was added. The reaction mixture was allowed to warm to room temperature and stirred for 3 h. The reaction was quenched with saturated sodium bicarbonate solution and the resulting mixture was extracted with ethyl acetate. The combined extracts were dried over anhydrous sodium sulfate and concentrated. Purification of the residue by flash column chromatography on silica gel provided compound (1.1 g, 47.4% yield) as a light yellow solid.

321

(S)-4-Methoxybenzyl 4-methyl-2-((S)—N-(((2-methyl-2-(prop-2-yn-1-yloxy)propanoyl)oxy)methyl)-2-(2-morpholinoacetamido)-4-phenylbutanamido)pentanoate

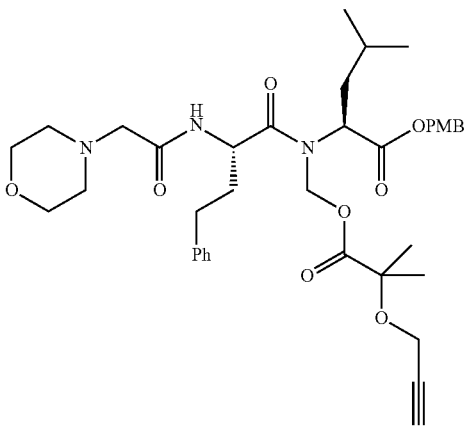

322

To a light yellow solution of (S)-4-methoxybenzyl 4-methyl-2-((S)-2-(2-morpholinoacetamido)-4-phenylbutanamido)pentanoate (2.16 g, 4.0 mmol) in THF (15 mL) at −50° C. was added KHMDS solution (1 M in THF, 5.0 mL, 5.0 mmol) dropwise maintaining the internal reaction temperature below −50° C. The mixture was stirred for 10 min and a solution of iodomethyl 2-methyl-2-(prop-2-ynyloxy)propanoate (1.58 g, 5.6 mmol) in THF (5.0 mL) was added dropwise. The reaction mixture was allowed to warm to room temperature and stirred for 3 h. The reaction was quenched with methanol (3 mL) and then diluted with ethyl acetate. The resulting mixture was washed with brine and the aqueous layer was extracted with ethyl acetate. The combined organic layers were dried over anhydrous sodium sulfate and concentrated under reduced pressure. The resulting oil was purified by flash column chromatography on silica gel (hexanes/ethyl acetate=9:1 to 7:3) to afford compound (major spot, 1.9 g, 68.5% yield) as a colorless oil.

((S)—N—((S)-4-methyl-1-((S)-1-((S)-4-methyl-1-((R)-2-methyloxiran-2-yl)-1-oxopentan-2-ylamino)-1-oxo-3-phenylpropan-2-ylamino)-1-oxopentan-2-yl)-2-(2-morpholinoacetamido)-4-phenylbutanamido)methyl 3-(1-PEG$_{20K}$/4-Arm-1H-1,2,3-triazol-4-yl)propanoate

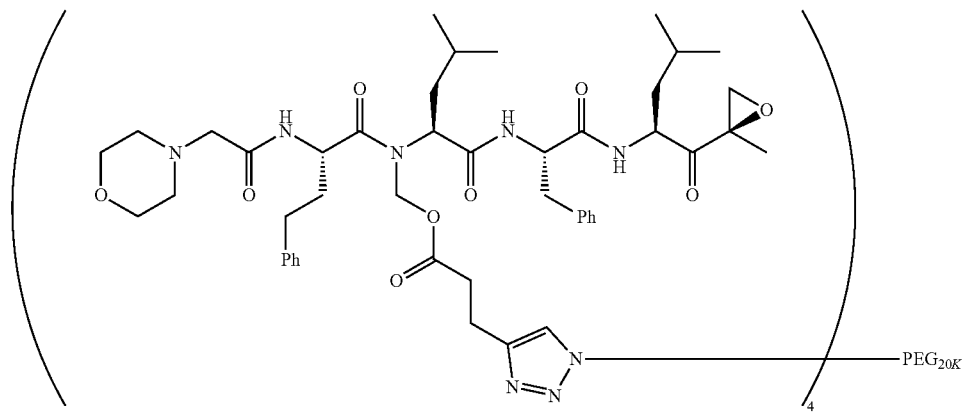

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl pent-4-ynoate and PEG$_{20K}$-(N$_3$)$_4$ (Creative PEGworks Catalog # PSB-493) were reacted following General PEGylation Conditions, Method C.

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl pent-4-ynoate

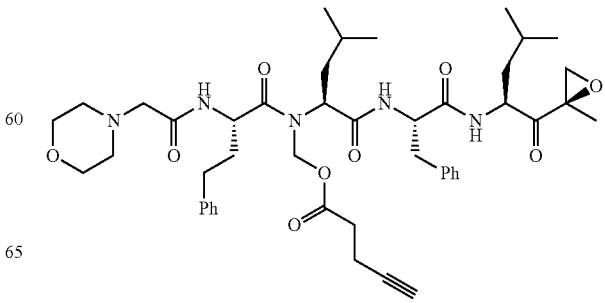

Prepared according to procedures described above from iodomethyl pent-4-ynoate.

(3S,6S,9S,12S)-9-benzyl-6-isobutyl-14-methyl-12-
((R)-2-methyloxirane-2-carbonyl)-2-(2-morpholino-
acetyl)-4,7,10-trioxo-3-phenethyl-2,5,8,11-tetraaza-
pentadecyl 3-(1-PEG$_{20K}$/4-Arm-1H-1,2,3-triazol-4-
yl)propanoate

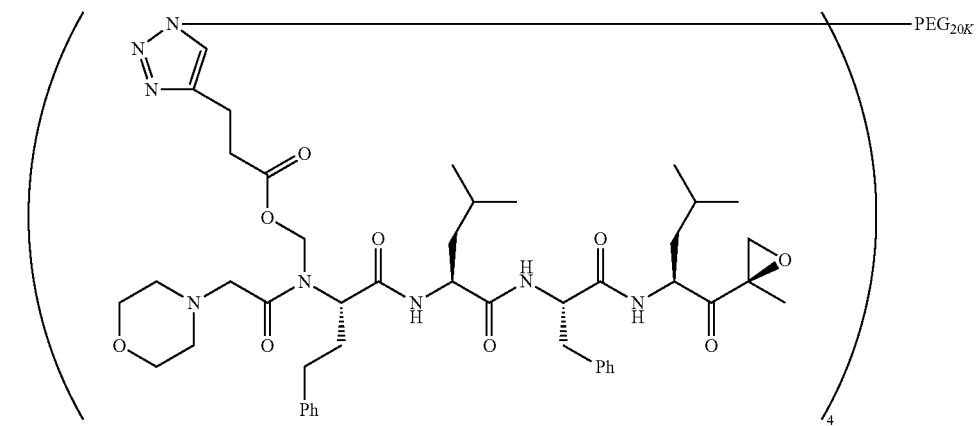

(3S,6S,9S,12S)-9-Benzyl-6-isobutyl-14-methyl-12-((R)-2-methyloxirane-2-carbonyl)-2-(2-morpholinoacetyl)-4,7,10-trioxo-3-phenethyl-2,5,8,11-tetraazapentadecyl pent-4-ynoate and PEG$_{20k}$-(N$_3$)$_4$ (Creative PEGworks Catalog # PSB-93) were reacted following General PEGylation Conditions, Method C.

(3S,6S,9S,12S)-9-Benzyl-6-isobutyl-14-methyl-12-
((R)-2-methyloxirane-2-carbonyl)-2-(2-morpholino-
acetyl)-4,7,10-trioxo-3 phenethyl-2,5,8,11-tetraaza-
pentadecyl pent-4-ynoate

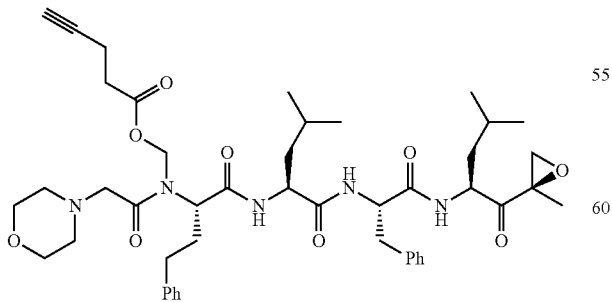

Prepared according to procedures described above from iodomethyl pent-4-ynoate.

((S)—N-((3)-4-methyl-1-((S)-1-((S)-4-methyl-1-((R)-2-methyloxiran-2-yl)-1-oxopentan-2-ylamino)-1-oxo-3-phenylpropan-2-ylamino)-1-oxopentan-2-yl)-2-(2-morpholinoacetamido)-4-phenylbutanamido)methyl 3-(1-PEG$_{20K}$/4-Arm-1H-1,2,3-triazol-4 yl)benzoate

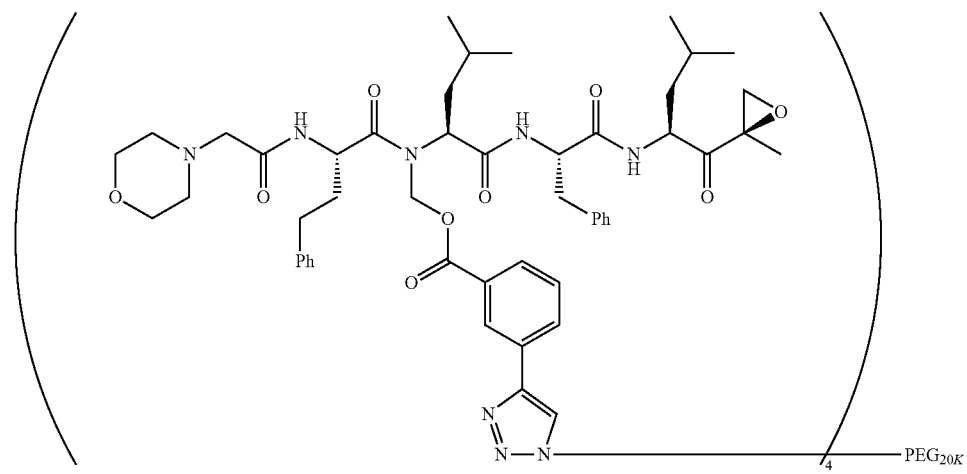

((S)—N—((S)-4-Methyl-1-(((S)-1-(((S)-1-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl 3-ethynylbenzoate and PEG$_{20k}$-(N$_3$)$_4$ (Creative PEGworks Catalog # PSB-493) were reacted following General PEGylation Conditions, Method C.

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl 3-ethynylbenzoate

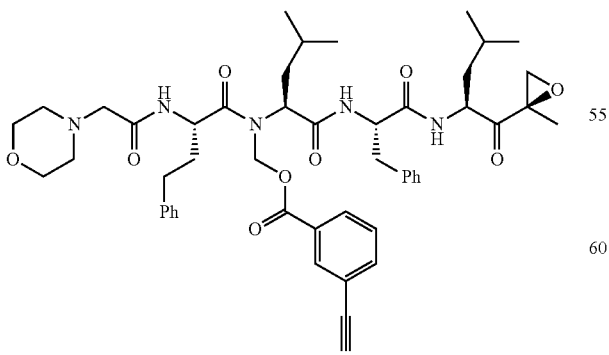

Prepared according to procedures described above, from iodomethyl 3-ethynylbenzoate.

(3S,6S,9S,12S)-9-benzyl-6-isobutyl-14-methyl-12-
((R)-2-methyloxirane-2-carbonyl)-2-(2-morpholino-
acetyl)-4,7,10-trioxo-3-phenethyl-2,5,8,11-tetraaza-
pentadecyl 3-(1-PEG$_{20K}$/4-Arm-1H-1,2,3-triazol-4-
yl)benzoate

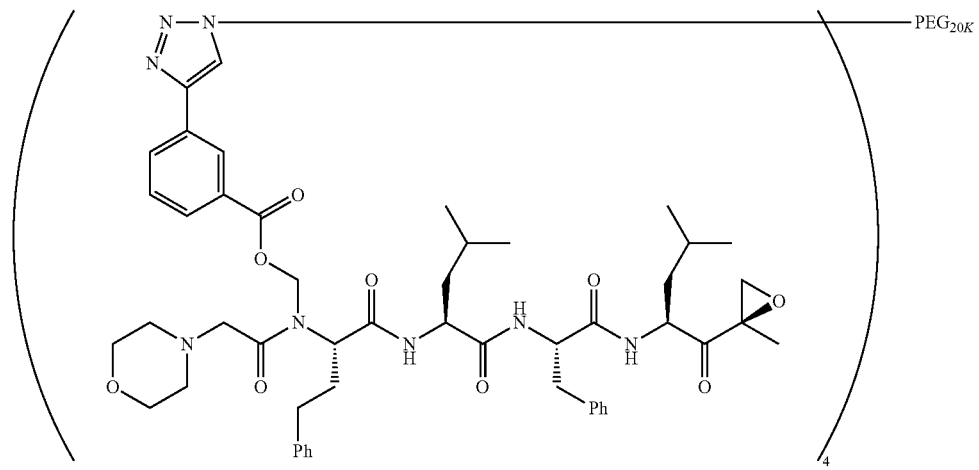

(3S,6S,9S,20S)-9-Benzyl-6-isobutyl-14-methyl-12-((R)-
2-methyloxirane-2-carbonyl)-2-(2-morpholinoacetyl)-4,7,
10-trioxo-3-phenethyl-2,5,8,11-tetraazapentadecyl 3-ethy-
nylbenzoate and PEG$_{20k}$-(N$_3$)$_4$ (Creative PEGworks Catalog
PSB-493) were reacted following General PEGylation
Conditions, Method C.

(3S,6S,9S,12S)-9-Benzyl-6-isobutyl-14-methyl-12-
((R)-2-methyloxirane-2-carbonyl)-2-(2-morpholino-
acetyl)-4,7,10-trioxo-3-phenethyl-2,5,8,11-tetraaza-
pentadecyl 3-ethynylbenzoate

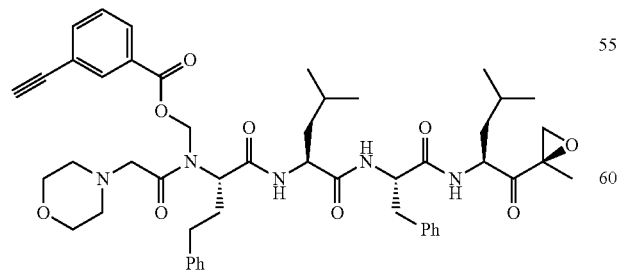

Prepared according to procedures described above, from
iodomethyl 3-ethynylbenzoate.

((S)—N—((S)-4-methyl-1-((S)-1-((S)-4-methyl-1-
((R)-2-methyloxiran-2-yl)-1-oxopentan-2-ylamino)-
1-oxo-3-phenylpropan-2-ylamino)-1-oxopentan-2-
yl)-2-(2-morpholinoacetamido)-4-
phenylbutanamido)methyl 4-(methyl((1-PEG$_{20K}$/4-
Arm-1H-1,2,3-triazol-4-yl)methyl)amino)-4-
oxobutanoate

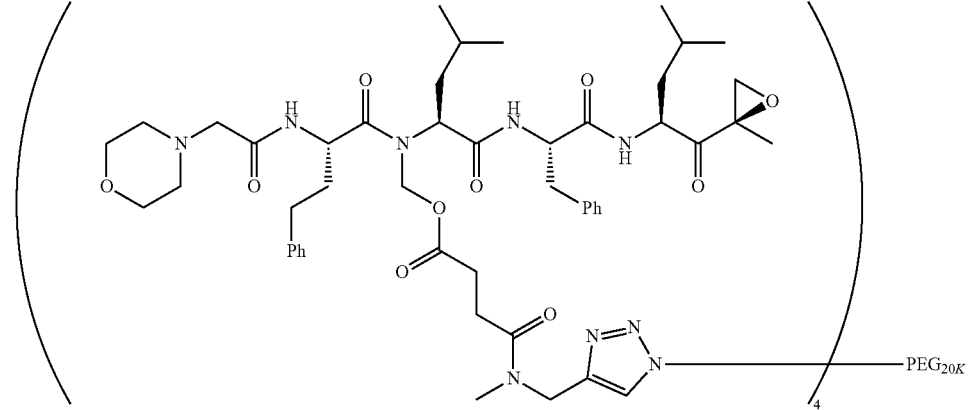

((S)—N—((S)-4-Methyl-1-(((S)-1-(((S)-4-methyl-1-
((R)-2-methyloxiran-2-yl)-1-oxopentan-2-yl)amino)-1-oxo-
3-phenylpropan-2-yl)amino)-1-oxopentan-2-yl)-2-(2-mor-
pholinoacetamido)-4-phenylbutanamido)methyl 4-(methyl
(prop-2-yn-1-yl)amino)-4-oxobutanoate and PEG$_{20K}$-(N$_3$)$_4$
(Creative PEGworks Catalog # PSB-493) were reacted
following General PEGylation Conditions, Method C.

((S)—N—((S)-4-Methyl-1-(((S)-1-(((S)-4-methyl-1-
((R)-2-methyloxiran-2-yl)-1-oxopentan-2-yl)amino)-
1-oxo-3-phenylpropan-2-yl)amino)-1-oxopentan-2-
yl)-2-(2-morpholinoacetamido)-4-
phenylbutanamido)methyl 4-(methyl(prop-2-yn-1-
yl)amino)-4-oxobutanoate

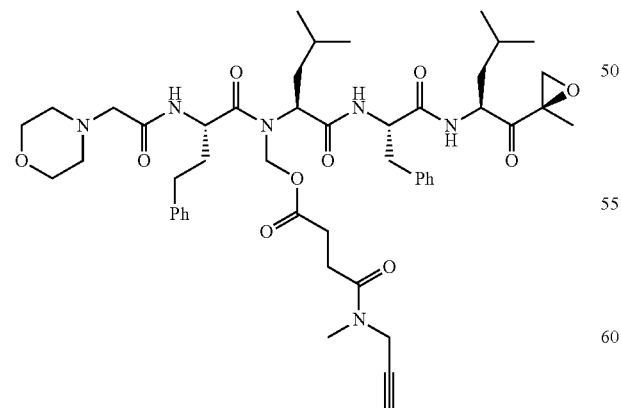

Prepared according to procedures described above, from
iodomethyl 4-(methyl(prop-2-yn-1-yl)amino)-4-oxobutano-
ate.

(3S,6S,9S,12S)-9-benzyl-6-isobutyl-14-methyl-12-
((R)-2-methyloxirane-2-carbonyl)-2-(2-morpholino-
acetyl)-4,7,10-trioxo-3-phenethyl-2,5,8,11-tetraaza-
pentadecyl 4-(methyl((1-PEG$_{20K}$/4-Arm-1H-1,2,3-
triazol-4-yl)methyl)amino)-4-oxobutanoate

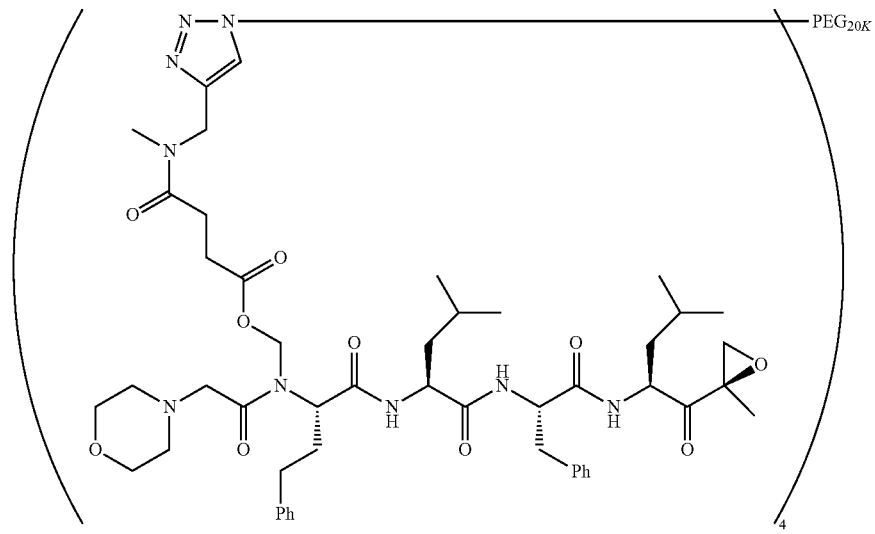

(3S,6S,9S,12S)-9-Benzyl-6-isobutyl-14-methyl-12-((R)-2-methyloxirane-2-carbonyl)-2-(2-morpholinoacetyl)-4,7,10-trioxo-3-phenethyl-2,5,8,11-tetraazapentadecyl 4-(methyl(prop-2-yn-1-yl)amino)-4-oxobutanoate and PEG$_{20k}$-(N$_3$)$_4$ (Creative PEGworks Catalog # PSB-493) were reacted following General PEGylation Conditions, Method C.

(3S,6S,9S,12S)-9-Benzyl-6-isobutyl-14-methyl-12-
((R)-2-methyloxirane-2-carbonyl)-2-(2-morpholino-
acetyl)-4,7,10-trioxo-3-phenethyl-2,5,8,11-teraaza-
pentadecyl 4-(methyl(prop-2-yn-1-yl)amino)-4-
oxobutanoate

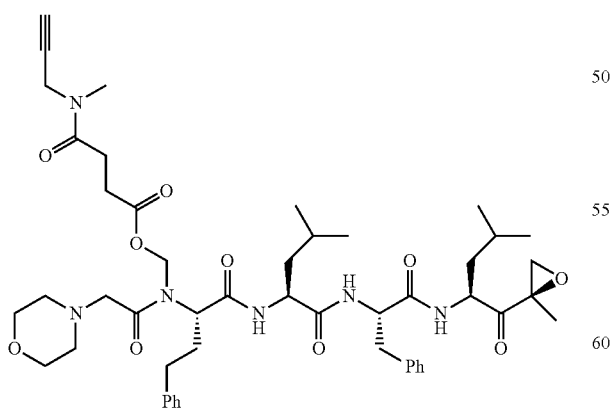

Prepared according to procedures described above, from iodomethyl 4-(methyl(prop-2-yn-1-yl)amino)-4-oxobutanoate.

((S)—N—((S)-4-methyl-1-((S)-1-((S)-4-methyl-1-((R)-2-methyloxiran-1-yl)-1-oxopentan-2-ylamino)-1-oxo-3-phenylpropan-2-ylamino)-1-oxopentan-2-yl)-2-(2-morpholinoacetamido)-4-phenylbutanamido)methyl 6-(N-PEG$_{20K}$/4-Arm-amino)-6-oxohexanoate

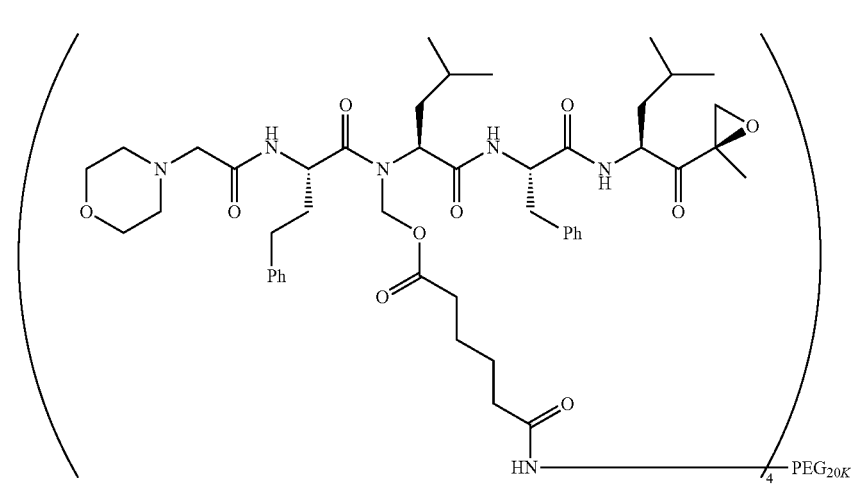

(4S,7S,10S)-7-Benzyl-10-isobutyl-2-methyl-4-((R)-2-methyloxirane-2-carbonyl)-11-((S)-2-(2-morpholinoacetamido)-4-phenylbutanoyl)-6,9,14-trioxo-13-oxa-5,8,11-triazanonadecane-19-oic acid and PEG$_{20K}$-(N$_3$)$_4$ (Creative PEGworks Catalog # PSB-493) were reacted following General PEGylation Conditions, Method C.

(4S,7S,10S)-7-Benzyl-10-isobutyl-2-methyl-4-((R)-2-methyloxirane-2-carbonyl)-11-((S)-2-(2-morpholinoacetamido)-4-phenylbutanoyl)-6,9,14-trioxo-13-oxa-5,8,11-triazanonadecane-19-oic Acid

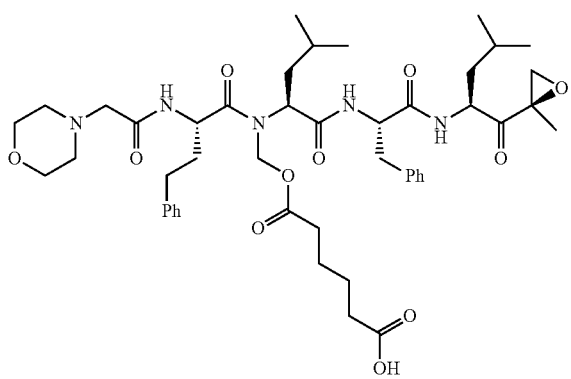 [SMILES: CC(C)C[C@H](NC(=O)[C@H](Cc1ccccc1)NC(=O)[C@H](CC(C)C)N(COC(=O)CCCCC(=O)O)C(=O)[C@H](CCc1ccccc1)NC(=O)CN1CCOCC1)C(=O)[C@@]1(C)CO1]

Prepared according to procedures described above, from benzyl (iodomethyl) adipate.

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-1-yl)amino)-1-oxopentan-2-yl)-2-(2-morpholinoacetamido)-4-phenylbutanamido)methyl Pivalate

(S)-Benzyl 2-((S)-2-((tert-butoxycarbonyl)amino)-4-phenylbutanamido)-4-methylpentanoate (1)

Figure 45:
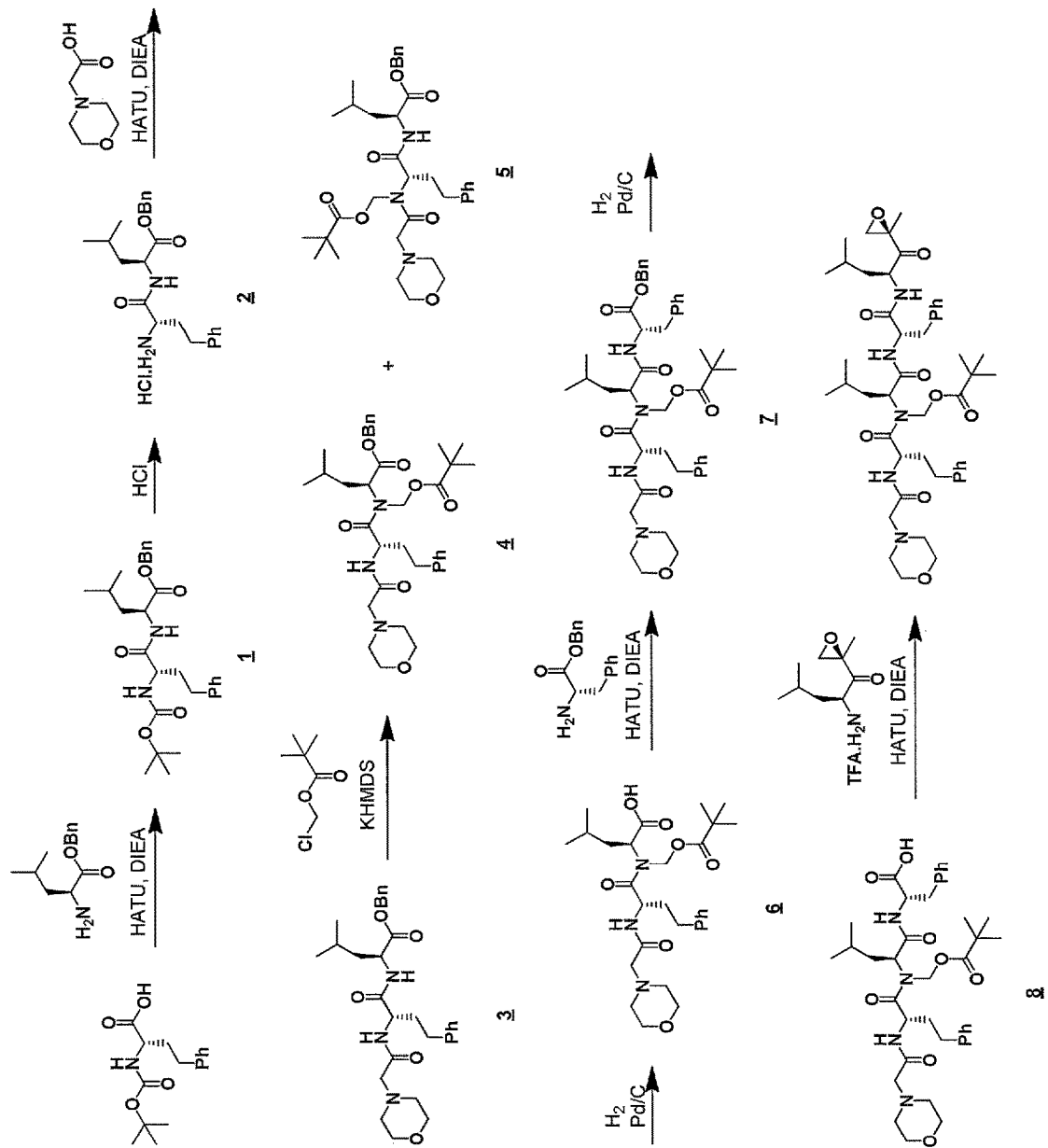
FIG. 45 is a scheme showing the synthesis of an embodiment of N-acyloxymethyl prodrug of an epoxy ketone proteasome inhibitor.

Referring to FIG. 45, DIPEA (2 mL, 12 mmol, 2.7 eq) was added to a mixture of Boc-HoPhe-OH (1.25 g, 4.4 mmol, 1 eq). H-Leu-OBn.TsOH (1.75 g, 4.5 mmol, 1.0 eq) and HATU (2 g, 5 mmol, 1.1 eq) in CH$_2$Cl$_2$ (50 mL) and the mixture was stirred for four hours at RT. The mixture was poured into 0.5N aq. HCl and extracted twice with CH$_2$Cl$_2$. The combined organic extracts were dried over Na$_2$SO$_4$ and concentrated in vacuo. The residue was purified by chromatography (SiO$_2$, 0-30% EtOAc in heptanes) and product (2.7 g, 100%) was isolated as a colorless oil.

(S)-Benzyl 2-((S)-2-amino-4-phenylbutanamido)-4-methylpentanoate Hydrochloride (2)

Referring to FIG. 45, 4N HCl in dioxane (6 mL, 24 mmol, 10 eq) was added to a solution of (S)-benzyl 2-((S)-2-((tert-butoxycarbonyl)amino)-4-phenylbutanamido)-4-methylpentanoate (1.2 g, 2.48 mmol) in dioxane (20 mL) and the solution was stirred overnight at RT. Analysis showed starting material was still present. 4N HCl in dioxane (6 mL, 24 mmol, 10 eq) was added and the solution was stirred for another 5 hours at RT after which is was concentrated in vacuo to yield the HCl-salt (1.0 g, 96%) as a white solid.

(S)-Benzyl 4-methyl-2-((S)-(2-morpholinoacetamido)-4-phenylbutanamido)pentanoate (3)

Referring to FIG. 45, DIPEA (592 µL, 3.6 mmol, 2.6 eq) was added to a mixture of (S)-benzyl 2-((S)-2-amino-4-phenylbutanamido)-4-methylpentanoate hydrochloride (600 mg, 1.4 mmol), 2-morpholinoacetic acid (312 mg, 2.1 mmol, 1.5 eq) and HATU (816 mg, 2.1 mmol, 1.5 eq) in $CH_2Cl_2$ (25 mL) and the mixture was stirred overnight at RT. The reaction mixture was washed with water and the aqueous layer was extracted once with $CH_2Cl_2$. The combined organic extracts were dried over $Na_2SO_4$ and concentrated in vacuo. The residue was purified by chromatography ($SiO_2$, 0-100%/EtOAc in heptanes, followed by 10% MeOH in EtOAc) to yield product (700 mg, 98%) as a yellow oil.

(S)-Benzyl 4-methyl-2-((S)-2-(2-morpholinoacetamido)-4-phenyl-N-((pivaloyloxy)methyl)butanamido) pentanoate (4)

Referring to FIG. 45, KHMDS (0.5 M in toluene) (3.3 mL, 1.6 mmol, 1.2 eq) was added drop wise to a solution of (S)-benzyl 4-methyl-2-((S)-2-(2-morpholinoacetamido)-4-phenylbutanamido)pentanoate (700 mg, 1.3 mmol) in THF (26 mL) at −50° C., keeping the temperature below −45° C. The mixture was stirred for 10 minutes at −45° C., chloromethyl pivalate (750 µL, 5.2 mmol, 4 eq) was added and the reaction mixture was allowed to reach RT over three hours. MeOH (500 µL) was added and after five minutes the mixture was poured into brine and extracted three times with EtOAc. The combined organic extracts were dried over $Na_2SO_4$ and concentrated in vacuo. The residue was purified by chromatography ($SiO_2$, 0-100% EtOAc in heptanes) to yield benzyl ester 4 (240 mg, 30%) as a colorless oil and isomer 5 (30 mg, 4%) also as a colorless oil.

(S)-4-Methyl-2-((S)-2-(2-morpholinoacetamido)-4-phenyl-N-((pivaloyloxy)methyl)butanamido)pentanoic Acid (6)

Referring to FIG. 45, a slurry of Pd/C (10%) (200 mg) in MeOH/water (9:1) (10 mL) was added to a solution of (S)-benzyl 4-methyl-2-((S)-2-(2-morpholinoacetamido)-4-phenyl-N-((pivaloyloxy)methyl)butanamido) pentanoate (440 mg, 0.7 mmol) in MeOH (100 mL) and the suspension was stirred overnight under an atmosphere of hydrogen at RT. The reaction mixture was filtered over Celite, washed with MeOH and concentrated in vacuo to yield product (345 mg, 92%) as a colorless oil.

(S)-Benzyl 2-((S)-4-methyl-2-((S)-2-(2-morpholinoacetamido-4-phenyl-N-((pivaloyloxy)methyl)butanamido) pentanamido)-3-phenylpropanoate (7)

Referring to FIG. 45, DIPEA (270 µL, 1.6 mmol, 2.5 eq) was added to a mixture of acid (S)-4-methyl-2-((S)-2-(2-morpholinoacetamido)-4-phenyl-N-((pivaloyloxy)methyl)butanamido)pentanoic acid (345 mg, 0.64 mmol), H-Phe-OBn (283 mg, 0.97 mmol, 1.5 eq) and HATU (370 mg, 0.97 mmol, 1.5 eq) in $CH_2Cl_2$ (10 mL) and the mixture was stirred for four hours at RT. The mixture was poured into water and extracted twice with $CH_2C_2$. The combined organic extracts were dried over $Na_2SO_4$ and concentrated in vacuo. The residue was purified by chromatography ($SiO_2$, 0-80% EtOAc in heptanes) and product (330 mg, 67%) was isolated as a colorless oil.

(S)-2-((S)-Methyl-2-((S)-2-(2-morpholinoacetamido)-4-phenyl-N-((pivaloyloxy)methyl)butanamido)pentanamido)-3-phenylpropanoic Acid (8)

Referring to FIG. 45, a slurry of Pd/C (10%) (150 mg) in MeOH/water (9:1) (2 mL) was added to a solution of benzyl ester (S)-benzyl 2-((S)-4-methyl-2-((S)-2-(2-morpholinoacetamido)-4-phenyl-N-((pivaloyloxy)methyl)butanamido) pentanamido)-3-phenylpropanoate (320 mg, 0.41 mmol) in MeOH (15 mL) and the suspension was stirred overnight under an atmosphere of hydrogen at RT. The reaction mixture was filtered over Celite, washed with MeOH and concentrated in vacuo to yield product (289 mg, 102%) as a white foam.

Referring to FIG. 45, DIPEA (170 µL, 1.0 mmol, 2.5 eq) was added to a mixture of (S)-2-((S)-4-methyl-2-((S)-2-(2-morpholinoacetamido)-4-phenyl-N-((pivaloyloxy)methyl)butanamido) pentanamido)-3-phenylpropanoic acid (289 mg, 0.41 mmol), (S)-2-Amino-4-methyl-1-((R)-2-methyloxiran-2-yl)pentan-1-one 2,2,2-trifluoroacetate (165 mg, 0.61 mmol, 1.5 eq) and HATU (234 mg, 0.61 mmol, 1.5 eq) in $CH_2Cl_2$ (4 mL) and the mixture was stirred for three hours at RT. The mixture was poured into water and extracted once with $CH_2Cl_2$. The organic extract was dried over $Na_2SO_4$ and concentrated in vacuo. The residue was purified by chromatography ($SiO_2$, 0-90% EtOAc in heptanes) to yield product (purity 90%). This sample was purified again by $SiO_2$-chromatography (0 to 2% MeOH in $CH_2Cl_2$) yielding product (114 mg, 33%).

(3S,6S,9S,12S)-9-benzyl-6-isobutyl-14-methyl-12-((R)-2-methyloxirane-2-carbonyl)-2-(2 morpholino-acetyl)-4,7,10-trioxo-3-phenethyl-2,5,8,11-tetraaza-pentadecyl 6-(N-PEG$_{20K}$/4-Arm-amino)-6-oxohexanoate

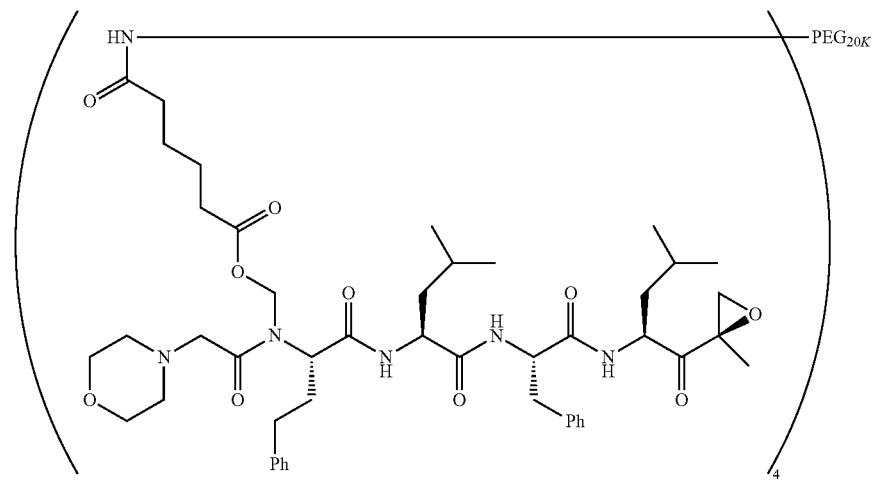

(4S,7S,10S,13S)-7-Benzyl-10-isobutyl-2-methyl-4-((R)-2-methyloxirane-2-carbonyl)-14-(2-morpholinoacetyl)-6,9,12,17-tetraoxo-13-phenethyl-16-oxa-5,8,11,14-tetraazadocosan-22-oic acid and PEG$_{20K}$-(N$_3$)$_4$ (Creative PEGworks Catalog # PSB-493) were reacted following General PEGylation Conditions, Method C.

(4S,7S,10S,13S)-7-Benzyl-O-isobutyl-2-methyl-4-((R)-2-methyloxirane-2-carbonyl)-14-(2-morpholinoacetyl)-6,9,12,17-tetraoxo-13-phenethyl-16-oxa-5,8,11,14-tetraazadocosan-22-oic Acid

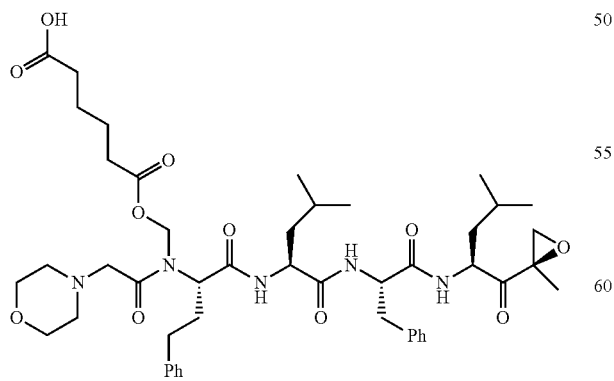

Prepared according to procedures described above, from benzyl (iodomethyl) adipate.

(3S,6S,9S,12S)-9-benzyl-6-isobutyl-14-methyl-12-((R)-2-methyloxirane-2-carbonyl)-2-(2-morpholinoacetyl)-4,7,10-trioxo-3-phenethyl-2,5,8,11-tetraazapentadecyl 2-methyl-2-((1-PEG$_{20K}$/4-Arm-1H-1,2,3-triazol-5-yl)methoxy)propanoate

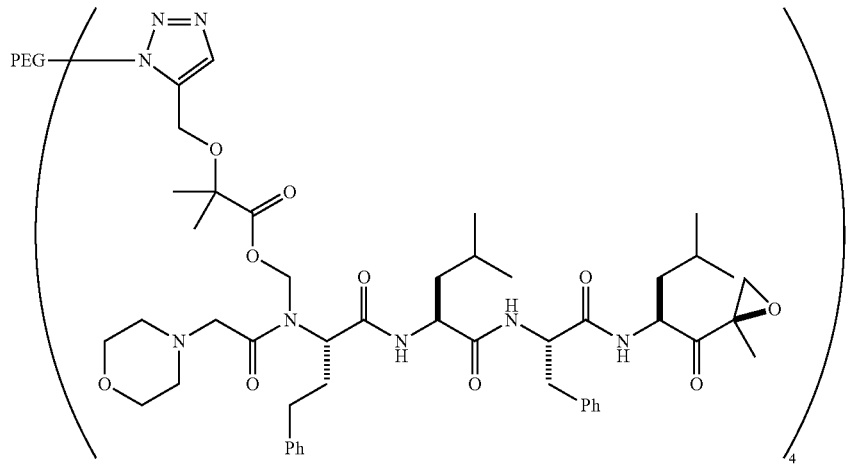

(3S,6S,9S,12S)-9-Benzyl-6-isobutyl-14-methyl-12-((R)-2-methyloxirane-2-carbonyl)-2-(2-morpholinoacetyl)-4,7,10-trioxo-3-phenethyl-2,5,8,11-tetraazapentadecyl 2-methyl-2-(prop-2-yn-1-yloxy)propanoate and PEG$_{20k}$-(N$_3$)$_4$ (Creative PEGworks Catalog # PSB-493) were reacted following General PEGylation Conditions, Method C.

(3S,6S,9S,12S)-9-Benzyl-6-isobutyl-14-methy-12-((R)-2-methyloxirane-2-carbonyl)-2-(2-morpholinoacetyl)-4,7,10-trioxo-3-phenethyl-2,5,8,11-tetraazapentadecyl 2-methyl-2-(prop-2-yn-1-yloxy)propanoate

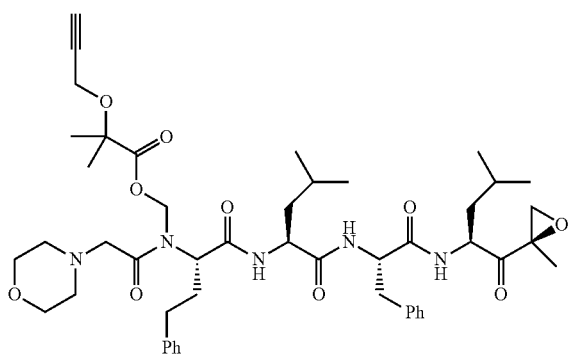 [SMILES: C#CCOC(C)(C)C(=O)OCN(C(=O)CN1CCOCC1)[C@@H](CCc1ccccc1)C(=O)N[C@@H](CC(C)C)C(=O)N[C@@H](Cc1ccccc1)C(=O)N[C@@H](CC(C)C)C(=O)[C@@]1(C)CO1]

Prepared according to procedures described above, from iodomethyl 2-methyl-2-(prop-2-yn-1-yloxy)propanoate.

(3S,6S,9S,12S)-9-Benzyl-6-isobutyl-14-methyl-12-((R)-2-methyloxirane-2-carbonyl)-2-(2-morpholinoacetyl)-4,7,10-trioxo-3-phenethyl-2,5,8,11-tetraazapentadecyl 4-(((1-PEG$_{20K}$/4-Arm-1H-1,2,3-triazol-4-yl)methyl)amino)-4-oxobutanoate

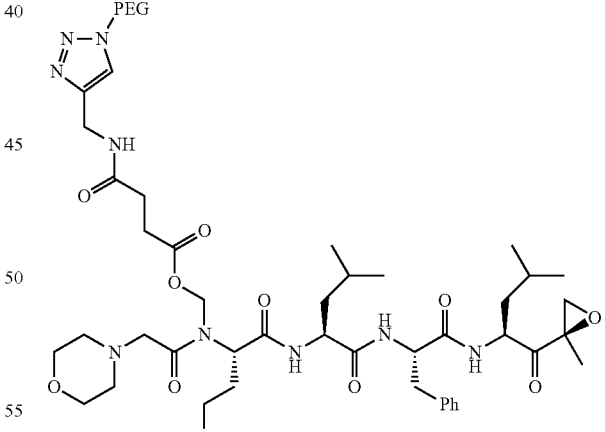

(3S,6S,9S,12S)-9-Benzyl-6-isobutyl-14-methyl-12-((R)-2-methyloxirane-2-carbonyl)-2-(2-morpholinoacetyl)-4,7,10-trioxo-3-phenethyl-2,5,8,11-tetraazapentadecyl 4-oxo-4-(prop-2-yn-1-ylamino)butanoate and PEG$_{20k}$-(N$_3$)$_4$ (Creative PEGworks Catalog # PSB-493) were reacted following General PEGylation Conditions, Method C.

341

(3S,6S,9S,12S)-9-Benzyl-6-isobutyl-14-methyl-12-((R)-2-methyloxirane-2-carbonyl)-2-(2-morpholino-acetyl)-4,7,10-trioxo-3-phenethyl-2,5,8,11-tetraaza-pentadecyl 4-oxo-4-(prop-2-yn-1-ylamino)butanoate

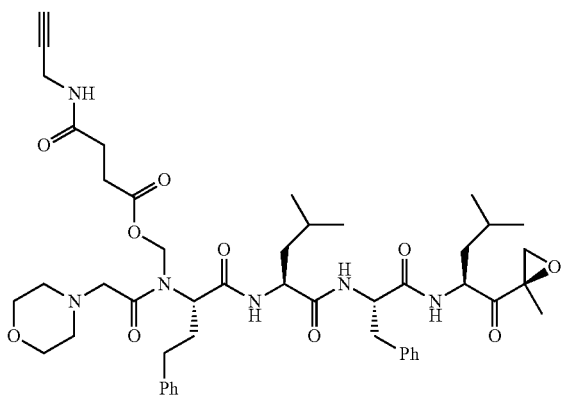

Prepared according to procedures described above, from iodomethyl 4-oxo-4-(prop-2-yn-1-yl amino)butanoate.

((S)—N—((S)-4-Methyl-1-(((S)-1-(((S)-4-methyl-1-((R)-2-methyloxiran-2-yl)-1-oxopentan-2-yl)amino)-1-oxo-3 phenylpropan-2-yl)amino)-1-oxopentan-2-yl)-2-(2-morpholinoacetamido)-4-phenylbutanamido)methyl 4-(((1-PEG-1H-1,2,3-triazol-4-yl)methyl)amino)-4-oxobutanoate

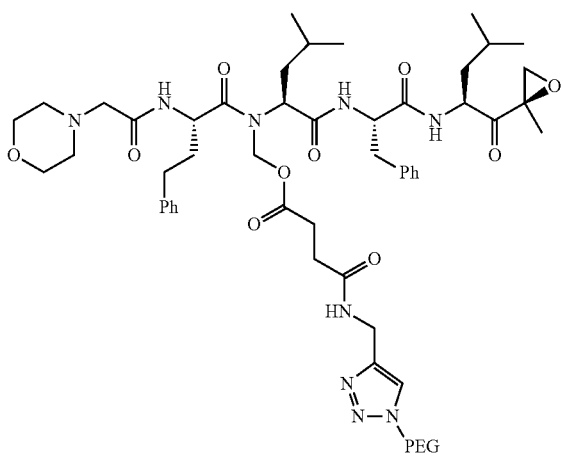

342

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl 4-oxo-4-(prop-2-yn-1-ylamino)butanoate and $PEG_{20K}$-$(N_3)_4$ (Creative PEGworks Catalog # PSB-493) were reacted following General PEGylation Conditions, Method C.

((S)—N—((S)-4-Methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-(2-morpholinoacetamido)-4-phenylbutanamido)methyl 4-oxo-4-(prop-2-yn-1-ylamino)butanoate

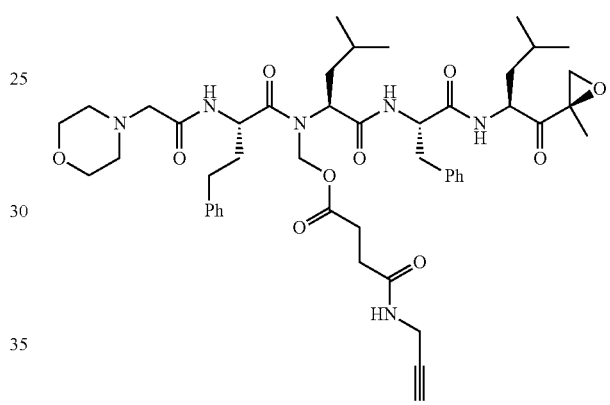

Prepared according to procedures described above, from iodomethyl 4-oxo-4-(prop-2-yn-1-ylamino)butanoate.

Iodohydrin Esters/Carbonates

Preparation of (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexa-decan-15-yl 3-(1-$PEG_{20K}$/4-Arm-1H-1,2,3-triazol-4-yl)propanoate

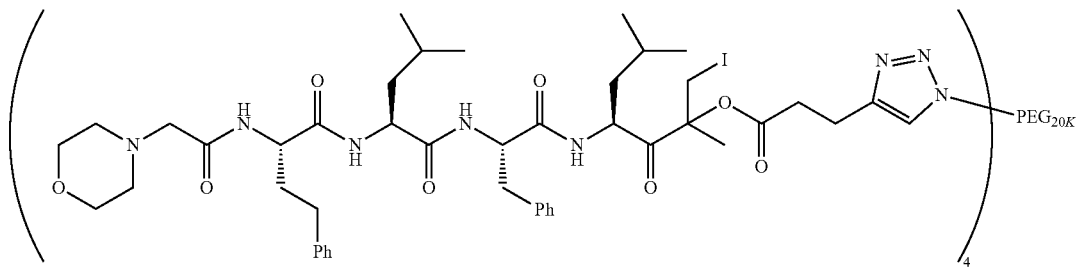

PEGylation accomplished with standard PEGylation procedure disclosed above. ¹H NMR (DMSO-$d_6$): δ 8.32 (d, J=9.0 Hz, 1H), 8.12 (d, J=8.5 Hz, 1H), 8.02 (d, J=8.0 Hz, 1H), 7.88-7.85 (m, 2H), 7.28-7.08 (m, 10H), 4.89-4.83 (m, 1H), 4.57-4.29 (m, 6H), 3.83-3.32 (m, 593H), 2.96-2.90 (m, 4H), 2.84-2.73 (m, 2H), 2.54-2.42 (m, 6H), 1.89-1.75 (m, 2H), 1.58-1.30 (m, 9H), 0.85-0.76 (m, 12H).

(4S,7S,10S,13S,15S)-10-benzyl-16-iodo-7,13-di-isobutyl-15-methyl-1-morpholino-2,5,8,11,14-pentaoxo-4-phenethyl-3,6,9,12-tetraazahexadecan-15-yl pent-4-ynoate

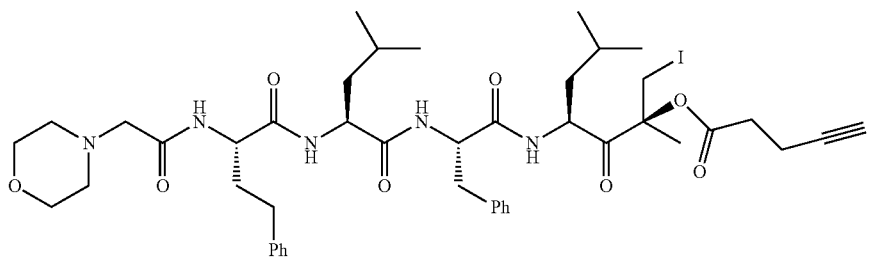

(2S)—N—((S)-1-((2S,4S)-2-hydroxy-1-iodo-2,6-dimethyl-3-oxoheptan-4-ylcarbamoyl)-2-phenylethyl)-2-((S)-2-(2-morpholinoacetamido)-4-phenylbutanamido)-4-methylpentanamide (1.18 g, 1.39 mmol) was dissolved in DMF. DMAP (19.2 mg, 0.139 mmol), 4-pentynoic acid (205 mg, 2.09 mmol) and DCC (430 mg, 2.09 mmol) were added. The mixture was stirred at room temperature for 16 hours and then diluted with 200 mL EtOAc. The organic phase was washed with 1N HCl (50 ml), brine (50 mL), and saturated NaHCO₃ solution. The organic layer was dried over anhydrous MgSO₄ and concentrated under reduced pressure. The crude product was purified by prep HPLC to afford 539 mg of product as a white solid.

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl 2-(4-2-oxoethoxy)acetate

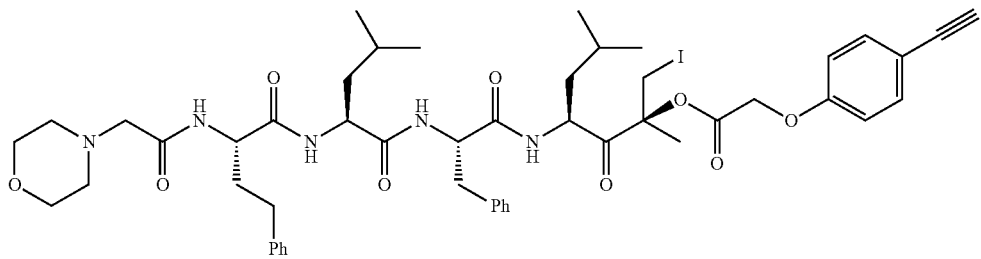 [SMILES: C#Cc1ccc(OCC(=O)O[C@](C)(CI)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)cc1]

Prepared according to the procedure for the compound above, except from 2-(4-ethynylphenoxy)acetic acid and (2S)—N—((S)-1-((2S,4S)-2-hydroxy-1-iodo-2,6-dimethyl-3-oxoheptan-4-ylcarbamoyl)-2-phenylethyl)-2-((S)-2-(2-morpholinoacetamido)-4-phenylbutanamido)-4-methylpentanamide.

(2S)—N—((S)-1-((2S,4S)-2-hydroxy-1-iodo-2,6-dimethyl-3-oxoheptan-4-ylcarbamoyl)-2-phenylethyl)-2-((S)-2-(2-morpholinoacetamido)-4-phenylbutanamido)-4-methylpentanamide

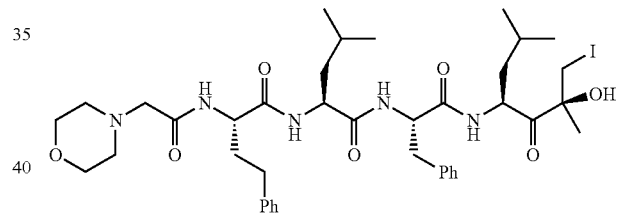

Cerium chloride heptahydrate (488 mg, 1.32 mmol) and sodium iodide (423 mg, 2.82 mmol) were added to Compound A (1.0 g, 1.39 mmol) dissolved in acetonitrile (50 mL). The reaction mixture was stirred at room temperature for 16 hours after which HPLC analysis showed complete conversion. Saturated sodium hydrogensulfite solution (50 mL) was added and the resulting mixture was extracted with EtOAc (200 mL). The organic phase was separated, washed with brine (50 mL), dried over anhydrous MgSO₄ and concentrated under reduced pressure to afford product as a light yellow solid (1.18 g, 100% yield).

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl 3-(1-PEG$_{20K}$/4-Arm-1H-1,2,3-triazol-4-yl)propanoate

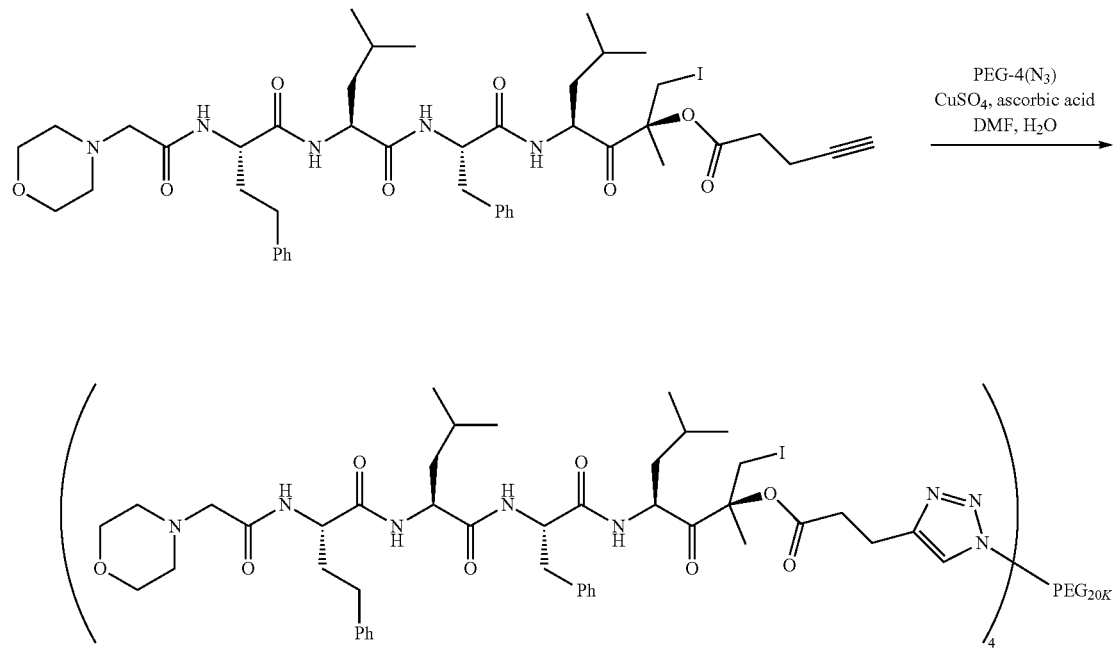

(4S,7S,10S,13S,15S)-10-Benzyl-16-iodo-7,13-diisobutyl-5-methyl-1-morpholino-2,5,8,11,14-pentaoxo-4-phenethyl-3,6,9,12-tetraazahexadecan-15-yl pent-4-ynoate and PEG$_{20K}$-(N$_3$)$_4$ (Creative PEGworks Catalog # PSB-493) were reacted following General PEGylation Conditions, Method C; $^1$H NMR (DMSO-d$_6$): δ 8.32 (d, J=9.0 Hz, 1H), 8.12 (d, J=8.5 Hz, 1H), 8.02 (d, J=8.0 Hz, 1H), 7.88-7.85 (m, 2H), 7.28-7.08 (m, 10H), 4.89-4.83 (m, 1H), 4.57-4.29 (m, 6H), 3.83-3.32 (m, 593H), 2.96-2.90 (m, 4H), 2.84-2.73 (m, 2H), 2.54-2.42 (m, 6H), 1.89-1.75 (m, 2H), 1.58-1.30 (m, 9H), 0.85-0.76 (m, 12H); PEG Loading (NMR): 3.2/4 Arms, 9.6% small molecule.

Preparation of (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 2-((1-PEG$_{20K}$/4-Arm-1H-1,2,3-triazol-4-yl)methoxy)acetate Prepared similarly as above from (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 2-(prop-2-yn-1-yloxy)acetate. (4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 2-(prop-2-yn-1-yloxy)acetate and PEG$_{20K}$-(N$_3$)$_4$ (Creative PEGworks Catalog # PSB-493) were reacted following General PEGylation Conditions, Method C; $^1$H NMR (DMSO-d$_6$): δ 8.37 (d, J=8.5 Hz, 1H), 8.12 (d, J=8.0 Hz, 1H), 8.08 (s, 1H), 8.03 (d, J=8.5 Hz, 1H), 7.88 (d, J=8.5 Hz, 1H), 7.28-7.08 (m, 10H), 4.89-4.83 (m, 1H), 4.64 (s, 2H), 4.57-4.50 (m, 4H), 4.37-4.28 (m, 2H), 4.24 (s, 2H), 3.92-3.78 (m, 4H), 3.65-3.30 (m, 638H), 2.99-2.91 (m, 3H), 2.80-2.76 (m, 1H), 2.50-2.42 (m, 6H), 1.89-1.75 (m, 2H), 1.59-1.32 (m, 9H), 0.85-0.77 (m, 12H).

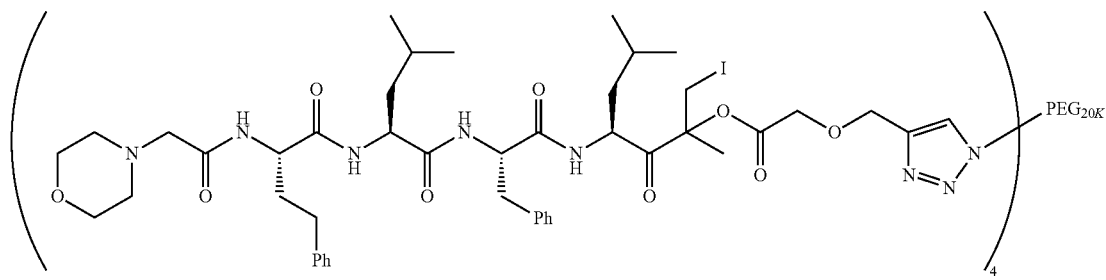

Preparation of (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl ((1-PEG$_{20K}$/4-Arm-1H-1,2,3-triazol-4-yl)methyl) carbonate

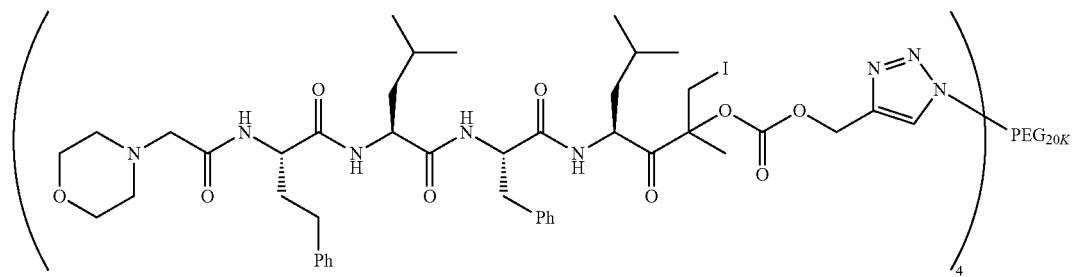

PEGylation accomplished with standard PEGylation procedure disclosed above. (4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl prop-2-yn-1-yl carbonate and PEG$_{20k}$-(N$_3$)$_4$ (Creative PEGworks Catalog # PSB-493) were reacted following General PEGylation Conditions, Method C; PEG Loading (NMR): 2.9/4 Arms, 8.7% small molecule.

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-(1-PEG$_{20K}$/4-Arm-1H-1,2,3-triazol-4-yl)benzyl Carbonate

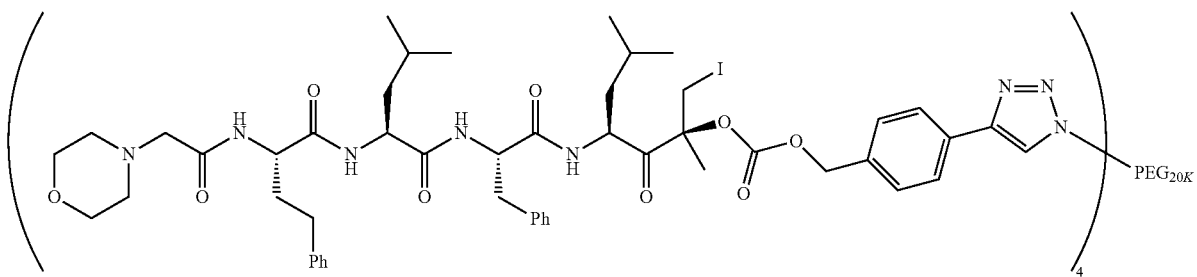

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-ethynylbenzyl carbonate and PEG$_{20k}$-(N$_3$)$_4$ (Creative PEGworks Catalog # PSB-493) were reacted following General PEGylation Conditions, Method C.; PEG Loading (NMR): 3/4 Arms, 8.9% small molecule.

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl 4-ethynylbenzyl Carbonate

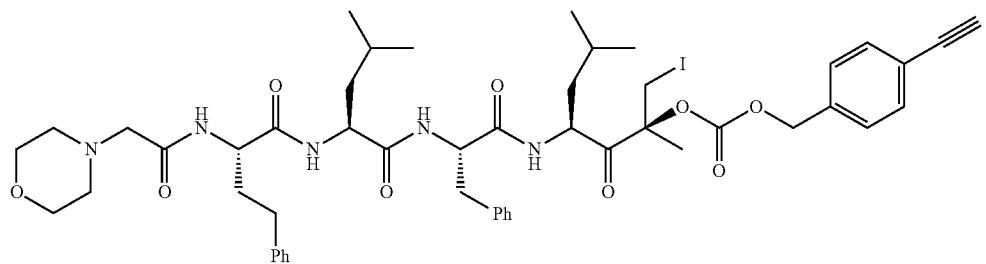 [SMILES: C#Cc1ccc(COC(=O)O[C@](C)(CI)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)cc1]

Prepared as according to methods described above, from (4-ethynylphenyl)methanol and (2S)—N—((S)-1-((2S,4S)-2-hydroxy-1-iodo-2,6-dimethyl-3-oxoheptan-4-ylcarbamoyl)-2-phenylethyl)-2-((S)-2-(2-morpholinoacetamido)-4-phenylbutanamido)-4-methylpentanamide.

(4S,7S,10S,13S,15S)-10-benzyl-16-iodo-7,13-di-isobutyl-15-methyl-1-morpholino-2,5,8,11,14-pentaoxo-4-phenethyl-3,6,9,12-tetraazahexadecan-15-yl ((1-PEG$_{20K}$/4-Arm)-1H-1,2,3-triazol-4-yl)methyl Succinate

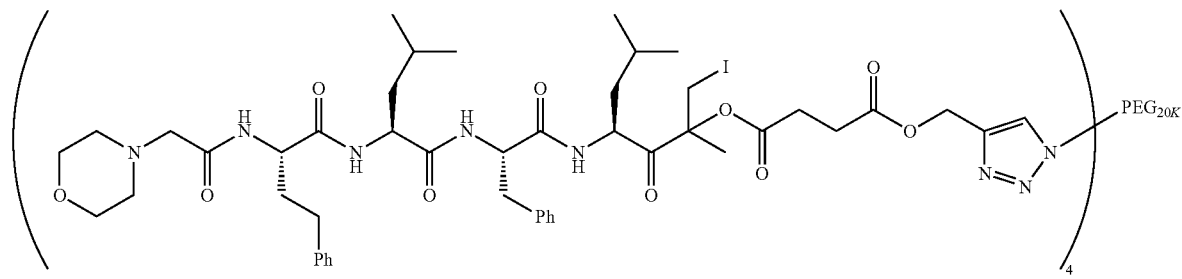

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl prop-2-yn-1-yl succinate and PEG$_{20K}$-(N$_3$)$_4$ (Creative PEGworks Catalog # PSB-493) were reacted following General PEGylation Conditions. Method C.

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl prop-2-yn-1-yl Succinate

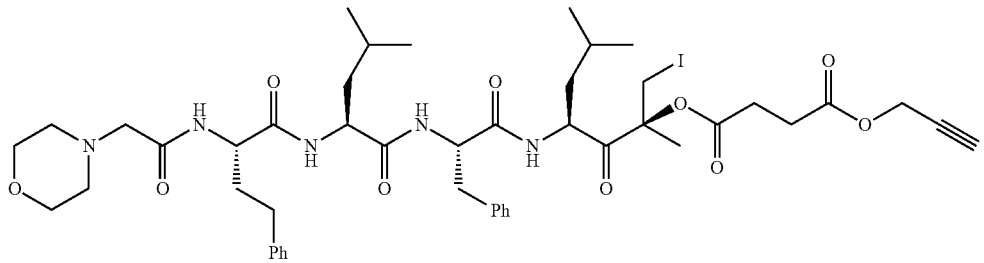 [SMILES: C#CCOC(=O)CCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S,15S)-10-benzyl-16-iodo-7,13-di-isobutyl-15-methyl-1-morpholino-2,5,8,11,14-pentaoxo-4-phenethyl-3,6,9,12-tetraazahexadecan-15-yl 2-(4-(1-PEG$_{20K}$/4-Arm-1H-1,2,3-triazol-4-yl)phenoxy)acetate

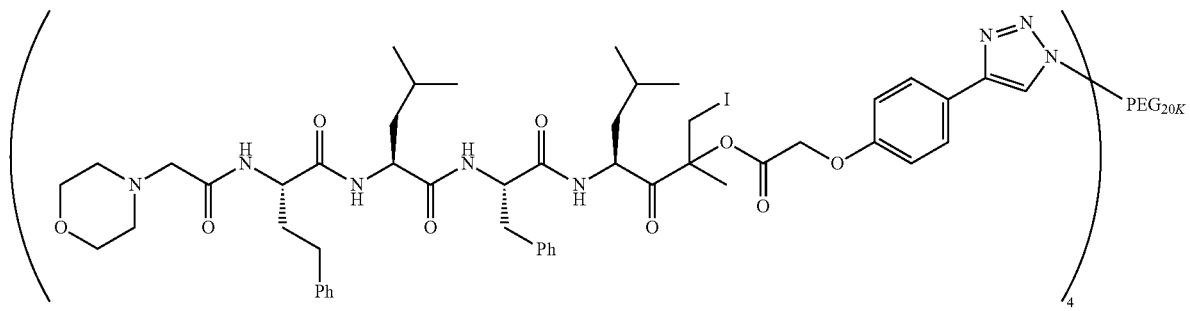

(4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 2-(4-ethynylphenoxy)acetate and PEG$_{20k}$-(N$_3$)$_4$ (Creative PEGworks Catalog # PSB-93) were reacted following General PEGylation Conditions, Method C; PEG Loading (NMR): 3.2/4 Arms, 9.5% small molecule.

(4S,7S,10S,13S,15S)-10-benzyl-16-iodo-7,13-di-isobutyl-15-methyl-yl)-morpholino-2,5,8,11,14-pentaoxo-4-phenethyl-3,6,9,12-tetraazahexadecan-15-yl 4-(2-(methyl ((1-PEG$_{20K}$/4-Arm-1H-1,2,3-triazol-4-yl)methyl)amino)-2-oxoethylamino)-4-oxobutanoate

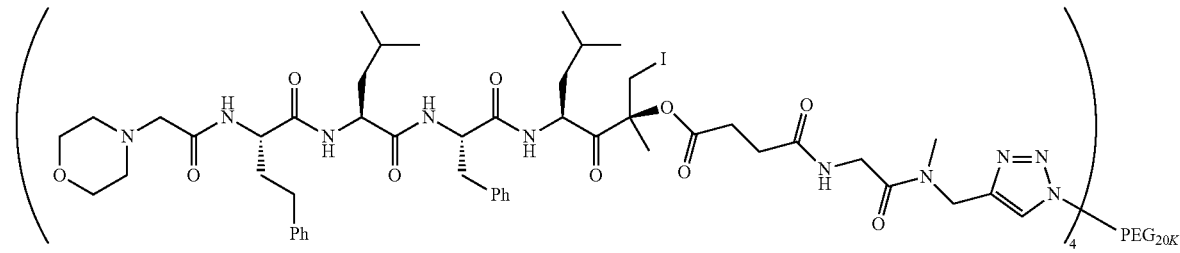

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-((2-(methyl(prop-2-yn-1-yl)amino)-2-oxoethyl)amino)-4-oxobutanoate and PEG$_{20K}$-(N$_3$)$_4$ (Creative PEGworks Catalog # PSB-493) were reacted following General PEGylation Conditions, Method C; PEG Loading (NMR): 3.8/4 Arms, 11.1% small molecule.

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-((2-(methyl(prop-2-yn-1-yl)amino)-2-oxoethyl)amino)-4-oxobutanoate

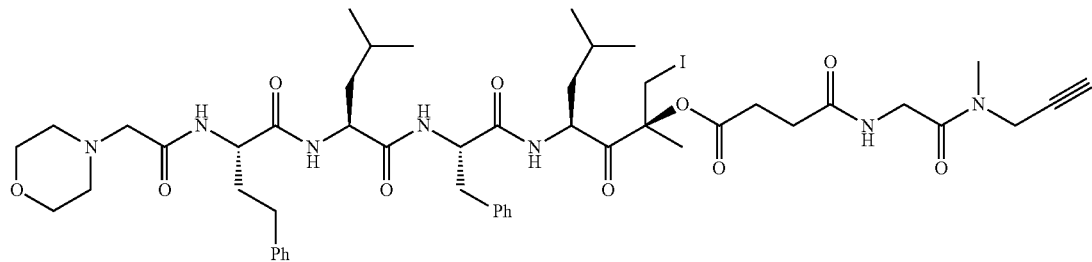 [SMILES: C#CCN(C)C(=O)CNC(=O)CCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 4-((1-PEG$_{20K}$/4-Arm-1H-1,2,3-triazol-4-yl)methylamino)-4-oxobutanoate

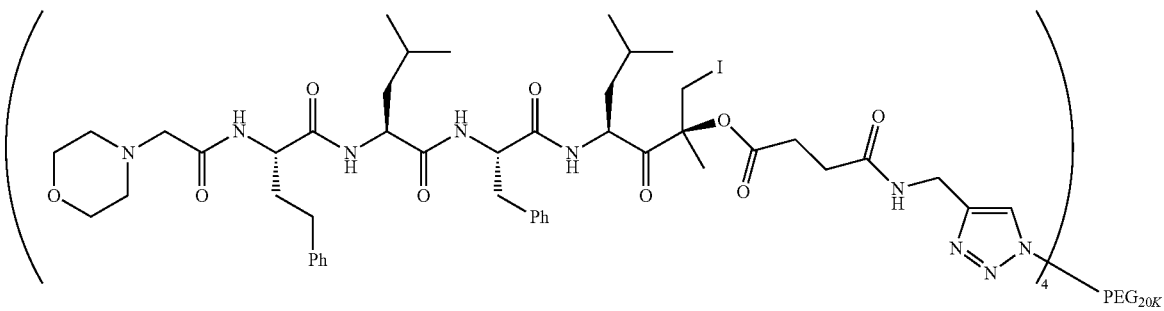

(4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 2-(2-((1-PEG$_{20K}$/4-Arm-1H-1,2,3-triazol-4-yl)methylamino)-2-oxoethoxy)acetate

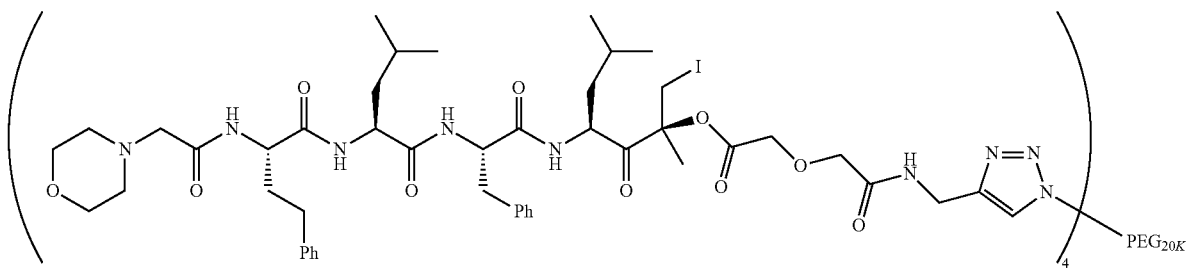

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 2-(2-oxo-2-(prop-2-yn-1-ylamino)ethoxy)acetate and PEG$_{20k}$-(N$_3$)$_4$ (Creative PEGworks Catalog # PSB-493) were reacted following General PEGylation Conditions, Method C; PEG Loading (NMR): 3.7/4 Arms, 10.9% small molecule.

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 2-(2-oxo-2-(prop-2-yn-1-ylamino)ethoxy)acetate

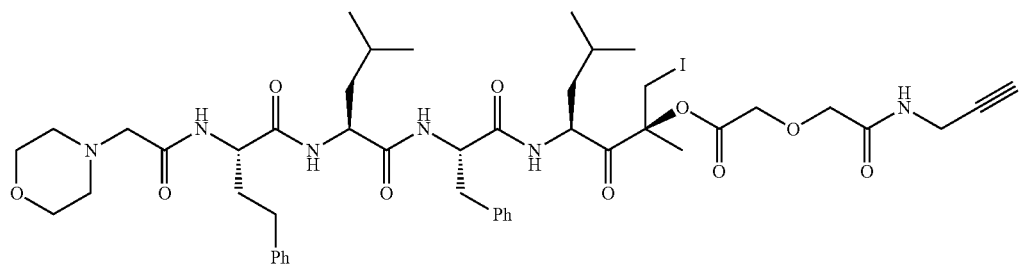 [SMILES: C#CCNC(=O)COCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 4-(3-(1-PEG$_{20K}$/4-Arm-1H-1,2,3-triazol-4-yl)propanamido)butanoate

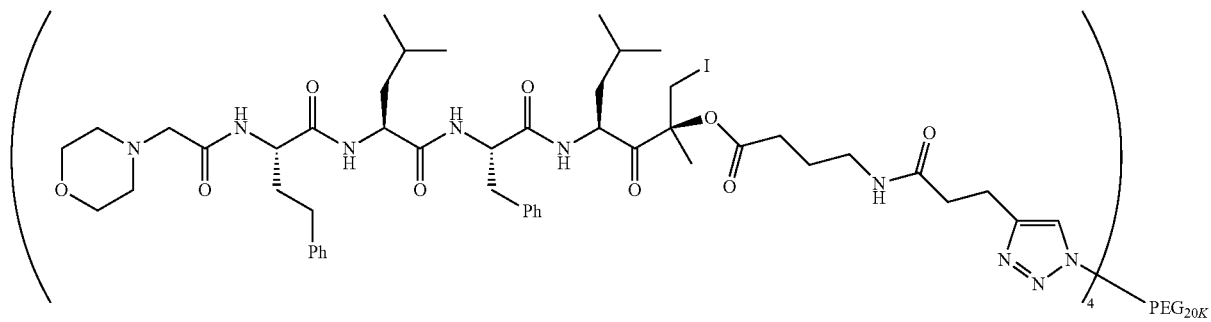

(4S,7S,10S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-(pent-4-ynamido)butanoate and PEG$_{20k}$-(N$_3$)$_4$ (Creative PEGworks Catalog # PSB-493) were reacted following General PEGylation Conditions, Method C; PEG Loading (NMR): 2.4/4 Arms, 7.1% Compound A.

(4S,7S,10S,13S,15S)-10-Benzyl-16-iodo-7,13-di-
isobutyl-15-methyl-1-morpholino-2,5,8,11,14-pen-
taoxo-4-phenethyl-3,6,9,12-tetraazahexadecan-15-yl
4-(pent-4-ynamido)butanoate

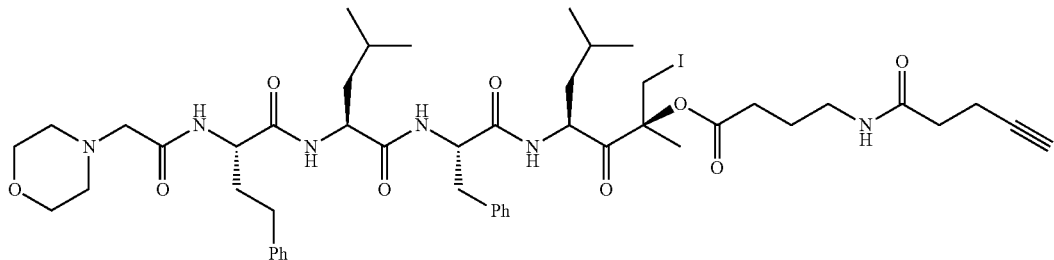 [SMILES: C#CCCC(=O)NCCCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S,15S)-10-benzyl-16-iodo-7,13-di-
isobutyl-15-methyl-1-morpholino-2,5,8,11,14-pen-
taoxo-4-phenethyl-3,6,9,12-tetraazahexadecan-15-yl
4-(1-PEG$_{20K}$/4-Arm-1H-1,2,3-triazol-4-yl)butyl Car-
bonate

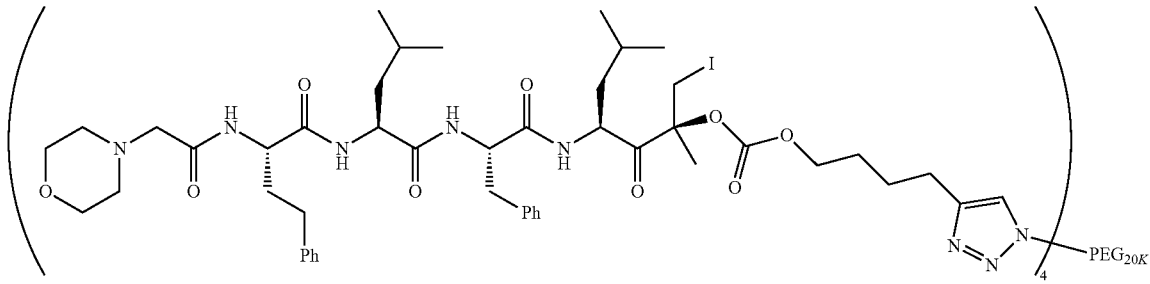

(4S,7S,10S,13S,5S)-10-Benzyl-16-iodo-7,13-diisobutyl-
15-methyl-1-morpholino-2,5,8,11,14-pentaoxo-4-phen-
ethyl-3,6,9,12-tetraazahexadecan-15-yl hex-5-yn-1-yl car-
bonate and PEG$_{20k}$-(N$_3$)$_4$ (Creative PEGworks Catalog #
PSB-493) were reacted following General PEGylation Con-
ditions, Method C.

(4S,7S,10S,13S,15S)-10-Benzyl-16-iodo-7,13-di-
isobutyl-15-methyl-1-morpholino-2,5,8,11,14-pen-
taoxo-4-phenethyl-3,6,9,12-tetraazahexadecan-15-yl
hex-5-yn-1-yl Carbonate

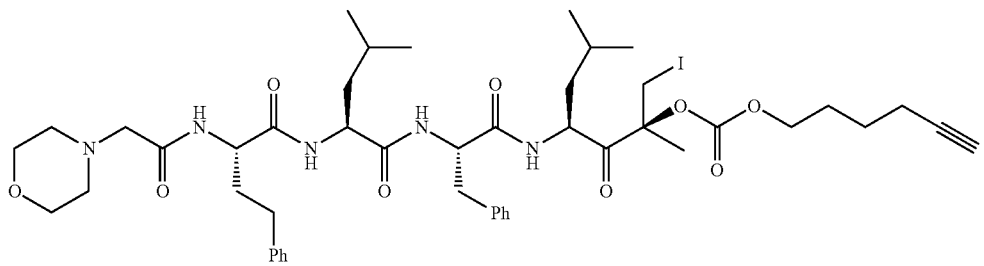 [SMILES: C#CCCCCOC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Prepared according to methods described above from
hexyn-1-ol and (2S)—N—((S)-1-((2S,4S)-2-hydroxy-1-
iodo-2,6-dimethyl-3-oxoheptan-4-ylcarbamoyl)-2-phenyl-
ethyl)-2-((S)-2-(2-morpholinoacetamido)-4-phenylbutana-
mido)-4-methylpentanamide.

(4S,7S,10S,13S,15S)-10-benzyl-16-iodo-7,13-di-isobutyl-15-methyl-1-morpholino-2,5,8,11,14-pentaoxo-4-phenethyl-3,6,9,12-tetraazahexadecan-15-yl 3-(3-1-PEG$_{20K}$/4-Arm-1H-1,2,3-triazol-4-yl)propanamido)propanoate

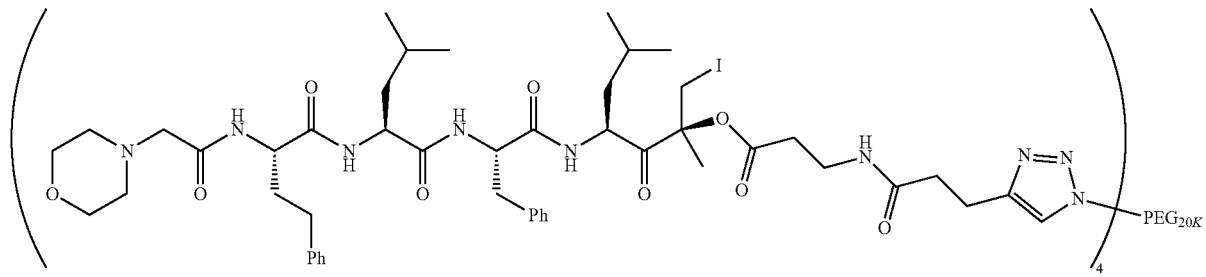

(4S,7S,10S,13S,15 S)-10-Benzyl-16-iodo-7,13-diisobutyl-15-methyl-1-morpholino-2,5,8,11,14-pentaoxo-1-phenethyl-3,6,9,12-tetraazahexadecan-15-yl 3-(pent-4-ynamido)propanoate and PEG$_{20k}$-(N$_3$)$_4$ (Creative PEGworks Catalog # PSB-493) were reacted following General PEGylation Conditions, Method C; PEG Loading (NMR): 3.2/4 Arms, 9.5% small molecule.

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 3-(pent-4-ynamido)propanoate

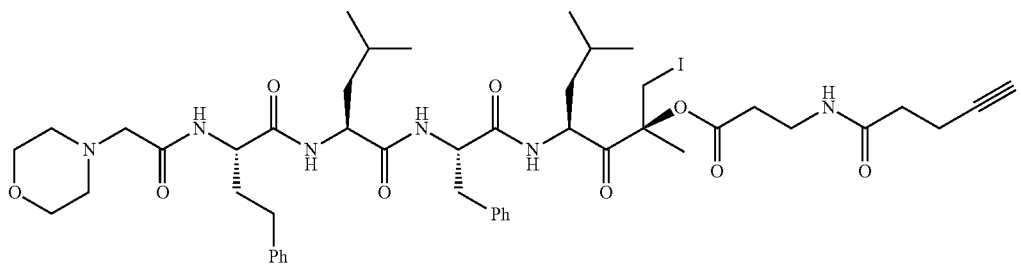 [SMILES: C#CCCC(=O)NCCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S 13S)-10-benzyl-16-iodo-7,13-diisobutyl-15-methyl-1-morpholino-2,5,8,11,14-pentaoxo-4-phenethyl-3,6,9,12-tetraazahexadecan-15-yl 4-(PEG$_{20K}$/4-Arm-amino)-4-oxobutanoate

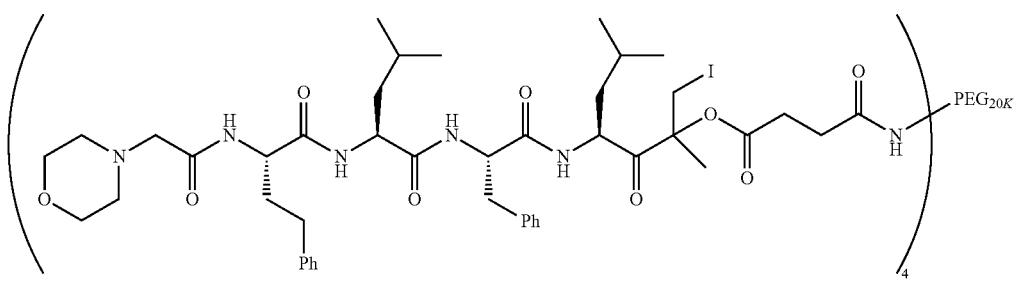

(4S,7S,10S,13S)-10-benzyl-16-iodo-7,13-diisobutyl-15-methyl-1-morpholino-2,5,8,11,14-pentaoxo-4-phenethyl-3,6,9,12-tetraazahexadecan-15-yl 2-(2-((1-PEG$_{20K}$/4-Arm-1H-1,2,3-triazol-4-yl)methoxy)acetamido)acetate

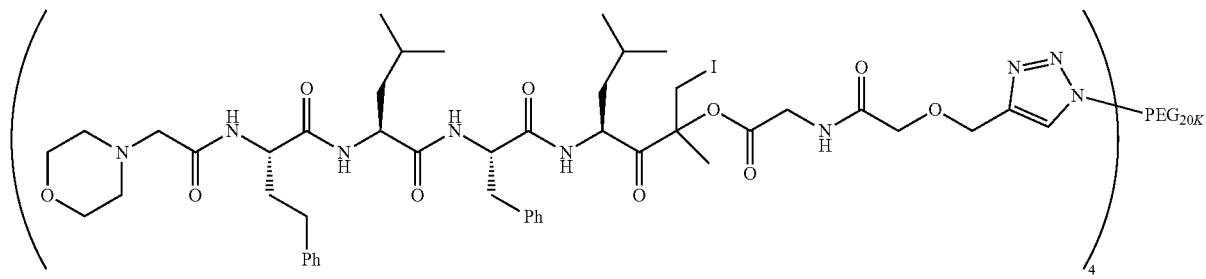

(4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 4-(2-(1-PEG$_{20K}$/4-Arm-1H-1,2,3-triazol-4-yl)ethylamino)-4-oxobutanoate

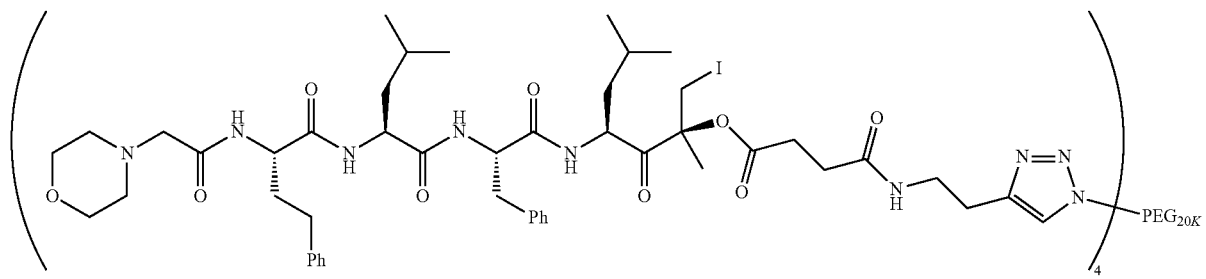

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-(but-3-yn-1-ylamino)-4-oxobutanoate and PEG$_{20k}$-(N$_3$)$_4$ (Creative PEGworks Catalog # PSB-493) were reacted following General PEGylation Conditions, Method C; PEG Loading (NMR): 3.1/4 Arms, 9.2% small molecule.

(4S,7S,10S,13S,15S)-10-Benzyl-16-iodo-7,13-diisobutyl-15-methyl-1-morpholino-2,5,8,11,14-pentaoxo-4-phenethyl-3,6,9,12-tetraazahexadecan-15-yl 4-(but-3-yn-1-ylamino)-4-oxobutanoate

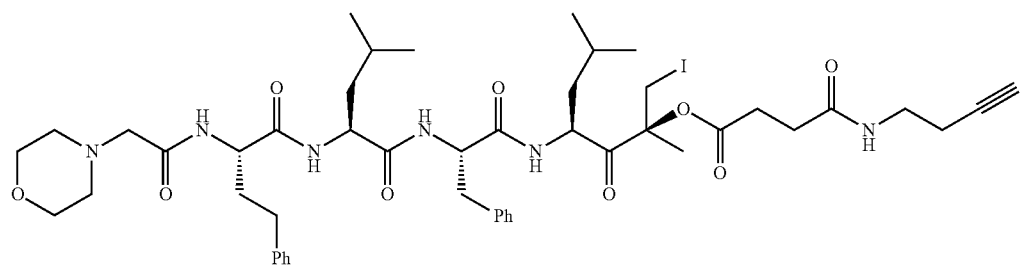 [SMILES: C#CCCNC(=O)CCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl 4-(((1-PEG₂₀ₖ/4-Arm-1H-1,2,3-triazol-4-yl)methyl)amino)-4-oxobutanoate

4-((4-Methoxybenzyl)oxy)-4-oxobutanoic Acid

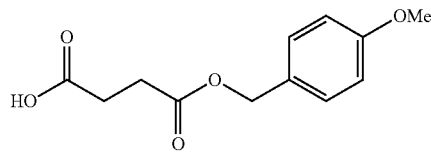 [SMILES: COc1ccc(COC(=O)CCC(=O)O)cc1]

To a solution of succinic anhydride (10 g, 0.1 mol) in CH3CN (200 mL) were added (4-methoxyphenyl)methanol (69.0 g, 0.5 mol) and DMAP (12.2 g, 0.1 mol). The reaction mixture was stirred for 3 h at about 30° C. and then diluted with water (700 mL). The resulting mixture was adjusted to pH=10 with saturated Na2CO3 solution and washed with ethyl acetate (300 mL×4) to remove an excess of (4-methoxyphenyl)methanol. The aqueous phase was adjusted to pH=2 with saturated citric acid solution and then extracted with ethyl acetate (200 mL×2). The combined extracts were dried over anhydrous Na2SO4 and concentrated to give product (21.0 g, 88% yield) as a white solid.

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl 4-methoxybenzyl Succinate (21)

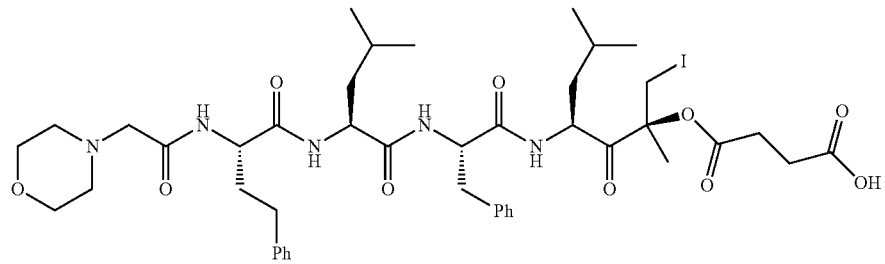

Figure 43:
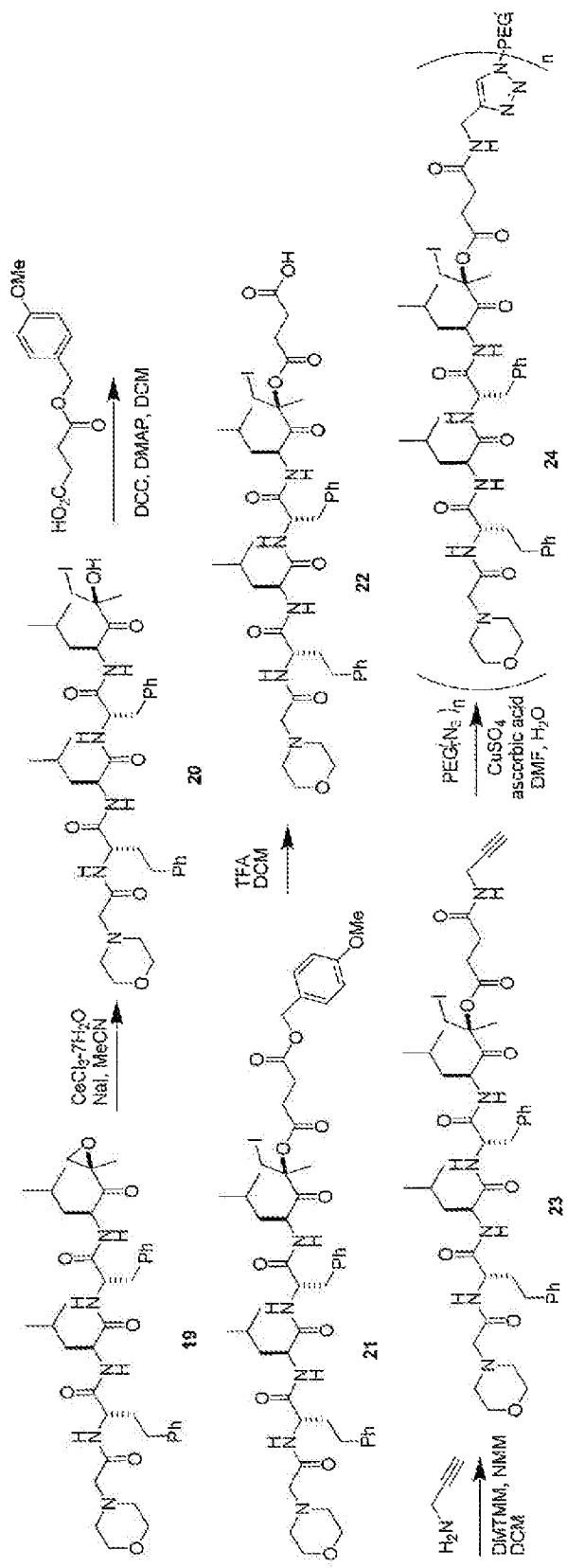
FIG. 43 is a scheme showing the synthesis of an embodiment of an iodohydrin ester prodrug of an epoxy ketone proteasome inhibitor conjugated to a multi-arm PEG.

Referring to FIG. 43, to a solution of compound (S)—N—((S)-1-(((2S,4S)-2-hydroxy-1-iodo-2,6-dimethyl-3-oxoheptan-4-yl)amino)-1-oxo-3-phenylpropan-2-yl)-4-methyl-2-((S)—N-methyl-2-(2-morpholinoacetamido)-4-phenylbutanamido)pentanamide (20, 1.5 g, 1.77 mmol) in DCM (10 mL) were added 4-((4-methoxybenzyl)oxy)-4-oxobutanoic acid (2.1 g, 8.81 mmol), DCC (1.82 g, 8.82 mmol) and DMAP (1.08 g, 8.84 mmol). The reaction mixture was stirred for 3 h at 30° C. (TLC analysis showed very little of 19 was left). The mixture was diluted with DCM (100 mL) and then filtered. The filtrate was washed with saturated citric acid solution (50 mL×2) and saturated NaHCO₃ solution (50 mL×3), dried over anhydrous Na₂SO₄ and concentrated. The residue was purified by flash column chromatography (EtOAc/DCM=1:15 to 2:1) to give product (1.7 g, 90% yield) as a yellow powder.

(4S,7S,10S,13S,15S)-10-Benzyl-15-(iodomethyl)-7,13-diisobutyl-15-methyl-1-morpholino-2,5,8,11,14,17-hexaoxa-4-phenethyl-16-oxa-3,6,9,12-tetraaza-icosan-20-oic Acid (22)

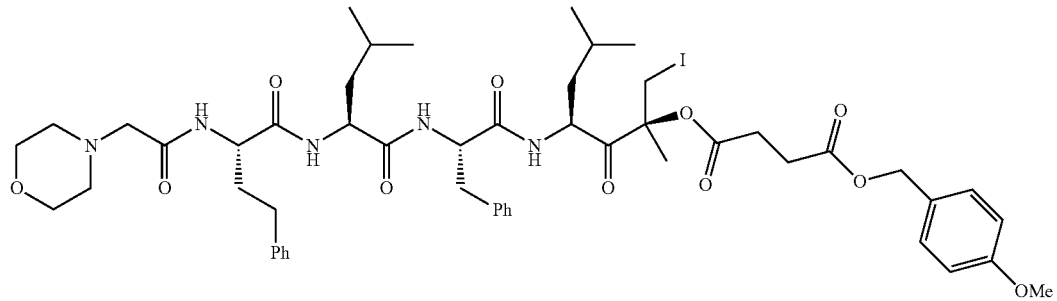 [SMILES: COc1ccc(COC(=O)CCC(=O)O[C@](C)(CI)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)cc1]

Referring to FIG. 43, TFA (6 mL) was added dropwise to a solution of compound (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 4-methoxybenzyl succinate (21, 1.7 g, 1.59 mmol) in DCM (30 mL) at 0° C. and the reaction mixture was allowed to warm to room temperature and stirred for 0.5 h. TFA was removed under reduced pressure and the residue was dissolved in DCM (50 mL). The resulting mixture was washed with water (40 mL×3) and brine (50 mL), dried over anhydrous Na2SO4 and concentrated to give product (quantitative without further purification).

(4S,7S,10S,13S,15S)-10-Benzyl-16-iodo-7,13-di-isobutyl-15-methyl-1-morpholino-2,5,8,11,14-pentaoxo-4-phenethyl-3,6,9,12-tetraazahexadecan-15-yl 4-oxo-4-(prop-2-yn-1-ylamino)butanoate (23)

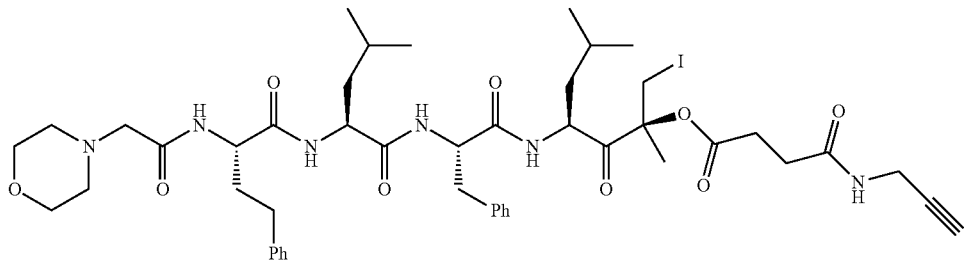 [SMILES: C#CCNC(=O)CCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Referring to FIG. 43, to a solution of compound (4S,7S,10S,13S,15S)-10-benzyl-15-(iodomethyl)-7,13-diisobutyl-15-methyl-1-morpholino-2,5,8,11,14,17-hexaoxo-4-phenethyl-16-oxa-3,6,9,12-tetraazaicosan-20-oic acid (4, 0.95 g, 1.0 mmol) in DCM (15 mL) at 0° C. were added prop-2-yn-1-amine (88 mg, 1.6 mmol) and 4-(4,6-dimethoxy-1,3,5-triazin-2-yl)-4-methylmorpholinium chloride (587 mg, 2.1 mmol). The mixture was adjusted to pH=7~8 with NMM (0.1 N in DCM) immediately and then allowed to warm to room temperature and stirred for 1 h (TLC analysis showed starting material disappeared). The mixture was diluted with DCM (60 mL) and the resulting mixture was washed with saturated citric acid solution (40 mL×2) and saturated NaHCO3 solution (40 mL×2), dried over anhydrous Na2SO4 and concentrated. The residue was purified by flash column chromatography (EtOAc:DCM=1:15 to 3:2) to give product (650 mg, 66% yield) as a white solid.

Referring to FIG. 43, (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 4-oxo-4-(prop-2-yn-1-ylamino)butanoate and $PEG_{20K}$-$(N_3)_4$ (Creative PEGworks Catalog # PSB-493) were reacted following General PEGylation Conditions, Method C to give product 24.

(4S,7S,10S,3S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl 3-(1-$PEG_{20K}$/4-Arm-1H-1,2,3-triazol-4-yl)benzoate

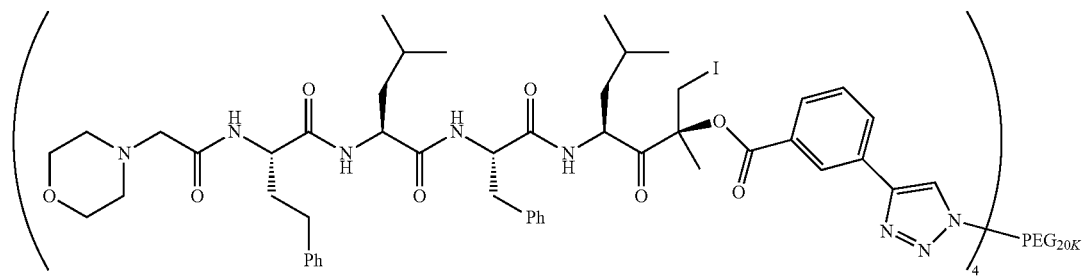

(4S,7S,10S,13S,15S)-10-benzyl-16-iodo-7,13-di-
isobutyl-15-methyl-1-morpholino-2,5,8,11,14-pen-
taoxo-4-phenethyl-3,6,9,12-tetraazahexadecan-15-yl
2-(3-(1-PEG$_{20K}$/4-Arm-1H-1,2,3-triazol-4-yl)pro-
panamido)acetate

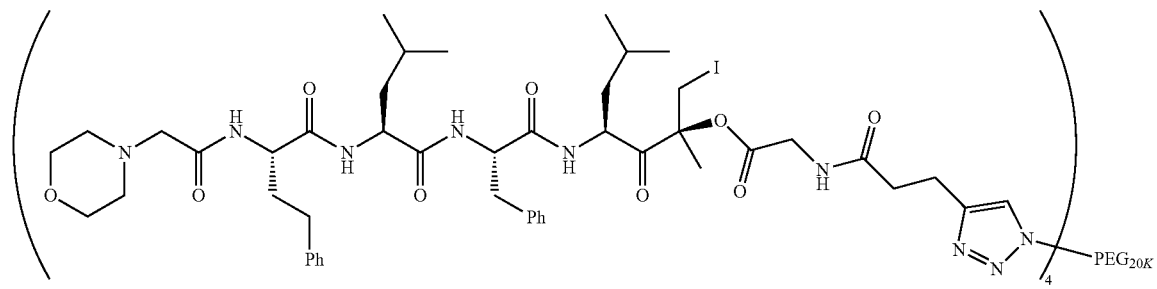

(4S,7S,10S,13S,15S)-10-Benzyl-16-iodo-7,13-diisobu-
tyl-15-methyl-1-morpholino-2,5,8,11,14-pentaoxo-4-phen-
ethyl-3,6,9,12-tetraazahexadecan-15-yl 2-(pent-4-ynamido)
acetate and PEG$_{20k}$-(N$_3$)$_4$ (Creative PEGworks Catalog #
PSB-493) were reacted following General PEGylation Con-
ditions, Method C; PEG Loading (NMR): 2.7/4 Arms, 8.0%
small molecule.

(4S,7S,10S,13S,15S)-10-Benzyl-16-iodo-7,13-di-
isobutyl-15-methyl-1-morpholino-2,5,8,11,14-pen-
taoxo-4-phenethyl-3,6,9,12-tetraazahexadecan-15-yl
2-(pent-4-ynamido)acetate

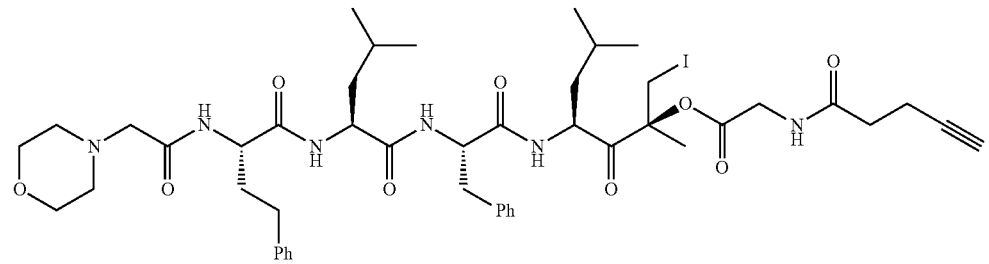 [SMILES: C#CCCC(=O)NCC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(4S,7S,10S,13S)-10-benzyl-16-iodo-7,13-diisobutyl-
15-methyl-1-morpholino-2,5,8,11,14-pentaoxo-4-
phenethyl-3,6,9,12-tetraazahexadecan-15-yl 2-(2-(1-
PEG$_{20K}$/4-Arm-1H-1,2,3-triazol-4-yl)acetamido)
acetate

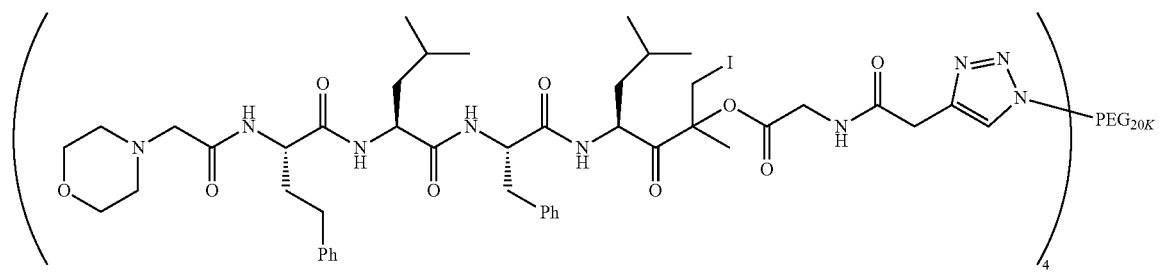

(4S,7S,10S,13S)-10-benzyl-16-iodo-7,13-diisobutyl-15-methyl-1-morpholino-2,5,8,11,14-pentaoxo-4-phenethyl-3,6,9,12-tetraazahexadecan-15-yl (1-PEG$_{20K}$/8-Arm Hexaglycerin-1H-1,2,3-triazol-4-yl)methyl Carbonate

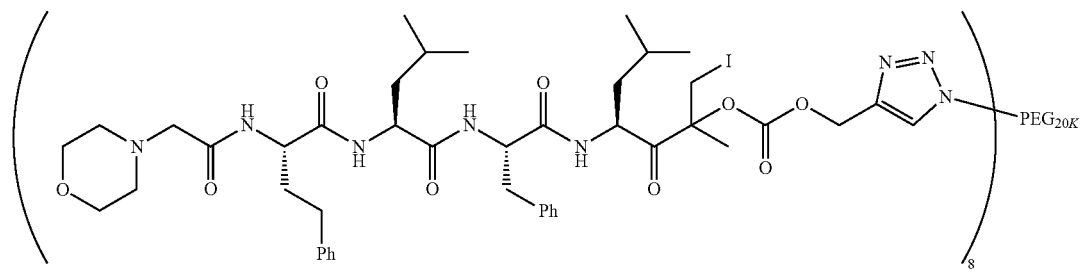

(4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl prop-2-yn-1-yl Carbonate

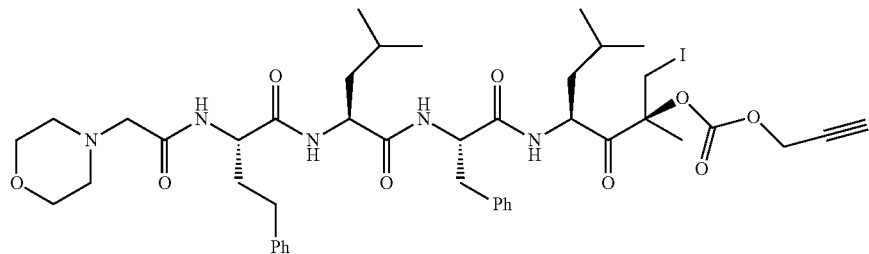 [SMILES: C#CCOC(=O)O[C@](C)(CI)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

(2S)—N—((S)-1-((2S,4S)-2-hydroxy-1-iodo-2,6-dimethyl-3-oxoheptan-4-ylcarbamoyl)-2-phenylethyl)-2-((S)-2-(2-morpholinoacetamido)-4-phenylbutanamido)-4-methylpentanamide (1.18 g, 1.39 mmol) was dissolved in dichloromethane. DMAP (1.92 g, 13.9 mmol) was added and the mixture cooled to 0° C. Phosgene solution (20% in toluene, 3.75 mL, 5.52 mmol) was added dropwise and the reaction stirred at 0° C. for 30 minutes. Propargyl alcohol (0.802 ml, 13.9 mmol) was added and the mixture stirred at room temperature for 16 hours. The reaction was diluted with 200 mL dichloromethane, washed with 1N HCl (50 ml) and brine (50 mL), dried over anhydrous MgSO$_4$ and concentrated under reduced pressure. The residue was purified by prep HPLC to afford 230 mg of white solid. $^1$H NMR (DMSO-d$_6$): δ 8.37 (d, J=8.5 Hz, 1H), 8.18 (s, 1H), 8.12 (d, J=8.0 Hz, 1H), 8.03 (d, J=8.5 Hz, 1H), 7.88 (d, J=8.5 Hz, 1H), 7.28-7.08 (m, 10H), 5.19 (s, 2H), 4.89-4.83 (m, 1H), 4.57-4.51 (m, 4H), 4.37-4.28 (m, 2H), 3.87-3.79 (m, 4H), 3.65-3.31 (m, 793H), 2.96-2.90 (m, 4H), 2.80-2.76 (m, 1H), 2.50-2.42 (m, 6H), 1.89-75 (m, 2H), 1.58-1.30 (m, 9H), 0.86-0.74 (m, 12H).

Sulfonate Carbonates and Sulfonate Esters (4S,7S,10S,13S)-10-benzyl-7,13-diisobutyl-15-methyl-15-(((1-PEG$_{20K}$/4-Arm-1H-1,2,3-triazol-4-yl)methoxy)carbonyloxy)-1-morpholino-2,5,8,11,14-pentaoxo-4-phenethyl-3,6,9,12-tetraazahexadecan-16-yl Methanesulfonate

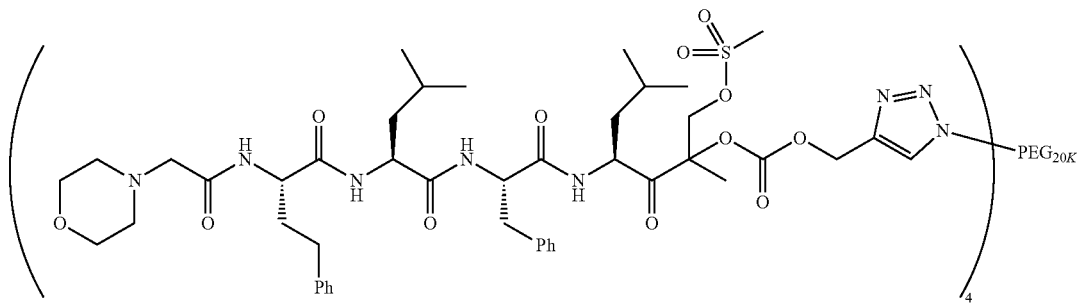

(4S,7S,10S,13S)-10-Benzyl-7,13-diisobutyl-15-methyl-1-morpholino-2,5,8,11,14-pentaoxo-4-phenethyl-15-(((prop-2-yn-1-yloxy)carbonyl)oxy)-3,6,9,12-tetraazahexadecan-16-yl methanesulfonate and PEG$_{20K}$-(N$_3$)$_4$ (Creative PEGworks Catalog # PSB-493) were reacted following General PEGylation Conditions, Method C; $^1$H NMR (DMSO-d$_6$): δ 8.36-8.32 (m, 1H), 8.16-7.84 (m, 4H), 7.26-7.06 (m, 10H), 5.21-5.09 (m, 2H), 4.87-4.82 (m, 1H), 4.64-4.51 (m, 6H), 4.38-4.02 (m, 4H), 3.82-3.79 (m, 2H), 3.65-3.35 (m, 463H), 3.01-2.75 (m, 4H), 2.47-2.39 (m, 2H), 1.91-1.71 (m, 2H), 1.65-1.45 (m, 5H), 1.41-1.30 (m, 2H), 0.86-0.77 (m, 12H).

(4S,7S,10S,13S)-10-Benzyl-7,13-diisobutyl-15-methyl-1-morpholino-2,5,8,11,14-pentaoxo-4-phenethyl-15-(((prop-2-yn-1-yloxy)carbonyl)oxy)-3,6,9,12-tetraazahexadecan-16-yl Methanesulfonate

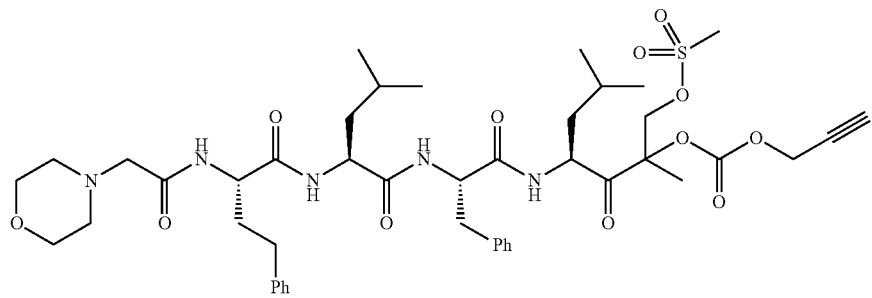 [SMILES: C#CCOC(=O)OC(C)(COS(C)(=O)=O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Prepared according to the procedure for (4S,7S,10S,13S,15S)-10-benzyl-16-iodo-7,13-diisobutyl-15-methyl-1-morpholino-2,5,8,11,14-pentaoxo-4-phenethyl-3,6,9,12-tetraazahexadecan-15-yl prop-2-yn-1-yl carbonate, except using propargyl alcohol and (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl methanesulfonate.

(4S,7S,10S,13S)-10-benzyl-15-(ethoxycarbonyloxy)-7,13-diisobutyl-15-methyl-1-morpholino-2,5,8,11,14-pentaoxo-4-phenethyl-3,6,9,12-tetraazahexadecan-16-yl 3-((1-PEG$_{20K}$/4-Arm-1H-1,2,3-triazol-4-yl)methylcarbamoyl)benzenesulfonate

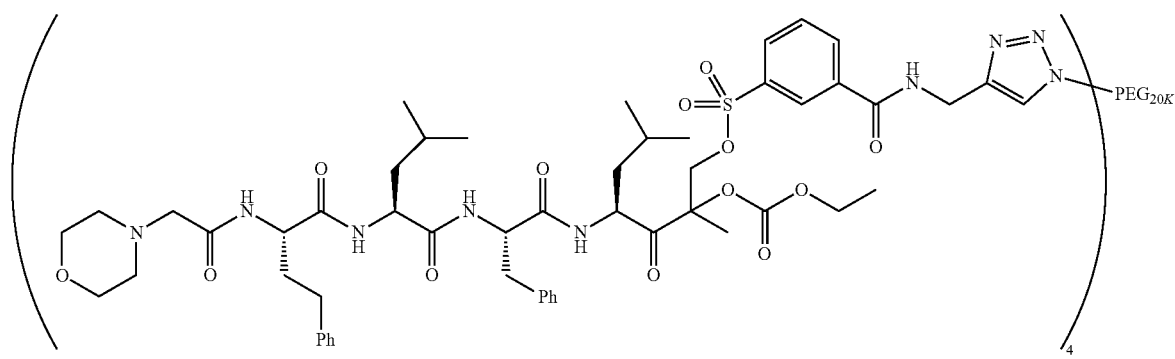

(4S,7S,10S,13S)-10-Benzyl-15-((ethoxycarbonyl)oxy)-7,13-diisobutyl-15-methyl-1-morpholino-2,5,8,11,14-pentaoxo-4-phenethyl-3,6,9,12-tetraazahexadecan-16-yl 3-(prop-2-yn-1-ylcarbamoyl)benzenesulfonate and PEG$_{20k}$-(N$_3$)$_4$ (Creative PEGworks Catalog # PSB-493) were reacted following General PEGylation Conditions, Method C; $^1$H NMR (DMSO-d$_6$): δ 9.42 (t, J=7.0 Hz, 1H), 8.41 (t, J=2.0 Hz, 1H), 8.29 (d, J=8 Hz, 1H), 8.09-8.05 (m, 4H), 7.98 (s, 1H), 7.79 (t, J=8 Hz, H), 7.29-7.05 (m, 11H), 4.82-4.77 (m, 1H), 4.54-4.48 (m, 5H), 4.41-4.29 (m, 3H), 4.05-3.94 (m, 5H), 3.08 (t, J=5 Hz, 3H), 3.69-3.46 (m, 507H), 2.93-2.87 (m, 1H), 2.76-2.70 (m, 1H), 1.92-1.73 (m, 2H), 1.60-1.26 (m, 9H), 1.16 (t, J=8.5 Hz, 3H), 0.86-0.75 (m, 12H); PEG Loading (NMR): 3.6/4 Arms, 10.6% small molecule.

(4S,7S,10S,13S)-10-benzyl-7,13-diisobutyl-15-methyl-16-(3-((1-PEG$_{20K}$/4-Arm-1H-1,2,3-triazol-4-yl)methylcarbamoyl)phenylsulfonyloxy)-1-morpholino-2,5,8,11,14-pentaoxo-4-phenethyl-3,6,9,12-tetraazahexadecan-15-yl 4-(2-amino-2-oxoethylamino)-4-oxobutanoate

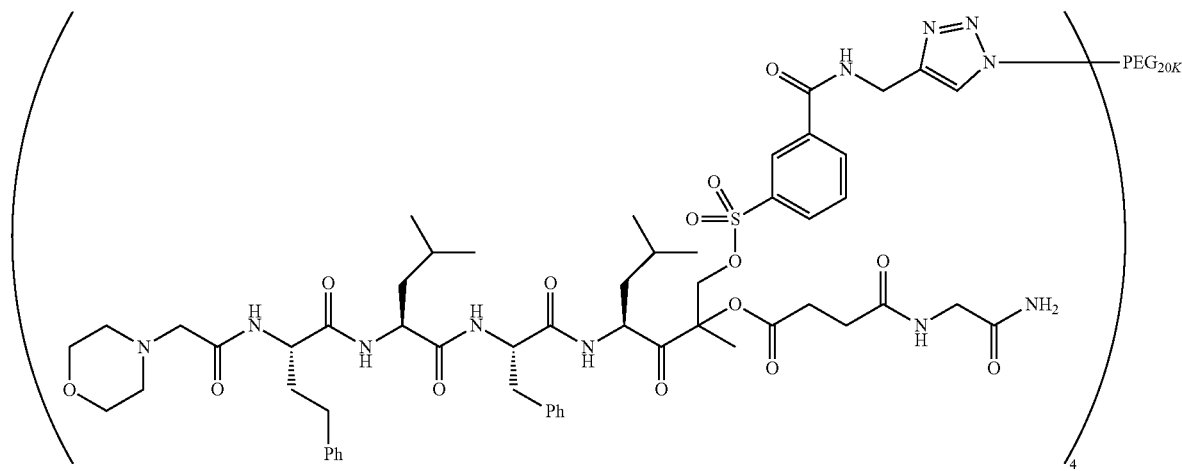

(4S,7S,10S,13S)-10-Benzyl-7,13-diisobutyl-15-methyl-1-morpholino-2,5,8,11,14-pentaoxo-4-phenethyl-16-(((3-(prop-2-yn-1-ylcarbamoyl)phenyl)sulfonyl)oxy)-3,6,9,12-tetraazahexadecan-15-yl 4-((2-amino-2-oxoethyl)amino)-4-oxobutanoate and PEG$_{20k}$-(N$_3$)$_4$ (Creative PEGworks Catalog # PSB-493) were reacted following General PEGylation Conditions, Method C; PEG Loading (NMR): 0.78/4 Arms, 2.3% small molecule.

(4S,7S,10S,13S)-10-Benzyl-7,13-diisobutyl-15-
methyl-1-morpholino-2,5,8,11,14-pentaoxo-4-phen-
ethyl-16-(((3-(prop-2-yn-1-ylcarbamoyl)phenyl)
sulfonyl)oxy)-3,6,9,12-tetraazahexadecan-15-yl
4-((2-amino-2-oxoethyl)amino)-4-oxobutanoate

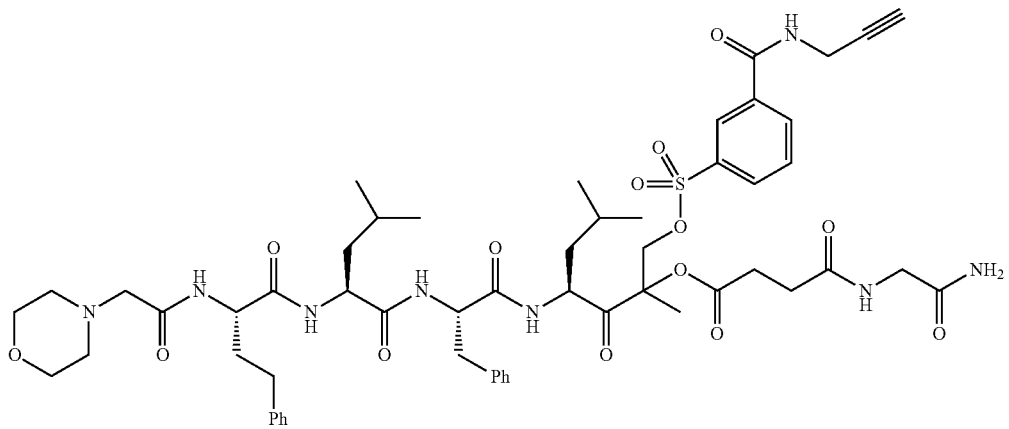 [SMILES: C#CCNC(=O)c1cccc(S(=O)(=O)OCC(C)(OC(=O)CCC(=O)NCC(N)=O)C(=O)[C@H](CC(C)C)NC(=O)[C@H](Cc2ccccc2)NC(=O)[C@H](CC(C)C)NC(=O)[C@H](CCc2ccccc2)NC(=O)CN2CCOCC2)c1]

(7S,10S,13S,16S)-10-benzyl-7,13-diisobutyl-5-
methyl-19-morpholino-6,9,12,15,18-pentaoxo-16-
phenethyl-3-oxa-2-thia-2,2-dioxo-8,11,14,17-tet-
raazanonadecane-5-yl 4-((1-PEG$_{20K}$/4-Arm-1H-1,2,
3-triazol-4-yl)methylamino)-4-oxobutanoate

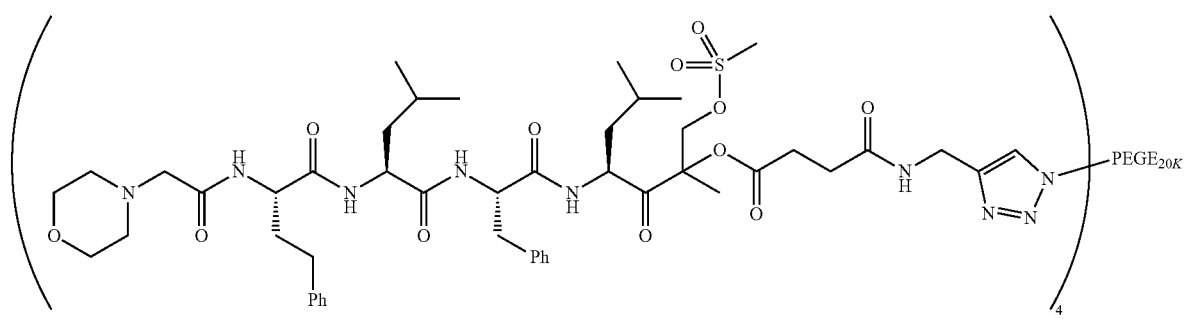

(4S,7S,10S,13S)-10-Benzyl-7,13-diisobutyl-15-methyl-
1-morpholino-2,5,8,11,14-pentaoxo-15-(4-oxo-4-(prop-2-
yn-1-ylamino)butanamido)-4-phenethyl-3,6,9,12-tetraaza-
hexadecan-16-yl methanesulfonate and PEG$_{20K}$-(N$_3$)$_4$
(Creative PEGworks Catalog # PSB-493) were reacted
following General PEGylation Conditions, Method C; $^1$H
NMR (DMSO-d$_6$): δ 8.43-7.96 (m, 5H), 7.88-7.86 (m, 1H),
7.26-7.04 (m, 10H), 4.86-4.80 (m, 1H), 4.59-4.26 (m, 8H),
3.82-3.78 (m, 4H), 3.66-3.35 (m, 598H), 3.20 (s, 2H),
2.99-2.91 (m, 2H), 2.80-2.59 (m, 2H), 2.47-2.40 (m, 6H),
1.90-1.72 (m, 2H), 1.62-1.30 (m, 9H), 0.86-0.77 (m, 12H);
PEG Loading (NMR): 2.8/4 Arms, 8.4% small molecule.

(4S,7S,10S,13S)-10-Benzyl-7,13-diisobutyl-15-methyl-1-morpholino-2,5,8,11,14-pentaoxo-15-(4-oxo-4-(prop-2-yn-1-ylamino)butanamido)-4-phenethyl-3,6,9,12-tetraazahexadecan-16-yl Methanesulfonate

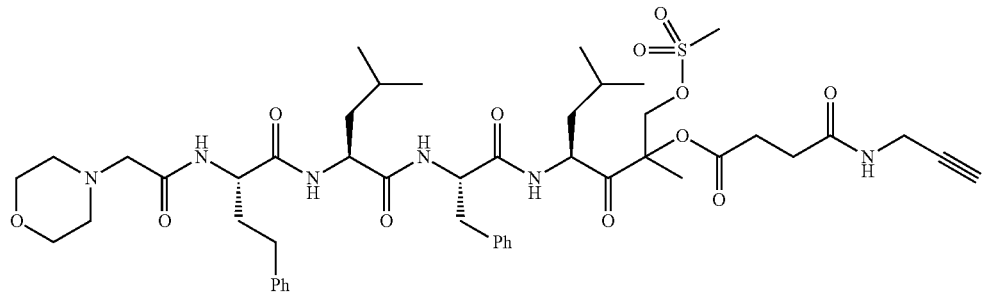 [SMILES: C#CCNC(=O)CCC(=O)OC(C)(COS(C)(=O)=O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Prepared according to methods described above, using 4-oxo-4-(prop-2-yn-1-ylamino)butanoic acid and (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl methanesulfonate.

(4S,7S,10S,13S)— O-benzyl-7,13-diisobutyl-15-methyl-15-(((1-PEG$_{20K}$/4-Arm-1H-1,2,3-triazol-4-yl)methoxy)carbonyloxy)-1-morpholino-2,5,8,11,14-pentaoxo-4-phenethyl-3,6,9,12-tetraazahexadecan-16-yl 4-methylbenzenesulfonate

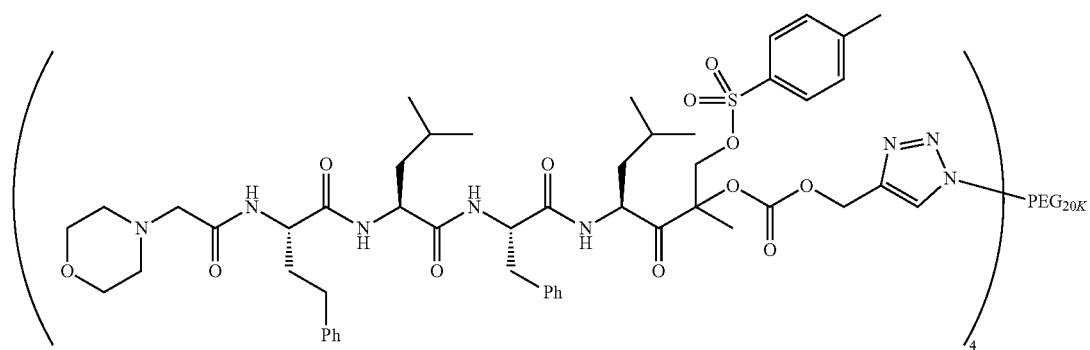

(4S,7S,10S,13S)-10-Benzyl-7,13-diisobutyl-15-methyl-1-morpholino-2,5,8,11,14-pentaoxo-4-phenethyl-15-(((prop-2-yn-1-yloxy)carbonyl)oxy)-3,6,9,12-tetraazahexadecan-16-yl 4-methylbenzenesulfonate and PEG$_{20K}$-(N$_3$)$_4$ (Creative PEGworks Catalog # PSB-493) were reacted following General PEGylation Conditions, Method C; $^1$H NMR [(CD$_3$)$_2$SO] δ 8.37-8.26 (m, 1H), 8.16-8.11 (m, 1H), 8.04-7.99 (m, 2H), 7.92-7.85 (m, 11H), 7.80-7.75 (m, 2H), 7.52-7.45 (m, 2H), 7.26-7.08 (m, 10H), 5.14-5.06 (m, 1H), 4.80-4.73 (m, 1H), 4.55-4.46 (m, 4H), 4.40-4.29 (m, 2H), 3.82-3.78 (m, 4H), 3.66-3.35 (m, 456H), 3.00-2.72 (m, 4H), 2.43-2.38 (m, 6H), 1.90-1.75 (m, 2H), 1.58-1.23 (m, 9H), 0.85-0.72 (m, 12H); PEG Loading (NMR): 3.5/4 Arms, 10.4% small molecule.

(4S,7S,10S,13S)-10-Benzyl-7,13-diisobutyl-15-methyl-1-morpholino-2,5,8,11,14-pentaoxo-4-phenethyl-15-(((prop-2-yn-1-yloxy)carbonyl)oxy)-3,6,9,12-tetraazahexadecan-16-yl 4-methylbenzenesulfonate

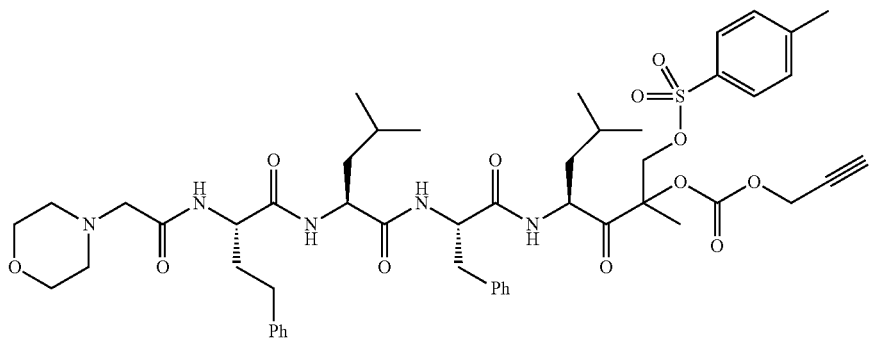 [SMILES: C#CCOC(=O)OC(C)(COS(=O)(=O)c1ccc(C)cc1)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Prepared according to procedures described above, from propargyl alcohol and (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl benzenesulfonate.

(4S,7S,10S,13S)-10-benzyl-7,13-diisobutyl-15-methyl-1-morpholino-2,5,8,11,14-pentaoxo-4-phenethyl-16-(tosyloxy)-3,6,9,12-tetraazahexadecan-15-yl 4-((1-PEG$_{20K}$/4-Arm-1H-1,2,3-triazol-4-yl)methylamino)-4-oxobutanoate

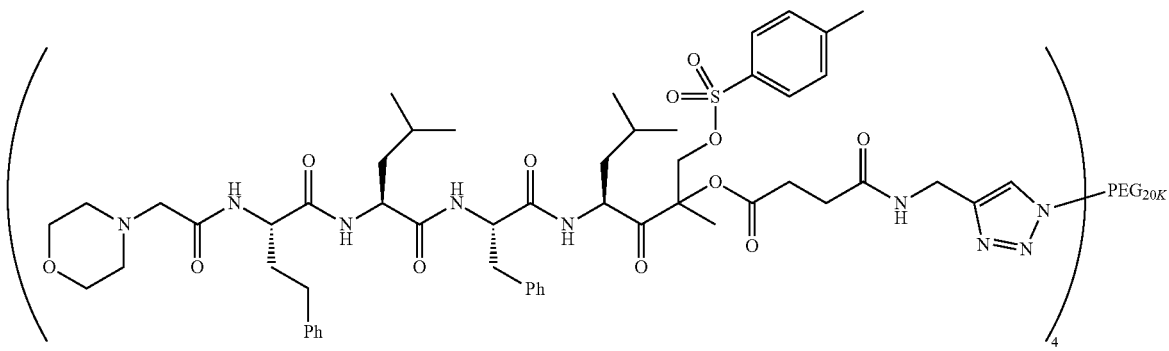

(4S,7S,10S,13S)-10-Benzyl-7,3-diisobutyl-15-methyl-1-morpholino-2,5,8,11,14-pentaoxo-4-phenethyl-16-(tosyloxy)-3,6,9,12-tetraazahexadecan-15-yl 4-oxo-4-(prop-2-yn-1-ylamino)butanoate and PEG$_{20K}$-(N$_3$)$_4$ (Creative PEGworks Catalog # PSB-493) were reacted following General PEGylation Conditions, Method C; $^1$H NMR (DMSO-d$_6$): δ 8.41-7.95 (m, 5H), 7.86-7.73 (m, 3H), 7.46-7.42 (m, 2H), 7.26-7.10 (m, 10H), 5.15-5.10 (m, 1H), 4.77-4.70 (m, 1H), 4.58-4.43 (m, 4H), 4.37-4.21 (m, 4H), 4.04 (d, J=8.5 Hz, 1H), 3.97 (d, J=8.5 Hz, 1H), 3.78-3.75 (m, 4H), 3.64-3.30 (m, 513H), 3.00-2.71 (m, 4H), 2.45-2.27 (m, 9H), 1.91-1.73 (m, 2H), 1.65-1.02 (m, 9H), 0.88-0.72 (m, 12H); PEG Loading (NMR): 3.2/4 Arms, 9.4% small molecule.

(4S,7S,10S,13S)-10-Benzyl-7,13-diisobutyl-15-methyl-1-morpholino-2,5,8,11,14-pentaoxo-4-phenethyl-16-(tosyloxy)-3,6,9,12-tetraazahexadecan-15-yl 4-oxo-4-(prop-2-yn-1-ylamino)butanoate 2-((S)-2-(2-morpholinoacetamido)-4-phenylbutanamido)pentanamide (19.5 mg, 0.024 mmol) and 4-arm 20K PEG azide (104.0 mg, 0.0051 mmol) was added 1.2 mL of DMF and the resultant slurry was stirred at RT. In a separate vial a mixture of $Cu(SO_4)\cdot 5H_2O$ (6.1 mg, 0.024 mmol) and

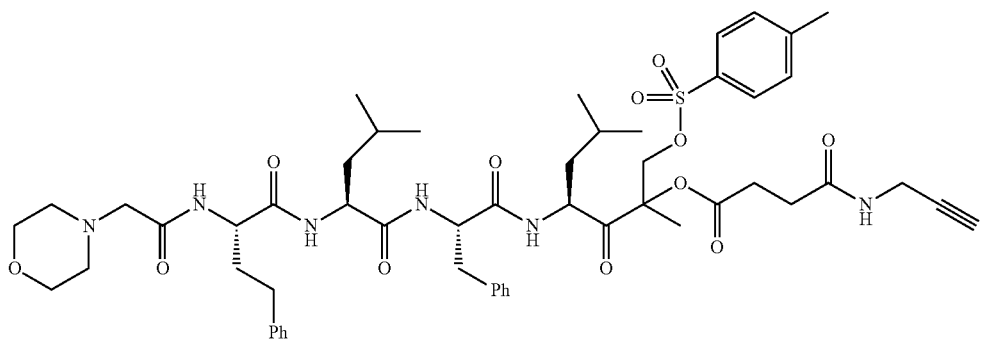 [SMILES: C#CCNC(=O)CCC(=O)OC(C)(COS(=O)(=O)c1ccc(C)cc1)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

Prepared according to procedures described above, from 4-oxo-4-(prop-2-yn-1-ylamino)butanoic acid and (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl benzenesulfonate.

Hydrazones (S)-4-Methyl-N—((S)-1-(((S,Z)-4-methyl-1-(2-(3-(1-PEG$_{20K}$/4-Arm-1H-1,2,3-triazol-4-yl)propanoyl)hydrazono)-1-((S)-2-methyloxiran-2-yl)pentan-2-yl)amino)-1-oxo-3-phenylpropan-2-yl)-2-((S)-2-(2-morpholinoacetamido)-4-phenylbutanamido)pentanamide sodium ascorbate (10.2 mg, 0.052 mmol) was dissolved in 0.7 mL water, yielding a yellow-brown solution. The copper solution was rapidly added to the stirred DMF slurry to produce a cloudy golden yellow solution that gradually clarified over time. A viscous homogeneous solution was obtained within 20 min. After 18 hr at RT the reaction mixture had transitioned to the characteristic blue-green color of Cu(II). Analysis of the mixture at this point by LC/MS showed complete consumption of alkyne starting material and the generation of a new UV-active PEG having an MS signature distinct from the starting azide. The solution was purified by direct injection onto a C8 prep LC column eluting with a neutral water/acetonitrile gradient.

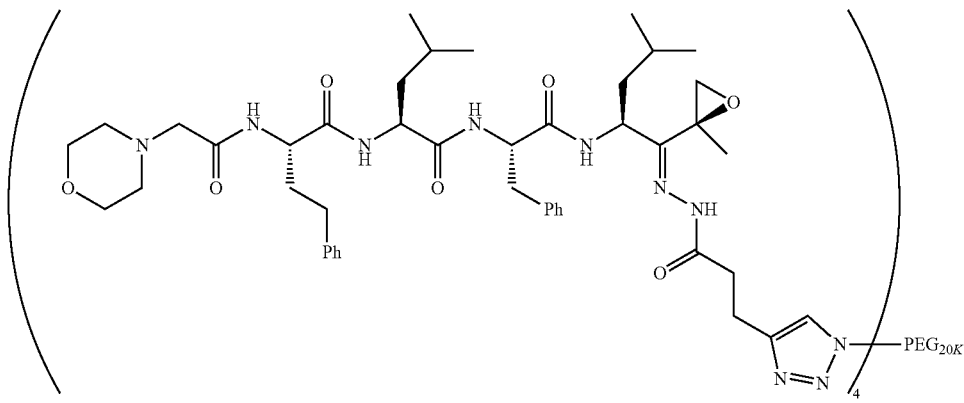

To a solid mixture of (S)-4-methyl-N—((S)-1-(((S,Z)-4-methyl-1-((S)-2-methyloxiran-2-yl)-1-(2-(pent-4-ynoyl)hydrazono)pentan-2-yl)amino)-1-oxo-3-phenylpropan-2-yl)-

The product-containing fractions were combined, concentrated to remove MeCN, and lyophilized to produce a fluffy white solid (0.017 g, 14% theory if 4-fold conjugate).

383

(S)-4-methyl-N—((S)-1-(((S,Z)-4-Methyl-1-((S)-2-methyloxiran-2-yl)-1-(2-(pent-4-ynoyl)hydrazono)pentan-2-yl)amino)-1-oxo-3-phenylpropan-2-yl)-2-((S)-2-(2-morpholinoacetamido)-4-phenylbutanamido)pentanamide

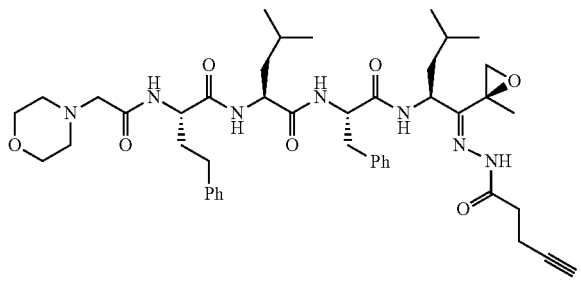 [SMILES: C#CCCC(=O)N/N=C(/[C@H](CC(C)C)NC(=O)[C@H](Cc1ccccc1)NC(=O)[C@H](CC(C)C)NC(=O)[C@H](CCc1ccccc1)NC(=O)CN1CCOCC1)[C@@]1(C)CO1]

To a solution of (S)-4-methyl-N—((S)-1-(((S)-4-methyl-1-((R)-2-methyloxiran-2-yl)-1-oxopentan-2-yl)amino)-1-oxo-33-phenylpropan-2-yl)-2-((S)-2-(2-morpholinoacetamido)-4-phenylbutanamido)pentanamide (2.0 g, 2.78 mmol) in MeOH (100 mL) were added pent-4-ynehydrazide (0.37 g, 3.34 mmol) and TFA (8 drops). The reaction mixture was stirred at room temperature for four days. LC-MS analysis showed ~40% conversion. The mixture was poured into saturated NaHCO$_3$ (120 mL) and then extracted with DCM (200 mL). The organic layer was dried over anhydrous Na$_2$SO$_4$ and concentrated under reduced pressure. The residue was purified by preparative HPLC on C-18 column using 0.1% ammonia water/acetonitrile gradient 50%-75%, 20 min) to give compound as a white powder (300 mg, 13.3% yield); $^1$H NMR (CDCl$_3$, 300 MHz): δ 7.68-7.55 (m, 1H), 7.31-6.85 (m, 12H), 6.79-6.69 (m, 1H), 4.89-4.75 (m, 2H), 4.55-4.19 (m, 2H), 3.78 (br s, 4H), 3.20-2.68 (m, 6H), 2.65-2.45 (m, 8H), 2.05 (m, 3H), 1.55 (m, 7H), 1.35 (s, 3H), 0.89 (m, 12H).

Pent-4-ynehydrazide

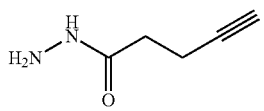

384

Methyl pent-4-ynoate (1.5 g, 13.4 mmol) was dissolved in hydrazine hydrate (85%, 10 mL). The reaction mixture was stirred at room temperature overnight. Removal of the volatiles under reduced pressure gave compound as a white solid (1.4 g, 93% yield); $^1$H NMR (CDCl$_3$, 300 MHz): δ 7.58 (br s, 1H), 3.68 (br s, 2H), 2.53 (m, 2H), 2.41 (m, 2H), 2.01 (m, 1H).

(4S,7S,10S,13S,Z)-10-Benzyl-7,13-diisobutyl-14-((S)-2-methyloxiran-2-yl)-1-morpholino-2,5,8,11,17-pentaoxo-4-phenethyl-3,6,9,12,15,16-hexaazahenicos-14-en-21-oic Acid (31)

5-Hydrazinyl-5-oxopentanoic Acid (30)

Figure 44:
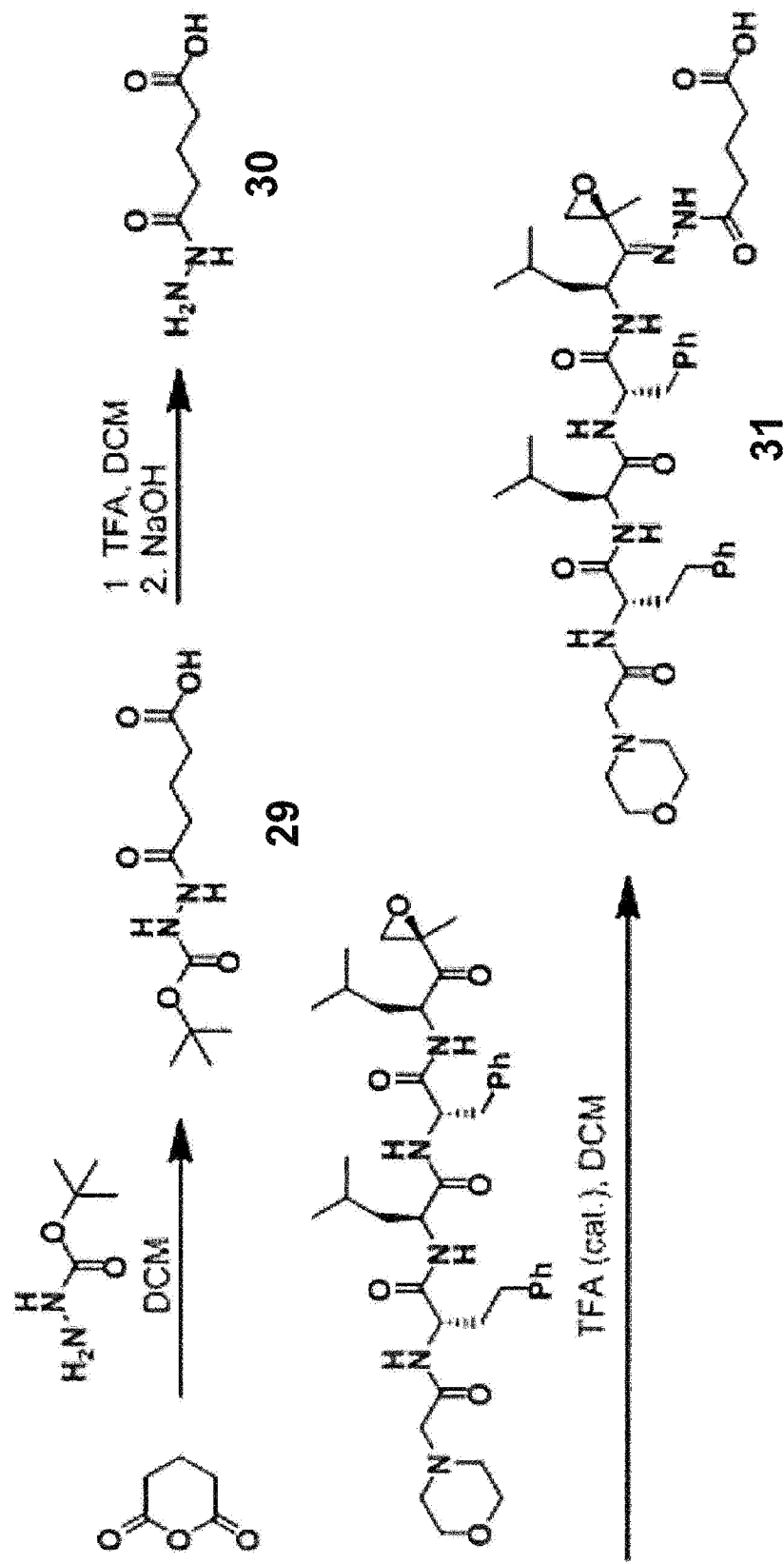
FIG. 44 is a scheme showing the synthesis of an embodiment of a precursor to an acyl hydrazone prodrug of an epoxy ketone proteasome inhibitor.

Referring to FIG. 44, glutaric anhydride (2.23 g, 2.0 mmol) and t-butyl carbazate (2.58 g, 2.0 mmol) in DCM (15 mL) were stirred at room temperature overnight. The solution was concentrated to provide a colorless thick oil (1). The oil was dissolved in DCM (10 mL), trifluoroacetic acid (10 ml) added, and the mixture stirred at room temperature for 1 hour. The solution was concentrated, the residue dissolved in water (2 ml), neutralized to pH=5 with aqueous sodium hydroxide (1N) and extracted with ethyl acetate. The extract was dried (Na$_2$SO$_4$) and evaporated to give product as foam.

Referring to FIG. 44, 5-hydrazinyl-5-oxopentanoic acid (2, 0.600 g, 4.14 mmol), (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (1.97 g, 2.74 mmol) and TFA (100 µl) in methanol (20 ml) were stirred at room temperature for 5 days. The mixture was evaporated and the residue purified by prep HPLC (C18 column, acetonitrile/water) to give product as an oil; (601 mg, 29%).

Cyclodextrin Conjugates (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 2,6-dimethyl-4-((1-β-cyclodextrin-1H-1,2,3-triazol-4-yl)methoxy)benzenesulfonate

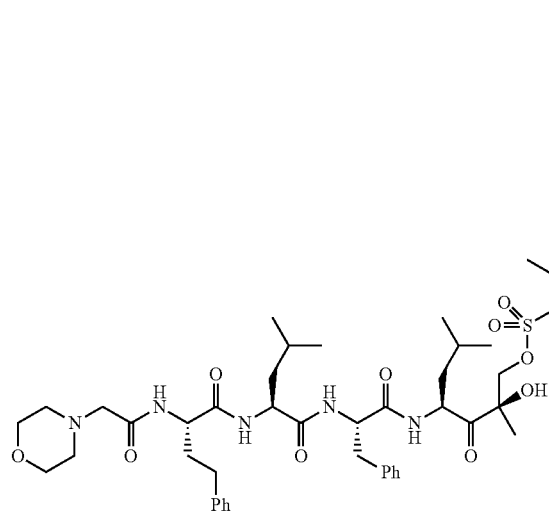
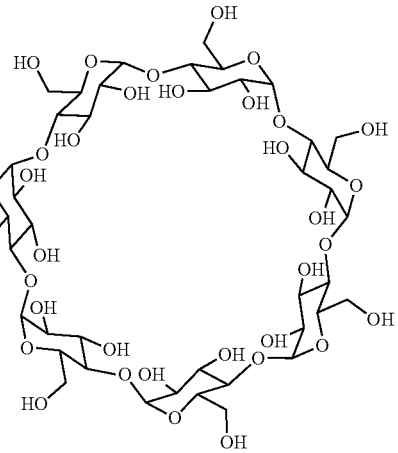

Copper sulfate (0.1 M aqueous solution, 1.8 eq.) was added to (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl 4-(allyloxy)-2,6-dimethylbenzenesulfonate (1.5 eq.), 6-monodeoxy-6-monoazido-β-cyclodextrin (1 eq.) and ascorbic acid (3.6 eq.) in DMF (7 mL/g β-cyclodextrin) and water (3.5 mL/g b-cyclodextrin) at room temperature. The resultant mixture was stirred overnight at room temperature. The crude solution was submitted for preparative HPLC on a C18 column using a 0.1% formic acid water/acetonitrile gradient (25% B→65% B over 60 min.). Fractions were combined on the basis of LC/MS analysis. Acetonitrile was largely stripped from the combined solution at 25° C. and the resultant concentrate was frozen and lyophilized.

Example 2—Cyclization Rate of PEG-Conjugates

The rate of cyclization and displacement can be controlled, for example, by tuning the electron density of the sulfonate linker group. Sulfonate linker groups having a variety of electron rich and electron poor groups listed in Table F, above, were investigated.

The release capabilities of PEG conjugates was assessed by quantitation of epoxy ketone protease inhibitors released in a basic buffer solution, by NMR, and by MALDI-TOF NMR. Some examples of PEG conjugates produced are shown in Table I.

Proteolytic cleavage of examples of PEG conjugates was assessed via non-cleavable conjugates (liver homogenate), where the remaining active epoxy ketone protease inhibitor is estimated from metabolite loss. A 2 kDa conjugate had a proteolytic $t_{1/2}$ of <1 hr; while a 20 kDa-4 Arm conjugate had a proteolytic $t_{1/2}$ of greater than 6 hrs. Very long $t_{1/2}$ conjugates can be obtained, for example with PEG 40 kDa conjugates.

Figure 7:
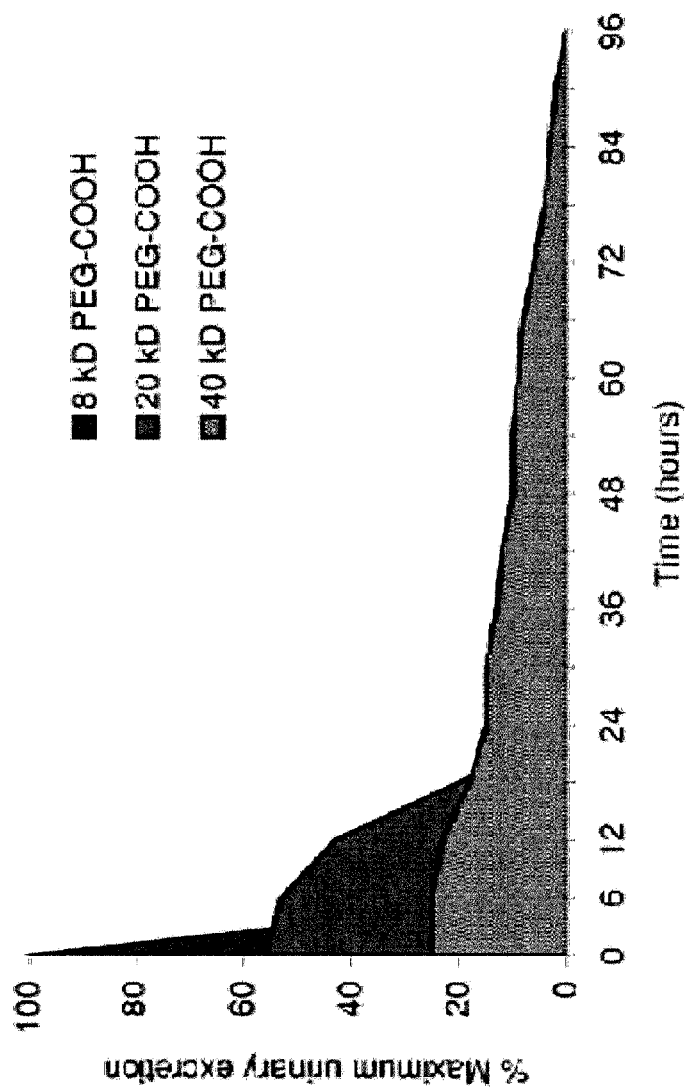
FIG. 7 is a graph showing the effect of PEG size on renal clearance.
Figure 8:
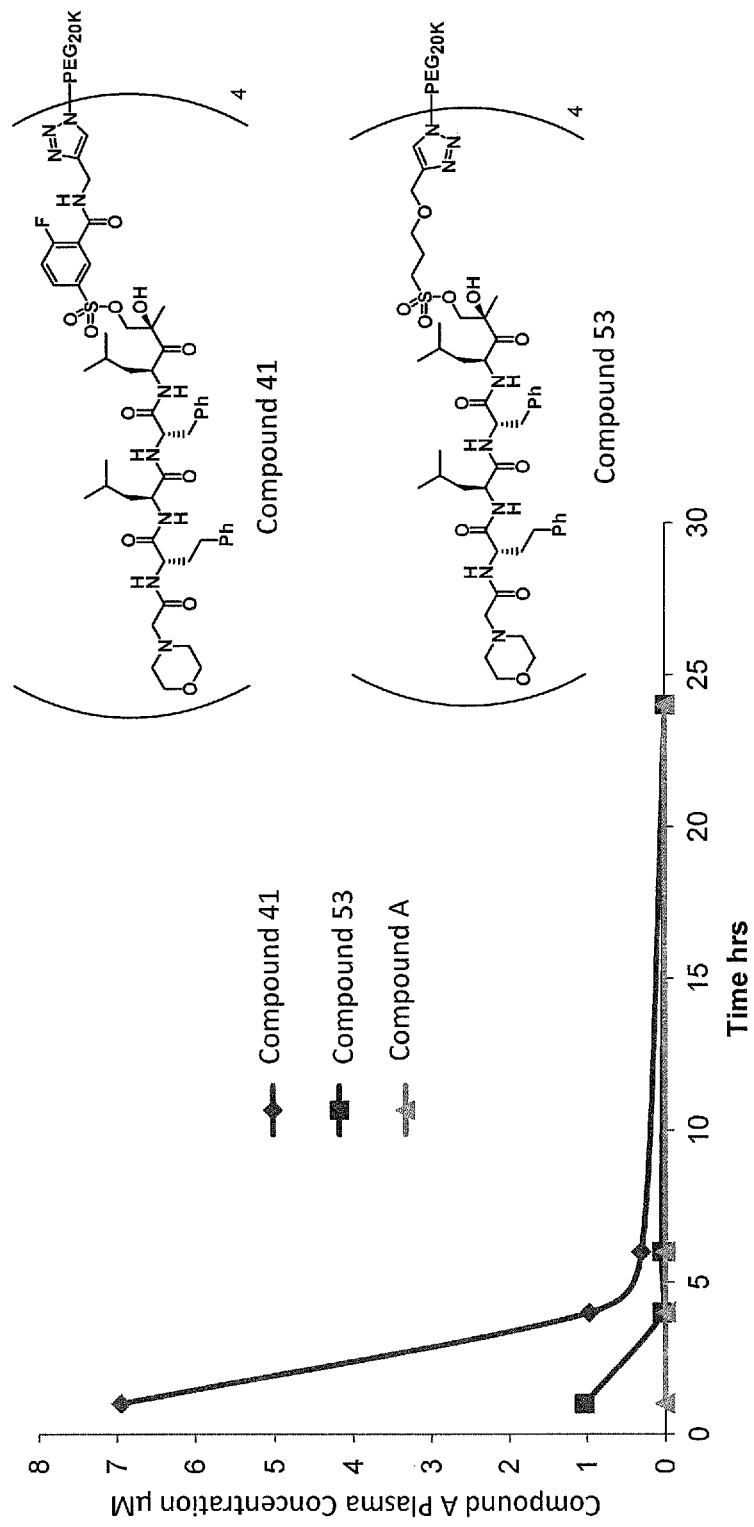
FIG. 8 is a line graph showing the plasma levels of embodiments of epoxy ketone protease inhibitor and inhibitor PEG-conjugates. High plasma concentrations were observed for PEG conjugates with significantly extended half life for PEG conjugate compound 41.
Figure 9:
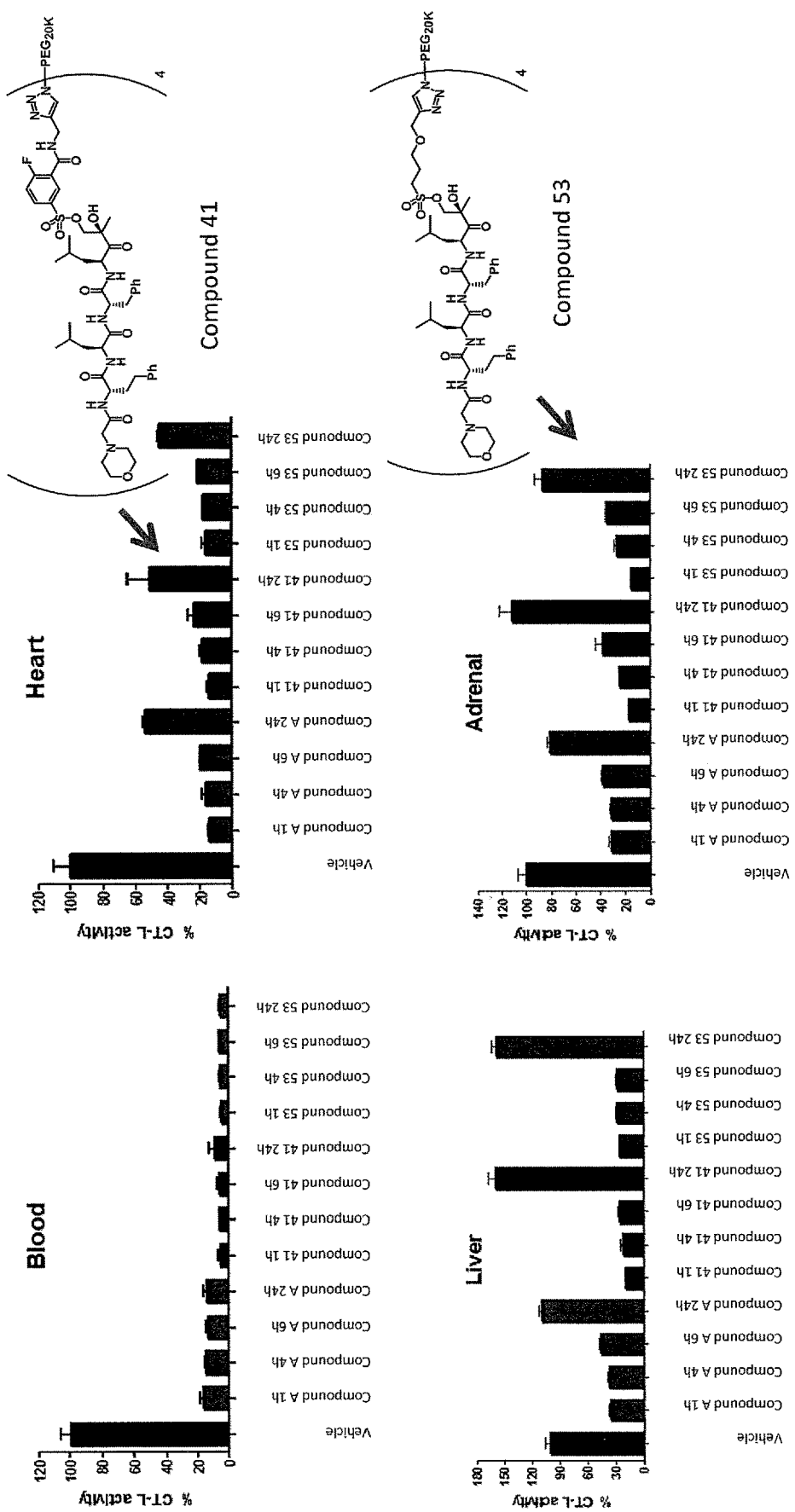
FIG. 9 is a bar graph showing in vivo mouse PD results for embodiments of epoxy ketone protease inhibitor PEG-conjugates.

PEG size can have an effect on renal clearance, as shown in FIG. 7. In some embodiments, it is believed that a PEG having a molecular weight of about or greater than 30,000 can decrease rapid renal clearance and allow for passive tumor accumulation of its corresponding PEG conjugate. For example, referring to FIG. 8, in in vivo mouse PK studies, relatively high plasma levels of an epoxy kinase protease inhibitor was observed for its corresponding PEG conjugates, and $t_{1/2}$ for conjugate 41 was significantly extended. Referring to FIG. 9, in vivo mouse PD studies showed that there was proteasome recovery even though PK studies suggested high epoxy kinase protease inhibitor levels.

TABLE I

| Entry | Structure | MW | Arms |
|---|---|---|---|
| 1 | (structure with PEG$_{20K}$) | 23916.6 | 4 |
| 2 | (structure with PEG$_{20K}$) | 24232.8 | 4 |

Example 3—Properties of PEG Conjugates

Figure 5:
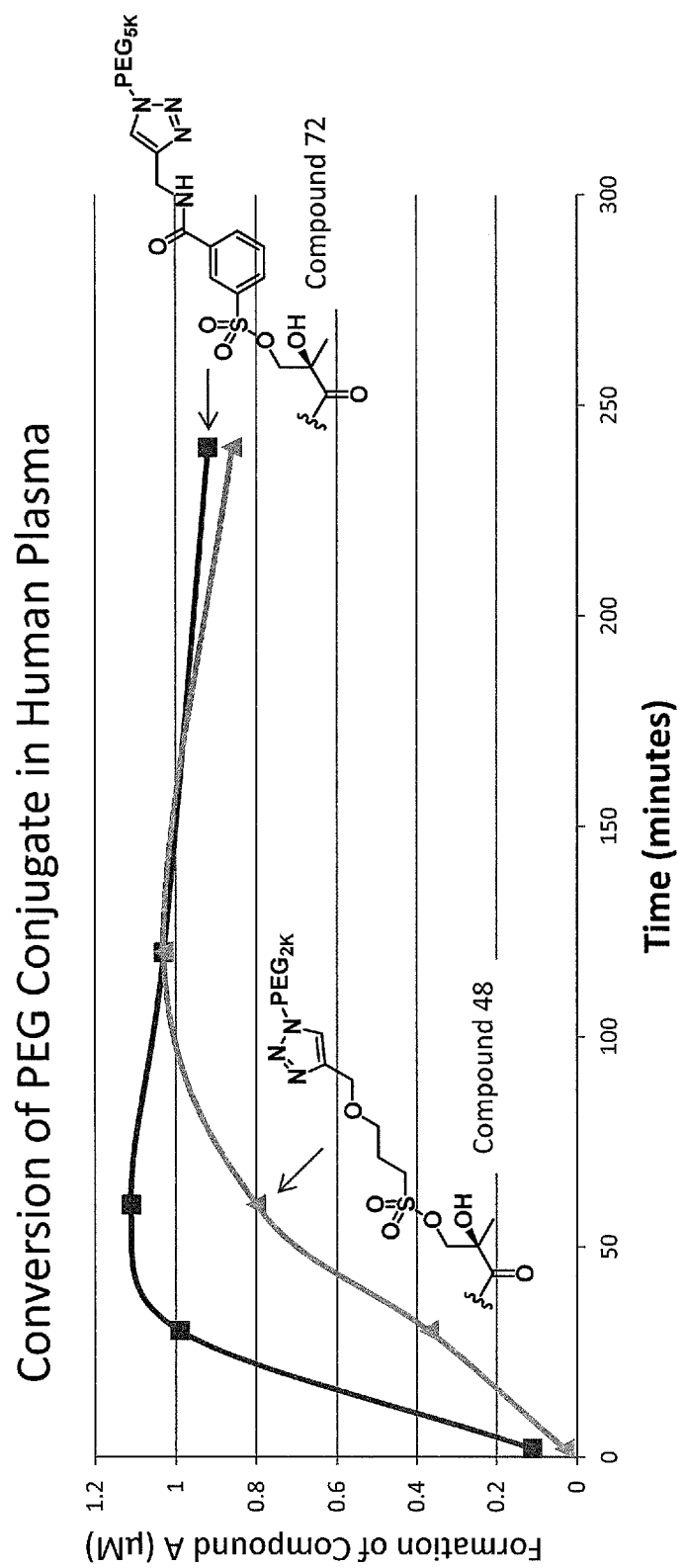
FIG. 5 is a line graph showing rates of re-formation of an active epoxy ketone protease inhibitor from embodiments of epoxy ketone protease inhibitor prodrugs in human plasma, where the re-formation rate is adjustable by tuning a linker group's electron density.
Figure 6:
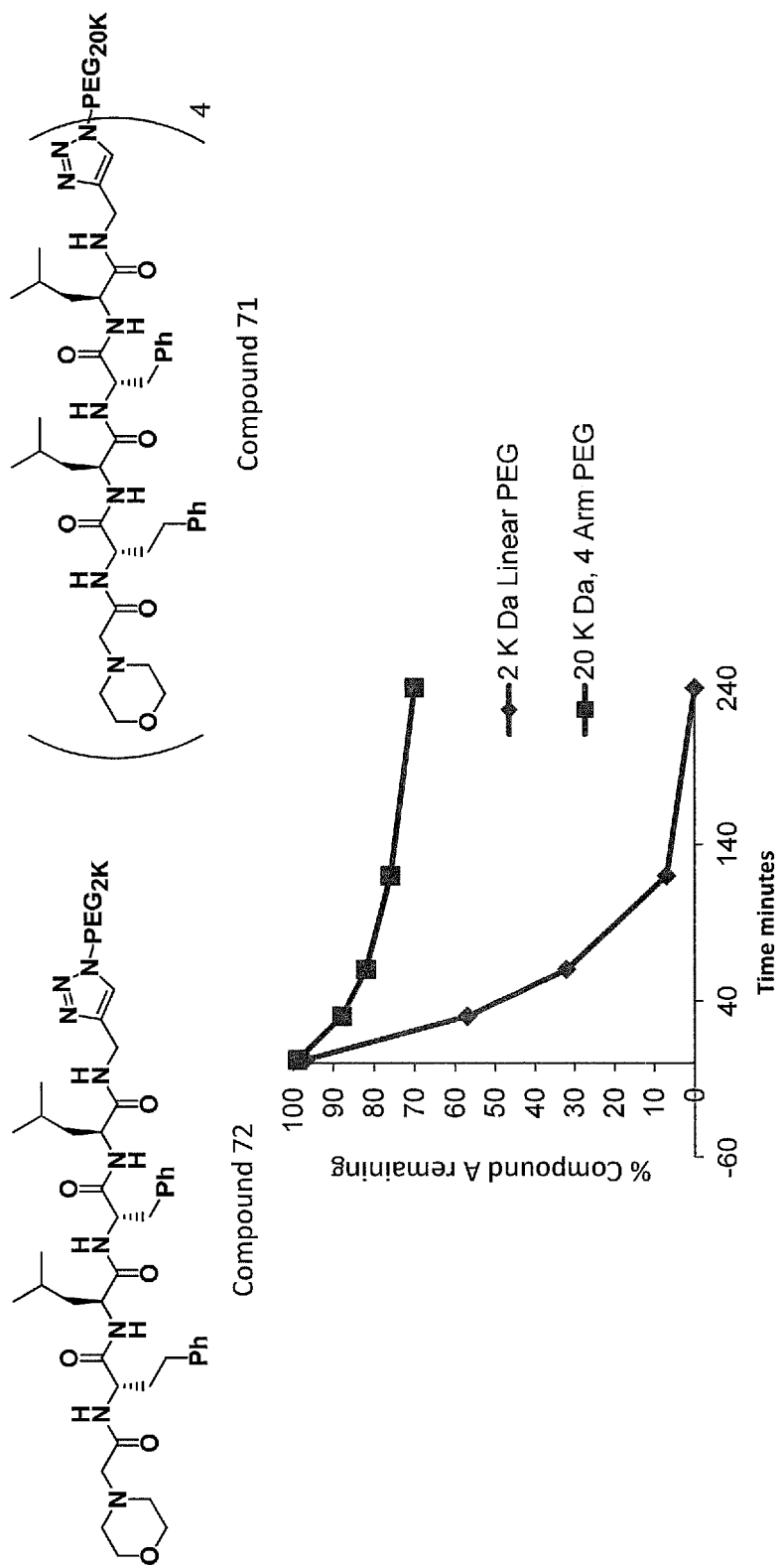
FIG. 6 is a line graph showing proteolytic cleavage assessed via non-cleavable conjugates (liver homogenate), where the remaining active epoxy ketone protease inhibitor is estimated from metabolite loss. A 2 kDa conjugate had a proteolytic $t_{1/2}$ of <1 hr; while a 20 kDa-4 Arm conjugate had a proteolytic $t_{1/2}$ of greater than 6 hrs.

The release capabilities of PEG conjugates can be assessed by quantitation of epoxy ketone protease inhibitors released in a basic buffer solution, by NMR, and by MALDI-TOF NMR. Reformation rates of various examples of PEG conjugates were measured and are shown, for example, in FIG. 4. FIG. 5 shows the rates of re-formation of an active epoxy ketone protease inhibitor from examples of epoxy ketone protease inhibitor prodrugs in human plasma, where the re-formation rate is adjustable by tuning a linker group's electron density.

Figure 10:
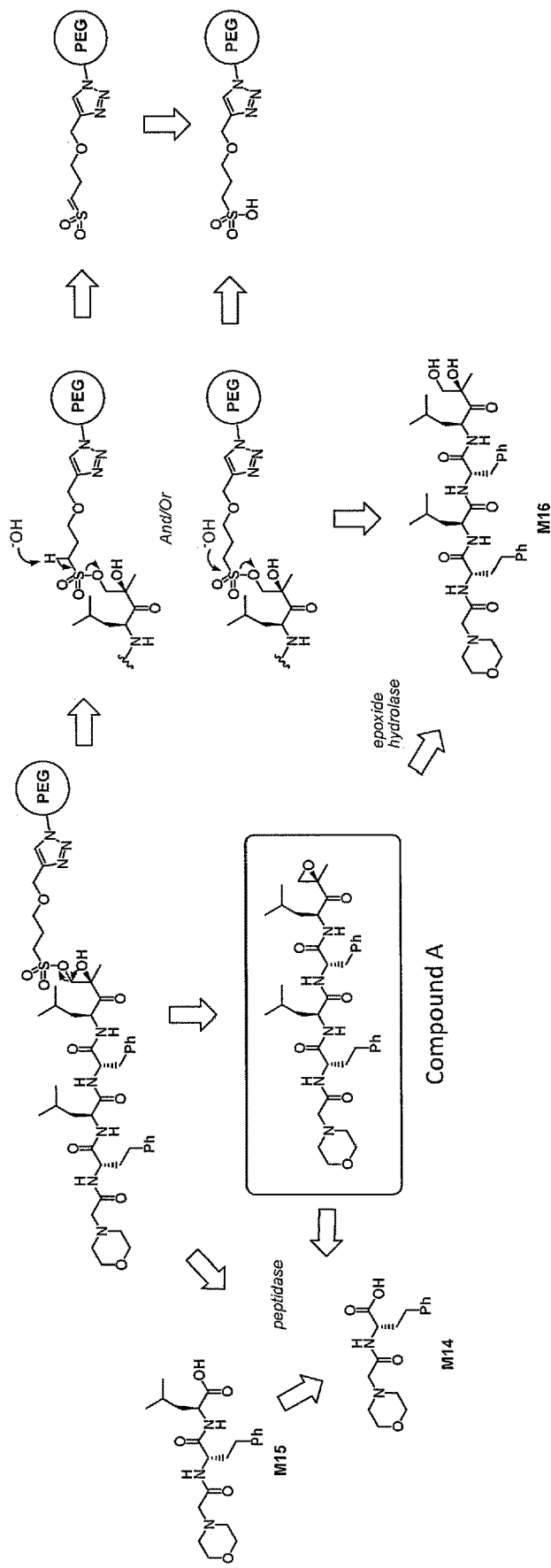
FIG. 10 is a scheme showing that proteolytic cleavage is reduced by increasing PEG size and/or branching and that cleavage of the epoxide moiety was observed for aliphatic sulfonate linkers in embodiments of epoxy ketone protease inhibitor PEG-conjugates.

Referring to FIG. 10, proteolytic cleavage can be reduced by increasing PEG size and/or branching. With aliphatic sulfonate linkers, cleavage of the epoxide moiety to diol M16 was observed, possibly due to steric considerations.

Example 4—Exemplifications of PEG-Conjugates

Exemplary PEG conjugates and their respective molecular weight, loading percentage, solubility, amount of drug/mL, and percent conversion to drug in human plasma are listed in Tables J and K.

TABLE J
| Structure | MW | Loading % | Solubility (mg/mL) | mg drug/mL |
|---|---|---|---|---|
| 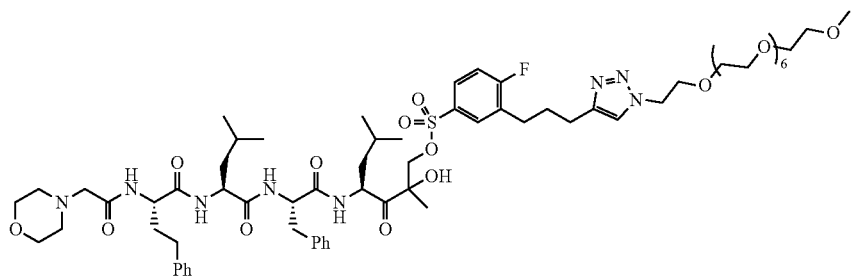 | 1368.63 | 53 | | |
| 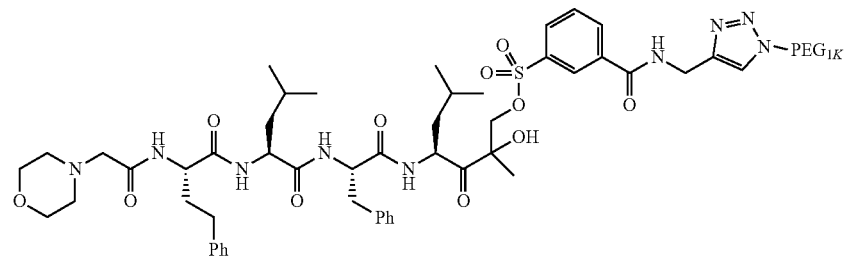 | 2029.42 | 36 | | |
| 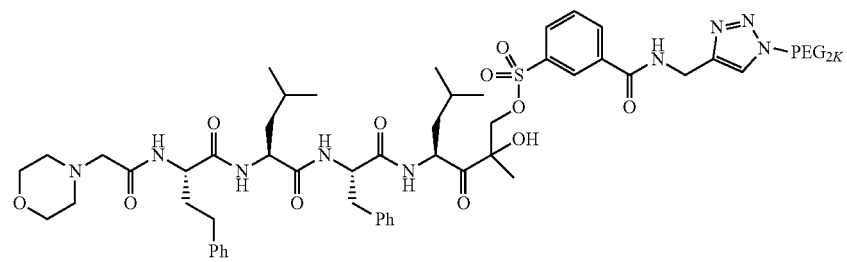 | 3042.63 | 24 | 72.93 | 17.5 |
| 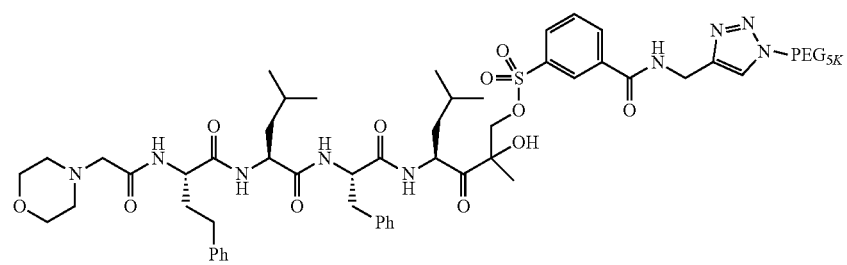 | 6038.2 | 12 | 188.05 | 22.6 |
| 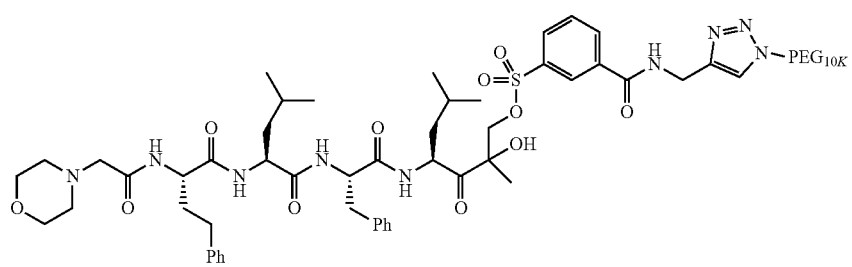 | 11060.2 | 6.5 | | |

TABLE J-continued

| Structure | MW | Loading % | Solubility (mg/mL) | mg drug/mL |
|---|---|---|---|---|
| 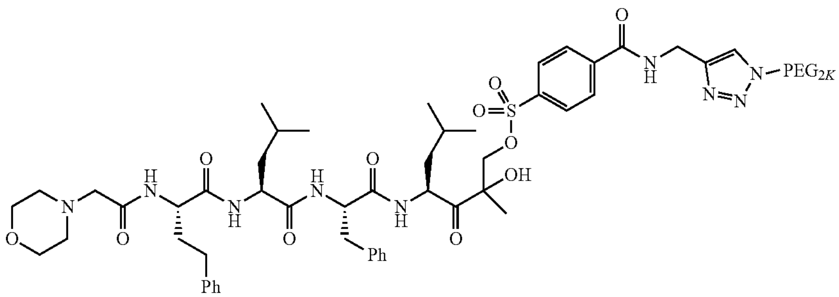 | 3042.63 | 24 | | |
| 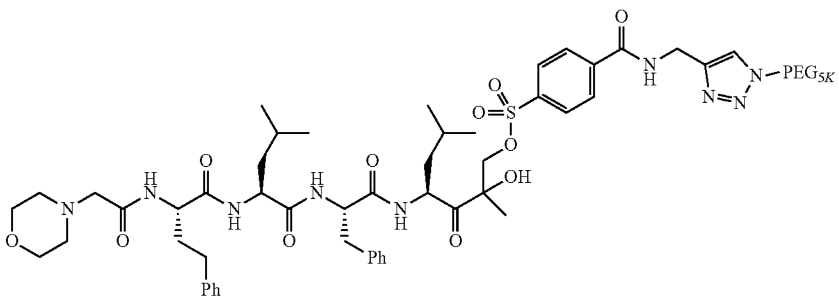 | 6038.2 | 12 | | |
| | 3060.62 | 0.24 | | |
| | 3060.62 | 24 | | |
| 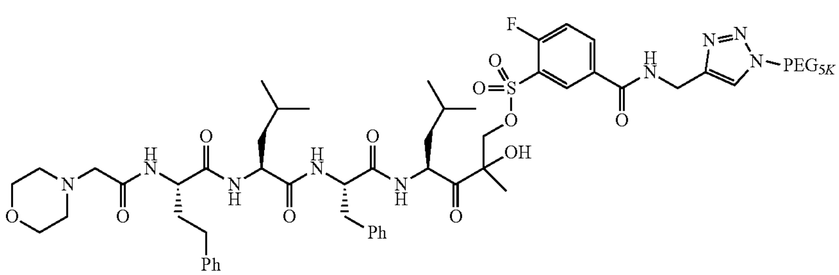 | 6056.19 | 12 | | |

TABLE J-continued

| Structure | MW | Loading % | Solubility (mg/mL) | mg drug/mL |
|---|---|---|---|---|
| 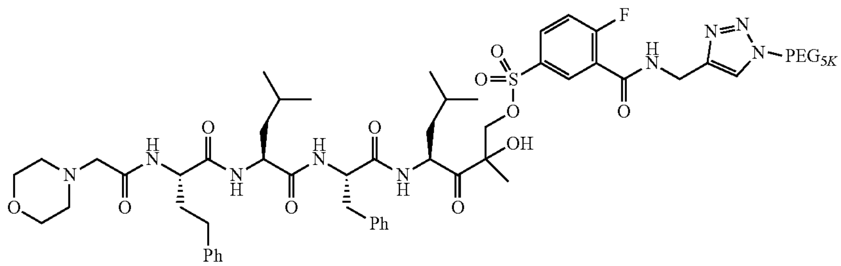 | 6056.19 | 12 | | |
| 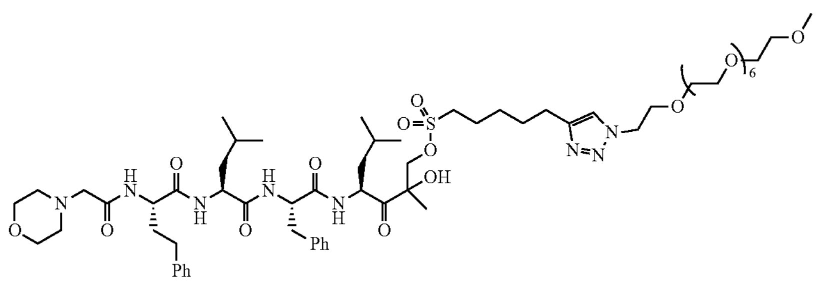 | 1307.59 | 55 | | |
| 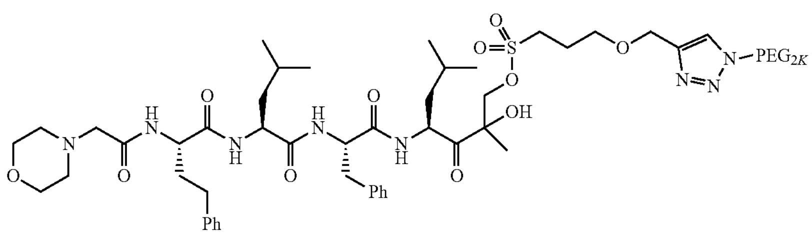 | 2981.59 | 24 | 143.71 | 34.5 |
| 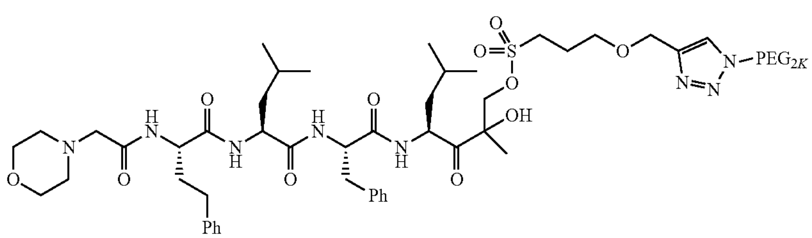 | 5977.16 | 12 | | |
| 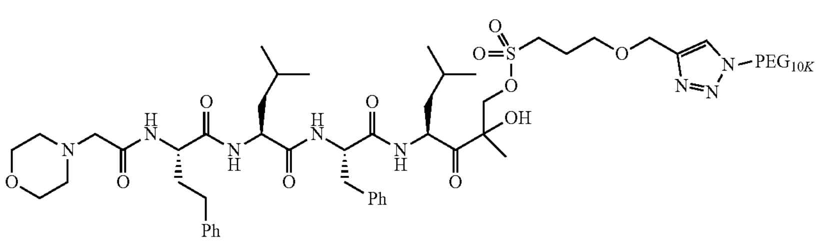 | 10999.15 | | | |

TABLE J-continued
| Structure | MW | Loading % | Solubility (mg/mL) | mg drug/mL |
|---|---|---|---|---|
| 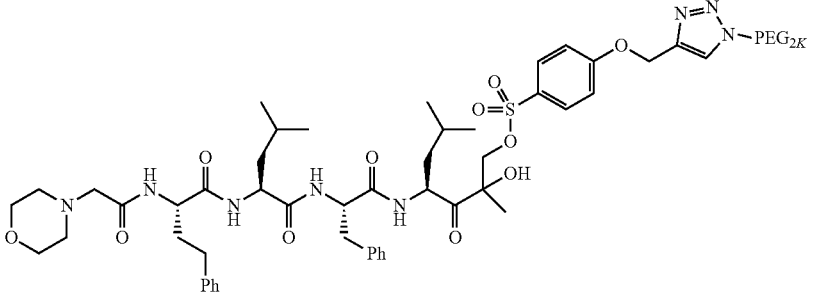 | 3015.6 | | | |
| 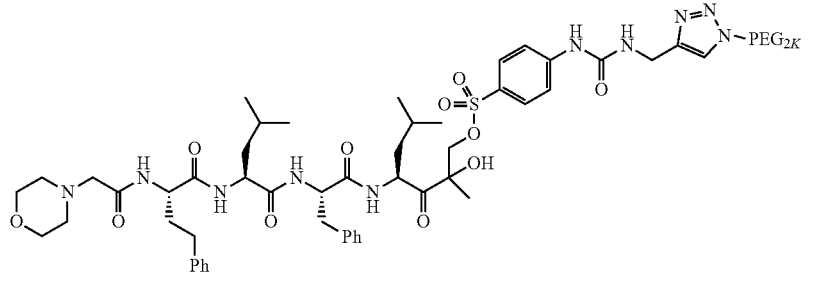 | 3057.64 | | | |
| 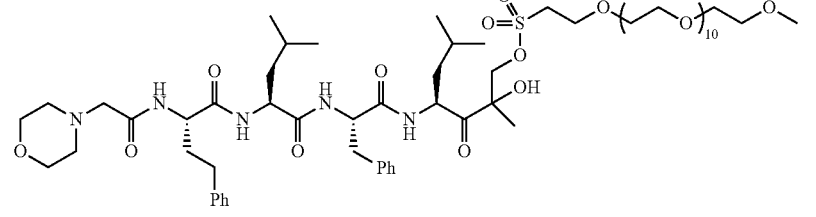 | 1344.65 | 54 | | |
| 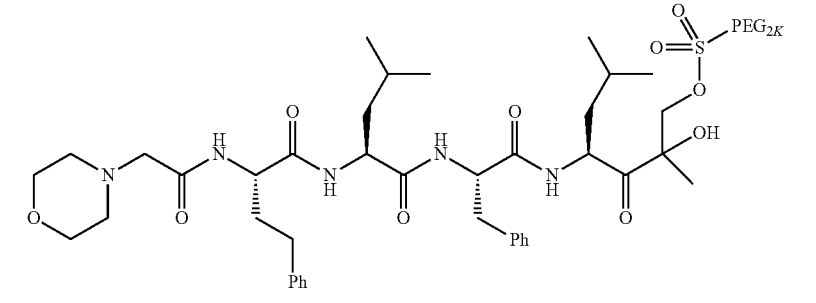 | 2842.43 | 25 | | |
| 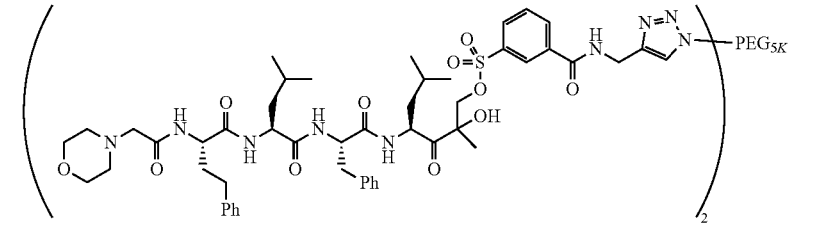 | 7052.4 | 20 | | |

TABLE J-continued
| Structure | MW | Loading % | Solubility (mg/mL) | mg drug/mL |
|---|---|---|---|---|
| 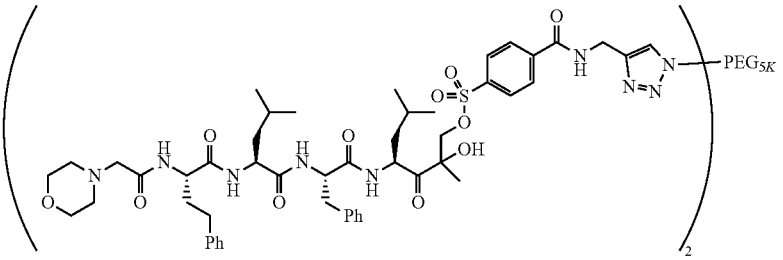 | 7052.4 | 20 | | |
| 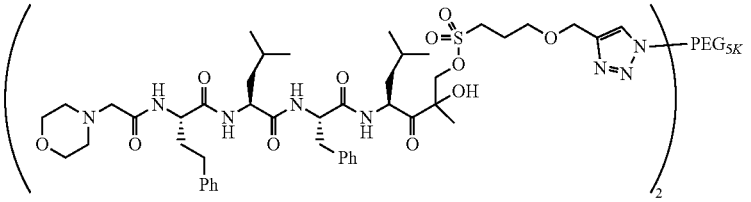 | 6930.32 | | | |
| 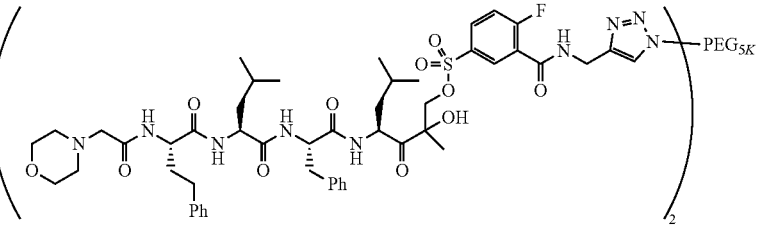 | 7088.38 | | | |
| 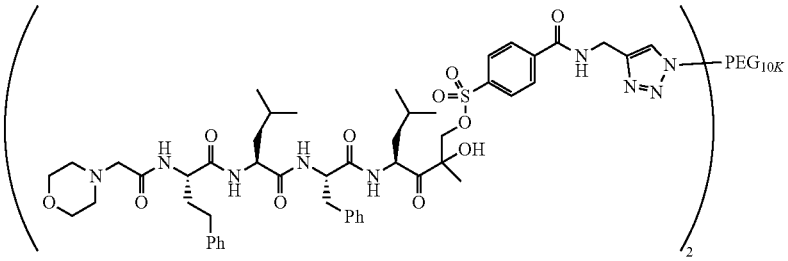 | 14116.81 | s20 | | |
| 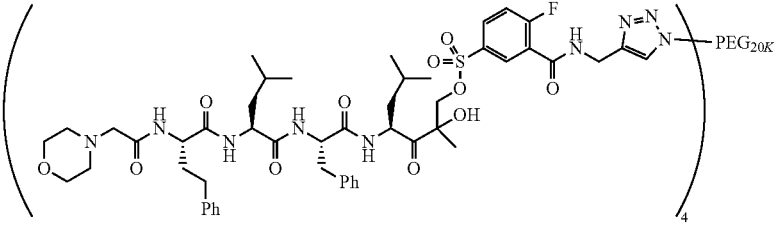 | 24232.76 | 12 | | |
| 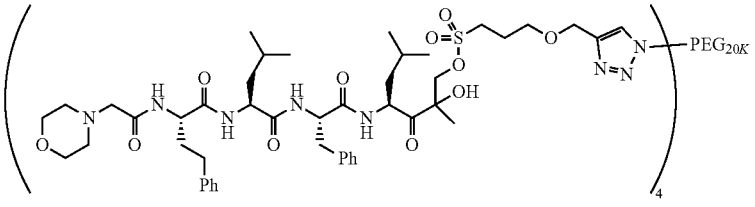 | 23916.63 | | | |

TABLE J-continued

| Structure | MW | Loading % | Solubility (mg/mL) | mg drug/mL |
|---|---|---|---|---|
| (structure with PEG₁₀ₖ) | 13872.65 | | | |
| (structure) | 1383.64 | | | |
| (structure with PEG₂ₖ) | 3057.64 | | | |
| (structure with PEG₂₀ₖ) | 24220.84 | | | |

TABLE J-continued
| Structure | MW | Loading % | Solubility (mg/mL) | mg drug/mL |
|---|---|---|---|---|
| 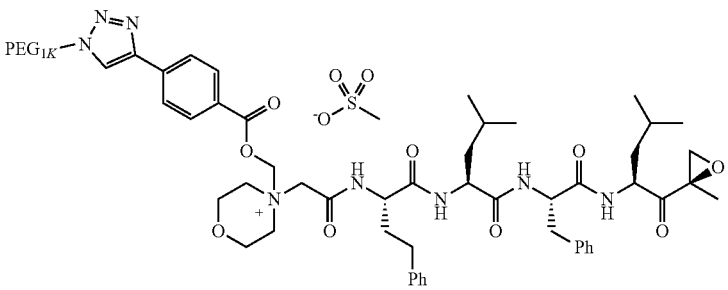 | 2044.43 | | | |
| 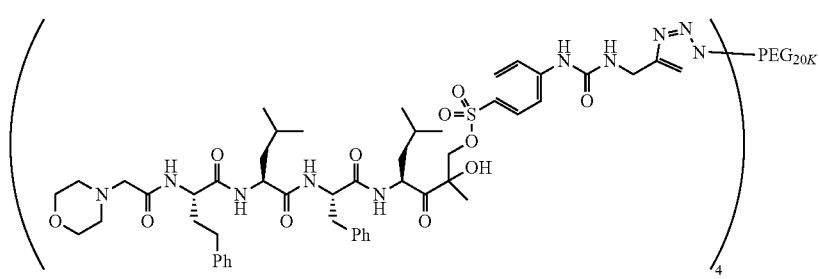 | 24220.85 | | | |
| 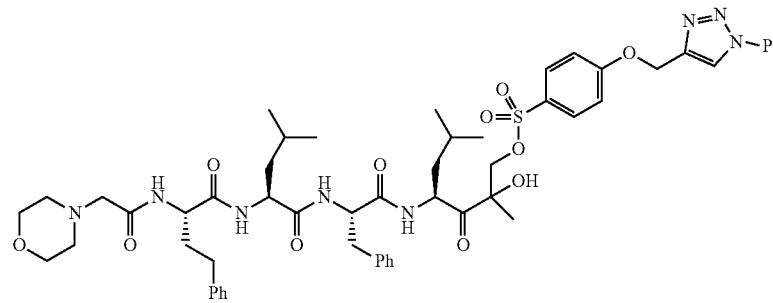 | 6011.16 | | | |
| 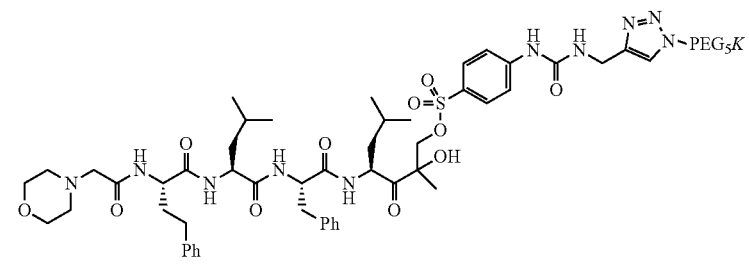 | 6053.22 | | | |
| 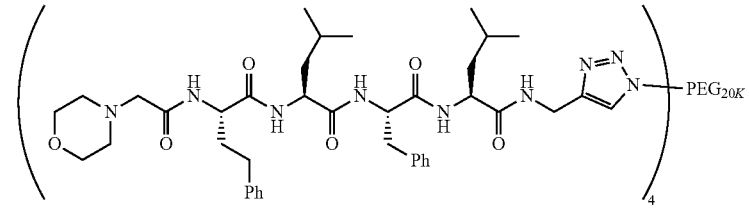 | 23191.8 | | | |

TABLE J-continued
| Structure | MW | Loading % | Solubility (mg/mL) | mg drug/mL |
|---|---|---|---|---|
| 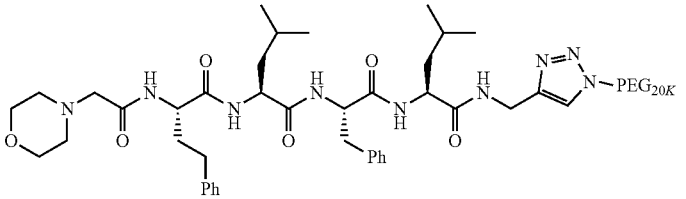 | 2800.38 | | | |
| 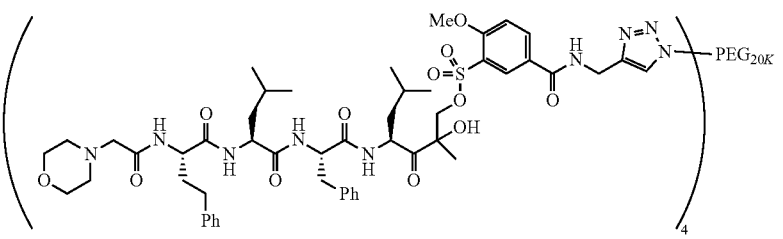 | 24280.9 | | | |
| 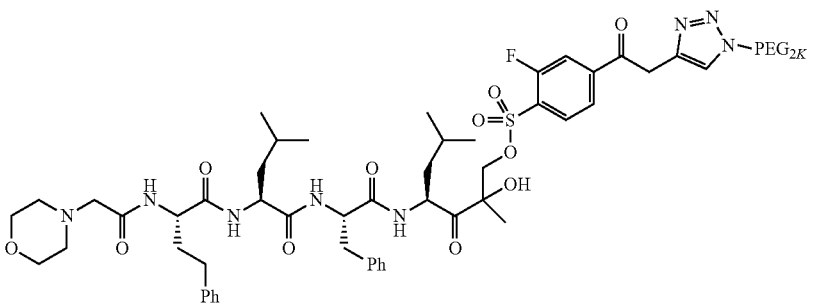 | 3033.6 | | | |
| 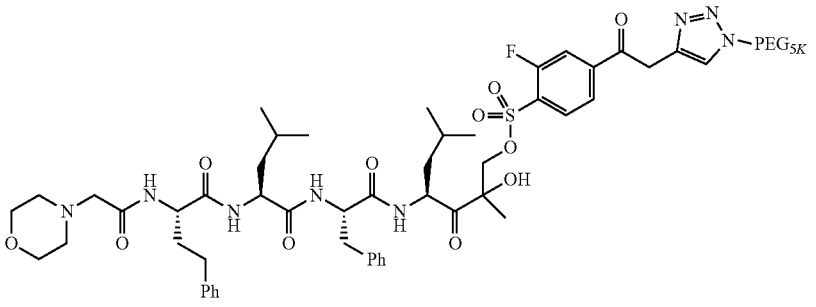 | 6029.17 | | | |
| 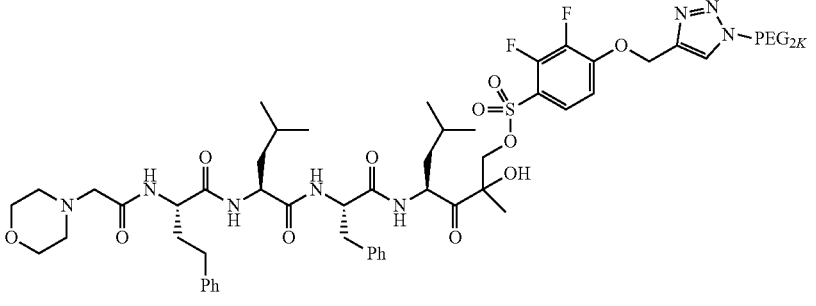 | 3051.59 | | | |

TABLE J-continued
| Structure | MW | Loading % | Solubility (mg/mL) | mg drug/mL |
|---|---|---|---|---|
| 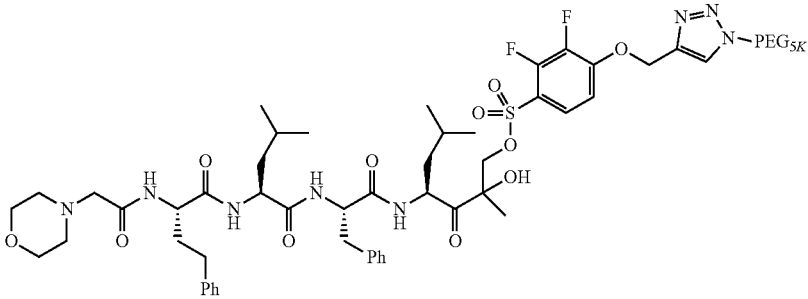 | 6047.16 | | | |
| 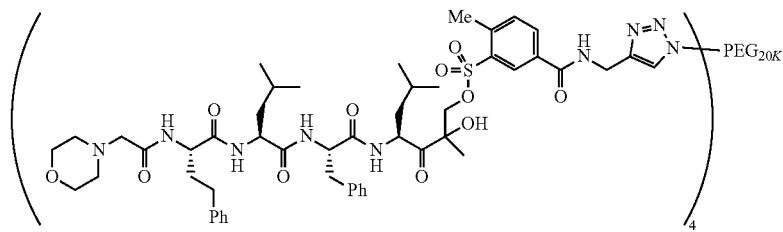 | 24216.9 | | | |
| 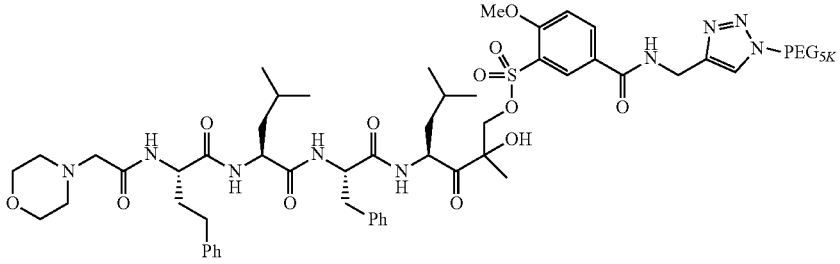 | 6068.23 | | | |
| 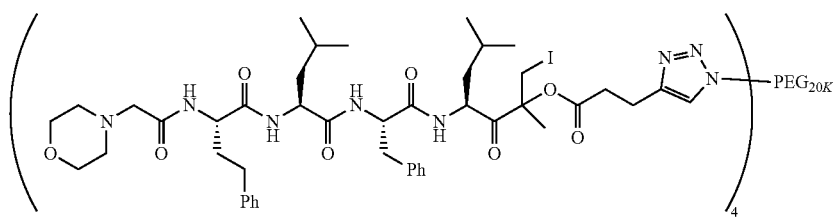 | 24035.79 | | | |
| 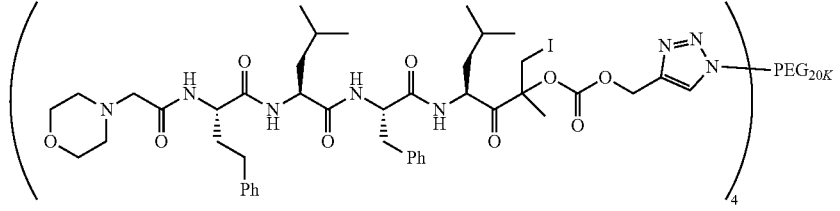 | 24043.68 | | | |
| 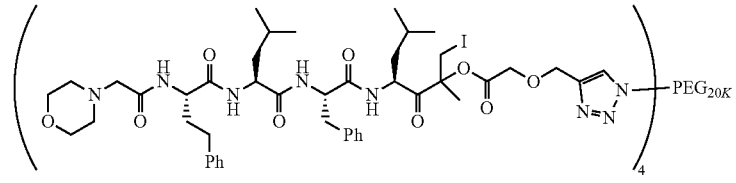 | 24099.79 | | | |

TABLE K

| Structure | Conversion to drug in Human Plasma (%) | | | | |
|---|---|---|---|---|---|
| | 2 min | 30 min | 1 hr | 2 hr | 4 hr |
| (structure 1) | 7 | 63 | 100 | 95 | 80 |
| (structure 2) | 17 | 79 | 108 | 102 | 80 |

TABLE K-continued
| Structure | Conversion to drug in Human Plasma (%) | | | | |
|---|---|---|---|---|---|
| | 2 min | 30 min | 1 hr | 2 hr | 4 hr |
| 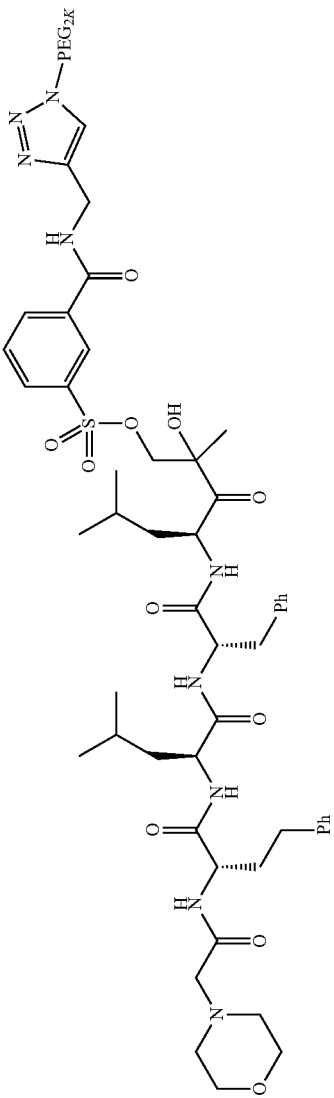 | 36 | 101 | 109 | 110 | 80 |
| 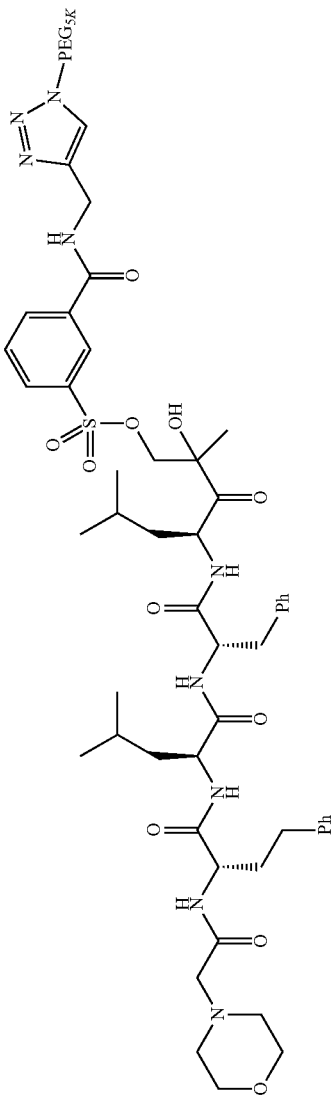 | 11 | 99 | 111 | 103 | 92 |

TABLE K-continued

| Structure | Conversion to drug in Human Plasma (%) | | | | |
|---|---|---|---|---|---|
| | 2 min | 30 min | 1 hr | 2 hr | 4 hr |
| (structure with PEG₁₀K) | | | | | |
| (structure with PEG₂ₖ) | 13 | 92 | 104 | 102 | 80 |

TABLE K-continued
| Structure | Conversion to drug in Human Plasma (%) | | | | |
|---|---|---|---|---|---|
| | 2 min | 30 min | 1 hr | 2 hr | 4 hr |
| 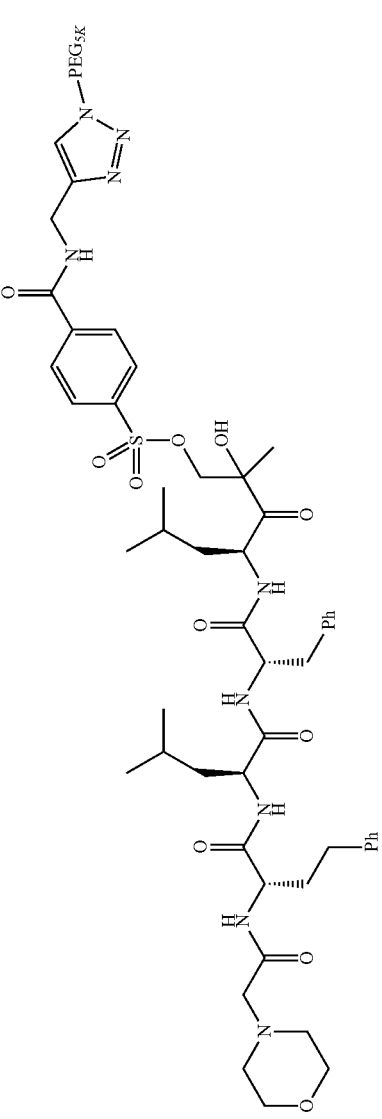 | | | | | |
| 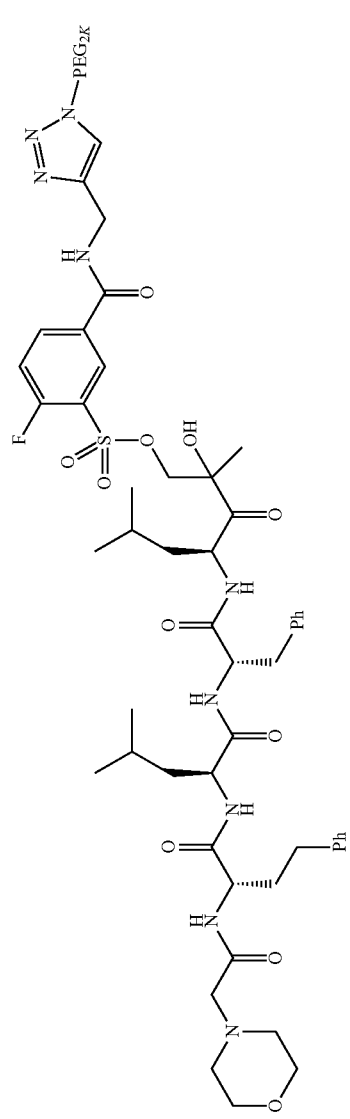 | 39 | 100 | 100 | 94 | 80 |

TABLE K-continued
| Structure | Conversion to drug in Human Plasma (%) | | | | |
|---|---|---|---|---|---|
| | 2 min | 30 min | 1 hr | 2 hr | 4 hr |
| 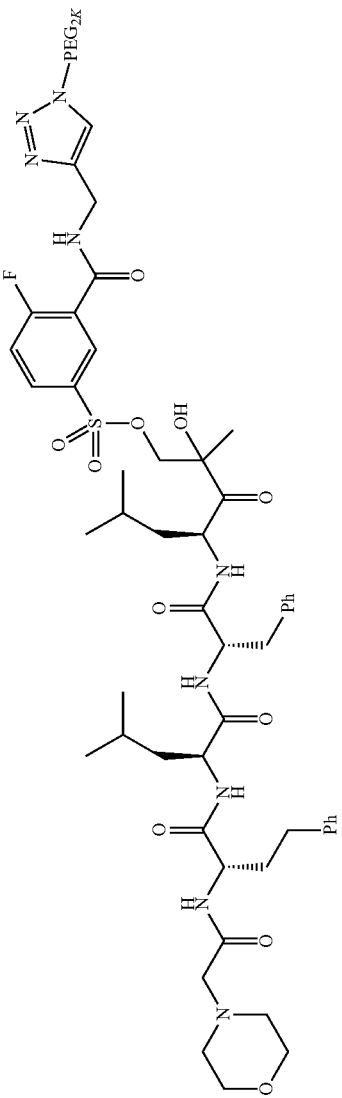 | 14 | 99 | 133 | 118 | 113 |
| 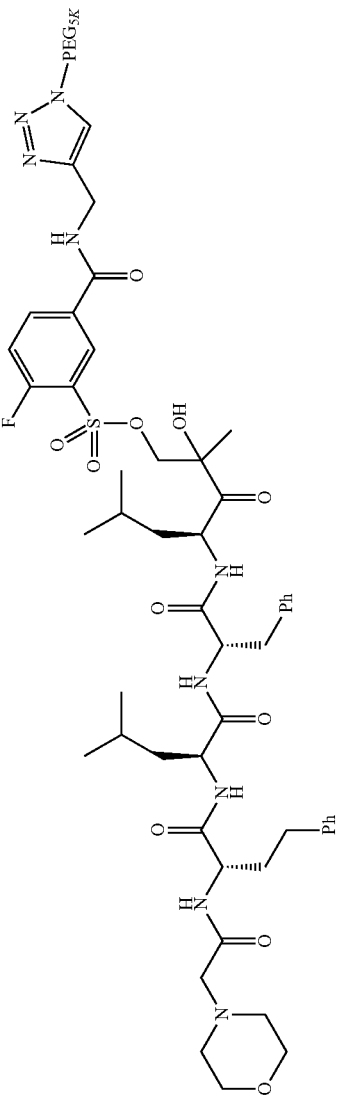 | | | | | |

TABLE K-continued

| Structure | Conversion to drug in Human Plasma (%) | | | | |
|---|---|---|---|---|---|
| | 2 min | 30 min | 1 hr | 2 hr | 4 hr |
| (structure with PEG5K-triazole-fluorobenzamide-sulfonate linked to peptide with Leu, Phe, Leu, homoPhe, morpholine acetamide) | | | | | |
| (structure with methoxy-PEG6-triazole-propyl sulfonate linked to peptide with Leu, Phe, Leu, homoPhe, morpholine acetamide) | 2 | 18 | 58 | 90 | 80 |

TABLE K-continued

| Structure | Conversion to drug in Human Plasma (%) | | | | |
|---|---|---|---|---|---|
| | 2 min | 30 min | 1 hr | 2 hr | 4 hr |
| (structure with PEG2K) | 3 | 37 | 80 | 103 | 86 |
| (structure with PEG5K) | | | | | |
| (structure with PEG10K) | | | | | |

TABLE K-continued
| Structure | Conversion to drug in Human Plasma (%) |
| --- | --- |
| | 2 min / 30 min / 1 hr / 2 hr / 4 hr |
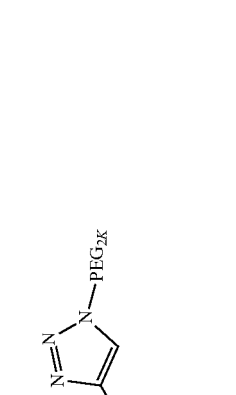

TABLE K-continued

TABLE K-continued

| Structure | Conversion to drug in Human Plasma (%) | | | | |
|---|---|---|---|---|---|
| | 2 min | 30 min | 1 hr | 2 hr | 4 hr |

TABLE K-continued
| Structure | Conversion to drug in Human Plasma (%) | | | | |
|---|---|---|---|---|---|
| | 2 min | 30 min | 1 hr | 2 hr | 4 hr |
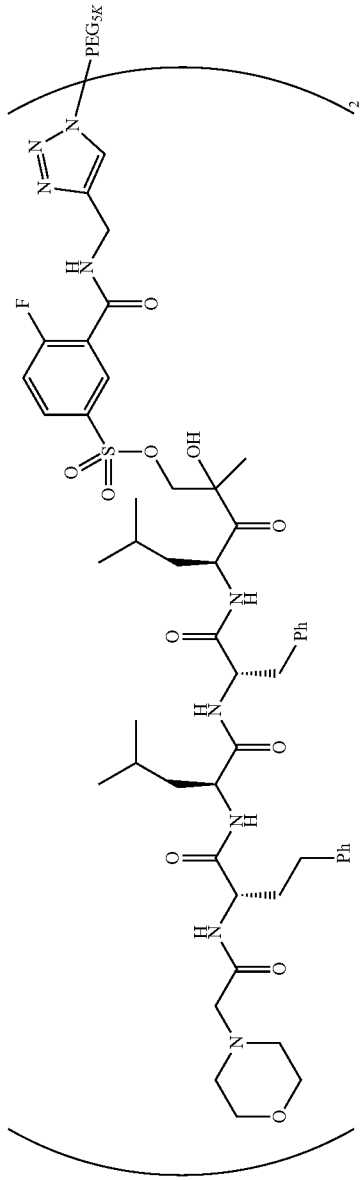
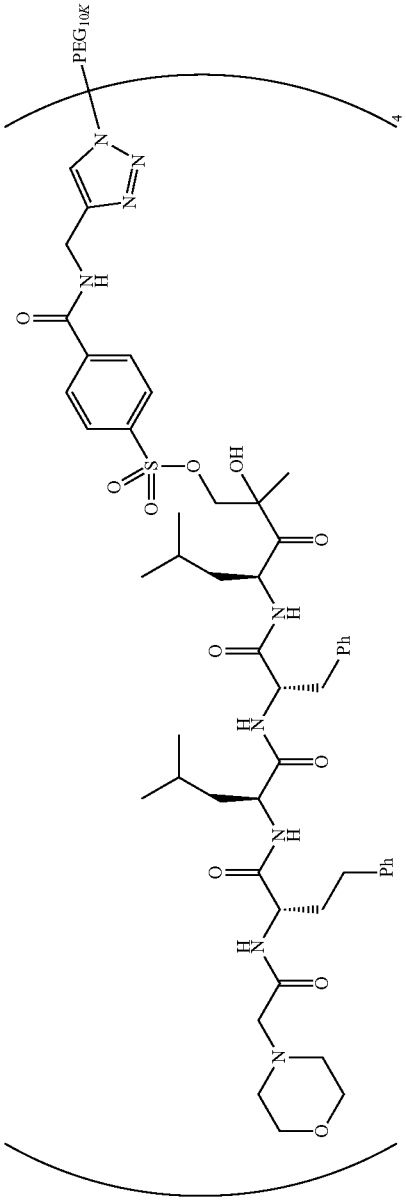

TABLE K-continued

| Structure | Conversion to drug in Human Plasma (%) | | | |
|---|---|---|---|---|
| | 2 min | 30 min | 1 hr | 2 hr | 4 hr |

TABLE K-continued

| Structure | Conversion to drug in Human Plasma (%) | | | |
|---|---|---|---|---|
| | 2 min | 30 min | 1 hr | 2 hr | 4 hr |

TABLE K-continued
| Structure | Conversion to drug in Human Plasma (%) |
|---|---|
| | 2 min / 30 min / 1 hr / 2 hr / 4 hr |
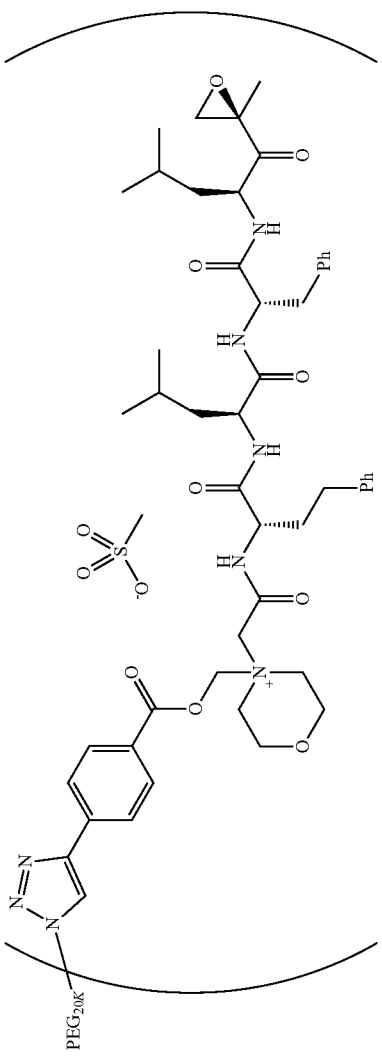

TABLE K-continued
| Structure | Conversion to drug in Human Plasma (%) | | | |
|---|---|---|---|---|
| | 2 min | 30 min | 1 hr | 2 hr | 4 hr |
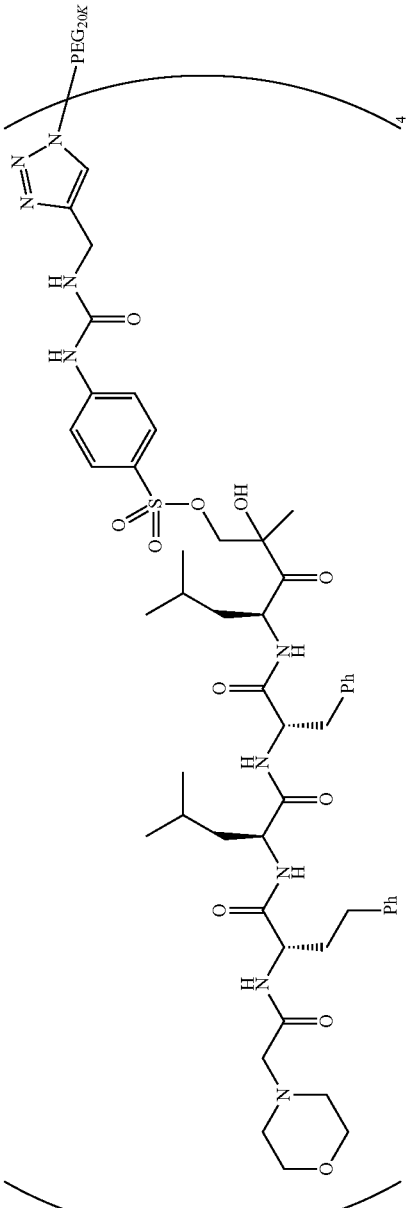

TABLE K-continued

| Structure | Conversion to drug in Human Plasma (%) | | | | |
|---|---|---|---|---|---|
| | 2 min | 30 min | 1 hr | 2 hr | 4 hr |

TABLE K-continued

| Structure | Conversion to drug in Human Plasma (%) | | | |
|---|---|---|---|---|
| | 2 min | 30 min | 1 hr | 2 hr | 4 hr |

TABLE K-continued
| Structure | Conversion to drug in Human Plasma (%) | | | |
|---|---|---|---|---|
| | 2 min | 30 min | 1 hr | 2 hr | 4 hr |
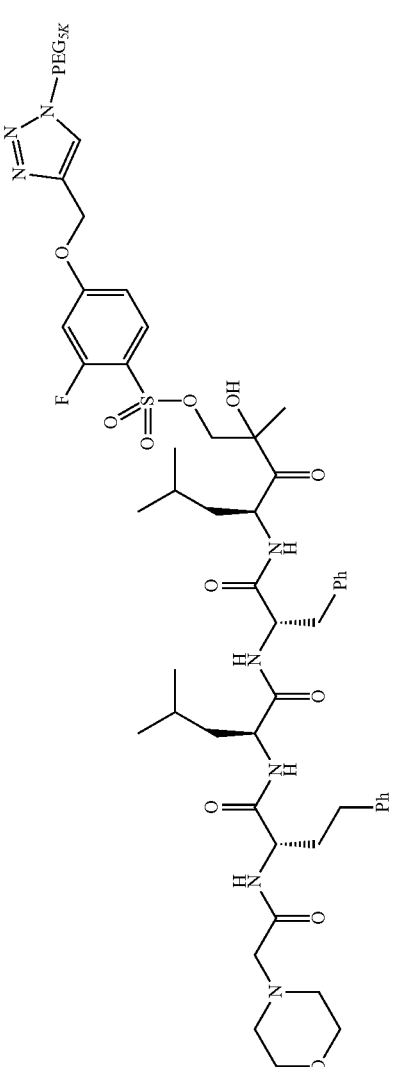
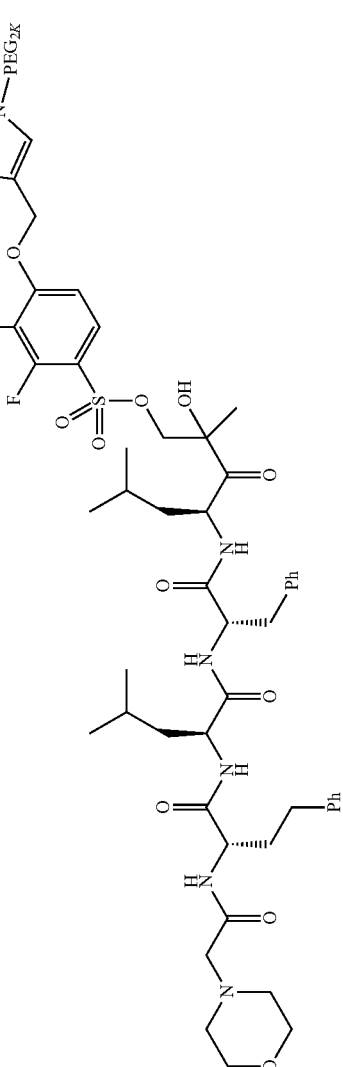

TABLE K-continued
| Structure | Conversion to drug in Human Plasma (%) | | | |
|---|---|---|---|---|
| | 2 min | 30 min | 1 hr | 2 hr | 4 hr |
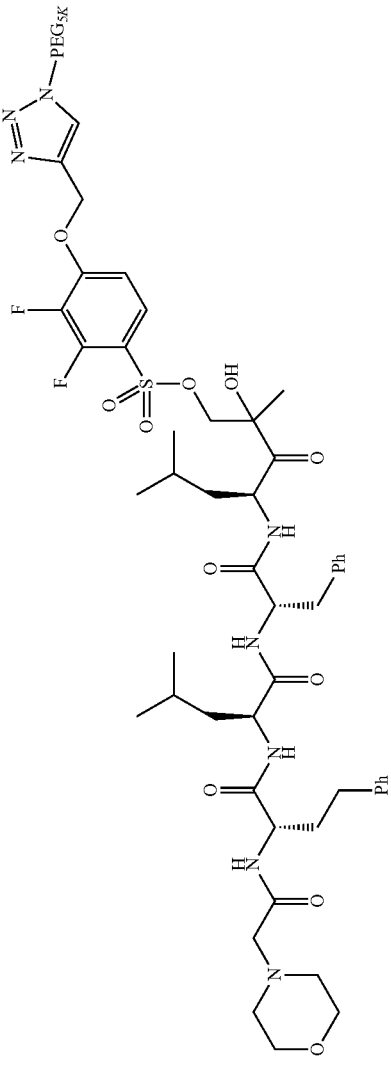

TABLE K-continued

| Structure | Conversion to drug in Human Plasma (%) | | | |
|---|---|---|---|---|
| | 2 min | 30 min | 1 hr | 2 hr | 4 hr |

TABLE K-continued
| Structure | Conversion to drug in Human Plasma (%) |  |  |  |
|---|---|---|---|---|
|  | 2 min | 30 min | 1 hr | 2 hr | 4 hr |
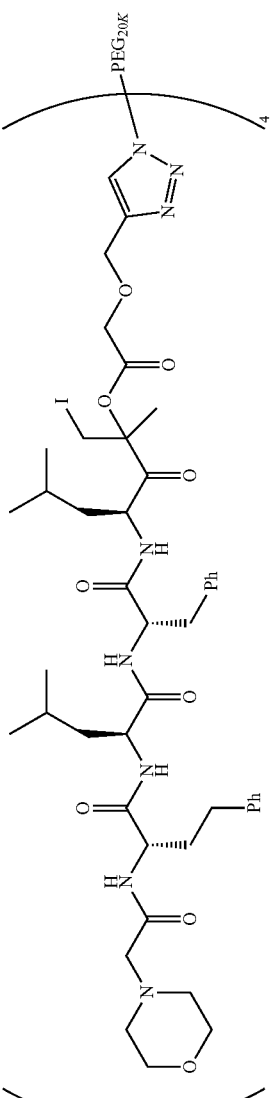

TABLE L
Conversion of Small Molecule-PEG Prodrug to Compound A in Human Plasma
1 µM Prodrug in Human Plasma
Incubation times: 0, 1, 2, 4, 6 and 24 hours
Mass Spec Quantitation of Compound A
| Compound | Structure | Prodrug $t_{1/2}$ (hrs) |
|---|---|---|
| 53 | 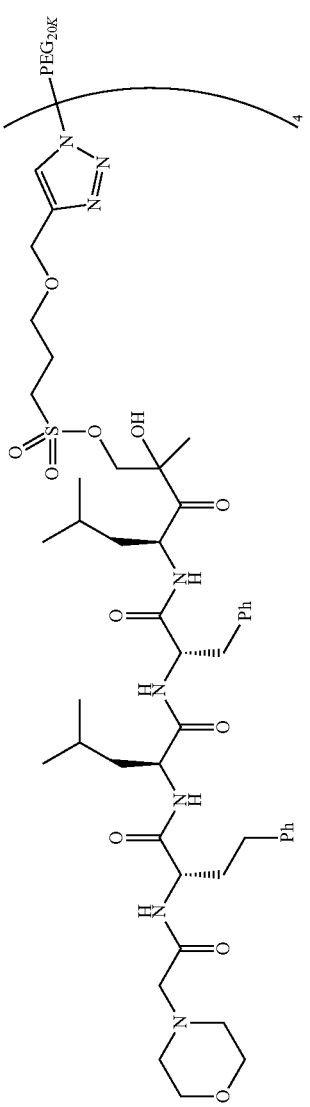 | 1.3 |
| 74 | 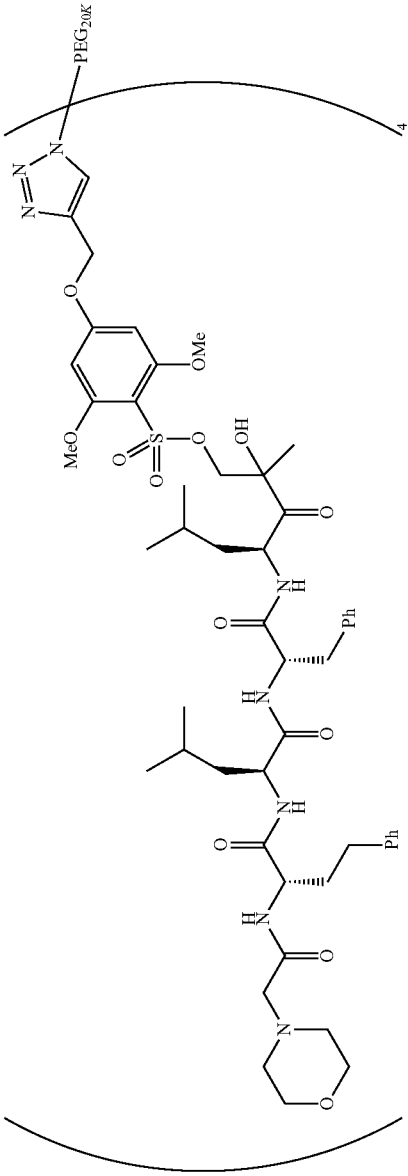 | 267 |

TABLE L-continued
Conversion of Small Molecule-PEG Prodrug to Compound A in Human Plasma
1 µM Prodrug in Human Plasma
Incubation times: 0, 1, 2, 4, 6 and 24 hours
Mass Spec Quantitation of Compound A
| Compound | Structure | Prodrug $t_{1/2}$ (hrs) |
|---|---|---|
| 75 | 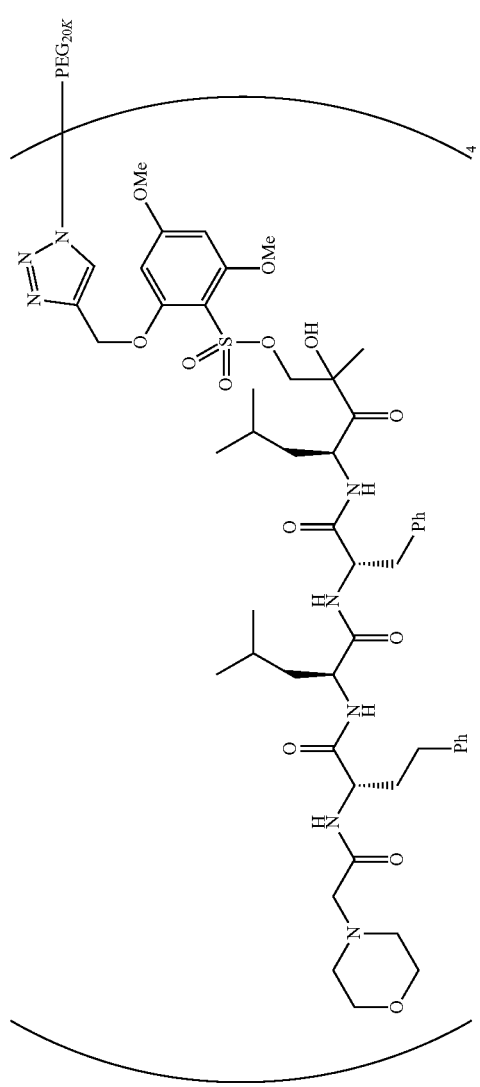 | 503 |
| 63 | 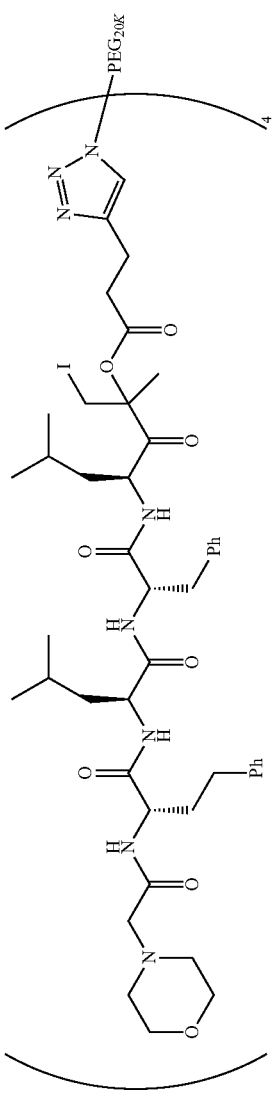 | 59 |

TABLE L-continued
Conversion of Small Molecule-PEG Prodrug to Compound A in Human Plasma
1 µM Prodrug in Human Plasma
Incubation times: 0, 1, 2, 4, 6 and 24 hours
Mass Spec Quantitation of Compound A
| Compound | Structure | Prodrug $t_{1/2}$ (hrs) |
|---|---|---|
| 65 | 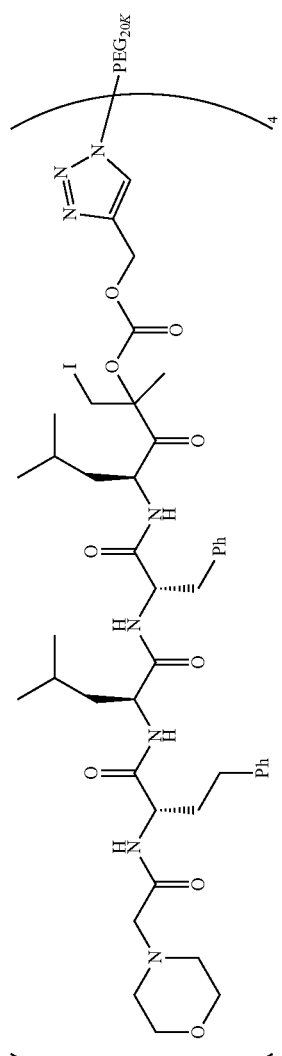 | 24 |
| 64 | 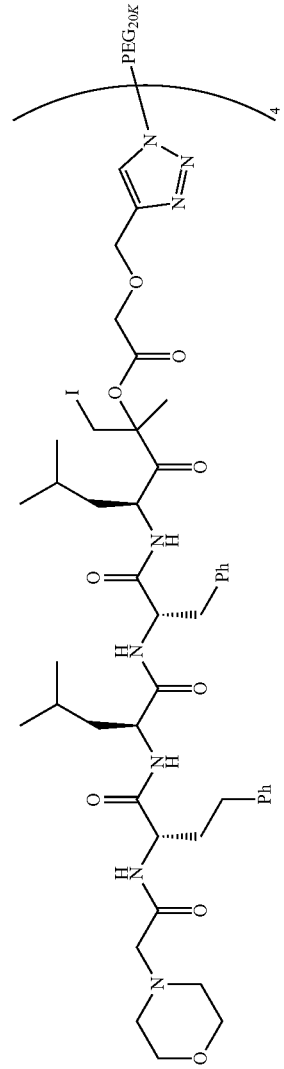 | 31 |
| 98 | 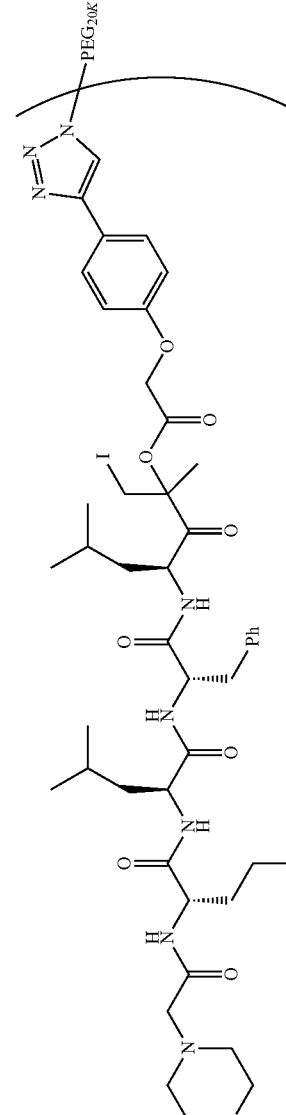 | 836 |

TABLE L-continued

Conversion of Small Molecule-PEG Prodrug to Compound A in Human Plasma
1 μM Prodrug in Human Plasma
Incubation times: 0, 1, 2, 4, 6 and 24 hours
Mass Spec Quantitation of Compound A

| Compound | Structure | Prodrug $t_{1/2}$ (hrs) |
|---|---|---|
| 99 | 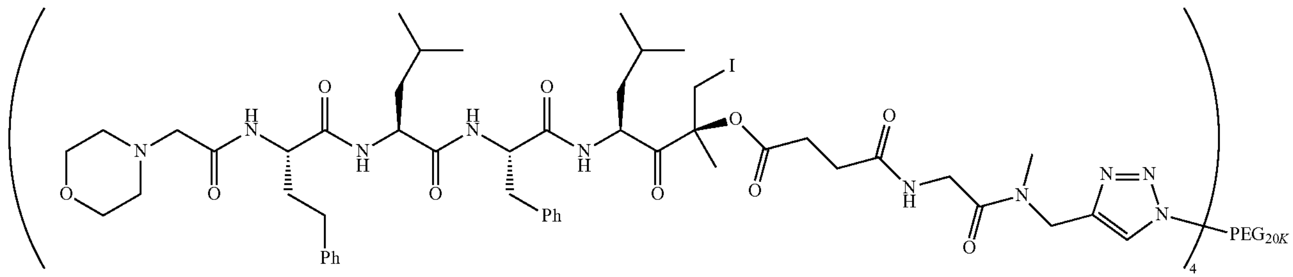 | 3.9 |
| 100 | 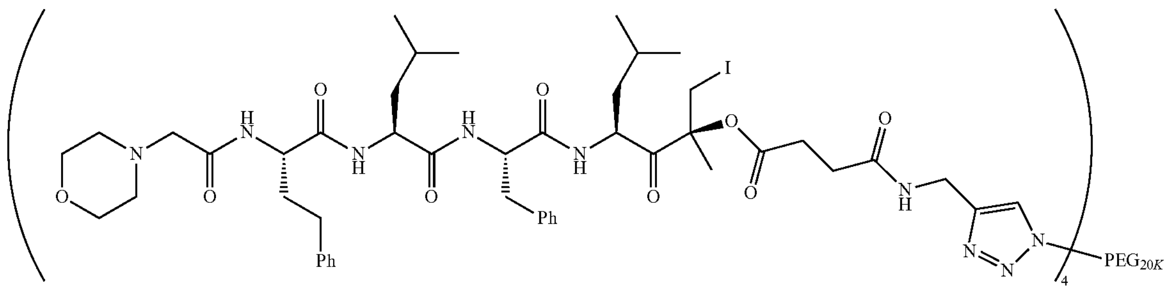 | 4.7 |
| 101 | 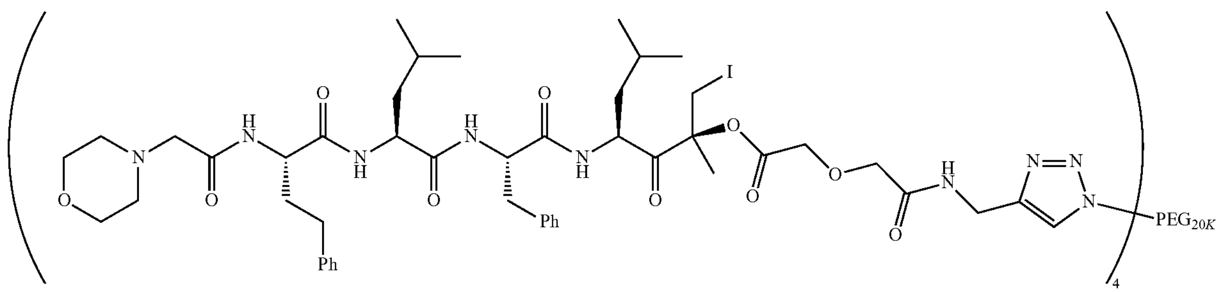 | 3.3 |

TABLE L-continued

Conversion of Small Molecule-PEG Prodrug to Compound A in Human Plasma
1 μM Prodrug in Human Plasma
Incubation times: 0, 1, 2, 4, 6 and 24 hours
Mass Spec Quantitation of Compound A

| Compound | Structure | Prodrug $t_{1/2}$ (hrs) |
|---|---|---|
| 102 | 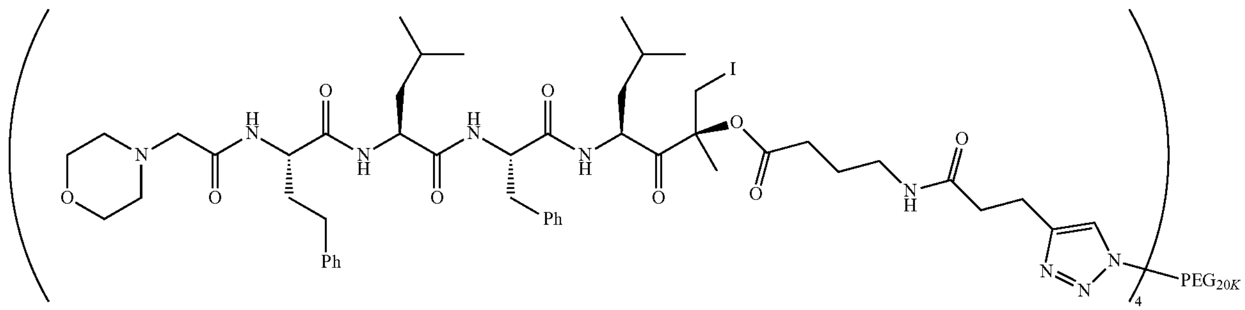 | 42 |
| 103 | 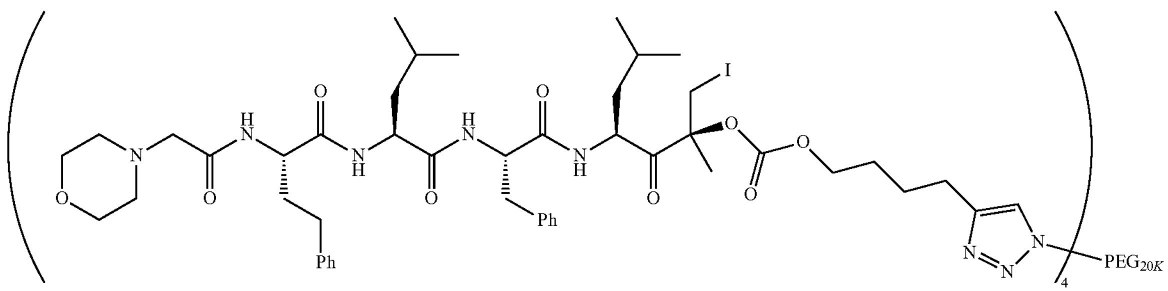 | 42 |
| 104 | 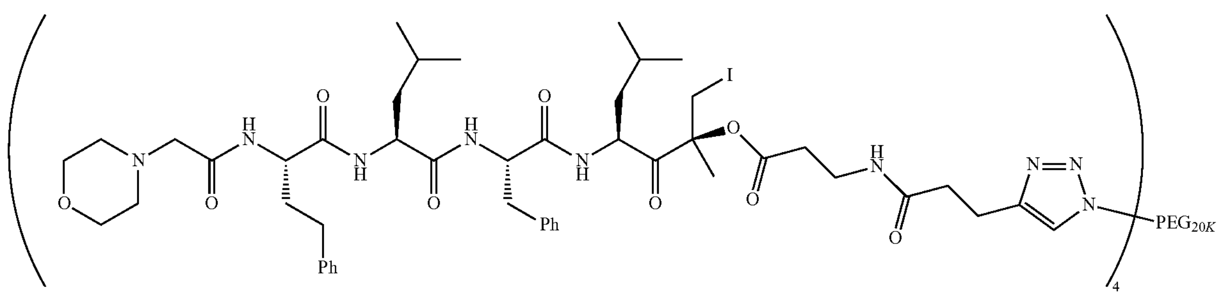 | 32 |

TABLE L-continued

Conversion of Small Molecule-PEG Prodrug to Compound A in Human Plasma
1 μM Prodrug in Human Plasma
Incubation times: 0, 1, 2, 4, 6 and 24 hours
Mass Spec Quantitation of Compound A

| Compound | Structure | Prodrug $t_{1/2}$ (hrs) |
|---|---|---|
| 134 | 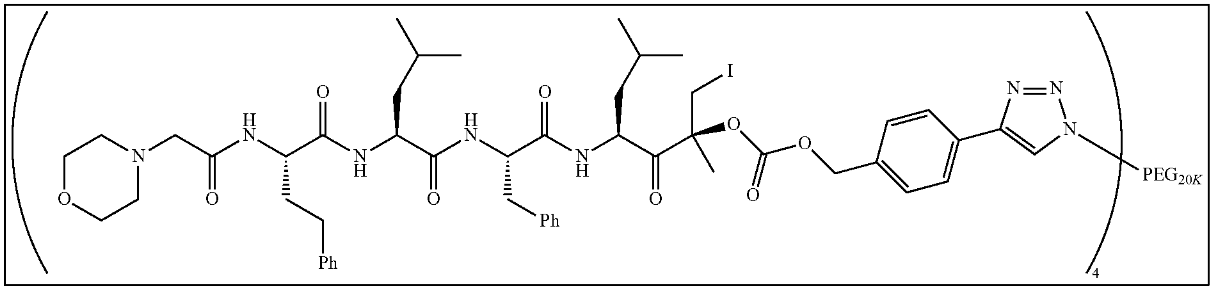 | 33 |
| 135 | 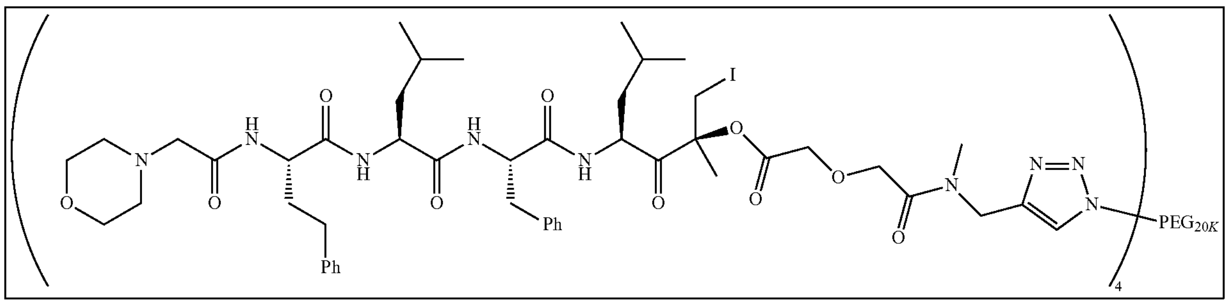 | 25 |
| 136 | 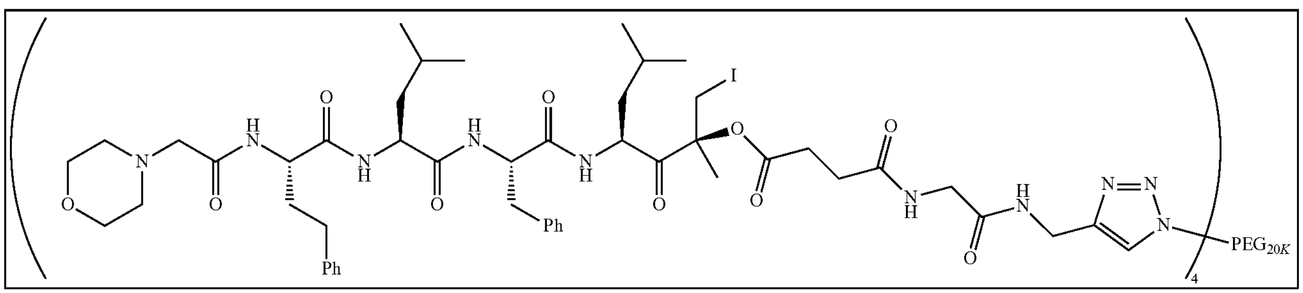 | 0.7 |

TABLE L-continued

Conversion of Small Molecule-PEG Prodrug to Compound A in Human Plasma
1 μM Prodrug in Human Plasma
Incubation times: 0, 1, 2, 4, 6 and 24 hours
Mass Spec Quantitation of Compound A

| Compound | Structure | Prodrug $t_{1/2}$ (hrs) |
|---|---|---|
| 106 | 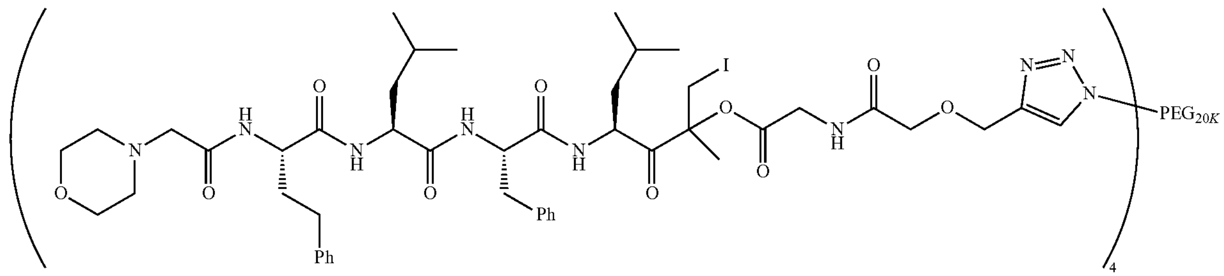 | 30 |
| 107 | 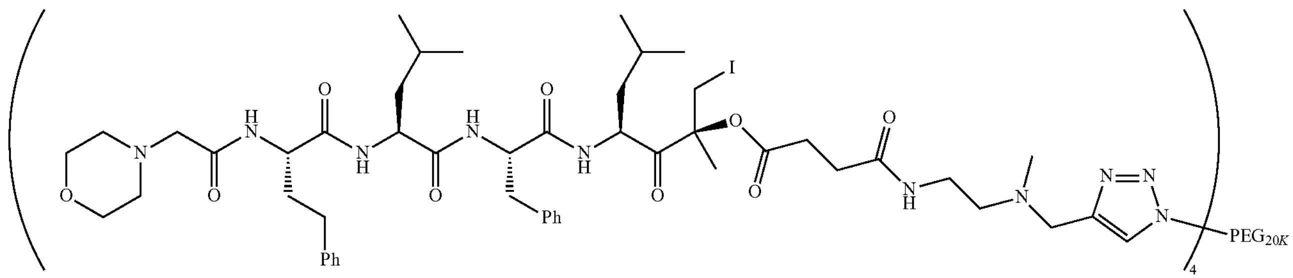 | 5.5 |
| 108 | 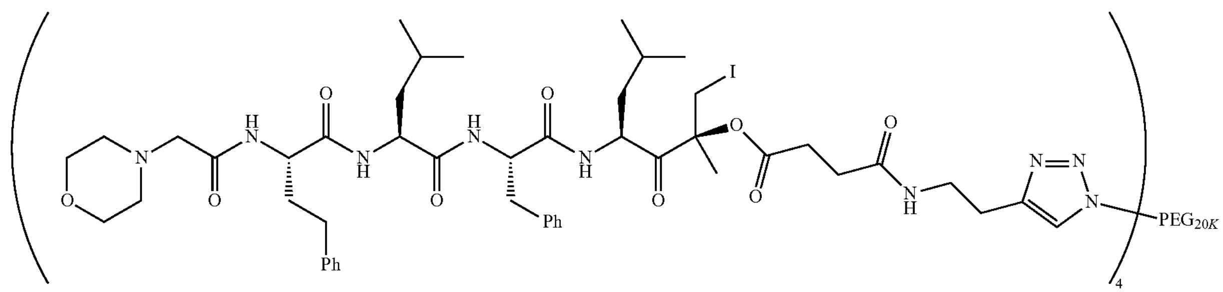 | 10.4 |

TABLE L-continued

Conversion of Small Molecule-PEG Prodrug to Compound A in Human Plasma
1 μM Prodrug in Human Plasma
Incubation times: 0, 1, 2, 4, 6 and 24 hours
Mass Spec Quantitation of Compound A

| Compound | Structure | Prodrug $t_{1/2}$ (hrs) |
|---|---|---|
| 109 | 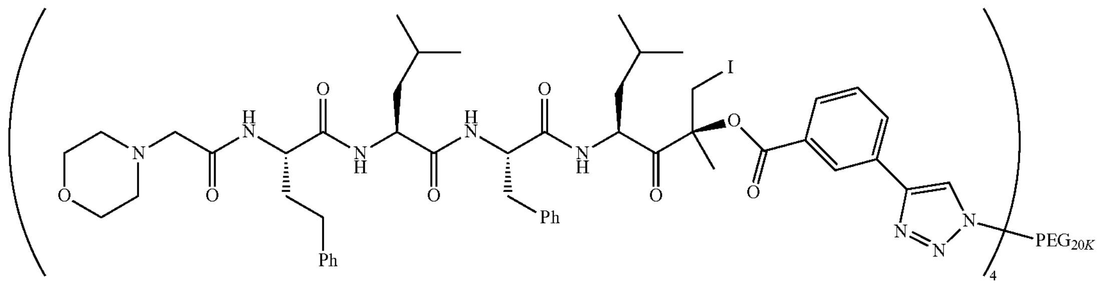 | 112 |
| 110 | 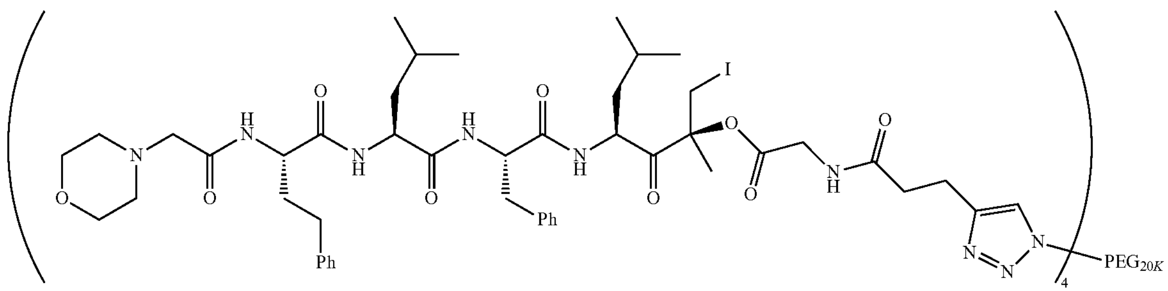 | 29 |

TABLE L-continued

Conversion of Small Molecule-PEG Prodrug to Compound A in Human Plasma
1 µM Prodrug in Human Plasma
Incubation times: 0, 1, 2, 4, 6 and 24 hours
Mass Spec Quantitation of Compound A

| Compound | Structure | Prodrug $t_{1/2}$ (hrs) |
|---|---|---|
| 120 | (structure shown) | 12 |

TABLE M
Pharmacokinetic Comparison of Compound A and Prodrug Compound in Mouse
| Compound | Structure | Time (hr) | [Cmpd A] (μM) |
|---|---|---|---|
| Cmpd A | 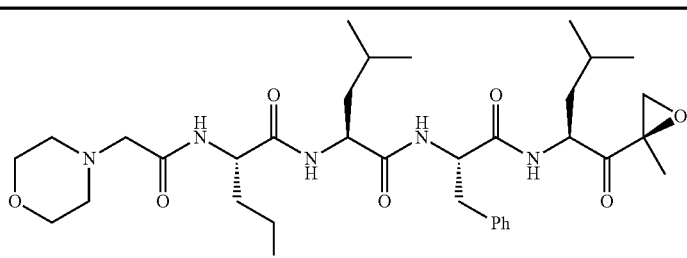 Dose: 5 mg/kg | 1<br>4<br>6<br>24 | 0.008<br>BLOQ<br>BLOQ<br>BLOQ |
| 74 | 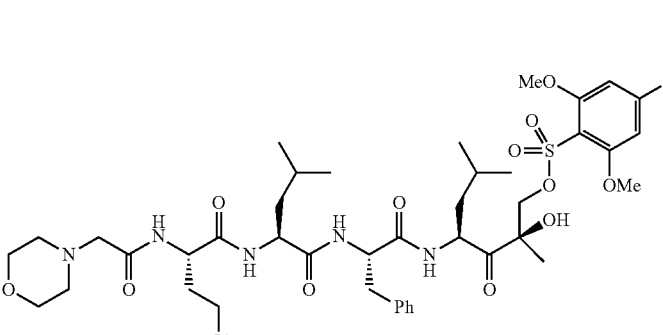 Dose: 5 mg/kg | 1<br>4<br>6<br>24 | 2.873<br>0.793<br>0.354<br>BLOQ |
(BLOQ = below level of quantitation)
TABLE N
Buffer Conversion Rates of Prodrugs to Compound B
| Compound | Structure | Buffer pH = 7.4<br>% Conversion @ 1 hour |
|---|---|---|
| 20-1 | 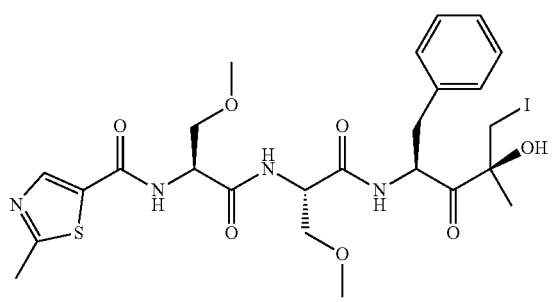 | 24 |

TABLE N-continued

Buffer Conversion Rates of Prodrugs to Compound B

| Compound | Structure | Buffer pH = 7.4 % Conversion @ 1 hour |
|---|---|---|
| 20-2 | 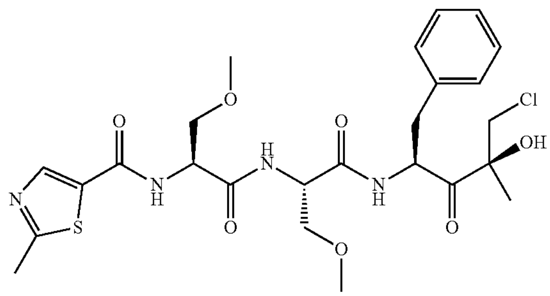 [SMILES: COC[C@H](NC(=O)c1cnc(C)s1)C(=O)N[C@@H](COC)C(=O)N[C@@H](Cc1ccccc1)C(=O)[C@](C)(O)CCl] | 0 |
| 20-3 | 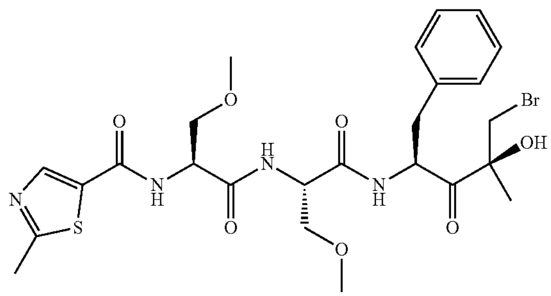 [SMILES: COC[C@H](NC(=O)c1cnc(C)s1)C(=O)N[C@@H](COC)C(=O)N[C@@H](Cc1ccccc1)C(=O)[C@](C)(O)CBr] | 23 |
| 20-4 | 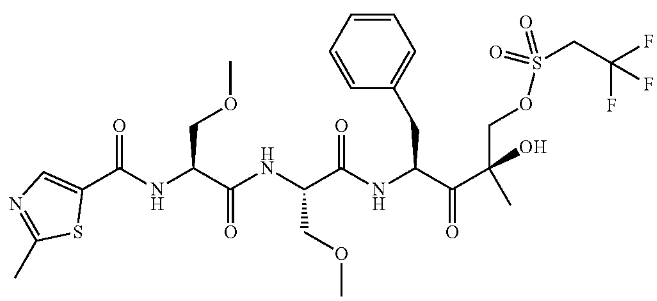 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)CC(F)(F)F] | 21.2 |
| 20-5 | 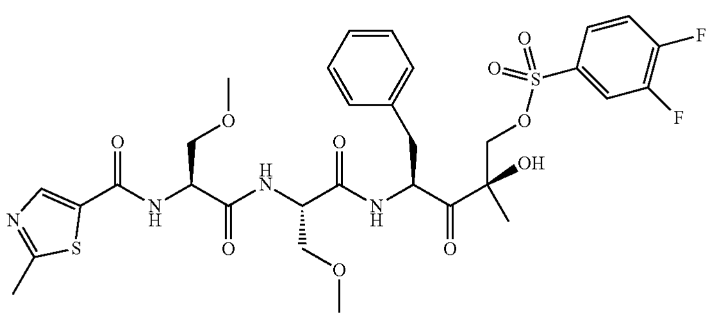 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(F)c(F)c1] | 13.2 |
| 20-6 | 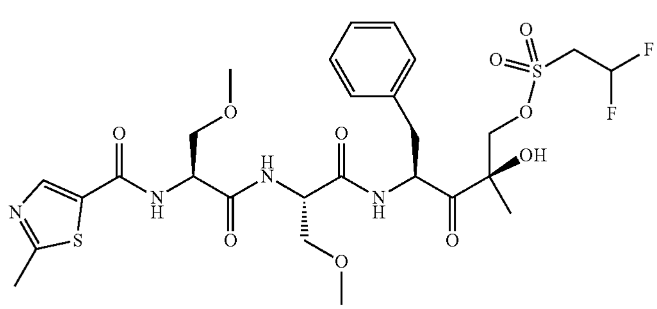 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)CC(F)F] | 5.7 |

TABLE N-continued

Buffer Conversion Rates of Prodrugs to Compound B

| Compound | Structure | Buffer pH = 7.4 % Conversion @ 1 hour |
|---|---|---|
| 23 | 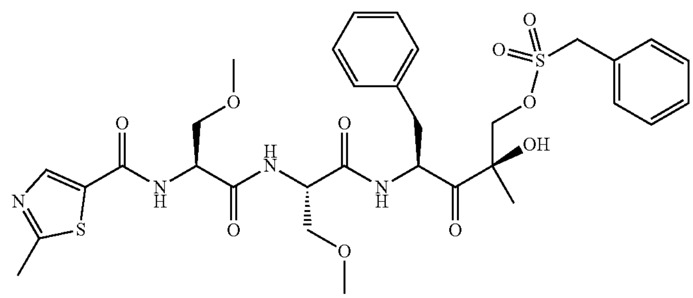 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)Cc1ccccc1] | 9.6 |
| 20-8 | 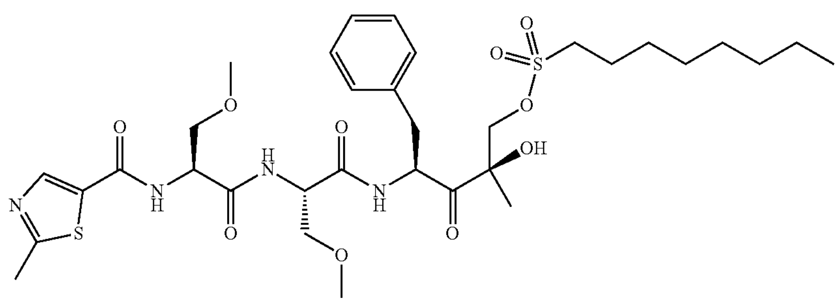 [SMILES: CCCCCCCCS(=O)(=O)OC[C@@](C)(O)C(=O)[C@H](Cc1ccccc1)NC(=O)[C@H](COC)NC(=O)[C@H](COC)NC(=O)c1cnc(C)s1] | 10.8 |
| 22 | 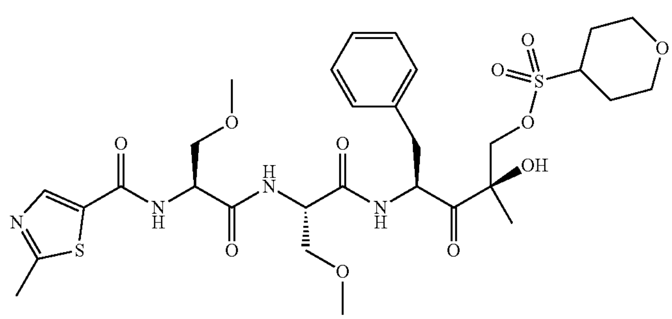 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)C1CCOCC1] | 9.8 |
| 21 | 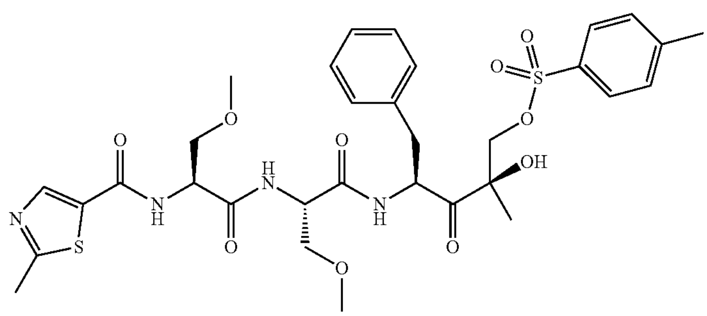 [SMILES: COC[C@H](NC(=O)c1cnc(C)s1)C(=O)N[C@@H](COC)C(=O)N[C@@H](Cc1ccccc1)C(=O)[C@](C)(O)COS(=O)(=O)c1ccc(C)cc1] | 20.3 |

TABLE N-continued

Buffer Conversion Rates of Prodrugs to Compound B

| Compound | Structure | Buffer pH = 7.4 % Conversion @ 1 hour |
|---|---|---|
| 20-7 | 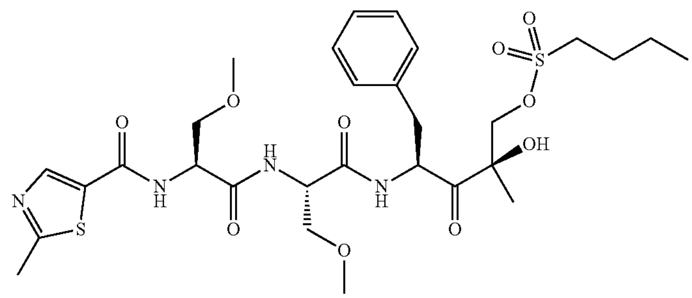 [SMILES: CCCCS(=O)(=O)OC[C@@](C)(O)C(=O)[C@H](Cc1ccccc1)NC(=O)[C@H](COC)NC(=O)[C@H](COC)NC(=O)c1cnc(C)s1] | 4.2 |

TABLE O

Conversion of Prodrugs by Human Liver S9 over Time

| Compound | Structure | Human Liver S9 % Conversion @ 1 hour |
|---|---|---|
| 20-10 | 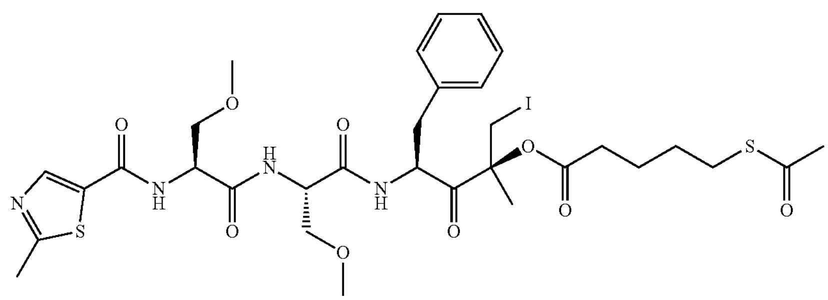 | 3 |
| 20-13 | 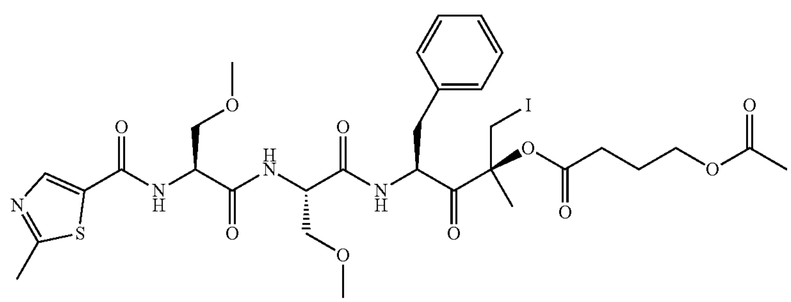 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCCOC(C)=O] | 11 |
| 20-15 | 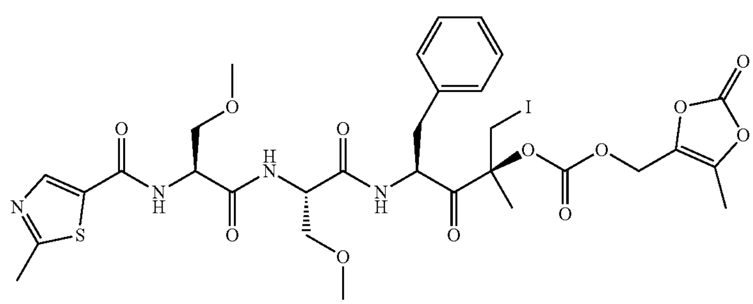 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)OCc1oc(=O)oc1C] | 30 |

TABLE O-continued

Conversion of Prodrugs by Human Liver S9 over Time

| Compound | Structure | Human Liver S9 % Conversion @ 1 hour |
|---|---|---|
| 20-16 | 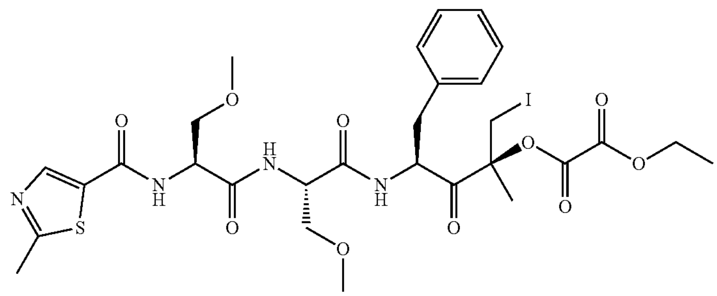 [SMILES: CCOC(=O)C(=O)O[C@](C)(CI)C(=O)[C@H](Cc1ccccc1)NC(=O)[C@H](COC)NC(=O)[C@H](COC)NC(=O)c1cnc(C)s1] | 24 |
| 20-17 | 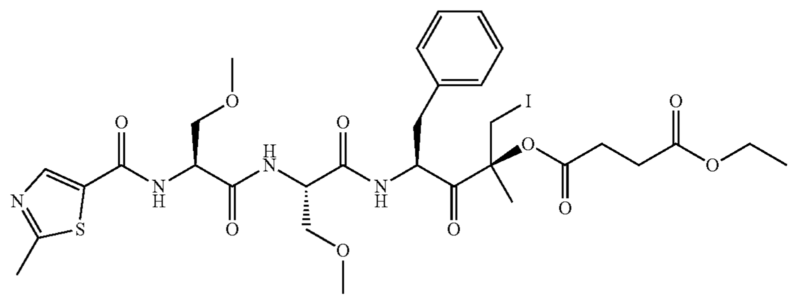 [SMILES: CCOC(=O)CCC(=O)O[C@](C)(CI)C(=O)[C@H](Cc1ccccc1)NC(=O)[C@H](COC)NC(=O)[C@H](COC)NC(=O)c1cnc(C)s1] | 1 |
| 20-19 | 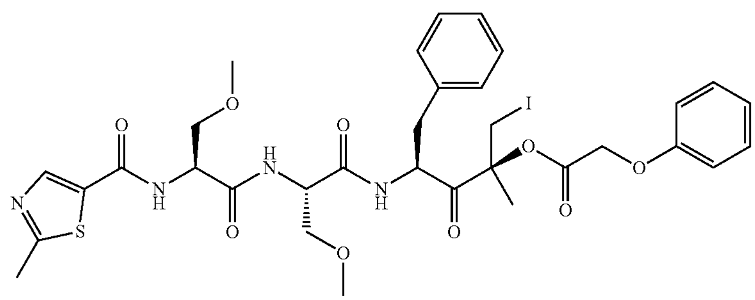 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)COc1ccccc1] | 7 |
| 20-22 | 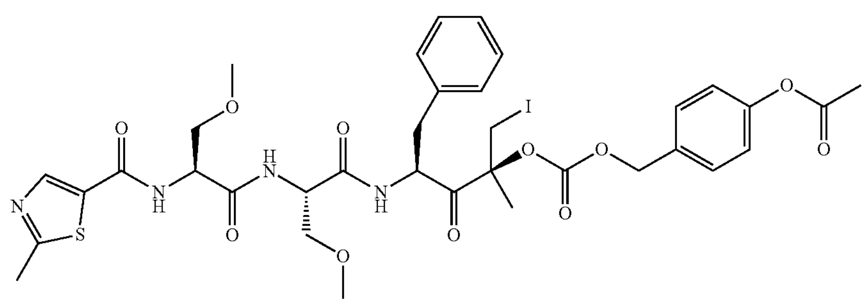 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)OCc1ccc(OC(C)=O)cc1] | 28 |
| 20-23 | 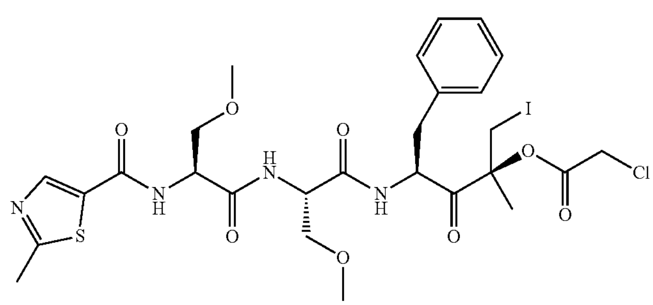 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)CCl] | 22 |

TABLE O-continued

Conversion of Prodrugs by Human Liver S9 over Time

| Compound | Structure | Human Liver S9 % Conversion @ 1 hour |
|---|---|---|
| 20-24 | 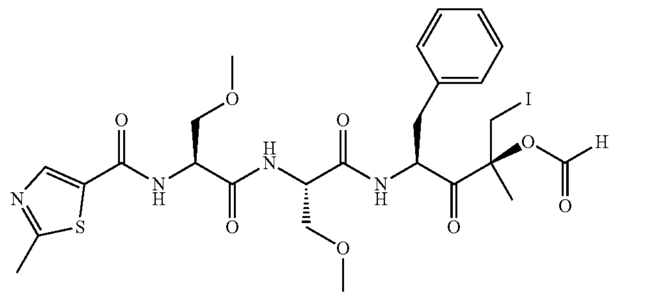 [SMILES: COC[C@H](NC(=O)c1cnc(C)s1)C(=O)N[C@@H](COC)C(=O)N[C@@H](Cc1ccccc1)C(=O)[C@@](C)(CI)OC=O] | 29 |
| 20-25 | 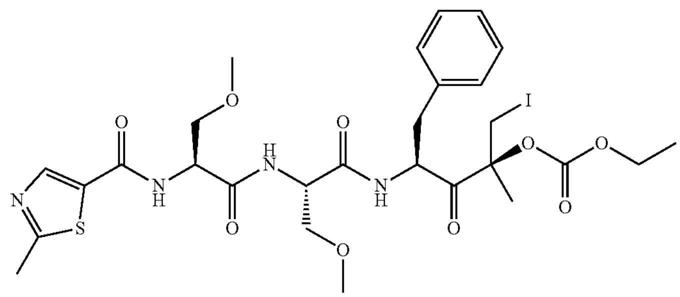 [SMILES: CCOC(=O)O[C@](C)(CI)C(=O)[C@H](Cc1ccccc1)NC(=O)[C@H](COC)NC(=O)[C@H](COC)NC(=O)c1cnc(C)s1] | 14 |
| 20-26 | 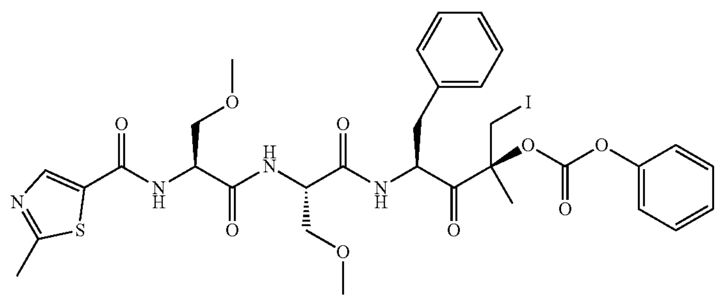 [SMILES: COC[C@H](NC(=O)c1cnc(C)s1)C(=O)N[C@@H](COC)C(=O)N[C@@H](Cc1ccccc1)C(=O)[C@@](C)(CI)OC(=O)Oc1ccccc1] | 32 |

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A compound having the formula:

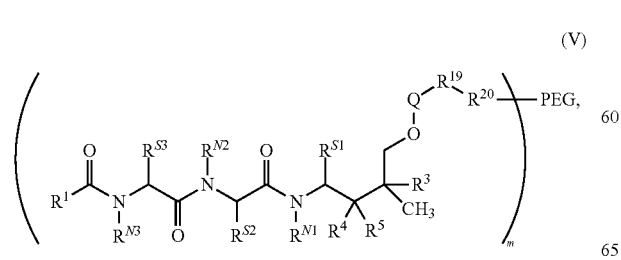

(V)

or a pharmaceutically acceptable salt thereof;

wherein

Q is selected from: —$SO_2$—; and —P(=O)—$OR^{16}$—;

$R^{19}$ is a divalent spacer which comprises of one or more of the following moieties:

heteroatom, alkylene chain, heteroalkylene chain, polyheteroalkylene chain, alkenylene chain, arylene having 6-10 ring atoms, heteroarylene having from 5-10 ring atoms wherein 1-3 of the ring atoms are independently selected from N, NH, N—C1-C6 alkyl, O, and S, heterocycloalkylene having 3-9 ring atoms wherein 1-3 of the ring atoms are independently selected from N, NH, N—C1-C6 alkyl, O, and S, —OC(=O)—, —C(=O)O—, —NHC(=O)—, —C(=O)NH—, —N($C_{1-6}$ alkyl)C(=O), —C(=O)N($C_{1-6}$ alkyl)-, —C(=O)—, —NHC(=O)NH—, cyclodextrin, human serum albumin, amino acid, and hydrazine, wherein arylene having 6-10 ring atoms, heteroarylene having from 5-10 ring atoms, and heterocycloalkylene having 3-9 ring atoms are each optionally substituted with 1, 2, or 3 substituents each independently selected from the group consisting of halo, cyano, nitro, hydroxyl, $C_{1-6}$ alkoxy, heteroalkyl, $C_{6-10}$ aryloxy, $C_{7-12}$ aralkoxy, $CF_3$, quaternary ammonium ion, sugar, $C_{1-6}$ alkyl, —C(═O)(C$_{1-6}$ alkyl), —SO$_2$(C$_{1-6}$ alkyl), —C(═O)O(C$_{1-6}$ alkyl), —C(═O)O(heteroalkyl), —C(═O)NH(C$_{1-6}$ alkyl), —C(═O)NH(heteroalkyl), —C(═O)(phenyl), —SO$_2$(phenyl), and phosphate;

R$^{20}$ is absent or

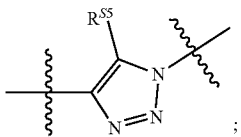

;

R$^{S5}$ is H, C$_{1-6}$alkyl, C$_{1-6}$hydroxyalkyl, C$_{1-6}$alkoxyC$_{1-6}$alkyl, C$_{6-10}$aryl, or C$_{7-12}$aralkyl, each of which is optionally substituted with a group selected from amide, amine, carboxylic acid or a pharmaceutically acceptable salt thereof, carboxyl ester, thiol, and thioether;

R$^1$ has formula (II):

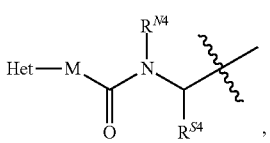

(II)

wherein Het is heterocyclyl that includes from 5-6 ring atoms, wherein at least one ring atom is a nitrogen atom selected from —N(H)—, —N(M)-, or —N(C$_1$-C$_3$ alkyl)-; and M is C$_1$-C$_{12}$ alkyl; or R$^3$ is hydroxyl or activated hydroxyl;

R$^4$ and R$^5$, together with the carbon atom to which both are attached, form a carbonyl group;

R$^{S1}$, R$^{S2}$, R$^{S3}$, and R$^{S4}$ are each independently selected from C$_{1-6}$alkyl, C$_{1-6}$hydroxyalkyl, C$_{1-6}$alkoxy, C$_{1-6}$alkyl, C$_{6-10}$aryl, and C$_{7-12}$aralkyl, each of which is optionally substituted with a group selected from amide, amine, carboxylic acid or a pharmaceutically acceptable salt thereof, carboxyl ester, thiol, and thioether;

R$^{N1}$, R$^{N2}$, R$^{N3}$, and R$^{N4}$ are each independently selected from H and R$^{14}$;

each R$^{14}$ is, independently, a moiety that is removable at a pH>7 or in the presence of an esterase;

R$^{16}$ is C$_{1-6}$alkyl, C$_{1-6}$haloalkyl, heteroalkyl, C$_{6-10}$aryl, C$_{7-12}$aralkyl, C$_{3-7}$cycloalkyl, heteroaryl having from 5-10 ring atoms, or heterocyclyl having from 3-7 ring atoms, each of which is optionally substituted with from 1-2 R$^a$;

R$^a$ at each occurrence is, independently selected from halo, cyano, C$_{1-6}$ alkoxy, heteroalkyl, C$_{6-10}$ aryloxy, C$_{7-12}$ aralkoxy, CF$_3$, C$_{1-6}$ alkyl, —C(═O)(C$_{1-6}$ alkyl), —SO$_2$(C$_{1-6}$ alkyl), —C(═O)O(C$_{1-6}$ alkyl), —C(═O)O(heteroalkyl), —C(═O)NH(C$_{1-6}$ alkyl), —C(═O)NH(C$_{1-6}$ alkyl)-C(═O)NH$_2$, —C(═O)NH(heteroalkyl), —C(═O)(phenyl), and —SO$_2$(phenyl); and m is 2-10.

2. The compound of claim 1, wherein Het is:

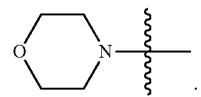

.

3. The compound according to claim 1, wherein M is CH$_2$.

4. The compound according to claim 1, wherein R$^3$ is an activated hydroxyl.

5. The compound according to claim 4 wherein R$^3$ is:

—OC(═O)—R$^{22}$—R$^{20}$-PEG, wherein:

R$^{22}$ is a divalent spacer comprising one or more of the following moieties: heteroatom, alkylene chain, heteroalkylene chain, polyheteroalkylene chain, alkenylene chain, arylene having 6-10 ring atoms, heteroarylene having from 5-10 ring atoms, heterocycloalkylene having 3-9 ring atoms, —OC(═O)—, —C(═O)O—, —NHC(═O)—, —C(═O)NH—, —N(C$_{1-6}$ alkyl)C(═O), —C(═O)N(C$_{1-6}$ alkyl)-, —C(═O)—, —NHC(═O)NH—, cyclodextrin, human serum albumin, amino acid, or hydrazine, wherein arylene having 6-10 ring atoms, heteroarylene having from 5-10 ring atoms, and heterocycloalkylene having 3-9 ring atoms are each optionally substituted with 1, 2, or 3 substituents each independently selected from the group consisting of halo, cyano, nitro, hydroxyl, C$_{1-6}$ alkoxy, heteroalkyl, C$_{6-10}$ aryloxy, C$_{7-12}$ aralkoxy, CF$_3$, quaternary ammonium ion, sugar, C$_{1-6}$ alkyl, —C(═O)(C$_{1-6}$ alkyl), —SO$_2$(C$_{1-6}$ alkyl), —C(═O)O(C$_{1-6}$ alkyl), —C(═O)O(heteroalkyl), —C(═O)NH(C$_{1-6}$ alkyl), —C(═O)NH(heteroalkyl), —C(═O)(phenyl), —SO$_2$(phenyl), and phosphate;

R$^{20}$ is

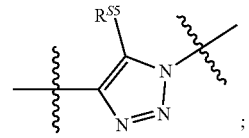

;

R$^{S5}$ is H, C$_{1-6}$alkyl, C$_{1-6}$hydroxyalkyl, C$_{1-6}$alkoxyC$_{1-6}$alkyl, C$_{6-10}$aryl, or C$_{7-12}$aralkyl, each of which is optionally substituted with a group selected from amide, amine, carboxylic acid or a pharmaceutically acceptable salt thereof, carboxyl ester, thiol, and thioether.

6. The compound according to claim 1, wherein each of R$^{N1}$, R$^{N2}$, R$^{N3}$, and R$^{N4}$ is H.

7. The compound of claim 1, wherein Q is SO$_2$.

8. The compound of claim 1, wherein m is 2, 4, or 8.

9. The compound according to claim 1, wherein R$^3$ is OH.

10. The compound according to claim 1, wherein R$^{19}$ is a divalent spacer comprising one or more of the following moieties: heteroatom, alkylene chain, —NHC(═O)—, —C(═O)NH—, heteroalkylene chain, phenylene, indolylene, indolinylene, thiophenylene, or furanylene, wherein phenylene, indolylene, indolinylene, thiophenylene, and furanylene are optionally substituted with 1, 2, or 3 substituents each independently selected from the group consisting of halo, C$_{1-6}$ alkoxy, heteroalkyl, CF$_3$, and C$_{1-6}$ alkyl.

11. The compound of claim 10, wherein when $R^{19}$ comprises either of —NHC(=O)— or —C(=O)NH—, the —NHC(=O)— or —C(=O)NH— of $R^{19}$ is linked to PEG.

12. The compound according to claim 1, wherein $R^{19}$ is

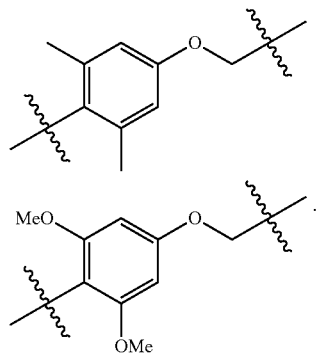 or

13. The compound according to claim 1, wherein PEG is $PEG_{20K}$.

14. The compound according to claim 1, wherein $R^{S5}$ is H.

15. The compound of claim 1, wherein $R^{S1}$ and $R^{S3}$ are each independently $C_{1-6}$alkyl, and $R^{S2}$ and $R^{S4}$ are each independently $C_{7-12}$aralkyl.

16. The compound of claim 1, wherein the compound is a prodrug of:

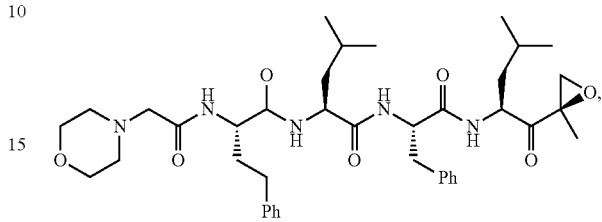

or a pharmaceutically acceptable salt thereof.

17. A compound according to claim 1, wherein the compound is selected from the group consisting of:

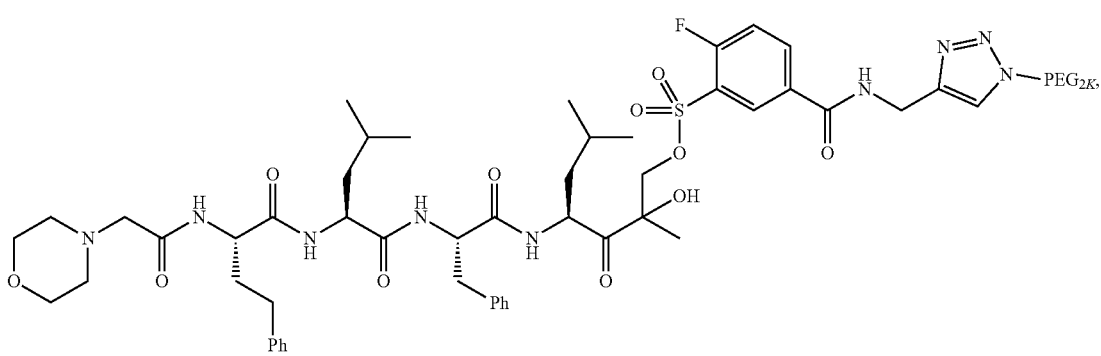

27

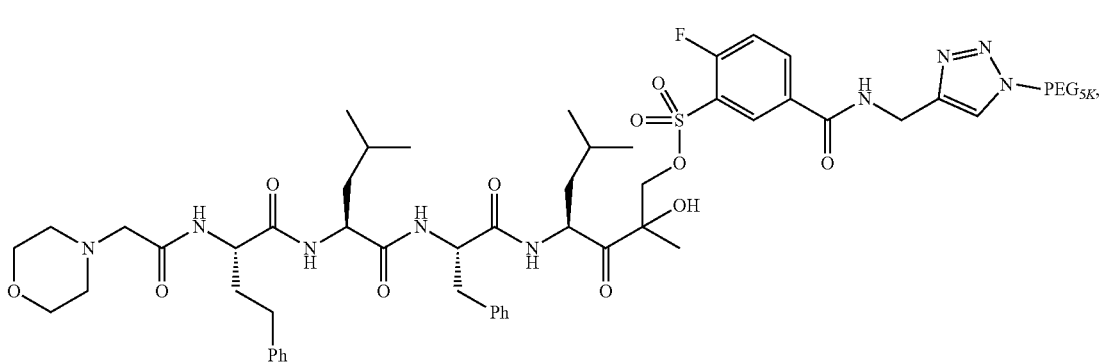

28

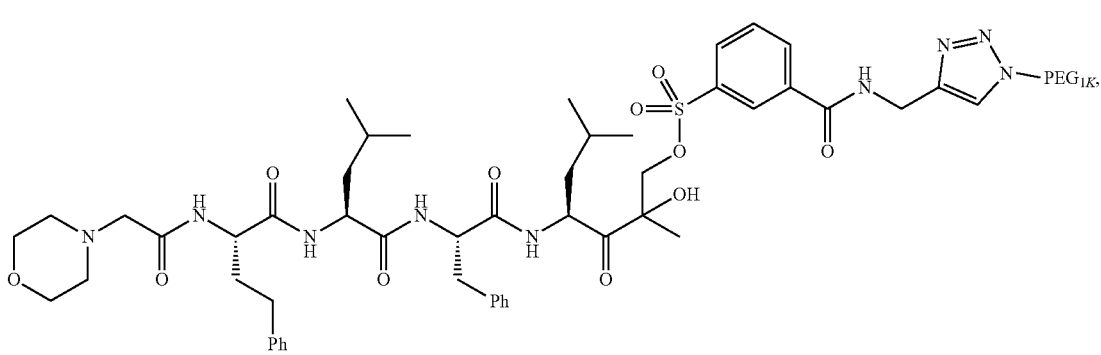

29

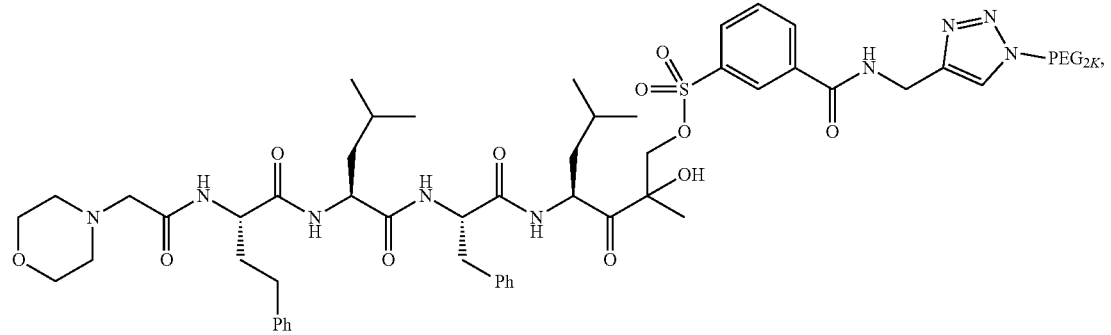
30
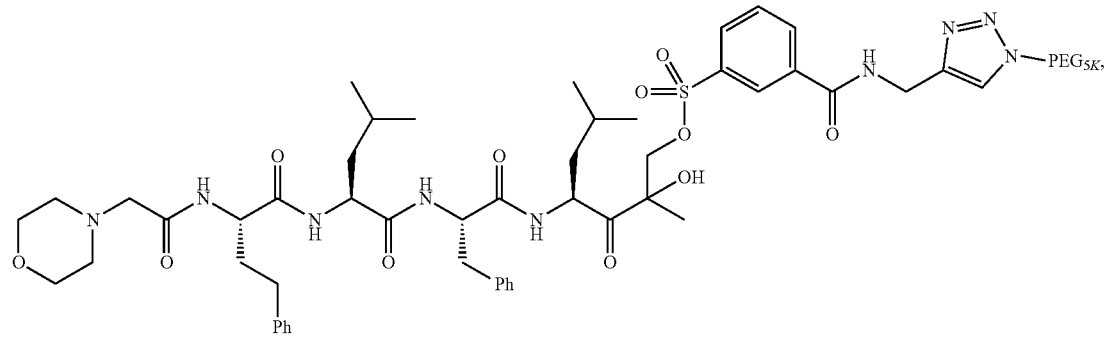
31
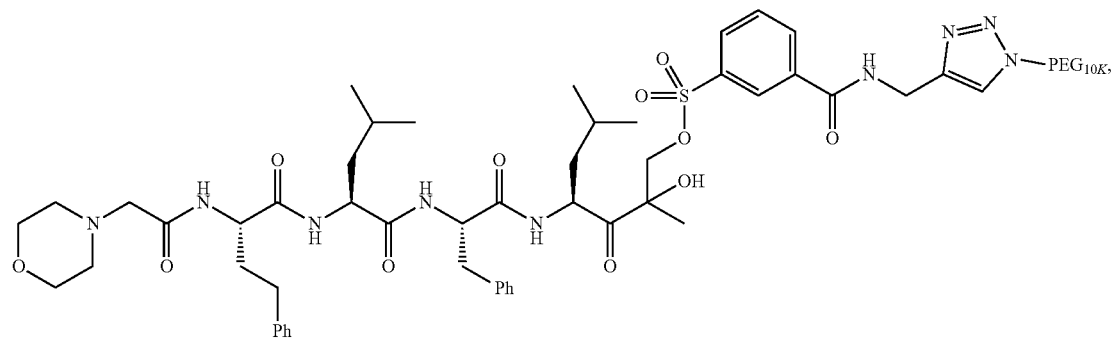
32
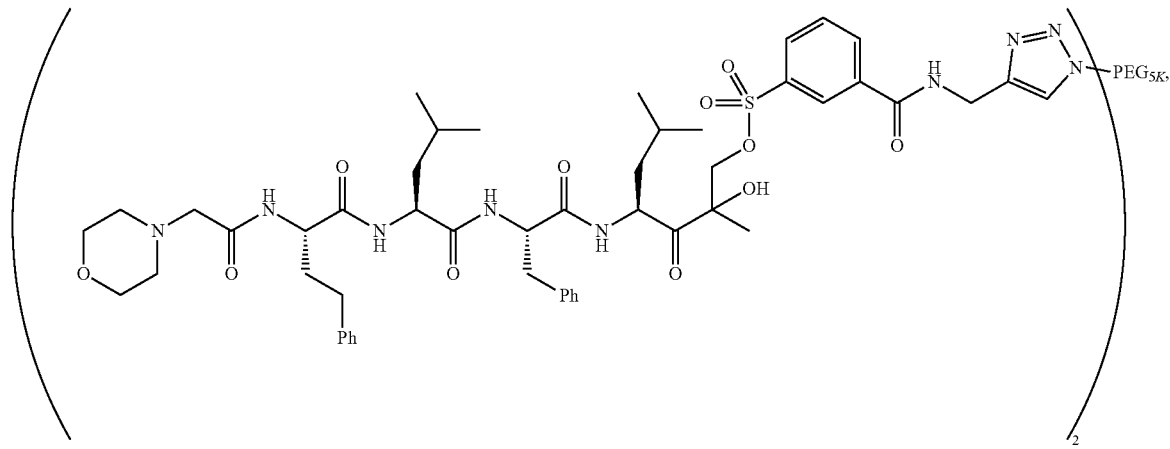
33

-continued
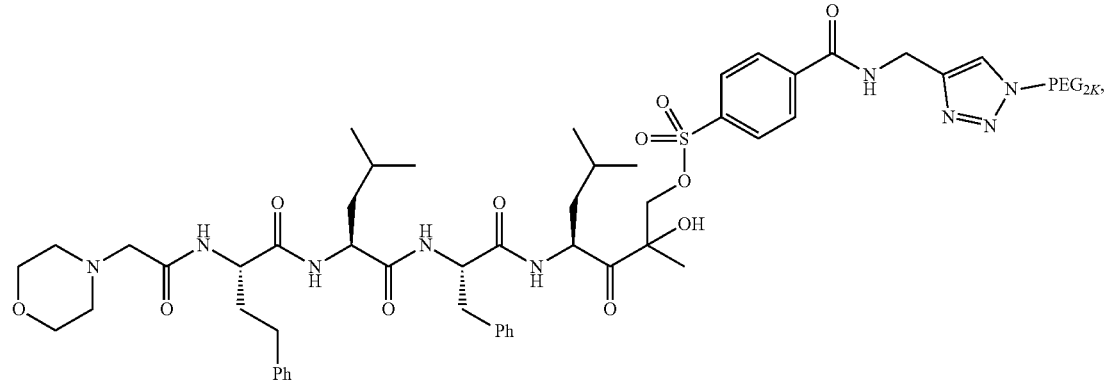
34
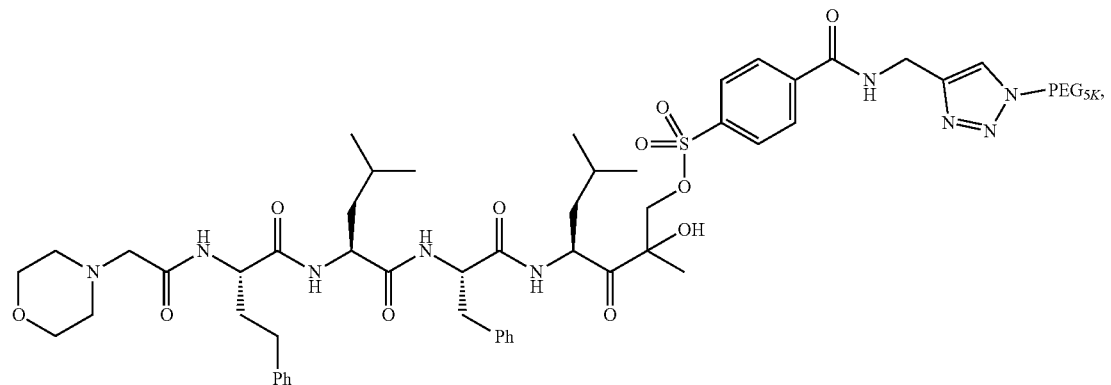
35
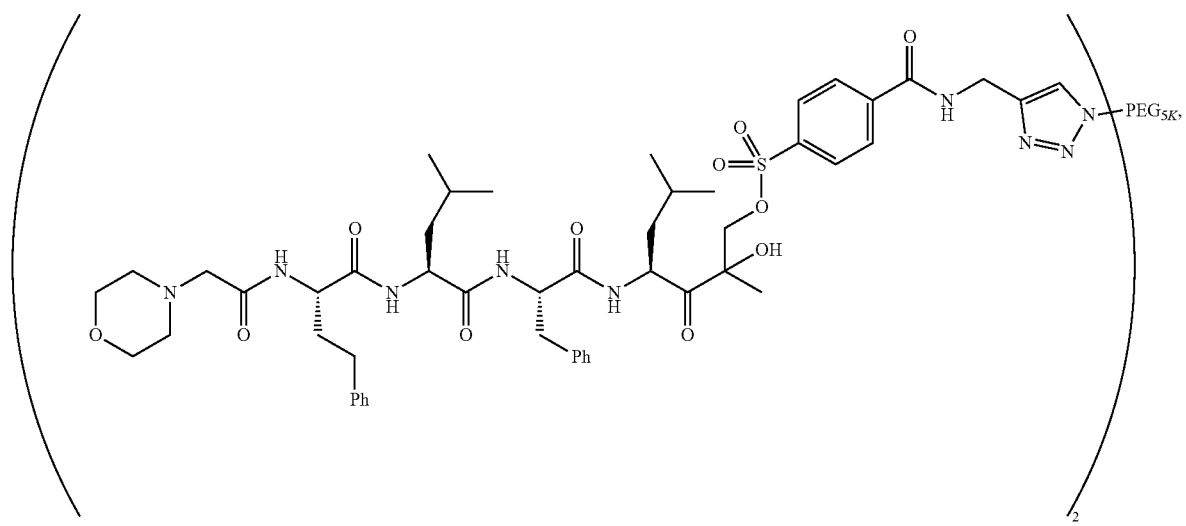
36

-continued
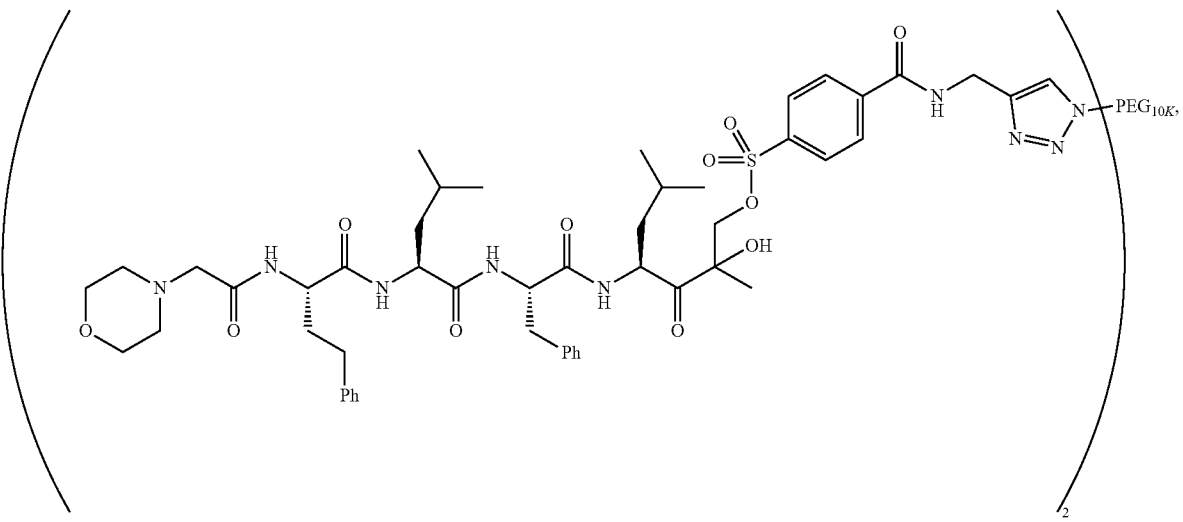
37
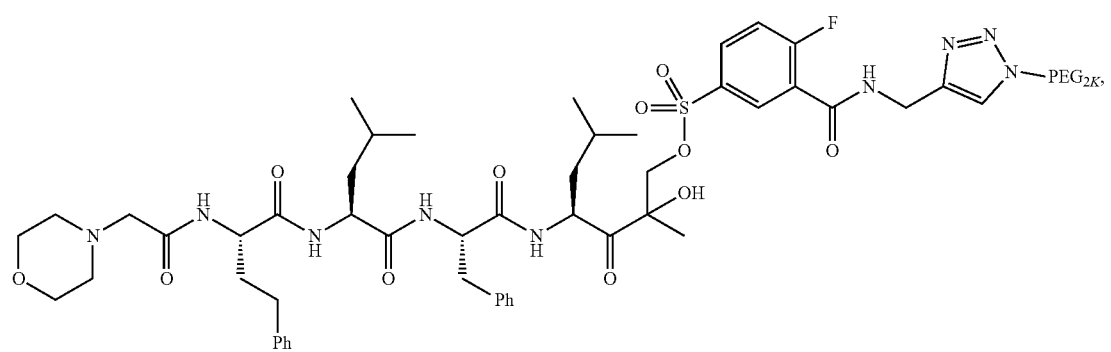
38
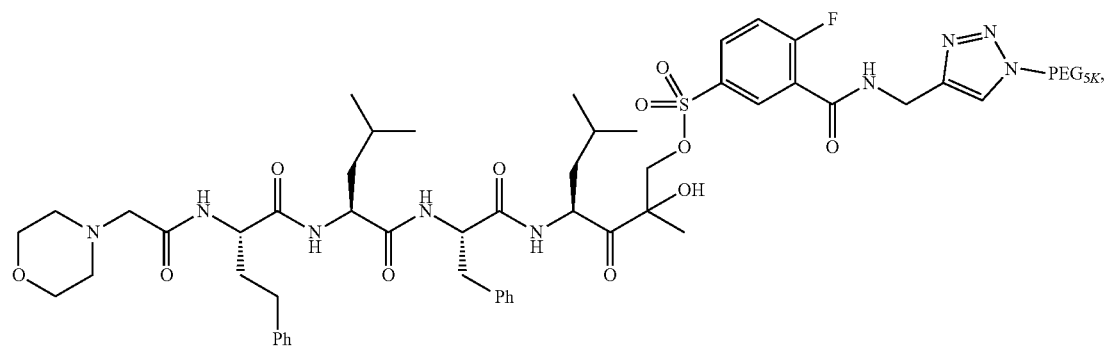
39
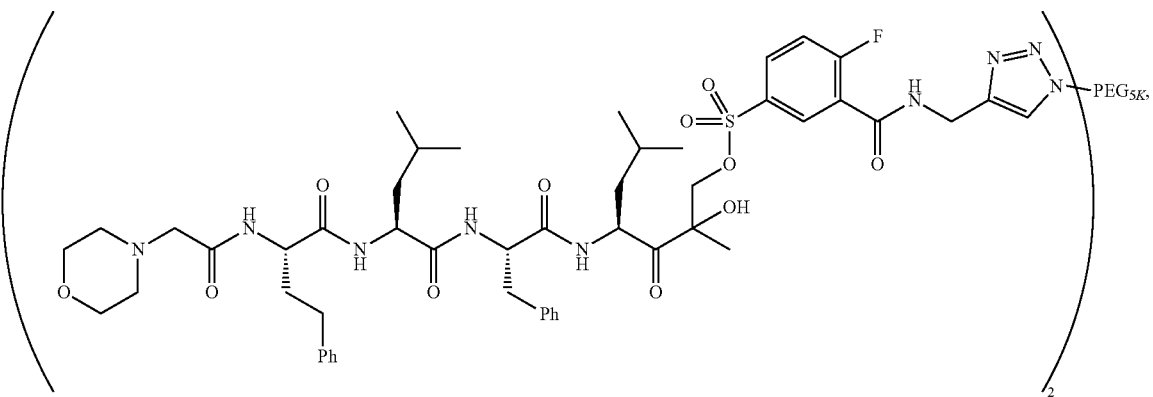
40

41
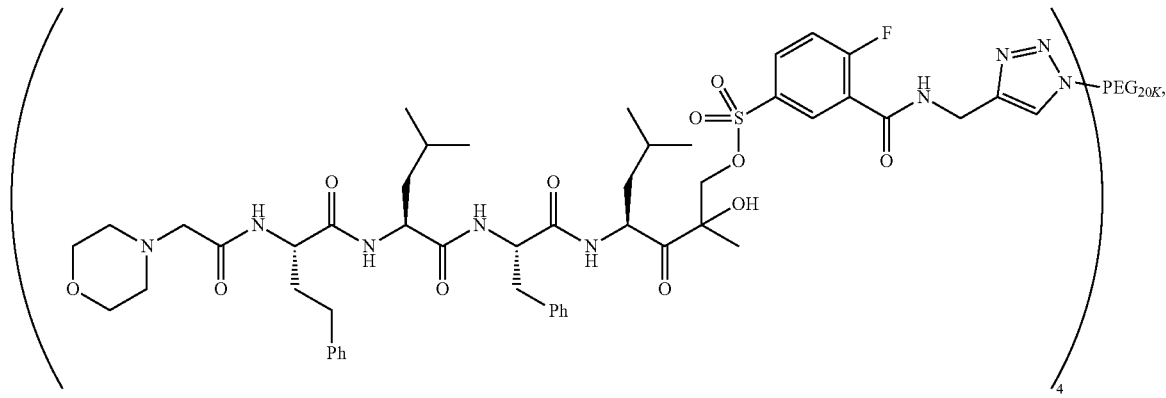
42
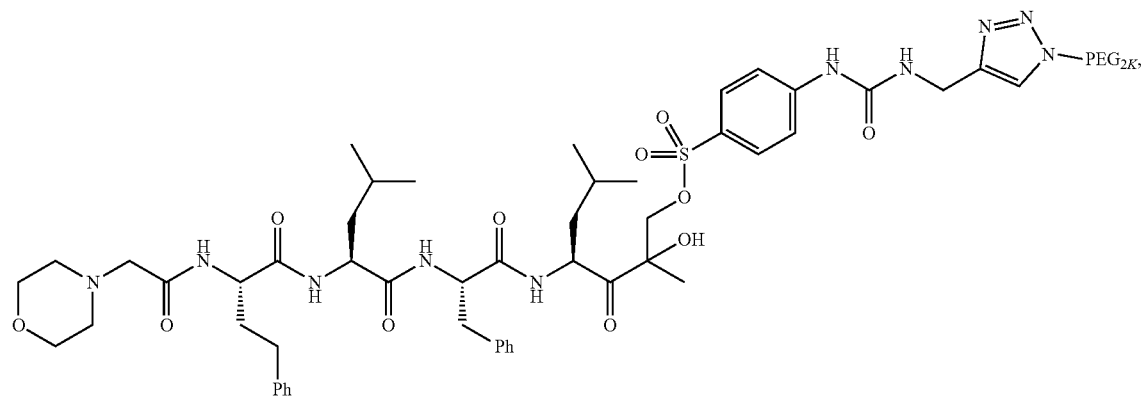
43
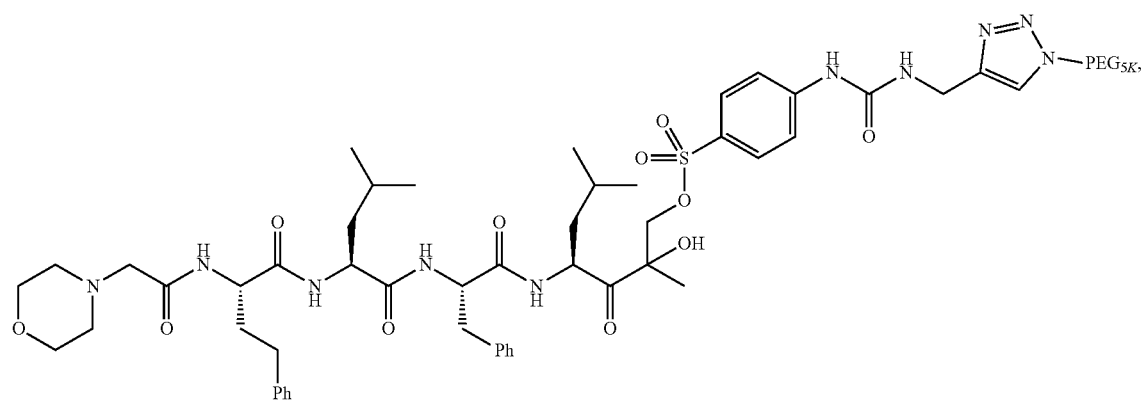
44
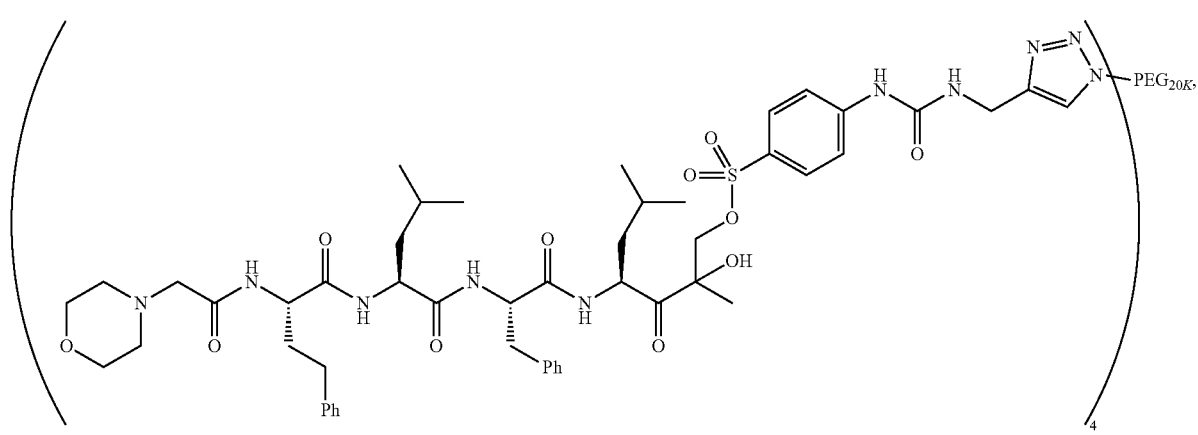

-continued
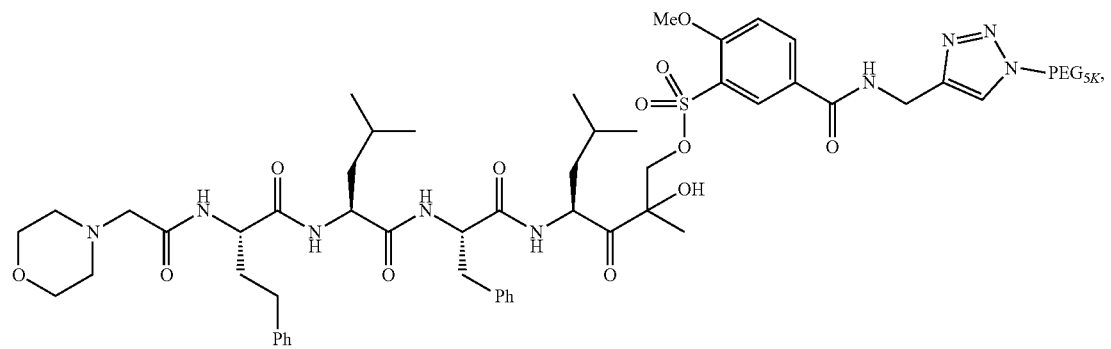
45
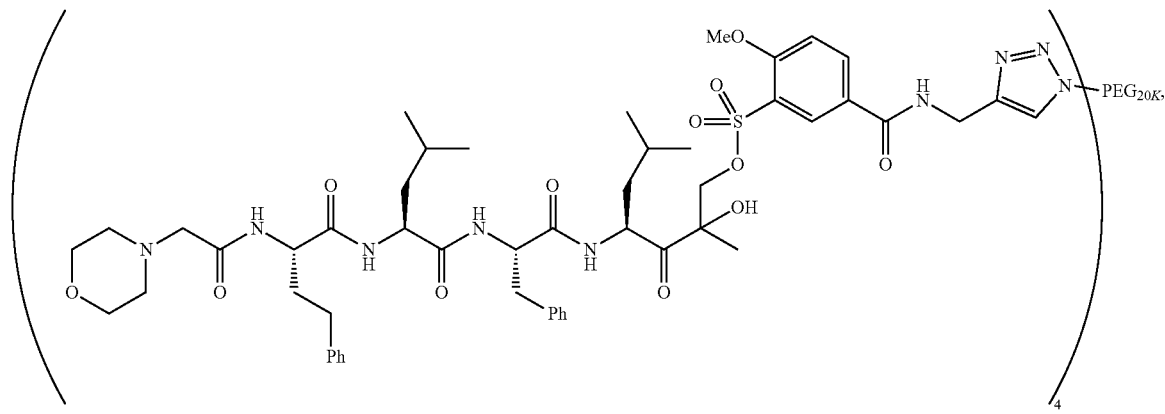
46
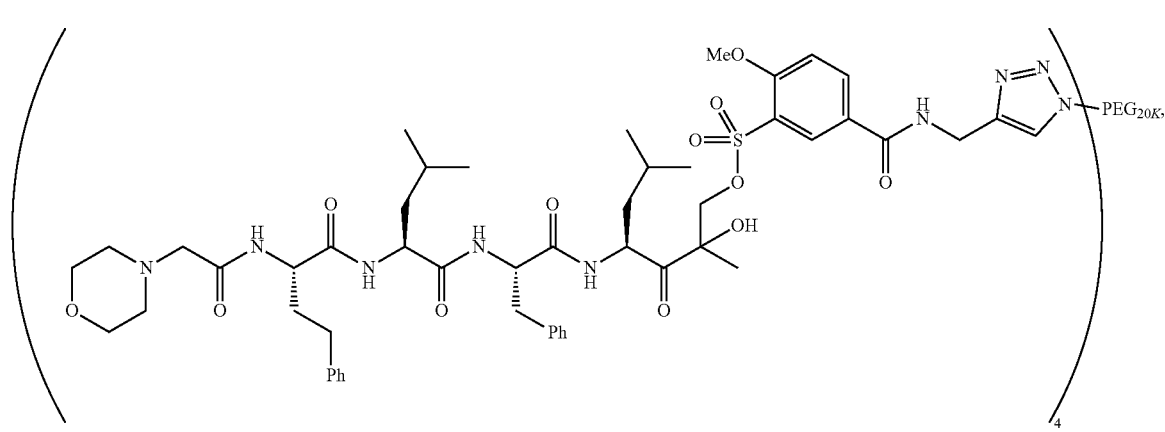
47
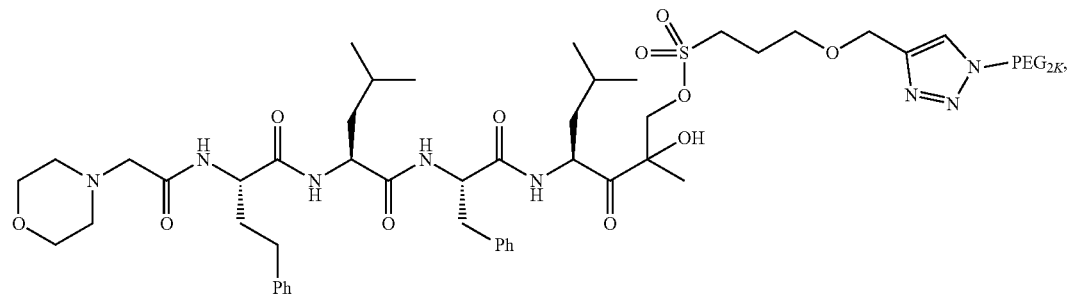
48

-continued
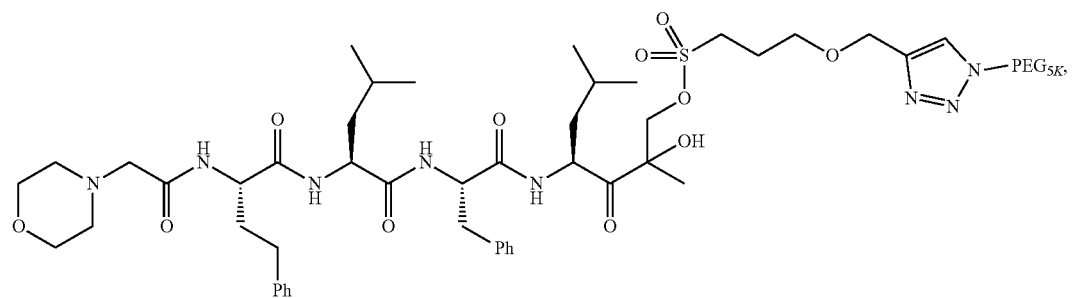
49
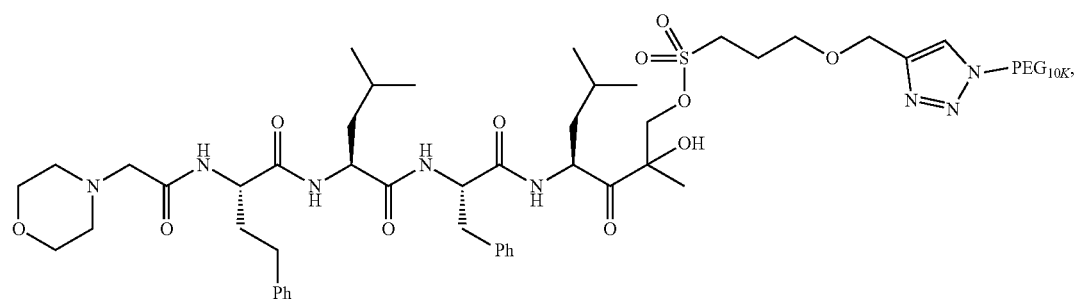
50
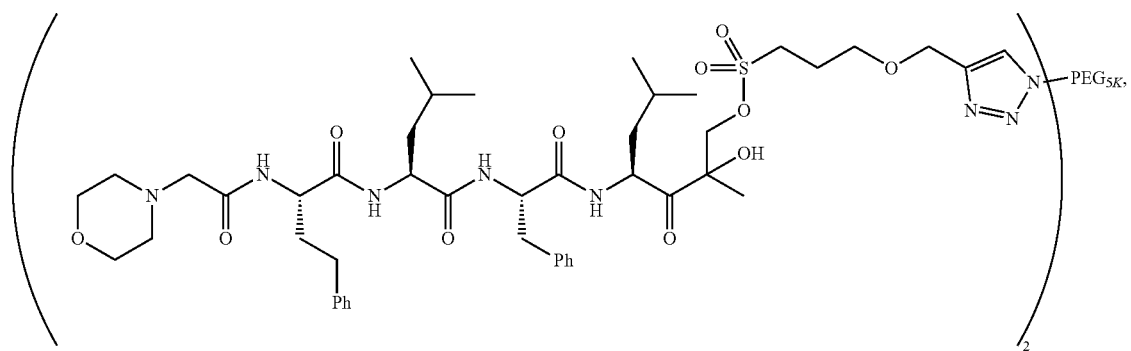
51
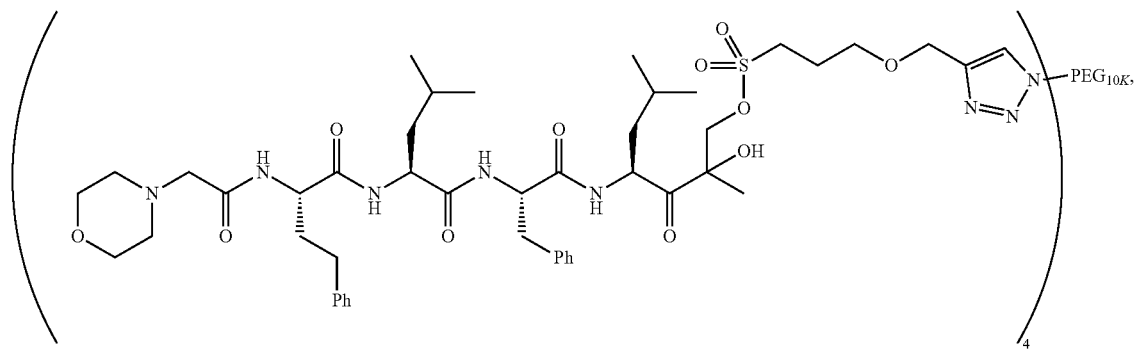
52

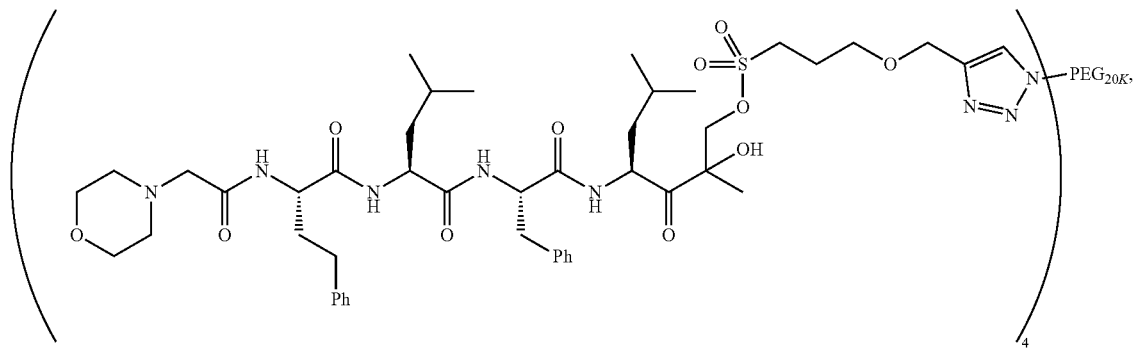
53
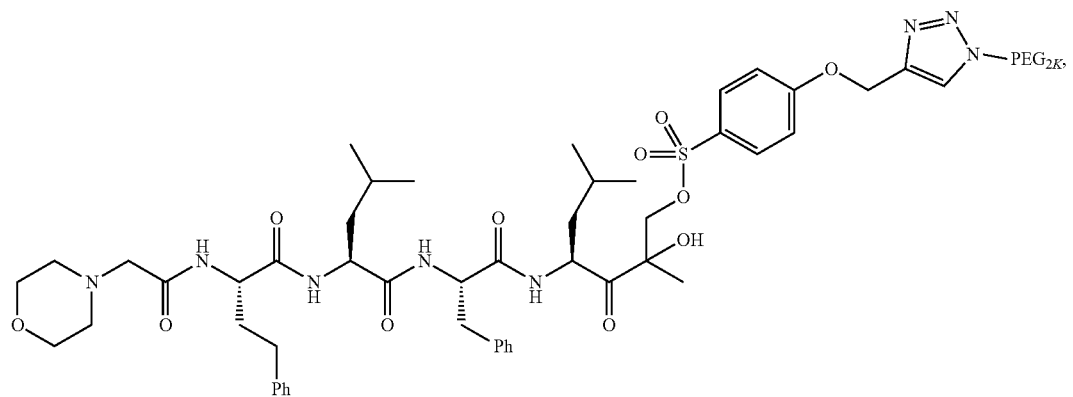
54
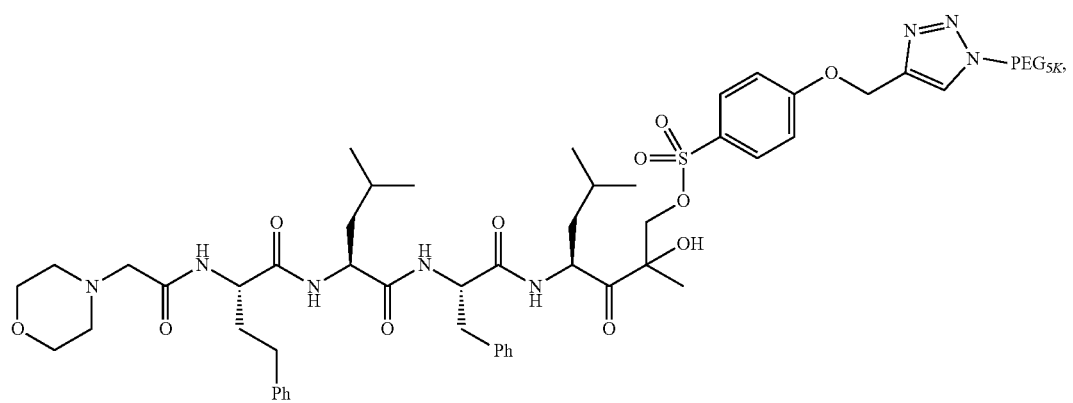
55
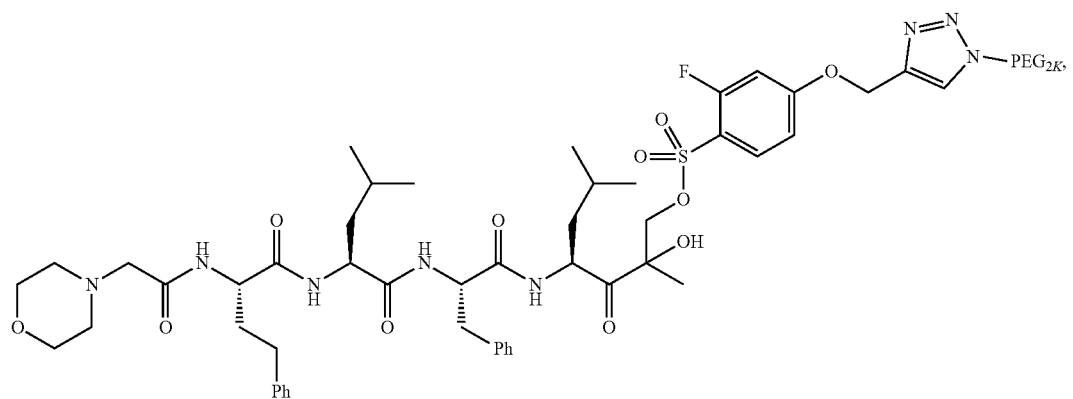
56

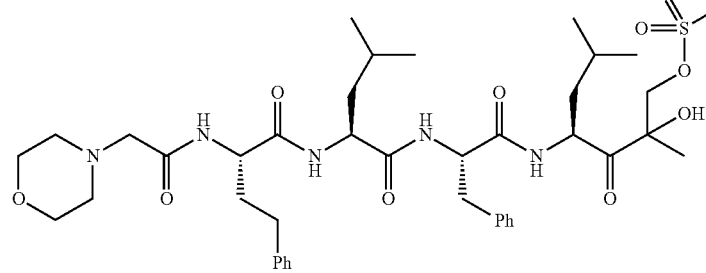
57
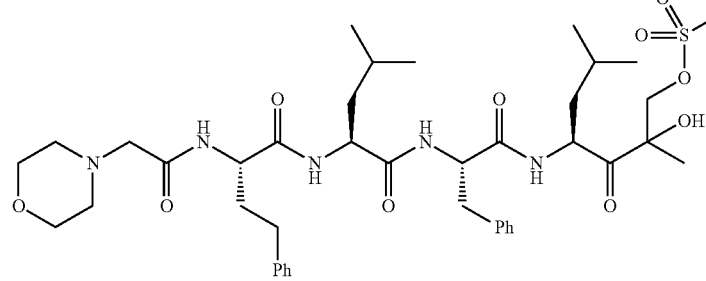
58
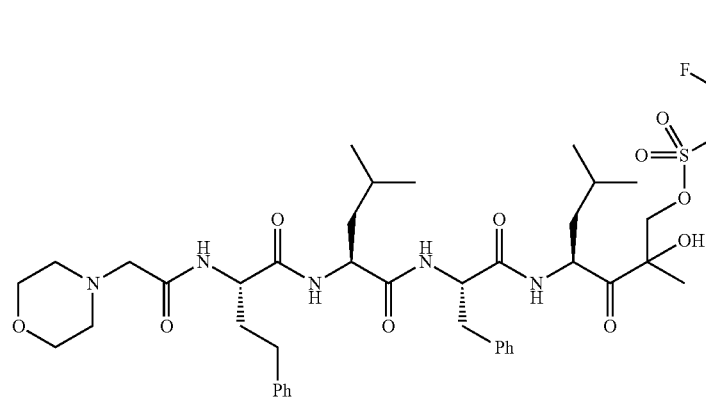
59
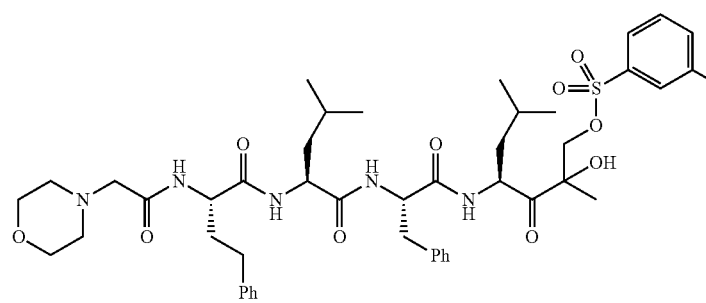
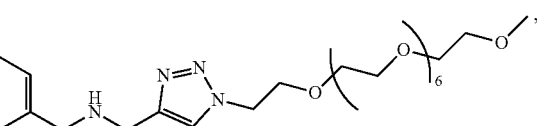
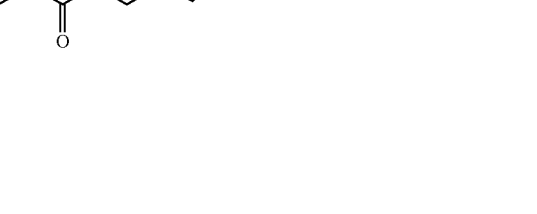
66

-continued
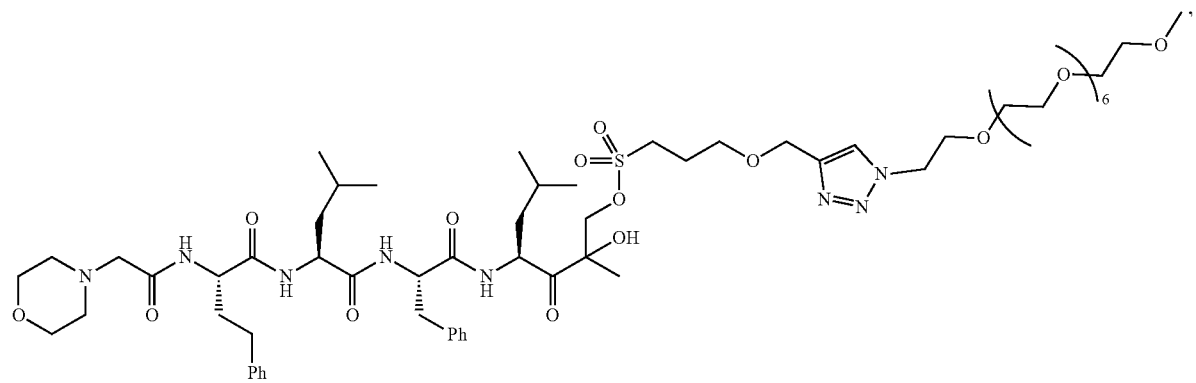
67
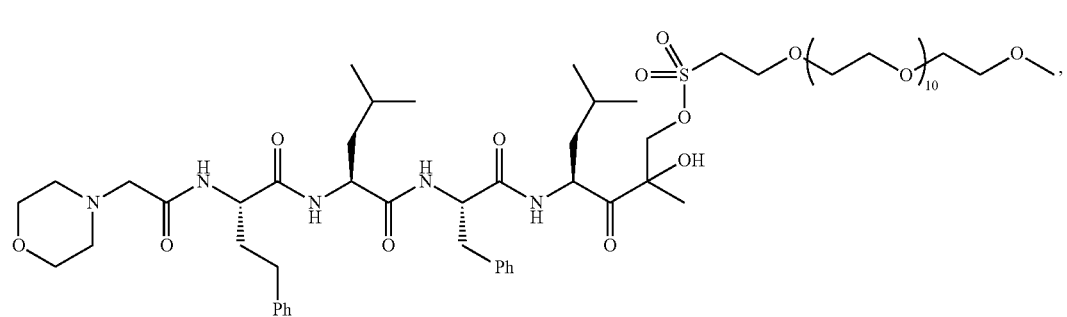
68
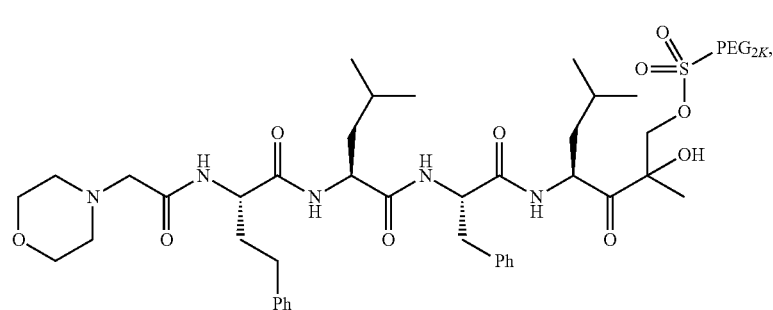
69
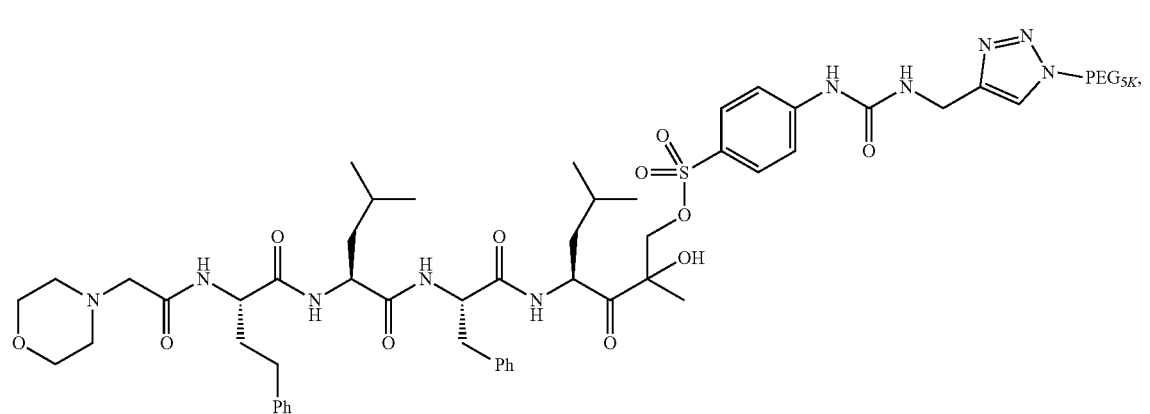
73

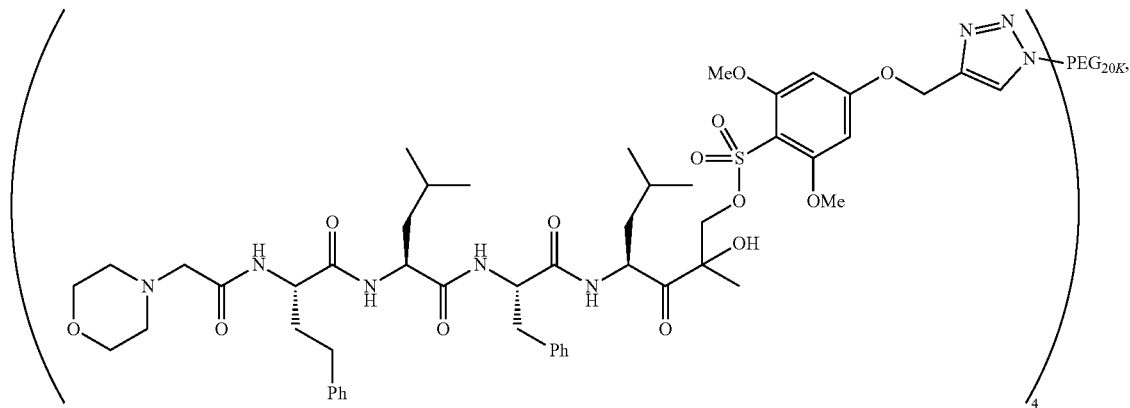
74
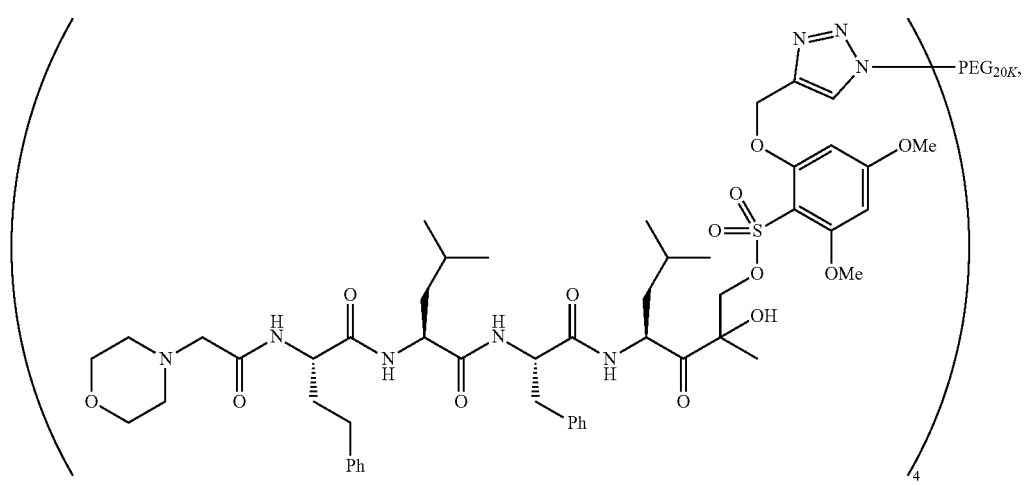
75
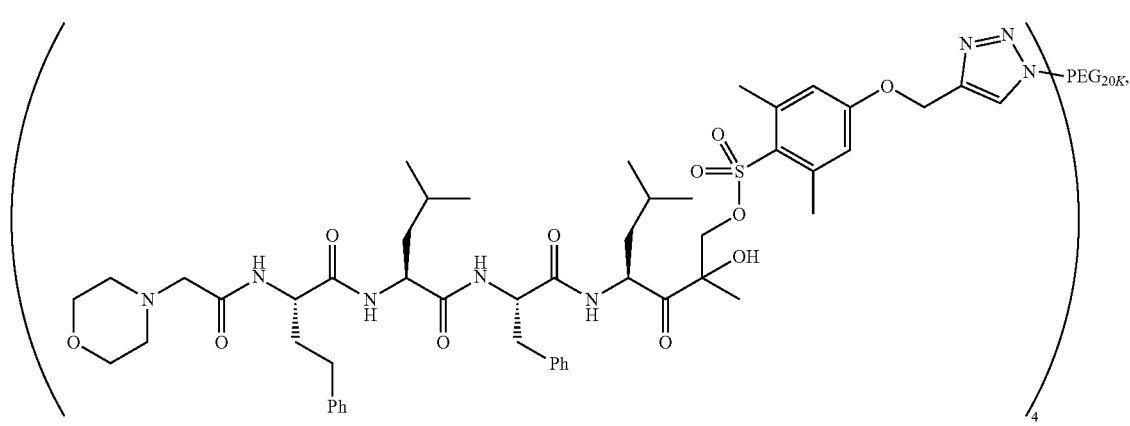
76

-continued
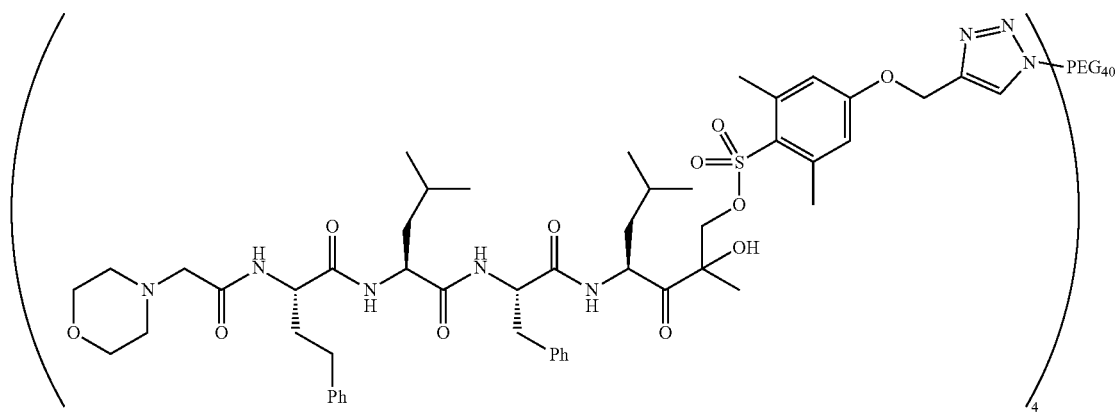
77
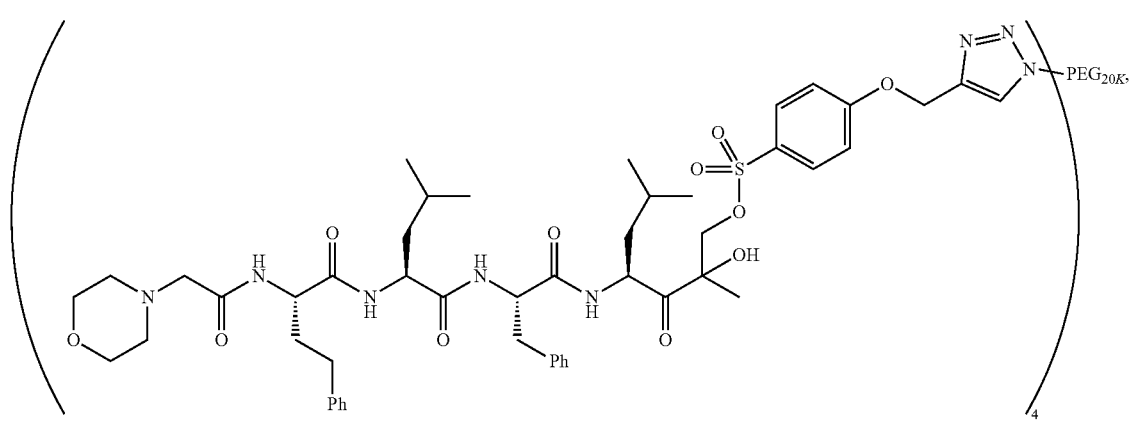
78
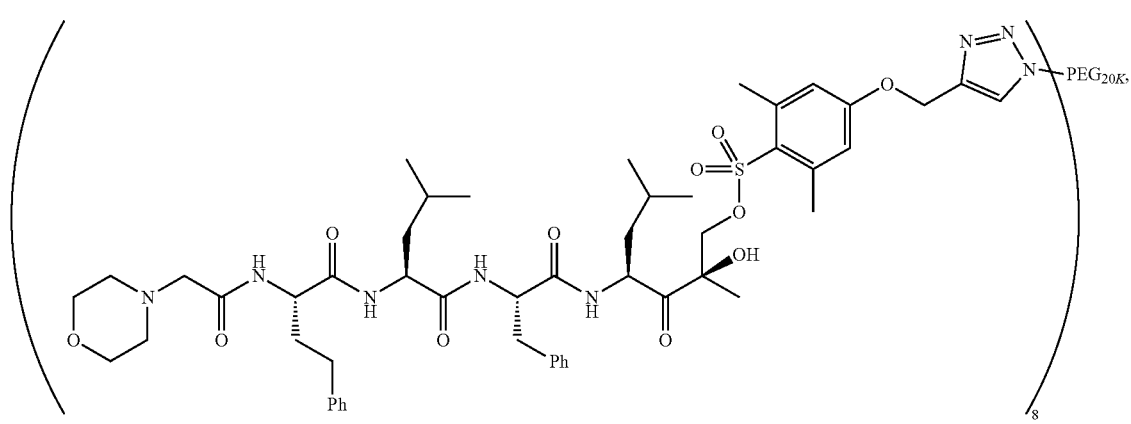
79
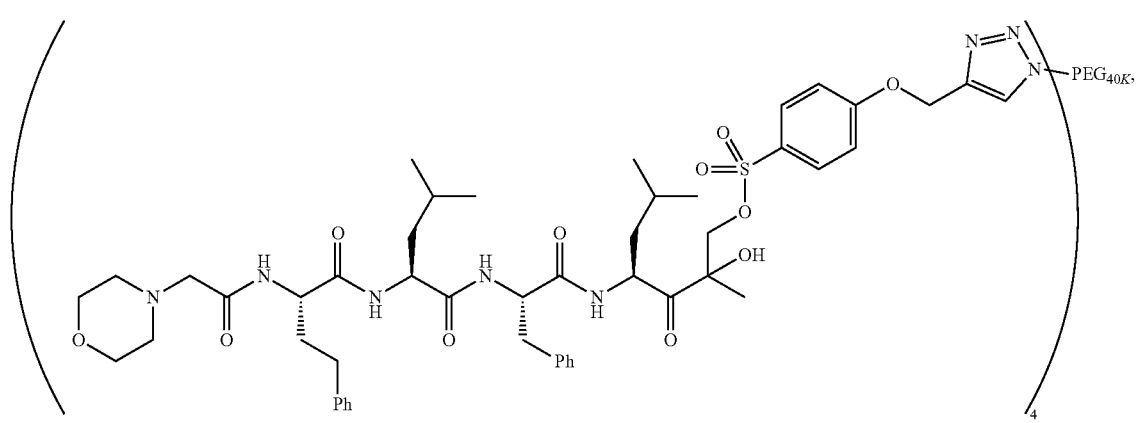
80

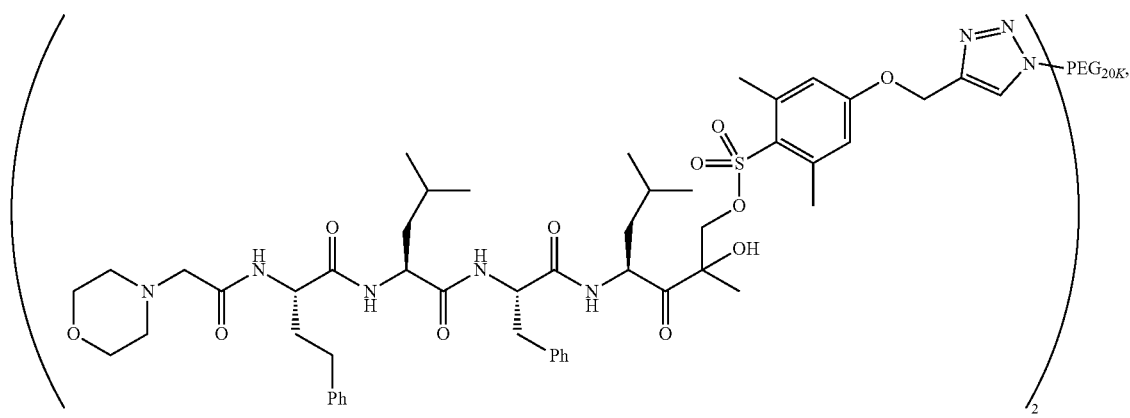
81
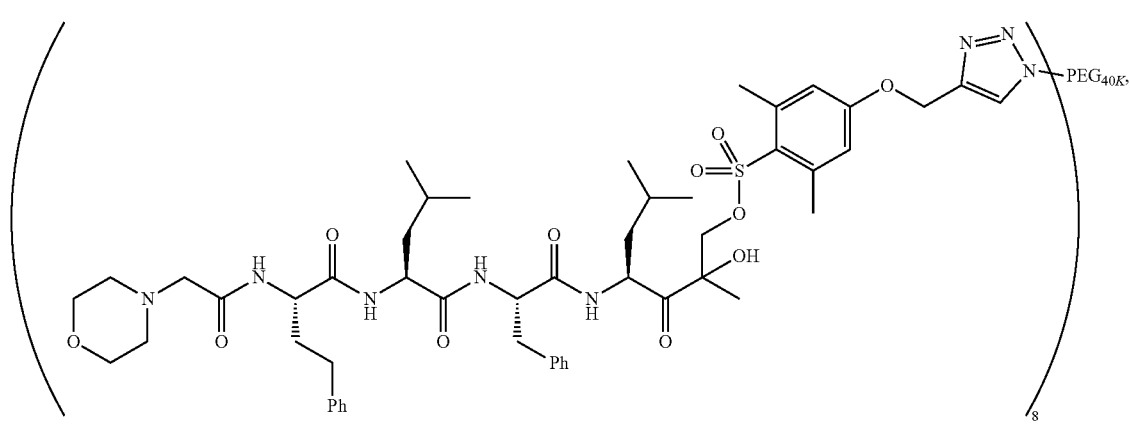
82
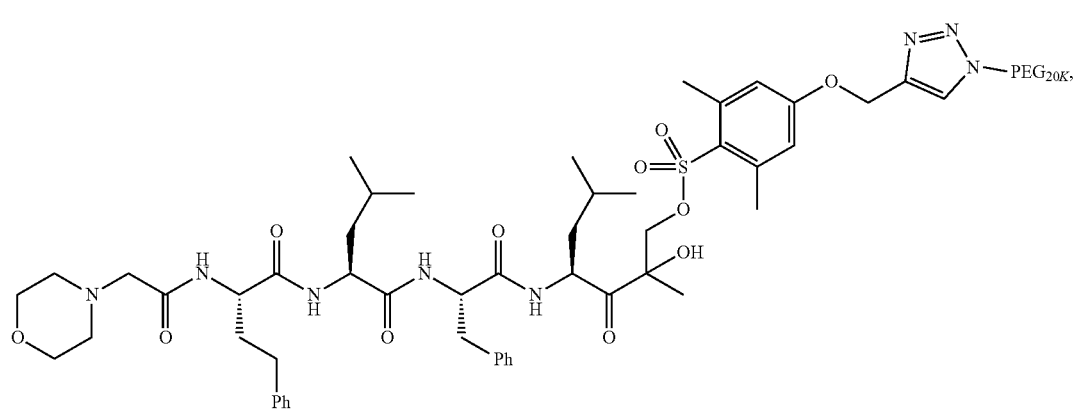
83
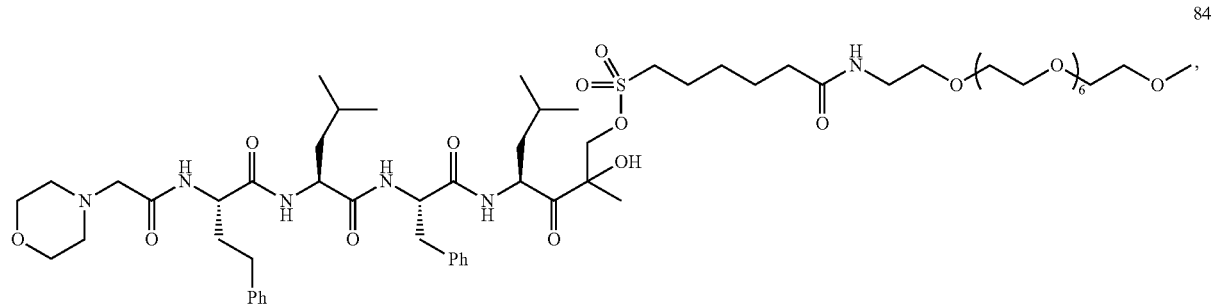
84

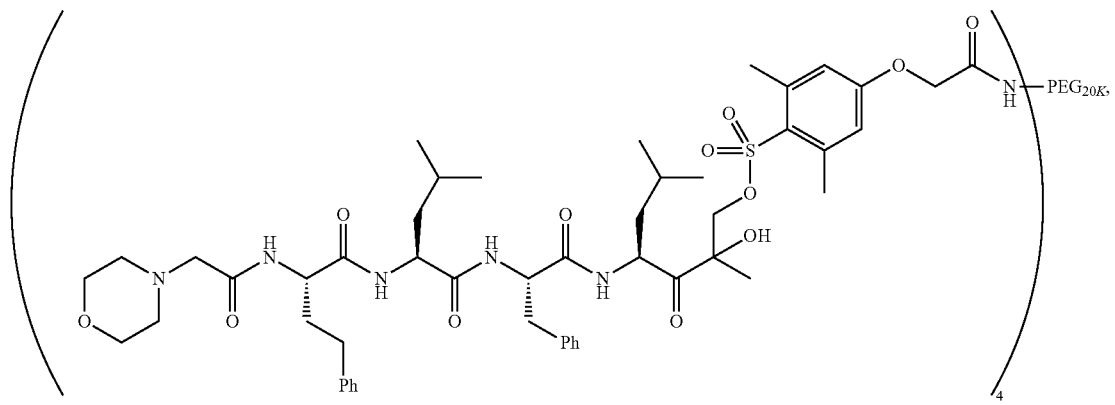
85
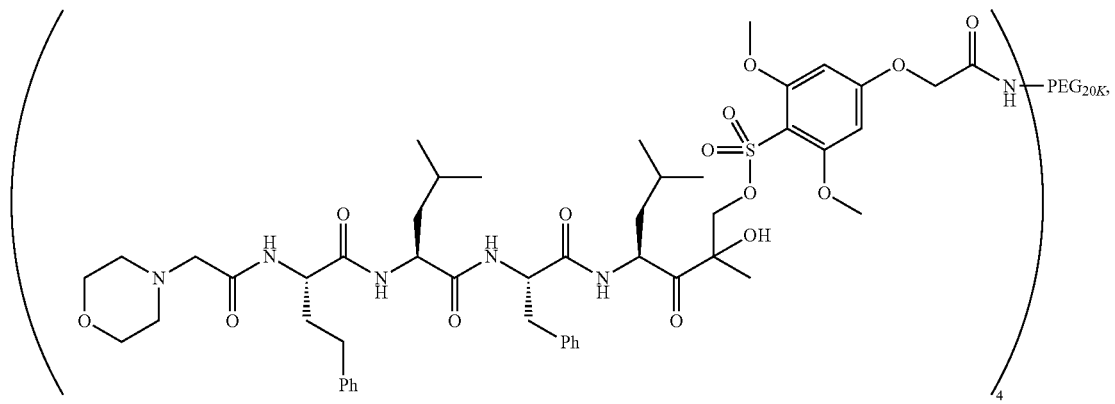
86
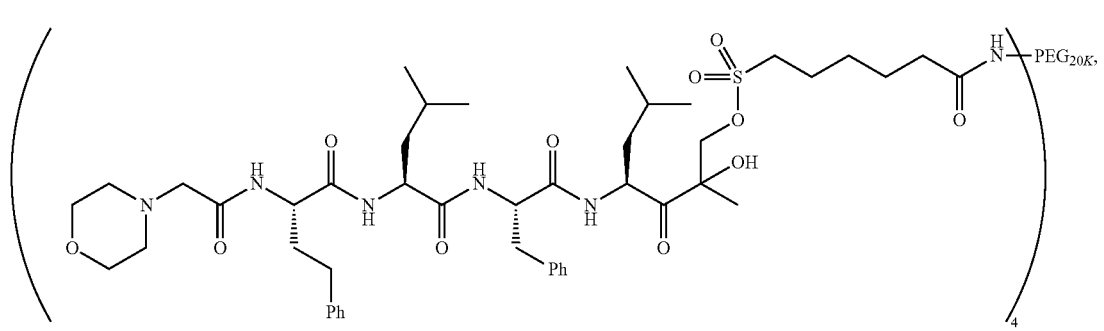
87
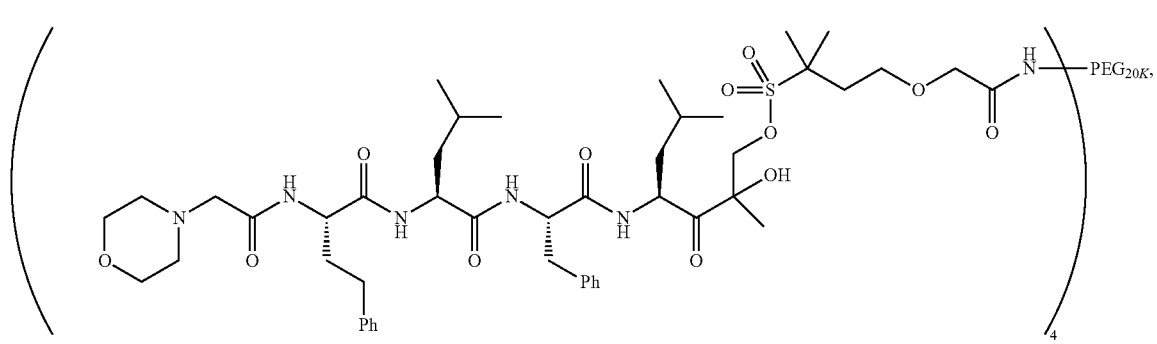
88

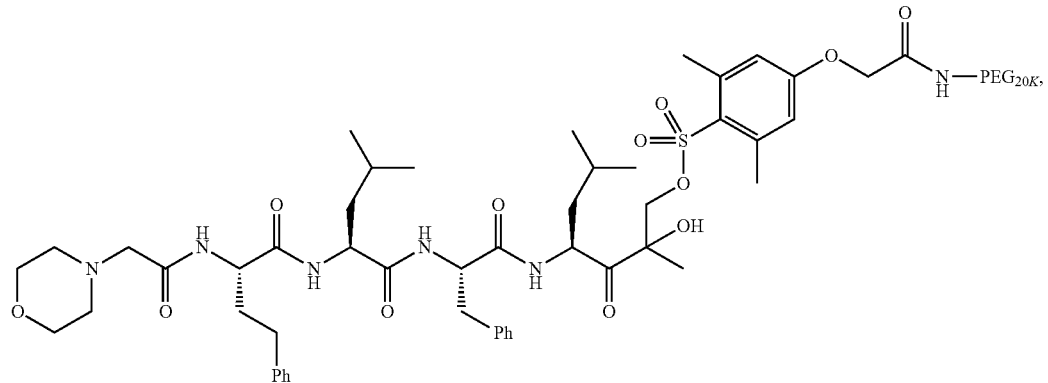
89
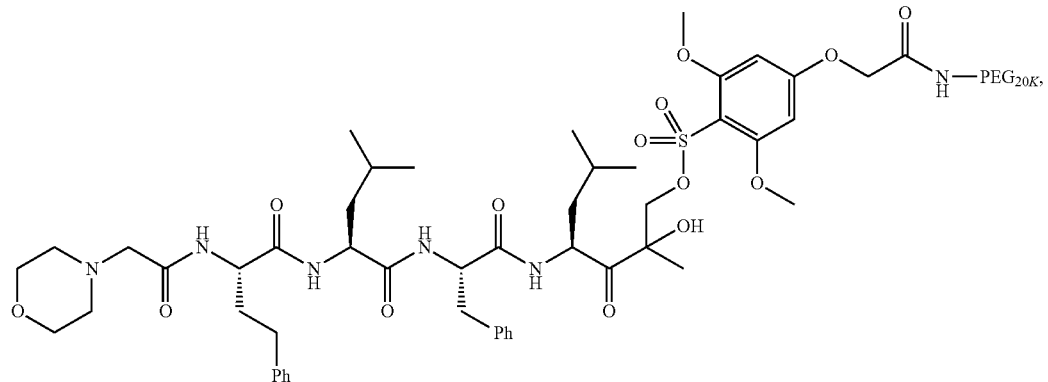
90
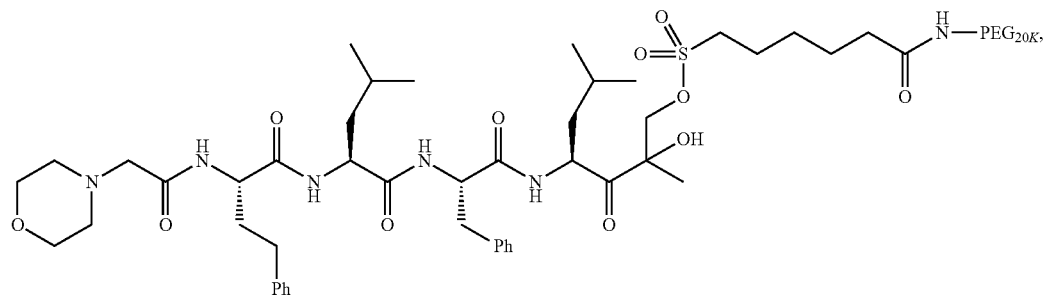
91
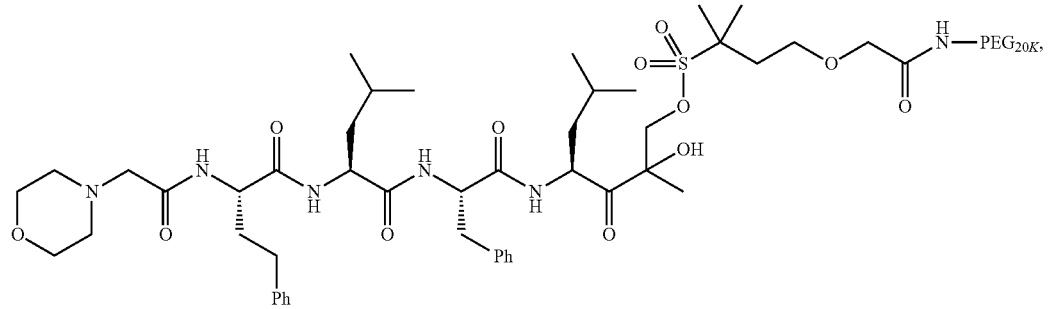
92

93
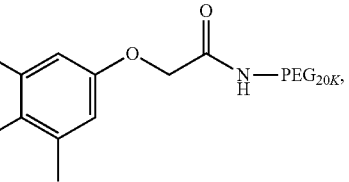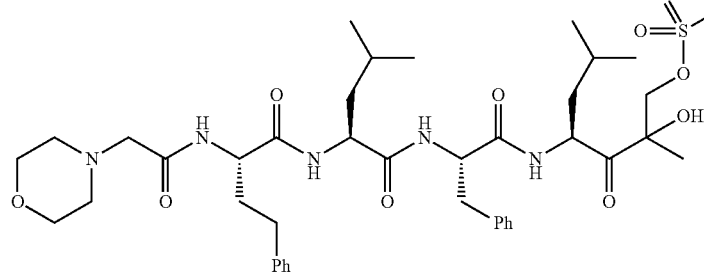
94
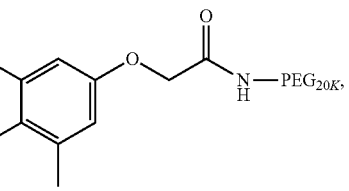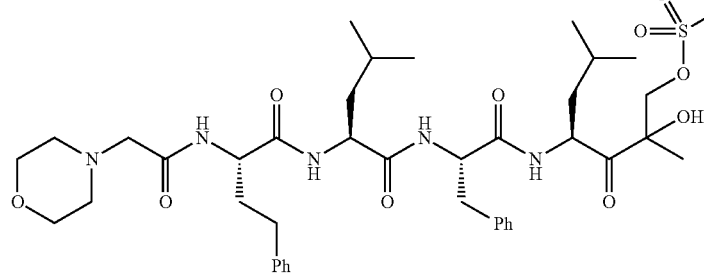
95
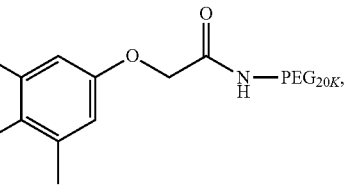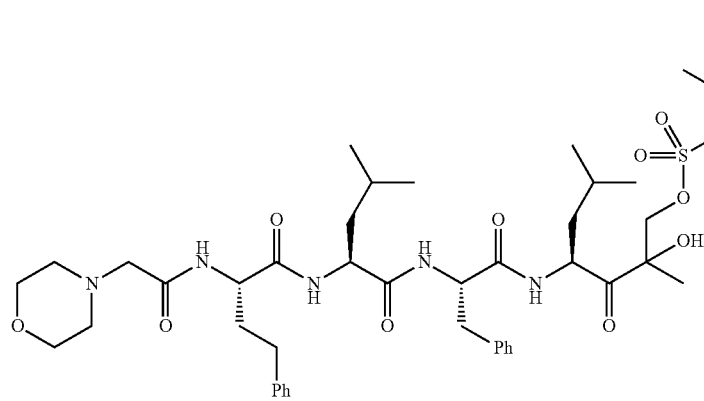
96
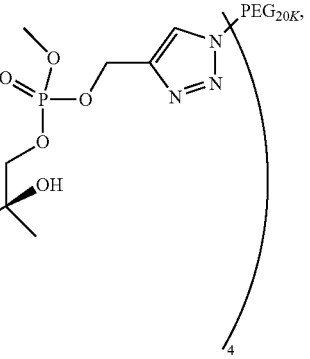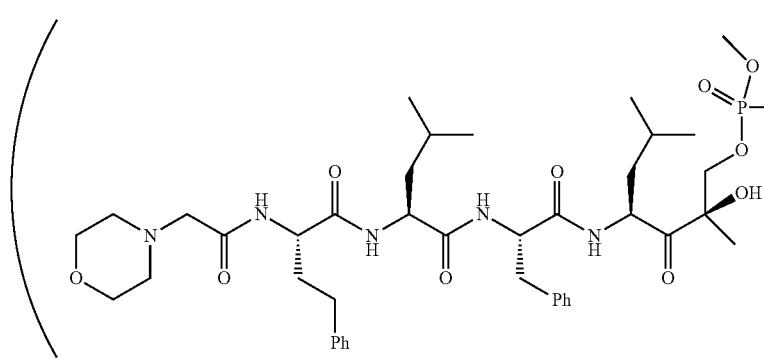

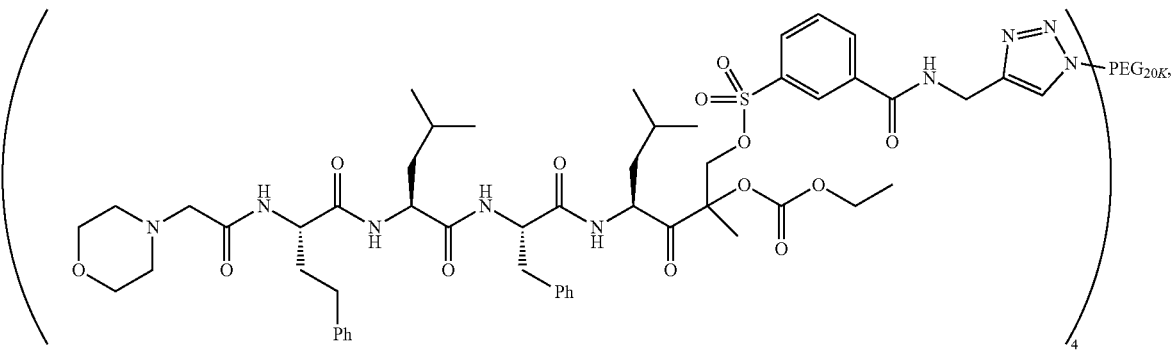

114

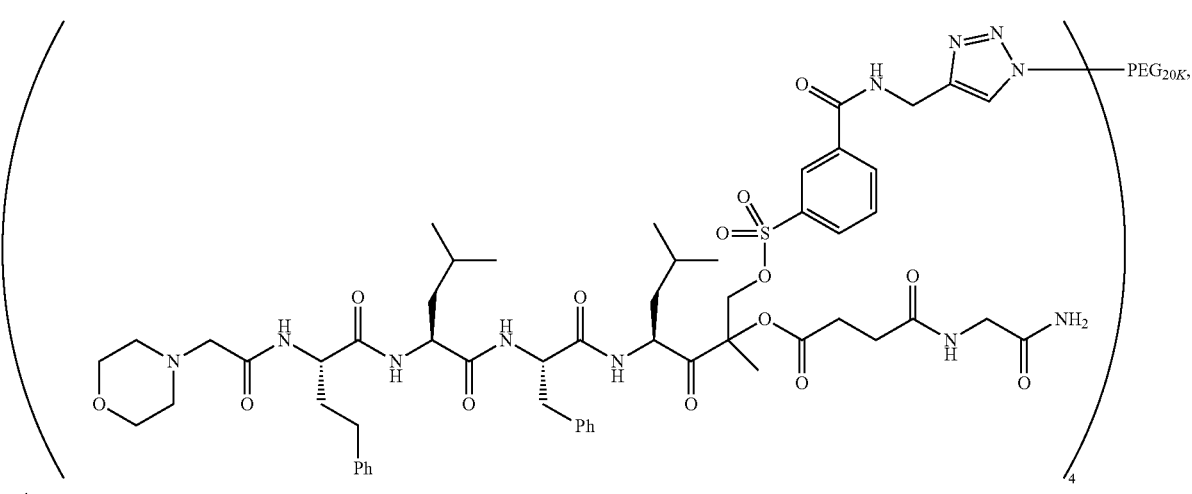

115 and

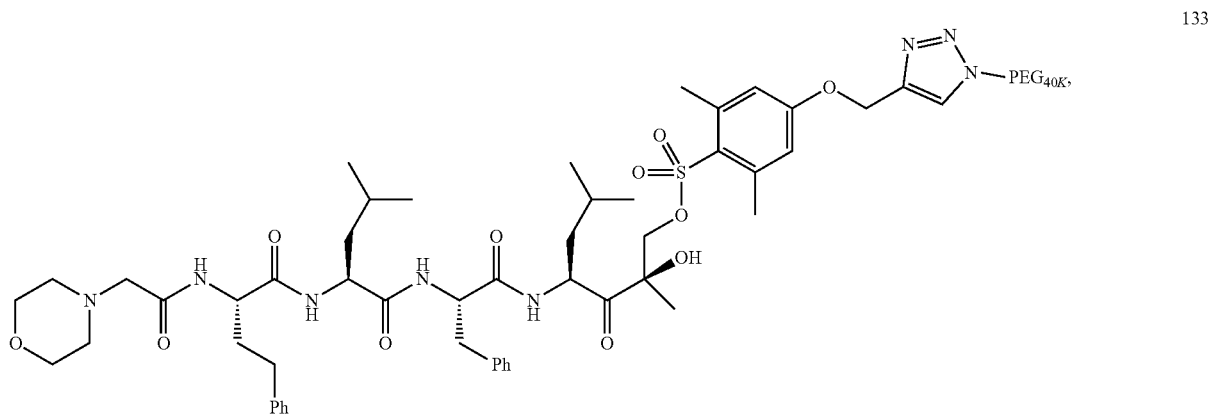

133 or a pharmaceutically acceptable salt thereof.

18. A pharmaceutical composition comprising a compound as claimed in claim 1, and a pharmaceutically acceptable carrier.

19. The compound according to claim 1, wherein the PEG has PEG architecture 2B or 2C; and/or the PEG has a molecular weight selected from the group consisting of: greater than 1 kDa, 1 kDa, greater than 2 kDa, 2 kDa, greater than 5 kDa, 5 kDa, greater than 10 kDa, 10 kDa, greater than 20 kDa, 20 kDa, greater than 30 kDa, 30 kDa, greater than 40 kDa, 40 kDa, and greater than 50 kDa.

* * * * *